United States Patent
Olszewski et al.

(10) Patent No.: US 10,988,484 B2
(45) Date of Patent: *Apr. 27, 2021

(54) GLUCOSE UPTAKE INHIBITORS

(71) Applicant: Kadmon Corporation, LLC, New York, NY (US)

(72) Inventors: Kellen L. Olszewski, Brooklyn, NY (US); Ji-In Kim, Princeton, NJ (US); Masha V. Poyurovsky, New York, NY (US); Kevin G. Liu, West Windsor, NJ (US); Anthony Barsotti, New York, NY (US); Koi Morris, Plainsboro, NJ (US)

(73) Assignee: Kadmon Corporation, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/397,043

(22) Filed: Apr. 29, 2019

(65) Prior Publication Data
US 2019/0315772 A1    Oct. 17, 2019

Related U.S. Application Data

(63) Continuation of application No. 15/737,911, filed as application No. PCT/US2016/039365 on Jun. 24, 2016, now Pat. No. 10,273,248.

(60) Provisional application No. 62/185,223, filed on Jun. 26, 2015.

(51) Int. Cl.
| | |
|---|---|
| *C07D 471/04* | (2006.01) |
| *C07D 491/04* | (2006.01) |
| *C07D 495/04* | (2006.01) |
| *C07D 487/04* | (2006.01) |
| *C07D 513/04* | (2006.01) |
| *A61K 45/06* | (2006.01) |
| *A61K 31/519* | (2006.01) |
| *A61K 31/52* | (2006.01) |
| *A61K 31/5377* | (2006.01) |
| *C07D 473/34* | (2006.01) |
| *C07D 491/048* | (2006.01) |
| *A61P 35/04* | (2006.01) |

(52) U.S. Cl.
CPC .......... *C07D 513/04* (2013.01); *A61K 31/519* (2013.01); *A61K 31/52* (2013.01); *A61K 31/5377* (2013.01); *A61K 45/06* (2013.01); *A61P 35/04* (2018.01); *C07D 471/04* (2013.01); *C07D 473/34* (2013.01); *C07D 487/04* (2013.01); *C07D 491/04* (2013.01); *C07D 491/048* (2013.01); *C07D 495/04* (2013.01)

(58) Field of Classification Search
CPC .. C07D 471/04; C07D 491/04; C07D 495/04; C07D 487/04; C07D 513/04
See application file for complete search history.

(56) References Cited

U.S. PATENT DOCUMENTS

| | | |
|---|---|---|
| 2010/0216789 A1 | 8/2010 | Nagarathnam et al. |
| 2012/0238540 A1 | 9/2012 | Holcomb et al. |
| 2012/0277206 A1 | 11/2012 | Shaginian et al. |
| 2012/0329780 A1 | 12/2012 | Thormann et al. |
| 2019/0060314 A1* | 2/2019 | Olszewski ........... C07D 239/70 |

FOREIGN PATENT DOCUMENTS

WO    2014/040499 A2    3/2012

* cited by examiner

*Primary Examiner* — Laura L Stockton
(74) *Attorney, Agent, or Firm* — Fox Rothschild LLP

(57) ABSTRACT

Provided herein are compounds that modulate glucose uptake activity and are useful for treating cancer, autoimmune diseases, inflammation, infectious diseases, and metabolic diseases. In certain embodiments, the compounds modulate glucose uptake activity by modulating cellular components, including, but not limited to those related to glycolysis and the known transporters/co-transporters of glucose such as GLUT1 and other GLUT family members/alternative hexose transporters. In certain embodiments, the compounds have the structure of formula I:

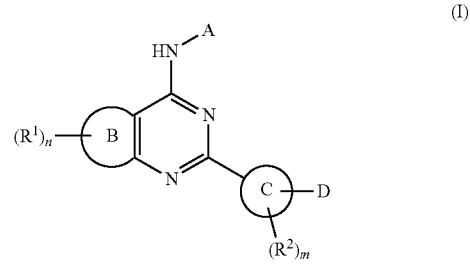

wherein the variables have the values disclosed herein.

7 Claims, 9 Drawing Sheets

| | IC50 (μM) |
|---|---|
| Ex. 7 | 0.063 |
| CQ | 0.062 |

| | IC50 (μM) |
|---|---|
| Ex. 23 | 0.077 |
| Ex. 24 | 0.078 |
| Ex. 7 | 0.11 |

| IC50 (µM) | Glycolysis | IL-17 | Proliferation |
|---|---|---|---|
| Ex. 7 | 0.155 | 1.313 | 3.901 |
| Ex. 31 | 0.049 | 0.359 | 2.247 |
| Ex. 70 | 0.043 | 0.062 | 2.495 |
| Ex. 51 | 0.039 | 0.073 | 0.835 |
| Ex. 81 | 0.048 | 0.158 | 1.259 |

GLUCOSE UPTAKE INHIBITORS

FIELD OF THE INVENTION

This invention provides compounds that modulate glucose uptake activity. Compounds of the invention are useful for treating diseases, including cancer, autoimmune diseases and inflammation, infectious diseases, and metabolic diseases.

BACKGROUND OF THE INVENTION

Glucose represents a central nutrient for many organisms, and control of glucose signaling and consumption is tightly regulated. Accordingly, many disease states are associated with defects in this regulation and therefore may be susceptible to therapeutic intervention using glucose uptake inhibitors. Glucose uptake inhibitors may have utility in disease areas such as oncology, autoimmunity and inflammation, infection diseases/virology, and metabolic disease.

SUMMARY OF THE INVENTION

Compounds useful according to the present invention include those having the formula I:

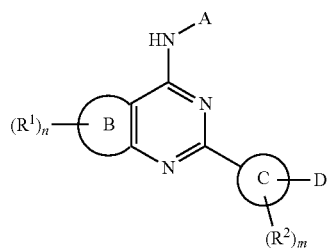

wherein:
A is selected from the group consisting of:

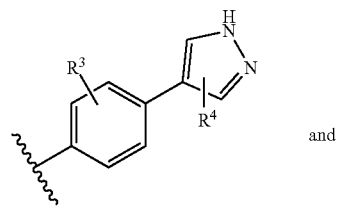

and

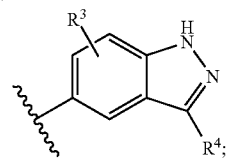

Ring B is a five- or six-membered ring containing 1 or 2 heteroatoms selected from the group consisting of N, O and S;
Ring C is a five- or six-membered aryl or heteroaryl ring containing from 0 to 2 heteroatoms selected from the group consisting of N, O and S;
each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;
n is selected from 0, 1, or 2;
each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;
m is selected from 0, 1, or 2;
$R^3$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl;
$R^4$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl; and
D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—$R^7$, and —NH—$(CH_2)_y$—$NR^5R^6$;
y is selected from 1, 2, or 3;
$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl,
or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and
$R^7$ is selected from the group consisting of aryl, heteroaryl, and a hetercyclic group.

The invention is based, at least in part, on the discovery of compounds that modulate glucose uptake activity. In one embodiment, the compounds of the invention are useful for treating cancer. In another embodiment, the compounds are useful for treating autoimmune diseases. In another embodiment, the compounds are useful for treating inflammation. In another embodiment, the compounds are useful for treating infectious diseases. In another embodiment, the compounds are useful for treating metabolic diseases. In certain embodiments, the compounds modulate glucose uptake activity by modulating cellular components, including, but not limited to those related to glycolysis and the known transporters of glucose such as GLUT1 and other GLUT family members.

DESCRIPTION OF THE DRAWINGS

FIG. 4A shows relative cell number and $IC_{50}$ values. FIG. 4B shows the percentage cell death (relative to number of cells plated).

FIG. 5A shows $IC_{50}$ values for the compound of Example 31−/+$H_2O_2$. FIG. 5B shows the percentage cell death following indicated treatments.

FIG. 6A shows the $IC_{50}$ for cell proliferation. FIG. 6B shows the $LD_{50}$ for cell death.

FIG. 7A shows blood cultures of *P. falciparum* (HB3 strain; 2% initial parasitemia; 1% hematocrit; O+ blood) that were seeded in 96-well culture plates and treated with the varying concentrations of the compound of Example 7 and chloroquine (CQ) in 0.1% DMSO for 48 hours. The cultures were harvested and DNA quantitated using the standard Sybr Green I fluorescence assay. FIG. 7B shows cultures that were seeded as above and treated with varying concentrations of the indicated compounds for 48 hours. The culture medium was harvested and extracellular lactic acid was quantified by LC-MS.

In FIG. 8A, left panel, human CD4 positive T cells were activated for 24 hours prior to a one hour treatment with the indicated glucose uptake inhibitors combined with 10 µM oligomycin (the same conditions used for the glycolysis assay in HT1080 cells described below). In FIG. 8A, right panel, human CD4 T cells were activated for 48 hours in the presence of the glucose uptake inhibitors. IL-17 secreted into the supernatant was measured by ELISA (R&D systems). Proliferation was measured by Cell Titer Glo (Promega). FIG. 8B lists the IC50 values (µM) for the glucose uptake inhibitors against activated T cell glycolysis, IL-17 secretion and proliferation.

DETAILED DESCRIPTION OF THE INVENTION

Figure 1:
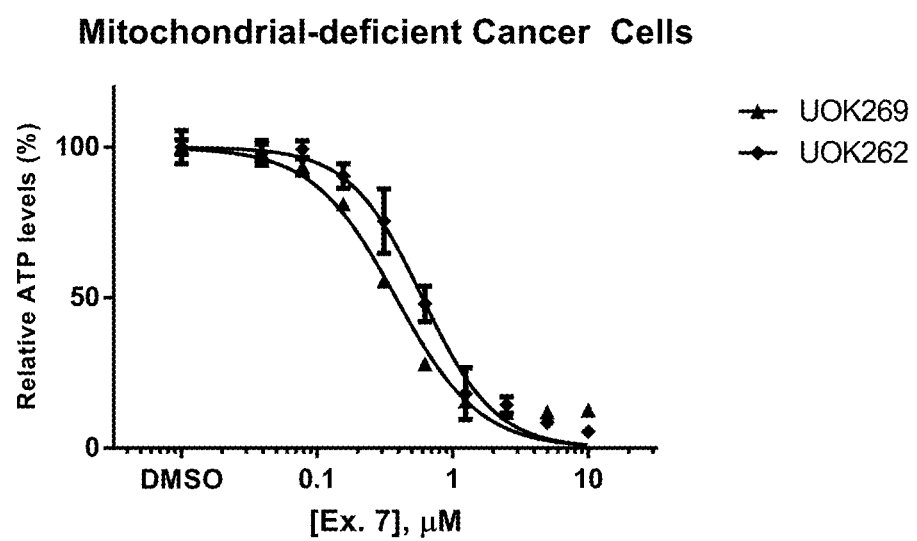
FIG. 1 shows two mitochondrial deficient cell lines (UOK262, UOK269) treated with a dose-curve of the compound of Example 7 for one hour. Cellular ATP levels were measured by Cell Titer Glo (Promega).

Glucose represents a central nutrient for many organisms, and control of glucose signaling and consumption is tightly regulated. Accordingly, many disease states are associated with defects in this regulation and therefore may be susceptible to therapeutic intervention using glucose uptake inhibitors. Glucose uptake inhibitors have utility in disease areas such as oncology, autoimmunity and inflammation, infection diseases/virology, and metabolic disease.

One of the emerging hallmarks of cancer is reprogramming of cancer cell metabolism. In order to meet the energetic demands of cell growth and division, cancer cells adopt the process of "aerobic glycolysis." While normal cells maintain a low rate of glycolysis, followed by full oxidization of pyruvate in the mitochondria, cancer cells rely on an increased rate of glycolysis followed by lactic acid fermentation (even in the presence of oxygen). Since mitochondrial oxidation phosphorylation generates more ATP than glycolysis alone, cancer cells rely heavily on increased rates of glucose consumption. One common way cancer cells achieve this goal is through the up-regulation of glucose transporters. In fact, many well-characterized oncogenes are thought to up-regulate both glycolytic enzymes and glucose transporters. Furthermore, the increased rate of glucose consumption displayed by the majority of tumors has already been employed in the field of diagnostics. Because of this cancer wide-phenomenon, one standard technique for imaging tumors is through the use of PET imaging of a radio-labelled glucose analog ($^{18}$FDG) (Hanahan, D. and R. A. Weinberg, *Hallmarks of cancer: the next generation*. Cell, 2011. 144(5): p. 646-74.) Taken together, it is predicted that inhibition of glucose uptake should affect cancer cells from a wide variety of tumor types while having little effect on normal cells.

Like cancer cells, activated T effector cells switch to the process of aerobic glycolysis to meet their energetic demands (MacIver, N. J., R. D. Michalek, and J. C. Rathmell, *Metabolic regulation of T lymphocytes*. Annu Rev Immunol, 2013. 31: p. 259-83.) Since hyper-activation of helper T-cells (e.g. Th17, Th2, Th1) play a large role in autoimmune disorders and inflammation, decreasing the rate of glycolysis in these cells would be predicted to curb their secretion of inflammatory cytokines. In addition, as inhibition of glucose uptake activates AMPK, a master regulator of T regulatory cells (Michalek, R. D., et al., *Cutting edge: distinct glycolytic and lipid oxidative metabolic programs are essential for effector and regulatory CD4+ T cell subsets*. J Immunol, 2011. 186(6): p. 3299-303)), the use of glucose uptake inhibitors would also be predicted to increase the T regulatory cell population (which suppress inflammation), thereby "rebalancing" the immune system. In addition to T cells, other cells of the immune system (including but not limited to macrophages, dendritic cells and B cells) rely heavily on glycolysis for their development, activation and effector functions. Thus it is predicted that glucose uptake inhibitors will have utility as immunesuppressants and may provide benefit in many autoimmune and inflammatory conditions.

Many infectious agents (including viruses, parasites, etc.) rely heavily on glucose consumption for growth and expansion and therefore the use of the glucose uptake inhibitors disclosed herein will be useful for inhibiting infectious diseases. In particular, the malaria parasites of the genus *Plasmodia* rely exclusively on glucose for energy production. These parasites infect red blood cells and induce a vast increase in glucose uptake modulated through the host cell GLUT1 transporters. Subsequent to transport of glucose into the red blood cells, parasites must also transport glucose across its own cellular membrane through additional, para-site-encoded hexose transporters such as *Plasmodium falciparum* hexose transporter 1 (PfHT1). Interfering with glucose uptake at either step with the compounds disclosed herein is predicted to have anti-malarial activity. In addition to malaria, many other infectious agents also hijack the mammalian cellular machinery to support their own growth, often targeting host glucose metabolism. For example, the activity of the glucose transporter GLUT1 is critically important for the infection and replication of HIV-1 in cultured T cells (Loisel-Meyer, S., et al., *Glut1-mediated glucose transport regulates HIV infection*. Proc Natl Acad Sci USA, 2012. 109(7): p. 2549-54). The induction of glucose uptake has also been noted in other viruses, such as the substantial increase in GLUT4 levels in human cytomegalovirus-infected fibroblasts (Yu, Y., T. G. Maguire, and J. C. Alwine, *Human cytomegalovirus activates glucose transporter 4 expression to increase glucose uptake during infection*. J Virol, 2011. 85(4): p. 1573-80). Given that infectious disease causing agents often rely on glucose metabolism, the use of the glucose uptake inhibitors (that target host and/or parasite cellular components) disclosed herein against these dieases is promising.

Hyperglycemia resulting from diabetes mellitus can lead to various long-term consequences. Because certain cells rely solely on passive glucose transporters (where glucose flows down a concentration gradient), such cells consume damaging levels of glucose under these conditions. Inhibitors of glucose uptake (particular those that inhibit GLUT1) could protect such cells from damage. For example, the compounds disclosed herein may have utility in both diabetic retinopathy (Lu, L., et al., *Suppression of GLUT1; a new strategy to prevent diabetic complications*. J Cell Physiol, 2013. 228(2): p. 251-7) and nephropathy (Marques, T., et al., *Association of single nucleotide polymorphisms in the gene encoding GLUT1 and diabetic nephropathy in Brazilian patients with type 1 diabetes mellitus*. Clin Chim Acta, 2015).

Compounds useful according to the present invention include those having the formula I:

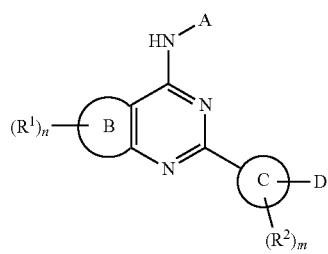

wherein:
A is selected from the group consisting of:

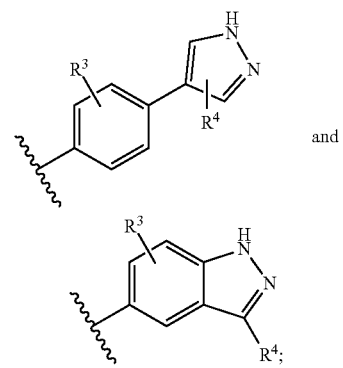

Ring B is a five- or six-membered ring containing 1 or 2 heteroatoms selected from the group consisting of N, O and S;
Ring C is a five- or six-membered aryl or heteroaryl ring containing from 0 to 2 heteroatoms selected from the group consisting of N, O and S;
each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;
n is selected from 0, 1, or 2;
each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

m is selected from 0, 1, or 2;
$R^3$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl;
$R^4$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl; and
D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—$R^7$, and —NH—$(CH_2)_y$—$NR^5R^6$;
y is selected from 1, 2, or 3;
$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl,
or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and
$R^7$ is selected from the group consisting of aryl, heteroaryl, and a hetercyclic group.

In certain preferred embodiments, the sub-structure

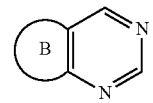

is selected from the group consisting of but not limited to:

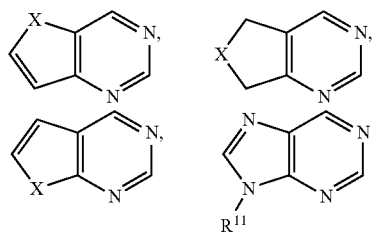

wherein X is selected from O and S, and $R^{11}$ is selected from H and $C_1$ to $C_6$ alkyl

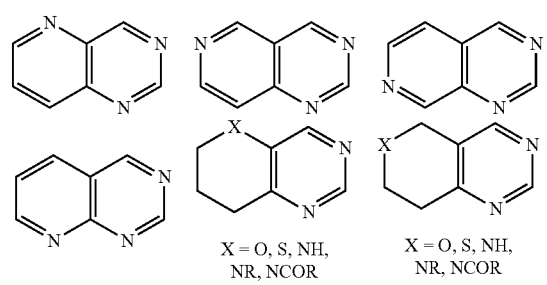

-continued

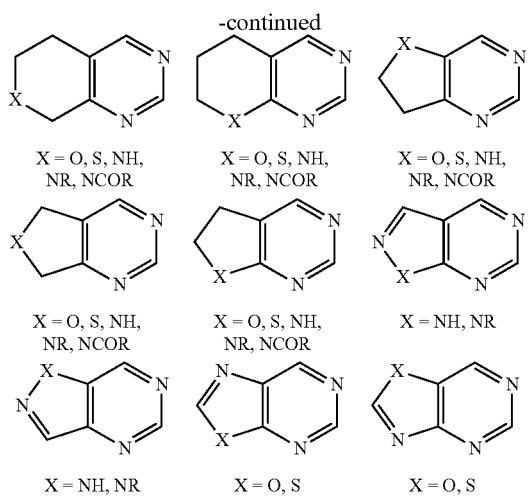

wherein R is selected from $C_1$-$C_6$ alkyl, $C_3$-$C_6$ cycloalkyl, aryl, and heterocycle.

In certain preferred embodiments, the present invention relates to a compound having the formula II:

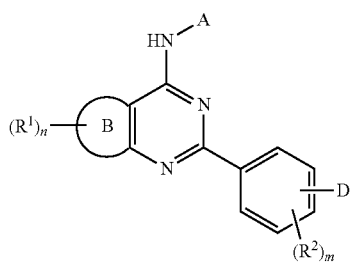

wherein:
A is selected from the group consisting of:

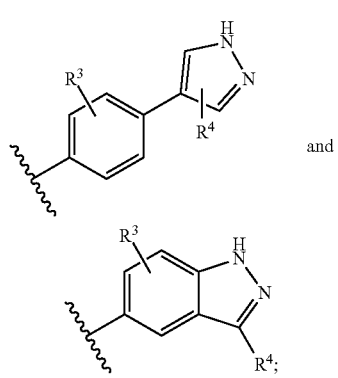

Ring B is a five- or six-membered ring containing 1 or 2 heteroatoms selected from the group consisting of N, O and S;
each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;
n is selected from 0, 1, or 2;
each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;
m is selected from 0, 1, or 2;

$R^3$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl;
$R^4$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl; and
D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—$R^7$, and —NH—$(CH_2)_y$—$NR^5R^6$;
y is selected from 1, 2, or 3;
$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl,
or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and
$R^7$ is selected from the group consisting of aryl, heteroaryl, and a hetercyclic group.

In other preferred embodiments, the present invention relates to a compound having the formula $III_a$ or $III_b$:

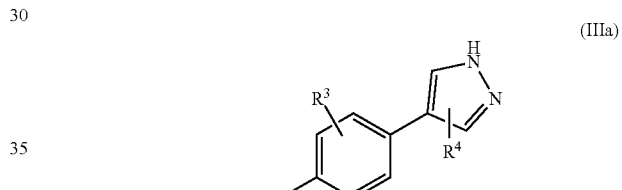

(IIIa)

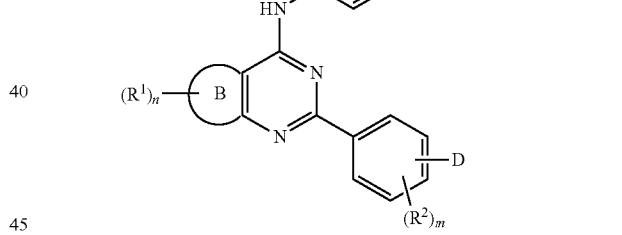

(IIIb)

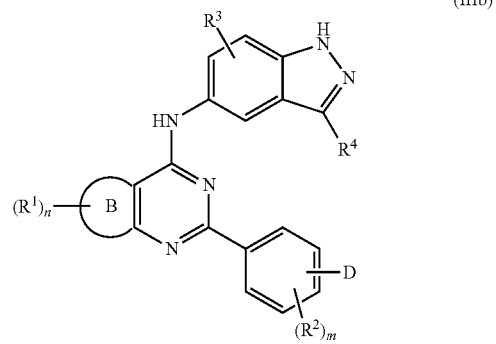

wherein:
Ring B is a five- or six-membered ring containing 1 or 2 heteroatoms selected from the group consisting of N, O and S;
each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

n is selected from 0, 1, or 2;
each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;
m is selected from 0, 1, or 2;
$R^3$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl;
$R^4$ is selected from the group consisting of halo, $C_1$-$C_6$ alkyl, $C_2$-$C_6$ alkenyl, $C_1$-$C_6$ alkoxy, $C_3$-$C_6$ cycloalkyl, hydroxy, amino, cyano and $C_1$-$C_3$ perfluoro alkyl; and
D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—$R^7$, and —NH—$(CH_2)_y$—$NR^5R^6$;
y is selected from 1, 2, or 3;
$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl,
or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and
$R^7$ is selected from the group consisting of aryl, heteroaryl, and a hetercyclic group.

As used herein, the definition of each expression, e.g. alkyl, m, n, R, etc., when it occurs more than once in any structure, is intended to be independent of its definition elsewhere in the same structure.

The term "heteroatom" as used herein means an atom of any element other than carbon or hydrogen. Preferred heteroatoms are nitrogen, oxygen, and sulfur.

The term "alkyl" refers to the radical of saturated aliphatic groups, including straight-chain alkyl groups and branched-chain alkyl groups. In preferred embodiments, a straight chain or branched chain alkyl has 10 or fewer carbon atoms in its backbone (e.g., $C_1$-$C_{10}$ for straight chain, $C_3$-$C_{10}$ for branched chain). Likewise, preferred cycloalkyls have from 3-10 carbon atoms in their ring structure, and more preferably have 3 to 6 carbons in the ring structure.

The term "cycloalkyl" refers to saturated, carbocyclic groups having from 3 to 7 carbons in the ring. Preferred cycloalkyl groups include cyclopropyl, cyclobutyl, cyclopentyl and cyclohexyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles", "heteroaromatics" or "heteroaryl". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, aryls and/or heterocyclic groups.

The terms "heterocyclyl" or "heterocyclic group" refer to 3- to 10-membered ring structures, more preferably 5- or 6-membered rings, whose ring structures include one to four heteroatoms. Heterocycles can also be polycycles. Heterocyclic groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$. The term "halogen" or "halo" designates —F, —Cl, —Br or —I, and preferably —F, —Cl, or —Br. The term "hydroxyl" means —OH.

The terms "amine" and "amino" refer to both unsubstituted and substituted amines, e.g., a moiety that can be represented by the general formula:

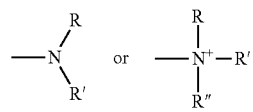

wherein R, R' and R" each independently represent H, alkyl, alkenyl, alkynyl, aralkyl, aryl, and heterocyclic groups, and most preferably H or lower alkyl.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. The term lower alkoxy refers to an alkoxy group having from 1 to 6 carbon atoms.

The term "oxo" as used herein refers to an oxygen atom that has a double bond to a another atom, particularly to carbon.

It will be understood that "substituted", "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above.

Certain compounds of the present invention may exist in particular geometric or stereoisomeric forms. The present invention contemplates all such compounds, including cis- and trans-isomers, R- and S-enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention.

Certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this context, refers to the relatively non-toxic, inorganic and organic acid addition salts of compounds of the present invention. Representative salts include the hydrochloride, hydrobromide, sulfate, bisulfate, phosphate, nitrate, acetate, stearate, laurate, benzoate, lactate, phosphate, tosylate, citrate, maleate, fumarate, succinate, tartrate, napthylate, and mesylate salts and the like. (See, for example, Berge et al. "Pharmaceutical Salts", *J. Pharm. Sci.* (1977) 66:1-19).

In other cases, the compounds of the present invention may contain one or more acidic functional groups and, thus, are capable of forming pharmaceutically-acceptable salts with pharmaceutically-acceptable bases. Representative salts include alkali or alkaline earth salts such as lithium, sodium, potassium, calcium, magnesium salts and the like. Representative organic amines useful for the formation of base addition salts include ethylamine, diethylamine, ethylenediamine, ethanolamine, diethanolamine, piperazine and the like. (See, for example, Berge et al., supra).

In another aspect of the present invention there is provided a method of treating a patient suffering from a disease comprising administering to a patient in need of such treatment a therapeutically effective amount of a compound of the present invention. The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment, e.g. reasonable side effects applicable to any medical treatment.

Glucose uptake inhibitors of the invention inhibit tumor cell growth and metastasis and angiogenesis, and are useful for treating neoplastic diseases. Neoplastic diseases include any malignant growth or tumor caused by abnormal or uncontrolled cell division, and may spread to other parts of the body through the lymphatic system or the blood stream. Neoplastic disease includes, without limitiation, lymphoma (a neoplasm of lymph tissue that is usually malignant), carcinoma (any malignant tumor derived from epithelial tissue), leukemia (malignant neoplasm of blood-forming tissues; characterized by abnormal proliferation of leukocytes), sarcoma (a usually malignant tumor arising from connective tissue (bone or muscle etc.), and blastoma (malignancy in precursor cells). Nonlimiting examples include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer. In particular, the compounds of the present invention inhibit tumors with a defined genetic background that render cancer cells more reliant on glycolysis. Non-limiting examples include genetic mutations in TCA cycle components Fumarate Hydratase (FH), Succinate Dehydrogenase (SDH), and mitochondrial encoded complex I mutations. Mutations in FH underlie an inherited cancer disease termed leiomyomatosis renal cell carcinoma (HLRCC). Kidney tumors associated with this disease are aggressive and have the tendency to metastasize early. Tumor cell lines derived from such tumors are extremely dependent on glucose uptake for survival (Yang et al, *Cancer Genet Cytogenet.* 2010 Jan. 1; 196(1): 45-55.). Germline mutations in SDH have been observed in patients with hereditary paragangliomas and phaeochromocytomas (Belinksi et al, *Front Oncol.* 2013 May 17; 3:117.). Germline mutations in SDH have also been associated with renal neoplasia (Gill, *Pathology* (June 2012) 44(4), pp. 285-292) and cell lines derived from such tumors consume very little oxygen and thus are predicted to be completely dependent on glycolysis for survival.

In certain embodiments, a glucose uptake inhibitor of the invention is used as part of a rational combination therapy. Other compounds or therapies to be used with a glucose uptake inhibitor of the invention include, but are not limited to, $H_2O_2$, Vitamin C (pharmacological-dose), Ionizing Radiation, Beta-lapachone, AEQ501, ARQ761 (prodrug), Elesclemol, Menadione, Bleomycin, Cisplatinum, Apatone (IC-MedTech) (Menadione+Vitamin C), Imexon, Antamycin A, Paraquat, MPP, Caged $H_2O_2$, Mustard Gas-Mustargen, methchlorethamine), Melphalan (ALkeran), NOV-002, Pyrogallol, Acetaminophen, Dimethylfumarate (DMF) and its metabolite methylhydrogenfumarate (MHF), Apaziquone/E0quin, E09, and CPI-613 (AKGDH inhibitor).

Glucose uptake inhibitors of the invention may be co-administered with other antineoplastic agents, including chemotherapeutic agents and radiation. Anti-neoplastic agents can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, antisurvival agents, biological response modifiers, anti-hormones, steroids and anti-angiogenesis agents. Examples of alkylating agents include, but are not limited to, cisplatin, cyclophosphamide, melphalan, and dacarbazine. Examples of antimetabolites include, but are not limited to, doxorubicin, daunorubicin, and paclitaxel, gemcitabine. Non-limiting examples of topoisomerase inhibitors are irinotecan (CPT-11), aminocamptothecin, camptothecin, DX-8951f, and topotecan (topoisomerase I) and etoposide (VP-16) and teniposide (VM-26) (topoisomerase II). When the anti-neoplastic agent is radiation, the source of the radiation can be either external (e.g., external beam radiation therapy—EBRT) or internal (i.e., brachytherapy—BT) to the patient being treated. The dose of anti-neoplastic agent administered depends on numerous factors, including, for example, the type of agent, the type and severity tumor being treated and the route of administration of the agent. It should be emphasized, however, that the present invention is not limited to any particular dose.

Glucose uptake inhibitors in this invention could be co-administered with an anti-angiogenic agent, for example a small molecule or biological molecule that targets a vascular endothelial growth factor (e.g., VEGF) or its receptor (e.g., VEGFR1, VEGFR2). In another embodiment, the compound is co-administered with an antagonist of the human EGFR related family of receptor tyrosine kinases (HER1/EGFR (epidermal growth factor receptor)/c-erbB1, HER2/c-erbB2, HER3/c-erbB3 and HER4/c-erbB4).

Glucose uptake inhibitors in this invention could be further co-administered with other agents that deplete cellular ATP or energy. Examples of such agents include, but are not limited to: metformin, phenformin, pyrvinium, rotenone.

The glucose uptake inhibitors could be co-administered with cell death inducing agents, which could include but are not limited to: BCL2 family inhibitors (e.g.: ABT737, ABT263, ABT199, obatoclax), SMAC family mimetics, TRAIL agonists, ferroptosis inducing agents (e.g.: sorafenib, erastin) and ER stress inducers.

In certain embodiments, a glucose uptake inhibitor of the invention is used to treat inflammation, including, but not limited to, asthma, idiopathic pulmonary fibrosis, liver fibrosis, renal fibrosis, LAM, nephrogenic systemic fibrosis, arthritis (especially rheumatoid arthritis and/or psoriatic arthritis and/or juvenile arthritis), sepsis and/or other autoimmune diseases such as but not limited to atherosclerosis, psoriasis, systemic lupus erythematosus, lupus nephritis, chronic graft vs. host disease, acute graft vs. host disease, multiple sclerosis, myasthenia gravis or symptoms of any of these, as well as one or more IBD, such as Crohn's disease, scleroderma, granulomatous colitis, ulcerative colitis, lymphocyte colitis, collagenous colitis and/or Coeliac disease, insulin-dependent diabetes mellitus, acquired immunodeficiency syndrome ("AIDS"), hemolytic anemias, rheumatic fever, Guillain-Barre syndrome and CIDP, thyroiditis, Graves' disease, glomerulonephritis, autoimmune hepatitis, cardiovascular inflammation, renal inflammation, and arteriosclerosis. In addition, the glucose uptake inhibitors disclosed herein may also be used as immunosuppressants for preventing rejection of transplanted organs.

Glucose uptake inhibitors in this invention can be co-administered with a corticosteroid hormone, anti-inflammatory drugs and cytokine targeting agents to achieve a better therapeutic activity on relieving/reducing the symptoms associated with autoimmune conditions. Examples of corticosteroid hormone include, but are not limited to, prednisolone, prednisone, hydrocortisone, methylprednisolone, and dexamethasone, cortisol, cortisone, triamcinolone, betamethasone, etc.

In certain embodiments, glucose uptake inhibitors of the invention are used to treat parasitic or viral infections, including, but not limited to, acute malaria and African trypanosomiasis, HIV, HCMV, tuberculosis, herpes virus.

In certain embodiments, a glucose uptake inhibitor of the invention is used to treat metabolic disease. In another embodiment of the invention, a glucose uptake inhibitor is used to reduce or prevent hyperglycemia. In an embodiment of the invention, a glucose uptake inhibitor is used to treat diabetic retinopathy or diabetic nephropathy. Metabolic diseases or conditions include, without limitation, diabetes (type 1 and type 2), insulin resistance, metabolic syndrome, hyperinsulinemia, nonalcoholic steatohepatitis (NASH), dyslipidemia, and hypercholesterolemia, obesity, hypertension, retinal degeneration, retinal detachment, cardiovascular diseases including vascular disease, atherosclerosis, coronary heart disease, cerebrovascular disease, heart failure and peripheral vascular disease in a subject.

When used for treatment of metabolic conditions, compounds in this invention could be co-administered with other agents used for treatment of metabolic disease. Non-limiting examples for these are: biguanides (including, but not limited to metformin), which reduce hepatic glucose output and increase uptake of glucose by the periphery, SGLT inhibitors, insulin secretagogues (including but not limited to sulfonylureas and meglitinides) which trigger or enhance insulin release by pancreatic β-cells, and PPARγ, PPARα, and PPARα/γ modulators (e.g., thiazolidinediones such as pioglitazone and rosiglitazone). Further examples may include statins, lipid lowering drugs such as MTP inhibitors and LDLR upregulators, antihypertensive agents such as angiotensin antagonists, e.g., losartan, irbesartan, olmesartan, candesartan, and telmisartan, calcium channel antagonists, e.g. lacidipine, ACE inhibitors, e.g., enalapril, and β-andrenergic blockers (β-blockers), e.g., atenolol, labetalol, and nebivolol.

In the methods of the invention, the compound of Formula I, and particularly Formula II, IIIa, or IIIb, can be administered by routes commonly known in the art. This includes oral administration, or any other convenient route. The compound of Formula I may also be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, transmucosal, rectally, by inhalation, or topically, particularly to the ears, nose, eyes, or skin. The mode of administration is left to the discretion of the practitioner. In most instances, administration will result in the release of a compound into the bloodstream.

In specific embodiments, it may be desirable to administer a compound locally. This may be achieved, for example, and not by way of limitation, by local infusion, topical application, by injection, by means of a catheter, by means of a suppository, or by means of an implant, said implant being of a porous, non-porous, or gelatinous material, including membranes, such as sialastic membranes, or fibers. In such instances, administration may selectively target a local tissue without substantial release of a compound into the bloodstream.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

In another embodiment, a compound is delivered in a vesicle, in particular a liposome (see Langer, 1990, Science 249:1527-1533; Treat et al., in Liposomes in the Therapy of Infectious Disease and Bacterial infection, Lopez-Berestein and Fidler (eds.), Liss, New York, pp. 353-365 (1989); Lopez Berestein, ibid., pp. 317-327; see generally ibid.).

In another embodiment, a compound is delivered in a controlled release system (see, e.g., Goodson, in Medical Applications of Controlled Release, supra, vol. 2, pp. 115-138 (1984)). Examples of controlled-release systems are discussed in the review by Langer, 1990, Science 249:1527-1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105).

The present invention provides a method of treating breast cancer in a subject. The term subject, as used herein, refers to the animal being treated, wherein the animal can be a mammal such as a human.

For the treatment of tumors, the therapeutically effective amount of the compound of Formula I, and particularly Formula II, IIIa, or IIIb, is the dose of this compound, or of a pharmaceutically acceptable salt thereof, that provides a therapeutic benefit in the treatment or management of a tumor, delays or minimizes one or more symptoms associated with a tumor, or enhances the therapeutic efficacy of another therapeutic agent used in the treatment or management of a tumor. The therapeutically effective amount may be an amount that reduces or inhibits the growth of breast cancer. A person skilled in the art would recognize that the therapeutically effective amount may vary depending on known factors such as the pharmacodynamic characteristics of the particular active ingredient and its mode and route of administration; age, sex, health and weight of the recipient; nature and extent of symptoms; kind of concurrent treatment, frequency of treatment and the effect desired. A person skilled in the art would also recognize that the therapeutically effective amount, or dose, of the compound of Formula I, Formula II, Formula $III_a$, or Formula $III_b$ can be determined based on the disclosures in this patent application and common knowledge in the art.

The amount of a compound, or the amount of a composition comprising a compound, that will be effective in the treatment and/or management of a tumor can be determined by standard clinical techniques. In vitro or in vivo assays may optionally be employed to help identify optimal dosage ranges.

A compound of the present invention, and its pharmaceutically acceptable salts, may be formulated in a pharmaceutical composition. In certain embodiments provided herein, the composition may comprise said compound and a pharmaceutically acceptable carrier, excipient, or diluent. The pharmaceutical compositions provided herein can be in any form that allows for the composition to be administered to a subject, including, but not limited to a human, and formulated to be compatible with an intended route of administration.

The ingredients of compositions provided herein may be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutically acceptable carriers, excipients and diluents include those approved by a regulatory agency of the Federal or a state government or listed in the U.S. Pharmacopeia or other generally recognized pharmacopeia for use in animals, and more particularly in humans. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions can comprise excipients that are well known in the art and are listed, for example, in the U.S. Pharmacopeia (USP) SP (XXI)/NF (XVI). In general, lactose free compositions comprise an active ingredient, a binder/filler, and a lubricant in pharmaceutically compatible and pharmaceutically acceptable amounts. Preferred lactose free dosage forms comprise a compound, microcrystalline cellulose, pre-gelatinized starch, and magnesium stearate.

Further provided herein are anhydrous pharmaceutical compositions and dosage forms comprising one or more compounds, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions. Compositions and dosage forms that comprise lactose and at least one compound that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are compositions and dosage forms that comprise one or more agents that reduce the rate by which a compound will decompose. Such agents, which are referred to herein as "stabilizers," include, but are not limited to, antioxidants such as ascorbic acid, pH buffers, or salt buffers.

The compositions and single unit dosage forms can take the form of solutions, suspensions, emulsions, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Such compositions and dosage forms will contain a therapeutically effective amount of a compound, preferably in purified form, together with a suitable amount of carrier so as to provide the form for proper administration to the patient.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation, if necessary. For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL® PH 101, AVICEL® PH 103 AVICEL® RC 581, AVICEL® PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL® RC 581. Suitable anhydrous or low moisture excipients or additives include AVICEL® PH 103™ and Starch 1500 LM.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB 0 SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Most controlled release formulations are designed to initially release an amount of drug (active ingredient) that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

The invention now being generally described, it will be more readily understood by reference to the following examples, which are included merely for the purposes of illustration of certain aspects and embodiments of the present invention, and are not intended to limit the invention.

EXAMPLES

Abbreviations used in the following examples and preparations include:
Ac₂O acetic anhydride
AcOH acetic acid
Bn Benzyl
Celite® diatomaceous earth
DCM dichloromethane
DIEA di-isopropylethylamine
DMAP 4-dimethylamino pyridine
DME 1,2-dimethoxylethane
DMF dimethylformamide
DMSO dimethyl sulfoxide
EDC 1-(3-dimethylaminopropyl)-3-ethylcarbodimide hydrochloride
EtOAc ethyl acetate
EtOH ethyl alcohol or ethanol
Et₂O ethyl ether
Et₃N triethylamine
g grams
HOBt 1-hydroxybenzotriazole
HPLC high pressure liquid chromatography
h hour(s)
MeCN acetonitrile
min minute(s)
MeOH methyl alcohol or methanol
mL milliliter
mmol millimoles
MS mass spectrometry
NMR nuclear magnetic resonance
iPrOH iso-propanol
PyBOP® benzotriazol-1-yl-oxytripyrrolidinophosphonium
rt room temperature
s singlet
t triplet
THF tetrahydrofuran Mass spectrometry was recorded on an LC-MS: Shimadzu 2000 LCMS. Unless otherwise stated all mass spectrometry was run in ESI mode.

¹H NMR spectra were recorded on a Bruker 400 or 500 MHz machine using MestReNova software.

Insofar as the synthesis of the following examples of compounds of the present invention is not explicitly described in such example, the synthesis is as described herein in general terms and the appropriate starting material can be easily selected for synthesizing the compound of the example.

Example 1

2-(3-(4-((4-(1H-pyrazol-4-yl)phenyl)amino)-5,7-dihydrofuro[3,4-d]pyrimidin-2-yl)phenoxy)-N-iso-propylacetamide

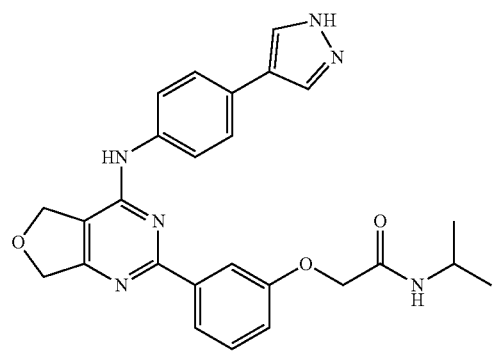 [SMILES: CC(C)NC(=O)COc1cccc(-c2nc3c(c(Nc4ccc(-c5cn[nH]c5)cc4)n2)COC3)c1]

Example 1A (Z)-3-hydroxy-2-(4-nitrophenyl)acrylaldehyde

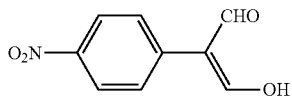 [SMILES: O=C/C(=C\O)c1ccc([N+](=O)[O-])cc1]

To stirring anhydrous DMF (20 mL) was added dropwise over 25 min POCl₃ (25.4 g, 165.61 mmol, 15.4 mL) at 0-10° C. After the addition was complete, it was noted that the reaction mixture was red and somewhat viscous. At this point, 4-nitrophenylacetic acid (10.0 g, 11.04 mmol) was added to the reaction and the mixture was heated to and stirred at 90° C. After about 5 min after the addition of the acid, the reaction mixture became a yellow suspension which gradually turned into a red-orange viscous liquid. After 90 min of heating, LC-MS showed one peak. At this point, the mixture was cooled to rt then placed in an ice bath and quenched dropwise with about 110 mL water that was cooled to 0° C. After the quench, the solution was basified with 1N NaOH until the pH of the solution was around 10. The mixture was then carried out directly for next step reaction. MS (ES+) m/e 194 (M+H)+.

Example 1B 4-(4-Nitrophenyl)-1H-pyrazole

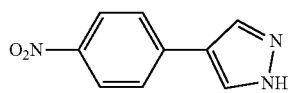

To the basic solution of (Z)-3-hydroxy-2-(4-nitrophenyl) acrylaldehyde was added hydrazine (2.65 g, 82.8 mmol, 2.6 mL). The mixture was heated at 80° C. and checked by LC-MS. After 1 h, a brown precipitate was noted in the reaction vessel. LC-MS at this point showed the correct mass for the pyrazole and that the reaction was not completed yet. Heating was continued overnight then the LC-MS was checked again. The reaction was complete at this point. The reaction mixture was cooled to rt and filtered. The brown filter cake was washed with water and left on the filter to remove most of the water. Then the wet filter cake was placed on a rotovap to remove most of the water still remaining (at least 30 g) in the material. There yielded 10.3 g of the solid as the crude pyrazole. The material was then recrystallized from EtOH/ACN to give 5.96 g of dark brown crystals. The mother liquor was concentrated to remove most of the liquid. ACN was added to the mixture and the mixture was heated at 77° C. to dissolve the solid. Additional ACN was added as necessary to effect the dissolution. The solution was cooled and the resulting crystals filtered to give an additional 2.35 g of product. Total yield is 8.31 g (80%). $^1$H NMR (400 MHz, DMSO-$d_6$) δ 13.19 (b, 1H), 8.29 (s, 2H), 8.20 (d, J=8.8 Hz, 2H), 7.88 (d, J=8.8 Hz, 2H). MS (ES+) m/e 190 (M+H)+.

Example 1C 4-(1H-pyrazol-4-yl)aniline

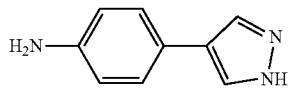

To a suspension of 4-(4-Nitrophenyl)-1H-pyrazole (8.3 g, 43.88 mmol) in MeOH/DME (2:1 v/v) was added 10% Pd/C (wet, 415 mg). The reaction flask was purged with vacuum then filled with H$_2$ from a balloon. This was done a total of 3 times. The reaction mixture was stirred at rt and checked by LC-MS for formation of the amine. After stirring for 2.5 at rt, LC-MS and tlc showed that there is a minor amount of SM in the reaction. An additional amount of catalyst (200 mg) was added to the reaction mixture and the reaction vessel was filled with H$_2$ as before. The reaction was checked after 2 h for disappearance of the remaining SM. At this time, the reaction was complete. The mixture was filtered on Celite and the Celite was washed with MeOH. The solvent was removed in vacuo to give 6.59 g (94%) of a yellow solid. $^1$H NMR (400 MHz, DMSO-$d_6$) δ 12.68 (b, 1H), 7.80 (s, 2H), 7.23 (d, J=8.0 Hz, 2H), 6.54 (d, J=8.0 Hz, 2H), 4.97 (s, 2H). MS (ES+) m/e 160 (M+H)+.

Example 1D 2-chloro-N-isopropylacetamide

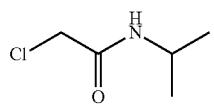

To a solution of propan-2-amine (5.9 g, 0.1 mol) in DCM (500 mL) was added 2-chloroacetyl chloride (11.1 g, 0.1 mol) drop wise at 0° C. The mixture was stirred at room temperature for 2 hrs. Then the mixture was quenched with water. The organic phase was washed with saturated brine, dried with anhydrous Na$_2$SO$_4$, filtered and concentrated in vacuum to give the product title compound (6.30 g) as a light yellow oil. $^1$H NMR (400 MHz, DMSO-$d_6$) δ 6.37 (b, 1H), 4.14-4.02 (m, 1H), 1.20 (d, J=6.8 Hz, 6H).

Example 1E 2-(3-bromophenoxy)-N-isopropylacetamide

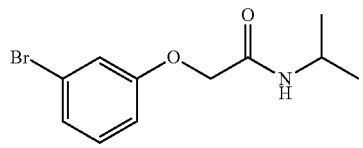

To a mixture of K$_2$CO$_3$ (13.8 g, 100 mmol) and 3-bromophenol (8.5 g, 50 mmol) in CH$_3$CN (100 mL) was stirred at room temperature for 30 min. Then 2-chloro-N-isopropylacetamide (6.3 g, 46 mmol) was added. The mixture was heated at reflux overnight. After LCMS showed the reaction was completed, the mixture was filtered and the filtrate was concentrated. The residue was dissolved in DCM and washed with NaOH solution, the organic phase was dried and concentrated to give the title compound (8.0 g) as a white solid. $^1$H NMR (400 MHz, DMSO-$d_6$) δ 7.21-7.12 (m, 3H), 6.87-6.85 (m, 1H), 6.30 (b, 1H), 4.44 (s, 2H), 4.25-4.15 (m, 1H), 1.20 (d, J=6.8 Hz, 6H).

Example 1F

N-isopropyl-2-(3-(4,4,5,5-tetramethyl-1,3,2-dioxaborolan-2-yl)phenoxy)acetamide

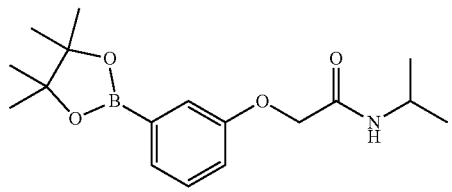 [SMILES: CC(C)NC(=O)COc1cccc(B2OC(C)(C)C(C)(C)O2)c1]

To a mixture of 2-(3-bromophenoxy)-N-isopropylacetamide (39.00 g, 143.31 mmol, 1.00 Eq), KOAc (28.13 g, 286.62 mmol) and 4,4,5,5-tetramethyl-2-(4,4,5,5-tetramethyl-1,3,2-dioxaborolan-2-yl)-1,3,2-dioxabrolane (47.31 g, 186.30 mmol) in dioxane (1 L) was added Pd(dppf)Cl$_2$ (5.32 g, 7.17 mmol) at room temperature under N$_2$. Then the reaction mixture was heated to 90° C. for 4 h. After LCMS showed the starting material was consumed completely, the mixture was filtered and the filtrate was concentrated. The residue was purified by column flash to provide the title compound (30 g) as a white solid. $^1$H NMR (400 MHz, DMSO-$d_6$) δ 7.48-7.27 (m, 3H), 7.03-7.01 (m, 1H), 6.41 (b, 1H), 4.48 (s, 2H), 4.24-4.15 (m, 1H), 1.20 (d, J=6.8 Hz, 6H). MS (ES+) m/e 320 (M+H)+.

Example 1G

N-(4-(1H-pyrazol-4-yl)phenyl)-2-chloro-5,7-dihydrofuro[3,4-d]pyrimidin-4-amine

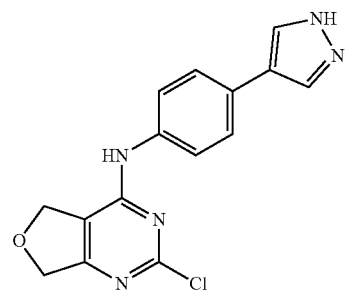 [SMILES: Clc1nc2c(c(Nc3ccc(-c4cn[nH]c4)cc3)n1)COC2]

A mixture of 2,4-dichloro-5,7-dihydrofuro[3,4-d]pyrimidine (300 mg, 1.57 mmol), 4-(1H-pyrazol-4-yl)aniline (250 mg, 1.57 mmol), and diisopropylethylamine (0.55 mL, 3.14 mmol) in DMF (3.14 mL) was heated at 100° C. for 5 h. TLC showed the reaction was complete. The mixture was then diluted with water. The resulted yellow precipitate was filtered and washed with water and dried in vacuo to provide 480 mg (97%) title compound which was used directly for next step reaction without further purification.

Example 1H 2-(3-(4-((4-(1H-pyrazol-4-yl)phenyl)amino)-5,7-dihydrofuro[3,4-d]pyrimidin-2-yl)phenoxy)-N-isopropylacetamide

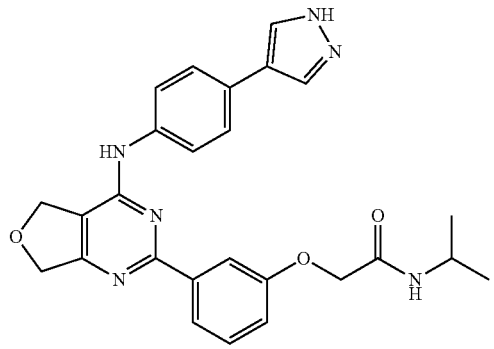 [SMILES: CC(C)NC(=O)COc1cccc(-c2nc3c(c(Nc4ccc(-c5cn[nH]c5)cc4)n2)COC3)c1]

A mixture of N-(4-(1H-pyrazol-4-yl)phenyl)-2-chloro-5,7-dihydrofuro[3,4-d]pyrimidin-4-amine (50.0 mg, 0.16 mmol), N-isopropyl-2-(3-(4,4,5,5-tetramethyl-1,3,2-dioxaborolan-2-yl)phenoxy)acetamide (50.9 mg, 0.16 mmol), Pd(PPh$_3$)$_4$ (18.4 mg, 0.02 mmol), saturated Na$_2$CO$_3$ (0.16 mL), water (0.16 mL), and dioxane (1.59 mL) was heated at 180° C. in a pressure tube for 2 h. The mixture was cooled to rt, concentrated, redissolved in DMSO and purified by reverse-phase HPLC to provide 16 mg (21%) of the title product.

$^1$H NMR (500 MHz, DMSO-d6) δ 9.30 (s, 1H), 8.07 (s, 2H), 8.03-7.92 (m, 3H), 7.81 (d, J=8.6 Hz, 2H), 7.67 (d, J=8.6 Hz, 2H), 7.44 (t, J=8.2 Hz, 1H), 7.15-7.07 (m, 1H), 5.08 (s, 2H), 4.95 (s, 2H), 4.53 (s, 2H), 3.99 (dq, J=13.3, 6.6 Hz, 1H), 1.10 (d, J=6.6 Hz, 6H). MS (ES+) m/e 471 (M+H)+.

Example 2

N-(3-(4-((4-(1H-pyrazol-4-yl)phenyl)amino)-5,7-dihydrofuro[3,4-d]pyrimidin-2-yl)phenyl)-2-morpholinoacetamide

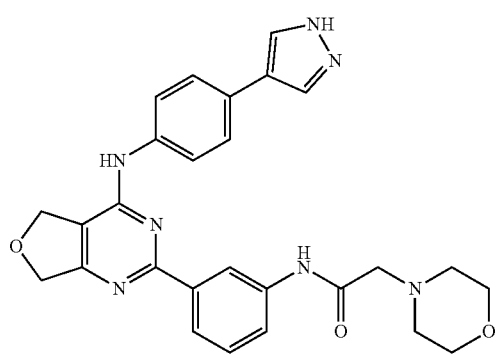 [SMILES: O=C(CN1CCOCC1)Nc1cccc(-c2nc3c(c(Nc4ccc(-c5cn[nH]c5)cc4)n2)COC3)c1]

Example 2A 2-morpholino-N-(3-(4,4,5,5-tetramethyl-1,3,2-dioxaborolan-2-yl)phenyl)acetamide

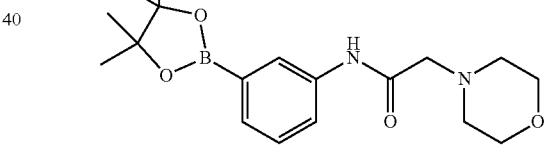

To a solution of 3-(4,4,5,5-tetramethyl-1,3,2-dioxaborolan-2-yl)aniline, 3-aminophenylboronic acid pinacol ester, (600 mg, 2.74 mmol) and 2-morpholinoacetic acid hydrochloride, morpholineacetic acid HCl (522 mg, 0.2.88 mmol) in dry DMF (13.7 mL) was added TEA (831 mg, 2.74 mmol, 1.15 mL) followed by HATU (1.04 g, 2.74 mmol) at rt. The mixture was stirred and checked by LC-MS. After 4 h of stirring, the LC-MS showed the reaction was complete. The mixture was poured into water and extracted with EtOAc. The aqueous layer was separated and extracted 2× more with EtOAc. The combined organic layers were washed with water twice and dried over sodium sulfate. The solution was decanted from the drying agent and concentrated in vacuo to give 1.02 g of an off-white solid. The material was dissolved in a minimum amount of DCM and was loaded onto a 24 g column. Column chromatography (10% EtOAc/Hexanes to 70% EtOAc/Hexanes gradient) gave 630 mg, 65%, of an off-white solid as the product. LC-MS shows the correct mass for the product.

Example 2B

N-(3-(4-((4-(1H-pyrazol-4-yl)phenyl)amino)-5,7-dihydrofuro[3,4-d]pyrimidin-2-yl)phenyl)-2-morpholinoacetamide

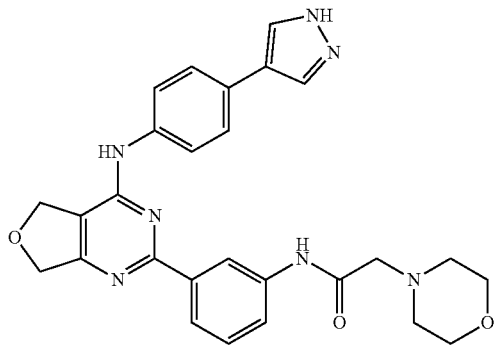 [SMILES: O=C(CN1CCOCC1)Nc1cccc(-c2nc3c(c(Nc4ccc(-c5cn[nH]c5)cc4)n2)COC3)c1]

A mixture of N-(4-(1H-pyrazol-4-yl)phenyl)-2-chloro-5,7-dihydrofuro[3,4-d]pyrimidin-4-amine (25.0 mg, 0.08 mmol), 2-morpholino-N-(3-(4,4,5,5-tetramethyl-1,3,2-dioxaborolan-2-yl)phenyl)acetamide (27.6 mg, 0.08 mmol), Pd(PPh$_3$)$_4$ (9.2 mg, 0.01 mmol), saturated Na$_2$CO$_3$ (0.08 mL), water (0.08 mL), and dioxane (0.8 mL) was heated at 180° C. in a pressure tube for 2 h. The mixture was cooled to rt, concentrated, redissolved in DMSO and purified by reverse-phase HPLC to provide 8 mg (20%) of the title product. $^1$H NMR (500 MHz, DMSO-d6) δ 10.83 (s, 1H), 9.24 (s, 1H), 8.34 (d, J=8.6 Hz, 2H), 8.06 (s, 2H), 7.81 (d, J=8.5 Hz, 2H), 7.74 (d, J=8.7 Hz, 2H), 7.67 (d, J=8.5 Hz, 2H), 5.08 (s, 2H), 4.94 (s, 2H), 4.24 (s, 2H), 3.90 (d, J=50.4 Hz, 4H), 3.39 (d, J=82.5 Hz, 4H). MS (ES+) m/e 498 (M+H)+.

Example 3

2-(3-(4-((4-(1H-pyrazol-4-yl)phenyl)aminoguro[3,2-d]pyrimidin-2-yl)phenoxy)-N-isopropylacetamide

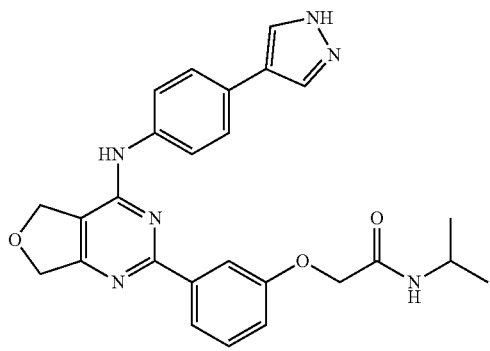 [SMILES: CC(C)NC(=O)COc1cccc(-c2nc3c(c(Nc4ccc(-c5cn[nH]c5)cc4)n2)COC3)c1]

Example 3A

N-(4-(1H-pyrazol-4-yl)phenyl)-2-chlorofuro[3,2-d]pyrimidin-4-amine

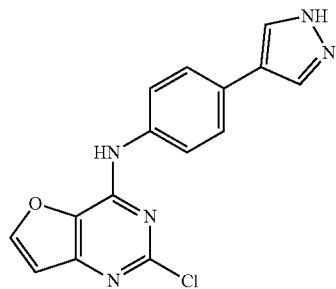

A mixture of 2,4-dichlorofuro[3,2-d]pyrimidine (150 mg, 0.79 mmol), 4-(1H-pyrazol-4-yl)aniline (126.3 mg, 0.79 mmol), and diisopropylethylamine (0.28 mL, 1.59 mmol) in DMF (1.59 mL) was heated at 100° C. for 5 h. TLC showed the reaction was complete. The mixture was then diluted with water. The resulted yellow precipitate was filtered and washed with water and dried in vacuo to provide 210 mg (85%) title compound which was used directly for next step reaction without further purification.

Example 3B 2-(3-(4-((4-(1H-pyrazol-4-yl)phenyl)aminoguro[3,2-d]pyrimidin-2-yl)phenoxy)-N-isopropylacetamide

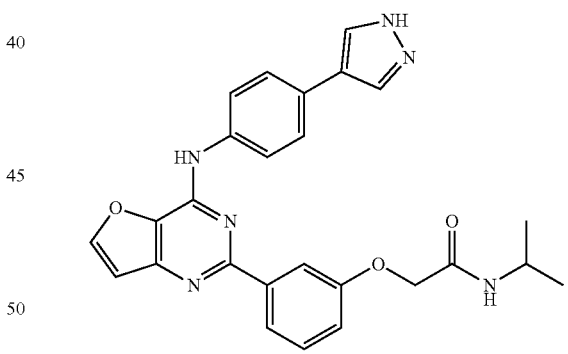

A mixture of N-(4-(1H-pyrazol-4-yl)phenyl)-2-chlorofuro[3,2-d]pyrimidin-4-amine (25.0 mg, 0.08 mmol), N-isopropyl-2-(3-(4,4,5,5-tetramethyl-1,3,2-dioxaborolan-2-yl)phenoxy)acetamide (25.4 mg, 0.08 mmol), Pd(PPh$_3$)$_4$ (9.2 mg, 0.01 mmol), saturated Na$_2$CO$_3$ (0.08 mL), water (0.08 mL), and dioxane (0.8 mL) was heated at 180° C. in a pressure tube for 2 h. The mixture was cooled to rt, concentrated, redissolved in DMSO and purified by reverse-phase HPLC to provide 12 mg (32%) of the title product. $^1$H NMR (500 MHz, DMSO-d6) δ 10.17 (s, 1H), 8.43 (d, J=2.1 Hz, 1H), 8.08 (s, 2H), 8.07-7.90 (m, 5H), 7.69 (d, J=8.6 Hz, 2H), 7.45 (t, J=7.9 Hz, 1H), 7.16 (d, J=2.1 Hz, 1H), 7.10 (dd, J=8.2, 1.9 Hz, 1H), 6.43-6.30 (m, 1H), 4.55 (s, 2H), 4.00 (m, 1H), 1.11 (d, J=6.6 Hz, 6H). MS (ES+) m/e 469 (M+H)+.

Example 4

N-(3-(4-((4-(1H-pyrazol-4-yl)phenyl)aminoguro[3,2-d]pyrimidin-2-yl)phenyl)-2-morpholinoacetamide

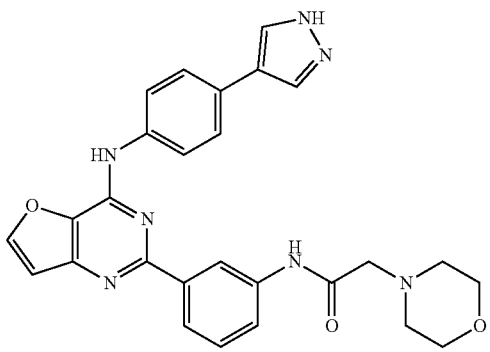

A mixture of N-(4-(1H-pyrazol-4-yl)phenyl)-2-chloro-furo[3,2-d]pyrimidin-4-amine (25.0 mg, 0.08 mmol), N-isopropyl-2-(3-(4,4,5,5-tetramethyl-1,3,2-dioxaborolan-2-yl)phenoxy)acetamide (27.6 mg, 0.08 mmol), Pd(PPh$_3$)$_4$ (9.2 mg, 0.01 mmol), saturated Na$_2$CO$_3$ (0.08 mL), water (0.08 mL), and dioxane (0.8 mL) was heated at 180° C. in a pressure tube for 2 h. The mixture was cooled to rt, concentrated, redissolved in DMSO and purified by reverse-phase HPLC to provide 23 mg (58%) of the title product. $^1$H NMR (500 MHz, DMSO-d6) δ 10.86 (s, 1H), 10.15 (s, 1H), 8.51-8.29 (m, 3H), 8.08 (s, 2H), 7.95 (d, J=8.6 Hz, 2H), 7.76 (d, J=8.7 Hz, 2H), 7.69 (d, J=8.6 Hz, 2H), 7.14 (d, J=2.1 Hz, 1H), 4.26 (s, 2H), 3.90 (d, J=45.5 Hz, 4H), 3.41 (d, J=78.4 Hz, 4H). MS (ES+) m/e 496 (M+H)+.

Example 5

2-(3-(6-((4-(1H-pyrazol-4-yl)phenyl)amino)-9-methyl-9H-purin-2-yl)phenoxy)-N-isopropylacetamide

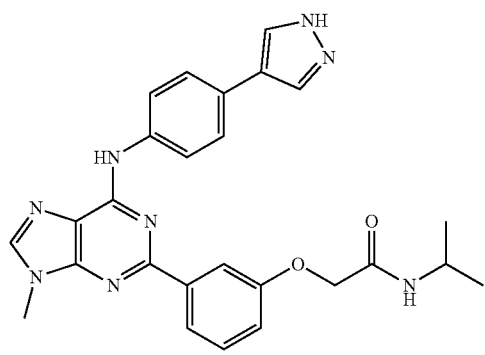 [SMILES: CC(C)NC(=O)COc1cccc(-c2nc(Nc3ccc(-c4cn[nH]c4)cc3)c3ncn(C)c3n2)c1]

Example 5A

N-(4-(1H-pyrazol-4-yl)phenyl)-2-chloro-9-methyl-9H-purin-6-amine

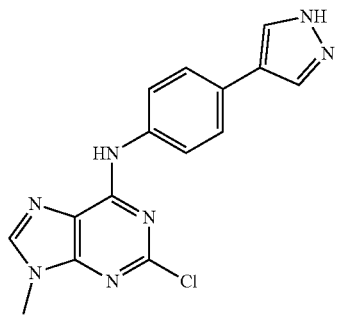 [SMILES: Cn1cnc2c(Nc3ccc(-c4cn[nH]c4)cc3)nc(Cl)nc21]

A mixture of 2,6-dichloro-9-methyl-9H-purine (150 mg, 0.74 mmol), 4-(1H-pyrazol-4-yl)aniline (117.6 mg, 0.74 mmol), and diisopropylethylamine (0.26 mL, 1.48 mmol) in DIVIF (1.48 mL) was heated at 100° C. for 5 h. TLC showed the reaction was complete. The mixture was then diluted with water. The resulted yellow precipitate was filtered and washed with water and dried in vacuo to provide 220 mg (91%) title compound which was used directly for next step reaction without further purification

Example 5B 2-(3-(6-((4-(1H-pyrazol-4-yl)phenyl)amino)-9-methyl-9H-purin-2-yl)phenoxy)-N-isopropylacetamide

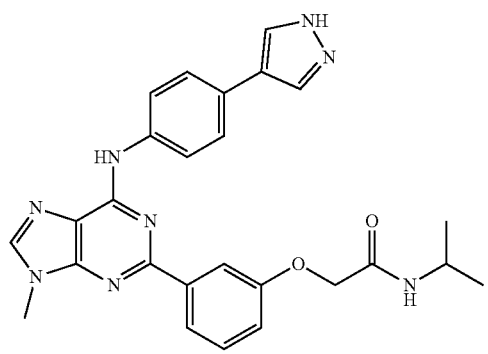 [SMILES: CC(C)NC(=O)COc1cccc(-c2nc(Nc3ccc(-c4cn[nH]c4)cc3)c3ncn(C)c3n2)c1]

A mixture of N-(4-(1H-pyrazol-4-yl)phenyl)-2-chloro-9-methyl-9H-purin-6-amine (24.5 mg, 0.08 mmol), N-isopropyl-2-(3-(4,4,5,5-tetramethyl-1,3,2-dioxaborolan-2-yl)phenoxy)acetamide (24.5 mg, 0.08 mmol), Pd(PPh$_3$)$_4$ (9.2 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide 14 mg (38%) of the title product. $^1$H NMR (500 MHz, DMSO-d6) δ 9.97 (s, 1H), 8.34 (s, 1H), 8.19-8.04 (m, 6H), 7.99 (d, J=8.0 Hz, 1H), 7.66 (d, J=8.6 Hz, 2H), 7.45 (t, J=8.1 Hz, 1H), 7.09 (dd, J=8.2, 1.7 Hz, 1H), 4.57 (s, 2H), 4.01 (dq, J=13.3, 6.6 Hz, 1H), 3.88 (s, 3H), 1.11 (d, J=6.6 Hz, 6H). MS (ES+) m/e 483 (M+H)+.

Example 6

N-(3-(6-((4-(1H-pyrazol-4-yl)phenyl)amino)-9-methyl-9H-purin-2-yl)phenyl)-2-morpholinoacetamide

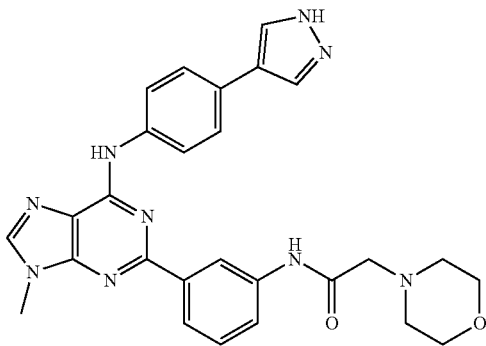 [SMILES: Cn1cnc2c(Nc3ccc(-c4cn[nH]c4)cc3)nc(-c3cccc(NC(=O)CN4CCOCC4)c3)nc21]

A mixture of N-(4-(1H-pyrazol-4-yl)phenyl)-2-chloro-9-methyl-9H-purin-6-amine (24.5 mg, 0.08 mmol), 2-morpholino-N-(3-(4,4,5,5-tetramethyl-1,3,2-dioxaborolan-2-yl)phenyl)acetamide (27.6 mg, 0.08 mmol), Pd(PPh$_3$)$_4$ (9.2 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide 25 mg (62%) of the title product. $^1$H NMR (500 MHz, DMSO-d6) δ 10.88 (s, 1H), 9.95 (s, 1H), 8.45 (d, J=8.8 Hz, 2H), 8.35 (s, 1H), 8.11-8.03 (m, 4H), 7.77 (d, J=8.8 Hz, 2H), 7.67 (d, J=8.6 Hz, 2H), 6.64 (s, 8H), 4.27 (s, 2H), 3.87 (s, 8H), 3.42 (d, J=74.4 Hz, 5H), 2.55 (s, 1H). MS (ES+) m/e 510 (M+H)+.

Example 7

2-(3-(4-((4-(1H-pyrazol-4-yl)phenyl)amino)thieno[3,2-d]pyrimidin-2-yl)phenoxy)-N-isopropylacetamide

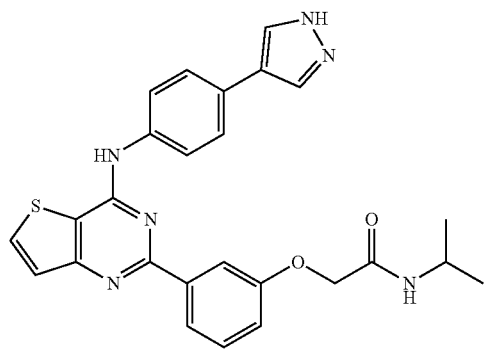 [SMILES: CC(C)NC(=O)COc1cccc(-c2nc(Nc3ccc(-c4cn[nH]c4)cc3)c3sccc3n2)c1]

Example 7A

N-(4-(1H-pyrazol-4-yl)phenyl)-2-chlorothieno[3,2-d]pyrimidin-4-amine

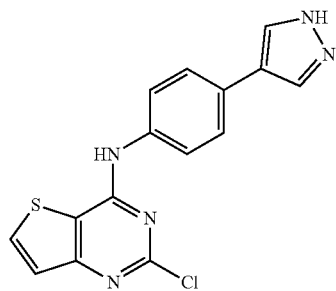 [SMILES: Clc1nc(Nc2ccc(-c3cn[nH]c3)cc2)c2sccc2n1]

A mixture of 2,4-dichlorothieno[3,2-d]pyrimidine (150 mg, 0.73 mmol), 4-(1H-pyrazol-4-yl)aniline (116.4 mg, 0.73 mmol), and diisopropylethylamine (0.26 mL, 1.48 mmol) in DMF (1.48 mL) was heated at 100° C. for 5 h. TLC showed the reaction was complete. The mixture was then diluted with water. The resulted yellow precipitate was filtered and washed with water and dried in vacuo to provide 220 mg (94%) title compound which was used directly for next step reaction without further purification.

Example 7B 2-(3-(4-((4-(1H-pyrazol-4-yl)phenyl)amino)thieno[3,2-d]pyrimidin-2-yl)phenoxy)-N-isopropylacetamide

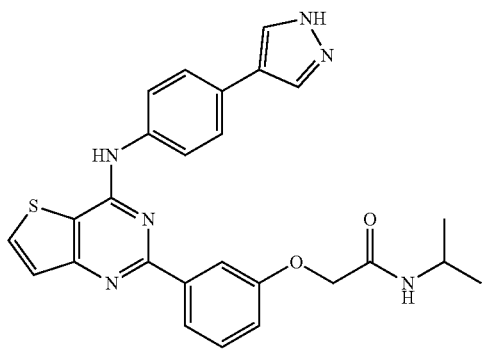 [SMILES: CC(C)NC(=O)COc1cccc(-c2nc(Nc3ccc(-c4cn[nH]c4)cc3)c3sccc3n2)c1]

A mixture of N-(4-(1H-pyrazol-4-yl)phenyl)-2-chlorothieno[3,2-d]pyrimidin-4-amine (24.5 mg, 0.08 mmol), N-isopropyl-2-(3-(4,4,5,5-tetramethyl-1,3,2-dioxaborolan-2-yl)phenoxy)acetamide (24.3 mg, 0.08 mmol), Pd(PPh$_3$)$_4$ (9.2 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide 11 mg (30%) of the title product. $^1$H NMR (500 MHz, DMSO-d6) δ 10.13 (s, 1H), 8.32 (d, J=5.3 Hz, 1H), 8.11 (s, 2H), 8.06-7.96 (m, 3H), 7.88 (d, J=8.2 Hz, 2H), 7.72 (d, J=8.4 Hz, 2H), 7.55 (d, J=5.4 Hz, 1H), 7.48 (t, J=7.9 Hz, 1H), 7.14 (d, J=7.6 Hz, 1H), 4.56 (s, 2H), 4.04-3.94 (m, 1H), 1.11 (d, J=6.6 Hz, 6H). MS (ES+) m/e 485 (M+H)+.

Example 8

N-(3-(4-((4-(1H-pyrazol-4-yl)phenyl)amino)thieno[3,2-d]pyrimidin-2-yl)phenyl)-2-morpholinoacetamide

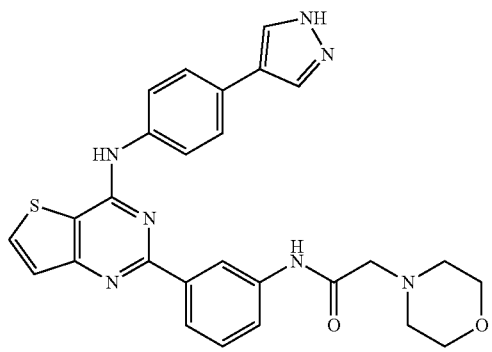

A mixture of N-(4-(1H-pyrazol-4-yl)phenyl)-2-chlorothieno[3,2-d]pyrimidin-4-amine (25.0 mg, 0.08 mmol), 2-morpholino-N-(3-(4,4,5,5-tetramethyl-1,3,2-dioxaborolan-2-yl)phenyl)acetamide (26.4 mg, 0.08 mmol), Pd(PPh$_3$)$_4$ (9.2 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide 11 mg (30%) of the title product. $^1$H NMR (500 MHz, DMSO-d6) δ 10.94 (s, 1H), 10.25 (s, 1H), 8.36 (dd, J=27.2, 7.0 Hz, 3H), 8.12 (s, 2H), 7.86 (d, J=8.3 Hz, 2H), 7.79 (d, J=8.6 Hz, 2H), 7.73 (d, J=8.4 Hz, 2H), 7.55 (s, 1H), 6.77 (s, 2H), 4.27 (s, 2H), 3.91 (d, J=35.9 Hz, 4H), 3.41 (d, J=77.1 Hz, 4H). MS (ES+) m/e 512 (M+H)+.

Example 9

N-(4-(1H-pyrazol-4-yl)phenyl)-2-chlorothieno[3,2-d]pyrimidin-4-amine

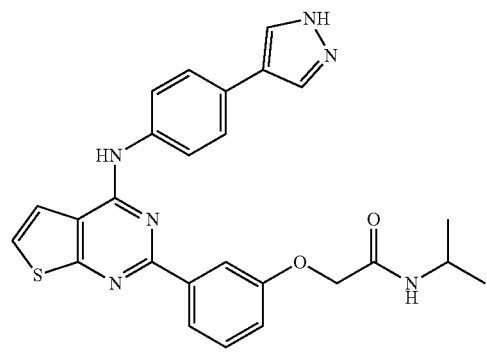 [SMILES: CC(C)NC(=O)COc1cccc(-c2nc(Nc3ccc(-c4cn[nH]c4)cc3)c3ccsc3n2)c1]

Example 9A

N-(4-(1H-pyrazol-4-yl)phenyl)-2-chlorothieno[2,3-d]pyrimidin-4-amine

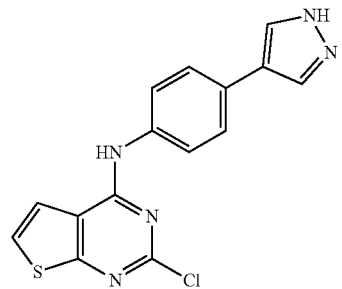 [SMILES: Clc1nc(Nc2ccc(-c3cn[nH]c3)cc2)c2ccsc2n1]

A mixture of 2,4-dichlorothieno[2,3-d]pyrimidine (150 mg, 0.73 mmol), 4-(1H-pyrazol-4-yl)aniline (116.4 mg, 0.73 mmol), and diisopropylethylamine (0.26 mL, 1.48 mmol) in DMF (1.48 mL) was heated at 100° C. for 5 h. TLC showed the reaction was complete. The mixture was then diluted with water. The resulted yellow precipitate was filtered and washed with water and dried in vacuo to provide 230 mg (96%) title compound which was used directly for next step reaction without further purification.

Example 9B

2-(3-(4-((4-(1H-pyrazol-4-yl)phenyl)amino)thieno[2,3-d]pyrimidin-2-yl)phenoxy)-N-isopropylacetamide

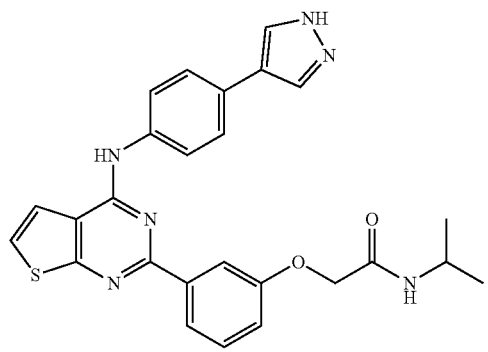 [SMILES: CC(C)NC(=O)COc1cccc(-c2nc(Nc3ccc(-c4cn[nH]c4)cc3)c3ccsc3n2)c1]

A mixture of N-(4-(1H-pyrazol-4-yl)phenyl)-2-chlorothieno[2,3-d]pyrimidin-4-amine (24.5 mg, 0.08 mmol), N-isopropyl-2-(3-(4,4,5,5-tetramethyl-1,3,2-dioxaborolan-2-yl)phenoxy)acetamide (24.3 mg, 0.08 mmol), Pd(PPh$_3$)$_4$ (9.2 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide 4 mg (11%) of the title product. $^1$H NMR (500 MHz, DMSO-d6) δ 9.79 (s, 1H), 8.10 (s, 2H), 8.06-7.99 (m, 3H), 7.94 (t, J=7.7 Hz, 3H), 7.73 (dd, J=11.8, 7.3 Hz, 3H), 7.45 (t, J=7.9 Hz, 1H), 7.10 (d, J=10.0 Hz, 1H), 4.56 (s, 3H), 4.01 (m, 2H), 1.12 (d, J=6.6 Hz, 6H). MS (ES+) m/e 485 (M+H)+.

Example 10

N-(3-(4-((4-(1H-pyrazol-4-yl)phenyl)amino)thieno[2,3-d]pyrimidin-2-yl)phenyl)-2-morpholinoacetamide

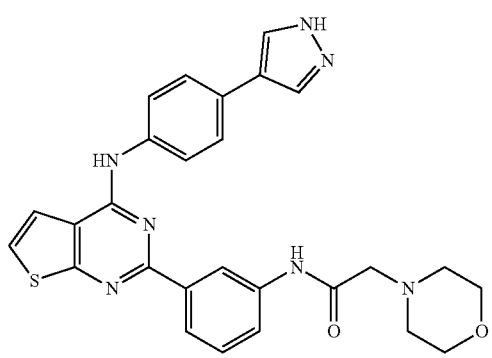 [SMILES: O=C(CN1CCOCC1)Nc1cccc(-c2nc(Nc3ccc(-c4cn[nH]c4)cc3)c3ccsc3n2)c1]

A mixture of N-(4-(1H-pyrazol-4-yl)phenyl)-2-chlorothieno[2,3-d]pyrimidin-4-amine (24.5 mg, 0.08 mmol), 2-morpholino-N-(3-(4,4,5,5-tetramethyl-1,3,2-dioxaborolan-2-yl)phenyl)acetamide (26.4 mg, 0.08 mmol), Pd(PPh$_3$)$_4$ (9.2 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide 4 mg (11%) of the title product. $^1$H NMR (500 MHz, DMSO-d6) δ 10.87 (s, 1H), 9.76 (s, 1H), 8.41 (d, J=8.7 Hz, 2H), 8.10 (s, 2H), 7.93 (dd, J=12.1, 7.3 Hz, 3H), 7.74 (dd, J=20.1, 8.6 Hz, 5H), 4.26 (s, 2H), 3.90 (d, J=59.4 Hz, 4H), 3.40 (d, J=85.7 Hz, 4H). MS (ES+) m/e 512 (M+H)+.

Example 11

2-(3-(4-((1H-indazol-5-yl)amino)-5,7-dihydrofuro[3,4-d]pyrimidin-2-yl)phenoxy)-N-isopropylacetamide

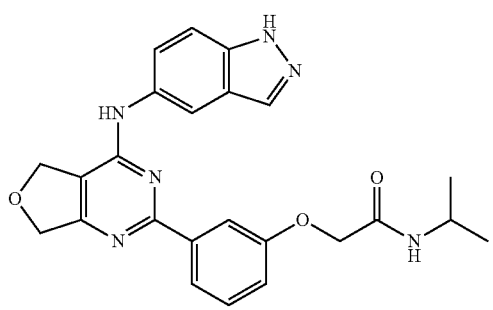 [SMILES: CC(C)NC(=O)COc1cccc(-c2nc3c(c(Nc4ccc5[nH]ncc5c4)n2)COC3)c1]

Example 11A 2-chloro-N-(1H-indazol-5-yl)-5,7-dihydrofuro[3,4-d]pyrimidin-4-amine

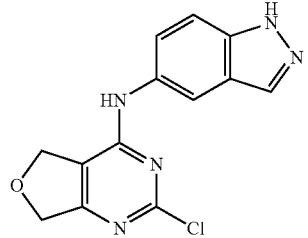 [SMILES: Clc1nc2c(c(Nc3ccc4[nH]ncc4c3)n1)COC2]

A mixture of 2,4-dichloro-5,7-dihydrofuro[3,4-d]pyrimidine (90 mg, 0.47 mmol), 1H-indazol-5-amine (62.7 mg, 0.47 mmol), and diisopropylethylamine (0.16 mL, 0.94 mmol) in DMF (0.94 mL) was heated at 100° C. for 5 h. TLC showed the reaction was complete. The mixture was then diluted with water. The resulted yellow precipitate was filtered and washed with water and dried in vacuo to provide 120 mg (89%) title compound which was used directly for next step reaction without further purification.

Example 11B 2-(3-(4-((1H-indazol-5-yl)amino)-5,7-dihydrofuro[3,4-d]pyrimidin-2-yl)phenoxy)-N-isopropylacetamide

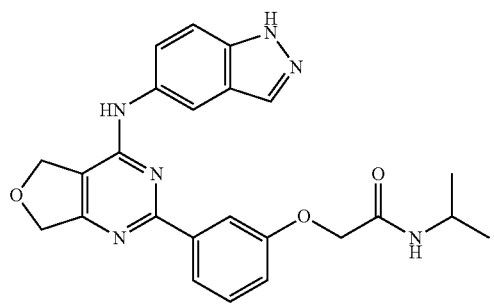 [SMILES: CC(C)NC(=O)COc1cccc(-c2nc3c(c(Nc4ccc5[nH]ncc5c4)n2)COC3)c1]

A mixture of 2-chloro-N-(1H-indazol-5-yl)-5,7-dihydrofuro[3,4-d]pyrimidin-4-amine (25 mg, 0.09 mmol), N-isopropyl-2-(3-(4,4,5,5-tetramethyl-1,3,2-dioxaborolan-2-yl)phenoxy)acetamide (27.74 mg, 0.08 mmol), Pd(PPh$_3$)$_4$ (9.2 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product. $^1$H NMR (500 MHz, DMSO-d6) δ 9.31 (s, 1H), 8.18 (s, 1H), 8.12 (s, 1H), 8.01-7.89 (m, 3H), 7.67-7.55 (m, 2H), 7.42 (t, J=7.9 Hz, 1H), 7.22 (s, 1H), 7.16-7.05 (m, 2H), 7.02 (s, 1H), 5.01 (s, 2H), 4.93 (s, 2H), 4.51 (s, 2H), 3.98 (m, 1H), 1.10 (d, J=6.6 Hz, 6H). MS (ES+) m/e 445 (M+H)+.

Example 12

N-(3-(4-((1H-indazol-5-yl)amino)-5,7-dihydrofuro[3,4-d]pyrimidin-2-yl)phenyl)-2-morpholinoacetamide

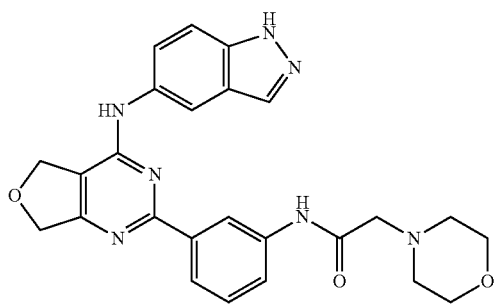 [SMILES: O=C(CN1CCOCC1)Nc1cccc(-c2nc3c(c(Nc4ccc5[nH]ncc5c4)n2)COC3)c1]

A mixture of 2-chloro-N-(1H-indazol-5-yl)-5,7-dihydrofuro[3,4-d]pyrimidin-4-amine (25 mg, 0.09 mmol), 2-morpholino-N-(3-(4,4,5,5-tetramethyl-1,3,2-dioxaborolan-2-yl)phenyl)acetamide (30.1 mg, 0.09 mmol), Pd(PPh$_3$)$_4$ (10.4 mg, 0.01 mmol), saturated Na$_2$CO$_3$ (0.09 mL), water (0.08 mL), and dioxane (0.9 mL) was heated at 180° C. in microwave for 2 h. The mixture was cooled to rt, concentrated, redissolved in DMSO and purified by reverse-phase HPLC to provide the title product. $^1$H NMR (500 MHz, DMSO-d6) δ 10.87 (s, 1H), 9.31 (s, 1H), 8.31 (d, J=8.7 Hz, 2H), 8.14 (s, 1H), 8.11 (s, 1H), 7.72 (d, J=8.7 Hz, 2H), 7.64 (d, J=8.4 Hz, 1H), 7.59 (d, J=8.9 Hz, 1H), 5.00 (s, 2H), 4.92 (s, 2H), 4.24 (s, 2H), 3.90 (s, 4H), 3.38 (s, 4H). MS (ES+) m/e 472 (M+H)+.

Example 13

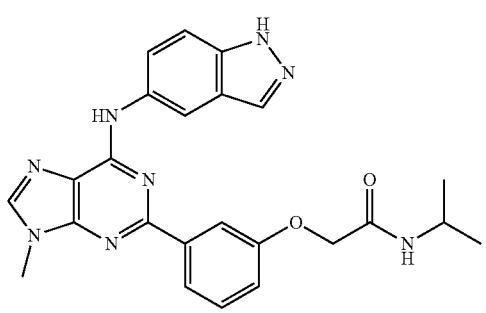 [SMILES: CC(C)NC(=O)COc1cccc(-c2nc(Nc3ccc4[nH]ncc4c3)c3ncn(C)c3n2)c1]

A mixture of 2-chloro-N-(1H-indazol-5-yl)-9-methyl-9H-purin-6-amine (25 mg, 0.08 mmol), N-isopropyl-2-(3-(4,4,5,5-tetramethyl-1,3,2-dioxaborolan-2-yl)phenoxy)acetamide (26.6 mg, 0.09 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product. $^1$H NMR (500 MHz, DMSO-d6) δ 9.93 (s, 1H), 8.46 (s, 1H), 8.31 (s, 1H), 8.08 (d, J=33.7 Hz, 3H), 7.96 (d, J=7.4 Hz, 1H), 7.89 (d, J=8.8 Hz, 1H), 7.57 (d, J=8.7 Hz, 1H), 7.44 (t, J=8.1 Hz, 1H), 4.55 (s, 2H), 4.07-3.94 (m, 1H), 3.87 (s, 3H), 1.11 (d, J=6.5 Hz, 6H). MS (ES+) m/e 457 (M+H)+.

Example 14

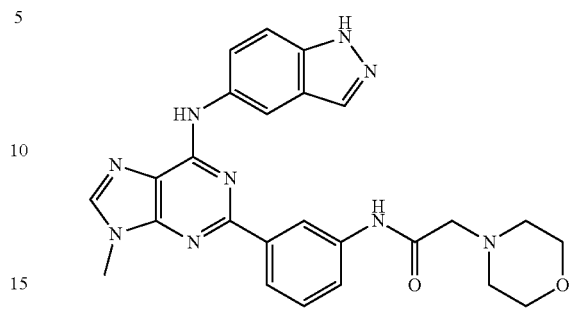

A mixture of 2-chloro-N-(1H-indazol-5-yl)-9-methyl-9H-purin-6-amine (25 mg, 0.08 mmol), 2-morpholino-N-(3-(4,4,5,5-tetramethyl-1,3,2-dioxaborolan-2-yl)phenyl)acetamide (28.9 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product. $^1$H NMR (500 MHz, DMSO-d6) δ 10.86 (s, 1H), 9.92 (s, 1H), 8.48-8.37 (m, 3H), 8.30 (s, 1H), 8.11 (s, 1H), 7.89 (d, J=10.7 Hz, 1H), 7.75 (d, J=8.8 Hz, 2H), 7.58 (d, J=8.9 Hz, 1H), 4.74 (b, 4H), 4.25 (s, 2H), 3.97 (m, 1H), 3.86 (s, 3H), 3.40 (d, J=57.4 Hz, 4H). MS (ES+) m/e 484 (M+H)+.

Example 15

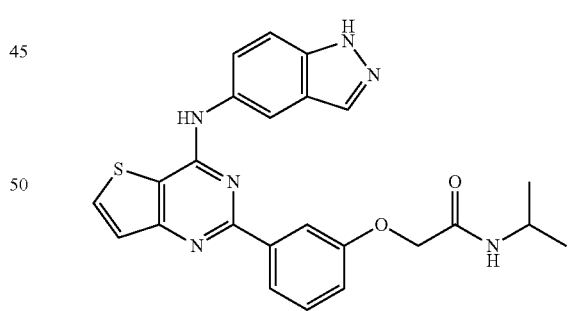

A mixture of 2-chloro-N-(1H-indazol-5-yl)thieno[3,2-d]pyrimidin-4-amine (25 mg, 0.08 mmol), N-isopropyl-2-(3-(4,4,5,5-tetramethyl-1,3,2-dioxaborolan-2-yl)phenoxy)acetamide (26.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product. MS (ES+) m/e 459 (M+H)+.

Example 16

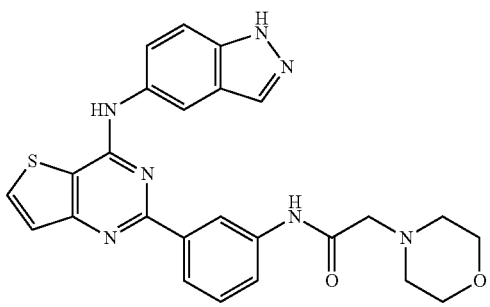 [SMILES: O=C(CN1CCOCC1)Nc1cccc(-c2nc(Nc3ccc4[nH]ncc4c3)c3sccc3n2)c1]

A mixture of 2-chloro-N-(1H-indazol-5-yl)thieno[3,2-d]pyrimidin-4-amine (25 mg, 0.08 mmol), 2-morpholino-N-(3-(4,4,5,5-tetramethyl-1,3,2-dioxaborolan-2-yl)phenyl)acetamide (28.7 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (14 mg, 35%). MS (ES+) m/e 486 (M+H)+.

Example 17

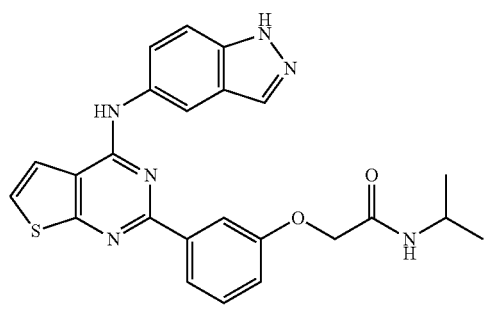 [SMILES: CC(C)NC(=O)COc1cccc(-c2nc(Nc3ccc4[nH]ncc4c3)c3ccsc3n2)c1]

A mixture of 2-chloro-N-(1H-indazol-5-yl)thieno[2,3-d]pyrimidin-4-amine (25 mg, 0.08 mmol), N-isopropyl-2-(3-(4,4,5,5-tetramethyl-1,3,2-dioxaborolan-2-yl)phenoxy)acetamide (26.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (11 mg, 29%). MS (ES+) m/e 459 (M+H)+.

Example 18

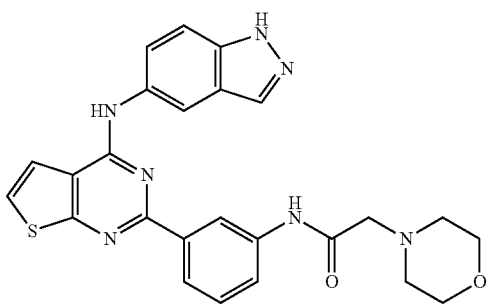 [SMILES: O=C(CN1CCOCC1)Nc1cccc(-c2nc(Nc3ccc4[nH]ncc4c3)c3ccsc3n2)c1]

A mixture of 2-chloro-N-(1H-indazol-5-yl)thieno[2,3-d]pyrimidin-4-amine (25 mg, 0.08 mmol), 2-morpholino-N-(3-(4,4,5,5-tetramethyl-1,3,2-dioxaborolan-2-yl)phenyl)acetamide (28.7 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (16 mg, 40%). MS (ES+) m/e 486 (M+H)+

Example 19

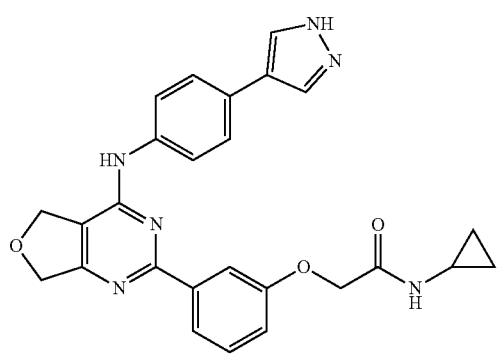 [SMILES: O=C(COc1cccc(-c2nc3c(c(Nc4ccc(-c5cn[nH]c5)cc4)n2)COC3)c1)NC1CC1]

A mixture of N-(4-(1H-pyrazol-4-yl)phenyl)-2-chloro-5,7-dihydrofuro[3,4-d]pyrimidin-4-amine (25 mg, 0.08 mmol), N-cyclopropyl-2-(3-(4,4,5,5-tetramethyl-1,3,2-dioxaborolan-2-yl)phenoxy)acetamide (27.7 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (6 mg, 15%). MS (ES+) m/e 469 (M+H)+.

Example 20

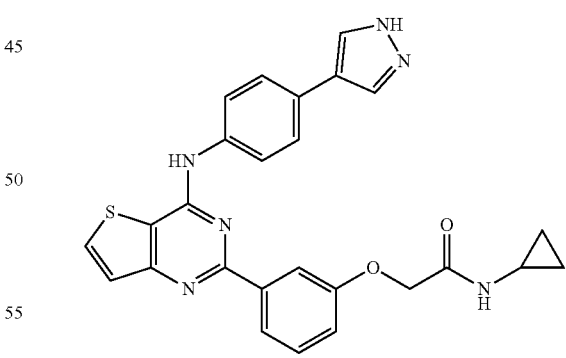

A mixture of N-(4-(1H-pyrazol-4-yl)phenyl)-2-chlorothieno[3,2-d]pyrimidin-4-amine (25 mg, 0.08 mmol), N-cyclopropyl-2-(3-(4,4,5,5-tetramethyl-1,3,2-dioxaborolan-2-yl)phenoxy)acetamide (26.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (17 mg, 45%). MS (ES+) m/e 483 (M+H)+.

Example 21

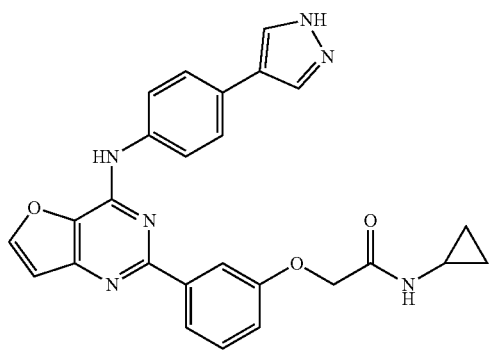 [SMILES: O=C(COc1cccc(-c2nc(Nc3ccc(-c4cn[nH]c4)cc3)c3occc3n2)c1)NC1CC1]

A mixture of N-(4-(1H-pyrazol-4-yl)phenyl)-2-chloro-furo[3,2-d]pyrimidin-4-amine (25 mg, 0.08 mmol), N-cyclopropyl-2-(3-(4,4,5,5-tetramethyl-1,3,2-dioxaborolan-2-yl)phenoxy)acetamide (27.9 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (22 mg, 55%). MS (ES+) m/e 467 (M+H)+.

Example 22

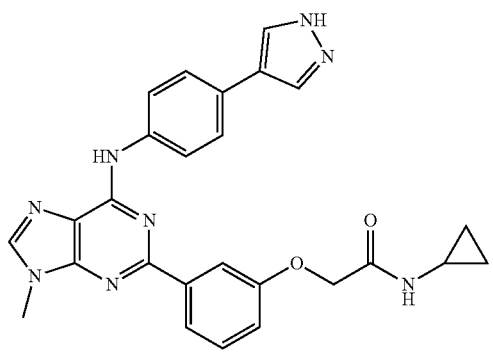 [SMILES: Cn1cnc2c(Nc3ccc(-c4cn[nH]c4)cc3)nc(-c3cccc(OCC(=O)NC4CC4)c3)nc21]

A mixture of N-(4-(1H-pyrazol-4-yl)phenyl)-2-chloro-9-methyl-9H-purin-6-amine (25 mg, 0.08 mmol), N-cyclopropyl-2-(3-(4,4,5,5-tetramethyl-1,3,2-dioxaborolan-2-yl)phenoxy)acetamide (27.9 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product. MS (ES+) m/e 481 (M+H)+.

Example 23

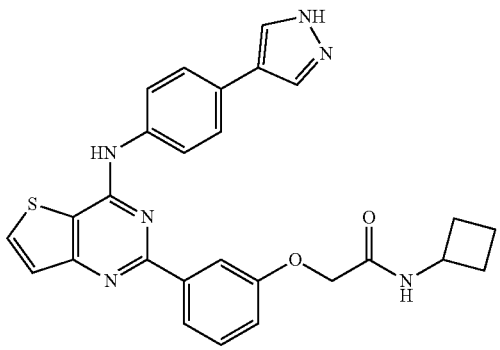 [SMILES: O=C(COc1cccc(-c2nc(Nc3ccc(-c4cn[nH]c4)cc3)c3occc3n2)c1)NC1CCC1]

A mixture of N-(4-(1H-pyrazol-4-yl)phenyl)-2-chlorothieno[3,2-d]pyrimidin-4-amine (25 mg, 0.08 mmol), N-cyclobutyl-2-(3-(4,4,5,5-tetramethyl-1,3,2-dioxaborolan-2-yl)phenoxy)acetamide (25.2 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (16 mg, 42%). $^1$H NMR (500 MHz, DMSO-d6) δ 10.11 (s, 1H), 8.40 (d, J=8.0 Hz, 1H), 8.32 (d, J=5.4 Hz, 1H), 8.11 (s, 2H), 8.08-7.99 (m, 2H), 7.88 (d, J=8.5 Hz, 2H), 7.71 (d, J=8.6 Hz, 2H), 7.55 (d, J=5.4 Hz, 1H), 7.48 (t, J=7.9 Hz, 1H), 7.19-7.12 (m, 1H), 6.45-6.26 (m, 1H), 4.56 (s, 2H), 4.40-4.22 (m, 2H), 2.14 (m, 2H), 2.02 (m, 2H), 1.72-1.53 (m, 2H). MS (ES+) m/e 497 (M+H)+.

Example 24

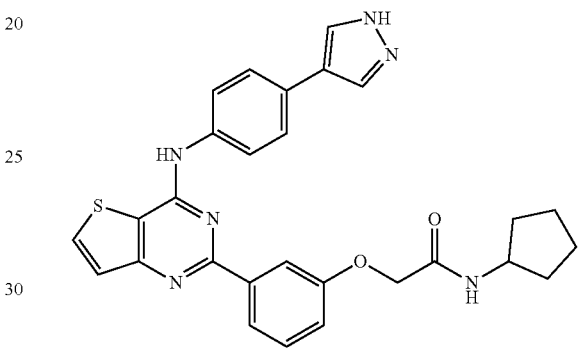

A mixture of N-(4-(1H-pyrazol-4-yl)phenyl)-2-chlorothieno[3,2-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (26.3 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (11 mg, 28%). $^1$H NMR (500 MHz, DMSO-d6) δ 10.06 (s, 1H), 8.31 (d, J=5.4 Hz, 1H), 8.15-8.05 (m, 3H), 8.02 (d, J=7.8 Hz, 2H), 7.88 (d, J=8.5 Hz, 2H), 7.71 (d, J=8.6 Hz, 2H), 7.55 (d, J=5.4 Hz, 1H), 7.47 (t, J=8.2 Hz, 1H), 7.17-7.07 (m, 1H), 4.57 (s, 2H), 4.12 (m, 1H), 1.88-1.77 (m, 2H), 1.71-1.59 (m, 2H), 1.55-1.39 (m, 4H). MS (ES+) m/e 511 (M+H)+.

Example 25

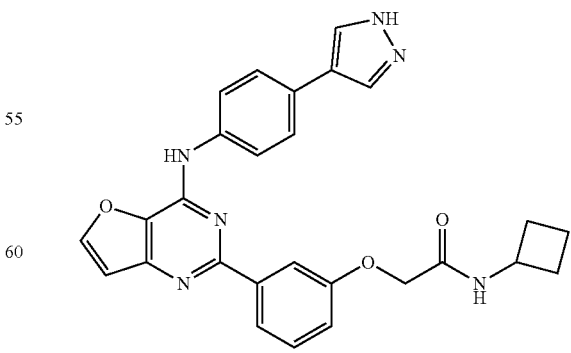

A mixture of N-(4-(1H-pyrazol-4-yl)phenyl)-2-chloro-furo[3,2-d]pyrimidin-4-amine (25 mg, 0.08 mmol), N-cyclobutyl-2-(3-(4,4,5,5-tetramethyl-1,3,2-dioxaborolan-2-yl)

phenoxy)acetamide (26.6 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (11 mg, 28%). $^1$H NMR (500 MHz, DMSO-d6) δ 10.18 (s, 1H), 8.43 (d, J=2.1 Hz, 1H), 8.40 (d, J=8.0 Hz, 1H), 8.08 (s, 2H), 8.04-7.98 (m, 2H), 7.95 (d, J=8.6 Hz, 2H), 7.69 (d, J=8.6 Hz, 2H), 7.45 (t, J=7.9 Hz, 1H), 7.16 (d, J=2.2 Hz, 1H), 7.10 (dd, J=7.9, 2.2 Hz, 1H), 4.55 (s, 2H), 4.33 (m, 1H), 2.15 (m, 2H), 2.10-1.98 (m, 2H), 1.70-1.53 (m, 2H). MS (ES+) m/e 480 (M+H)+.

phenoxy)acetamide (25.3 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (9 mg, 24%). $^1$H NMR (500 MHz, DMSO-d6) δ 9.79 (s, 1H), 8.42 (d, J=8.0 Hz, 1H), 8.10 (s, 2H), 8.08-8.01 (m, 2H), 8.00-7.90 (m, 3H), 7.81-7.69 (m, 3H), 7.45 (t, J=7.9 Hz, 1H), 7.11 (dd, J=8.5, 2.3 Hz, 1H), 4.55 (s, 2H), 4.33 (m, 1H), 2.22-2.11 (m, 2H), 2.10-1.97 (m, 2H), 1.62 (m, 2H). MS (ES+) m/e 497 (M+H)+.

Example 28

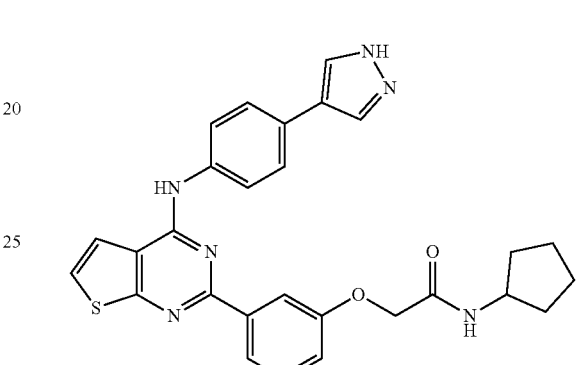

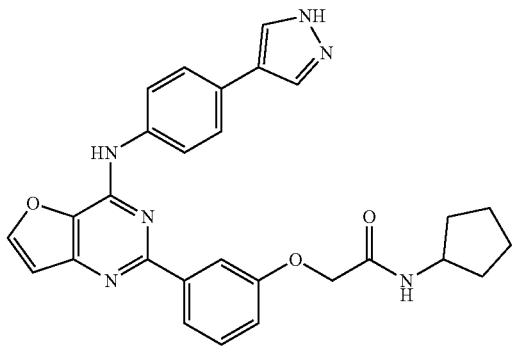 [SMILES: O=C(COc1cccc(-c2nc(Nc3ccc(-c4cn[nH]c4)cc3)c3occc3n2)c1)NC1CCCC1]

Example 26

A mixture of N-(4-(1H-pyrazol-4-yl)phenyl)-2-chlorofuro[3,2-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (27.7 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (12 mg, 29%). $^1$H NMR (500 MHz, DMSO-d6) δ 10.17 (s, 1H), 8.43 (s, 1H), 8.07 (d, J=9.4 Hz, 3H), 8.02-7.98 (m, 2H), 7.95 (d, J=8.6 Hz, 2H), 7.68 (d, J=8.6 Hz, 2H), 7.45 (t, J=8.1 Hz, 1H), 7.15 (d, J=2.1 Hz, 1H), 7.12-7.06 (m, 1H), 4.56 (s, 2H), 4.12 (m, 1H), 1.81 (m, 2H), 1.71-1.58 (m, 2H), 1.48 (m, 4H). MS (ES+) m/e 494 (M+H)+.

A mixture of N-(4-(1H-pyrazol-4-yl)phenyl)-2-chlorothieno[2,3-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (26.3 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (9 mg, 23%). $^1$H NMR (500 MHz, DMSO-d6) δ 9.78 (s, 1H), 8.09 (s, 4H), 8.02 (dd, J=4.0, 2.3 Hz, 2H), 7.94 (t, J=7.5 Hz, 3H), 7.73 (dd, J=12.4, 7.3 Hz, 3H), 7.45 (t, J=8.1 Hz, 1H), 7.10 (dd, J=8.1, 1.9 Hz, 1H), 4.57 (s, 2H), 4.13 (m, 1H), 1.82 (m, 2H), 1.65 (m, 2H), 1.49 (m, 4H). MS (ES+) m/e 511 (M+H)+.

Example 29

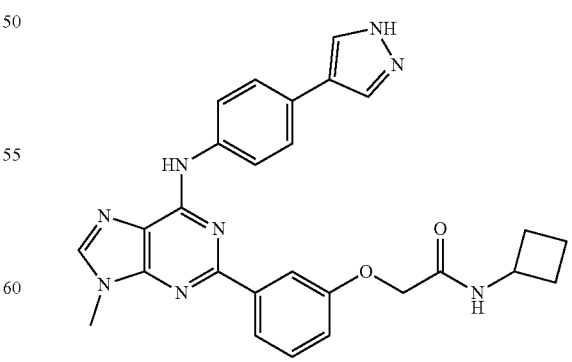

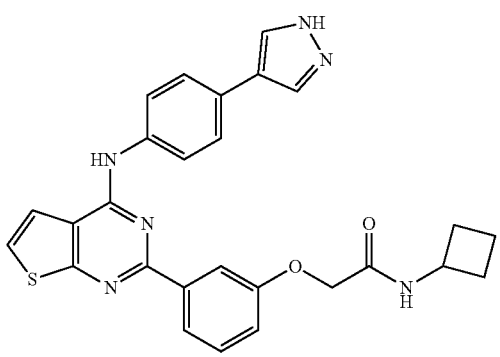 [SMILES: O=C(COc1cccc(-c2nc(Nc3ccc(-c4cn[nH]c4)cc3)c3ccsc3n2)c1)NC1CCC1]

Example 27

A mixture of N-(4-(1H-pyrazol-4-yl)phenyl)-2-chlorothieno[2,3-d]pyrimidin-4-amine (25 mg, 0.08 mmol), N-cyclobutyl-2-(3-(4,4,5,5-tetramethyl-1,3,2-dioxaborolan-2-yl)

A mixture of N-(4-(1H-pyrazol-4-yl)phenyl)-2-chloro-9-methyl-9H-purin-6-amine (25 mg, 0.08 mmol), N-cyclobutyl-2-(3-(4,4,5,5-tetramethyl-1,3,2-dioxaborolan-2-yl)phenoxy)acetamide (25.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (19 mg, 50%). $^1$H NMR (500 MHz, DMSO-d6) δ 9.98 (s, 1H), 8.41 (d, J=8.0 Hz, 1H), 8.35 (s, 1H), 8.07 (s, 6H), 7.66 (d, J=8.7 Hz, 2H), 7.46 (t, J=8.1 Hz, 1H), 7.09 (dd, J=7.8, 2.1 Hz, 1H), 4.57 (s, 2H), 4.33 (m, 2H), 2.22-2.10 (m, 2H), 2.09-1.95 (m, 2H), 1.62 (m, 2H). MS (ES+) m/e 495 (M+H)+.

180° C. in microwave for 2 h. The mixture was cooled to rt, concentrated, redissolved in DMSO and purified by reverse-phase HPLC to provide the title product (6 mg, 16%). $^1$H NMR (500 MHz, DMSO-d6) δ 9.30 (s, 1H), 8.40 (d, J=7.9 Hz, 1H), 8.08 (s, 2H), 7.97 (d, J=7.9 Hz, 2H), 7.82 (m, 2H), 7.67 (d, J=8.5 Hz, 2H), 7.44 (t, J=7.9 Hz, 1H), 7.11 (d, J=7.8 Hz, 1H), 5.09 (s, 2H), 4.96 (s, 2H), 4.53 (s, 2H), 4.32 (m, 1H), 2.14 (m, 2H), 2.03 (m, 2H), 1.62 (m, 2H). MS (ES+) m/e 483 (M+H)+.

Example 32

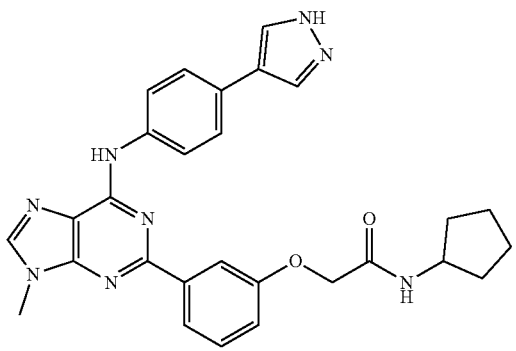 [SMILES: Cn1cnc2c(Nc3ccc(-c4cn[nH]c4)cc3)nc(-c3cccc(OCC(=O)NC4CCCC4)c3)nc21]

Example 30

A mixture of N-(4-(1H-pyrazol-4-yl)phenyl)-2-chloro-9-methyl-9H-purin-6-amine (25 mg, 0.08 mmol), N-cyclopentyl-2-(3-(4,4,5,5-tetramethyl-1,3,2-dioxaborolan-2-yl)phenoxy)acetamide (26.5 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (18 mg, 46%). $^1$H NMR (500 MHz, DMSO-d6) δ 9.96 (s, 1H), 8.33 (s, 1H), 8.06 (m, 7H), 7.66 (d, J=8.6 Hz, 2H), 7.45 (t, J=8.0 Hz, 1H), 7.15-6.99 (m, 1H), 4.58 (s, 2H), 4.22-4.05 (m, 1H), 3.88 (s, 3H), 1.81 (m, 2H), 1.63 (m, 2H), 1.55-1.38 (m, 4H). MS (ES+) m/e 509 (M+H)+.

Example 31

A mixture of N-(4-(1H-pyrazol-4-yl)phenyl)-2-chloro-5,7-dihydrofuro[3,4-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (26.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product. $^1$H NMR (500 MHz, DMSO-d6) δ 9.28 (s, 1H), 8.07 (s, 3H), 7.96 (d, J=6.7 Hz, 2H), 7.82 (d, J=8.4 Hz, 2H), 7.67 (d, J=8.5 Hz, 2H), 7.44 (t, J=8.1 Hz, 1H), 7.10 (d, J=8.3 Hz, 1H), 6.36 (dd, J=15.5, 7.1 Hz, 1H), 5.09 (s, 2H), 4.95 (s, 2H), 4.54 (s, 3H), 4.11 (m, 1H), 1.80 (m, 2H), 1.64 (m, 2H), 1.54-1.37 (m, 4H). MS (ES+) m/e 497 (M+H)+.

Example 33

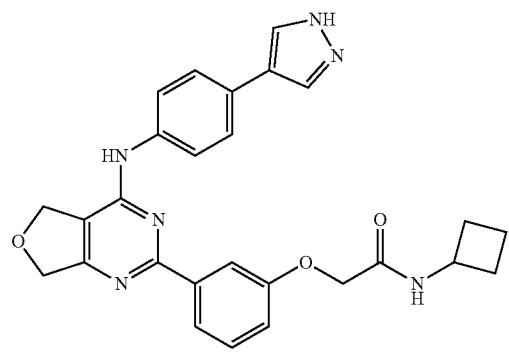 [SMILES: O=C(COc1cccc(-c2nc3c(c(Nc4ccc(-c5cn[nH]c5)cc4)n2)COC3)c1)NC1CCC1]

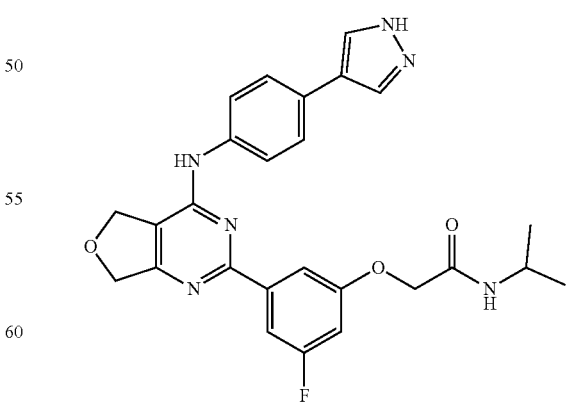

A mixture of N-(4-(1H-pyrazol-4-yl)phenyl)-2-chloro-5,7-dihydrofuro[3,4-d]pyrimidin-4-amine (25 mg, 0.08 mmol), N-cyclobutyl-2-(3-(4,4,5,5-tetramethyl-1,3,2-dioxaborolan-2-yl)phenoxy)acetamide (26.4 mg, 0.08 mmol), Pd(PPh$_3$)$_4$ (9.6 mg, 0.01 mmol), saturated Na$_2$CO$_3$ (0.08 mL), water (0.08 mL), and dioxane (0.8 mL) was heated at A mixture of N-(4-(1H-pyrazol-4-yl)phenyl)-2-chloro-5,7-dihydrofuro[3,4-d]pyrimidin-4-amine (25 mg, 0.08 mmol), 2-(3-fluoro-5-(4,4,5,5-tetramethyl-1,3,2-dioxaborolan-2-yl)phenoxy)-N-isopropylacetamide (25.4 mg, 0.08 mmol), Pd(PPh₃)₄ (9.6 mg, 0.01 mmol), saturated Na₂CO₃ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (14 mg, 31%). ¹H NMR (500 MHz, DMSO-d6) δ 9.33 (s, 1H), 8.08 (s, 2H), 8.03 (d, J=7.9 Hz, 1H), 7.83 (s, 1H), 7.77 (d, J=8.4 Hz, 2H), 7.70-7.61 (m, 3H), 7.00 (d, J=10.5 Hz, 1H), 5.08 (s, 2H), 4.95 (s, 2H), 4.57 (s, 2H), 3.99 (m, 1H), 1.10 (d, J=6.6 Hz, 6H). MS (ES+) m/e 489 (M+H)+.

Example 34

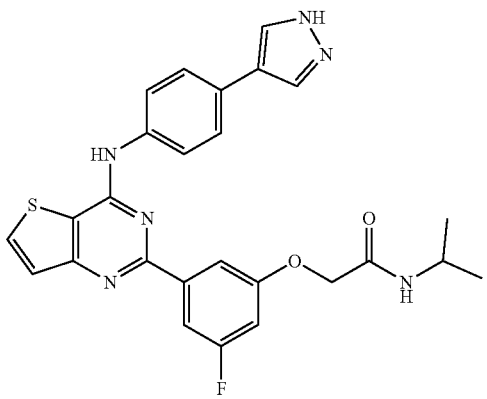 [SMILES: CC(C)NC(=O)COc1cc(F)cc(-c2nc(Nc3ccc(-c4cn[nH]c4)cc3)c3sccc3n2)c1]

A mixture of N-(4-(1H-pyrazol-4-yl)phenyl)-2-chlorothieno[3,2-d]pyrimidin-4-amine (25 mg, 0.08 mmol), 2-(3-fluoro-5-(4,4,5,5-tetramethyl-1,3,2-dioxaborolan-2-yl)phenoxy)-N-isopropylacetamide (25.7 mg, 0.08 mmol), Pd(PPh₃)₄ (9.6 mg, 0.01 mmol), saturated Na₂CO₃ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product. ¹H NMR (500 MHz, DMSO-d6) δ 10.02 (s, 1H), 8.31 (d, J=5.4 Hz, 1H), 8.12 (s, 2H), 8.04 (d, J=7.9 Hz, 1H), 7.91 (s, 1H), 7.85 (d, J=8.4 Hz, 1H), 7.72 (t, J=10.1 Hz, 2H), 7.55 (d, J=5.4 Hz, 1H), 7.01 (d, J=10.5 Hz, 1H), 4.59 (s, 2H), 4.00 (m, 1H), 1.12 (d, J=6.6 Hz, 6H). MS (ES+) m/e 503 (M+H)+.

Example 35

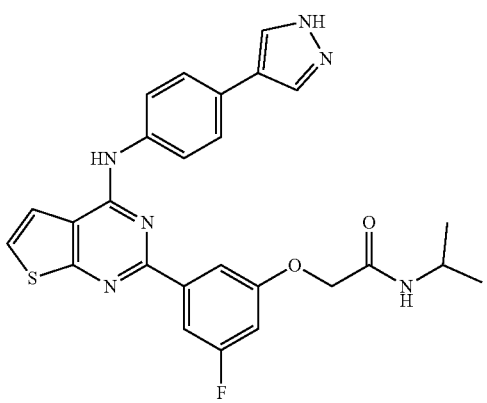 [SMILES: CC(C)NC(=O)COc1cc(F)cc(-c2nc(Nc3ccc(-c4cn[nH]c4)cc3)c3ccsc3n2)c1]

A mixture of N-(4-(1H-pyrazol-4-yl)phenyl)-2-chlorothieno[2,3-d]pyrimidin-4-amine (25 mg, 0.08 mmol), 2-(3-fluoro-5-(4,4,5,5-tetramethyl-1,3,2-dioxaborolan-2-yl)phenoxy)-N-isopropylacetamide (25.7 mg, 0.08 mmol), Pd(PPh₃)₄ (9.6 mg, 0.01 mmol), saturated Na₂CO₃ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (9 mg, 23%). ¹H NMR (500 MHz, DMSO-d6) δ 9.84 (s, 1H), 8.11 (s, 2H), 8.05 (d, J=7.9 Hz, 1H), 7.97-7.84 (m, 4H), 7.77 (d, J=6.0 Hz, 1H), 7.72 (d, J=8.4 Hz, 3H), 7.00 (d, J=10.4 Hz, 1H), 4.59 (s, 2H), 4.00 (m, 1H), 1.12 (d, J=6.5 Hz, 6H). MS (ES+) m/e 503 (M+H)+.

Example 36

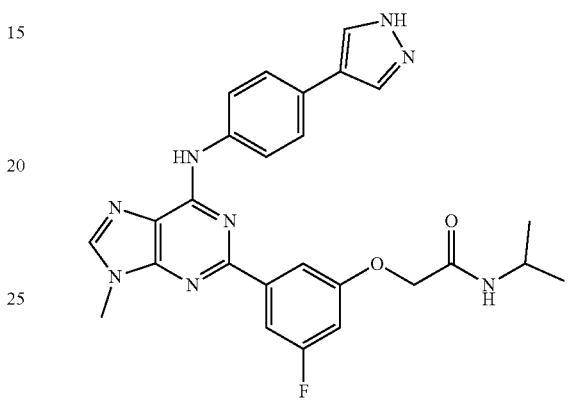

A mixture of N-(4-(1H-pyrazol-4-yl)phenyl)-2-chloro-9-methyl-9H-purin-6-amine (25 mg, 0.08 mmol), 2-(3-fluoro-5-(4,4,5,5-tetramethyl-1,3,2-dioxaborolan-2-yl)phenoxy)-N-isopropylacetamide (25.9 mg, 0.08 mmol), Pd(PPh₃)₄ (9.6 mg, 0.01 mmol), saturated Na₂CO₃ (0.08 mL), water (0.08 mL), and dioxane (0.8 mL) was heated at 180° C. in microwave for 2 h. The mixture was cooled to rt, concentrated, redissolved in DMSO and purified by reverse-phase HPLC to provide the title product (8 mg, 21%). ¹H NMR (500 MHz, DMSO-d6) δ 10.04 (s, 1H), 8.37 (s, 1H), 8.15-7.97 (m, 4H), 7.91 (s, 1H), 7.77 (d, J=9.5 Hz, 1H), 7.66 (d, J=7.6 Hz, 2H), 6.98 (d, J=10.0 Hz, 1H), 4.60 (s, 2H), 4.00 (m, 1H), 3.88 (s, 3H), 1.11 (d, J=6.0 Hz, 6H). MS (ES+) m/e 501 (M+H)+.

Example 37

2-(3-(4-((4-(1H-pyrazol-4-yl)phenyl)amino)-5,7-dihydrofuro[3,4-d]pyrimidin-2-yl)phenoxy)-1-morpholinoethan-1-one

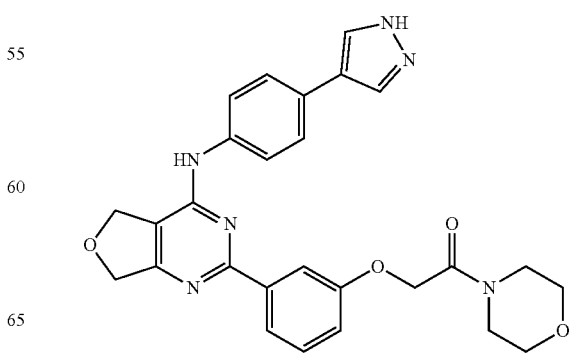

Example 37A 2-chloro-1-morpholinoethan-1-one

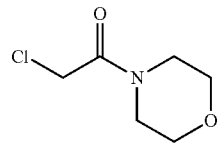

To morpholine (466 mg, 5.36 mmol) in DCM (13.4 mL) at 0° C., was added 2-chloroacetyl chloride (300 mg, 2.68 mmol) in DCM. The mixture was then stirred at r.t. for 1 h. The precipitate was filtered and the filtrate was concentrated to provide the title compound as an oil (300 mg, 68%). MS (ES+) m/e 164 (M+H)+.

Example 37B 1-morpholino-2-(3-(4,4,5,5-tetramethyl-1,3,2-dioxaborolan-2-yl)phenoxy)ethan-1-one

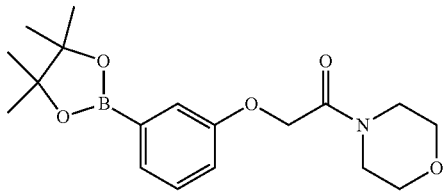 [SMILES: CC1(C)OB(c2cccc(OCC(=O)N3CCOCC3)c2)OC1(C)C]

A mixture of 3-(4,4,5,5-tetramethyl-1,3,2-dioxaborolan-2-yl)phenol (300 mg, 1.36 mmol), 2-chloro-1-morpholinoethan-1-one (223 mg, 1.36) and $K_2CO_3$ (283 mg, 2.04 mmol) in DMF (4.5 mL) was heated at 90° C. overnight, diluted with EtOAc, washed with water (2×) and brine, dried over Na2SO4, concentrated, and purified by chromatography with EtOAc/Hex to provide the title compound (201 mg, 42%) as a white solid. MS (ES+) m/e 348 (M+H)+.

Example 37C 2-(3-(4-((4-(1H-pyrazol-4-yl)phenyl)amino)-5,7-dihydrofuro[3,4-d]pyrimidin-2-yl)phenoxy)-1-morpholinoethan-1-one

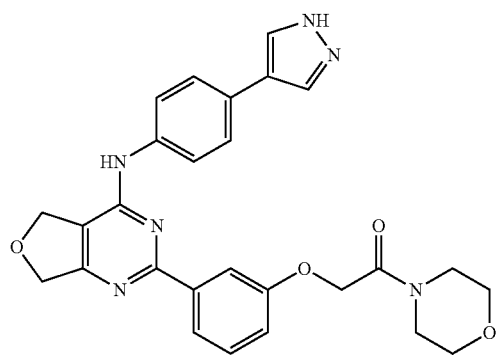 [SMILES: O=C(COc1cccc(-c2nc3c(c(Nc4ccc(-c5cn[nH]c5)cc4)n2)COC3)c1)N1CCOCC1]

A mixture of N-(4-(1H-pyrazol-4-yl)phenyl)-2-chloro-5,7-dihydrofuro[3,4-d]pyrimidin-4-amine (20 mg, 0.06 mmol), 1-morpholino-2-(3-(4,4,5,5-tetramethyl-1,3,2-dioxaborolan-2-yl)phenoxy)ethan-1-one (22 mg, 0.06 mmol), tetrakis(triphenylphosphine)palladium(0) (7.4 mg, 0.01 mmol), dioxane (0.64 mL), water (0.06 mL), and saturated $Na_2CO_3$ (0.06 mL) was heated at 100° C. overnight. The mixture was concentrated in vacuo to remove the volatiles. The residue was dissolved in DMSO and purified by reverse-phase HPLC to provide the title compound (9 mg, 28%). $^1$H NMR (500 MHz, DMSO-$d_6$) δ 9.31 (s, 1H), 8.07 (s, 2H), 7.94 (d, J=7.7 Hz, 1H), 7.87 (t, J=2.0 Hz, 1H), 7.84-7.77 (m, 2H), 7.67 (dd, J=9.2, 2.7 Hz, 2H), 7.43 (t, J=7.9 Hz, 1H), 7.08 (dd, J=8.1, 2.8 Hz, 1H), 5.09 (d, J=2.7 Hz, 2H), 5.01-4.88 (m, 4H), 3.57 (m, 4H), 3.47 (m, 4H). MS (ES+) m/e 499 (M+H)+.

Example 38

2-(3-(4-((4-(1H-pyrazol-4-yl)phenyl)amino)thieno[3,2-d]pyrimidin-2-yl)phenoxy)-1-morpholinoethan-1-one

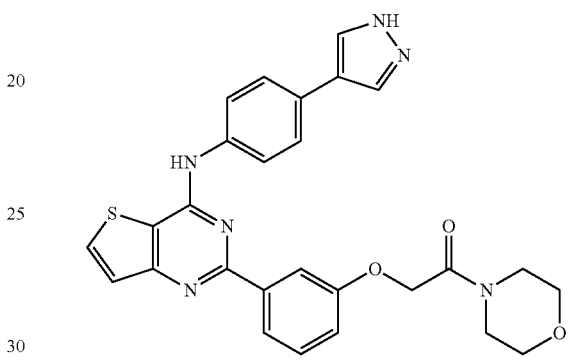

A mixture of N-(4-(1H-pyrazol-4-yl)phenyl)-2-chlorothieno[3,2-d]pyrimidin-4-amine (20 mg, 0.06 mmol), 1-morpholino-2-(3-(4,4,5,5-tetramethyl-1,3,2-dioxaborolan-2-yl)phenoxy)ethan-1-one (22 mg, 0.06 mmol), tetrakis(triphenylphosphine)palladium(0) (7.4 mg, 0.01 mmol), dioxane (0.64 mL), water (0.06 mL), and saturated $Na_2CO_3$ (0.06 mL) was heated at 100° C. overnight. The mixture was concentrated in vacuo to remove the volatiles. The residue was dissolved in DMSO and purified by reverse-phase HPLC to provide the title compound (10 mg, 32%). $^1$H NMR (400 MHz, DMSO-$d_6$) δ 9.78 (s, 1H), 8.10 (s, 2H), 8.01 (d, J=7.8 Hz, 1H), 7.94 (dq, J=9.0, 3.2, 2.7 Hz, 4H), 7.76-7.68 (m, 3H), 7.44 (t, J=8.0 Hz, 1H), 7.07 (dd, J=8.2, 2.7 Hz, 1H), 4.94 (s, 2H), 3.61-3.45 (m, 8H). MS (ES+) m/e 513 (M+H)+.

Example 39

2-(3-(4-((4-(1H-pyrazol-4-yl)phenyl)amino)thieno[2,3-d]pyrimidin-2-yl)phenoxy)-1-morpholinoethan-1-one

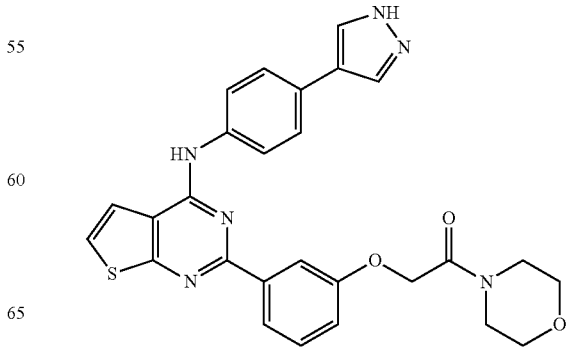

A mixture of N-(4-(1H-pyrazol-4-yl)phenyl)-2-chlorothieno[2,3-d]pyrimidin-4-amine (20 mg, 0.06 mmol), 1-morpholino-2-(3-(4,4,5,5-tetramethyl-1,3,2-dioxaborolan-2-yl)phenoxy)ethan-1-one (21 mg, 0.06 mmol), tetrakis(triphenylphosphine)palladium(0) (7.4 mg, 0.01 mmol), dioxane (0.64 mL), water (0.06 mL), and saturated $Na_2CO_3$ (0.06 mL) was heated in microwave at 180° C. for 2 h. The mixture was concentrated in vacuo to remove the volatiles. The residue was dissolved in DMSO and purified by reverse-phase HPLC to provide the title compound (12 mg, 38%). $^1$H NMR (400 MHz, DMSO-$d_6$) δ 10.18 (s, 1H), 8.33 (dd, J=5.4, 2.2 Hz, 1H), 8.10 (d, J=6.9 Hz, 2H), 8.04-7.91 (m, 2H), 7.90-7.80 (m, 2H), 7.75-7.69 (m, 2H), 7.57 (t, J=5.3 Hz, 1H), 7.47 (td, J=8.0, 2.7 Hz, 1H), 7.12 (dd, J=8.1, 2.8 Hz, 1H), 4.95 (s, 2H), 3.68-3.40 (m, 8H). MS (ES+) m/e 513 (M+H)$^+$.

Example 40

2-(3-(4-((4-(1H-pyrazol-4-yl)phenyl)amino)thieno[3,2-d]pyrimidin-2-yl)phenoxy)-N-methylacetamide

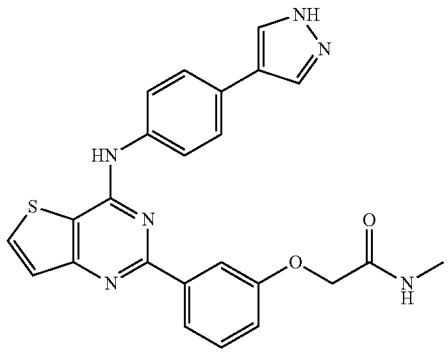 [SMILES: CNC(=O)COc1cccc(-c2nc(Nc3ccc(-c4cn[nH]c4)cc3)c3sccc3n2)c1]

Example 40A 2-chloro-N-methylacetamide

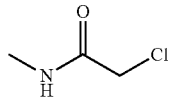

To methylamine hydrochloride (896 mg, 13.3 mmol) and $Na_2CO_3$ (5630 mg, 53 mmol) in water (26 mL) at ° C. was added 2-chloroacetyl chloride (1500 mg, 13.3 mmol). The mixture was stirred at r.t. for 1 h and extracted with EtOAc (2×). The combined organic layers were dried over $Na_2SO_4$ and concentrated to provide the title compound (1200 mg, 84%).

Example 40B

N-methyl-2-(3-(4,4,5,5-tetramethyl-1,3,2-dioxaborolan-2-yl)phenoxy)acetamide

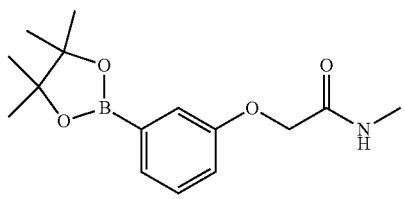

A mixture of 3-(4,4,5,5-tetramethyl-1,3,2-dioxaborolan-2-yl)phenol (250 mg, 1.14 mmol), 2-chloro-N-methylacetamide (122 mg, 1.14) and $K_2CO_3$ (236 mg, 1.70 mmol) in DMF (3.8 mL) was heated at 80° C. overnight, diluted with EtOAc, washed with water (2×) and brine, dried over Na2SO4, concentrated, and purified by chromatography with EtOAc/Hex to provide the title compound (160 mg, 48%). MS (ES+) m/e 292 (M+H)$^+$.

Example 40C 2-(3-(4-((4-(1H-pyrazol-4-yl)phenyl)amino)thieno[3,2-d]pyrimidin-2-yl)phenoxy)-N-methylacetamide

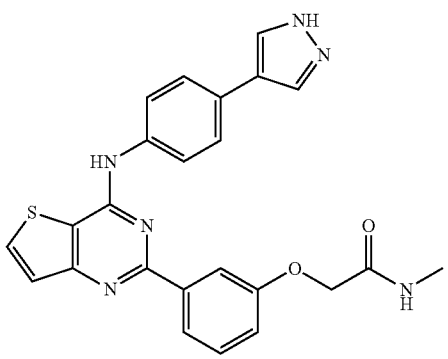 [SMILES: CNC(=O)COc1cccc(-c2nc(Nc3ccc(-c4cn[nH]c4)cc3)c3sccc3n2)c1]

A mixture of N-(4-(1H-pyrazol-4-yl)phenyl)-2-chlorothieno[3,2-d]pyrimidin-4-amine (20 mg, 0.06 mmol), 1-morpholino-2-(3-(4,4,5,5-tetramethyl-1,3,2-dioxaborolan-2-yl)phenoxy)ethan-1-one (18 mg, 0.06 mmol), tetrakis(triphenylphosphine)palladium(0) (7.4 mg, 0.01 mmol), dioxane (0.64 mL), water (0.06 mL), and saturated Na2CO3 (0.06 mL) was heated in microwave at 180° C. for 2 h. The mixture was concentrated in vacuo to remove the volatiles. The residue was dissolved in DMSO and purified by reverse-phase HPLC to provide the title compound (13 mg, 47%). $^1$H NMR (400 MHz, DMSO-$d_6$) δ 9.79 (s, 1H), 8.16-8.15 (m, 1H), 8.10 (s, 2H), 8.06-8.02 (m, 2H), 7.97-7.91 (m, 3H), 7.77-7.71 (m, 3H), 7.46 (t, J=7.9 Hz, 1H), 7.11 (ddd, J=8.2, 2.6, 1.0 Hz, 1H), 4.60 (s, 2H), 2.69 (d, J=4.6 Hz, 3H). MS (ES+) m/e 457 (M+H)$^+$.

Example 41

2-(3-(4-((4-(1H-pyrazol-4-yl)phenyl)amino)thieno[3,2-d]pyrimidin-2-yl)phenoxy)-N-propylacetamide

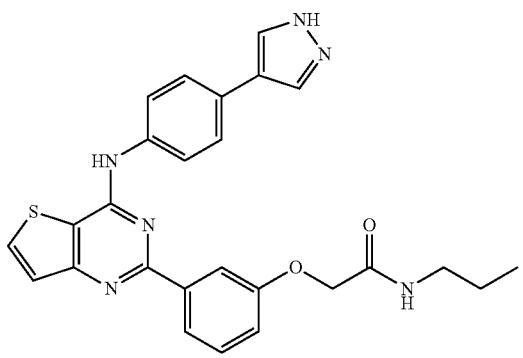 [SMILES: CCCNC(=O)COc1cccc(-c2nc(Nc3ccc(-c4cn[nH]c4)cc3)c3sccc3n2)c1]

Example 41A 2-chloro-N-propylacetamide

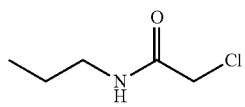

To propan-1-amine hydrochloride (1269 mg, 13.3 mmol) and Na2CO3 (5630 mg, 53 mmol) in water (26 mL) at 0° C. was added 2-chloroacetyl chloride (1500 mg, 13.3 mmol). The mixture was stirred at r.t. for 1 h and extracted with EtOAc (2×). The combined organic layers were dried over $Na_2SO_4$ and concentrated to provide the title compound (1500 mg, 83%).

Example 41B

N-propyl-2-(3-(4,4,5,5-tetramethyl-1,3,2-dioxaborolan-2-yl)phenoxy)acetamide

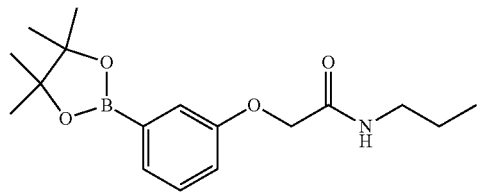 [SMILES: CCCNC(=O)COc1cccc(B2OC(C)(C)C(C)(C)O2)c1]

A mixture of 3-(4,4,5,5-tetramethyl-1,3,2-dioxaborolan-2-yl)phenol (250 mg, 1.14 mmol), 2-chloro-N-propylacetamide (154 mg, 1.14) and $K_2CO_3$ (236 mg, 1.70 mmol) in DMF (3.8 mL) was heated at 80° C. overnight, diluted with EtOAc, washed with water (2×) and brine, dried over $Na_2SO_4$, concentrated, and purified by chromatography with EtOAc/Hex to provide the title compound (160 mg, 48%). MS (ES+) m/e 320 (M+H)+.

Example 41C 2-(3-(4-((4-(1H-pyrazol-4-yl)phenyl)amino)thieno[3,2-d]pyrimidin-2-yl)phenoxy)-N-propylacetamide

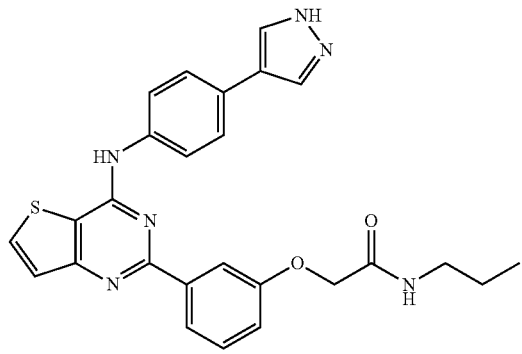 [SMILES: CCCNC(=O)COc1cccc(-c2nc(Nc3ccc(-c4cn[nH]c4)cc3)c3sccc3n2)c1]

A mixture of n-(4-(1h-pyrazol-4-yl)phenyl)-2-chlorothieno[3,2-d]pyrimidin-4-amine (20 mg, 0.06 mmol), n-propyl-2-(3-(4,4,5,5-tetramethyl-1,3,2-dioxaborolan-2-yl)phenoxy)acetamide (19 mg, 0.06 mmol), tetrakis(triphenylphosphine)palladium(0) (7.4 mg, 0.01 mmol), dioxane (0.64 ml), water (0.06 ml), and saturated $Na_2CO_3$ (0.06 ml) was heated in microwave at 180° c. for 2 h. The mixture was concentrated in vacuo to remove the volatiles. the residue was dissolved in dmso and purified by reverse-phase HPLC to provide the title compound (9 mg, 30%). 1H NMR (400 mHz, DMSO-d6) δ 9.78 (s, 1h), 8.19 (t, J=5.9 Hz, 1h), 8.10 (s, 2H), 8.06-8.02 (m, 2H), 7.94 (dd, j=8.8, 6.6 Hz, 3H), 7.76-7.69 (m, 3H), 7.66-7.54 (m, 1H), 7.46 (t, J=7.9 Hz, 1H), 7.11 (ddd, J=8.1, 2.6, 1.0 Hz, 1H), 4.59 (s, 2H), 3.19-3.06 (m, 2H), 1.47 (H, J=7.3 Hz, 2h), 0.83 (t, J=7.4 Hz, 3H). MS (ES+) m/e 485 (M+H)+.

Example 42

2-(3-(4-((4-(1H-pyrazol-4-yl)phenyl)amino)-5,7-dihydrofuro[3,4-d]pyrimidin-2-yl)phenoxy)-N-methylacetamide

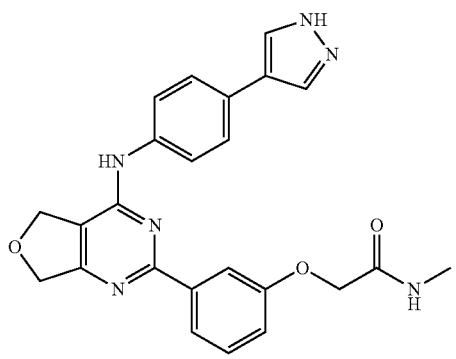 [SMILES: CNC(=O)COc1cccc(-c2nc3c(c(Nc4ccc(-c5cn[nH]c5)cc4)n2)COC3)c1]

A mixture of N-(4-(1H-pyrazol-4-yl)phenyl)-2-chloro-5,7-dihydrofuro[3,4-d]pyrimidin-4-amine (20 mg, 0.06 mmol), N-methyl-2-(3-(4,4,5,5-tetramethyl-1,3,2-dioxaborolan-2-yl)phenoxy)acetamide (18 mg, 0.06 mmol), tetrakis(triphenylphosphine)palladium(0) (7.4 mg, 0.01 mmol), dioxane (0.64 mL), water (0.06 mL), and saturated $Na_2CO_3$ (0.06 mL) was heated in microwave at 180° C. for 2 h. The mixture was concentrated in vacuo to remove the volatiles. The residue was dissolved in DMSO and purified by reverse-phase HPLC to provide the title compound (6 mg, 21%). 1H NMR (400 MHz, DMSO-d6) δ 9.29 (s, 1H), 8.20-8.06 (m, 3H), 8.01-7.93 (m, 2H), 7.81 (d, J=8.4 Hz, 2H), 7.74-7.63 (m, 2H), 7.45 (t, J=8.1 Hz, 1H), 7.11 (ddd, J=8.1, 2.5, 1.1 Hz, 1H), 5.09 (s, 2H), 4.96 (t, J=2.7 Hz, 2H), 4.57 (s, 2H), 2.68 (d, J=4.6 Hz, 3H). MS (ES+) m/e 443 (M+H)+.

Example 43

N-(3-(4-((4-(1H-pyrazol-4-yl)phenyl)amino)thieno[3,2-d]pyrimidin-2-yl)phenyl)nicotinamide

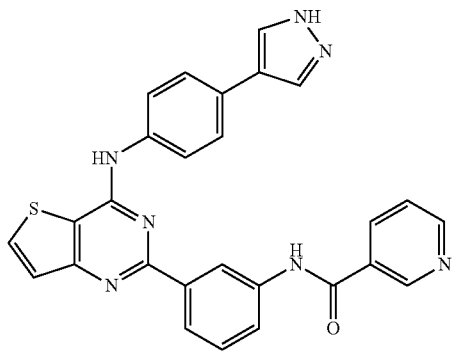 [SMILES: O=C(Nc1cccc(-c2nc(Nc3ccc(-c4cn[nH]c4)cc3)c3sccc3n2)c1)c1cccnc1]

Example 43A

N-(3-(4,4,5,5-tetramethyl-1,3,2-dioxaborolan-2-yl)phenyl)nicotinamide

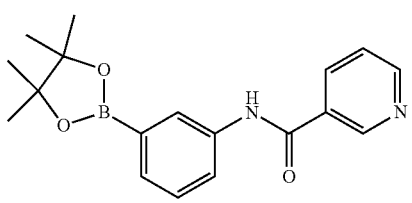 [SMILES: CC1(C)OB(c2cccc(NC(=O)c3cccnc3)c2)OC1(C)C]

To nicotinoyl chloride hydrochloride (325 mg, 1.83 mmol) and iPrNEt2 (0.64 mL, 3.65 mmol) in DCM (18 mL) at 0 C was added 3-(4,4,5,5-tetramethyl-1,3,2-dioxaborolan-2-yl)aniline (400 mg, 1.83 mmol). The mixture was stirred at rt for 3 h, washed with water. The organic layer was dried over Na$_2$SO$_4$ and concentrated and purified by chromatography with 30-100% EtOAc/Hex to provide the title compound (291 mg, 49%). $^1$H NMR (400 MHz, DMSO-d$_6$) δ 10.50 (s, 1H), 9.19 (d, J=2.4 Hz, 1H), 8.82 (dd, J=4.9, 1.7 Hz, 1H), 8.38 (dt, J=8.0, 2.0 Hz, 1H), 8.17 (d, J=2.4 Hz, 1H), 8.02 (dt, J=7.9, 2.0 Hz, 1H), 7.63 (dd, J=8.0, 4.8 Hz, 1H), 7.46 (dt, J=15.2, 7.2 Hz, 2H), 1.37 (s, 12H). MS (ES+) m/e 325 (M+H)$^+$.

Example 43B

N-(3-(4-((4-(1H-pyrazol-4-yl)phenyl)amino)thieno[3,2-d]pyrimidin-2-yl)phenyl)nicotinamide

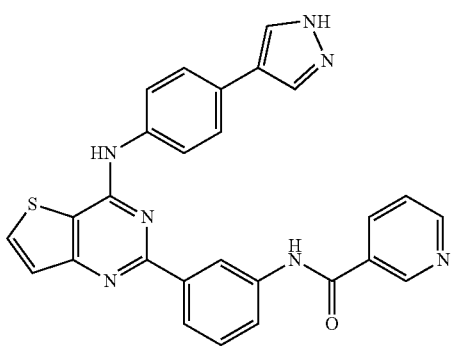 [SMILES: O=C(Nc1cccc(-c2nc(Nc3ccc(-c4cn[nH]c4)cc3)c3sccc3n2)c1)c1cccnc1]

A mixture of N-(4-(1H-pyrazol-4-yl)phenyl)-2-chlorothieno[3,2-d]pyrimidin-4-amine (20 mg, 0.06 mmol), N-(3-(4,4,5,5-tetramethyl-1,3,2-dioxaborolan-2-yl)phenyl)nicotinamide (20 mg, 0.06 mmol), tetrakis(triphenylphosphine)palladium(0) (7 mg, 0.01 mmol), dioxane (0.64 mL), water (0.06 mL), and saturated Na$_2$CO$_3$ (0.06 mL) was heated in microwave at 180° C. for 2 h. The mixture was concentrated in vacuo to remove the volatiles. The residue was dissolved in DMSO and purified by reverse-phase HPLC to provide the title compound (23 mg, 78%). MS (ES+) m/e 490 (M+H)$^+$.

Example 44

2-(3-(4-((4-(1H-pyrazol-4-yl)phenyl)amino)-5,7-dihydrofuro[3,4-d]pyrimidin-2-yl)phenoxy)-N-propylacetamide

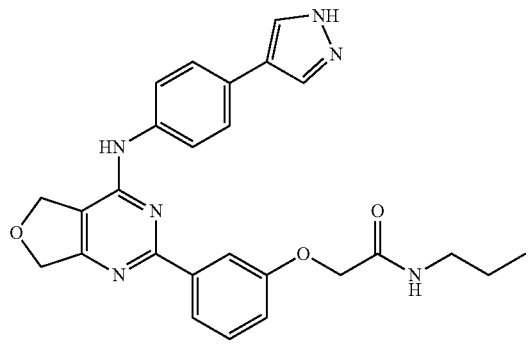 [SMILES: CCCNC(=O)COc1cccc(-c2nc3c(c(Nc4ccc(-c5cn[nH]c5)cc4)n2)COC3)c1]

A mixture of N-(4-(1H-pyrazol-4-yl)phenyl)-2-chloro-5,7-dihydrofuro[3,4-d]pyrimidin-4-amine (20 mg, 0.06 mmol), N-propyl-2-(3-(4,4,5,5-tetramethyl-1,3,2-dioxaborolan-2-yl)phenoxy)acetamide (20 mg, 0.06 mmol), tetrakis(triphenylphosphine)palladium(0) (7 mg, 0.01 mmol), dioxane (0.64 mL), water (0.06 mL), and saturated Na$_2$CO$_3$ (0.06 mL) was heated in microwave at 180° C. for 2 h. The mixture was concentrated in vacuo to remove the volatiles. The residue was dissolved in DMSO and purified by reverse-phase HPLC to provide the title compound (5 mg, 17%). $^1$H NMR (400 MHz, DMSO-d$_6$) δ 9.29 (s, 1H), 8.17 (t, J=5.9 Hz, 1H), 8.07 (s, 2H), 7.97 (d, J=7.0 Hz, 2H), 7.81 (d, J=8.2 Hz, 2H), 7.67 (d, J=8.3 Hz, 2H), 7.44 (t, J=8.0 Hz, 1H), 7.16-7.07 (m, 1H), 5.09 (s, 2H), 4.96 (d, J=2.5 Hz, 2H), 4.57 (s, 2H), 3.11 (q, J=6.7 Hz, 2H), 1.44 (p, J=7.2 Hz, 2H), 0.82 (t, J=7.4 Hz, 3H). MS (ES+) m/e 471 (M+H)$^+$.

Example 45

2-(3-(4-((4-(1H-pyrazol-4-yl)phenyl)amino)thieno[2,3-d]pyrimidin-2-yl)phenoxy)-N-methylacetamide

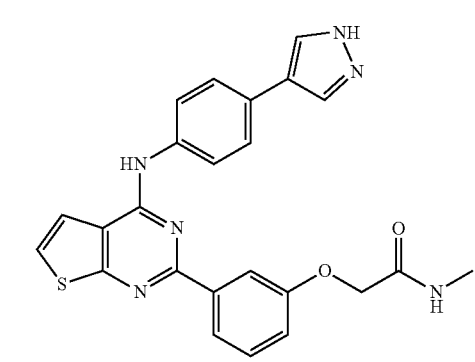 [SMILES: CNC(=O)COc1cccc(-c2nc(Nc3ccc(-c4cn[nH]c4)cc3)c3ccsc3n2)c1]

A mixture of N-(4-(1H-pyrazol-4-yl)phenyl)-2-chlorothieno[2,3-d]pyrimidin-4-amine (20 mg, 0.06 mmol), N-methyl-2-(3-(4,4,5,5-tetramethyl-1,3,2-dioxaborolan-2-yl)phenoxy)acetamide (17 mg, 0.06 mmol), tetrakis(triphenylphosphine)palladium(0) (7 mg, 0.01 mmol), dioxane (0.64 mL), water (0.06 mL), and saturated Na$_2$CO$_3$ (0.06 mL) was heated in microwave at 180° C. for 2 h. The mixture was concentrated in vacuo to remove the volatiles. The residue was dissolved in DMSO and purified by reverse-phase HPLC to provide the title compound (12 mg, 43%). MS (ES+) m/e 457 (M+H)$^+$.

Example 46

2-(3-(4-((4-(1H-pyrazol-4-yl)phenyl)amino)thieno[2,3-d]pyrimidin-2-yl)phenoxy)-N-propylacetamide

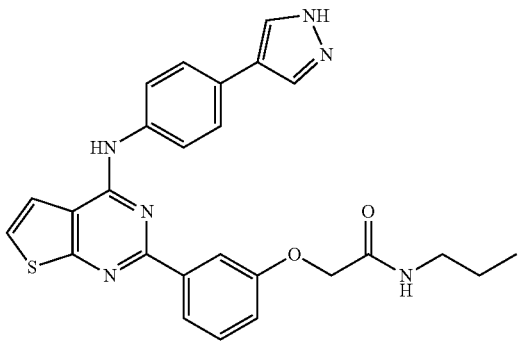 [SMILES: CCCNC(=O)COc1cccc(-c2nc(Nc3ccc(-c4cn[nH]c4)cc3)c3ccsc3n2)c1]

A mixture of N-(4-(1H-pyrazol-4-yl)phenyl)-2-chlorothieno[2,3-d]pyrimidin-4-amine (20 mg, 0.06 mmol), N-propyl-2-(3-(4,4,5,5-tetramethyl-1,3,2-dioxaborolan-2-yl)phenoxy)acetamide (19 mg, 0.06 mmol), tetrakis(triphenylphosphine)palladium(0) (7 mg, 0.01 mmol), dioxane (0.64 mL), water (0.06 mL), and saturated Na$_2$CO$_3$ (0.06 mL) was heated in microwave at 180° C. for 2 h. The mixture was concentrated in vacuo to remove the volatiles. The residue was dissolved in DMSO and purified by reverse-phase HPLC to provide the title compound (10 mg, 34%). $^1$H NMR (400 MHz, DMSO-d$_6$) δ 10.11 (s, 1H), 8.33 (dd, J=10.7, 5.5 Hz, 1H), 8.14 (d, J=21.2 Hz, 3H), 8.07-7.98 (m, 2H), 7.88 (d, J=8.3 Hz, 2H), 7.71 (d, J=8.3 Hz, 2H), 7.56 (d, J=5.3 Hz, 1H), 7.48 (t, J=8.0 Hz, 1H), 7.19-7.07 (m, 1H), 4.59 (s, 2H), 2.69 (d, J=4.7 Hz, 3H). MS (ES+) m/e 485 (M+H)$^+$.

Example 47

N-(3-(4-((4-(1H-pyrazol-4-yl)phenyl)amino)-5,7-dihydrofuro[3,4-d]pyrimidin-2-yl)phenyl)nicotinamide

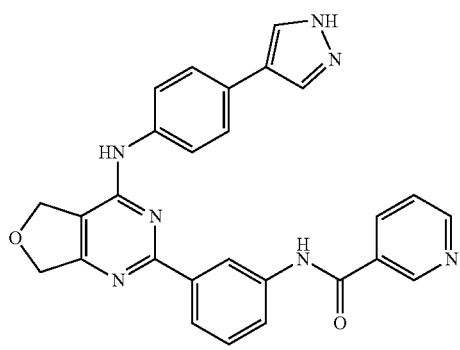 [SMILES: O=C(Nc1cccc(-c2nc3c(c(Nc4ccc(-c5cn[nH]c5)cc4)n2)COC3)c1)c1cccnc1]

A mixture of N-(4-(1H-pyrazol-4-yl)phenyl)-2-chloro-5,7-dihydrofuro[3,4-d]pyrimidin-4-amine (20 mg, 0.06 mmol), N-(3-(4,4,5,5-tetramethyl-1,3,2-dioxaborolan-2-yl)phenyl)nicotinamide (21 mg, 0.06 mmol), tetrakis(triphenylphosphine)palladium(0) (7 mg, 0.01 mmol), dioxane (0.64 mL), water (0.06 mL), and saturated Na$_2$CO$_3$ (0.06 mL) was heated in microwave at 180° C. for 2 h. The mixture was concentrated in vacuo to remove the volatiles. The residue was dissolved in DMSO and purified by reverse-phase HPLC to provide the title compound (15 mg, 49%). MS (ES+) m/e 476 (M+H)$^+$.

Example 48

2-(3-(4-((4-(1H-pyrazol-4-yl)phenyl)amino)pyrido[3,2-d]pyrimidin-2-yl)phenoxy)-N-isopropylacetamide

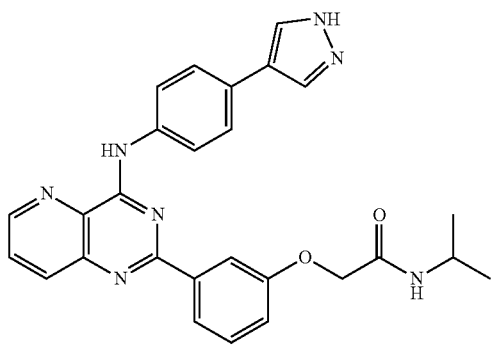 [SMILES: CC(C)NC(=O)COc1cccc(-c2nc(Nc3ccc(-c4cn[nH]c4)cc3)c3ncccc3n2)c1]

Example 48A

N-(4-(1H-pyrazol-4-yl)phenyl)-2-chloropyrido[3,2-d]pyrimidin-4-amine

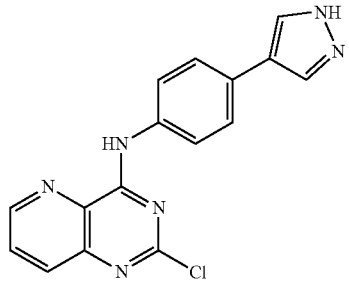 [SMILES: Clc1nc(Nc2ccc(-c3cn[nH]c3)cc2)c2ncccc2n1]

A mixture of 2,4-dichloropyrido[3,2-d]pyrimidine (300 mg, 1.50 mmol), 4-(1H-pyrazol-4-yl)aniline (239, 1.50 mmol), and iPr2NEt (0.52 mL, 0.74 mmol) in DMF (3.0 mL) was heated at 100 C for 5 h, cooled to rt, and diluted with water. The precipitate formed was collected by filtration and washed with water and dried in vacuo to provide the title compound (480 mg, 99%). MS (ES+) m/e 323 (M+H)$^+$.

Example 48B 2-(3-(4-((4-(1H-pyrazol-4-yl)phenyl)amino)pyrido[3,2-d]pyrimidin-2-yl)phenoxy)-N-isopropylacetamide

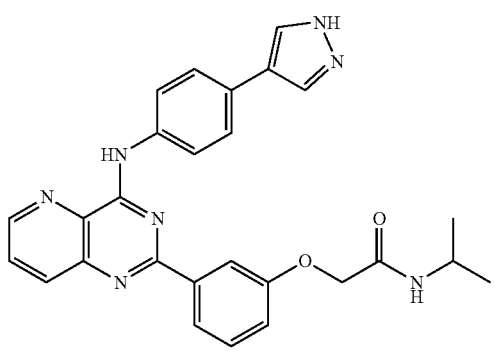 [SMILES: CC(C)NC(=O)COc1cccc(-c2nc(Nc3ccc(-c4cn[nH]c4)cc3)c3ncccc3n2)c1]

A mixture of N-(4-(1H-pyrazol-4-yl)phenyl)-2-chloropyrido[3,2-d]pyrimidin-4-amine (25 mg, 0.08 mmol), N-isopropyl-2-(3-(4,4,5,5-tetramethyl-1,3,2-dioxaborolan-2-yl)phenoxy)acetamide (25 mg, 0.08 mmol), tetrakis(triphenylphosphine)palladium(0) (9 mg, 0.01 mmol), dioxane (0.77 mL), water (0.08 mL), and saturated $Na_2CO_3$ (0.08 mL) was heated in microwave at 180° C. for 2 h. The mixture was concentrated in vacuo to remove the volatiles. The residue was dissolved in DMSO and purified by reverse-phase HPLC to provide the title compound (20 mg, 54%). $^1$H NMR (400 MHz, DMSO-$d_6$) δ 10.53 (s, 1H), 8.94 (dd, J=4.2, 1.5 Hz, 1H), 8.30 (dd, J=8.5, 1.6 Hz, 1H), 8.14 (ddd, J=28.1, 5.4, 1.9 Hz, 7H), 8.07-7.93 (m, 2H), 7.80-7.69 (m, 2H), 7.51 (t, J=8.0 Hz, 1H), 7.21-7.13 (m, 1H), 4.58 (s, 3H), 4.01 (dt, J=8.1, 6.5 Hz, 4H), 1.12 (d, J=6.6 Hz, 6H). MS (ES+) m/e 480 (M+H)$^+$.

Example 49

2-(3-(4-((4-(1H-pyrazol-4-yl)phenyl)amino)pyrido[3,2-d]pyrimidin-2-yl)phenoxy)-N-cyclobutylacetamide

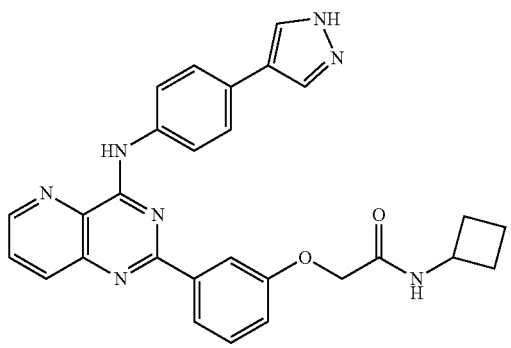 [SMILES: O=C(COc1cccc(-c2nc(Nc3ccc(-c4cn[nH]c4)cc3)c3ncccc3n2)c1)NC1CCC1]

A mixture of N-(4-(1H-pyrazol-4-yl)phenyl)-2-chloropyrido[3,2-d]pyrimidin-4-amine (25 mg, 0.08 mmol), N-cyclobutyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated $Na_2CO_3$ (0.08 mL) was heated in microwave at 180° C. for 2 h. The mixture was concentrated in vacuo to remove the volatiles. The residue was dissolved in DMSO and purified by reverse-phase HPLC to provide the title compound (22 mg, 62%). $^1$H NMR (400 MHz, DMSO-$d_6$) δ 10.52 (s, 1H), 8.94 (dd, J=4.2, 1.5 Hz, 1H), 8.44 (d, J=8.0 Hz, 1H), 8.30 (dd, J=8.4, 1.6 Hz, 1H), 8.21-8.08 (m, 8H), 7.97 (dd, J=8.5, 4.2 Hz, 1H), 7.74 (d, J=8.6 Hz, 3H), 7.51 (t, J=8.2 Hz, 1H), 7.17 (dd, J=8.2, 2.6 Hz, 1H), 4.58 (s, 3H), 4.37-4.29 (m, 3H), 218-2.12 (m, 2H), 2.10-1.98 (m, 2H), 1.67-1.58 (m, 3H). MS (ES+) m/e 492 (M+H)$^+$.

Example 50

N-(3-(4-((4-(1H-pyrazol-4-yl)phenyl)amino)pyrido[3,2-d]pyrimidin-2-yl)phenyl)-2-morpholinopropanamide

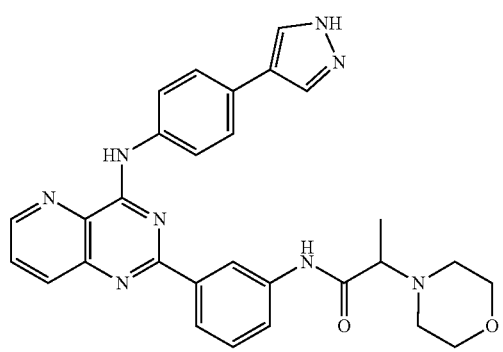 [SMILES: CC(C(=O)Nc1cccc(-c2nc(Nc3ccc(-c4cn[nH]c4)cc3)c3ncccc3n2)c1)N1CCOCC1]

Example 50A

N-(3-bromophenyl)-2-morpholinopropanamide

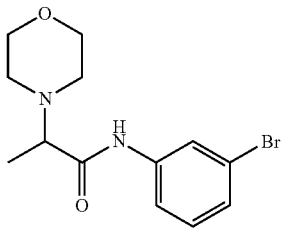 [SMILES: CC(C(=O)Nc1cccc(Br)c1)N1CCOCC1]

To a solution of 2-morpholinopropanoic acid hydrochloride (97 mg, 0.50 mmol) in dry DMF (2.5 mL) was added 3-bromoaniline (86 mg, 0.50 mmol, 0.054 mL) followed by TEA (201 mg, 1.99 mmol, 0.277 mL) and HATU (189 mg, 0.50 mmol). The reaction mixture was stirred overnight at r.t. after which point LC-MS shows one major peak corresponding to the desired product mass. The reaction mixture was diluted with water and extracted with EtOAc twice. The combined organic layers were washed twice with water, dried over sodium sulfate, decanted from the drying agent, and concentrated in vacuo to give 1.33 g of brown oil. The oil was dissolved in a minimum amount of DCM and subjected to column chromatography (Hexanes to EtOAc gradient) to give the title compound (1.00 g, 79%) as a viscous light brown oil.

MS (ES+) m/e 312/314 (M+H)$^+$.

Example 50B 2-morpholino-N-(3-(4,4,5,5-tetramethyl-1,3,2-dioxaborolan-2-yl)phenyl)propanamide

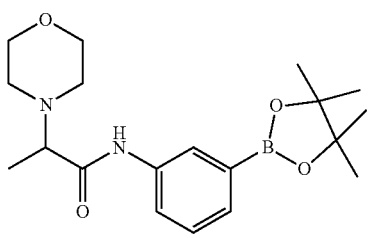 [SMILES: CC(C(=O)Nc1cccc(B2OC(C)(C)C(C)(C)O2)c1)N1CCOCC1]

To a solution of N-(3-bromophenyl)-2-morpholinopropanamide (470 mg, 1.50 mmol) in 1,4-dioxane (7.5 mL) in a 20 mL vial was added bis(pinacolato)diboron (457 mg, 1.80 mmol), KOAc (622 mg, 4.50 mmol) and PdCl$_2$(dppf) (55 mg, 0.075 mmol). The reaction was heated at 90° C. for 18 h after which LC-MS showed all of the starting bromide was consumed and one major peak corresponding to the desired product mass was present. The mixture was cooled and diluted with water. The aqueous mixture was extracted twice with EtOAc and the combined organic layers were dried over sodium sulfate, decanted from the drying agent, and concentrated in vacuo to give 740 mg of brown oil. The oil was dissolved in DCM and column chromatography (Hexanes to EtOAc gradient) afforded the title compound (400 mg, 74%) as a beige solid. $^1$H NMR (400 MHz, DMSO-d$_6$) δ 9.82 (s, 1H), 7.96 (d, J=2.2 Hz, 1H), 7.78 (dt, J=8.0, 1.8 Hz, 1H), 7.40-7.29 (m, 2H), 3.61 (t, J=4.6 Hz, 4H), 3.20 (q, J=6.8 Hz, 1H), 2.60-2.41 (m, 4H), 1.30 (s, 12H), 1.19 (d, J=6.9 Hz, 3H). MS (ES+) m/e 361 (M+H)$^+$.

Example 50C

N-(3-(4-((4-(1H-pyrazol-4-yl)phenyl)amino)pyrido[3,2-d]pyrimidin-2-yl)phenyl)-2-morpholinopropanamide

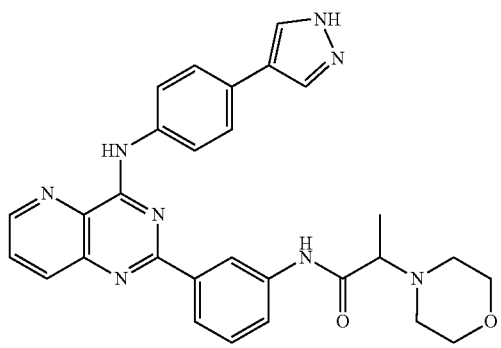 [SMILES: CC(C(=O)Nc1cccc(-c2nc(Nc3ccc(-c4cn[nH]c4)cc3)c3ncccc3n2)c1)N1CCOCC1]

A mixture of N-(4-(1H-pyrazol-4-yl)phenyl)-2-chloropyrido[3,2-d]pyrimidin-4-amine (25 mg, 0.08 mmol), 2-morpholino-N-(3-(4,4,5,5-tetramethyl-1,3,2-dioxaborolan-2-yl)phenyl)propanamide (28 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (17 mg, 48%). $^1$H NMR (400 MHz, DMSO-d$_6$) δ 10.96 (s, 1H), 10.48 (s, 1H), 8.95 (dd, J=4.2, 1.5 Hz, 1H), 8.86 (t, J=1.9 Hz, 1H), 8.28 (dt, J=8.5, 2.1 Hz, 2H), 8.25-8.19 (m, 2H), 8.10 (s, 2H), 7.97 (dd, J=8.5, 4.2 Hz, 1H), 7.82 (dd, J=8.0, 2.2 Hz, 1H), 7.76-7.70 (m, 2H), 7.59 (t, J=7.9 Hz, 1H), 4.15 (q, J=6.9 Hz, 1H), 4.08-3.64 (m, 4H), 3.61-3.11 (m, 4H), 1.64 (d, J=6.9 Hz, 3H). MS (ES+) m/e 521 (M+H)$^+$.

Example 51

2-(3-(4-((4-(1H-pyrazol-4-yl)phenyl)amino)pyrido[3,2-d]pyrimidin-2-yl)phenoxy)-N-cyclopentylacetamide

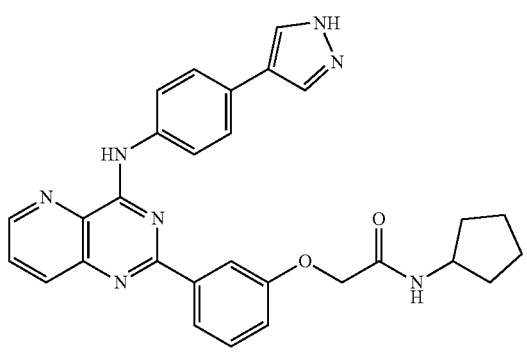 [SMILES: O=C(COc1cccc(-c2nc(Nc3ccc(-c4cn[nH]c4)cc3)c3ncccc3n2)c1)NC1CCCC1]

A mixture of A mixture of N-(4-(1H-pyrazol-4-yl)phenyl)-2-chloropyrido[3,2-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (27 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (19 mg, 49%). $^1$H NMR (400 MHz, DMSO-d$_6$) δ 10.65 (s, 1H), 8.96 (dd, J=4.3, 1.5 Hz, 1H), 8.31 (dd, J=8.5, 1.6 Hz, 1H), 8.23-8.05 (m, 7H), 7.98 (dd, J=8.5, 4.2 Hz, 1H), 7.80-7.69 (m, 2H), 7.52 (t, J=7.9 Hz, 1H), 7.18 (dd, J=8.1, 2.6 Hz, 1H), 6.36 (ddd, J=15.9, 6.0, 2.3 Hz, 1H), 4.60 (s, 2H), 4.20-4.00 (m, 1H), 1.89-1.73 (m, 2H), 1.67-1.61 (m, 2H), 1.55-1.35 (m, 4H). MS (ES+) m/e 506 (M+H)$^+$.

Example 52

2-(3-(4-((4-(1H-pyrazol-4-yl)phenyl)amino)pyrido[2,3-d]pyrimidin-2-yl)phenoxy)-N-isopropylacetamide

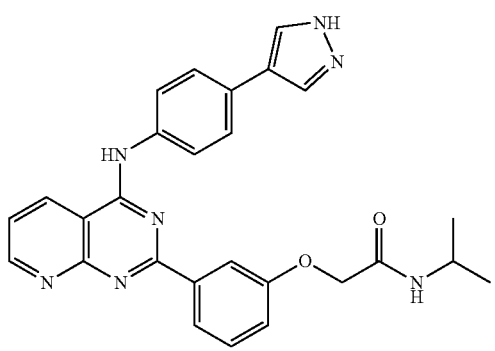 [SMILES: CC(C)NC(=O)COc1cccc(-c2nc(Nc3ccc(-c4cn[nH]c4)cc3)c3cccnc3n2)c1]

Example 52A

N-(4-(1H-pyrazol-4-yl)phenyl)-2-chloropyrido[2,3-d]pyrimidin-4-amine

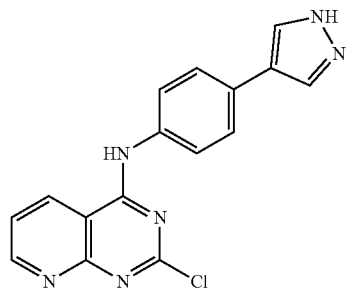 [SMILES: Clc1nc(Nc2ccc(-c3cn[nH]c3)cc2)c2cccnc2n1]

A mixture of N-(4-(1H-pyrazol-4-yl)phenyl)-2-chloropyrido[2,3-d]pyrimidin-4-amine (300 mg, 1.50 mmol), 4 4-(1H-pyrazol-4-yl)aniline (239, 1.50 mmol), and iPr$_2$NEt (0.52 mL, 0.74 mmol) in DMF (3.0 mL) was heated at 100 C for 5 h, cooled to rt, and diluted with water. The precipitate formed was collected by filtration and washed with water and dried in vacuo to provide the title compound (405 mg, 99%). MS (ES+) m/e 323 (M+H)$^+$.

Example 52B 2-(3-(4-((4-(1H-pyrazol-4-yl)phenyl)amino)pyrido[2,3-d]pyrimidin-2-yl)phenoxy)-N-isopropylacetamide

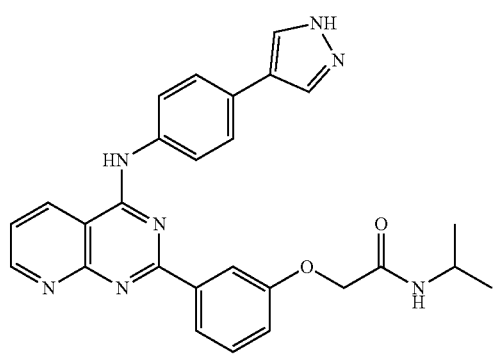 [SMILES: CC(C)NC(=O)COc1cccc(-c2nc(Nc3ccc(-c4cn[nH]c4)cc3)c3cccnc3n2)c1]

A mixture of N-(4-(1H-pyrazol-4-yl)phenyl)-2-chloropyrido[2,3-d]pyrimidin-4-amine (25 mg, 0.08 mmol), N-isopropyl-2-(3-(4,4,5,5-tetramethyl-1,3,2-dioxaborolan-2-yl)phenoxy)acetamide (25 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (21 mg, 59%). MS (ES+) m/e 480 (M+H)$^+$.

Example 53

2-(3-(4-((4-(1H-pyrazol-4-yl)phenyl)amino)pyrido[3,2-d]pyrimidin-2-yl)phenoxy)-N-isobutylacetamide

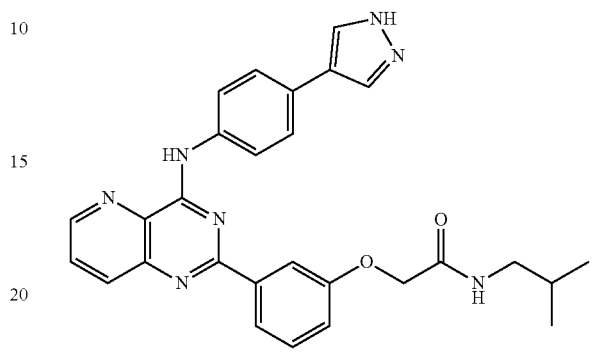

A mixture of N-(4-(1H-pyrazol-4-yl)phenyl)-2-chloropyrido[3,2-d]pyrimidin-4-amine (25 mg, 0.08 mmol), N-isobutyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (25 mg, 65%). $^1$H NMR (400 MHz, DMSO-d$_6$) δ 10.62 (s, 1H), 8.95 (dd, J=4.2, 1.5 Hz, 1H), 8.31 (dd, J=8.4, 1.5 Hz, 1H), 8.22-8.06 (m, 8H), 7.98 (dd, J=8.5, 4.2 Hz, 1H), 7.76-7.70 (m, 2H), 7.52 (t, J=7.9 Hz, 1H), 7.25-7.13 (m, 1H), 4.64 (s, 2H), 2.98 (t, J=6.5 Hz, 2H), 1.75 (dt, J=13.6, 6.8 Hz, 1H), 0.82 (d, J=6.7 Hz, 6H). MS (ES+) m/e 494 (M+H)$^+$.

Example 54

2-(3-(4-((4-(1H-pyrazol-4-yl)phenyl)amino)-1-methyl-1H-pyrazolo[3,4-d]pyrimidin-6-yl)phenoxy)-N-cyclobutylacetamide

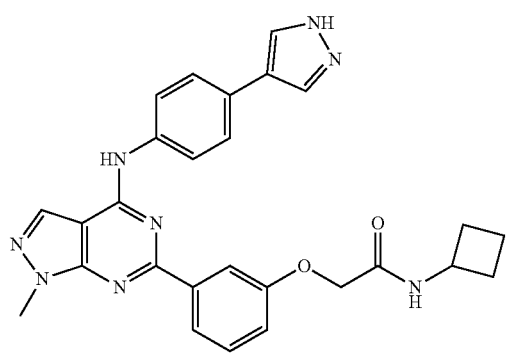 [SMILES: Cn1ncc2c(Nc3ccc(-c4cn[nH]c4)cc3)nc(-c3cccc(OCC(=O)NC4CCC4)c3)nc21]

Example 54A

N-(4-(1H-pyrazol-4-yl)phenyl)-6-chloro-1-methyl-1H-pyrazolo[3,4-d]pyrimidin-4-amine

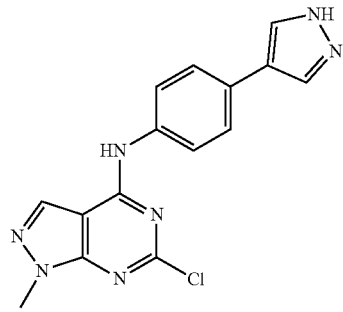 [SMILES: Cn1ncc2c(Nc3ccc(-c4cn[nH]c4)cc3)nc(Cl)nc21]

A mixture of 4,6-dichloro-1-methyl-1H-pyrazolo[3,4-d]pyrimidine (300 mg, 1.50 mmol), 4-(1H-pyrazol-4-yl)aniline (235, 1.50 mmol), and iPr2NEt (0.52 mL, 0.74 mmol) in DMF (3.0 mL) was heated at 100 C for 5 h, cooled to rt, and diluted with water. The precipitate formed was collected by filtration and washed with water and dried in vacuo to provide the title compound (470 mg, 98%). $^1$H NMR (400 MHz, DMSO-$d_6$) δ 12.95 (s, 1H), 10.48 (s, 1H), 8.26 (d, J=61.6 Hz, 2H), 7.95 (s, 1H), 7.84-7.51 (m, 4H), 3.91 (s, 3H). MS (ES+) m/e 326 (M+H)$^+$.

Example 54B 2-(3-(4-((4-(1H-pyrazol-4-yl)phenyl)amino)-1-methyl-1H-pyrazolo[3,4-d]pyrimidin-6-yl)phenoxy)-N-cyclobutylacetamide

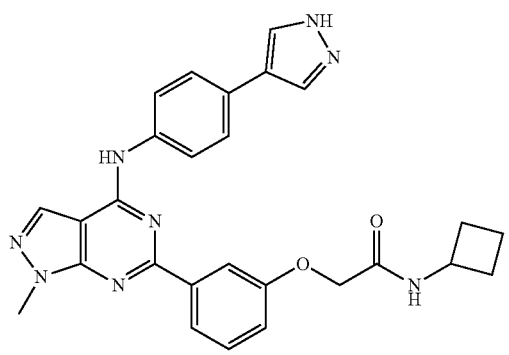 [SMILES: Cn1ncc2c(Nc3ccc(-c4cn[nH]c4)cc3)nc(-c3cccc(OCC(=O)NC4CCC4)c3)nc21]

A mixture of N-(4-(1H-pyrazol-4-yl)phenyl)-6-chloro-1-methyl-1H-pyrazolo[3,4-d]pyrimidin-4-amine (25 mg, 0.08 mmol), N-cyclobutyl-2-(3-(4,4,5,5-tetramethyl-1,3,2-dioxaborolan-2-yl)phenoxy)acetamide (24 mg, 0.08 mmol), tetrakis(triphenylphosphine)palladium(0) (9 mg, 0.01 mmol), dioxane (0.77 mL), water (0.08 mL), and saturated Na2CO3 (0.08 mL) was heated in microwave at 180° C. for 2 h. The mixture was concentrated in vacuo to remove the volatiles. The residue was dissolved in DMSO and purified by reverse-phase HPLC to provide the title compound (26 mg, 69%). $^1$H NMR (400 MHz, DMSO-$d_6$) δ 10.18 (s, 1H), 8.41 (d, J=8.0 Hz, 1H), 8.12-8.09 (m, 2H), 7.95 (d, J=7.9 Hz, 2H), 7.76-7.69 (m, 2H), 7.68-7.53 (m, 4H), 7.49-7.44 (m, 1H), 7.13 (ddd, J=8.1, 2.6, 1.1 Hz, 1H), 4.57 (s, 2H), 4.33 (q, J=8.2 Hz, 1H), 4.04 (s, 3H), 2.19-2.10 (m, 2H), 2.08-1.96 (m, 2H), 1.70-1.55 (m, 2H). MS (ES+) m/e 495 (M+H)$^+$.

Example 55

2-(3-(4-((4-(1H-pyrazol-4-yl)phenyl)amino)-1-methyl-1H-pyrazolo[3,4-d]pyrimidin-6-yl)phenoxy)-N-isopropylacetamide

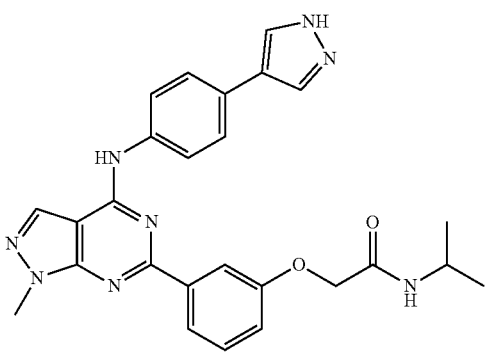 [SMILES: CC(C)NC(=O)COc1cccc(-c2nc(Nc3ccc(-c4cn[nH]c4)cc3)c3cnn(C)c3n2)c1]

A mixture of N-(4-(1H-pyrazol-4-yl)phenyl)-6-chloro-1-methyl-1H-pyrazolo[3,4-d]pyrimidin-4-amine (25 mg, 0.08 mmol), N-isopropyl-2-(3-(4,4,5,5-tetramethyl-1,3,2-dioxaborolan-2-yl)phenoxy)acetamide (24 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (16 mg, 74%). $^1$H NMR (400 MHz, DMSO-$d_6$) δ 10.17 (s, 1H), 8.30 (s, 1H), 8.14-8.06 (m, 4H), 8.02-7.94 (m, 3H), 7.76-7.66 (m, 2H), 7.47 (t, J=8.0 Hz, 1H), 7.20-7.08 (m, 1H), 4.57 (s, 2H), 4.10-3.95 (m, 4H), 1.11 (d, J=6.6 Hz, 6H). MS(ES+) m/e 483 (M+H)$^+$.

Example 56

2-(3-(4-((4-(1H-pyrazol-4-yl)phenyl)amino)-1-methyl-1H-pyrazolo[3,4-d]pyrimidin-6-yl)phenoxy)-N-cyclopentylacetamide

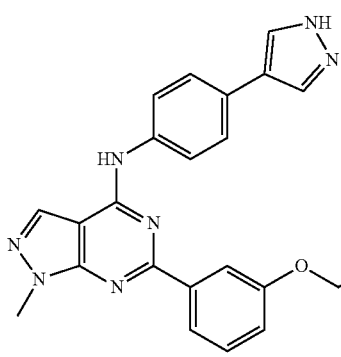

A mixture of N-(4-(1H-pyrazol-4-yl)phenyl)-6-chloro-1-methyl-1H-pyrazolo[3,4-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (21 mg, 54%). $^1$H NMR (500 MHz, DMSO-$d_6$) δ 10.17 (s, 1H), 8.31 (b, 1H), 8.10 (d, J=9.2 Hz, 4H), 7.95 (d, J=8.0 Hz, 2H), 7.72 (d, J=8.3 Hz, 2H), 7.46 (t, J=7.6 Hz, 1H), 7.30 (t, J=7.8 Hz, 1H), 7.17-7.07 (m, 1H), 7.01-6.90 (m, 1H), 4.58 (s, 2H), 4.44 (s, 1H), 4.19-3.96 (m, 4H), 1.89-1.33 (m, 8H). MS(ES+) m/e 509 (M+H)$^+$.

Example 57

2-(3-(4-((4-(1H-pyrazol-4-yl)phenyl)amino)-1-methyl-1H-pyrazolo[3,4-d]pyrimidin-6-yl)phenoxy)-N-isobutylacetamide

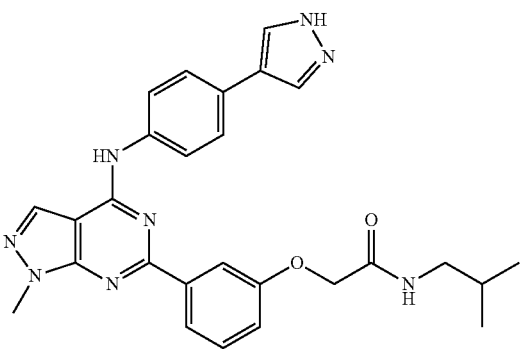 [SMILES: CC(C)CNC(=O)COc1cccc(-c2nc(Nc3ccc(-c4cn[nH]c4)cc3)c3cnn(C)c3n2)c1]

A mixture of N-(4-(1H-pyrazol-4-yl)phenyl)-6-chloro-1-methyl-1H-pyrazolo[3,4-d]pyrimidin-4-amine (25 mg, 0.08 mmol), N-isobutyl-2-(3-(4,4,5,5-tetramethyl-1,3,2-dioxaborolan-2-yl)phenoxy)acetamide (25 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (19 mg, 50%). $^1$H NMR (500 MHz, DMSO-$d_6$) δ 10.18 (s, 1H), 8.31 (s, 1H), 8.17 (t, J=6.0 Hz, 1H), 8.10 (dd, J=7.7, 5.8 Hz, 4H), 7.95 (d, J=8.1 Hz, 2H), 7.76-7.69 (m, 2H), 7.47 (t, J=8.0 Hz, 1H), 7.16-7.10 (m, 1H), 4.62 (s, 2H), 3.00-2.94 (m, 3H), 1.75 (dh, J=13.3, 6.7 Hz, 1H), 0.81 (d, J=6.6 Hz, 6H). MS(ES+) m/e 497 (M+H)$^+$.

Example 58

2-(3-(7-((4-(1H-pyrazol-4-yl)phenyl)amino)-1-methyl-1H-pyrazolo[4,3-d]pyrimidin-5-yl)phenoxy)-N-isopropylacetamide

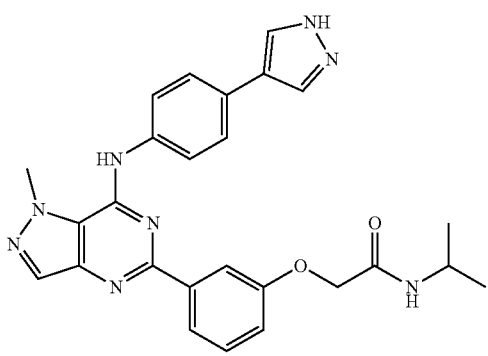 [SMILES: CC(C)NC(=O)COc1cccc(-c2nc(Nc3ccc(-c4cn[nH]c4)cc3)c3c(cnn3C)n2)c1]

Example 58A

N-(4-(1H-pyrazol-4-yl)phenyl)-5-chloro-1-methyl-1H-pyrazolo[4,3-d]pyrimidin-7-amine

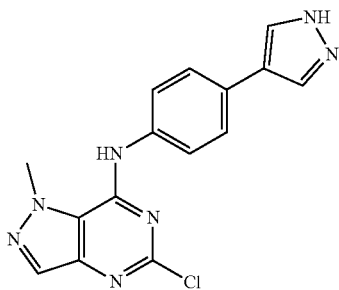 [SMILES: Cn1ncc2nc(Cl)nc(Nc3ccc(-c4cn[nH]c4)cc3)c21]

A mixture of 5,7-dichloro-1-methyl-1H-pyrazolo[4,3-d]pyrimidine (300 mg, 1.50 mmol), 4-(1H-pyrazol-4-yl)aniline (235, 1.50 mmol), and iPr$_2$NEt (0.52 mL, 0.74 mmol) in DMF (3.0 mL) was heated at 100 C for 5 h, cooled to rt, and diluted with water. The precipitate formed was collected by filtration and washed with water and dried in vacuo to provide the title compound (465 mg, 97%). MS(ES+) m/e 326 (M+H)$^+$.

Example 58B 2-(3-(7-((4-(1H-pyrazol-4-yl)phenyl)amino)-1-methyl-1H-pyrazolo[4,3-d]pyrimidin-5-yl)phenoxy)-N-isopropylacetamide

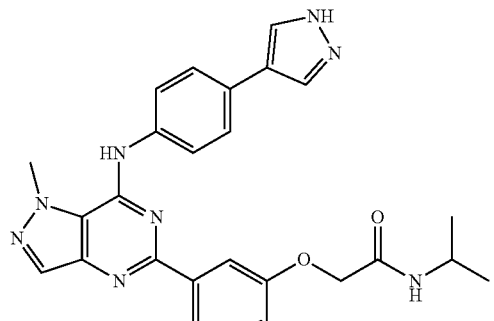

A mixture of N-(4-(1H-pyrazol-4-yl)phenyl)-5-chloro-1-methyl-1H-pyrazolo[4,3-d]pyrimidin-7-amine (25 mg, 0.08 mmol), N-isopropyl-2-(3-(4,4,5,5-tetramethyl-1,3,2-dioxaborolan-2-yl)phenoxy)acetamide (25 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (13 mg, 35%). $^1$H NMR (400 MHz, DMSO-$d_6$) δ 8.89 (s, 1H), 8.60 (s, 1H), 8.21 (s, 2H), 8.12-8.02 (m, 3H), 7.89 (d, J=8.5 Hz, 2H), 7.80 (d, J=8.2 Hz, 2H), 7.55-7.47 (m, 1H), 7.17 (dd, J=8.2, 2.5 Hz, 1H), 4.63 (s, 2H), 4.33 (s, 3H), 4.09 (dp, J=15.7, 8.7, 7.7 Hz, 2H), 1.21 (d, J=6.6 Hz, 6H). MS (ES+) m/e 483 (M+H)$^+$.

Example 59

2-(3-(7-((4-(1H-pyrazol-4-yl)phenyl)amino)-1-methyl-1H-pyrazolo[4,3-d]pyrimidin-5-yl)phenoxy)-N-cyclobutylacetamide

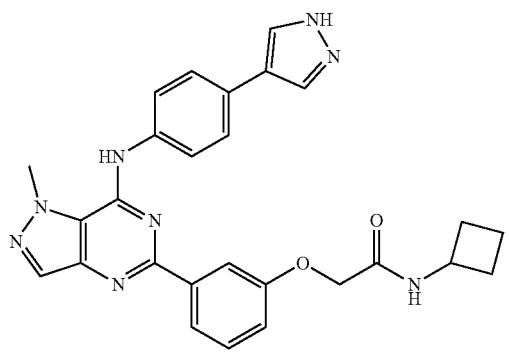 [SMILES: Cn1ncc2nc(-c3cccc(OCC(=O)NC4CCC4)c3)nc(Nc3ccc(-c4cn[nH]c4)cc3)c21]

A mixture of N-(4-(1H-pyrazol-4-yl)phenyl)-5-chloro-1-methyl-1H-pyrazolo[4,3-d]pyrimidin-7-amine (25 mg, 0.08 mmol), N-cyclobutyl-2-(3-(4,4,5,5-tetramethyl-1,3,2-dioxaborolan-2-yl)phenoxy)acetamide (25 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (12 mg, 32%). $^1$H NMR (400 MHz, DMSO-d$_6$) δ 8.86 (s, 1H), 8.57 (s, 1H), 8.37 (d, J=8.0 Hz, 1H), 8.10 (s, 2H), 8.00-7.91 (m, 2H), 7.78 (d, J=8.3 Hz, 2H), 7.70 (d, J=8.4 Hz, 2H), 7.42 (t, J=7.9 Hz, 1H), 7.07 (dd, J=8.1, 2.5 Hz, 1H), 4.52 (s, 2H), 4.32 (h, J=8.2 Hz, 1H), 4.23 (s, 3H), 2.14 (qt, J=5.9, 3.6 Hz, 2H), 2.02 (pd, J=9.3, 2.4 Hz, 2H), 1.61 (qd, J=10.8, 10.3, 7.1 Hz, 2H). MS (ES+) m/e 495 (M+H)$^+$.

Example 60

2-(3-(7-((4-(1H-pyrazol-4-yl)phenyl)amino)-1-methyl-1H-pyrazolo[4,3-d]pyrimidin-5-yl)phenoxy)-N-cyclopentylacetamide

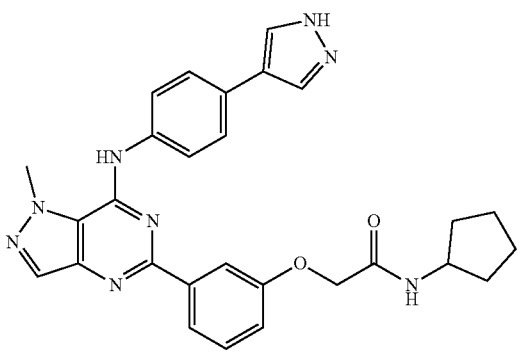 [SMILES: Cn1ncc2nc(-c3cccc(OCC(=O)NC4CCCC4)c3)nc(Nc3ccc(-c4cn[nH]c4)cc3)c21]

A mixture of N-(4-(1H-pyrazol-4-yl)phenyl)-5-chloro-1-methyl-1H-pyrazolo[4,3-d]pyrimidin-7-amine (25 mg, 0.08 mmol), N-cyclopentyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na2CO3 (0.08 mL) was heated in microwave at 180° C. for 2 h. The mixture was concentrated in vacuo to remove the volatiles. The residue was dissolved in DMSO and purified by reverse-phase HPLC to provide the title compound (10 mg, 26%). $^1$H NMR (400 MHz, DMSO-d$_6$) δ 8.83 (s, 1H), 8.55 (s, 1H), 8.09 (s, 2H), 8.03 (d, J=7.6 Hz, 1H), 7.98-7.92 (m, 2H), 7.78 (d, J=8.5 Hz, 2H), 7.70 (d, J=8.3 Hz, 2H), 7.40 (t, J=7.9 Hz, 1H), 7.05 (dd, J=8.2, 2.6 Hz, 1H), 4.53 (s, 2H), 4.22 (s, 3H), 4.11 (p, J=7.2 Hz, 1H), 1.88-1.74 (m, 2H), 1.65-1.61 (m, 2H), 1.51-1.43 (m, 4H). MS (ES+) m/e 509 (M+H)$^+$.

Example 61

2-(3-(7-((4-(1H-pyrazol-4-yl)phenyl)amino)-1-methyl-1H-pyrazolo[4,3-d]pyrimidin-5-yl)phenoxy)-N-isobutylacetamide

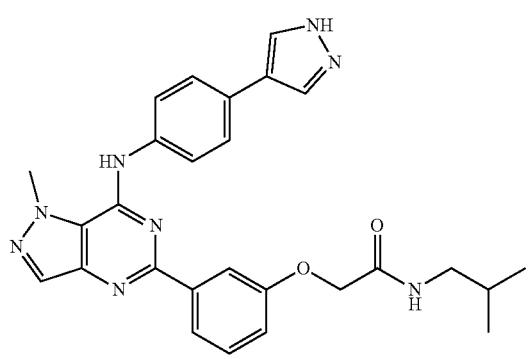 [SMILES: CC(C)CNC(=O)COc1cccc(-c2nc(Nc3ccc(-c4cn[nH]c4)cc3)c3c(cnn3C)n2)c1]

A mixture of N-(4-(1H-pyrazol-4-yl)phenyl)-5-chloro-1-methyl-1H-pyrazolo[4,3-d]pyrimidin-7-amine (25 mg, 0.08 mmol), N-isobutyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na$_2$CO$_3$ (0.08 mL) was heated in microwave at 180° C. for 2 h. The mixture was concentrated in vacuo to remove the volatiles. The residue was dissolved in DMSO and purified by reverse-phase HPLC to provide the title compound (12 mg, 31%). $^1$H NMR (500 MHz, DMSO-d$_6$) δ 8.85 (s, 1H), 8.57 (s, 1H), 8.11 (d, J=13.4 Hz, 3H), 7.98-7.91 (m, 2H), 7.77 (d, J=8.6 Hz, 2H), 7.70 (d, J=8.5 Hz, 2H), 7.41 (t, J=7.9 Hz, 1H), 7.07 (dd, J=8.1, 2.6 Hz, 1H), 4.58 (s, 2H), 4.23 (s, 3H), 2.96 (t, J=6.5 Hz, 2H), 1.74 (hept, J=6.7 Hz, 1H), 0.80 (d, J=6.7 Hz, 6H). MS (ES+) m/e 497 (M+H)$^+$.

Example 62

2-(3-(4-((4-(1H-pyrazol-4-yl)phenyl)amino)pyrido[3,4-d]pyrimidin-2-yl)phenoxy)-N-isopropylacetamide

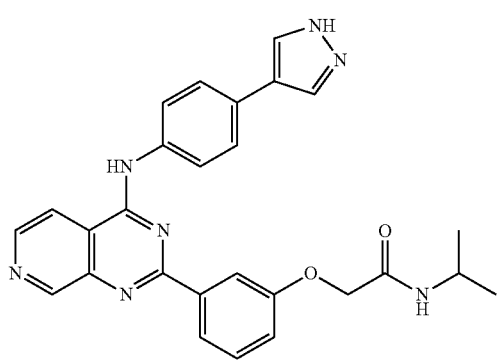 [SMILES: CC(C)NC(=O)COc1cccc(-c2nc(Nc3ccc(-c4cn[nH]c4)cc3)c3ccncc3n2)c1]

Example 62A

N-(4-(1H-pyrazol-4-yl)phenyl)-2-chloropyrido[3,4-d]pyrimidin-4-amine

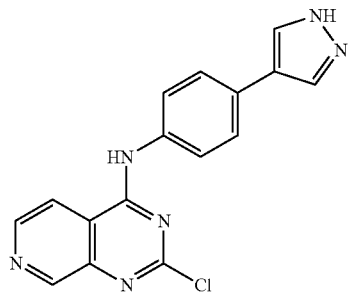 [SMILES: Clc1nc(Nc2ccc(-c3cn[nH]c3)cc2)c2ccncc2n1]

A mixture of 2,4-dichloropyrido[3,4-d]pyrimidine (250 mg, 1.25 mmol), 4-(1H-pyrazol-4-yl)aniline (199, 1.25 mmol), and iPr₂NEt (0.44 mL, 2.50 mmol) in DMF (2.5 mL) was heated at 100 C for 5 h, cooled to rt, and diluted with water. The precipitate formed was collected by filtration and washed with water and dried in vacuo to provide the title compound (400 mg, 99%). MS (ES+) m/e 323 (M+H)$^+$.

Example 62B 2-(3-(4-((4-(1H-pyrazol-4-yl)phenyl)amino)pyrido[3,4-d]pyrimidin-2-yl)phenoxy)-N-isopropylacetamide

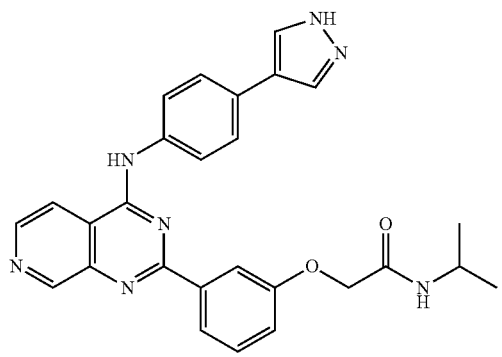 [SMILES: CC(C)NC(=O)COc1cccc(-c2nc(Nc3ccc(-c4cn[nH]c4)cc3)c3ccncc3n2)c1]

A mixture of N-(4-(1H-pyrazol-4-yl)phenyl)-2-chloropyrido[3,4-d]pyrimidin-4-amine (25 mg, 0.08 mmol), N-isopropyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na₂CO₃ (0.08 mL) was heated in microwave at 180° C. for 2 h. The mixture was concentrated in vacuo to remove the volatiles. The residue was dissolved in DMSO and purified by reverse-phase HPLC to provide the title compound (10 mg, 27%). ¹H NMR (400 MHz, DMSO-d₆) δ 10.28 (s, 1H), 9.26 (s, 1H), 8.73 (d, J=5.6 Hz, 1H), 8.51 (d, J=5.7 Hz, 1H), 8.21-8.06 (m, 4H), 8.00 (dd, J=10.9, 8.2 Hz, 3H), 7.82-7.73 (m, 2H), 7.49 (t, J=8.1 Hz, 1H), 7.16 (dd, J=8.2, 2.5 Hz, 1H), 4.57 (s, 2H), 4.09-3.94 (m, 1H), 1.11 (d, J=6.6 Hz, 6H). MS (ES+) m/e 480 (M+H)$^+$.

Example 63

2-(3-(4-((4-(1H-pyrazol-4-yl)phenyl)amino)pyrido[3,4-d]pyrimidin-2-yl)phenoxy)-N-cyclobutylacetamide

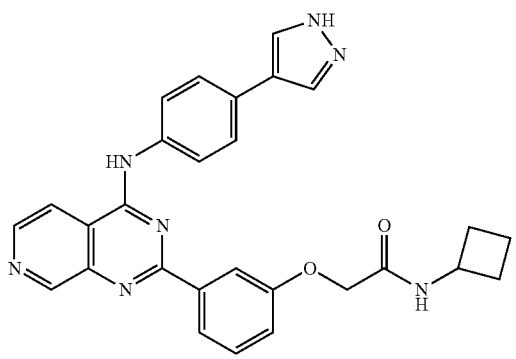 [SMILES: O=C(COc1cccc(-c2nc(Nc3ccc(-c4cn[nH]c4)cc3)c3ccncc3n2)c1)NC1CCC1]

A mixture of N-(4-(1H-pyrazol-4-yl)phenyl)-2-chloropyrido[3,4-d]pyrimidin-4-amine (25 mg, 0.08 mmol), N-cyclobutyl-2-(3-(4,4,5,5-tetramethyl-1,3,2-dioxaborolan-2-yl)phenoxy)acetamide (26 mg, 0.08 mmol), tetrakis(triphenylphosphine)palladium(0) (9 mg, 0.01 mmol), dioxane (0.77 mL), water (0.08 mL), and saturated Na₂CO₃ (0.08 mL) was heated in microwave at 180° C. for 2 h. The mixture was concentrated in vacuo to remove the volatiles. The residue was dissolved in DMSO and purified by reverse-phase HPLC to provide the title compound (11 mg, 29%). ¹H NMR (400 MHz, DMSO-d₆) δ 10.28 (s, 1H), 9.26 (s, 1H), 8.73 (d, J=5.6 Hz, 1H), 8.51 (d, J=5.7 Hz, 1H), 8.43 (d, J=8.0 Hz, 1H), 8.13 (s, 2H), 8.11-8.07 (m, 2H), 7.99 (d, J=8.3 Hz, 2H), 7.77 (d, J=8.3 Hz, 2H), 7.49 (t, J=8.0 Hz, 1H), 7.19-7.13 (m, 1H), 7.06 (t, J=8.1 Hz, 1H), 6.41-6.31 (m, 2H), 4.57 (s, 2H), 4.36-4.22 (m, 2H), 2.18-1.96 (m, 4H), 1.68-1.55 (m, 2H). MS (ES+) m/e 492 (M+H)$^+$.

Example 64

2-(3-(4-((4-(1H-pyrazol-4-yl)phenyl)amino)pyrido[3,4-d]pyrimidin-2-yl)phenoxy)-N-cyclopentylacetamide

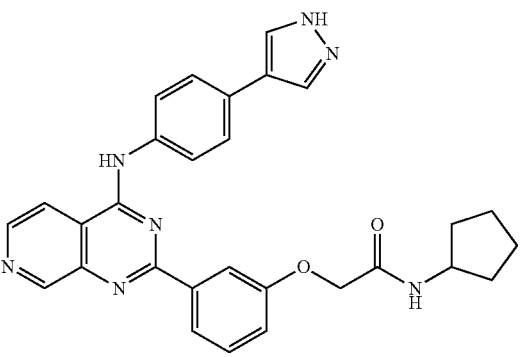 [SMILES: O=C(COc1cccc(-c2nc(Nc3ccc(-c4cn[nH]c4)cc3)c3ccncc3n2)c1)NC1CCCC1]

A mixture of N-(4-(1H-pyrazol-4-yl)phenyl)-2-chloropyrido[3,4-d]pyrimidin-4-amine (25 mg, 0.08 mmol), N-cyclopentyl-2-(3-(4,4,5,5-tetramethyl-1,3,2-dioxaborolan-2-yl)phenoxy)acetamide (26 mg, 0.08 mmol), tetrakis (triphenylphosphine)palladium(0) (9 mg, 0.01 mmol), dioxane (0.77 mL), water (0.08 mL), and saturated Na₂CO₃ (0.08 mL) was heated in microwave at 180° C. for 2 h. The mixture was concentrated in vacuo to remove the volatiles. The residue was dissolved in DMSO and purified by reverse-phase HPLC to provide the title compound (11 mg, 29%). ¹H NMR (400 MHz, DMSO-d₆) δ 10.28 (s, 1H), 9.26 (s, 1H), 8.73 (d, J=5.6 Hz, 1H), 8.51 (d, J=5.7 Hz, 1H), 8.18-8.06 (m, 5H), 8.03-7.96 (m, 2H), 7.81-7.74 (m, 2H), 7.48 (t, J=8.0 Hz, 1H), 7.19-7.10 (m, 1H), 4.58 (s, 2H), 4.13 (h, J=7.2 Hz, 1H), 1.86-1.78 (m, 2H), 1.65 (ddt, J=8.5, 6.2, 2.8 Hz, 2H), 1.55-1.42 (m, 4H). MS (ES+) m/e 506 (M+H)⁺.

Example 65

2-(3-(7-((4-(1H-pyrazol-4-yl)phenyl)amino)thiazolo [5,4-d]pyrimidin-5-yl)phenoxy)-N-isopropylacetamide

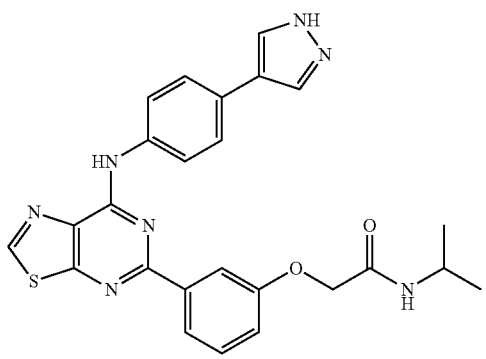 [SMILES: CC(C)NC(=O)COc1cccc(-c2nc(Nc3ccc(-c4cn[nH]c4)cc3)c3ncsc3n2)c1]

Example 65A

N-(4-(1H-pyrazol-4-yl)phenyl)-5-chlorothiazolo[5,4-d]pyrimidin-7-amine

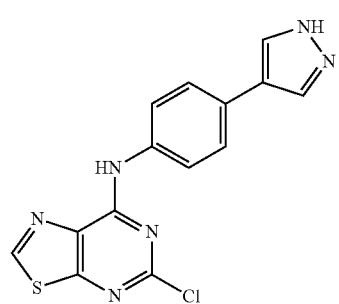 [SMILES: Clc1nc(Nc2ccc(-c3cn[nH]c3)cc2)c2ncsc2n1]

A mixture of 5,7-dichlorothiazolo[5,4-d]pyrimidine (300 mg, 1.46 mmol), 4-(1H-pyrazol-4-yl)aniline (233, 1.46 mmol), and iPr₂NEt (0.51 mL, 2.93 mmol) in DMF (2.9 mL) was heated at 100° C. for 5 h, cooled to rt, and diluted with water. The precipitate formed was collected by filtration and washed with water and dried in vacuo to provide the title compound (470 mg, 98%). MS (ES+) m/e 329 (M+H)⁺.

Example 65B 2-(3-(7-((4-(1H-pyrazol-4-yl)phenyl)amino)thiazolo [5,4-d]pyrimidin-5-yl)phenoxy)-N-isopropylacetamide

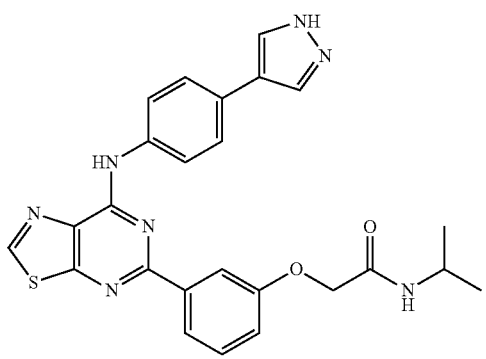 [SMILES: CC(C)NC(=O)COc1cccc(-c2nc(Nc3ccc(-c4cn[nH]c4)cc3)c3ncsc3n2)c1]

A mixture of N-(4-(1H-pyrazol-4-yl)phenyl)-5-chlorothiazolo[5,4-d]pyrimidin-7-amine (25 mg, 0.08 mmol), N-isopropyl-2-(3-(4,4,5,5-tetramethyl-1,3,2-dioxaborolan-2-yl) phenoxy)acetamide (24 mg, 0.08 mmol), tetrakis (triphenylphosphine)palladium(0) (9 mg, 0.01 mmol), dioxane (0.77 mL), water (0.08 mL), and saturated Na₂CO₃ (0.08 mL) was heated in microwave at 180° C. for 2 h. The mixture was concentrated in vacuo to remove the volatiles. The residue was dissolved in DMSO and purified by reverse-phase HPLC to provide the title compound (7 mg, 19%). ¹H NMR (400 MHz, DMSO-d₆) δ 10.31 (s, 1H), 9.40 (s, 1H), 8.16-7.95 (m, 6H), 7.69 (d, J=8.3 Hz, 2H), 7.66-7.51 (m, 2H), 7.46 (t, J=8.0 Hz, 1H), 7.16-7.06 (m, 1H), 4.56 (s, 2H), 4.03-3.97 (m, 2H), 1.11 (d, J=6.6 Hz, 6H). MS (ES+) m/e 486 (M+H)⁺.

Example 66

2-(3-(7-((4-(1H-pyrazol-4-yl)phenyl)amino)thiazolo [5,4-d]pyrimidin-5-yl)phenoxy)-N-cyclobutylacetamide

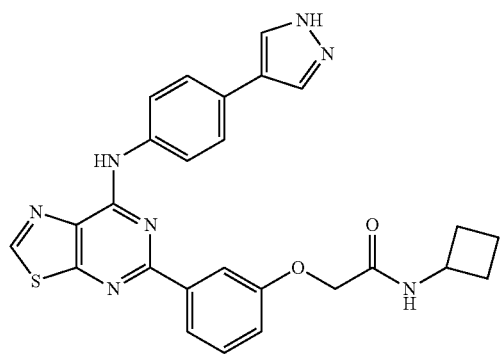 [SMILES: O=C(COc1cccc(-c2nc(Nc3ccc(-c4cn[nH]c4)cc3)c3ncsc3n2)c1)NC1CCC1]

A mixture of N-(4-(1H-pyrazol-4-yl)phenyl)-5-chlorothiazolo[5,4-d]pyrimidin-7-amine (25 mg, 0.08 mmol), N-cyclobutyl-2-(3-(4,4,5,5-tetramethyl-1,3,2-dioxaborolan-2-yl) phenoxy)acetamide (24 mg, 0.08 mmol), tetrakis (triphenylphosphine)palladium(0) (9 mg, 0.01 mmol), dioxane (0.77 mL), water (0.08 mL), and saturated Na₂CO₃ (0.08 mL) was heated in microwave at 180° C. for 2 h. The mixture was concentrated in vacuo to remove the volatiles.

The residue was dissolved in DMSO and purified by reverse-phase HPLC to provide the title compound (8 mg, 21%). ¹H NMR (400 MHz, DMSO-$d_6$) δ 10.31 (s, 1H), 9.40 (s, 1H), 8.41 (d, J=8.0 Hz, 1H), 8.14-7.97 (m, 6H), 7.69 (d, J=8.5 Hz, 2H), 7.47 (t, J=7.9 Hz, 1H), 7.13 (dd, J=8.3, 2.6 Hz, 1H), 4.56 (s, 2H), 4.32 (h, J=8.4 Hz, 1H), 2.17-2.00 (m, 4H), 1.65-1.58 (m, 2H). MS (ES+) m/e 498 (M+H)⁺.

Example 67

2-(3-(7-((4-(1H-pyrazol-4-yl)phenyl)amino)thiazolo[5,4-d]pyrimidin-5-yl)phenoxy)-N-cyclopentylacetamide

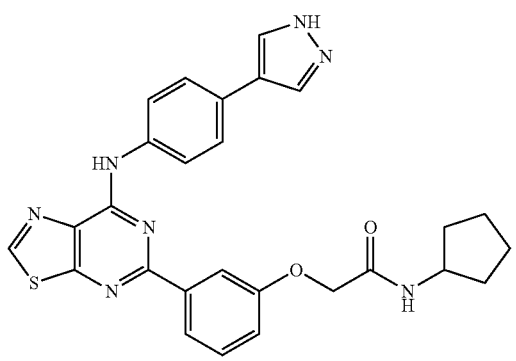 [SMILES: O=C(COc1cccc(-c2nc(Nc3ccc(-c4cn[nH]c4)cc3)c3ncsc3n2)c1)NC1CCCC1]

A mixture of N-(4-(1H-pyrazol-4-yl)phenyl)-5-chlorothiazolo[5,4-d]pyrimidin-7-amine (25 mg, 0.08 mmol), N-cyclopentyl-2-(3-(4,4,5,5-tetramethyl-1,3,2-dioxaborolan-2-yl)phenoxy)acetamide (24 mg, 0.08 mmol), tetrakis(triphenylphosphine)palladium(0) (9 mg, 0.01 mmol), dioxane (0.77 mL), water (0.08 mL), and saturated Na₂CO₃ (0.08 mL) was heated in microwave at 180° C. for 2 h. The mixture was concentrated in vacuo to remove the volatiles. The residue was dissolved in DMSO and purified by reverse-phase HPLC to provide the title compound (6 mg, 16%). ¹H NMR (400 MHz, DMSO-$d_6$) δ 10.31 (s, 1H), 9.40 (s, 1H), 8.20-7.96 (m, 8H), 7.69 (d, J=8.6 Hz, 2H), 7.46 (t, J=8.1 Hz, 1H), 7.12 (dd, J=8.1, 2.6 Hz, 1H), 4.57 (s, 2H), 4.14-4.08 (m, 1H), 1.83-1.63 (m, 4H), 1.51-1.45 (m, 4H). MS (ES+) m/e 512 (M+H)⁺.

Example 68

2-(3-(7-((4-(1H-pyrazol-4-yl)phenyl)amino)thiazolo[5,4-d]pyrimidin-5-yl)phenoxy)-N-isobutylacetamide

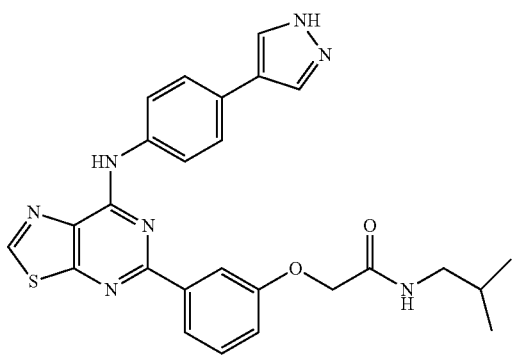 [SMILES: CC(C)CNC(=O)COc1cccc(-c2nc(Nc3ccc(-c4cn[nH]c4)cc3)c3ncsc3n2)c1]

A mixture of N-(4-(1H-pyrazol-4-yl)phenyl)-5-chlorothiazolo[5,4-d]pyrimidin-7-amine (25 mg, 0.08 mmol), N-isobutyl-2-(3-(4,4,5,5-tetramethyl-1,3,2-dioxaborolan-2-yl)phenoxy)acetamide (24 mg, 0.08 mmol), tetrakis(triphenylphosphine)palladium(0) (9 mg, 0.01 mmol), dioxane (0.77 mL), water (0.08 mL), and saturated Na₂CO₃ (0.08 mL) was heated in microwave at 180° C. for 2 h. The mixture was concentrated in vacuo to remove the volatiles. The residue was dissolved in DMSO and purified by reverse-phase HPLC to provide the title compound (10 mg, 26%). ¹H NMR (400 MHz, DMSO-$d_6$) δ 10.31 (s, 1H), 9.40 (s, 1H), 8.17 (t, J=6.0 Hz, 1H), 8.12-7.99 (m, 6H), 7.69 (d, J=8.3 Hz, 2H), 7.46 (t, J=8.1 Hz, 1H), 7.13 (dd, J=8.2, 2.5 Hz, 1H), 4.61 (s, 2H), 2.97 (t, J=6.5 Hz, 2H), 1.75 (hept, J=6.7 Hz, 1H), 0.81 (d, J=6.7 Hz, 6H). MS (ES+) m/e 500 (M+H)⁺.

Example 69

N-(3-(4-((4-(1H-pyrazol-4-yl)phenyl)amino)-5,7-dihydrofuro[3,4-d]pyrimidin-2-yl)phenyl)-5-chloronicotinamide

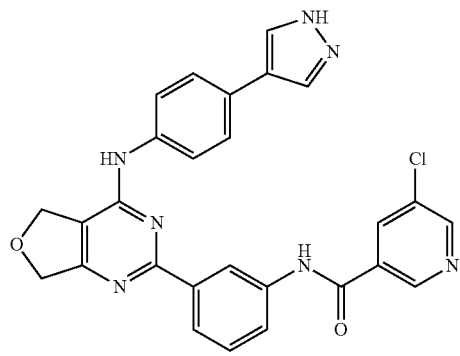 [SMILES: O=C(Nc1cccc(-c2nc3c(c(Nc4ccc(-c5cn[nH]c5)cc4)n2)COC3)c1)c1cncc(Cl)c1]

Example 69A 5-chloro-N-(3-(4,4,5,5-tetramethyl-1,3,2-dioxaborolan-2-yl)phenyl)nicotinamide

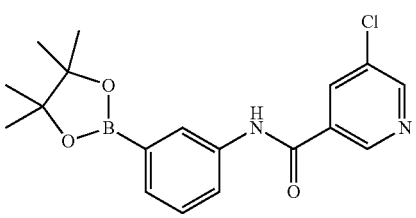 [SMILES: CC1(C)OB(c2cccc(NC(=O)c3cncc(Cl)c3)c2)OC1(C)C]

A mixture of 3-(4,4,5,5-tetramethyl-1,3,2-dioxaborolan-2-yl)aniline (700 mg, 3.20 mmol), 5-chloronicotinic acid (529.37 mg, 3.36 mmol) and HATU (1.83 g, 4.80 mmol) in DMF (7.00 mL) was stirred at 28° C. for 5 min. To the mixture was added DIPEA (827.14 mg, 6.40 mmol, 1.12 mL) and the mixture was stirred at 28° C. for 13 h. When TLC (petroleum ether/EtOAc=0:1, Rf=0.35) showed one main spot was detected, the mixture was diluted with EtOAc (50 mL) and washed with water (30 mL×3). The organic layer was dried over Na$_2$SO$_4$, filtered and concentrated under reduced pressure to give a residue. The residue was purified by column chromatography (SiO$_2$, petroleum ether/EtOAc=50:1 to 1:1) to give the title compound (461 mg, 40%) as a white solid. $^1$H NMR (400 MHz, DMSO-d$_6$) δ 10.50 (s, 1H), 9.06 (d, J=2.8 Hz, 1H), 8.83 (d, J=2.4 Hz, 1H), 8.47-8.46 (m, 1H), 8.08 (s, 1H), 7.96 (d, J=8.0 Hz, 1H), 7.44-7.38 (m, 2H), 1.31 (s, 12H).

Example 69B tert-butyl 4-(4-((tert-butoxycarbonyl)(2-(3-(5-chloronicotinamido)phenyl)-5,7-dihydrofuro[3,4-d]pyrimidin-4-yl)amino)phenyl)-1H-pyrazole-1-carboxylate

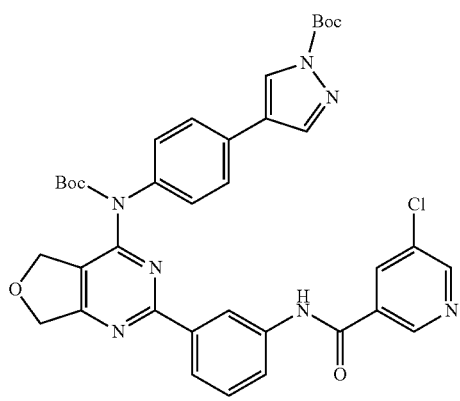 [SMILES: CC(C)(C)OC(=O)N(c1ccc(-c2cnn(C(=O)OC(C)(C)C)c2)cc1)c1nc(-c2cccc(NC(=O)c3cncc(Cl)c3)c2)nc2c1COC2]

To a mixture of 5-chloro-N-(3-(4,4,5,5-tetramethyl-1,3,2-dioxaborolan-2-yl)phenyl)nicotinamide (100 mg, 278.84 umol), tert-butyl 4-(4-((tert-butoxycarbonyl)(2-chloro-5,7-dihydrofuro[3,4-d]pyrimidin-4-yl)amino)phenyl)-1H-pyrazole-1-carboxylate (143.31 mg, 278.84 umol) in dioxane (4.00 mL) and H$_2$O (400.00 uL) were added K$_2$CO$_3$ (77.08 mg, 557.68 umol) and Pd(dppf)Cl$_2$ (20.40 mg, 27.88 umol). The mixture was stirred under N$_2$ at 100° C. for 16 h. TLC (petroleum ether/EtOAc=1:2, Rf=0.35) showed that one new main spot was detected. The mixture was diluted with water (30 mL), and extracted with EtOAc (30 mL×3). The organic layers were dried over Na$_2$SO$_4$, filtered and concentrated under reduced pressure to give a residue. The residue was purified by prep-TLC (petroleum ether/EtOAc=1:2) to give the title compound (mono-Boc product was obtained, 80 mg, crude) as a white solid. $^1$H NMR (400 MHz, DMSO-d$_6$) δ 12.97 (s, 1H), 10.66 (s, 1H), 9.07 (s, 1H), 8.85-8.84 (m, 1H), 8.74 (s, 1H), 8.46 (s, 1H), 8.24 (s, 1H), 7.95-7.89 (m, 3H), 7.70-7.66 (m, 2H), 7.46 (t, J=8.0 Hz, 1H), 7.29 (d, J=8.0 Hz, 1H), 5.06 (s, 2H), 4.84 (s, 2H), 1.44 (s, 6H).

Example 69C

N-(3-(4-((4-(1H-pyrazol-4-yl)phenyl)amino)-5,7-dihydrofuro[3,4-d]pyrimidin-2-yl)phenyl)-5-chloronicotinamide

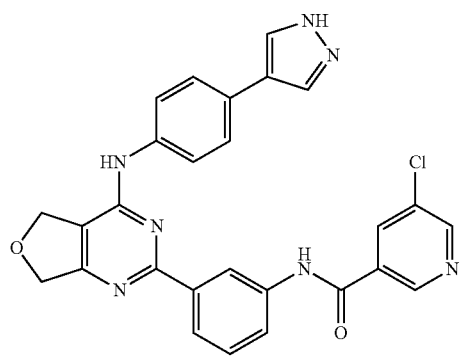 [SMILES: O=C(Nc1cccc(-c2nc3c(c(Nc4ccc(-c5cn[nH]c5)cc4)n2)COC3)c1)c1cncc(Cl)c1]

To a mixture of tert-butyl 4-(4-((tert-butoxycarbonyl)(2-(3-(5-chloronicotinamido)phenyl)-5,7-dihydrofuro[3,4-d]pyrimidin-4-yl)amino)phenyl)-1H-pyrazole-1-carboxylate (mono-Boc product, 77.00 mg) in CH$_2$Cl$_2$ (3.00 mL) was added HCl/dioxane (4 M, 3 mL). The mixture was stirred at 28° C. for 17 h. LCMS showed about 14% of starting material was remaining. An additional amount of HCl/dioxane (4 M, 2 mL) was added. The mixture was stirred at 28° C. for another 1.5 h. LCMS showed about 11% of starting material and about 75% of desired product. The mixture was concentrated under reduced pressure to give a residue. The residue was purified by prep-HPLC to give the title compound (24.60 mg, 38%) as a yellow solid. $^1$H NMR (400 MHz, DMSO-d$_6$) δ 12.92 (s, 1H), 10.70 (s, 1H), 9.24 (s, 1H), 9.11 (d, J=1.6 Hz, 1H), 8.86-8.85 (m, 2H), 8.51 (s, 1H), 8.12-8.10 (m, 2H), 7.94-7.85 (m, 4H), 7.67 (d, J=8.4 Hz, 2H), 7.52 (t, J=7.8 Hz, 1H), 5.09 (s, 2H), 4.96 (s, 2H). (ES+) m/e 510.1 (M+H)$^+$.

Example 70

2-(3-(4-((4-(1H-pyrazol-4-yl)phenyl)amino)-5,7-dihydrofuro[3,4-d]pyrimidin-2-yl)phenoxy)-N-(tert-butyl)acetamide dihydrochloride

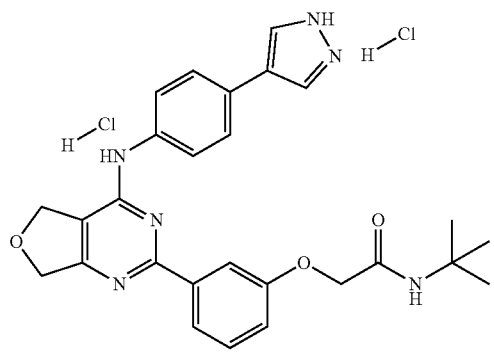

Example 70A

N-(tert-butyl)-2-chloroacetamide

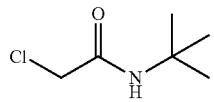

To the mixture of 2-methylpropan-2-amine (4.21 g, 57.55 mmol, 6.01 mL) and TEA (13.44 g, 132.81 mmol, 18.41 mL) in CH$_2$Cl$_2$ (100.00 mL) was added 2-chloroacetyl chloride (5.00 g, 44.27 mmol, 3.52 mL) drop-wise at 0° C. The mixture was stirred under N$_2$ at 23° C. for 3 h. TLC (petroleum ether/EtOAc=0:1, Rf=0.65) showed that one new main spot was detected. The mixture was diluted with CH$_2$Cl$_2$ (50 mL) and washed with water (50 mL×2), citric acid (10%, 50 mL×3), sat.NaHCO$_3$ (50 mL×2), brine (50 mL×2). The organic layer was dried over Na$_2$SO$_4$, filtered and concentrated under reduced pressure to give the title compound (3.49 g, crude) as a black brown solid which was used in the next step without further purification. $^1$H NMR (400 MHz, DMSO-d$_6$) δ 7.80 (s, 1H), 3.95 (s, 2H), 1.32 (s, 9H).

Example 70B 2-(3-bromophenoxy)-N-(tert-butyl)acetamide

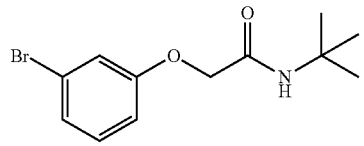 [SMILES: CC(C)(C)NC(=O)COc1cccc(Br)c1]

To a mixture of N-(tert-butyl)-2-chloroacetamide (3.48 g, 23.26 mmol) and 3-bromophenol (3.62 g, 20.93 mmol) in MeCN (40.00 mL) was added K$_2$CO$_3$ (6.43 g, 46.52 mmol). The mixture was stirred at 70° C. for 16 h. TLC (petroleum ether/EtOAc=5:1, Rf=0.62) showed one new main spot was detected. The reaction mixture was diluted with water (50 mL) and extracted with EtOAc (50 mL∴3). The combined organic layers were dried over Na$_2$SO$_4$, filtered, and concentrated under reduced pressure to give a residue. The residue was purified by column chromatography (SiO$_2$) to give the title compound (3.52 g, 53%) as a white solid. $^1$H NMR (400 MHz, DMSO-d$_6$) δ 7.55 (s, 1H), 7.25 (t, J=8.4 Hz, 1H), 7.15-7.13 (m, 2H), 6.95-6.93 (m, 1H), 4.43 (s, 2H), 1.28 (m, 9H).

Example 70C

N-(tert-butyl)-2-(3-(4,4,5,5-tetramethyl-1,3,2-dioxaborolan-2-yl)phenoxy)acetamide

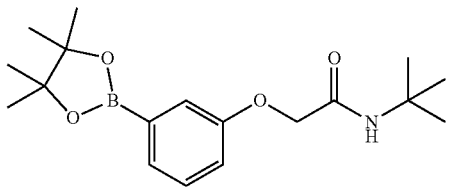 [SMILES: CC(C)(C)NC(=O)COc1cccc(B2OC(C)(C)C(C)(C)O2)c1]

To a mixture of 2-(3-bromophenoxy)-N-(tert-butyl)acetamide (3.50 g, 12.23 mmol) and 4,4,4',4',5,5,5',5'-octamethyl-2,2'-bi(1,3,2-dioxaborolane) (4.66 g, 18.35 mmol) in dioxane (70.00 mL) was added AcOK (2.40 g, 24.46 mmol), Pd(dppf)Cl$_2$ (447.44 mg, 611.50 umol). The mixture was stirred under N$_2$ at 90° C. for 16 h. TLC (petroleum ether/EtOAc=5:1, Rf=0.61) showed that one main spot was detected. The reaction mixture was diluted with water (50 mL) and the mixture was extracted with EtOAc (50 mL×3). The combined organic layers were dried over Na$_2$SO$_4$, filtered and concentrated under reduced pressure to give a residue. The residue was purified by column chromatography (SiO$_2$, petroleum ether/EtOAc=1:0 to 10:1) to give the title compound (3.88 g, 95%) as a white solid. $^1$H NMR (400 MHz, DMSO-d$_6$) δ 7.55 (s, 1H), 7.33-7.25 (m, 2H), 7.20-7.19 (m, 1H), 7.07-7.05 (m, 1H), 4.40 (s, 2H), 1.29-1.28 (m, 21H).

Example 70D

N-(tert-butyl)-2-(3-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)acetamide

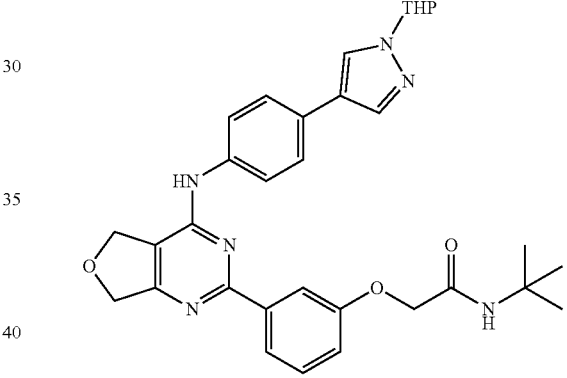

To a mixture of N-(tert-butyl)-2-(3-(4,4,5,5-tetramethyl-1,3,2-dioxaborolan-2-yl)phenoxy)acetamide (700.00 mg, 2.10 mmol) and 2-chloro-N-(4-(1-(tetrahydro-2H-pyran-2-yl)-1H-pyrazol-4-yl)phenyl)-5,7-dihydrofuro[3,4-d]pyrimidin-4-amine (751.96 mg, 1.89 mmol) in dioxane (15.00 mL), H$_2$O (1.50 mL) was added K$_2$CO$_3$ (580.48 mg, 4.20 mmol), Pd(dppf)Cl$_2$ (153.66 mg, 210.00 umol). The mixture was stirred under N$_2$ at 100° C. for 16 h. TLC (petroleum ether/EtOAc=1:2, Rf=0.63) showed one new main spot was detected. The reaction mixture was cooled to room temperature, diluted with water (40 mL) and the mixture was extracted with EtOAc (40 mL×3). The combined organic layers were washed with brine (30 mL×2), dried over Na$_2$SO$_4$, filtered, and concentrated under reduced pressure to give a residue. The residue was purified by column chromatography (SiO$_2$, petroleum ether/EtOAc=1:0 to 1:2) to give the title compound (760 mg, 58%) as a yellow solid. $^1$H NMR (400 MHz, DMSO-d$_6$) δ 9.24 (s, 1H), 8.35 (s, 1H), 7.96-7.94 (m, 3H), 7.82 (d, J=8.0 Hz, 2H), 7.66 (d, J=8.8 Hz, 2H), 7.52 (s, 1H), 7.43-7.39 (m, 1H), 7.09-7.07 (m, 1H), 5.41 (d, J=8.4 Hz, 1H), 5.08 (s, 2H), 4.94 (s, 2H), 4.49 (s, 2H), 3.96-3.94 (m, 1H), 3.68-3.62 (m, 1H), 2.19-2.10 (m, 1H), 1.97-1.94 (m, 2H), 1.70-1.65 (m, 1H), 1.57-1.56 (m, 2H), 1.30 (s, 9H).

Example 70E 2-(3-(4-((4-(1H-pyrazol-4-yl)phenyl)amino)-5,7-dihydrofuro[3,4-d]pyrimidin-2-yl)phenoxy)-N-(tert-butyl)acetamide

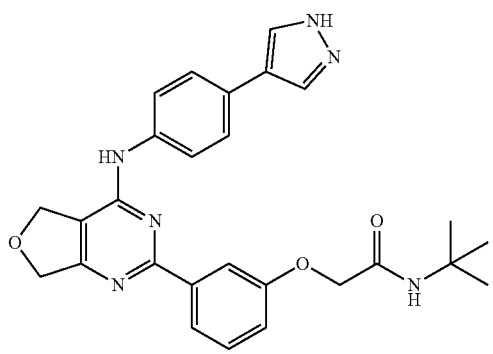 [SMILES: CC(C)(C)NC(=O)COc1cccc(-c2nc3c(c(Nc4ccc(-c5cn[nH]c5)cc4)n2)COC3)c1]

To a mixture of N-(tert-butyl)-2-(3-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)acetamide (760.00 mg, 1.34 mmol) in $CH_2Cl_2$ (30.00 mL) was added HCl/dioxane (4 M, 30.00 mL). The mixture was stirred at 20° C. for 5 h. LCMS showed it had about 83% of desired product and about 9.8% of starting material. The mixture was concentrated under reduced pressure to give a residue. The residue was purified by prep-HPLC (FA conditions) to give the title compound (195 mg, 30%) as an off-white solid. $^1$H NMR (400 MHz, DMSO-$d_6$) δ 9.24 (s, 1H), 7.96-7.93 (m, 4H), 7.80 (d, J=8.4 Hz, 2H), 7.65 (d, J=8.4 Hz, 2H), 7.54 (s, 1H), 7.42 (t, J=7.8 Hz, 1H), 7.08-7.06 (m, 1H), 5.07 (s, 2H), 4.93 (s, 2H), 4.48 (s, 2H), 1.29 (s, 9H).

Example 70F 2-(3-(4-((4-(1H-pyrazol-4-yl)phenyl)amino)-5,7-dihydrofuro[3,4-d]pyrimidin-2-yl)phenoxy)-N-(tert-butyl)acetamide dihydrochloride

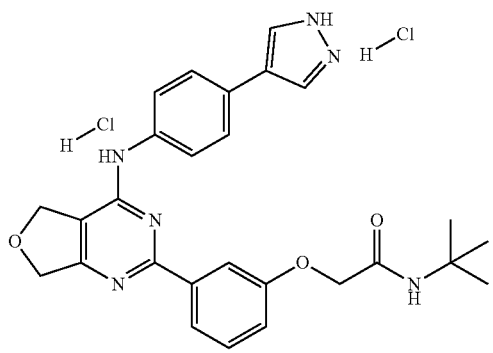

To the solution of 2-(3-(4-((4-(1H-pyrazol-4-yl)phenyl)amino)-5,7-dihydrofuro[3,4-d]pyrimidin-2-yl)phenoxy)-N-(tert-butyl)acetamide (193.00 mg, 398.31 umol) in THF (10.00 mL) was added HCl/dioxane (4 M, 497.89 uL). The mixture was stirred at 18° C. for 3 h. When a large amount of precipitate separated out after the addition of HCl/dioxane, Deionized water (50 mL) was added. The resulting mixture was concentrated under reduce pressure to remove the organic solvent. The aqueous layer was lyophilized to give the title compound (182.70 mg, 87%) as a deep yellow solid. $^1$H NMR (400 MHz, DMSO-$d_6$) δ 9.99 (s, 1H), 8.19 (s, 2H), 7.96-7.94 (m, 2H), 7.81 (d, J=8.4 Hz, 2H), 7.70 (d, J=8.8 Hz, 2H), 7.58 (s, 1H), 7.47 (t, J=8.0 Hz, 1H), 7.16-7.14 (m, 1H), 5.10 (s, 2H), 5.02 (s, 2H), 4.52 (s, 2H), 1.28 (s, 9H). (ES+) m/e 485.2 (M+H)$^+$.

Example 71

2-(3-(4-((4-(1H-pyrazol-4-yl)phenyl)amino)-5,7-dihydrofuro[3,4-d]pyrimidin-2-yl)phenoxy)-N,N-diethylacetamide

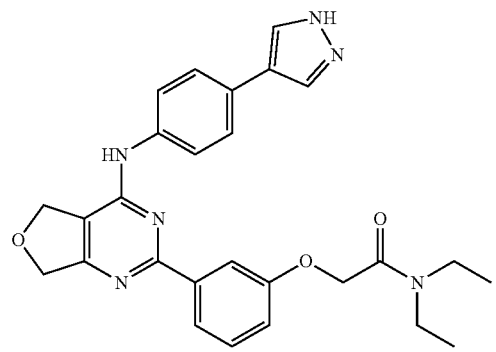 [SMILES: CCN(CC)C(=O)COc1cccc(-c2nc3c(c(Nc4ccc(-c5cn[nH]c5)cc4)n2)COC3)c1]

Example 71A 2-chloro-N,N-diethylacetamide

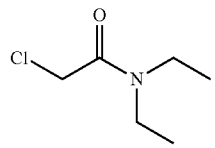

To the mixture of N-ethylethanamine (1.94 g, 26.57 mmol, 2.74 mL) and TEA (5.38 g, 53.12 mmol, 7.37 mL) in $CH_2Cl_2$ (30.00 mL) was added chloroacetyl chloride (2.00 g, 17.71 mmol, 1.41 mL) drop-wise at 0° C. The mixture was stirred at 28° C. for 2 h. TLC (petroleum ether/EtOAc=2:1, Rf=0.6) showed one new main spot was detected. The mixture was diluted with $CH_2Cl_2$ (30 mL) and washed with water (30 mL×2), citric acid (10%, 30 mL×3), sat.NaHCO$_3$ (30 mL×2), brine (30 mL×2). The organic layer was dried over $Na_2SO_4$, filtered and concentrated under reduced pressure to give the title compound (2.17 g, crude) as a black oil and it was then used into next step without further purification. $^1$H NMR (400 MHz, DMSO-$d_6$ (δ 4.32 (s, 2H), 3.31-3.24 (m, 4H), 1.14-1.11 (m, 3H), 1.04-0.99 (m, 3H).

Example 71B

N,N-diethyl-2-(3-(4,4,5,5-tetramethyl-1,3,2-dioxaborolan-2-yl)phenoxy)acetamide

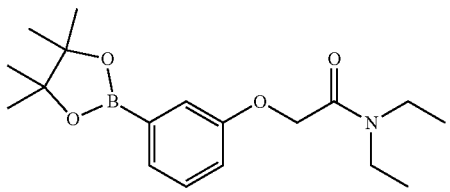 [SMILES: CCN(CC)C(=O)COc1cccc(B2OC(C)(C)C(C)(C)O2)c1]

To a mixture of 3-(4,4,5,5-tetramethyl-1,3,2-dioxaborolan-2-yl)phenol (1.00 g, 4.54 mmol), 2-chloro-N,N-diethylacetamide (883.06 mg, 5.90 mmol) in MeCN (30.00 mL) was added $K_2CO_3$ (1.25 g, 9.08 mmol). The mixture was stirred at 70° C. for 16 h. TLC (petroleum ether/EtOAc=3:1, Rf=0.45) showed one new main spot was detected. The reaction mixture was cooled to room temperature, diluted with water (30 mL) and the mixture was extracted with EtOAc (30 mL×3). The combined organic layers were dried over $Na_2SO_4$, filtered and concentrated under reduced pressure to give a residue. The residue was purified by column chromatography ($SiO_2$, petroleum ether/EtOAc=100:1 to 3:1) to give the title compound (1.01 g, 67%) as light yellow oil. $^1H$ NMR (400 MHz, DMSO-$d_6$) δ 7.31-7.23 (m, 2H), 7.11 (d, J=2.8 Hz, 1H), 7.03 (d, J=1.6 Hz, 1H), 4.78 (s, 2H), 3.29-3.26 (m, 4H), 1.28 (s, 12H), 1.14-1.11 (m, 3H), 1.04-1.02 (m, 3H).

Example 71C tert-butyl 4-(4-((tert-butoxycarbonyl)(2-(3-(2-(diethylamino)-2-oxoethoxy)phenyl)-5,7-dihydrofuro[3,4-d]pyrimidin-4-yl)amino)phenyl)-1H-pyrazole-1-carboxylate

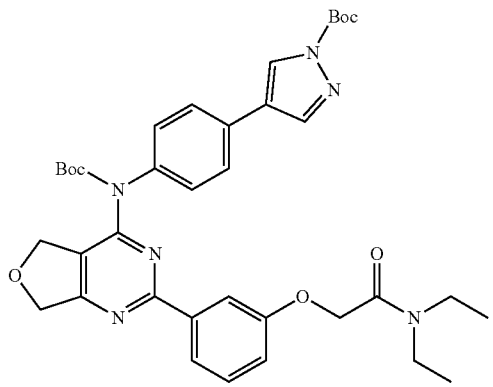 [SMILES: CCN(CC)C(=O)COc1cccc(-c2nc3c(c(N(C(=O)OC(C)(C)C)c4ccc(-c5cnn(C(=O)OC(C)(C)C)c5)cc4)n2)COC3)c1]

To a mixture of N,N-diethyl-2-(3-(4,4,5,5-tetramethyl-1,3,2-dioxaborolan-2-yl)phenoxy)acetamide (150.00 mg, 450.14 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (192.80 mg, 375.12 umol) in dioxane (3.00 mL), $H_2O$ (300.00 uL) was added $K_2CO_3$ (103.69 mg, 750.23 umol) and Pd(dppf)$Cl_2$ (27.45 mg, 37.51 umol). The mixture was stirred under $N_2$ at 100° C. for 16 h. TLC (petroleum ether/EtOAc=1:1, Rf=0.3) showed one new main spot was detected. The reaction mixture was cooled to room temperature, diluted with (30 mL) and the mixture was extracted with EtOAc (30 mL×3). Combined organic layers were dried over $Na_2SO_4$, filtered and concentrated under reduced pressure to give a residue. The residue was purified by prep-TLC (petroleum ether/EtOAc=1:1) to give the title compound (mono-Boc, 82.00 mg) as a light yellow solid. $^1H$ NMR (DMSO-$d_6$ 400 MHz) δ 12.97 (s, 1H), 8.24 (s, 1H), 7.96 (s, 1H), 7.77 (d, J=7.2 Hz, 1H), 7.66 (d, J=8.0 Hz, 3H), 7.37-7.35 (m, 1H), 7.27 (d, J=8.4 Hz, 2H), 7.02-7.00 (m, 1H), 5.03 (s, 2H), 4.86 (s, 2H), 4.76 (s, 2H), 3.17-3.08 (m, 4H), 1.46-1.44 (s, 9H), 1.19-1.10 (m, 6H).

Example 71D 2-(3-(4-((4-(1H-pyrazol-4-yl)phenyl)amino)-5,7-dihydrofuro[3,4-d]pyrimidin-2-yl)phenoxy)-N,N-diethylacetamide

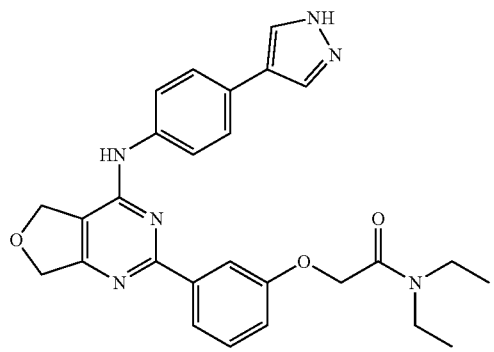 [SMILES: CCN(CC)C(=O)COc1cccc(-c2nc3c(c(Nc4ccc(-c5cn[nH]c5)cc4)n2)COC3)c1]

To the mixture of tert-butyl 4-(4-((tert-butoxycarbonyl)(2-(3-(2-(diethylamino)-2-oxoethoxy)phenyl)-5,7-dihydrofuro[3,4-d]pyrimidin-4-yl)amino)phenyl)-1H-pyrazole-1-carboxylate (mono-Boc, 65.00 mg) in $CH_2Cl_2$ (5.00 mL) was added HCl/dioxane (4 M, 3.00 mL). The mixture was stirred at 25° C. for 12 h. LCMS showed about 49% of desired product about 28% of starting material. Additional 2 mL HCl/dioxane (4 N) was added. Then the mixture was stirred at 30° C. for 7 h. LCMS showed only 11% of starting material remained. The reaction was concentrated under reduced pressure to give a residue. The residue was purified by prep-HPLC (FA conditions) to give the title compound (20.1 mg, 36%) as a white solid. $^1H$ NMR (DMSO-$d_6$ 400 MHz) δ 12.91 (s, 1H), 9.22 (s, 1H), 8.15 (s, 1H), 7.92 (d, J=8.0 Hz, 2H), 7.85 (s, 1H), 7.78 (d, J=8.4 Hz, 2H), 7.64 (d, J=8.4 Hz, 2H), 7.40 (t, J=8.0 Hz, 1H), 7.04-7.02 (m, 1H), 5.07 (s, 2H), 4.93 (s, 2H), 4.85 (s, 2H), 3.29-3.26 (m, 4H), 1.15-1.11 (m, 3H), 1.04-0.98 (m, 3H). (ES+) m/e 485.3 $(M+H)^+$.

Example 72

N-(3-(4-((4-(1H-pyrazol-4-yl)phenyl)amino)-5,7-dihydrofuro[3,4-d]pyrimidin-2-yl)phenyl)-6-methylnicotinamide

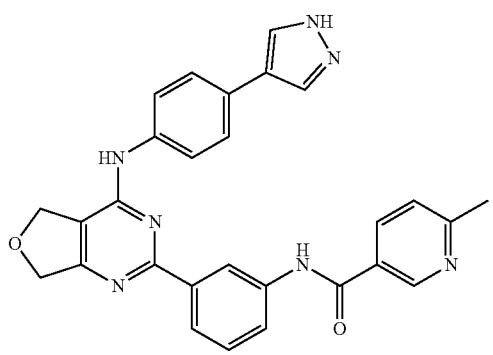 [SMILES: Cc1ccc(C(=O)Nc2cccc(-c3nc4c(c(Nc5ccc(-c6cn[nH]c6)cc5)n3)COC4)c2)cn1]

Example 72A 6-methyl-N-(3-(4,4,5,5-tetramethyl-1,3,2-dioxaborolan-2-yl)phenyl)nicotinamide

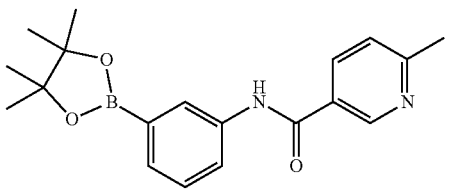

A mixture of 3-(4,4,5,5-tetramethyl-1,3,2-dioxaborolan-2-yl)aniline (700.00 mg, 3.20 mmol), 6-methylnicotinic acid (460.79 mg, 3.36 mmol) and HATU (1.83 g, 4.80 mmol) in DMF (7.00 mL) was stirred at 30° C. for 5 min, and then to the solution was added DIPEA (827.14 mg, 6.40 mmol, 1.12 mL). The mixture was stirred at 30° C. for 16 hour. LCMS showed that the starting material was consumed completely and one main peak with desired mass was detected. TLC (Petroleum ether/Ethyl acetate=1/2) indicated starting material was consumed completely and one new spot (Rf=0.5) formed. The reaction mixture was diluted with DCM (50 mL) and washed with $H_2O$ (50 mL×5), dried over $Na_2SO_4$, filtered and concentrated under reduced pressure to give a residue. The residue was purified by column chromatography (SiO$_2$, Petroleum ether/Ethyl acetate=1/1) to afford the title compound (1.00 g, 92%) as an off-white solid. $^1$H NMR (400 MHz, DMSO-d$_6$) δ 10.34 (s, 1H), 9.02 (d, J=2.0 Hz, 1H), 8.22 (dd, J=8.0 Hz, 2.4 Hz, 1H), 8.09 (d, J=1.6 Hz, 1H), 7.98-7.95 (m, 1H), 7.42-7.36 (m, 3H), 2.55 (s, 3H), 1.31 (s, 12H).

Example 72B tert-butyl 4-(4-((tert-butoxycarbonyl)(2-(3-(6-methylnicotinamido)phenyl)-5,7-dihydrofuro[3,4-d]pyrimidin-4-yl)amino)phenyl)-1H-pyrazole-1-carboxylate

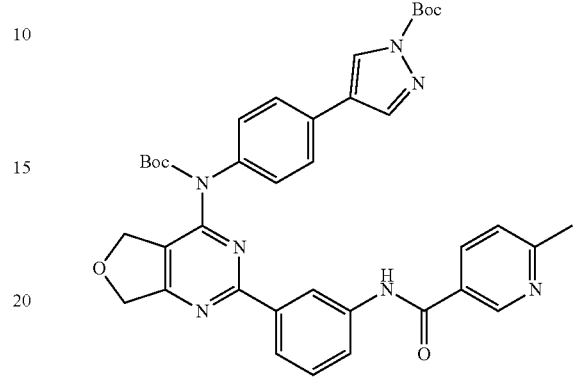

A mixture of 6-methyl-N-(3-(4,4,5,5-tetramethyl-1,3,2-dioxaborolan-2-yl)phenyl)nicotinamide (100.00 mg, 295.67 umol), tert-butyl 4-(4-((tert-butoxycarbonyl)(2-chloro-5,7-dihydrofuro[3,4-d]pyrimidin-4-yl)amino)phenyl)-1H-pyrazole-1-carboxylate (151.97 mg, 295.67 umol), $K_2CO_3$ (81.73 mg, 591.34 umol) and Pd(dppf)Cl$_2$ (21.63 mg, 29.57 umol) in dioxane (5.00 mL)/H$_2$O (500.00 uL) was degassed and purged with N$_2$ 3 times, and then the mixture was stirred at 95° C. for 16 hour under N$_2$ atmosphere. LCMS showed 6-methyl-N-(3-(4,4,5,5-tetramethyl-1,3,2-dioxaborolan-2-yl)phenyl)nicotinamidewas consumed completely and two main peaks with desired mass and de-Boc product were detected. Accordingly to the TLC (Petroleum ether/Ethyl acetate=1/2), the starting material was consumed completely and two main new spots (Rf=0.42, 0.2) formed. The reaction mixture was cooled to room temperature and quenched by addition of H$_2$O (50 mL), then the resulting mixture was extracted with EtOAc (50 mL×3). The combined organic layers were washed with brine (50 mL×3), dried over Na$_2$SO$_4$, filtered and concentrated under reduced pressure to give a residue. The residue was purified by prep-TLC (SiO$_2$, Petroleum ether/Ethyl acetate=1/2) to afford the title compound (60 mg, 27%) and de-Boc product (70 mg, 39%) both as off-white solids.

Example 72C

N-(3-(4-((4-(1H-pyrazol-4-yl)phenyl)amino)-5,7-dihydrofuro[3,4-d]pyrimidin-2-yl)phenyl)-6-methylnicotinamide

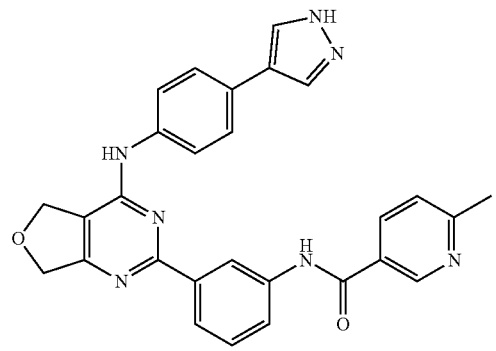 [SMILES: Cc1ccc(C(=O)Nc2cccc(-c3nc4c(c(Nc5ccc(-c6cn[nH]c6)cc5)n3)COC4)c2)cn1]

To a solution of tert-butyl 4-(4-((tert-butoxycarbonyl)(2-(3-(6-methylnicotinamido)phenyl)-5,7-dihydrofuro[3,4-d]pyrimidin-4-yl)amino)phenyl)-1H-pyrazole-1-carboxylate (60.00 mg, 86.99 umol, containing 70 mg de-Boc product) in DCM (3.00 mL) was added HCl/dioxane (4 M, 3.00 mL). The mixture was stirred at 30° C. for 16 hour. LCMS showed ~73% desired compound was detected by mass. The reaction mixture was concentrated under reduced pressure to remove solvent. The residue was purified by prep-HPLC (FA conditions) to afford the title compound (19.2 mg) as an off-white solid. $^1$H NMR (400 MHz, DMSO-$d_6$) δ 12.91 (s, 1H), 10.53 (s, 1H), 9.24 (s, 1H), 9.07 (s, 1H), 8.86 (s, 1H), 8.27 (dd, J=8.0 Hz, 2.4 Hz, 1H), 8.09 (d, J=7.6 Hz, 2H), 7.94-7.85 (m, 4H), 7.67 (d, J=8.8 Hz, 2H), 7.49 (t, J=8.0 Hz, 1H), 7.43 (d, J=8.0 Hz, 1H), 5.08 (s, 2H), 4.96 (s, 2H), 2.57 (s, 3H). (ES+) m/e 490.1 (M+H)$^+$.

Example 73

N-(3-(4-((4-(1H-pyrazol-4-yl)phenyl)amino)-5,7-dihydrofuro[3,4-d]pyrimidin-2-yl)phenyl)-5-methylnicotinamide

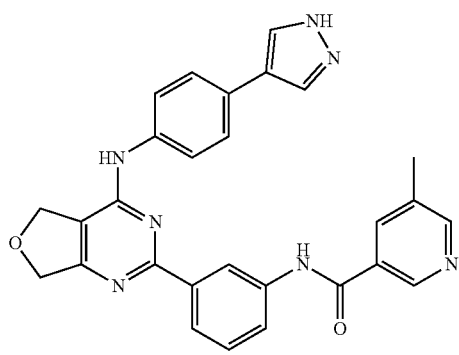 [SMILES: Cc1cncc(C(=O)Nc2cccc(-c3nc4c(c(Nc5ccc(-c6cn[nH]c6)cc5)n3)COC4)c2)c1]

Example 73A 5-methyl-N-(3-(4,4,5,5-tetramethyl-1,3,2-dioxaborolan-2-yl)phenyl)nicotinamide

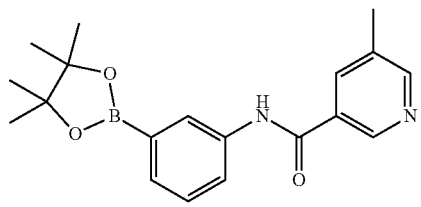 [SMILES: Cc1cncc(C(=O)Nc2cccc(B3OC(C)(C)C(C)(C)O3)c2)c1]

A mixture of 3-(4,4,5,5-tetramethyl-1,3,2-dioxaborolan-2-yl)aniline (700.00 mg, 3.20 mmol), 5-methylnicotinic acid (460.79 mg, 3.36 mmol) and HATU (1.83 g, 4.80 mmol) in DMF (7.00 mL) was stirred at 30° C. for 5 min, and then to this solution was added DIPEA (827.14 mg, 6.40 mmol, 1.12 mL). The mixture was stirred at 30° C. for 16 hour. LCMS showed 3-(4,4,5,5-tetramethyl-1,3,2-dioxaborolan-2-yl)aniline was consumed completely and one main peak with desired mass was detected. TLC (Petroleum ether/Ethyl acetate=1/2) indicated the same starting material was consumed completely and one new spot (Rf=0.49) appeared. The reaction mixture was diluted with DCM (50 mL) and washed with $H_2O$ (50 mL×5), dried over $Na_2SO_4$, filtered and concentrated under reduced pressure to give a residue. The residue was purified by column chromatography ($SiO_2$, Petroleum ether/Ethyl acetate=1/1) to afford the title compound (720 mg, 67%) as an off-white solid. $^1$H NMR (400 MHz, DMSO-$d_6$) δ 10.38 (s, 1H), 8.93 (d, J=2.0 Hz, 1H), 8.60 (d, J=1.6 Hz, 1H), 8.15 (s, 1H), 8.09 (d, J=2.0 Hz, 1H), 7.98-7.96 (m, 1H), 7.43-7.36 (m, 2H), 2.39 (s, 3H), 1.31 (s, 12H).

Example 73B tert-butyl 4-(4-((tert-butoxycarbonyl)(2-(3-(5-methylnicotinamido)phenyl)-5,7-dihydrofuro[3,4-d]pyrimidin-4-yl)amino)phenyl)-1H-pyrazole-1-carboxylate

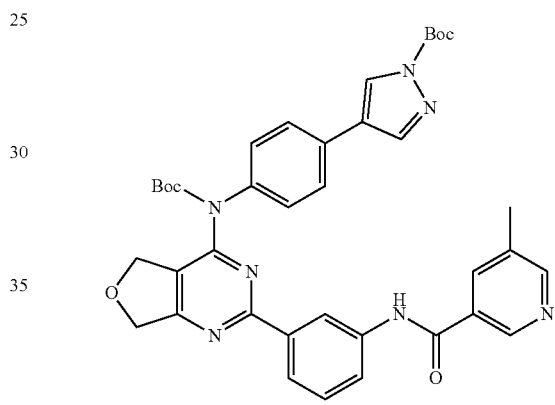

A mixture of 5-methyl-N-(3-(4,4,5,5-tetramethyl-1,3,2-dioxaborolan-2-yl)phenyl)nicotinamide (100.00 mg, 295.67 umol), tert-butyl 4-(4-((tert-butoxycarbonyl)(2-chloro-5,7-dihydrofuro[3,4-d]pyrimidin-4-yl)amino)phenyl)-1H-pyrazole-1-carboxylate (151.97 mg, 295.67 umol), $K_2CO_3$ (81.73 mg, 591.34 umol) and Pd(dppf)Cl$_2$ (21.63 mg, 29.57 umol) in dioxane (5.00 mL)/$H_2O$ (500.00 uL) was degassed and purged with $N_2$ 3 times, and then the mixture was stirred at 95° C. for 16 hour under $N_2$ atmosphere. LCMS showed that 5-methyl-N-(3-(4,4,5,5-tetramethyl-1,3,2-dioxaborolan-2-yl)phenyl)nicotinamide was consumed completely and one main peak with desired mass was detected. TLC (Petroleum ether/Ethyl acetate=1/2) indicated that the starting material was consumed completely and one main new spot (Rf=0.45) formed. The reaction mixture was cooled to room temperature and quenched by addition of $H_2O$ (50 mL), then the mixture was extracted with EtOAc (50 mL×3). The combined organic layers were washed with brine (50 mL×3), dried over $Na_2SO_4$, filtered and concentrated under reduced pressure to give a residue. The residue was purified by prep-TLC ($SiO_2$, Petroleum ether/Ethyl acetate=1/2) to afford the title compound (90 mg, 41%) as an off-white solid.

Example 73C

N-(3-(4-((4-(1H-pyrazol-4-yl)phenyl)amino)-5,7-dihydrofuro[3,4-d]pyrimidin-2-yl)phenyl)-5-methyl-nicotinamide

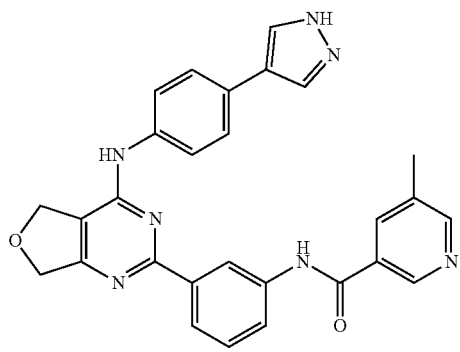 [SMILES: Cc1cncc(C(=O)Nc2cccc(-c3nc4c(c(Nc5ccc(-c6cn[nH]c6)cc5)n3)COC4)c2)c1]

To a solution of N-(3-(4-((4-(1H-pyrazol-4-yl)phenyl)amino)-5,7-dihydrofuro[3,4-d]pyrimidin-2-yl)phenyl)-5-methylnicotinamide (90.00 mg, 130.48 umol) in DCM (2.50 mL) was added HCl/dioxane (4 M, 2.50 mL). The mixture was stirred at 30° C. for 16 hour. LCMS showed ~71% conversion and the product had desired mass. The reaction mixture was concentrated under reduced pressure to remove the solvent. The residue was purified by prep-HPLC (FA condition) to afford the title compound (31.1 mg, 48%) as an off-white solid. $^1$H NMR (400 MHz, DMSO-$d_6$) δ 12.92 (s, 1H), 10.58 (s, 1H), 9.25 (s, 1H), 8.99 (s, 1H), 8.88 (s, 1H), 8.63 (d, J=1.6 Hz, 1H), 8.21 (s, 1H), 8.11 (d, J=8.0 Hz, 2H), 7.95-7.86 (m, 4H), 7.68 (d, J=8.8 Hz, 2H), 7.51 (t, J=8.0 Hz, 1H), 7.43 (d, J=8.0 Hz, 1H), 5.10 (s, 2H), 4.97 (s, 2H), 2.42 (s, 3H). (ES+) m/e 490.1 (M+H)$^+$.

Example 74

N-(3-(4-((4-(1H-pyrazol-4-yl)phenyl)amino)-5,7-dihydrofuro[3,4-d]pyrimidin-2-yl)phenyl)-4-methyl-nicotinamide

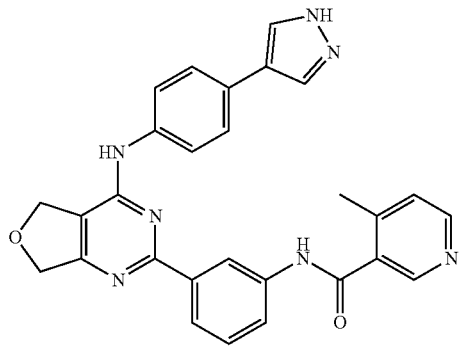

1.1.1
1.1.2

Example 74A 4-methyl-N-(3-(4,4,5,5-tetramethyl-1,3,2-dioxaborolan-2-yl)phenyl)nicotinamide

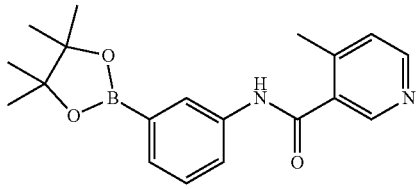 [SMILES: Cc1ccncc1C(=O)Nc1cccc(B2OC(C)(C)C(C)(C)O2)c1]

A mixture of 3-(4,4,5,5-tetramethyl-1,3,2-dioxaborolan-2-yl)aniline (300.00 mg, 1.37 mmol), 4-methylnicotinic acid (187.79 mg, 1.37 mmol) and HATU (780.97 mg, 2.06 mmol) in DMF (4.00 mL) was stirred at 30° C. for 5 min, then to this solution was added DIPEA (353.94 mg, 2.74 mmol, 478.30 uL). The mixture was stirred at 30° C. for 16 hour. LCMS showed that 3-(4,4,5,5-tetramethyl-1,3,2-dioxaborolan-2-yl)aniline was consumed completely and one main peak with desired mass was detected. TLC (Petroleum ether/Ethyl acetate=1/2) indicated the same starting material was consumed completely and one new spot (Rf=0.45) formed. The reaction mixture was diluted with DCM (50 mL) and washed with H$_2$O (50 mL×5), dried over Na$_2$SO$_4$, filtered and concentrated under reduced pressure to give a residue. The residue was purified by column chromatography (SiO$_2$, Petroleum ether/Ethyl acetate=1/1) to afford the title compound (330 mg, 71%) as an off-white solid. $^1$H NMR (400 MHz, DMSO-$d_6$) δ 10.47 (s, 1H), 8.65 (s, 1H), 8.54 (d, J=4.8 Hz, 1H), 8.14 (s, 1H), 7.83-7.81 (m, 1H), 7.44-7.36 (m, 3H), 2.42 (s, 3H), 1.31 (s, 12H).

Example 74B tert-butyl 4-(4-(((tert-butoxycarbonyl)(2-(3-(4-methylnicotinamido)phenyl)-5,7-dihydrofuro[3,4-d]pyrimidin-4-yl)amino)phenyl)-1H-pyrazole-1-carboxylate

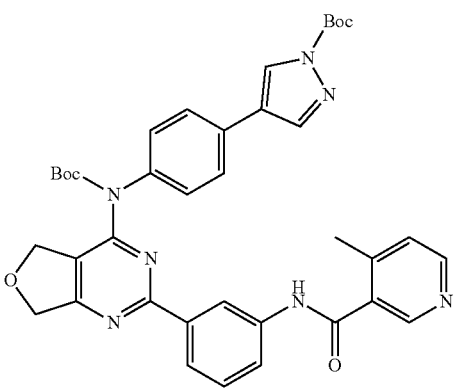 [SMILES: Cc1ccncc1C(=O)Nc1cccc(-c2nc3c(c(N(C(=O)OC(C)(C)C)c4ccc(-c5cnn(C(=O)OC(C)(C)C)c5)cc4)n2)COC3)c1]

A mixture of 4-methyl-N-(3-(4,4,5,5-tetramethyl-1,3,2-dioxaborolan-2-yl)phenyl)nicotinamide (165.00 mg, 487.86 umol), tert-butyl 4-(4-(((tert-butoxycarbonyl)(2-chloro-5,7-dihydrofuro[3,4-d]pyrimidin-4-yl)amino)phenyl)-1H-pyrazole-1-carboxylate (250.75 mg, 487.86 umol), K₂CO₃ (134.85 mg, 975.72 umol), Pd(dppf)Cl₂ (35.70 mg, 48.79 umol) in dioxane (5.00 mL)/H₂O (500.00 uL) was degassed and purged with N₂ 3 times, then the mixture was stirred at 100° C. for 16 hour under N₂ atmosphere. LCMS showed 4-methyl-N-(3-(4,4,5,5-tetramethyl-1,3,2-dioxaborolan-2-yl)phenyl)nicotinamide was consumed completely and two main peaks with desired mass and de-Boc product were detected. The reaction mixture was cooled to room temperature and quenched by addition of H₂O (50 mL), then the mixture was extracted with EtOAc (50 mL×3). The combined organic layers were washed with brine (50 mL×3), dried over Na₂SO₄, filtered and concentrated under reduced pressure to give a residue. The residue was purified by prep-TLC (SiO₂, Petroleum ether/Ethyl acetate=0/1) to afford the title compound (50 mg, 15%) and de-Boc product (150 mg, 52%) both as off-white solids.

Example 74C

N-(3-(4-((4-(1H-pyrazol-4-yl)phenyl)amino)-5,7-dihydrofuro[3,4-d]pyrimidin-2-yl)phenyl)-4-methylnicotinamide

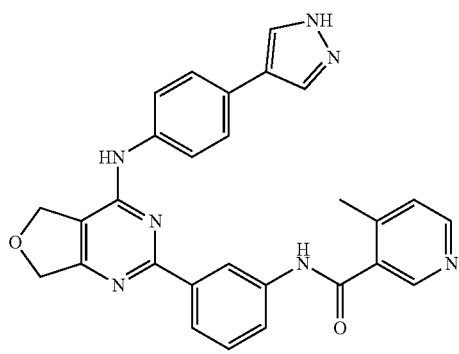 [SMILES: Cc1ccncc1C(=O)Nc1cccc(-c2nc3c(c(Nc4ccc(-c5cn[nH]c5)cc4)n2)COC3)c1]

To a solution of tert-butyl 4-(4-(((tert-butoxycarbonyl)(2-(3-(4-methylnicotinamido)phenyl)-5,7-dihydrofuro[3,4-d]pyrimidin-4-yl)amino)phenyl)-1H-pyrazole-1-carboxylate (50.00 mg, 72.49 umol) in DCM (2.50 mL) was added HCl/dioxane (4 N, 2.50 mL). The mixture was stirred at 30° C. for 16 hour. LCMS showed ~62% conversion and the desired compound mass was detected. The reaction mixture was concentrated under reduced pressure to remove solvent. The residue was purified by prep-HPLC (FA conditions) to afford title compound (54.9 mg) as a yellow solid. ¹H NMR (400 MHz, DMSO-d₆) δ 10.65 (s, 1H), 9.23 (s, 1H), 8.91 (s, 1H), 8.71 (s, 1H), 8.56 (d, J=4.8 Hz, 1H), 8.17-8.09 (m, 2H), 8.01 (s, 2H), 7.88 (d, J=8.8 Hz, 2H), 7.82 (d, J=8.4 Hz, 1H), 7.66 (d, J=8.8 Hz, 2H), 7.49 (t, J=8.0 Hz, 1H), 7.39 (d, J=4.2 Hz, 1H), 5.10 (s, 2H), 4.96 (s, 2H), 2.47 (s, 3H). (ES+) m/e 490.1 (M+H)⁺.

Example 75

N-(3-(4-((4-(1H-pyrazol-4-yl)phenyl)amino)-5,7-dihydrofuro[3,4-d]pyrimidin-2-yl)phenyl)-5-fluoronicotinamide

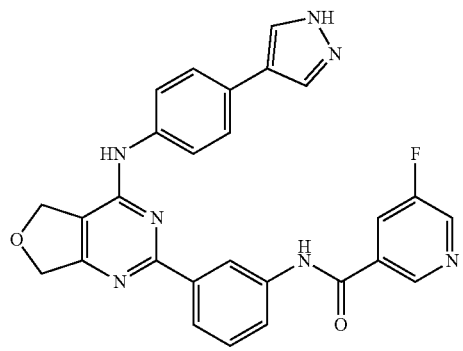

Example 75A 5-fluoro-N-(3-(4,4,5,5-tetramethyl-1,3,2-dioxaborolan-2-yl)phenyl)nicotinamide

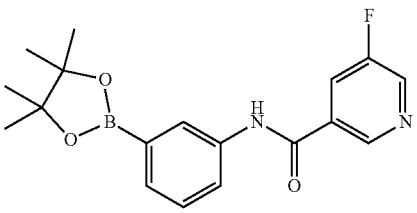 [SMILES: CC1(C)OB(c2cccc(NC(=O)c3cncc(F)c3)c2)OC1(C)C]

A mixture of 3-(4,4,5,5-tetramethyl-1,3,2-dioxaborolan-2-yl)aniline (300.00 mg, 1.37 mmol), 5-fluoronicotinic acid (193.21 mg, 1.37 mmol) and HATU (780.97 mg, 2.06 mmol) in DMF (4.00 mL) was stirred at 30° C. for 5 min, followed by addition of DIPEA (353.94 mg, 2.74 mmol, 478.30 uL). The mixture was stirred at 30° C. for 16 hour. LCMS showed the starting material was consumed completely and one main peak with desired mass was detected. TLC (Petroleum ether/Ethyl acetate=1/1) indicated 3-(4,4,5,5-tetramethyl-1,3,2-dioxaborolan-2-yl)aniline was consumed completely and one new spot (Rf=0.7) formed. The reaction mixture was diluted with CH₂Cl₂ (50 mL) and washed with H₂O (50 mL×5), dried over Na₂SO₄, filtered and concentrated under reduced pressure to give a residue. The residue was purified by column chromatography (SiO₂, Petroleum ether/Ethyl acetate=5/1) to afford the title compound (370 mg, 79%) as an off-white solid. ¹H NMR (400 MHz, DMSO-d₆) δ 10.48 (s, 1H), 9.01 (t, J=1.6 Hz, 1H), 8.79 (d, J=2.8 Hz, 1H), 8.26-8.23 (m, 1H), 8.09 (d, J=1.6 Hz, 1H), 7.98-7.95 (m, 1H), 7.45-7.38 (m, 2H), 1.31 (s, 12H).

Example 75B tert-butyl 4-(4-((tert-butoxycarbonyl)(2-(3-(5-fluoronicotinamido)phenyl)-5,7-dihydrofuro[3,4-d]pyrimidin-4-yl)amino)phenyl)-1H-pyrazole-1-carboxylate

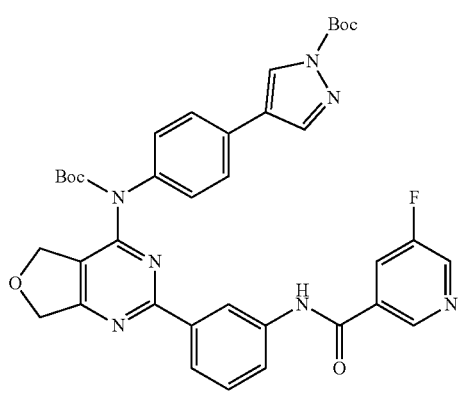

(i)

A mixture of 5-fluoro-N-(3-(4,4,5,5-tetramethyl-1,3,2-dioxaborolan-2-yl)phenyl)nicotinamide (167.00 mg, 488.06 umol), tert-butyl 4-(4-((tert-butoxycarbonyl)(2-chloro-5,7-dihydrofuro[3,4-d]pyrimidin-4-yl)amino)phenyl)-1H-pyrazole-1-carboxylate (250.85 mg, 488.06 umol), $K_2CO_3$ (134.91 mg, 976.12 umol) and $Pd(dppf)Cl_2$ (35.71 mg, 48.81 umol) in dioxane (5.00 mL)/$H_2O$ (500.00 uL) was degassed and purged with $N_2$ 3 times, then the mixture was stirred at 95° C. for 16 hour under $N_2$ atmosphere. LCMS showed tert-butyl 4-(4-((tert-butoxycarbonyl)(2-chloro-5,7-dihydrofuro[3,4-d]pyrimidin-4-yl)amino)phenyl)-1H-pyrazole-1-carboxylate was consumed completely and two main peaks with desired mass and de-Boc product were detected. TLC (Petroleum ether/Ethyl acetate=1/2) indicated that starting materials were consumed completely and two main new spots (Rf=0.7, 0.35) formed. The reaction mixture was cooled to room temperature and quenched by addition of $H_2O$ (50 mL), then the mixture was extracted with EtOAc (50 mL×3). The combined organic layers were washed with brine (50 mL×3), dried over $Na_2SO_4$, filtered and concentrated under reduced pressure to give a residue. The residue was purified by prep-TLC ($SiO_2$, Petroleum ether/Ethyl acetate=1/2) to afford the title compound (70 mg, 21%) and de-Boc product (180 mg, 62%) as off-white solids.

Example 75C

N-(3-(4-((4-(1H-pyrazol-4-yl)phenyl)amino)-5,7-dihydrofuro[3,4-d]pyrimidin-2-yl)phenyl)-5-fluoronicotinamide

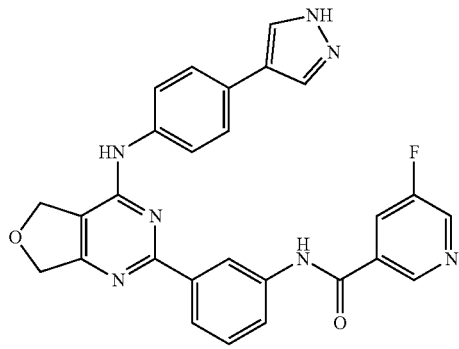 [SMILES: O=C(Nc1cccc(-c2nc3c(c(Nc4ccc(-c5cn[nH]c5)cc4)n2)COC3)c1)c1cncc(F)c1]

To a solution of tert-butyl 4-(4-((tert-butoxycarbonyl)(2-(3-(5-fluoronicotinamido)phenyl)-5,7-dihydrofuro[3,4-d]pyrimidin-4-yl)amino)phenyl)-1H-pyrazole-1-carboxylate (70.00 mg, 100.91 umol) (contain 180 mg) in $CH_2Cl_2$ (2.50 mL) was added HCl/dioxane (4 M, 2.50 mL). The mixture was stirred at 30° C. for 16 hour. LCMS showed ~60% coversion and the desired compound mass was detected. The reaction mixture was concentrated under reduced pressure to remove the solvent. The residue was purified by prep-HPLC (FA conditions) to afford the title compound (19.1 mg) as an off-white solid. $^1$H NMR (400 MHz, DMSO-$d_6$) δ 12.92 (s, 1H), 10.69 (s, 1H), 9.25 (s, 1H), 9.07 (s, 1H), 8.87 (s, 1H), 8.83 (d, J=2.8 Hz, 1H), 8.30 (d, J=9.2 Hz, 1H), 8.16-8.11 (m, 2H), 7.95-7.86 (m, 4H), 7.68 (d, J=8.8 Hz, 2H), 7.53 (t, J=8.0 Hz, 1H), 5.10 (s, 2H), 4.97 (s, 2H). (ES+) m/e 494.1 (M+H)$^+$.

Example 76

2-(3-(4-((4-(1H-pyrazol-4-yl)phenyl)amino)-5,7-dihydrofuro[3,4-d]pyrimidin-2-yl)phenoxy)-N-(pentan-3-yl)acetamide dihydrochloride

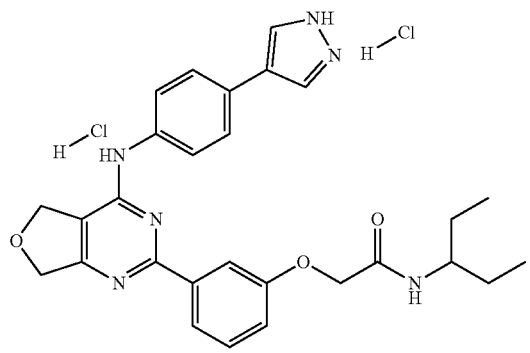

Example 76A 2-chloro-N-(pentan-3-yl)acetamide

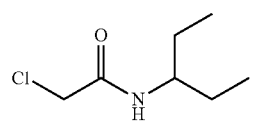

To a mixture of pentan-3-amine (5.79 g, 66.41 mmol, 7.72 mL) and TEA (13.44 g, 132.81 mmol, 18.41 mL) in $CH_2Cl_2$ (100.00 mL) was added 2-chloroacetyl chloride (5.00 g, 44.27 mmol, 3.52 mL) dropwise at 0° C. The mixture was stirred under $N_2$ at 23° C. for 3 h. TLC (petroleum ether/EtOAc=0:1, Rf=0.6) showed one new main spot. The mixture was diluted with $CH_2Cl_2$ (40 mL) and washed with water (50 mL×2), citric acid (10%, 50 mL×3), sat.NaHCO$_3$ (50 mL×2), brine (50 mL×2). The organic layer was dried over $Na_2SO_4$, filtered and concentrated under reduced pressure to give the title compound (5.21 g, crude) as a black brown solid. $^1$H NMR (400 MHz, DMSO-$d_6$) δ 7.89 (d, J=8.0 Hz, 1H), 4.02 (s, 2H), 3.55-3.48 (m, 1H), 1.48-1.42 (m, 2H), 1.36-1.30 (m, 2H), 0.81 (t, J=7.4 Hz, 6H).

Example 76B 2-(3-bromophenoxy)-N-(pentan-3-yl)acetamide

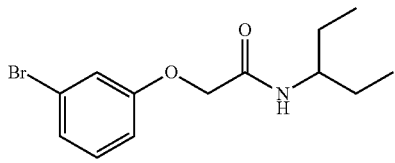 [SMILES: CCC(CC)NC(=O)COc1cccc(Br)c1]

To the mixture of 2-chloro-N-(pentan-3-yl)acetamide (2.00 g, 12.22 mmol) and 3-bromophenol (1.90 g, 11.00 mmol) in MeCN (40.00 mL) was added K$_2$CO$_3$ (3.38 g, 24.44 mmol). The mixture was stirred at 70° C. for 16 h. TLC (petroleum ether/EtOAc=2:1, Rf=0.72) showed one main spot was detected. The reaction mixture was diluted with water (50 mL) and extracted with EtOAc (50 mL×3). The combined organic layers were dried over Na$_2$SO$_4$, filtered and concentrated under reduced pressure to give a residue. The residue was purified by column chromatography (SiO$_2$) to give the title compound (2.41, 66%) as a light yellow solid. $^1$H NMR (400 MHz, DMSO-d$_6$) δ 7.74 (d, J=8.8 Hz, 1H), 7.25 (d, J=8.2 Hz, 1H), 7.15-7.13 (m, 2H), 6.98-6.95 (m, 1H), 4.53 (s, 2H), 3.62-3.55 (m, 1H), 1.47-1.32 (m, 4H), 0.78 (t, J=7.4 Hz, 6H).

Example 76C

N-(pentan-3-yl)-2-(3-(4,4,5,5-tetramethyl-1,3,2-dioxaborolan-2-yl)phenoxy)acetamide

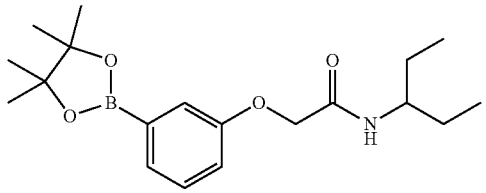 [SMILES: CCC(CC)NC(=O)COc1cccc(B2OC(C)(C)C(C)(C)O2)c1]

To a mixture of 2-(3-bromophenoxy)-N-(pentan-3-yl)acetamide (2.40 g, 7.99 mmol) and 4,4,4',4',5,5,5',5'-octamethyl-2,2'-bi(1,3,2-dioxaborolane) (3.05 g, 11.99 mmol) in dioxane (30.00 mL) was added Pd(dppf)Cl$_2$ (292.32 mg, 399.50 umol) and AcOK (1.57 g, 15.99 mmol). The mixture was stirred under N$_2$ at 90° C. for 16 h. TLC (petroleum ether/EtOAc=3:1, Rf=0.52) detected one new main spot. The reaction mixture was cooled to room temperature, diluted with water (50 mL) and the mixture was extracted with EtOAc (50 mL×3). The combined organic layers were dried over Na$_2$SO$_4$, filtered and concentrated under reduced pressure to give a residue. The residue was purified by column chromatography (SiO$_2$, petroleum ether/EtOAc=1:0 to 8:1) to give the title compound (3.05 g, 74%) as a light yellow solid. $^1$H NMR (400 MHz, DMSO-d$_6$) δ 7.72 (d, J=8.8 Hz, 1H), 7.33-7.25 (m, 2H), 7.21-7.20 (m, 1H), 7.08 (d, J=1.2 Hz, 1H), 4.49 (s, 2H), 3.64-3.58 (m, 1H), 1.46-1.33 (m, 4H), 1.28 (s, 12H), 0.79 (t, J=7.4 Hz, 6H).

Example 76D

N-(pentan-3-yl)-2-(3-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)acetamide

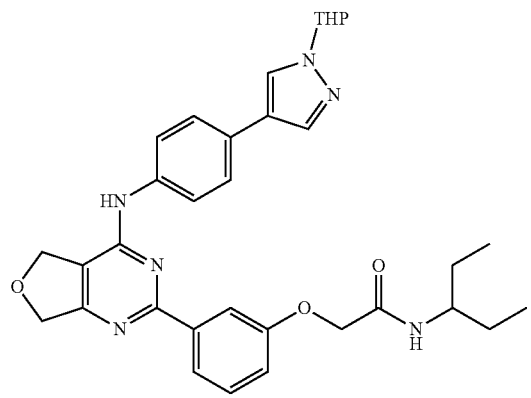

To the mixture of N-(pentan-3-yl)-2-(3-(4,4,5,5-tetramethyl-1,3,2-dioxaborolan-2-yl)phenoxy)acetamide (400.00 mg, 1.15 mmol) and 2-chloro-N-(4-(1-(tetrahydro-2H-pyran-2-yl)-1H-pyrazol-4-yl)phenyl)-5,7-dihydrofuro[3,4-d]pyrimidin-4-amine (434.66 mg, 1.09 mmol) in dioxane (15.00 mL) and H$_2$O (1.50 mL) was added K$_2$CO$_3$ (317.88 mg, 2.30 mmol), Pd(dppf)Cl$_2$ (84.15 mg, 115.00 umol). The mixture was stirred under N$_2$ at 100° C. for 6 h. TLC (petroleum ether/EtOAc=1:2, Rf=0.51) detected one new main spot. The mixture (two small experiments were combined together) was cooled to room temperature, diluted with water (40 mL) and the mixture was extracted with EtOAc (40 mL×3). The combined organic layers were washed with brine (40 mL×2), dried over Na$_2$SO$_4$, filtered and concentrated under reduced pressure to give a residue. The residue was purified by column chromatography (SiO$_2$, petroleum ether/EtOAc=1:0 to 1:1) to give the title compound (690 mg) as a yellow solid. $^1$H NMR (400 MHz, DMSO-d$_6$) δ 9.24 (s, 1H), 8.34 (s, 1H), 7.97-7.95 (m, 3H), 7.83-7.80 (m, 2H), 7.68-7.62 (m, 5H), 7.42-7.40 (m, 1H), 7.10 (d, J=8.0 Hz, 1H), 5.40 (d, J=9.6 Hz, 1H), 5.08 (s, 2H), 4.93 (s, 2H), 4.58 (s, 2H), 3.96-3.93 (m, 1H), 3.68-3.58 (m, 2H), 2.16-2.10 (m, 1H), 1.97-1.92 (m, 2H), 1.71-1.66 (m, 1H), 1.57-1.52 (m, 2H), 1.48-1.36 (m, 1H), 0.78 (t, J=7.4 Hz, 6H).

Example 76E 2-(3-(4-((4-(1H-pyrazol-4-yl)phenyl)amino)-5,7-dihydrofuro[3,4-d]pyrimidin-2-yl)phenoxy)-N-(pentan-3-yl)acetamide

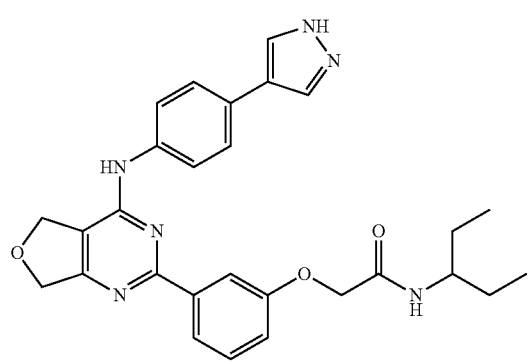 [SMILES: CCC(CC)NC(=O)COc1cccc(-c2nc3c(c(Nc4ccc(-c5cn[nH]c5)cc4)n2)COC3)c1]

To a mixture of N-(pentan-3-yl)-2-(3-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)acetamide (590.00 mg, 1.01 mmol) in CH₂Cl₂ (4.00 mL) was added HCl/dioxane (4 M, 6.00 mL). The mixture was stirred at 30° C. for 2.5 h. LCMS showed about 87% of desired product and 2% of starting material. The mixture was concentrated under reduced pressure to give a residue. The residue (about 100 mg crude product was used together) was purified by prep-HPLC (FA conditions). But HNMR showed the product contained some MeCN. The product was suspended in distilled water and the mixture was stirred at 95° C. for 16 h and collected by filtration. The product was resuspended in water and stirred at 120° C. for another 16 h and was lyophilized to provide the title compound (195 mg) as an off-white solid. $^1$H NMR (400 MHz, DMSO-$d_6$) δ 9.22 (s, 1H), 8.17 (s, 1H), 7.97-7.92 (m, 3H), 7.81-7.74 (m, 3H), 7.65 (d, J=8.4 Hz, 2H), 7.42 (t, J=8.0 Hz, 1H), 7.10-7.08 (m, 1H), 5.07 (s, 2H), 4.93 (s, 2H), 4.58 (s, 2H), 3.65-3.61 (m, 1H), 1.47-1.34 (m, 4H), 0.78 (t, J=7.4 Hz, 6H).

Example 76F 2-(3-(4-((4-(1H-pyrazol-4-yl)phenyl)amino)-5,7-dihydrofuro[3,4-d]pyrimidin-2-yl)phenoxy)-N-(pentan-3-yl)acetamide dihydrochloride

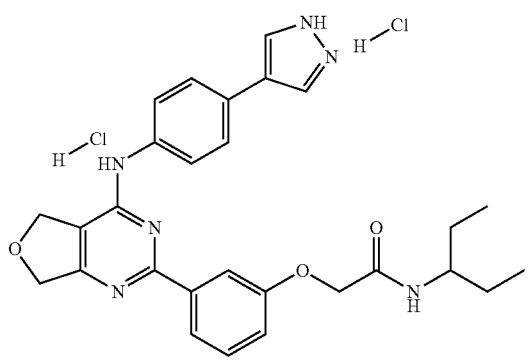

To the mixture of 2-(3-(4-((4-(1H-pyrazol-4-yl)phenyl)amino)-5,7-dihydrofuro[3,4-d]pyrimidin-2-yl)phenoxy)-N-(pentan-3-yl)acetamide (195.00 mg, 391.11 umol) in THF (300.00 mL) was added HCl/dioxane (4 M, 488.89 uL). The mixture was stirred at 18° C. for 16 h. Precipitates formed after the addition of HCl/dioxane. A small amount of mixture was concentrated under reduce pressure to provide a residue. HNMR showed the product was HCl salt. Deion water (20 mL) was added to the mixture. The resulting mixture was concentrated under reduce pressure to remove the organic solvent. To the mixture was added deion water (60 mL). The mixture was lyophilized to give the product as yellow solid. HNMR showed the product contained some organic solvents. The product was redissolved with deion water (50 mL) and CH₂Cl₂ (50 mL). The mixture was stirred at 18° C. for 13 h. Three layers were observed after standing for 30 min. Lactescence in middle layer was lyophilized to afford the title compound (135.1 mg) as a yellow solid. $^1$H NMR (400 MHz, DMSO-$d_6$) δ 9.54 (s, 1H), 8.11 (s, 2H), 7.94 (s, 2H), 7.82-7.76 (m, 3H), 7.68 (d, J=8.4 Hz, 2H), 7.45 (t, J=8.0 Hz, 1H), 7.13 (d, J=8.0 Hz, 2H), 5.08 (s, 2H), 4.97 (s, 2H), 4.59 (s, 2H), 3.63-3.61 (m, 1H), 1.47-1.34 (m, 4H), 0.78 (t, J=7.4 Hz, 6H). (ES+) m/e 499.3 (M+H)⁺.

Example 77

2-(3-(4-((4-(1H-pyrazol-4-yl)phenyl)amino)-5,7-dihydrofuro[3,4-d]pyrimidin-2-yl)phenoxy)-N-(sec-butyl)acetamide

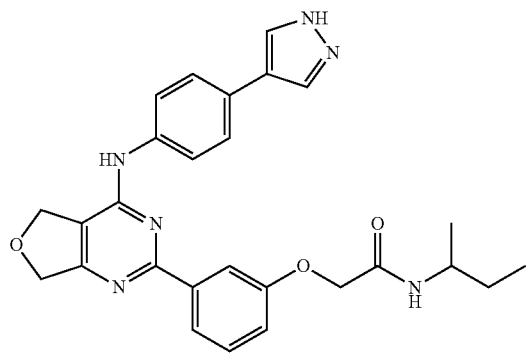 [SMILES: CCC(C)NC(=O)COc1cccc(-c2nc3c(c(Nc4ccc(-c5cn[nH]c5)cc4)n2)COC3)c1]

Example 77A

N-(sec-butyl)-2-chloroacetamide

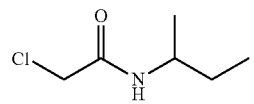

To the mixture of 2-methylpropan-1-amine (1.94 g, 26.57 mmol, 2.70 mL) and TEA (5.38 g, 53.12 mmol, 7.37 mL) in CH₂Cl₂ (30.00 mL) was added dropwise 2-chloroacetyl chloride (2.00 g, 17.71 mmol, 1.41 mL) at 0° C. The mixture was stirred at 28° C. for 2 h. TLC (petroleum ether/EtOAc=2:1, Rf=0.7) detected one new main spot. The mixture was diluted with CH₂Cl₂ (30 mL) and washed with water (40 mL×2), citric acid (10%, 40 mL×2), NaHCO₃ (40 mL×2), brine (40 mL×2). The organic layer was dried over Na₂SO₄, filtered and concentrated under reduced pressure to give the title compound (2.60 g, crude) as a black oil and used for the next step reaction without further purification. $^1$H NMR (400 MHz, DMSO-$d_6$) δ 8.00-7.98 (m, 1H), 4.00 (s, 2H), 3.71-3.61 (m, 1H), 1.43-1.36 (m, 2H), 1.03 (d, J=6.8 Hz, 3H), 0.82 (t, J=7.4 Hz, 3H).

Example 77B

N-(sec-butyl)-2-(3-(4,4,5,5-tetramethyl-1,3,2-dioxaborolan-2-yl)phenoxy)acetamide

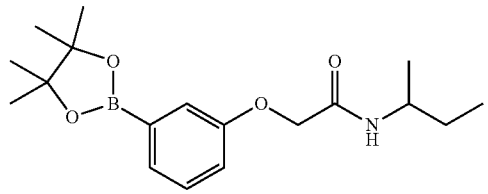 [SMILES: CCC(C)NC(=O)COc1cccc(B2OC(C)(C)C(C)(C)O2)c1]

To the mixture of 3-(4,4,5,5-tetramethyl-1,3,2-dioxaborolan-2-yl)phenol (1.00 g, 4.54 mmol) and N-(sec-butyl)-2-chloroacetamide (815.85 mg, 5.45 mmol) in MeCN (30.00 mL) was added K$_2$CO$_3$ (1.25 g, 9.08 mmol). The mixture was stirred at 70° C. for 16 h. TLC (petroleum ether/EtOAc=3:1, Rf=0.51) detected one new main spot. The reaction mixture was cooled to room temperature, diluted with water (30 mL) and the mixture was extracted with EtOAc (30 mL×3). The combined organic layers were dried over Na$_2$SO$_4$, filtered and concentrated under reduced pressure to give a residue. The residue was purified by column chromatography (SiO$_2$, petroleum ether/EtOAc=100:1 to 5:1) to give the title compound (481 mg, 32%) as a light yellow solid. $^1$H NMR (400 MHz, DMSO-d$_6$) δ 7.84-7.81 (m, 1H), 7.33-7.25 (m, 2H), 7.22-7.21 (m, 1H), 7.08-7.06 (m, 1H), 4.46 (s, 2H), 3.80-3.73 (m, 1H), 1.46-1.38 (m, 2H), 1.28 (s, 12H), 1.08-1.06 (m, 3H), 0.80 (t, J=7.4 Hz, 3H).

Example 77C tert-butyl 4-(4-((tert-butoxycarbonyl)(2-(3-(2-(sec-butylamino)-2-oxoethoxy)phenyl)-5,7-dihydrofuro[3,4-d]pyrimidin-4-yl)amino)phenyl)-1H-pyrazole-1-carboxylate

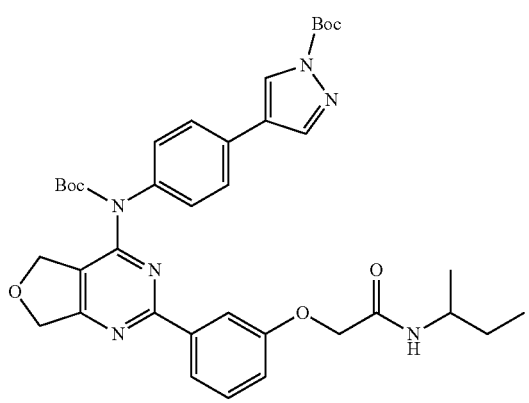 [SMILES: CCC(C)NC(=O)COc1cccc(-c2nc3c(c(N(C(=O)OC(C)(C)C)c4ccc(-c5cnn(C(=O)OC(C)(C)C)c5)cc4)n2)COC3)c1]

To the mixture of N-(sec-butyl)-2-(3-(4,4,5,5-tetramethyl-1,3,2-dioxaborolan-2-yl)phenoxy)acetamide (150.00 mg, 450.14 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (210.33 mg, 409.22 umol) in dioxane (3.00 mL), H$_2$O (300.00 uL) was added K$_2$CO$_3$ (113.12 mg, 818.44 umol) and Pd(dppf)Cl$_2$ (29.94 mg, 40.92 umol). The mixture was stirred under N$_2$ at 100° C. for 16 h. TLC (petroleum ether/EtOAc=1:2, Rf=0.35) detected one main new spot. The reaction mixture was cooled to room temperature, water (30 mL) was added and the mixture was extracted with EtOAc (30 mL×3). The combined organic layers were dried over Na$_2$SO$_4$, filtered and concentrated under reduced pressure to give a residue. The residue was purified by prep-TLC (petroleum ether/EtOAc=1:2) to give the title compound (190 mg, mono-Boc product) as a light yellow solid. $^1$H NMR (400 MHz, DMSO-d$_6$) δ 12.98 (s, 1H), 8.24 (s, 1H), 7.84 (s, 1H), 7.81-7.75 (m, 3H), 7.66 (d, J=8.8 Hz, 2H), 7.36-7.34 (m, 1H), 7.29-7.27 (m, 2H), 7.07-7.06 (m, 1H), 5.03 (s, 2H), 4.86 (s, 2H), 4.47 (s, 2H), 3.79-3.72 (m, 1H), 1.55-1.37 (m, 11H), 1.04 (d, J=6.8 Hz, 3H), 0.80-0.76 (m, 3H).

Example 77D 2-(3-(4-((4-(1H-pyrazol-4-yl)phenyl)amino)-5,7-dihydrofuro[3,4-d]pyrimidin-2-yl)phenoxy)-N-(sec-butyl)acetamide

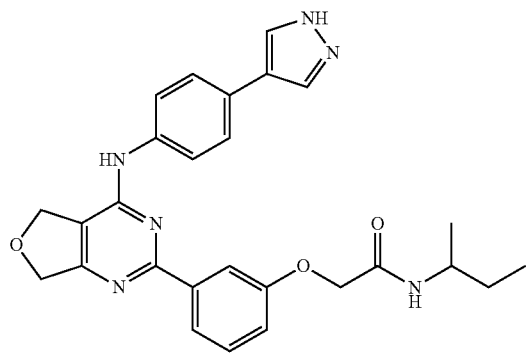 [SMILES: CCC(C)NC(=O)COc1cccc(-c2nc3c(c(Nc4ccc(-c5cn[nH]c5)cc4)n2)COC3)c1]

To a mixture of tert-butyl 4-(4-((tert-butoxycarbonyl)(2-(3-(2-(sec-butylamino)-2-oxoethoxy)phenyl)-5,7-dihydrofuro[3,4-d]pyrimidin-4-yl)amino)phenyl)-1H-pyrazole-1-carboxylate (mono-Boc product, 190.00 mg) in CH$_2$Cl$_2$ (6.00 mL) was added HCl/dioxane (4 M, 3.00 mL). The mixture was stirred at 28° C. for 11 h. LCMS showed about 58% of desired product and about 31% of starting material. To the mixture was added additional HCl/dioxane (4 M, 2 mL) and the mixture was stirred at 28° C. for another 5 h. LCMS showed about 75% of desired product and about 15% of starting material. The mixture was concentrated under reduced pressure to give a residue. The residue was purified by prep-HPLC (FA conditions) to give the title compound (27.30 mg, 17%) as a white solid. $^1$H NMR (400 MHz, DMSO-d$_6$) δ 12.90 (s, 1H), 9.22 (s, 1H), 8.17 (s, 1H), 7.97-7.79 (m, 4H), 7.80 (d, J=8.8 Hz, 2H), 7.65 (d, J=8.8 Hz, 2H), 7.42 (t, J=8.0 Hz, 1H), 7.10-7.08 (m, 1H), 5.07 (s, 2H), 4.93 (s, 2H), 4.55 (s, 2H), 3.83-3.78 (m, 1H), 1.44-1.40 (m, 1H), 1.06 (d, J=6.4 Hz, 3H), 0.79 (t, J=7.4 Hz, 3H). (ES+) m/e 485.2 (M+H)$^+$.

Example 78

2-(3-(4-((4-(1H-pyrazol-4-yl)phenyl)amino)-5,7-dihydrofuro[3,4-d]pyrimidin-2-yl)phenoxy)-N-isobutylacetamide

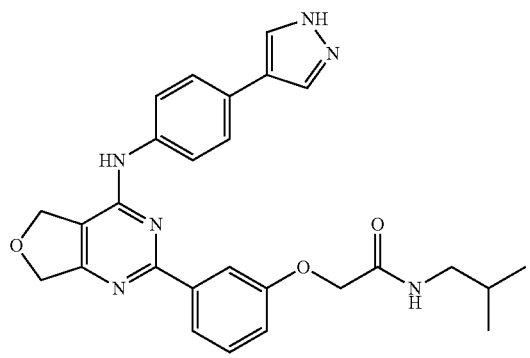 [SMILES: CC(C)CNC(=O)COc1cccc(-c2nc3c(c(Nc4ccc(-c5cn[nH]c5)cc4)n2)COC3)c1]

Example 78A 2-chloro-N-isobutylacetamide

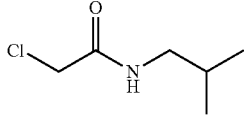

To the mixture of 2-methylpropan-1-amine (1.94 g, 26.57 mmol, 2.63 mL) and TEA (5.38 g, 53.12 mmol, 7.37 mL) in CH$_2$Cl$_2$ (30.00 mL) was added 2-chloroacetyl chloride (2.00 g, 17.71 mmol, 1.41 mL) dropwise at 0° C. The mixture was stirred at 28° C. for 2 h. TLC (petroleum ether/EtOAc=2:1, Rf=0.7) showed one new main spot. The mixture was diluted with CH$_2$Cl$_2$ (30 mL) and washed with water (40 mL×2), citric acid (10%, 40 mL×2), sat.NaHCO$_3$ (40 mL×2), brine (40 mL×2). The organic layer was dried over Na$_2$SO$_4$, filtered and concentrated under reduced pressure to give the title compound (1.83 g, crude) as a black oil which was used in the next step without further purification. $^1$H NMR (400 MHz, DMSO-d$_6$) δ 8.18-8.07 (m, 1H), 4.04 (s, 2H), 2.91 (t, J=6.4 Hz, 2H), 1.73-1.67 (m, 1H), 0.83 (t, J=6.0 Hz, 6H).

Example 78B

N-isobutyl-2-(3-(4,4,5,5-tetramethyl-1,3,2-dioxaborolan-2-yl)phenoxy)acetamide

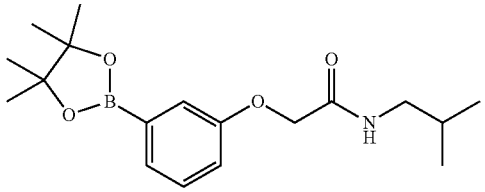 [SMILES: CC(C)CNC(=O)COc1cccc(B2OC(C)(C)C(C)(C)O2)c1]

To the mixture of 3-(4,4,5,5-tetramethyl-1,3,2-dioxaborolan-2-yl)phenol (1.00 g, 4.54 mmol) and 2-chloro-N-isobutylacetamide (815.13 mg, 5.45 mmol) in MeCN (30.00 mL) was added K$_2$CO$_3$ (1.25 g, 9.08 mmol). The mixture was stirred at 70° C. for 16 h. The reaction mixture was cooled to room temperature. Water (30 mL) was added and the mixture was extracted with EtOAc (30 mL×3). The combined organic layers were dried over Na$_2$SO$_4$, filtered and concentrated under reduced pressure to give a residue. The residue was purified by column chromatography (SiO$_2$, petroleum ether/EtOAc=100:1 to 5:1) to give the title compound (540 mg, 36%) as a light yellow solid. $^1$H NMR (400 MHz, DMSO-d$_6$) δ 8.08-8.05 (m, 1H), 7.33-7.26 (m, 2H), 7.22 (d, J=2.4 Hz, 1H), 7.09 (d, J=1.6 Hz, 1H), 4.48 (s, 2H), 2.96-2.91 (m, 2H), 1.76-1.67 (m, 1H), 1.29 (s, 12H), 0.82 (t, J=5.4 Hz, 6H).

Example 78C tert-butyl 4-(4-((tert-butoxycarbonyl)(2-(3-(2-(isobutylamino)-2-oxoethoxy)phenyl)-5,7-dihydrofuro[3,4-d]pyrimidin-4-yl)amino)phenyl)-1H-pyrazole-1-carboxylate

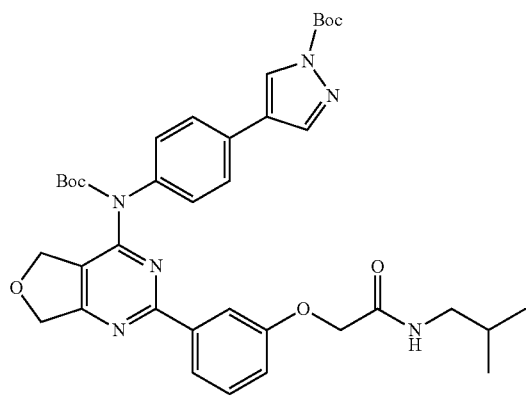 [SMILES: CC(C)CNC(=O)COc1cccc(-c2nc3c(c(N(C(=O)OC(C)(C)C)c4ccc(-c5cnn(C(=O)OC(C)(C)C)c5)cc4)n2)COC3)c1]

To the mixture of N-isobutyl-2-(3-(4,4,5,5-tetramethyl-1,3,2-dioxaborolan-2-yl)phenoxy)acetamide (200.00 mg, 600.19 umol), tert-butyl 4-(4-((tert-butoxycarbonyl)(2-chloro-5,7-dihydrofuro[3,4-d]pyrimidin-4-yl)amino)phenyl)-1H-pyrazole-1-carboxylate (280.44 mg, 545.63 umol) in dioxane (3.00 mL), H$_2$O (300.00 uL) was added K$_2$CO$_3$ (150.82 mg, 1.09 mmol) and Pd(dppf)Cl$_2$ (39.92 mg, 54.56 umol). The mixture was stirred under N$_2$ at 100° C. for 16 h. TLC (petroleum ether/EtOAc=1:2, Rf=0.35, 0.62) detected two main spots. The reaction mixture was cooled to room temperature. Water (30 mL) was added and the mixture was extracted with EtOAc (30 mL×3). The combined organic layers were dried over Na$_2$SO$_4$, filtered and concentrated under reduced pressure to give a residue. The residue was purified by prep-TLC (petroleum ether/EtOAc=1:2) to give the title compouund (65.00 mg, mono-Boc product: 136 mg) as a white solid. $^1$H NMR (400 MHz, DMSO-d$_6$) δ 12.98 (s, 1H), 8.24 (s, 1H), 8.10 (s, 1H), 7.97 (s, 1H), 7.82-7.76 (m, 2H), 7.70-7.66 (m, 2H), 7.37-7.33 (m, 2H), 7.29-7.27 (m, 1H), 7.09-7.06 (m, 1H), 5.03 (s, 2H), 4.91-4.86 (m, 2H), 4.49 (d, J=1.2 Hz, 2H), 2.98-2.92 (m, 2H), 1.76-1.66 (m, 1H), 1.43 (m, 4H), 0.80-0.79 (m, 6H).

Example 78D 2-(3-(4-((4-(1H-pyrazol-4-yl)phenyl)amino)-5,7-dihydrofuro[3,4-d]pyrimidin-2-yl)phenoxy)-N-isobutylacetamide

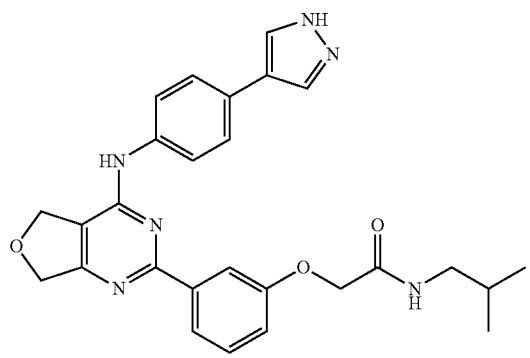 [SMILES: CC(C)CNC(=O)COc1cccc(-c2nc3c(c(Nc4ccc(-c5cn[nH]c5)cc4)n2)COC3)c1]

To a mixture of compound tert-butyl 4-(4-((tert-butoxycarbonyl)(2-(3-(2-(isobutylamino)-2-oxoethoxy)phenyl)-5,7-dihydrofuro[3,4-d]pyrimidin-4-yl)amino)phenyl)-1H-pyrazole-1-carboxylate (65 mg, 136 mg of mono-Boc product was used together) in CH$_2$Cl$_2$ (6.00 mL) was added HCl/dioxane (4 M, 3.00 mL). The mixture was stirred at 28° C. for 11 h. The mixture was concentrated under reduced pressure to give a residue. The residue was suspended with sat.NaHCO$_3$ (20 mL) and the mixture was extracted with EtOAc (30 mL×3). The organic layers were dried over Na$_2$SO$_4$, filtered and concentrated under reduced pressure to give a residue. The residue was purified by prep-HPLC (FA conditions) to afford the title compound (9.00 mg, 8%) as a white solid. $^1$H NMR (400 MHz, DMSO-d$_6$) δ 12.92 (s, 1H), 9.25 (s, 1H), 8.15-7.95 (m, 5H), 7.80 (d, J=8.8 Hz, 2H), 7.65 (d, J=8.4 Hz, 2H), 7.42 (d, J=8.0 Hz, 1H), 7.09 (d, J=6.4 Hz, 1H), 5.07 (s, 2H), 4.93 (s, 2H), 4.57 (s, 2H), 2.96 (t, J=6.4 Hz, 2H), 1.78-1.70 (m, 1H), 0.80 (d, J=6.8 Hz, 6H). (ES+) m/e 485.2 (M+H)$^+$.

Example 79

2-(3-(4-((4-(1H-pyrazol-4-yl)phenyl)amino)-5,7-dihydrofuro[3,4-d]pyrimidin-2-yl)phenoxy)-N-neopentylacetamide

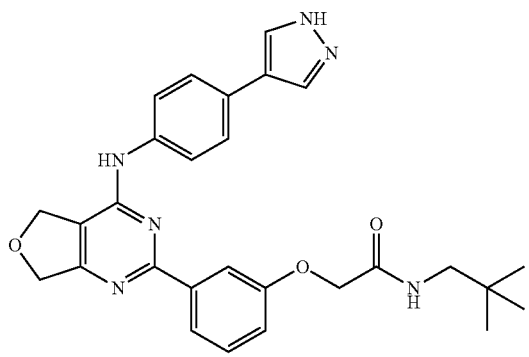 [SMILES: CC(C)(C)CNC(=O)COc1cccc(-c2nc3c(c(Nc4ccc(-c5cn[nH]c5)cc4)n2)COC3)c1]

Example 79A 2-chloro-N-neopentylacetamide

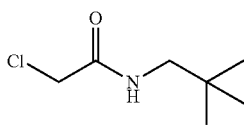

To a mixture of 2,2-dimethylpropan-1-amine (2.32 g, 26.57 mmol) and TEA (5.38 g, 53.12 mmol, 7.37 mL) in CH$_2$Cl$_2$ (30.00 mL) was added 2-chloroacetyl chloride (2.00 g, 17.71 mmol, 1.41 mL) dropwise at 0° C. The mixture was stirred at 25° C. for 2 h. The mixture was diluted with CH$_2$Cl$_2$ (30 mL) and washed with water (40 mL×2), citric acid (10%, 40 mL×2), sat.NaHCO$_3$ (40 mL×2), brine (40 mL×2). The organic layer was dried over Na$_2$SO$_4$, filtered and concentrated under reduced pressure to give the crude product (2.34 g, crude) as a black oil which was used in the next step reaction without further purification. $^1$H NMR (400 MHz, DMSO-d$_6$) δ 8.08 (s, 1H), 4.06 (s, 2H), 2.96-2.91 (m, 2H), 0.84 (s, 9H).

Example 79B

N-neopentyl-2-(3-(4,4,5,5-tetramethyl-1,3,2-dioxaborolan-2-yl)phenoxy)acetamide

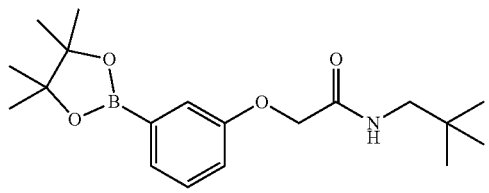 [SMILES: CC(C)(C)CNC(=O)COc1cccc(B2OC(C)(C)C(C)(C)O2)c1]

To the mixture of 2-chloro-N-neopentylacetamide (800.00 mg, 4.89 mmol) and 3-(4,4,5,5-tetramethyl-1,3,2-dioxaborolan-2-yl)phenol (978.01 mg, 4.45 mmol) in MeCN (20.00 mL) was added K$_2$CO$_3$ (1.23 g, 8.89 mmol). The mixture was stirred at 70° C. for 16 h. TLC (petroleum ether/EtOAc=3:1, Rf=0.55) showed one new main spot was detected. The reaction mixture was diluted with water (30 mL) and the mixture was extracted with EtOAc (30 mL×3). The combined organic layers were dried over Na$_2$SO$_4$, filtered and concentrated under reduced pressure to give a residue. The residue was purified by column chromatography (SiO$_2$, petroleum ether/EtOAc=1:1 to 5:1) to give the title compound (615 mg, 40%) as a yellow solid. $^1$H NMR (400 MHz, DMSO-d$_6$) δ 7.96-7.92 (m, 1H), 7.33-7.26 (m, 2H), 7.20 (d, J=2.4 Hz, 1H), 7.08 (d, J=8.0 Hz, 1H), 4.53 (s, 2H), 2.94-2.91 (m, 2H), 1.28 (s, 12H), 0.80 (s, 9H).

Example 79C tert-butyl 4-(4-((tert-butoxycarbonyl)(2-(3-(2-(neopentylamino)-2-oxoethoxy)phenyl)-5,7-dihydrofuro[3,4-d]pyrimidin-4-yl)amino)phenyl)-1H-pyrazole-1-carboxylate

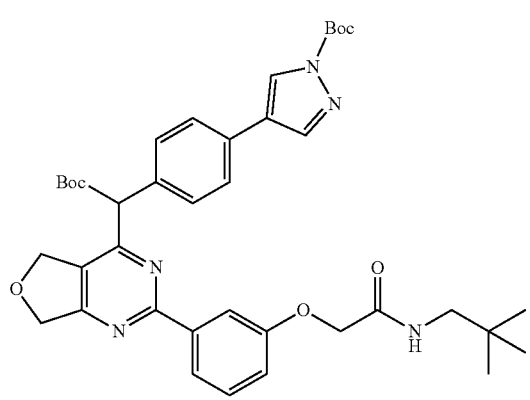 [SMILES: CC(C)(C)CNC(=O)COc1cccc(-c2nc3c(c(C(C(=O)OC(C)(C)C)c4ccc(-c5cnn(C(=O)OC(C)(C)C)c5)cc4)n2)COC3)c1]

To the mixture of N-neopentyl-2-(3-(4,4,5,5-tetramethyl-1,3,2-dioxaborolan-2-yl)phenoxy)acetamide (200.00 mg, 600.19 umol), tert-butyl 4-(4-((tert-butoxycarbonyl)(2-chloro-5,7-dihydrofuro[3,4-d]pyrimidin-4-yl)amino)phenyl)-1H-pyrazole-1-carboxylate (296.01 mg, 575.94 umol) in dioxane (3.00 mL), H₂O (300.00 uL) was added K₂CO₃ (159.20 mg, 1.15 mmol) and Pd(dppf)Cl₂ (42.14 mg, 57.59 umol). The mixture was stirred under N₂ at 100° C. for 16 h. TLC (petroleum ether/EtOAc=1:1.5, Rf=0.32, 0.78) detected two main spots (desired product and mono-Boc product). The reaction mixture was diluted with (30 mL) and the mixture was extracted with EtOAc (30 mL×3). The combined organic layers were dried over Na₂SO₄, filtered and concentrated under reduced pressure to give a residue. The residue was purified by prep-TLC (petroleum ether/EtOAc=1:2) to give the title compound (56.00 mg, mono-Boc: 122 mg) as a white solid.

Example 79D 2-(3-(4-((4-(1H-pyrazol-4-yl)phenyl)amino)-5,7-dihydrofuro[3,4-d]pyrimidin-2-yl)phenoxy)-N-neopentylacetamide

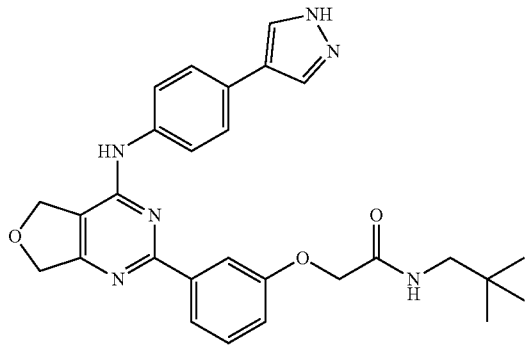 [SMILES: CC(C)(C)CNC(=O)COc1cccc(-c2nc3c(c(Nc4ccc(-c5cn[nH]c5)cc4)n2)COC3)c1]

To a mixture of tert-butyl 4-(4-((tert-butoxycarbonyl)(2-(3-(2-(neopentylamino)-2-oxoethoxy)phenyl)-5,7-dihydrofuro[3,4-d]pyrimidin-4-yl)amino)phenyl)-1H-pyrazole-1-carboxylate (56 mg, 122.00 mg of mono-Boc product was used together) in CH₂Cl₂ (4.00 mL) was added HCl/dioxane (4 M, 3.5 mL). The mixture was stirred at 25° C. for 17 h. LCMS showed 46% of desired product and 45% of starting material. To the mixture was added additional amount of HCl/dioxane (4M, 2 mL). The mixture was stirred at 25° C. for another 21 h. LCMS about 50% of desired product and about 37% of starting material. To the mixture was added HCl/dioxane (4M, 4 mL), then the mixture was stirred at 25° C. for another 3 h. LCMS showed 49% of desired product and 36% of starting material. The mixture was concentrated under reduced pressure to give a residue. The residue was purified by prep-HPLC (FA conditions) to give the title compound (19.50 mg, 13%) as an off-white solid. ¹H NMR (400 MHz, DMSO-d₆) δ 12.91 (s, 1H), 9.24 (s, 1H), 8.15 (s, 1H), 7.98-7.95 (m, 4H), 7.80 (d, J=8.8 Hz, 2H), 7.42 (d, J=8.2 Hz, 1H), 7.09 (d, J=8.8 Hz, 1H), 5.07 (s, 2H), 4.93 (s, 2H), 4.62 (s, 2H), 2.96 (d, J=6.0 Hz, 2H), 0.80 (s, 9H). (ES+) m/e 499.2 (M+H)⁺.

Example 80

N-(3-(4-((4-(1H-pyrazol-4-yl)phenyl)amino)-5,7-dihydrofuro[3,4-d]pyrimidin-2-yl)phenyl)-5-methoxynicotinamide

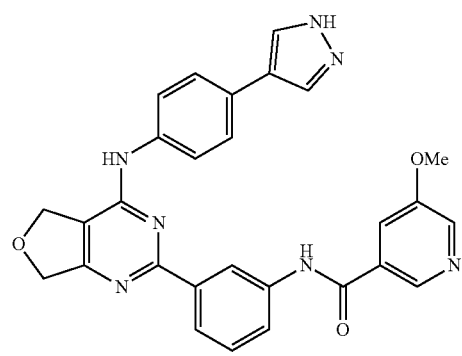 [SMILES: COc1cncc(C(=O)Nc2cccc(-c3nc4c(c(Nc5ccc(-c6cn[nH]c6)cc5)n3)COC4)c2)c1]

Example 80A 5-methoxy-N-(3-(4,4,5,5-tetramethyl-1,3,2-dioxaborolan-2-yl)phenyl)nicotinamide

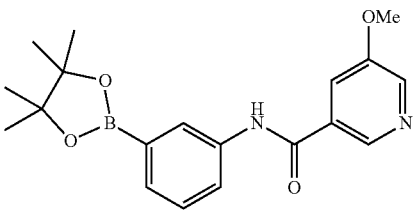 [SMILES: COc1cncc(C(=O)Nc2cccc(B3OC(C)(C)C(C)(C)O3)c2)c1]

A mixture of 3-(4,4,5,5-tetramethyl-1,3,2-dioxaborolan-2-yl)aniline (300.00 mg, 1.37 mmol), compound 5-methoxynicotinic acid (220.29 mg, 1.44 mmol) and HATU (781.37 mg, 2.06 mmol) in DMF (5.00 mL) was stirred for 10 min. To the mixture was added DIPEA (354.12 mg, 2.74 mmol, 478.54 uL). Then the mixture was stirred at 28° C. for 16 h. TLC (petroleum ether/EtOAc=1:1, Rf=0.55) detected one new main spot. The mixture was diluted with water (20 mL) and the mixture was extracted with EtOAc (30 mL×3). The organic layer was dried over Na₂SO₄, filtered and concentrated under reduced pressure to give a residue. The residue was purified by column chromatography (SiO₂, petroleum ether/EtOAc=50:1 to 3:1) to give the title compound (426 mg, 88%) as a light yellow solid. ¹H NMR (400 MHz, DMSO-d6) δ 10.39 (s, 1H), 8.73 (s, 1H), 8.47 (d, J=2.4 Hz, 1H), 8.08 (s, 1H), 7.98-7.95 (m, 1H), 7.88-7.87 (m, 1H), 7.44-7.39 (m, 2H), 3.92 (s, 3H), 1.31 (s, 12H).

Example 80B tert-butyl 4-(4-((tert-butoxycarbonyl)(2-(3-(5-methoxynicotinamido)phenyl)-5,7-dihydrofuro[3,4-d]pyrimidin-4-yl)amino)phenyl)-1H-pyrazole-1-carboxylate

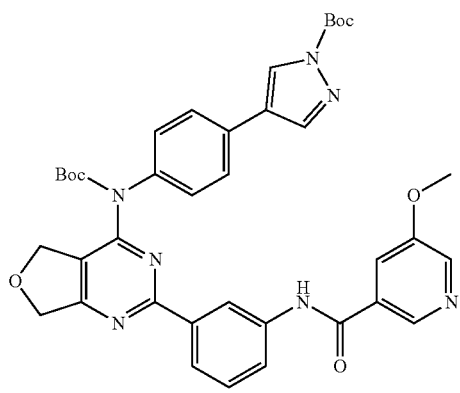 [SMILES: COc1cncc(C(=O)Nc2cccc(-c3nc4c(c(N(C(=O)OC(C)(C)C)c5ccc(-c6cnn(C(=O)OC(C)(C)C)c6)cc5)n3)COC4)c2)c1]

To a mixture of 5-methoxy-N-(3-(4,4,5,5-tetramethyl-1,3,2-dioxaborolan-2-yl)phenyl)nicotinamide (110.00 mg, 310.55 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (159.61 mg, 310.55 umol) in dioxane (3.00 mL), H$_2$O (300.00 uL) were added K$_2$CO$_3$ (85.84 mg, 621.10 umol) and Pd(dppf)Cl$_2$ (22.72 mg, 31.06 umol). The mixture was stirred under N$_2$ at 100° C. for 16 h. TLC (petroleum ether/EtOAc=0:1, Rf=0.55) detected one new main spot. The mixture was cooled to room temperature and diluted with water (30 mL). The mixture was extracted with EtOAc (30 mL×3). The organic layers were dried over Na$_2$SO$_4$, filtered and concentrated under reduced pressure to give a residue. The residue was purified by prep-TLC (petroleum ether/EtOAc=0:1) to give the tile compound (mono-Boc product, 95 mg, 50%) as a white solid. $^1$H NMR (400 MHz, DMSO-d$_6$) δ 12.98 (s, 1H), 10.56 (s, 1H), 8.74 (s, 2H), 8.50-8.49 (m, 1H), 8.25 (s, 1H), 7.96-7.89 (m, 4H), 7.68-7.66 (m, 2H), 7.46-7.42 (m, 1H), 7.30-7.28 (m, 2H), 5.06 (s, 2H), 4.84 (s, 2H), 3.92 (s, 3H), 1.44 (s, 9H).

Example 80C

N-(3-(4-((4-(1H-pyrazol-4-yl)phenyl)amino)-5,7-dihydrofuro[3,4-d]pyrimidin-2-yl)phenyl)-5-methoxynicotinamide

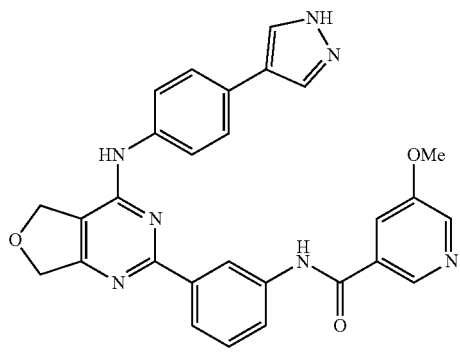 [SMILES: COc1cncc(C(=O)Nc2cccc(-c3nc4c(c(Nc5ccc(-c6cn[nH]c6)cc5)n3)COC4)c2)c1]

To a mixture of tert-butyl 4-(4-((tert-butoxycarbonyl)(2-(3-(5-methoxynicotinamido)phenyl)-5,7-dihydrofuro[3,4-d]pyrimidin-4-yl)amino)phenyl)-1H-pyrazole-1-carboxylate (95.00 mg, mono-Boc product) in CH$_2$Cl$_2$ (6.00 mL) was added TFA (2.00 mL). The mixture was stirred at 28° C. for 2 h. LCMS showed about 67% of desired product formed. The residue was concentrated under reduced pressure to give a residue. The residue was diluted with 2 M NaOH solution (20 mL) and the mixture was extracted with EtOAc (30 mL×3). The organic layers were dried over Na$_2$SO$_4$, filtered and concentrated under reduced pressure to give a residue. The residue was purified by prep-HPLC (FA conditions) to give the title compound (3.9 mg, 5%) as a light yellow solid. $^1$H NMR (400 MHz, DMSO-d$_6$) δ 10.60 (s, 1H), 9.27 (s, 1H), 8.86-8.78 (m, 2H), 8.49 (s, 1H), 8.35 (s, 1H), 8.11-7.85 (m, 7H), 7.66 (d, J=8.4 Hz, 2H), 7.51 (t, J=7.8 Hz, 1H), 5.08 (s, 2H), 4.95 (s, 2H), 3.93 (s, 3H). (ES+) m/e 506.2 (M+H)$^+$.

Example 81

2-(3-(4-((4-(1H-pyrazol-4-yl)phenyl)amino)-5,7-dihydrofuro[3,4-d]pyrimidin-2-yl)phenoxy)-N-(tert-pentyl)acetamide

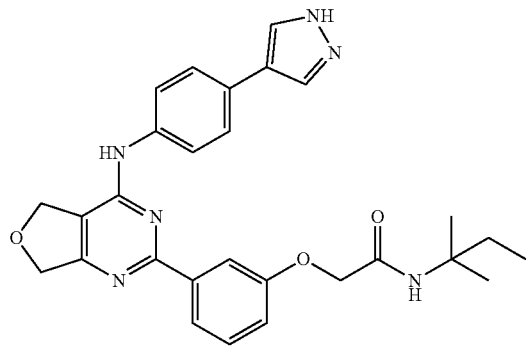 [SMILES: CCC(C)(C)NC(=O)COc1cccc(-c2nc3c(c(Nc4ccc(-c5cn[nH]c5)cc4)n2)COC3)c1]

Example 81A 2-chloro-N-(tert-pentyl)acetamide

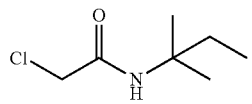

To a mixture of 2-methylbutan-2-amine (1.39 g, 15.94 mmol, 1.85 mL) and TEA (2.69 g, 26.56 mmol, 3.68 mL) in CH$_2$Cl$_2$ (30.00 mL) was added 2-chloroacetyl chloride (1.50 g, 13.28 mmol, 1.06 mL) dropwise at 0° C. The mixture was stirred at 23° C. for 2 h. The mixture was diluted with CH$_2$Cl$_2$ (30 mL) and washed with water (40 mL×2), citric acid (10%, 40 mL×2), NaHCO$_3$ (40 mL×2), brine (40 mL×2). The organic layer was dried over Na$_2$SO$_4$, filtered and concentrated under reduced pressure to give the title compound (1.96 g, crude) as yellow solid which was used in the next step reaction without further purification. $^1$H NMR (400 MHz, DMSO-d$_6$) δ 7.62 (s, 1H), 3.96 (s, 2H), 1.66-1.61 (m, 2H), 1.20 (s, 6H), 0.77 (t, J=7.6 Hz, 3H).

Example 81B

N-(tert-pentyl)-2-(3-(4,4,5,5-tetramethyl-1,3,2-dioxaborolan-2-yl)phenoxy)acetamide

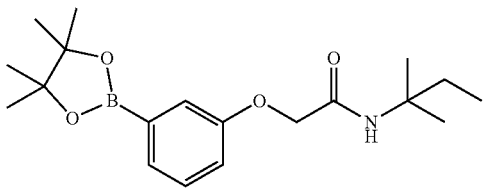 [SMILES: CCC(C)(C)NC(=O)COc1cccc(B2OC(C)(C)C(C)(C)O2)c1]

To the mixture of 2-chloro-N-(tert-pentyl)acetamide (800.00 mg, 4.89 mmol) and 3-(4,4,5,5-tetramethyl-1,3,2-dioxaborolan-2-yl)phenol (896.51 mg, 4.07 mmol) in MeCN (20.00 mL) was added $K_2CO_3$ (1.13 g, 8.15 mmol). The mixture was stirred at 70° C. for 16 h. TLC (petroleum ether/EtOAc=2:1, Rf=0.78) detected one new main spot. The reaction mixture was cooled to room temperature and diluted with water (30 mL). The mixture was extracted with EtOAc (30 mL×3). The combined organic layers were dried over $Na_2SO_4$, filtered and concentrated under reduced pressure to give a residue. The residue was purified by column chromatography ($SiO_2$, petroleum ether/EtOAc=1:1 to 8:1) to give the title compound (892 mg) as a yellow oil. $^1$H NMR (400 MHz, DMSO-$d_6$) δ 7.30-7.26 (m, 2H), 7.17-7.16 (m, 1H), 7.09-7.07 (m, 2H), 4.42 (s, 2H), 1.28-1.27 (m, 12H), 1.23 (s, 3H), 1.20 (s, 3H), 0.77 (t, J=7.4 Hz, 3H).

Example 81C tert-butyl (4-(1H-pyrazol-4-yl)phenyl)(2-(3-(2-oxo-2-(tert-pentylamino)ethoxy)phenyl)-5,7-dihydrofuro[3,4-d]pyrimidin-4-yl)carbamate

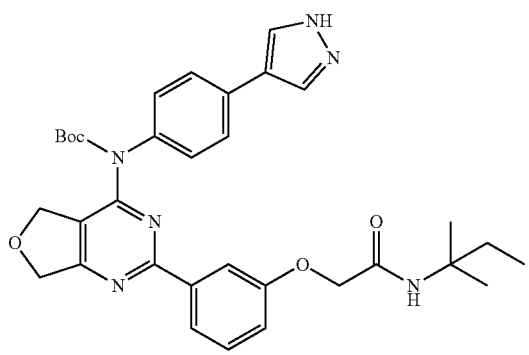 [SMILES: CCC(C)(C)NC(=O)COc1cccc(-c2nc3c(c(N(C(=O)OC(C)(C)C)c4ccc(-c5cn[nH]c5)cc4)n2)COC3)c1]

To the mixture of N-(tert-pentyl)-2-(3-(4,4,5,5-tetramethyl-1,3,2-dioxaborolan-2-yl)phenoxy)acetamide (150.00 mg, 431.95 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (201.83 mg, 392.68 umol) in dioxane (4.00 mL), $H_2O$ (400.00 uL) was added $K_2CO_3$ (108.55 mg, 785.36 umol) and $Pd(dppf)Cl_2$ (28.73 mg, 39.27 umol). The mixture was stirred under $N_2$ at 100° C. for 16 h. TLC (petroleum ether/EtOAc=1:1, Rf=0.34, 0.76) detected two main spots. The reaction mixture was cooled to room temperature and diluted with (20 mL). The resulting mixture was extracted with EtOAc (30 mL×3). The combined organic layers were dried over $Na_2SO_4$, filtered and concentrated under reduced pressure to give a residue. The residue was purified by prep-TLC (petroleum ether/EtOAc=1:1) to give the title compound (68.00 mg, mono-Boc product: 48 mg) as a white solid.

Example 81D 2-(3-(4-((4-(1H-pyrazol-4-yl)phenyl)amino)-5,7-dihydrofuro[3,4-d]pyrimidin-2-yl)phenoxy)-N-(tert-pentyl)acetamide

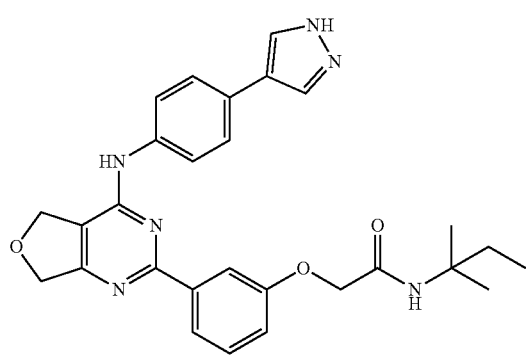 [SMILES: CCC(C)(C)NC(=O)COc1cccc(-c2nc3c(c(Nc4ccc(-c5cn[nH]c5)cc4)n2)COC3)c1]

To a mixture of tert-butyl (4-(1H-pyrazol-4-yl)phenyl)(2-(3-(2-oxo-2-(tert-pentylamino)ethoxy)phenyl)-5,7-dihydrofuro[3,4-d]pyrimidin-4-yl)carbamate (68.00 mg, 48 mg mono-Boc product was used together) in DMF (5.00 mL) and $CH_2Cl_2$ (1.00 mL) was added TFA (15.40 g, 135.06 mmol, 10.00 mL). The mixture was stirred at 25° C. for 16 h. LCMS showed about 34% of desired product and 51% of mono-Boc starting material. The mixture was concentrated under reduced pressure to remove $CH_2Cl_2$. The solution was diluted with sat.$NaHCO_3$ (30 mL) and extracted with EtOAc (30 mL×3). The organic layers were dried over $Na_2SO_4$, filtered and concentrated under reduced pressure to give a residue. The residue was purified by prep-HPLC (FA conditions) to give the title compound (6.8 mg) as a light yellow solid. $^1$H NMR (400 MHz, DMSO-$d_6$) δ 12.93 (s, 1H), 9.24 (s, 1H), 8.04-7.92 (m, 4H), 7.80 (d, J=8.4 Hz, 2H), 7.65 (d, J=8.0 Hz, 2H), 7.43-7.35 (m, 2H), 7.07 (d, J=7.2 Hz, 1H), 5.07 (s, 2H), 4.93 (s, 2H), 4.50 (s, 2H), 1.67-1.64 (m, 2H), 1.23 (s, 6H), 0.75 (t, J=7.2 Hz, 3H). (ES+) m/e 499.2 $(M+H)^+$.

Example 82

2-(3-(4-((4-(1H-pyrazol-4-yl)phenyl)amino)-5,7-dihydrofuro[3,4-d]pyrimidin-2-yl)phenoxy)-N-(3,3-difluorocyclobutyl)acetamide

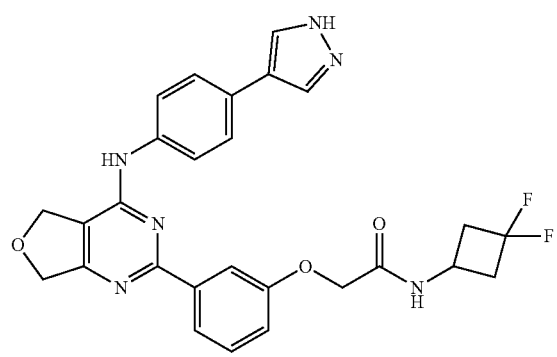 [SMILES: O=C(COc1cccc(-c2nc3c(c(Nc4ccc(-c5cn[nH]c5)cc4)n2)COC3)c1)NC1CC(F)(F)C1]

Example 82A 2-chloro-N-(3,3-difluorocyclobutyl)acetamide

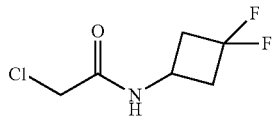 [SMILES: O=C(CCl)NC1CC(F)(F)C1]

To a mixture of 3,3-difluorocyclobutanamine (340.00 mg, 2.37 mmol, HCl) and TEA (456.80 mg, 4.51 mmol, 625.75 uL) in CH$_2$Cl$_2$ (15.00 mL) was added dropwise 2-chloroacetyl chloride (254.92 mg, 2.26 mmol, 179.52 uL) at 0° C. under N$_2$. The mixture was stirred at 23° C. for 2 h, diluted with CH$_2$Cl$_2$ (30 mL), and washed with water (40 mL×2), citric acid (10%, 40 mL×2), NaHCO$_3$ (40 mL×2), brine (40 mL×2). The organic layer was dried over Na$_2$SO$_4$, filtered and concentrated under reduced pressure to give the title compound (318 mg, crude) as a yellow solid and used in the next step reaction without further purification. $^1$H NMR (400 MHz, DMSO-d$_6$) δ 7.62 (s, 1H), 3.96 (s, 2H), 1.66-1.61 (m, 2H), 1.20 (s, 6H), 0.77 (t, J=7.6 Hz, 3H).

Example 82B

N-(3,3-difluorocyclobutyl)-2-(3-(4,4,5,5-tetramethyl-1,3,2-dioxaborolan-2-yl)phenoxy)acetamide

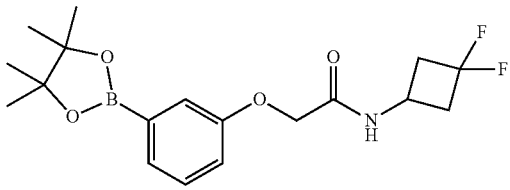 [SMILES: CC1(C)OB(c2cccc(OCC(=O)NC3CC(F)(F)C3)c2)OC1(C)C]

To a mixture of 2-chloro-N-(3,3-difluorocyclobutyl)acetamide (318.00 mg, 1.73 mmol) and 3-(4,4,5,5-tetramethyl-1,3,2-dioxaborolan-2-yl)phenol (380.72 mg, 1.73 mmol) in MeCN (15.00 mL) was added K$_2$CO$_3$ (478.21 mg, 3.46 mmol). The mixture was stirred at 70° C. for 15 h. TLC (petroleum ether/EtOAc=2:1, Rf=0.68) detected one new main spot. The reaction mixture was cooled to room temperature and diluted with water (40 mL). The resulting mixture was extracted with EtOAc (40 mL×3). The combined organic layers were dried over Na$_2$SO$_4$, filtered and concentrated under reduced pressure to give a residue. The residue was purified by column chromatography (SiO$_2$, petroleum ether/EtOAc=1:0 to 5:1) to give the title compound (172 mg, 12%) as a white solid. $^1$H NMR (400 MHz, DMSO-d$_6$) δ 7.30-7.26 (m, 2H), 7.17-7.16 (m, 1H), 7.09-7.07 (m, 2H), 4.42 (s, 2H), 1.28-1.27 (m, 12H), 1.23 (s, 3H), 1.20 (s, 3H), 0.77 (t, J=7.4 Hz, 3H).

Example 82C tert-butyl 4-(4-((tert-butoxycarbonyl)(2-(3-(2-((3,3-difluorocyclobutyl)amino)-2-oxoethoxy)phenyl)-5,7-dihydrofuro[3,4-d]pyrimidin-4-yl)amino)phenyl)-1H-pyrazole-1-carboxylate

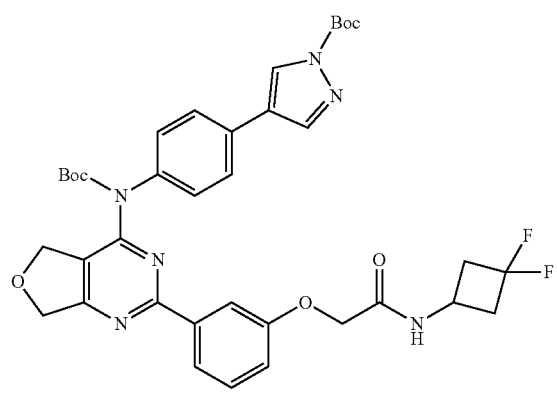 [SMILES: CC(C)(C)OC(=O)N(c1ccc(-c2cnn(C(=O)OC(C)(C)C)c2)cc1)c1nc(-c2cccc(OCC(=O)NC3CC(F)(F)C3)c2)nc2c1COC2]

To the mixture of N-(3,3-difluorocyclobutyl)-2-(3-(4,4,5,5-tetramethyl-1,3,2-dioxaborolan-2-yl)phenoxy)acetamide (150.00 mg, 408.50 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (174.96 mg, 340.42 umol) in dioxane (4.00 mL), H$_2$O (400.00 uL) was added K$_2$CO$_3$ (94.10 mg, 680.83 umol) and Pd(dppf)Cl$_2$ (24.91 mg, 34.04 umol). The mixture was stirred under N$_2$ at 100° C. for 15 h. TLC (petroleum ether/EtOAc=1:1, Rf=0.30, 0.76) detected two new main spots. The reaction mixture was cooled to room temperature and diluted with water (30 mL). The resulting mixture was extracted with EtOAc (30 mL×3). The combined organic layers were dried over Na$_2$SO$_4$, filtered and concentrated under reduced pressure to give a residue. The residue was purified by prep-TLC (petroleum ether/EtOAc=1:1) to give the title compound (62.00 mg, mono-Boc product: 30 mg) all as a light yellow solid.

Example 82D 2-(3-(4-((4-(1H-pyrazol-4-yl)phenyl)amino)-5,7-dihydrofuro[3,4-d]pyrimidin-2-Aphenoxy)-N-(3,3-difluorocyclobutyl)acetamide

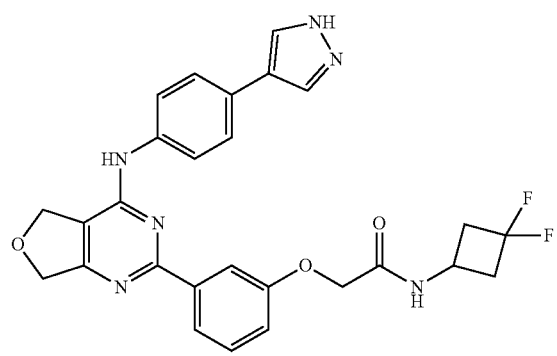 [SMILES: O=C(COc1cccc(-c2nc3c(c(Nc4ccc(-c5cn[nH]c5)cc4)n2)COC3)c1)NC1CC(F)(F)C1]

To a mixture of tert-butyl 4-(4-((tert-butoxycarbonyl)(2-(3-(2-((3,3-difluorocyclobutyl)amino)-2-oxoethoxy)phenyl)-5,7-dihydrofuro[3,4-d]pyrimidin-4-yl)amino)phenyl)-1H-pyrazole-1-carboxylate (62.00 mg, 13 mg mono-Boc product was used together) in CH$_2$Cl$_2$ (4.00 mL) was added HCl/dioxane (4 M, 8.00 mL). The mixture was stirred at 23° C. for 2 h. LCMS showed mono-Boc starting material was the major product. The mixture was stirred at 30° C. for another 2 h. LCMS showed that mono-Boc starting material remained and no peak of desired product formed. The mixture was concentrated under reduced pressure to give a residue. The residue was dissolved with CH$_2$Cl$_2$ (6 mL) and HCl/dioxane (8 mL) was added. The mixture was stirred at 30° C. for 3.5 h. LCMS showed about 33% of desired product and 35% of starting material. The mixture was concentrated under reduced pressure to give a residue. The residue was purified by prep-HPLC (FA conditions) to give the title compound (4.8 mg) as a light yellow solid. $^1$H NMR (400 MHz, DMSO-d$_6$) δ 12.93 (s, 1H), 9.27 (s, 1H), 8.67 (d, J=7.2 Hz, 1H), 8.45 (s, 1H), 7.98-7.96 (m, 4H), 7.80 (d, J=8.4 Hz, 2H), 7.65 (d, J=8.4 Hz, 2H), 7.44 (t, J=8.0 Hz, 1H), 7.12-7.09 (m, 1H), 5.07 (s, 2H), 4.94 (s, 2H), 4.58 (s, 2H), 4.21-4.17 (m, 1H), 2.88-2.84 (m, 2H), 2.75-2.69 (m, 2H). (ES+) m/e 519.1 (M+H)$^+$.

Example 83

2-(3-(4-((4-(1H-pyrazol-4-yl)phenyl)amino)-5,7-dihydrofuro[3,4-d]pyrimidin-2-yl)phenoxy)-N-(2,2,2-trifluoroethyl)acetamide

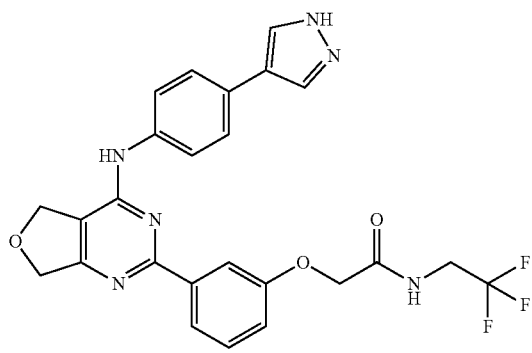 [SMILES: O=C(COc1cccc(-c2nc3c(c(Nc4ccc(-c5cn[nH]c5)cc4)n2)COC3)c1)NCC(F)(F)F]

Example 83A 2-chloro-N-(2,2,2-trifluoroethyl)acetamide

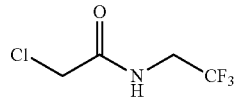

To a mixture of 2,2,2-trifluoroethanamine (1.58 g, 15.94 mmol, 1.25 mL) and TEA (2.69 g, 26.56 mmol, 3.68 mL, 2.00 eq) in CH$_2$Cl$_2$ (20.00 mL) was added dropwise 2-chloroacetyl chloride (1.50 g, 13.28 mmol, 1.06 mL) at 0° C. under N$_2$. The mixture was stirred at 23° C. for 2 h. The mixture was diluted with CH$_2$Cl$_2$ (30 mL) and washed with water (40 mL×2), citric acid (10%, 40 mL×2), NaHCO$_3$ (40 mL×2), brine (40 mL×2). The organic layer was dried over Na$_2$SO$_4$, filtered and concentrated under reduced pressure to give the title compound (780 mg, crude) as a yellow solid which was used for the next step reaction without further purification. $^1$H NMR (400 MHz, DMSO-d$_6$) δ 8.89 (s, 1H), 4.16 (s, 2H), 3.99-3.92 (m, 2H).

Example 83B 2-(3-(4,4,5,5-tetramethyl-1,3,2-dioxaborolan-2-yl)phenoxy)-N-(2,2,2-trifluoroethyl)acetamide

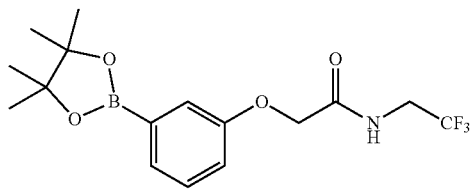 [SMILES: CC1(C)OB(c2cccc(OCC(=O)NCC(F)(F)F)c2)OC1(C)C]

To a mixture of 2-chloro-N-(2,2,2-trifluoroethyl)acetamide (500.00 mg, 2.85 mmol) and 3-(4,4,5,5-tetramethyl-1,3,2-dioxaborolan-2-yl)phenol (569.85 mg, 2.59 mmol) in MeCN (15.00 mL) was added K$_2$CO$_3$ (716.18 mg, 5.18 mmol). The mixture was stirred at 70° C. for 16 h. TLC (petroleum ether/EtOAc=2:1, Rf=0.68) detected one new main spot. The reaction mixture was cooled to room temperature and diluted with water (30 mL) and extracted with EtOAc (30 mL×3). The combined organic layers were dried over Na$_2$SO$_4$, filtered and concentrated under reduced pressure to give a residue. The residue was purified by column chromatography (SiO$_2$, petroleum ether/EtOAc=1:0 to 8:1) to give the title compound (728 mg, 62%) as a yellow solid. $^1$H NMR (400 MHz, DMSO-d$_6$) δ 8.79-8.76 (m, 1H), 7.34-7.24 (m, 3H), 7.09 (d, J=2.4 Hz, 1H), 4.59 (s, 2H), 3.94-3.93 (m, 2H), 1.28 (s, 12H).

Example 83C tert-butyl 4-(4-((tert-butoxycarbonyl)(2-(3-(2-oxo-2-((2,2,2-trifluoroethyl)amino)ethoxy)phenyl)-5,7-dihydrofuro[3,4-d]pyrimidin-4-yl)amino)phenyl)-1H-pyrazole-1-carboxylate

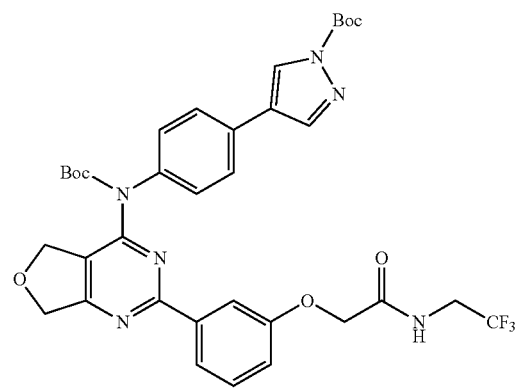 [SMILES: CC(C)(C)OC(=O)N(c1ccc(-c2cnn(C(=O)OC(C)(C)C)c2)cc1)c1nc(-c2cccc(OCC(=O)NCC(F)(F)F)c2)nc2c1COC2]

To the mixture of 2-(3-(4,4,5,5-tetramethyl-1,3,2-dioxaborolan-2-yl)phenoxy)-N-(2,2,2-trifluoroethyl)acetamide (150.00 mg, 417.65 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (178.88 mg, 348.04 umol) in dioxane (4.00 mL), H₂O (400.00 uL) was added K₂CO₃ (96.21 mg, 696.08 umol) and Pd(dppf)Cl₂ (25.47 mg, 34.80 umol). The mixture was stirred under N₂ at 100° C. for 16 h. TLC (petroleum ether/EtOAc=1:1, Rf=0.32, 0.76) showed two main spots. The reaction mixture was cooled to room temperature and diluted with (30 mL). The resulting mixture was extracted with EtOAc (30 mL×3). The combined organic layers were dried over Na₂SO₄, filtered and concentrated under reduced pressure to give a residue. The residue was purified by prep-TLC (petroleum ether/EtOAc=1:1) to give the title compound (71.00 mg, mono-Boc product: 36 mg) all as a light yellow solid.

Example 83D 2-(3-(4-((4-(1H-pyrazol-4-yl)phenyl)amino)-5,7-dihydrofuro[3,4-d]pyrimidin-2-yl)phenoxy)-N-(2,2,2-trifluoroethyl)acetamide

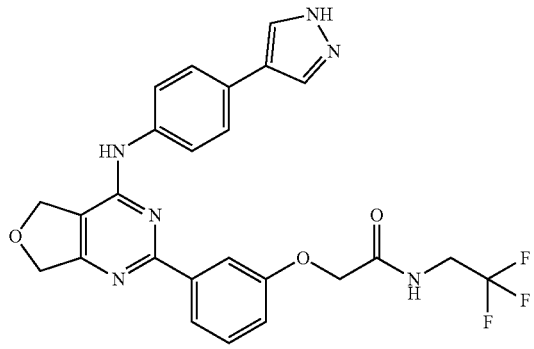 [SMILES: O=C(COc1cccc(-c2nc3c(c(Nc4ccc(-c5cn[nH]c5)cc4)n2)COC3)c1)NCC(F)(F)F]

To a mixture of tert-butyl 4-(4-((tert-butoxycarbonyl)(2-(3-(2-oxo-2-((2,2,2-trifluoroethyl)amino)ethoxy)phenyl)-5,7-dihydrofuro[3,4-d]pyrimidin-4-yl)amino)phenyl)-1H-pyrazole-1-carboxylate (71.00 mg, 36 mg mono-Boc product was used together) in CH₂Cl₂ (4.00 mL) was added HCl/dioxane (4 M, 8.00 mL). The mixture was stirred at 23° C. for 2 h. LCMS showed about 25% of desired product and 63% of mono-Boc starting material. The mixture was stirred at 30° C. for another 2 h. LCMS showed about 26% of desired product and 58% of mono-Boc starting material. The mixture was stirred at 30° C. for 3.5 h. LCMS showed about 43% of desired product and 47% of mono-Boc starting material. The mixture was concentrated under reduced pressure to give a residue. The residue was purified by prep-HPLC (FA conditions) to afford the title compound (19.3 mg) as a yellow solid. ¹H NMR (400 MHz, DMSO-d₆) δ 8.34 (s, 2H), 7.85-7.84 (m, 2H), 7.81-7.75 (m, 4H), 7.59 (d, J=8.2 Hz, 1H), 7.38 (d, J=7.2 Hz, 1H), 5.22-5.15 (m, 4H), 4.73 (s, 2H), 4.02-3.95 (m, 2H). (ES+) m/e 511.1 (M+H)⁺.

Example 84

2-(3-(4-((4-(1H-pyrazol-4-yl)phenyl)amino)-5,7-dihydrothieno[3,4-d]pyrimidin-2-yl)phenoxy)-N-isopropylacetamide

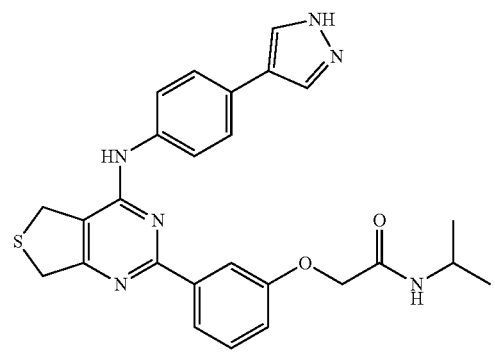 [SMILES: CC(C)NC(=O)COc1cccc(-c2nc3c(c(Nc4ccc(-c5cn[nH]c5)cc4)n2)CSC3)c1]

Example 84A 1-(tetrahydro-2H-pyran-2-yl)-4-(4,4,5,5-tetramethyl-1,3,2-dioxaborolan-2-yl)-1H-pyrazole

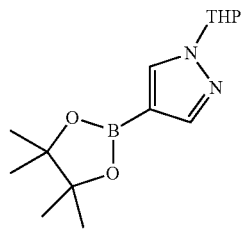

To a solution of 4-(4,4,5,5-tetramethyl-1,3,2-dioxaborolan-2-yl)-1H-pyrazole (10.00 g, 51.54 mmol) in CH₂Cl₂ (100.00 mL) was added DHP (8.67 g, 103.08 mmol, 9.42 mL) and TsOH.H₂O (4.90 g, 25.77 mmol). The mixture was stirred at 30° C. for 4 hour. LCMS showed 4-(4,4,5,5-tetramethyl-1,3,2-dioxaborolan-2-yl)-1H-pyrazolewas consumed completely and one main peak with desired mass was detected. The reaction mixture was concentrated under reduced pressure to remove solvent. The residue was diluted with sat.NaHCO₃ (35 mL) and the mixture was extracted with EtOAc (100 mL). The organic layer was dried over Na₂SO₄, filtered and concentrated under reduced pressure to give a residue. The residue was purified by column chromatography (SiO₂, Petroleum ether/Ethyl acetate=20/1 to 1/1) to afford the title compound (10.5 g, 73%) as colorless oil. ¹H NMR (400 MHz, DMSO-d₆) δ 8.06 (s, 1H), 7.62 (s, 1H), 5.44-5.41 (m, 1H), 3.94-3.89 (m, 1H), 3.76-3.58 (m, 2H), 3.46-3.41 (m, 1H), 2.15-2.06 (m, 1H), 1.95-1.84 (m, 2H), 1.76-1.40 (m, 9H), 1.26 (s, 12H).

Example 84B 4-(1-(tetrahydro-2H-pyran-2-yl)-1H-pyrazol-4-yl)aniline

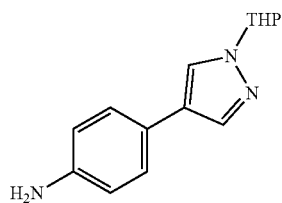

A mixture of 1-(tetrahydro-2H-pyran-2-yl)-4-(4,4,5,5-tetramethyl-1,3,2-dioxaborolan-2-yl)-1H-pyrazole (9.50 g, 34.15 mmol), 4-bromoaniline (5.58 g, 32.45 mmol), K$_2$CO$_3$ (9.44 g, 68.31 mmol) and Pd(dppf)Cl$_2$ (1.25 g, 1.71 mmol) in dioxane (100.00 mL)/H$_2$O (10.00 mL) was degassed and purged with N$_2$ 3 times, then the mixture was stirred at 100° C. for 16 hour under N$_2$ atmosphere. TLC (Petroleum ether/Ethyl acetate=1/1) showed starting materials were consumed completely, and there was a new spot (Rf=0.15). The reaction mixture was cooled to room temperature. After addition of water (200 mL) and EtOAc (200 mL), the mixture was stirred for 5 min. The resulting suspension was filtered through celatom, and the filtrate collected. The aqueous layer was extracted with EtOAc (200 mL×2). The combined organic layers were washed with brine (100 mL×2), dried over Na$_2$SO$_4$, filtered and concentrated to give a residue. The residue was purified by column chromatography (SiO$_2$, Petroleum ether/Ethyl acetate=1/0 to 1/2) to afford the title compound (7.5 g, 90%) as an off-white solid.

Example 84C 2,4-dichloro-5,7-dihydrothieno[3,4-d]pyrimidine

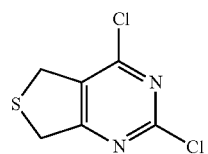 [SMILES: Clc1nc(Cl)c2c(n1)CSC2]

A mixture of 5,7-dihydrothieno[3,4-d]pyrimidine-2,4-diol (700.00 mg, 4.11 mmol) and DIPEA (1.06 g, 8.23 mmol, 1.44 mL) in POCl$_3$ (13.20 g, 86.09 mmol, 8.00 mL) was stirred at 80° C. for 2 hour under N$_2$ atmosphere. TLC (Petroleum ether/Ethyl acetate=5/1) showed starting materials were consumed completely, and there was a new spot (Rf=0.8) forming. The mixture was concentrated under reduced pressure to give a residue. And then ice water (30 mL) was poured into the residue. The resulting mixture was extracted with EtOAc (30 mL×2). The combined organic layers was washed with sat.NaHCO$_3$ (20 mL×2), dried over Na$_2$SO$_4$, filtered and concentrated to give the crude title compound (600 mg, 71%) as black brown oil.

Example 84E 2-chloro-N-(4-(1-(tetrahydro-2H-pyran-2-yl)-1H-pyrazol-4-yl)phenyl)-5,7-dihydrothieno[3,4-d]pyrimidin-4-amine

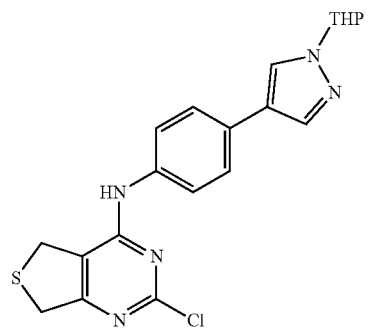

A mixture of 2,4-dichloro-5,7-dihydrothieno[3,4-d]pyrimidine (600.00 mg, 2.90 mmol), 4-(1-(tetrahydro-2H-pyran-2-yl)-1H-pyrazol-4-yl)aniline (704.94 mg, 2.90 mmol) and DIPEA (748.93 mg, 5.79 mmol, 1.01 mL) in n-BuOH (10.00 mL) was stirred at 100° C. for 16 hours under N$_2$ atmosphere. LCMS showed 2,4-dichloro-5,7-dihydrothieno[3,4-d]pyrimidinewas consumed completely and 90% of desired product was detected. The reaction mixture was concentrated under reduced pressure to remove n-BuOH. The residue was purified by column chromatography (SiO$_2$, Petroleum ether/Ethyl acetate=10/1 to 1/1) to afford the title compound (1.05 g, 87%) as a yellow solid.

Example 84F

N-isopropyl-2-(3-(4-((4-(1-(tetrahydro-2H-pyran-2-yl)-1H-pyrazol-4-yl)phenyl)amino)-5,7-dihydrothieno[3,4-cl]pyrimidin-2-yl)phenoxy)acetamide

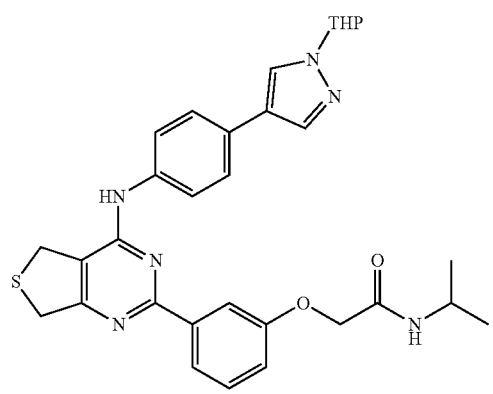

A mixture of 2-chloro-N-(4-(1-(tetrahydro-2H-pyran-2-yl)-1H-pyrazol-4-yl)phenyl)-5,7-dihydrothieno[3,4-d]pyrimidin-4-amine (210.00 mg, 507.34 umol), N-isopropyl-2-(3-(4,4,5,5-tetramethyl-1,3,2-dioxaborolan-2-yl)phenoxy)acetamide (161.94 mg, 507.34 umol), Pd(dppf)Cl$_2$ (37.12 mg, 50.73 umol) and K$_2$CO$_3$ (140.24 mg, 1.01 mmol) in dioxane (10.00 mL)/H₂O (1.00 mL) was degassed and purged with N₂ 3 times, and then the mixture was stirred at 95° C. for 16 hour under N₂ atmosphere. LCMS showed 2-chloro-N-(4-(1-(tetrahydro-2H-pyran-2-yl)-1H-pyrazol-4-yl)phenyl)-5,7-dihydrothieno[3,4-d]pyrimidin-4-amine was consumed completely and one new main peak with desired mass was detected. The reaction mixture was quenched by addition H₂O (30 mL) at 25° C. and the resulting mixture was extracted with EtOAc (30 mL×3). The combined organic layers were washed with brine (30 mL×3), dried over Na₂SO₄, filtered and concentrated under reduced pressure to give a residue. The residue was purified by prep-TLC (SiO₂, Petroleum ether/Ethyl acetate=1:2, Rf=0.35) to afford the title compound (120 mg) as a yellow solid.

Example 84G 2-(3-(4-((4-(1H-pyrazol-4-yl)phenyl)amino)-5,7-dihydrothieno[3,4-d]pyrimidin-2-yl)phenoxy)-N-isopropylacetamide

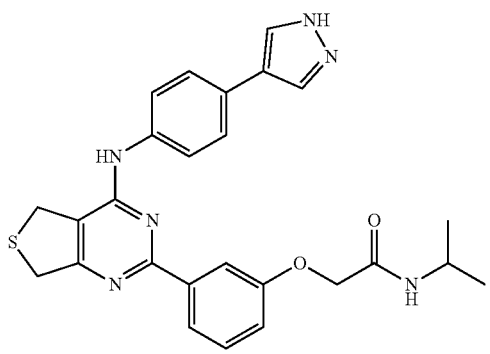 [SMILES: CC(C)NC(=O)COc1cccc(-c2nc3c(c(Nc4ccc(-c5cn[nH]c5)cc4)n2)CSC3)c1]

To a solution of N-isopropyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide (120.00 mg, 210.26 umol) in CH₂Cl₂ (1.00 mL) was added HCl/dioxane (4 M, 2.00 mL). The mixture was stirred at 25° C. for 16 hour. LCMS showed N-isopropyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide was consumed completely and a new main peak with the desired mass was detected. The reaction mixture was concentrated under reduced pressure to give a residue. The residue was purified by prep-HPLC (FA conditions). The title compound (10.4 mg) was obtained by lyophilization as an off-white solid. ¹H NMR (400 MHz, DMSO-d₆) δ 12.92 (s, 1H), 8.98 (s, 1H), 8.48 (s, 1H), 8.19 (s, 1H), 8.00-7.93 (m, 4H), 7.83 (d, J=8.4 Hz, 2H), 7.67 (d, J=8.4 Hz, 2H), 7.42 (t, J=8.0 Hz, 1H), 7.09 (dd, J=7.6, 1.6 Hz, 1H), 4.52 (s, 2H), 4.25-4.24 (m, 4H), 4.03-3.95 (m, 1H), 1.10 (d, J=6.4 Hz, 3H). (ES+) m/e 487.3 (M+H)⁺.

Example 85

2-(3-(4-((4-(1H-pyrazol-4-yl)phenyl)amino)-5,7-dihydrofuro[3,4-d]pyrimidin-2-yl)phenoxy)-N-phenylacetamide

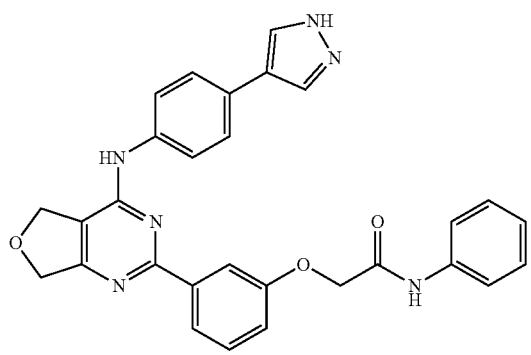 [SMILES: O=C(COc1cccc(-c2nc3c(c(Nc4ccc(-c5cn[nH]c5)cc4)n2)COC3)c1)Nc1ccccc1]

Example 85A 2-chloro-N-phenylacetamide

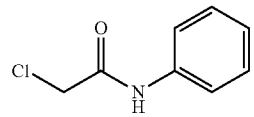 [SMILES: O=C(CCl)Nc1ccccc1]

To a solution of aniline (5.00 g, 53.69 mmol, 4.90 mL) and TEA (16.30 g, 161.07 mmol, 22.33 mL) in DCM (70.00 mL) was added dropwise 2-chloroacetyl chloride (6.06 g, 53.69 mmol, 4.27 mL) at 0° C. over 0.5 hr. Then the mixture was stirred at 25° C. for 3 hr. The reaction mixture was washed with H₂O (100 mL), HCl (1 M, 100 mL) and brine (100 mL), dried over Na₂SO₄, filtered and concentrated under reduced pressure to afford the title compound (7.5 g, crude) as a black-brown solid.

Example 85B

N-phenyl-2-(3-(4,4,5,5-tetramethyl-1,3,2-dioxaborolan-2-yl)phenoxy)acetamide

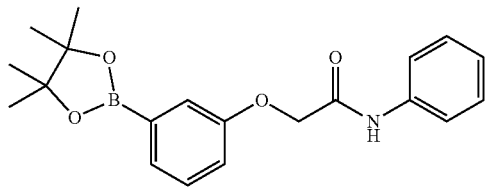 [SMILES: CC1(C)OB(c2cccc(OCC(=O)Nc3ccccc3)c2)OC1(C)C]

To a solution of 3-(4,4,5,5-tetramethyl-1,3,2-dioxaborolan-2-yl)phenol (1.00 g, 4.54 mmol) and 2-chloro-N-phenylacetamide (770.71 mg, 4.54 mmol) in MeCN (30.00 mL) was added K₂CO₃ (1.25 g, 9.08 mmol). The mixture was stirred at 80° C. for 16 hour. LCMS showed 3-(4,4,5,5-tetramethyl-1,3,2-dioxaborolan-2-yl)phenol was consumed completely and 48% peak with desired mass was detected. The reaction mixture was quenched by addition water (50 mL) and the resulting mixture was extracted with EtOAc (50 mL×2). The combined organic layers were washed with brine (50 mL×2), dried over Na$_2$SO$_4$, filtered and concentrated under reduced pressure to give a residue. The residue was purified by column chromatography (SiO$_2$, Petroleum ether/Ethyl acetate=50/1 to 1/1) to afford the title compound (0.95 g, 59%) as yellow oil. $^1$H NMR (400 MHz, DMSO-d$_6$) δ 8.34 (s, 1H), 7.64-7.61 (m, 2H), 7.53 (d, J=8.0 Hz, 1H), 7.46 (d, J=2.4 Hz, 1H), 7.41-7.37 (m, 3H), 7.20-7.16 (m, 1H), 7.13-7.10 (m, 1H), 4.67 (s, 2H), 1.38 (s, 12H).

Example 85C tert-butyl 4-(4-((tert-butoxycarbonyl)(2-(3-(2-oxo-2-(phenylamino)ethoxy)phenyl)-5,7-dihydrofuro[3,4-d]pyrimidin-4-yl)amino)phenyl)-1H-pyrazole-1-carboxylate

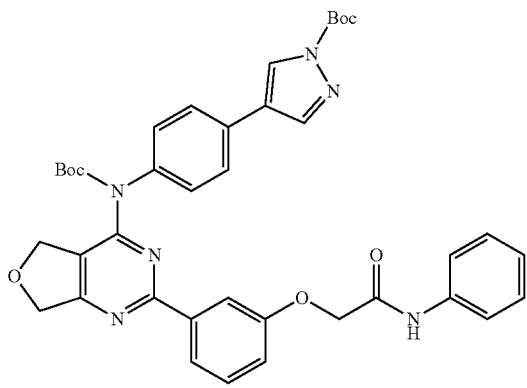 [SMILES: CC(C)(C)OC(=O)N(c1ccc(-c2cnn(C(=O)OC(C)(C)C)c2)cc1)c1nc(-c2cccc(OCC(=O)Nc3ccccc3)c2)nc2c1COC2]

A mixture of tert-butyl 4-(4-((tert-butoxycarbonyl)(2-chloro-5,7-dihydrofuro[3,4-d]pyrimidin-4-yl)amino)phenyl)-1H-pyrazole-1-carboxylate (200.00 mg, 389.13 umol), tert-butyl 4-(4-((tert-butoxycarbonyl)(2-chloro-5,7-dihydrofuro[3,4-d]pyrimidin-4-yl)amino)phenyl)-1H-pyrazole-1-carboxylate (137.45 mg, 389.13 umol), Pd(dppf)Cl$_2$ (28.47 mg, 38.91 umol) and K$_2$CO$_3$ (107.56 mg, 778.26 umol) in dioxane (5.00 mL)/H$_2$O (500.00 uL) was degassed and purged with nitrogen 3 times, then the mixture was stirred at 95° C. for 16 hour under N$_2$ atmosphere. LCMS showed tert-butyl 4-(4-((tert-butoxycarbonyl)(2-chloro-5,7-dihydrofuro[3,4-d]pyrimidin-4-yl)amino)phenyl)-1H-pyrazole-1-carboxylate was consumed completely and two main peaks with desired product (28%) and mono-Boc product (39%) masses were detected. TLC (Petroleum ether/Ethyl acetate=1/2) showed two main new spots (Rf=0.7, 0.32). The reaction mixture was cooled to room temperature and quenched by addition of H$_2$O (30 mL) at 25° C., then the resulting mixture was extracted with EtOAc (30 mL×3). The combined organic layers were washed with brine (30 mL×3), dried over Na$_2$SO$_4$, filtered and concentrated under reduced pressure to give a residue. The residue was purified by prep-TLC (SiO$_2$, Petroleum ether/Ethyl acetate=1:2) to afford the title compound (50.00 mg, 18%; LCMS: EW3123-101-P1D) and mono-Boc product (65.00 mg, 28%; LC-MS: EW3123-101-P1B) both as off-white solids.

Example 85D tert-butyl 4-(4-((tert-butoxycarbonyl)(2-(3-(2-oxo-2-(phenylamino)ethoxy)phenyl)-5,7-dihydrofuro[3,4-d]pyrimidin-4-yl)amino)phenyl)-1H-pyrazole-1-carboxylate

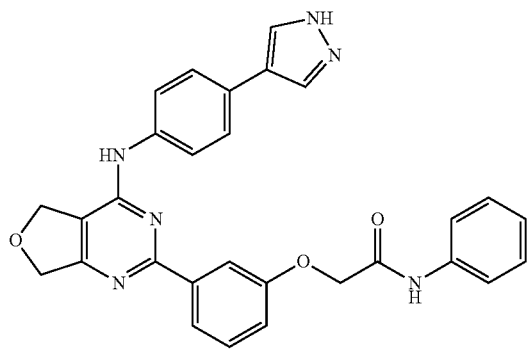 [SMILES: O=C(COc1cccc(-c2nc3c(c(Nc4ccc(-c5cn[nH]c5)cc4)n2)COC3)c1)Nc1ccccc1]

To a solution of tert-butyl 4-(4-((tert-butoxycarbonyl)(2-(3-(2-oxo-2-(phenylamino)ethoxy)phenyl)-5,7-dihydrofuro[3,4-d]pyrimidin-4-yl)amino)phenyl)-1H-pyrazole-1-carboxylate (65.00 mg, 107.50 umol) in CH$_2$Cl$_2$ (1.00 mL) was added HCl/dioxane (4 M, 2.00 mL). The mixture was stirred at 25° C. for 16 hour. LCMS showed ~32% peak with desired mass was detected. The reaction mixture was concentrated under reduced pressure to give a residue. The residue was purified by prep-HPLC (FA conditions). HNMR showed the solid contained dioxane. The solid was dissolved in 1 mL DMSO and distilled water (10 mL) was added. The suspension was filtered and washed with distilled water (10 mL). The title compound (4.5 mg) was obtained by lyophilization as an off-white solid. $^1$H NMR (400 MHz, DMSO-d$_6$) δ 12.92 (s, 1H), 10.14 (s, 1H), 9.24 (s, 1H), 8.16 (s, 1H), 8.02-7.93 (m, 3H), 7.82 (d, J=8.4 Hz, 2H), 7.66 (d, J=8.8 Hz, 4H), 7.46 (t, J=8.0 Hz, 1H), 7.32 (t, J=8.0 Hz, 2H), 7.16 (dd, J=8.4, 2.0 Hz, 1H), 7.09 (t, J=7.6 Hz, 1H), 5.08 (s, 2H), 4.95 (s, 2H), 4.80 (s, 2H). (ES+) m/e 505.3 (M+H)$^+$.

Example 86

2-(3-(4-((4-(1H-pyrazol-4-yl)phenyl)amino)-5,7-dihydrothieno[3,4-d]pyrimidin-2-yl)phenoxy)-N-cyclobutylacetamide

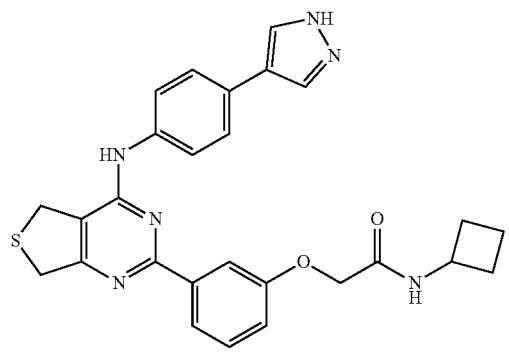 [SMILES: O=C(COc1cccc(-c2nc3c(c(Nc4ccc(-c5cn[nH]c5)cc4)n2)CSC3)c1)NC1CCC1]

Example 86A

N-cyclobutyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide

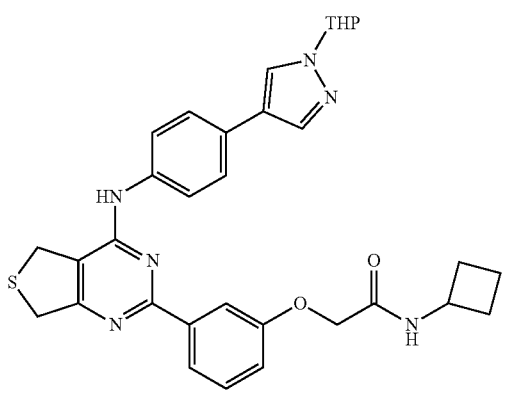

A mixture of 2-chloro-N-(4-(1-(tetrahydro-2H-pyran-2-yl)-1H-pyrazol-4-yl)phenyl)-5,7-dihydrothieno[3,4-d]pyrimidin-4-amine (200.00 mg, 483.19 umol), N-cyclobutyl-2-(3-(4,4,5,5-tetramethyl-1,3,2-dioxaborolan-2-yl)phenoxy)acetamide (160.04 mg, 483.19 umol), Pd(dppf)Cl$_2$ (35.36 mg, 48.32 umol) and K$_2$CO$_3$ (133.56 mg, 966.38 umol) in dioxane (5.00 mL)/H$_2$O (500.00 uL) was degassed and purged with N$_2$ 3 times, then the mixture was stirred at 95° C. for 16 hour under N$_2$ atmosphere. LCMS showed 2-chloro-N-(4-(1-(tetrahydro-2H-pyran-2-yl)-1H-pyrazol-4-yl)phenyl)-5,7-dihydrothieno[3,4-d]pyrimidin-4-aminewas consumed completely and ~76% peak with desired mass was detected. The reaction mixture was cooled to room temperature and quenched by addition H$_2$O (30 mL) at 25° C., then the resulting mixture was extracted with EtOAc (30 mL×3). The combined organic layers were washed with brine (30 mL×3), dried over Na$_2$SO$_4$, filtered and concentrated under reduced pressure to give a residue. The residue was purified by prep-TLC (SiO$_2$, Petroleum ether/Ethyl acetate=1:2, Rf=0.35) to afford the title compound (75 mg, 27%; LCMS: EW3123-109-P1C) as an off-white solid.

Example 86B 2-(3-(4-((4-(1H-pyrazol-4-yl)phenyl)amino)-5,7-dihydrothieno[3,4-d]pyrimidin-2-yl)phenoxy)-N-cyclobutylacetamide

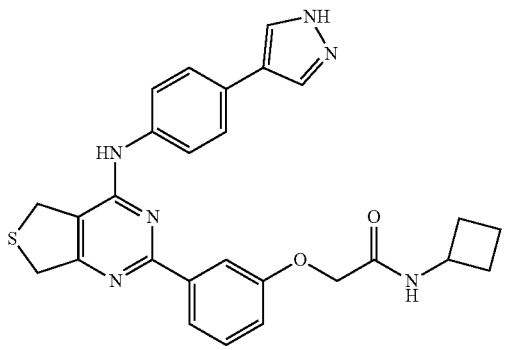 [SMILES: O=C(COc1cccc(-c2nc3c(c(Nc4ccc(-c5cn[nH]c5)cc4)n2)CSC3)c1)NC1CCC1]

To a solution of N-cyclobutyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide (75.00 mg, 128.71 umol) in CH$_2$Cl$_2$ (2.00 mL) was added HCl/dioxane (4 M, 4.00 mL). The mixture was stirred at 25° C. for 16 hour. LCMS showed ~65% peak with desired mass. The reaction mixture was concentrated under reduced pressure to give a residue. The residue was purified by prep-HPLC (FA conditions). The product of EW3123-99 was combined with the product of this page and residual MeCN was removed under reduced pressure. The title compound (12.7 mg) was obtained by lyophilization as an off-white solid. $^1$H NMR (400 MHz, DMSO-d$_6$) δ 8.98 (s, 1H), 8.40 (d, J=7.6 Hz, 2H), 8.07 (s, 2H), 7.95-7.93 (m, 2H), 7.82 (d, J=8.4 Hz, 2H), 7.66 (d, J=8.4 Hz, 2H), 7.42 (t, J=8.0 Hz, 1H), 7.10-7.07 (m, 1H), 4.51 (s, 2H), 4.32-4.23 (m, 5H), 2.14-2.00 (m, 4H), 1.63-1.60 (m, 2H). (ES+) m/e 499.3 (M+H)$^-$.

Example 87

2-(3-(4-((4-(1H-pyrazol-4-yl)phenyl)amino)-5,7-dihydrothieno[3,4-d]pyrimidin-2-yl)phenoxy)-N-cyclopentylacetamide

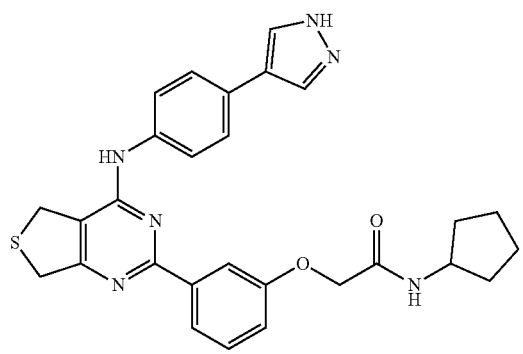 [SMILES: O=C(COc1cccc(-c2nc3c(c(Nc4ccc(-c5cn[nH]c5)cc4)n2)CSC3)c1)NC1CCCC1]

Example 87A

N-cyclopentyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide

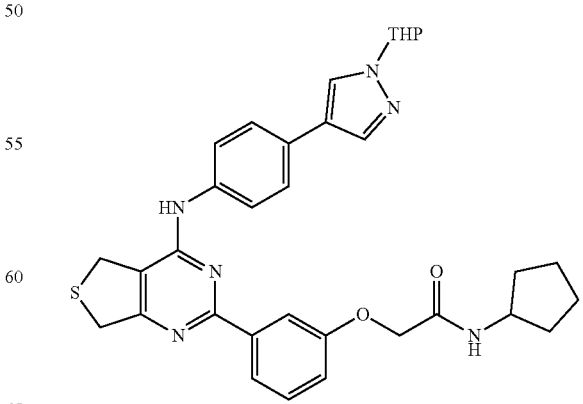

A mixture of 2-chloro-N-(4-(1-(tetrahydro-2H-pyran-2-yl)-1H-pyrazol-4-yl)phenyl)-5,7-dihydrothieno[3,4-d]pyrimidin-4-amine (200.00 mg, 483.19 umol), N-cyclopentyl-2-(3-(4,4,5,5-tetramethyl-1,3,2-dioxaborolan-2-yl)phenoxy)acetamide (166.81 mg, 483.19 umol), Pd(dppf)Cl$_2$ (35.36 mg, 48.32 umol), K$_2$CO$_3$ (133.56 mg, 966.38 umol) in dioxane (5.00 mL)/H$_2$O (500.00 uL) was degassed and purged with N$_2$ 3 times and the mixture was stirred at 95° C. for 16 hour under N$_2$ atmosphere. LCMS showed 2-chloro-N-(4-(1-(tetrahydro-2H-pyran-2-yl)-1H-pyrazol-4-yl)phenyl)-5,7-dihydrothieno[3,4-d]pyrimidin-4-aminewas consumed completely and ~63% peak with desired product was detected. The reaction mixture was cooled to room temperature and quenched by addition H$_2$O (30 mL) and the resulting mixture was extracted with EtOAc (30 mL×3). The combined organic layers were washed with brine (30 mL×3), dried over Na$_2$SO$_4$, filtered and concentrated under reduced pressure to give a residue. The residue was purified by prep-TLC (SiO$_2$, Petroleum ether/Ethyl acetate=1:2, Rf=0.35) to afford the title compound (70.00 mg, 24%) as an off-white solid.

Example 87B 2-(3-(4-((4-(1H-pyrazol-4-yl)phenyl)amino)-5,7-dihydrothieno[3,4-d]pyrimidin-2-yl)phenoxy)-N-cyclopentylacetamide

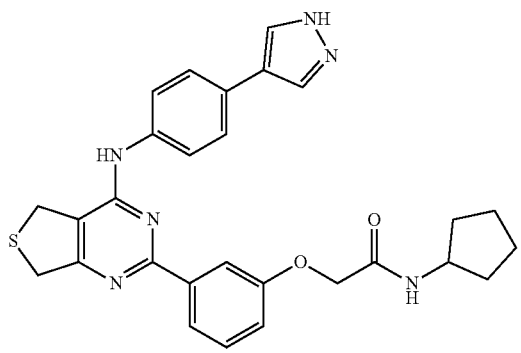 [SMILES: O=C(COc1cccc(-c2nc3c(c(Nc4ccc(-c5cn[nH]c5)cc4)n2)CSC3)c1)NC1CCCC1]

To a solution of N-cyclopentyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide (65.00 mg, 108.93 umol) in CH$_2$Cl$_2$ (2.00 mL) was added HCl/dioxane (4 M, 4.00 mL). The mixture was stirred at 25° C. for 16 hour. LCMS showed N-cyclopentyl-2-(3-(4-((4-(1-(tetrahydro-2H-pyran-2-yl)-1H-pyrazol-4-yl)phenyl)amino)-5,7-dihydrothieno[3,4-d]pyrimidin-2-yl)phenoxy)acetamide was consumed completely and ~52% peak with desired mass wasdetected. The reaction mixture was concentrated under reduced pressure to give a residue. The residue was purified by prep-HPLC (FA conditions). The product of EW3123-100 was combined with this page. The residual acetonitrile after prep-HPLC separation was removed under reduced pressure. The title compound (10.9 mg) was obtained by lyophilization as off-white solid. $^1$H NMR (400 MHz, DMSO-d$_6$) δ 8.98 (s, 1H), 8.42 (s, 2H), 8.07 (d, J=7.2 Hz, 2H), 7.95-7.93 (m, 2H), 7.82 (d, J=8.8 Hz, 2H), 7.67 (d, J=8.4 Hz, 2H), 7.42 (t, J=8.0 Hz, 1H), 7.10-7.08 (m, 1H), 4.53 (s, 2H), 4.25-4.24 (m, 4H), 4.12-4.10 (m, 1H), 1.81-1.80 (m, 2H), 1.63-1.62 (m, 2H), 1.51-1.46 (m, 4H). (ES+) m/e 513.3 (M+H)$^+$.

Example 88

2-(3-(4-((4-(1H-pyrazol-4-yl)phenyl)amino)-5,7-dihydrofuro[3,4-d]pyrimidin-2-yl)-5-fluorophenoxy)-N-(pentan-3-yl)acetamide

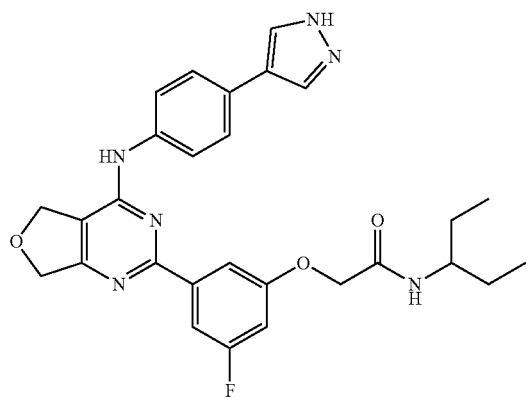 [SMILES: CCC(CC)NC(=O)COc1cc(F)cc(-c2nc3c(c(Nc4ccc(-c5cn[nH]c5)cc4)n2)COC3)c1]

Example 88A 2-chloro-N-(pentan-3-yl)acetamide

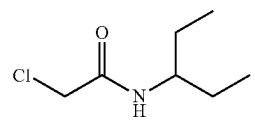

To a mixture of pentan-3-amine (2.32 g, 26.56 mmol, 3.09 mL) and TEA (5.38 g, 53.13 mmol, 7.36 mL) in CH$_2$Cl$_2$ (40.00 mL) was added dropwsie 2-chloroacetyl chloride (2.00 g, 17.71 mmol, 1.41 mL) at 0° C. The mixture was stirred at 23° C. for 2 h. The mixture was diluted with CH$_2$Cl$_2$ (40 mL) and washed with water (30 mL×2), citric acid (10%, 30 mL×2), NaHCO$_3$ (30 mL×2), brine (30 mL×2). The organic layer was dried over Na$_2$SO$_4$, filtered and concentrated under reduced pressure to give the title compound (2.47 g, crude) as a black brown solid and used in the next step without further purification. $^1$H NMR (400 MHz, DMSO-d$_6$) δ 7.89 (d, J=8.0 Hz, 1H), 4.02 (s, 2H), 3.55-3.48 (m, 1H), 1.47-1.42 (m, 2H), 1.36-1.31 (m, 2H), 0.81 (t, J=7.4 Hz, 6H).

Example 88B 2-(3-bromo-5-fluorophenoxy)-N-(pentan-3-yl)acetamide

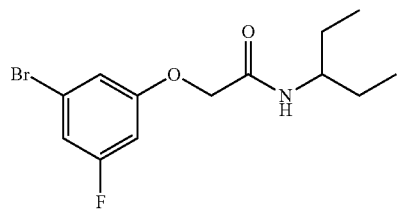 [SMILES: CCC(CC)NC(=O)COc1cc(F)cc(Br)c1]

To a mixture of 2-chloro-N-(pentan-3-yl)acetamide (500.00 mg, 3.06 mmol) and 3-bromo-5-fluoro-phenol (530.54 mg, 2.78 mmol) in MeCN (30.00 mL) was added K$_2$CO$_3$ (767.82 mg, 5.56 mmol). The mixture was stirred at 70° C. for 16 h. TLC (petroleum ether/EtOAc=5:1, Rf=0.57) showed one new main spot. The reaction mixture was cooled to room temperature and diluted with water (30 mL). The resulting mixture was extracted with EtOAc (30 mL×3). The combined organic layers were dried over Na$_2$SO$_4$, filtered and concentrated under reduced pressure to give a residue. The residue was purified by column chromatography (SiO$_2$, petroleum ether/EtOAc=1:0 to 8:1) to give the title compound (783 mg, 88%) as a yellow solid. $^1$H NMR (400 MHz, DMSO-d$_6$) δ 7.74 (d, J=8.8 Hz, 1H), 7.12 (d, J=8.0 Hz, 1H), 7.04 (s, 1H), 6.90-6.86 (m, 1H), 4.57 (s, 2H), 3.62-3.55 (m, 1H), 1.48-1.43 (m, 2H), 1.38-1.33 (m, 2H), 0.79 (t, J=7.2 Hz, 6H).

Example 88C 2-(3-fluoro-5-(4,4,5,5-tetramethyl-1,3,2-dioxaborolan-2-yl)phenoxy)-N-(pentan-3-yl)acetamide

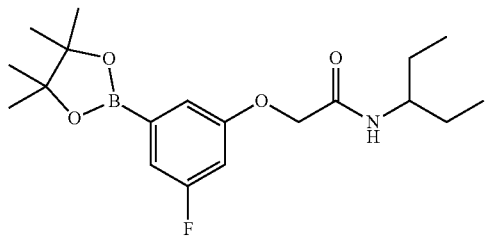 [SMILES: CCC(CC)NC(=O)COc1cc(F)cc(B2OC(C)(C)C(C)(C)O2)c1]

To a mixture of 2-(3-bromo-5-fluorophenoxy)-N-(pentan-3-yl)acetamide (780.00 mg, 2.45 mmol) and 4,4,4',4',5,5,5',5'-octamethyl-2,2'-bi(1,3,2-dioxaborolane) (933.23 mg, 3.68 mmol) in dioxane (8.00 mL) was added AcOK (480.89 mg, 4.90 mmol), Pd(dppf)Cl$_2$ (89.63 mg, 122.50 umol). The mixture was stirred under N$_2$ at 90° C. for 16 h. TLC (petroleum ether/EtOAc=5:1, Rf=0.35) showed two main spots. The reaction mixture was cooled to room temperature and diluted with (30 mL). The resulting mixture was extracted with EtOAc (30 mL×3). The combined organic layers were dried over Na$_2$SO$_4$, filtered and concentrated under reduced pressure to give a residue. The residue was purified column chromatography (SiO$_2$, petroleum ether/EtOAc=1:0 to 5:1) to give the title compound (767 mg) as a white solid. $^1$H NMR (400 MHz, DMSO-d$_6$) δ 7.76 (d, J=8.8 Hz, 1H), 7.06 (s, 1H), 6.95 (d, J=8.4 Hz, 2H), 4.54 (s, 2H), 3.64-3.57 (m, 1H), 1.46-1.43 (m, 2H), 1.39-1.33 (m, 2H), 1.28 (s, 12H), 0.79 (t, J=7.4 Hz, 6H).

Example 88D tert-butyl 4-(4-((tert-butoxycarbonyl)(2-(3-fluoro-5-(2-oxo-2-(pentan-3-ylamino)ethoxy)phenyl)-5,7-dihydrofuro[3,4-d]pyrimidin-4-yl)amino)phenyl)-1H-pyrazole-1-carboxylate

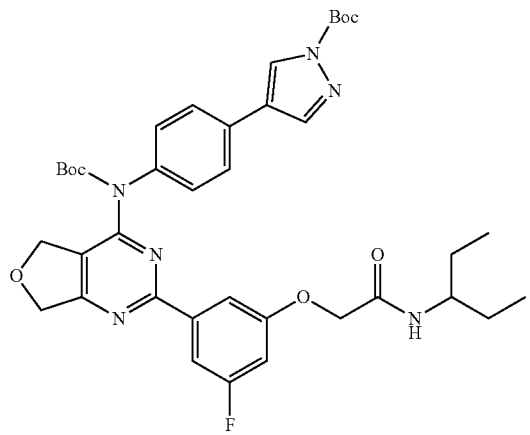 [SMILES: CCC(CC)NC(=O)COc1cc(F)cc(-c2nc3c(c(N(C(=O)OC(C)(C)C)c4ccc(-c5cnn(C(=O)OC(C)(C)C)c5)cc4)n2)COC3)c1]

To a mixture of 2-(3-fluoro-5-(4,4,5,5-tetramethyl-1,3,2-dioxaborolan-2-yl)phenoxy)-N-(pentan-3-yl)acetamide (300.00 mg, 821.36 umol) and tert-butyl 4-(4-((tert-butoxycarbonyl)(2-chloro-5,7-dihydrofuro[3,4-d]pyrimidin-4-yl)amino)phenyl)-1H-pyrazole-1-carboxylate (301.54 mg, 586.69 umol) in dioxane (5.00 mL), H$_2$O (500.00 uL) was added K$_2$CO$_3$ (162.17 mg, 1.17 mmol), Pd(dppf)Cl$_2$ (42.93 mg, 58.67 umol). The mixture was stirred under N$_2$ at 100° C. for 15 h. TLC (petroleum ether/EtOAc=1:2, Rf=0.78, 0.70, 0.36) showed that three spots were detected. LCMS showed the spot (Rf=0.78) was desired product. The reaction mixture was cooled to room temperature and diluted with water (30 mL). The resulting mixture was extracted with EtOAc (30 mL×3). The combined organic layers were dried over Na$_2$SO$_4$, filtered and concentrated under reduced pressure to give a residue. The residue was purified by column chromatography (SiO$_2$) to afford the title compound (56 mg, 8.5%) as a white solid.

Example 88E 2-(3-(4-((4-(1H-pyrazol-4-yl)phenyl)amino)-5,7-dihydrofuro[3,4-d]pyrimidin-2-yl)-5-fluorophenoxy)-N-(pentan-3-yl)acetamide

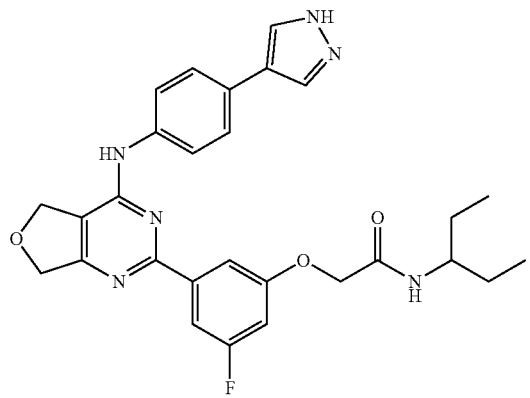 [SMILES: CCC(CC)NC(=O)COc1cc(F)cc(-c2nc3c(c(Nc4ccc(-c5cn[nH]c5)cc4)n2)COC3)c1]

To a mixture of tert-butyl 4-(4-((tert-butoxycarbonyl)(2-(3-fluoro-5-(2-oxo-2-(pentan-3-ylamino)ethoxy)phenyl)-5,7-dihydrofuro[3,4-d]pyrimidin-4-yl)amino)phenyl)-1H-pyrazole-1-carboxylate (56.00 mg) (52 mg mono-Boc product was used together) in CH$_2$Cl$_2$ (6.00 mL) was added TFA (10.00 mL). The mixture was stirred at 23° C. for 1.5 h. LCMS showed about 30% of the desired product and 31% of mono-Boc starting material. The mixture was stirred at 35° C. for another 2 h. LCMS showed about 28% desired product and 29% mono-Boc starting material. The mixture was concentrated under reduced pressure to give a residue. The solution was diluted with sat.NaHCO$_3$ (30 mL) and extracted with EtOAc (30 mL×3). The organic layers were dried over Na$_2$SO$_4$, filtered and concentrated under reduced pressure to give a residue. The residue was purified by prep-HPLC (FA conditions). Product was obtained as a white solid. Since HNMR showed that the solid contained acetonitrile, the product was suspended in distilled water and stirred at 95° C. for 16 h. HNMR showed MeCN was removed. The solution was filtered to afford solid which was washed with distilled water. The title compound (12.6 mg) was obtained by lyophilization as a white solid. $^1$H NMR (400 MHz, DMSO-d$_6$) δ 12.92 (s, 1H), 9.31 (s, 1H), 8.16 (s, 1H), 7.95 (s, 1H), 7.81-7.75 (m, 4H), 7.67-7.63 (m, 3H), 6.97 (d, J=10.4 Hz, 1H), 5.07 (s, 2H), 4.93 (s, 2H), 4.61 (s, 2H), 3.64-3.60 (m, 1H). (ES+) m/e 517.4 (M+H)$^+$.

Example 89

2-(3-(4-((4-(1H-pyrazol-4-yl)phenyl)amino)-5,7-dihydrofuro[3,4-d]pyrimidin-2-yl)phenoxy)-N-cyclohexylacetamide

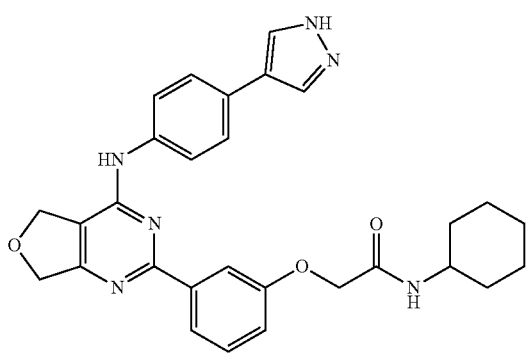 [SMILES: O=C(COc1cccc(-c2nc3c(c(Nc4ccc(-c5cn[nH]c5)cc4)n2)COC3)c1)NC1CCCCC1]

Example 89A 2-chloro-N-cyclohexylacetamide

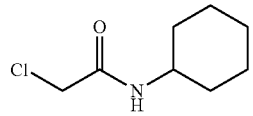 [SMILES: O=C(CCl)NC1CCCCC1]

To a solution of cyclohexanamine (5.00 g, 50.42 mmol, 5.75 mL) and TEA (15.31 g, 151.26 mmol, 20.97 mL) in DCM (70.00 mL) was added dropwise 2-chloroacetyl chloride (5.69 g, 50.42 mmol, 4.01 mL) at 0° C. over 0.5 hr. Then the mixture was stirred at 25° C. for 3 hr. The reaction mixture was washed with H$_2$O (100 mL), HCl (1 M, 100 mL) and brine (100 mL), dried over Na$_2$SO$_4$, filtered and concentrated under reduced pressure to afford the title compound (8.86 g, crude) as a black-brown solid.

Example 89B

N-cyclohexyl-2-(3-(4,4,5,5-tetramethyl-1,3,2-dioxaborolan-2-yl)phenoxy)acetamide

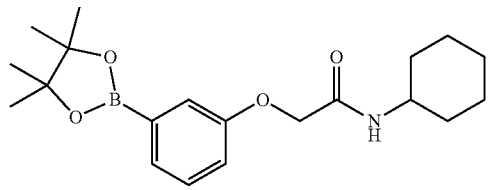 [SMILES: CC1(C)OB(c2cccc(OCC(=O)NC3CCCCC3)c2)OC1(C)C]

To a solution of 3-(4,4,5,5-tetramethyl-1,3,2-dioxaborolan-2-yl)phenol (500 mg, 2.27 mmol) and compound 2-chloro-N-cyclohexylacetamide3 (399.10 mg, 2.27 mmol) in MeCN (70.00 mL) was added K$_2$CO$_3$ (627.47 mg, 4.54 mmol). The mixture was stirred at 80° C. for 16 hour. TLC (Petroleum ether/Ethyl acetate=5/1) showed a new spot (Rf=0.35) was detected. LCMS showed 3-(4,4,5,5-tetramethyl-1,3,2-dioxaborolan-2-yl)phenol was consumed completely and ~37% peak with desired mass was detected. The reaction mixture was cooled to room temperature and quenched by addition water (50 mL). The resulting mixture was extracted with EtOAc (50 mL×2). The combined organic layers were washed with brine (50 mL×2), dried over Na$_2$SO$_4$, filtered and concentrated under reduced pressure to give a residue. The residue was purified by column chromatography (SiO$_2$, Petroleum ether/Ethyl acetate=50/1 to 1/1) to afford the title compound (550 mg, 67%) as a yellow solid. $^1$H NMR (400 MHz, DMSO-d$_6$) δ 7.49-7.48 (m, 1H), 7.40-7.33 (m, 2H), 7.05-7.02 (m, 1H), 6.49-6.47 (m, 1H), 4.51 (s, 2H), 3.93-3.87 (m, 1H), 1.97-1.93 (m, 2H), 1.77-1.72 (m, 2H), 1.67-1.61 (m, 2H), 1.37 (s, 12H), 1.26-1.17 (m, 4H).

Example 89C tert-butyl 4-(4-((tert-butoxycarbonyl)(2-(3-(2-(cyclohexylamino)-2-oxoethoxy)phenyl)-5,7-dihydrofuro[3,4-d]pyrimidin-4-yl)amino)phenyl)-1H-pyrazole-1-carboxylate

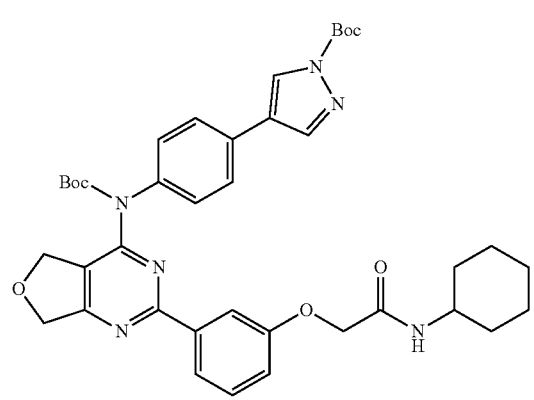 [SMILES: CC(C)(C)OC(=O)N(c1ccc(-c2cnn(C(=O)OC(C)(C)C)c2)cc1)c1nc(-c2cccc(OCC(=O)NC3CCCCC3)c2)nc2c1COC2]

A mixture of tert-butyl 4-(4-(((tert-butoxycarbonyl)(2-chloro-5,7-dihydrofuro[3,4-d]pyrimidin-4-yl)amino)phenyl)-1H-pyrazole-1-carboxylate (100.00 mg, 194.56 umol), N-cyclohexyl-2-(3-(4,4,5,5-tetramethyl-1,3,2-dioxaborolan-2-yl)phenoxy)acetamide (69.90 mg, 194.56 umol), Pd(PPh₃)₄ (22.48 mg, 19.46 umol) and K₃PO₄ (82.60 mg, 389.12 umol) in dioxane (5.00 mL)/H₂O (500.00 uL) was degassed and purged with N2 3 times and the mixture was stirred at 95° C. for 16 hour under N₂ atmosphere. LCMS showed tert-butyl 4-(4-(((tert-butoxycarbonyl)(2-chloro-5,7-dihydrofuro[3,4-d]pyrimidin-4-yl)amino)phenyl)-1H-pyrazole-1-carboxylate was consumed completely. TLC (Petroleum ether/Ethyl acetate=1/2) showed two main new spots (Rf=0.7, 0.35). The reaction mixture was cooled to room temperature and quenched by addition of H₂O (30 mL). Then the resulting mixture was extracted with EtOAc (30 mL×3). The combined organic layers were washed with brine (30 mL×3), dried over Na₂SO₄, filtered and concentrated under reduced pressure to give a residue. The residue was purified by prep-TLC (SiO₂, Petroleum ether/Ethyl acetate=1:2) to afford the title compound (50.00 mg) and mono-Boc product (110.00 mg) both as an off-white solid.

Example 89D 2-(3-(4-((4-(1H-pyrazol-4-yl)phenyl)amino)-5,7-dihydrofuro[3,4-d]pyrimidin-2-yl)phenoxy)-N-cyclohexylacetamide

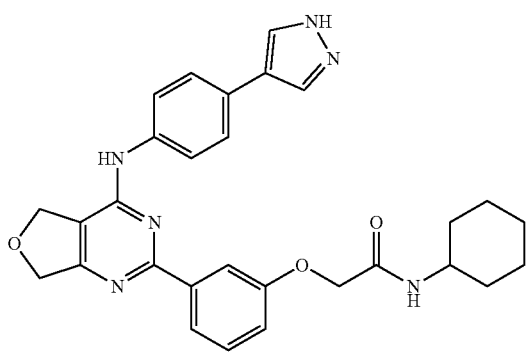 [SMILES: O=C(COc1cccc(-c2nc3c(c(Nc4ccc(-c5cn[nH]c5)cc4)n2)COC3)c1)NC1CCCCC1]

To a solution of tert-butyl 4-(4-(((tert-butoxycarbonyl)(2-(3-(2-(cyclohexylamino)-2-oxoethoxy)phenyl)-5,7-dihydrofuro[3,4-d]pyrimidin-4-yl)amino)phenyl)-1H-pyrazole-1-carboxylate (50.00 mg, 70.34 umol; contained 110 mg EW3123-108-P2) in CH₂Cl₂ (3.00 mL) was added HCl/dioxane (4 M, 6.00 mL). The mixture was stirred at 25° C. for 16 hour. LCMS showed ~29% desired compound and ~54% mono-Boc product. The reaction mixture was concentrated under reduced pressure to give a residue. The residue was washed with EtOAc (10 mL) to give an off-white solid. The solid was purified by prep-HPLC (FA conditions) to afford the title compound (7.6 mg) as an off-white solid. ¹H NMR (400 MHz, DMSO-d₆) δ 9.29 (s, 1H), 8.44 (s, 1H), 8.00-7.58 (m, 5H), 7.82 (d, J=8.8 Hz, 2H), 7.66 (d, J=8.4 Hz, 2H), 7.43 (t, J=8.4 Hz, 1H), 7.11-7.08 (m, 1H), 5.09 (s, 2H), 4.94 (s, 2H), 4.54 (s, 2H), 3.66-3.64 (m, 1H), 1.72-1.54 (m, 5H), 1.28-1.10 (m, 5H). (ES+) m/e 511.3 (M+H)⁺.

Example 90

2-(3-(4-((4-(1H-pyrazol-4-yl)phenyl)amino)-5,7-dihydrofuro[3,4-d]pyrimidin-2-yl)phenoxy)-N-(1,1,1-trifluoropropan-2-yl)acetamide

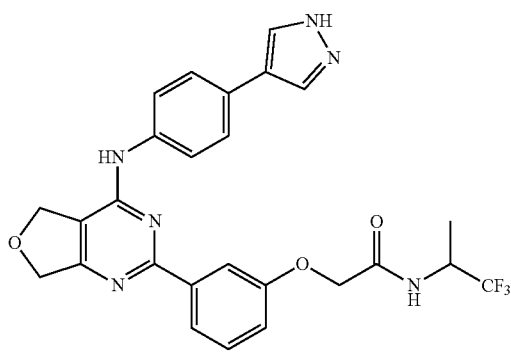 [SMILES: CC(NC(=O)COc1cccc(-c2nc3c(c(Nc4ccc(-c5cn[nH]c5)cc4)n2)COC3)c1)C(F)(F)F]

Example 90A 2-chloro-N-(1,1,1-trifluoropropan-2-yl)acetamide

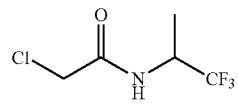

To a mixture of 1,1,1-trifluoropropan-2-amine (600.00 mg, 4.01 mmol, HCl) and TEA (803.51 mg, 7.94 mmol, 1.10 mL) in DCM (15.00 mL) was added 2-chloroacetyl chloride (448.41 mg, 3.97 mmol, 315.78 uL) dropwise at 0° C. The mixture was stirred under N₂ at 23° C. for 3 h. The reaction mixture was diluted with DCM (30 mL) and washed with water (30 mL×2), citric acid (10%, 30 mL), sat.NaHCO₃ (30 mL), brine (40 mL×2). The organic layer was dried over Na₂SO₄, filtered and concentrated under reduced pressure to afford the title compound as black oil which was used in the next step without further purification. ¹H NMR (400 MHz, DMSO-d₆) δ 8.80 (d, J=8.4 Hz, 1H), 4.64-4.54 (m, 1H), 4.11 (d, J=3.2 Hz, 2H), 1.25 (d, J=6.8 Hz, 3H).

Example 90B 2-(3-bromophenoxy)-N-(1,1,1-trifluoropropan-2-yl)acetamide

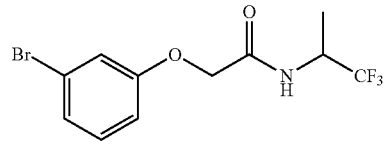 [SMILES: CC(NC(=O)COc1cccc(Br)c1)C(F)(F)F]

To a mixture of 2-chloro-N-(1,1,1-trifluoropropan-2-yl)acetamide (600.00 mg, 3.17 mmol) and 3-bromophenol (438.75 mg, 2.54 mmol) in MeCN (15.00 mL) was added K₂CO₃ (876.25 mg, 6.34 mmol). The mixture was stirred at 70° C. for 16 h. LCMS showed one main peak of desired product. The reaction mixture was cooled to room temperature and quenched by addition of H₂O (50 mL), then the resulting mixture was extracted with EtOAc (30 mL×3). The combined organic layers were washed with brine (30 mL×2), dried over Na$_2$SO$_4$, filtered and concentrated under reduced pressure to give a residue. The residue was purified by column chromatography (SiO$_2$, Petroleum ether/Ethyl acetate=50/1 to 1/1) to afford the title compound (530 mg, 62%; LCMS: EW3123-124-P1A) as a yellow solid.

Example 90C 2-(3-(4,4,5,5-tetramethyl-1,3,2-dioxaborolan-2-yl) phenoxy)-N-(1,1,1-trifluoropropan-2-yl)acetamide

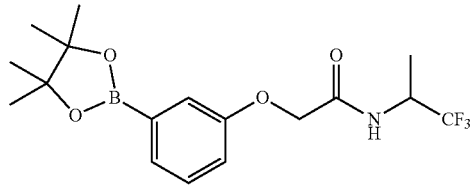 [SMILES: CC(NC(=O)COc1cccc(B2OC(C)(C)C(C)(C)O2)c1)C(F)(F)F]

A mixture of 2-(3-bromophenoxy)-N-(1,1,1-trifluoropropan-2-yl)acetamide (530.00 mg, 1.63 mmol), B$_2$(pin)$_2$ (455.31 mg, 1.79 mmol), Pd(dppf)Cl$_2$ (59.63 mg, 81.50 umol) and AcOK (319.94 mg, 3.26 mmol) in dioxane (20.00 mL) was degassed and purged with N$_2$ 3 times, then the mixture was stirred at 80° C. for 16 hour under N$_2$ atmosphere. LCMS showed one main peak with desired mass was detected. TLC (Petroleum ether/Ethyl acetate=3/1) showed two main new spots (Rf=0.35). The reaction mixture was cooled to room temperature. After addition of water (50 mL) and EtOAc (50 mL), the mixture was stirred for 5 min. The resulting suspension was filtered through celatom, and the filtrate was collected. The aqueous layer was extracted with EtOAc (50 mL×2). The combined organic layers were washed with brine (50 mL×2), dried over Na$_2$SO$_4$, filtered and concentrated under reduced pressure to give a residue. The residue was purified by column chromatography (SiO$_2$, Petroleum ether/Ethyl acetate=1/0 to 1/1) to afford product (500 mg) as a yellow solid. Purification by prep-TLC (Petroleum ether/Ethyl acetate=3/1) to afford the title compound (140 mg) as a white solid. $^1$H NMR (400 MHz, DMSO-d$_6$) δ 8.70 (d, J=9.2 Hz, 1H), 7.35-7.28 (m, 2H), 7.23 (d, J=2.4 Hz, 1H), 7.10-7.07 (m, 1H), 4.71-4.67 (m, 1H), 4.59 (s, 2H), 1.31 (s, 3H), 1.30 (s, 12H).

Example 90D tert-butyl 4-(4-((tert-butoxycarbonyl)(2-(3-(2-oxo-2-((1,1,1-trifluoropropan-2-yl)amino)ethoxy)phenyl)-5,7-dihydrofuro[3,4-d]pyrimidin-4-yl)amino)phenyl)-1H-pyrazole-1-carboxylate

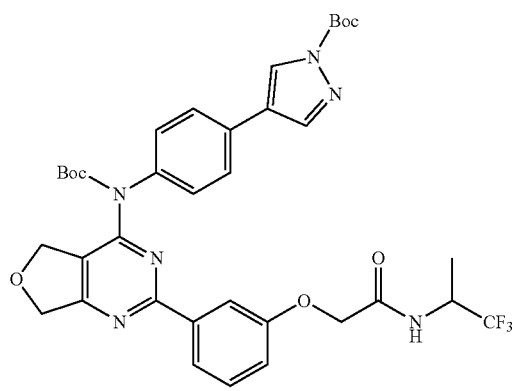 [SMILES: CC(NC(=O)COc1cccc(-c2nc3c(c(N(C(=O)OC(C)(C)C)c4ccc(-c5cnn(C(=O)OC(C)(C)C)c5)cc4)n2)COC3)c1)C(F)(F)F]

A mixture of tert-butyl 4-(4-((tert-butoxycarbonyl)(2-chloro-5,7-dihydrofuro[3,4-d]pyrimidin-4-yl)amino)phenyl)-1H-pyrazole-1-carboxylate (195.00 mg, 379.40 umol), 2-(3-(4,4,5,5-tetramethyl-1,3,2-dioxaborolan-2-yl)phenoxy)-N-(1,1,1-trifluoropropan-2-yl)acetamide (141.58 mg, 379.40 umol), Pd(dppf)Cl$_2$ (27.76 mg, 37.94 umol) and K$_2$CO$_3$ (104.87 mg, 758.80 umol) in dioxane (5.00 mL)/H$_2$O (500.00 uL) was degassed and purged with N$_2$ 3 times, then the mixture was stirred at 95° C. for 16 hour under N$_2$ atmosphere. LCMS showed ~20% starting material remained and ~40% desired compound was detected. The reaction mixture was cooled to room temperature and quenched by addition of H$_2$O (20 mL), then the resulting mixture was extracted with EtOAc (20 mL×3). The combined organic layers were washed with brine (20 mL×3), dried over Na$_2$SO$_4$, filtered and concentrated under reduced pressure to give a residue. The residue was purified by prep-TLC (SiO$_2$, Petroleum ether/Ethyl acetate=1:2, Rf=0.35) to afford the title compound (160.00 mg, 41%) and mono-Boc product (110.00 mg, 30%) both as an off-white solid.

Example 90E 2-(3-(4-((4-(1H-pyrazol-4-yl)phenyl)amino)-5,7-dihydrofuro[3,4-d]pyrimidin-2-yl)phenoxy)-N-(1,1,1-trifluoropropan-2-yl)acetamide

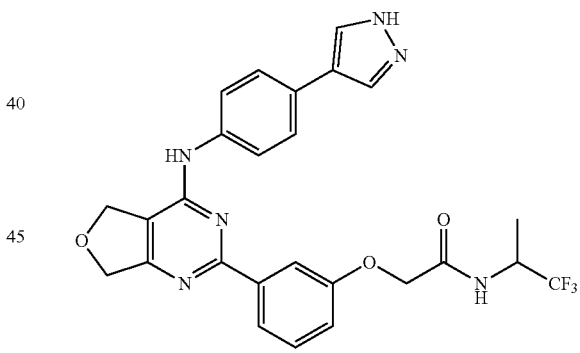

To a solution of tert-butyl 4-(4-((tert-butoxycarbonyl)(2-(3-(2-oxo-2-((1,1,1-trifluoropropan-2-yl)amino)ethoxy)phenyl)-5,7-dihydrofuro[3,4-d]pyrimidin-4-yl)amino)phenyl)-1H-pyrazole-1-carboxylate (160.00 mg, 154.54 umol, contain 110 mg mono-Boc product) in CH$_2$Cl$_2$ (3.00 mL) was added HCl/dioxane (4 M, 6.00 mL). The mixture was stirred at 25° C. for 16 hour. LCMS showed ~50% of desired compound and ~25% mono-Boc product. The reaction mixture was concentrated under reduced pressure to give a residue. The residue was purified by prep-HPLC (FA conditions) to afford the title compound (17.6 mg) as an off-white solid. $^1$H NMR (400 MHz, DMSO-d$_6$) δ 9.25 (s, 1H), 8.96 (d, J=9.2 Hz, 1H), 8.42 (s, 1H), 7.97-7.57 (m, 4H), 7.80 (d, J=8.4 Hz, 2H), 7.65 (d, J=8.4 Hz, 2H), 7.43 (t, J=8.4

Hz, 1H), 7.10-7.07 (m, 1H), 5.08 (s, 2H), 4.93 (s, 2H), 1.29 (d, J=6.8 Hz, 3H). (ES+) m/e 525.2 (M+H)+.

Example 91

N-(4-(1H-pyrazol-4-yl)phenyl)-2-(3-(((6-methylpyridin-3-yl)methyl)amino)phenyl)-5,7-dihydrofuro[3,4-d]pyrimidin-4-amine

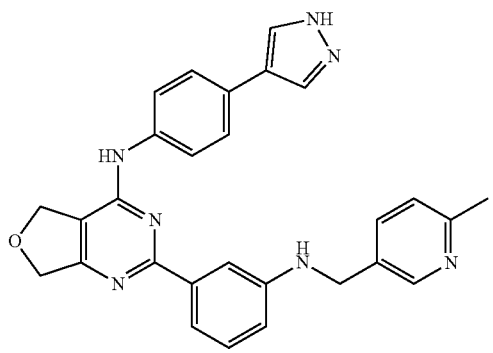 [SMILES: Cc1ccc(CNc2cccc(-c3nc4c(c(Nc5ccc(-c6cn[nH]c6)cc5)n3)COC4)c2)cn1]

Example 91A 2-(3-aminophenyl)-N-(4-(1-(tetrahydro-2H-pyran-2-yl)-1H-pyrazol-4-yl)phenyl)-5,7-dihydrofuro[3,4-d]pyrimidin-4-amine

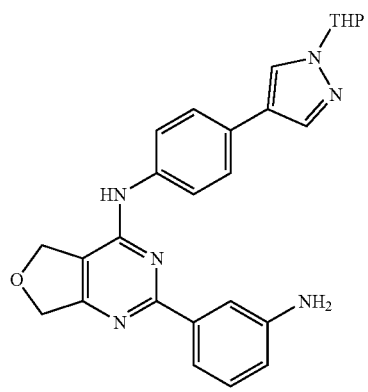

To a mixture of 2-chloro-N-(4-(1-(tetrahydro-2H-pyran-2-yl)-1H-pyrazol-4-yl)phenyl)-5,7-dihydrofuro[3,4-d]pyrimidin-4-amine (1.00 g, 2.51 mmol) and 3-(4,4,5,5-tetramethyl-1,3,2-dioxaborolan-2-yl)aniline (549.92 mg, 2.51 mmol) in dioxane (15.00 mL) and H$_2$O (1.50 mL) was added K$_2$CO$_3$ (693.81 mg, 5.02 mmol) and Pd(dppf)Cl$_2$ (183.66 mg, 251.00 umol). The mixture was stirred under N$_2$ at 90° C. for 16 h. TLC (petroleum ether/EtOAc=1:2, Rf=0.26) showed one new main spot. The reaction mixture was cooled to room temperature and diluted with water (50 mL). The mixture was extracted with EtOAc (60 mL×3). The combined organic layers were washed with brine (40 mL×2), dried over Na$_2$SO$_4$, filtered and concentrated under reduced pressure to give a residue. The residue was purified by column chromatography (silica gel, petroleum ether/EtOAc: 1:0 to 1:3) to give the title compound (505 mg, 44%) as a light yellow solid. $^1$H NMR (400 MHz, DMSO-d$_6$) δ 9.14 (s, 1H), 8.32 (s, 1H), 7.93 (s, 1H), 7.84 (d, J=8.4 Hz, 2H), 7.64 (t, J=9.0 Hz, 3H), 7.51 (d, J=7.6 Hz, 1H), 7.12 (t, J=7.8 Hz, 1H), 6.68 (d, J=6.4 Hz, 1H), 5.40 (d, J=10.0 Hz, 1H), 5.23 (s, 2H), 4.92 (s, 2H), 3.95 (d, J=10.4 Hz, 1H), 3.68-3.62 (m, 1H), 2.17-2.10 (m, 1H), 1.96-1.91 (m, 2H), 1.70-1.67 (m, 1H), 1.55 (s, 2H).

Example 91B

N-(4-(1H-pyrazol-4-yl)phenyl)-2-(3-(((6-methylpyridin-3-yl)methyl)amino)phenyl)-5,7-dihydrofuro[3,4-d]pyrimidin-4-amine

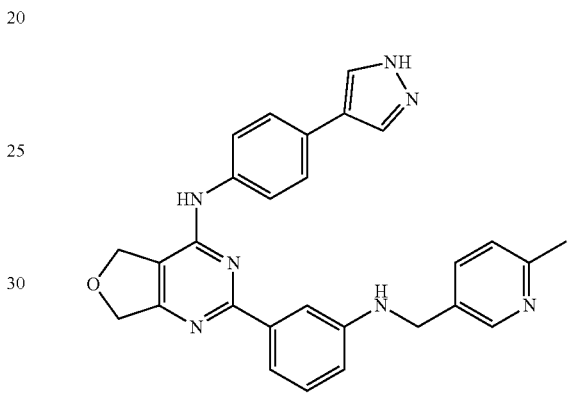

The mixture of 2-(3-aminophenyl)-N-(4-(1-(tetrahydro-2H-pyran-2-yl)-1H-pyrazol-4-yl)phenyl)-5,7-dihydrofuro[3,4-d]pyrimidin-4-amine (1 eq), aldehyde (1.5 eq) and AcOH (2 eq) in MeOH (3.00 mL) was stirred at 15° C. for 30 min. Then NaBH$_3$CN (5 eq) was added. The mixture was stirred at 15° C. for 15.5 h. TLC (CH$_2$Cl$_2$:CH$_3$OH=10:1) showed one new main spot. The reaction mixture was diluted with water (30 mL) and extracted with EtOAc (30 mL×3). The combined organic layers were washed with brine (20 mL×2), dried over Na$_2$SO$_4$, filtered and concentrated under reduced pressure to give a residue. The residue was purified by prep-TLC (CH$_2$Cl$_2$:CH$_3$OH=10:1) to give 2-(3-((pyridin-3-ylmethyl)amino)phenyl)-N-(4-(1-(tetrahydro-2H-pyran-2-yl)-1H-pyrazol-4-yl)phenyl)-5,7-dihydrofuro[3,4-d]pyrimidin-4-amine.

To the mixture of 2-(3-((pyridin-3-ylmethyl)amino)phenyl)-N-(4-(1-(tetrahydro-2H-pyran-2-yl)-1H-pyrazol-4-yl)phenyl)-5,7-dihydrofuro[3,4-d]pyrimidin-4-amine (1 eq) in CH$_2$Cl$_2$ (5.00 mL) was added HCl/dioxane (4 M, 5.00 mL). The mixture was stirred at 30° C. for 1 h. The mixture was concentrated under reduced pressure to give a residue. The residue was purified by prep-HPLC (FA) to get desired product. Yellow solid; Yield: 34% (two steps). $^1$H NMR (400 MHz, DMSO-d$_6$) δ 9.15 (s, 1H), 8.44 (s, 1H), 8.21 (s, 1H), 8.02 (s, 2H), 7.80 (d, J=8.4 Hz, 2H), 7.67 (s, 1H), 7.64-7.59 (m, 3H), 7.55 (d, J=7.6 Hz, 1H), 7.18-7.14 (m, 2H), 6.70 (d, J=7.6 Hz, 1H), 6.45 (t, J=6.0 Hz, 1H), 5.06 (s, 2H), 4.91 (s, 2H) 4.32 (d, J=5.6 Hz, 2H), 2.40 (s, 3H). (ES+) m/e 476.3 (M+H)+.

Example 92

N-(4-(1H-pyrazol-4-yl)phenyl)-2-(3-(((5-fluoropyridin-3-yl)methyl)amino)phenyl)-5,7-dihydrofuro[3,4-d]pyrimidin-4-amine

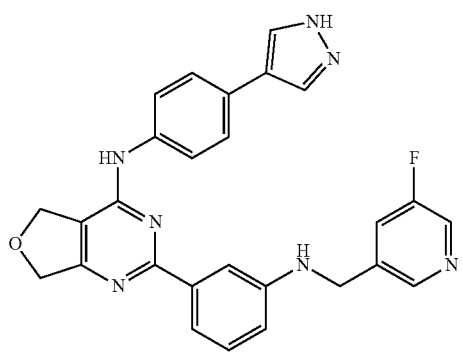 [SMILES: Fc1cncc(CNc2cccc(-c3nc4c(c(Nc5ccc(-c6cn[nH]c6)cc5)n3)COC4)c2)c1]

The title compound was prepared using essentially the same procedure for Example 127. Off-White solid; Yield: 32% (two steps). $^1$H NMR (400 MHz, DMSO-d$_6$) δ 12.90 (s, 1H), 9.16 (s, 1H), 8.48 (s, 1H), 8.42 (d, J=2.8 Hz, 1H), 8.14 (s, 1H), 7.91 (s, 1H), 7.80 (d, J=8.8 Hz, 2H), 7.69-7.57 (m, 5H), 7.19 (t, J=7.8 Hz, 1H), 6.71 (d, J=7.6 Hz, 1H), 6.53 (t, J=6.0 Hz, 1H), 5.06 (s, 2H), 4.91 (s, 2H), 4.43 (d, J=6.0 Hz, 2H). (ES+) m/e 480.2 (M+H)$^+$.

Example 93

N-(4-(1H-pyrazol-4-yl)phenyl)-2-(3-(((5-chloropyridin-3-yl)methyl)amino)phenyl)-5,7-dihydrofuro[3,4-d]pyrimidin-4-amine

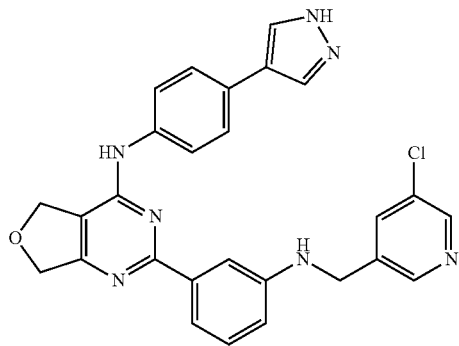 [SMILES: Clc1cncc(CNc2cccc(-c3nc4c(c(Nc5ccc(-c6cn[nH]c6)cc5)n3)COC4)c2)c1]

The title compound was prepared using essentially the same procedure for Example 127. Light Yellow solid; Yield: 6.5% (two steps). $^1$H NMR (400 MHz, DMSO-d6) δ 9.16 (s, 1H), 8.55 (s, 1H), 8.48 (d, J=2.4 Hz, 1H), 8.03 (s, 2H), 7.87 (s, 1H), 7.80 (d, J=8.4 Hz, 2H), 7.68 (s, 1H), 7.63-7.57 (m, 3H), 7.19 (t, J=7.8 Hz, 1H), 6.72 (d, J=8.0 Hz, 1H), 6.53 (t, J=6.2 Hz, 1H), 5.06 (s, 2H), 4.92 (s, 2H), 4.43 (d, J=5.6 Hz, 2H). (ES+) m/e 496.2 (M+H)$^+$.

Example 94

N-(4-(1H-pyrazol-4-yl)phenyl)-2-(3-(((5-methylpyridin-3-yl)methyl)amino)phenyl)-5,7-dihydrofuro[3,4-d]pyrimidin-4-amine

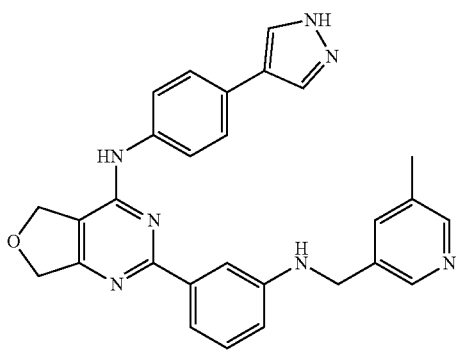 [SMILES: Cc1cncc(CNc2cccc(-c3nc4c(c(Nc5ccc(-c6cn[nH]c6)cc5)n3)COC4)c2)c1]

The title compound was prepared using essentially the same procedure for Example 127. Off-White solid; Yield: 35% (two steps). $^1$H NMR (400 MHz, DMSO-d$_6$) δ 12.9 (s, 1H), 9.15 (s, 1H), 8.39 (s, 1H), 8.26 (s 1H), 8.14 (s, 1H), 7.90 (s, 1H), 7.80 (d, J=8.8 Hz, 2H), 7.68 (s, 1H), 7.61 (d, J=8.8 Hz, 2H), 7.57 (s, 2H), 7.17 (t, J=8.0 Hz, 1H), 6.71 (d, J=8.4 Hz, 1H), 6.46 (t, J=6.0 Hz, 1H), 5.06 (s, 2H), 4.91 (s, 2H), 4.34 (d, J=6.0 Hz, 2H), 2.22 (s, 3H). (ES+) m/e 476.2 (M+H)$^+$.

Example 95

2-(5-(4-((4-(1H-pyrazol-4-yl)phenyl)amino)-5,7-dihydrofuro[3,4-d]pyrimidin-2-yl)-2-fluorophenoxy)-N-isopropylacetamide

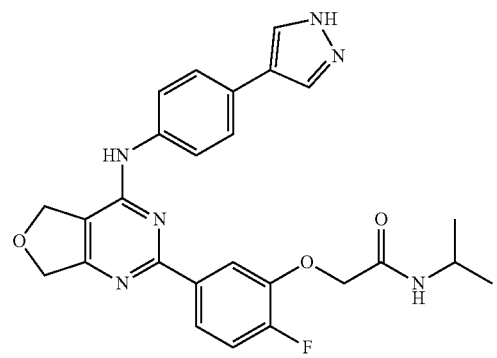 [SMILES: CC(C)NC(=O)COc1cc(-c2nc3c(c(Nc4ccc(-c5cn[nH]c5)cc4)n2)COC3)ccc1F]

Example 95A 2-(5-bromo-2-fluorophenoxy)-N-isopropylacetamide

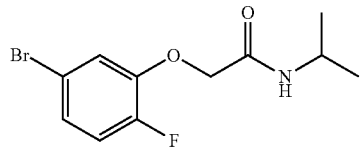 [SMILES: CC(C)NC(=O)COc1cc(Br)ccc1F]

To the mixture of 5-bromo-2-fluoro-phenol (600.00 mg, 3.14 mmol), 2-chloro-N-isopropylacetamide (510.90 mg, 3.77 mmol) in MeCN (15.00 mL) was added K₂CO₃ (867.96 mg, 6.28 mmol). The mixture was stirred at 70° C. for 16 h. LCMS showed one main peak of desired product. The reaction mixture was diluted with water (40 mL) and the mixture was extracted with EtOAc (40 mL×3). The combined organic layers were dried over Na₂SO₄, filtered and concentrated under reduced pressure to give a residue. The residue was purified by column chromatography (SiO2, petroleum ether/EtOAc=1:0 to 4:1) to give the title compound (900.00 mg, 98%) as light yellow solid. ¹H NMR (400 MHz, DMSO-d₆) δ 7.97 (d, J=7.2 Hz, 1H), 7.25-7.20 (m, 2H), 7.17-7.16 (m, 1H), 4.58 (s, 2H), 3.95-3.87 (m, 1H), 1.08 (d, J=6.8 Hz, 6H).

Example 95B 2-(2-fluoro-5-(4,4,5,5-tetramethyl-1,3,2-dioxaborolan-2-yl)phenoxy)-N-isopropylacetamide

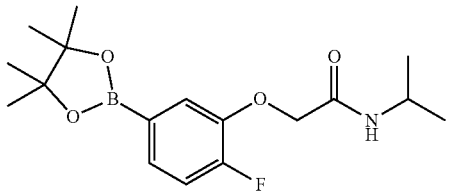 [SMILES: CC(C)NC(=O)COc1cc(B2OC(C)(C)C(C)(C)O2)ccc1F]

To the mixture of 2-(5-bromo-2-fluorophenoxy)-N-isopropylacetamide (900.00 mg, 3.10 mmol) and 4,4,4',4',5,5,5',5'-octamethyl-2,2'-bi(1,3,2-dioxaborolane) (1.18 g, 4.65 mmol) in dioxane (10.00 mL) was added AcOK (608.47 mg, 6.20 mmol) and Pd(dppf)Cl₂ (226.83 mg, 310.00 umol). The mixture was stirred under N₂ at 90° C. for 16 h. TLC (petroleum ether/EtOAc=2:1, Rf=0.59) showed one new main spot. The reaction mixture was diluted with water (40 mL) and the mixture was extracted with EtOAc (40 mL×3). The combined organic layers were washed with brine (30 mL×2), dried over Na₂SO₄, filtered and concentrated under reduced pressure to give a residue. The residue was purified by column chromatography (SiO₂, petroleum ether/EtOAc=1:0 to 2:1) to give the title compound (1.00 g, 95%) as a light yellow solid. ¹H NMR (400 MHz, DMSO-d₆) δ 8.00 (d, J=7.6 Hz, 1H), 7.29-7.20 (m, 3H), 4.54 (s, 2H), 3.95-3.90 (m, 1H), 1.28 (s, 12H), 1.07 (d, J=4.0 Hz, 6H).

Example 95C 2-(2-fluoro-5-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)-N-isopropylacetamide

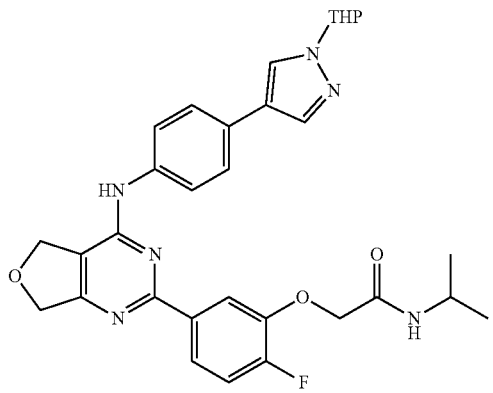

To the mixture of 2-chloro-N-(4-(1-(tetrahydro-2H-pyran-2-yl)-1H-pyrazol-4-yl)phenyl)-5,7-dihydrofuro[3,4-d]pyrimidin-4-amine (90.00 mg, 226.21 umol) and 2-(2-fluoro-5-(4,4,5,5-tetramethyl-1,3,2-dioxaborolan-2-yl)phenoxy)-N-isopropylacetamide (91.53 mg, 271.45 umol) in dioxane (4.00 mL), H₂O (400.00 uL) was added K₂CO₃ (62.53 mg, 452.42 umol) and Pd(dppf)Cl₂ (16.55 mg, 22.62 umol). The mixture was stirred under N₂ at 90° C. for 16 h. LCMS showed one main peak of desired product. The reaction mixture was diluted with (30 mL) and the mixture was extracted with EtOAc (30 mL×3). The combined organic layers were washed with brine (30 mL×2), dried over Na₂SO₄, filtered and concentrated under reduced pressure to give a residue. The residue was purified by prep-TLC (petroleum ether/EtOAc=1:3, Rf=0.23) to give the title compound (35.00 mg, 25%) as a light yellow solid.

Example 95D 2-(5-(4-((4-(1H-pyrazol-4-yl)phenyl)amino)-5,7-dihydrofuro[3,4-d]pyrimidin-2-yl)-2-fluorophenoxy)-N-isopropylacetamide

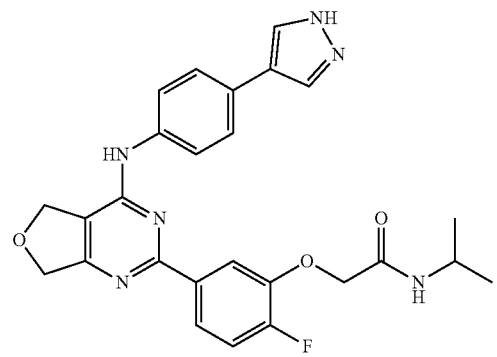 [SMILES: CC(C)NC(=O)COc1cc(-c2nc3c(c(Nc4ccc(-c5cn[nH]c5)cc4)n2)COC3)ccc1F]

To the solution of 2-(2-fluoro-5-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)-N-isopropylacetamide (35.00 mg, 61.12 umol) in CH₂Cl₂ (5.00 mL) was added HCl/dioxane (4 N, 5.00 mL). The mixture was stirred at 30° C. for 1 h. LCMS showed one main peak of desired product. The residue was concentrated under reduced pressure to give a residue. The residue was purified by prep-HPLC (FA conditions) to give the title compound (5.90 mg, 19%) as a white solid. ¹H NMR (400 MHz, DMSO-d₆) δ 12.90 (s, 1H), 9.23 (s, 1H), 8.16 (s, 1H), 8.04 (d, J=7.2 Hz, 1H), 7.99-7.93 (m, 3H), 7.79 (d, J=8.4 Hz, 2H), 7.65 (d, J=8.4 Hz, 2H), 7.38-7.33 (m, 1H), 5.07 (s, 2H), 4.92 (s, 2H), 4.64 (s, 2H), 4.00-3.91 (m, 1H), 1.06 (d, J=6.8 Hz, 6H). (ES+) m/e 489.2 (M+H)⁺.

Example 96

2-(5-(4-((4-(1H-pyrazol-4-yl)phenyl)amino)-5,7-dihydrofuro[3,4-d]pyrimidin-2-yl)-2-fluorophenoxy)-N-(tert-butyl)acetamide

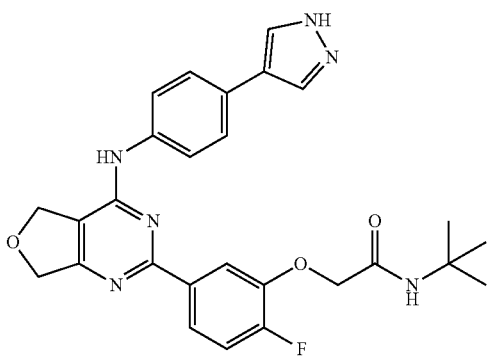 [SMILES: CC(C)(C)NC(=O)COc1cc(-c2nc3c(c(Nc4ccc(-c5cn[nH]c5)cc4)n2)COC3)ccc1F]

Example 96B 2-(5-bromo-2-fluorophenoxy)-N-(tert-butyl)acetamide

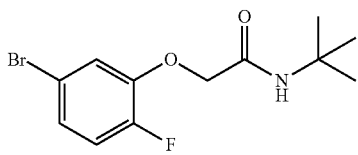 [SMILES: CC(C)(C)NC(=O)COc1cc(Br)ccc1F]

To the mixture of 5-bromo-2-fluoro-phenol (600.00 mg, 3.14 mmol) and N-(tert-butyl)-2-chloroacetamide (563.77 mg, 3.77 mmol) in MeCN (15.00 mL) was added K₂CO₃ (867.96 mg, 6.28 mmol). The mixture was stirred at 80° C. for 16 h. TLC (petroleum ether/EtOAc=2:1, Rf=0.7) showed one new main spot. The reaction mixture was cooled to room temperature and diluted with water (40 mL). The resulting mixture was extracted with EtOAc (40 mL×3). The combined organic layers were dried over Na₂SO₄, filtered and concentrated under reduced pressure to give a residue. The residue was purified by column chromatography (SiO₂, petroleum ether/EtOAc=1:0 to 4:1) to give the title compound (870.00 mg, 91%) as a light yellow solid. ¹H NMR (400 MHz, DMSO-d₆) δ 7.64 (s, 1H), 7.25-7.20 (m, 2H), 7.16-7.15 (m, 1H), 4.55 (s, 2H), 1.28 (m, 9H).

Example 96C

N-(tert-butyl)-2-(2-fluoro-5-(4,4,5,5-tetramethyl-1,3,2-dioxaborolan-2-yl)phenoxy)acetamide

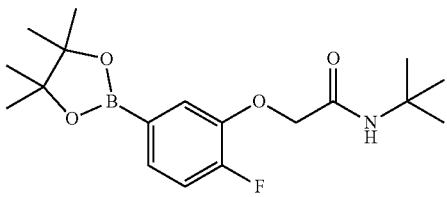 [SMILES: CC(C)(C)NC(=O)COc1cc(B2OC(C)(C)C(C)(C)O2)ccc1F]

To the mixture of compound 2-(5-bromo-2-fluorophenoxy)-N-(tert-butyl)acetamide (870.00 mg, 2.86 mmol) and 4,4,4',4',5,5,5',5'-octamethyl-2,2'-bi(1,3,2-dioxaborolane) (1.09 g, 4.29 mmol) in dioxane (15.00 mL) was added AcOK (561.36 mg, 5.72 mmol,) and Pd(dppf)Cl₂ (209.27 mg, 286.00 umol). The mixture was stirred under N₂ at 90° C. for 16 h. LCMS showed one main peak of desired product. The reaction mixture was cooled to room temperature and diluted with water (40 mL). The resulting mixture was extracted with EtOAc (40 mL×3). The combined organic layers were washed with brine (30 mL×2), dried over Na₂SO₄, filtered and concentrated under reduced pressure to give a residue. The residue was purified by column chromatography (SiO₂, petroleum ether/EtOAc=1:0 to 4:1) to give the title compound (870.00 mg, 87%) as a light yellow solid. ¹H NMR (400 MHz, DMSO-d₆) δ 7.69 (s, 1H), 7.27-7.19 (m, 3H), 7.07-7.05 (m, 1H), 4.51 (s, 2H), 1.29-1.28 (m, 21H).

Example 96D

N-(tert-butyl)-2-(2-fluoro-5-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)acetamide

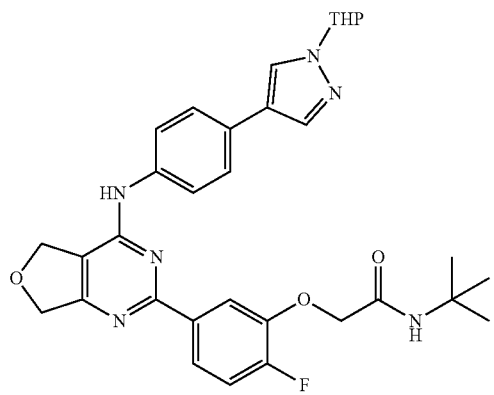

To the mixture of 2-chloro-N-(4-(1-(tetrahydro-2H-pyran-2-yl)-1H-pyrazol-4-yl)phenyl)-5,7-dihydrofuro[3,4-d]pyrimidin-4-amine (100.00 mg, 251.34 umol) and N-(tert-butyl)-2-(2-fluoro-5-(4,4,5,5-tetramethyl-1,3,2-dioxaborolan-2-yl)phenoxy)acetamide (132.41 mg, 377.01 umol) in dioxane (5.00 mL), H₂O (500.00 uL) was added K₂CO₃ (69.48 mg, 502.68 umol) and Pd(dppf)Cl₂ (18.39 mg, 25.13 umol). The mixture was stirred under N₂ at 90° C. for 16 h. LCMS showed one main peak of desired product. The reaction mixture was cooled to room temperature and diluted with (30 mL). The resulting mixture was extracted with EtOAc (30 mL×3). The combined organic layers were washed with brine (30 mL×2), dried over Na₂SO₄, filtered and concentrated under reduced pressure to give a residue. The residue was purified by prep-TLC (petroleum ether/EtOAc=1:3, Rf=0.23) to give the title compound (80.00 mg, 79% yield) as a light yellow solid.

Example 96E 2-(5-(4-((4-(1H-pyrazol-4-yl)phenyl)amino)-5,7-dihydrofuro[3,4-d]pyrimidin-2-yl)-2-fluorophenoxy)-N-(tert-butyl)acetamide

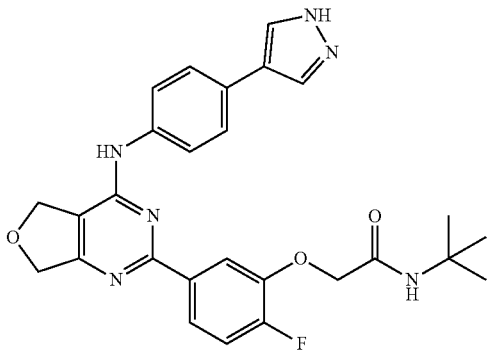 [SMILES: CC(C)(C)NC(=O)COc1cc(-c2nc3c(c(Nc4ccc(-c5cn[nH]c5)cc4)n2)COC3)ccc1F]

To the mixture of N-(tert-butyl)-2-(2-fluoro-5-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)acetamide (80.00 mg, 136.37 umol) in CH$_2$Cl$_2$ (5.00 mL) was added HCl/dioxane (4 N, 5.00 mL). The mixture was stirred at 30° C. for 1 h. LCMS showed one main peak of desired product. The reaction was concentrated under reduced pressure to give a residue. The residue was purified by prep-HPLC (FA conditions) to giv the title compound (10.7 mg, 15%) as a white solid. $^1$H NMR (400 MHz, DMSO-d$_6$) δ 9.25 (s, 1H), 8.16 (s, 1H), 8.05 (d, J=6.8 Hz, 1H), 7.96-7.93 (m, 2H), 7.80 (d, J=8.4 Hz, 2H), 7.67-7.64 (s, 3H), 7.37-7.32 (m, 1H), 5.07 (s, 2H), 4.92 (s, 2H), 4.61 (s, 2H), 1.27 (s, 9H). (ES+) m/e 503.2 (M+H)$^+$.

Example 97

2-(5-(4-((4-(1H-pyrazol-4-yl)phenyl)amino)-5,7-dihydrofuro[3,4-d]pyrimidin-2-yl)-2-fluorophenoxy)-N-(pentan-3-yl)acetamide

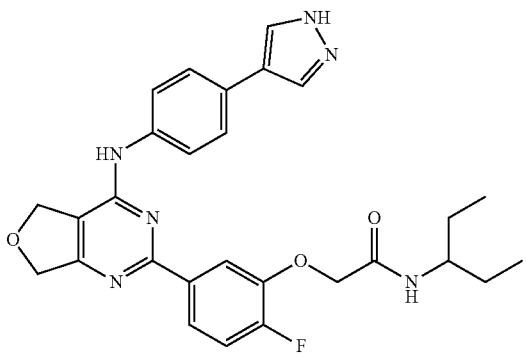 [SMILES: CCC(CC)NC(=O)COc1cc(-c2nc3c(c(Nc4ccc(-c5cn[nH]c5)cc4)n2)COC3)ccc1F]

Example 97A 2-(5-bromo-2-fluorophenoxy)-N-(pentan-3-yl)acetamide

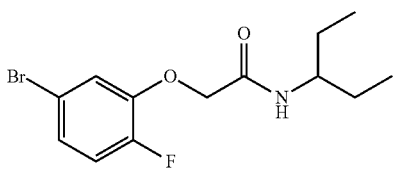 [SMILES: CCC(CC)NC(=O)COc1cc(Br)ccc1F]

To the mixture of 5-bromo-2-fluorophenol (600.00 mg, 3.14 mmol) and 2-chloro-N-(pentan-3-yl)acetamide (616.63 mg, 3.77 mmol) in MeCN (15.00 mL) was added K$_2$CO$_3$ (867.96 mg, 6.28 mmol). The mixture was stirred at 80° C. for 16 h. TLC (petroleum ether/EtOAc=2:1, Rf=0.67) showed one new main spot. The reaction mixture was cooled to room temperature and diluted with water (40 mL). The resulting mixture was extracted with EtOAc (40 mL×3). The combined organic layers were dried over Na$_2$SO$_4$, filtered and concentrated under reduced pressure to give a residue. The residue was purified by column chromatography (SiO$_2$, petroleum ether/EtOAc=1:0 to 4:1) to give the title compound (890.00 mg, 89%) as a light yellow solid. $^1$H NMR (400 MHz, DMSO-d$_6$) δ 7.82 (s, 1H), 7.23-7.15 (m, 3H), 4.65 (s, 2H), 3.62-3.56 (m, 1H), 1.48-1.43 (m, 2H), 1.37-1.32 (m, 2H), 0.80 (t, J=7.4 Hz, 6H).

Example 97B 2-(2-fluoro-5-(4,4,5,5-tetramethyl-1,3,2-dioxaborolan-2-yl)phenoxy)-N-(pentan-3-yl)acetamide

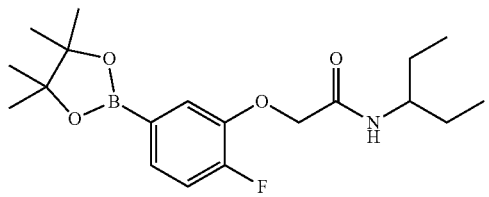 [SMILES: CCC(CC)NC(=O)COc1cc(B2OC(C)(C)C(C)(C)O2)ccc1F]

To the mixture of 2-(5-bromo-2-fluorophenoxy)-N-(pentan-3-yl)acetamide (890.00 mg, 2.80 mmol) and 4,4,4',4',5,5,5',5'-octamethyl-2,2'-bi(1,3,2-dioxaborolane) (1.07 g, 4.20 mmol) in dioxane (15.00 mL) was added AcOK (549.58 mg, 5.60 mmol) and Pd(dppf)Cl$_2$ (204.88 mg, 280.00 umol). The mixture was stirred under N$_2$ at 90° C. for 16 h. The reaction mixture was cooled to room temperature and diluted with water (40 mL). The resulting mixture was extracted with EtOAc (40 mL×3). The combined organic layers were washed with brine (30 mL×2), dried over Na$_2$SO$_4$, filtered and concentrated under reduced pressure to give a residue. The residue was purified by column chromatography (SiO$_2$, petroleum ether/EtOAc=1:0 to 5:1, TLC: petroleum ether/EtOAc=2:1, Rf=0.64) to give the title compound (900 mg, 88%) as a light yellow solid. $^1$H NMR (400 MHz, DMSO-d$_6$) δ 7.81 (d, J=8.8 Hz, 1H), 7.29-7.21 (m, 3H), 4.61 (s, 2H), 3.62-3.55 (m, 1H), 1.46-1.43 (m, 2H), 1.38-1.32 (m, 2H), 1.27 (s, 12H), 0.80 (t, J=7.4 Hz, 6H).

Example 97C 2-(2-fluoro-5-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)-N-(pentan-3-yl)acetamide

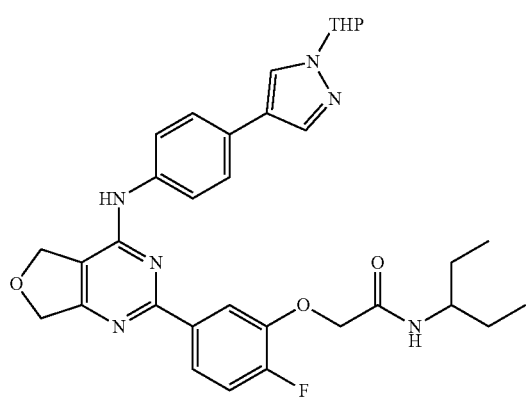

To the mixture of 2-chloro-N-(4-(1-(tetrahydro-2H-pyran-2-yl)-1H-pyrazol-4-yl)phenyl)-5,7-dihydrofuro[3,4-d]pyrimidin-4-amine (100.00 mg, 251.34 umol) and 2-(2-fluoro-5-(4,4,5,5-tetramethyl-1,3,2-dioxaborolan-2-yl)phenoxy)-N-(pentan-3-yl)acetamide (137.71 mg, 377.01 umol) in dioxane (5.00 mL), H$_2$O (500.00 uL) was added K$_2$CO$_3$ (69.48 mg, 502.68 umol) and Pd(dppf)Cl$_2$ (18.39 mg, 25.13 umol). The mixture was stirred under N$_2$ at 90° C. for 16 h. LCMS showed one main peak of desired product. The reaction mixture was cooled to room temperature and diluted with (30 mL). The resulting mixture was extracted with EtOAc (30 mL×3). The combined organic layers were washed with brine (30 mL×2), dried over Na$_2$SO$_4$, filtered and concentrated under reduced pressure to give a residue. The residue was purified by prep-TLC (petroleum ether/EtOAc=1:3, Rf=0.40) to give the title compound (63.00 mg, 38%) as a light yellow solid.

Example 97D 2-(5-(4-((4-(1H-pyrazol-4-yl)phenyl)amino)-5,7-dihydrofuro[3,4-d]pyrimidin-2-yl)-2-fluorophenoxy)-N-(pentan-3-yl)acetamide

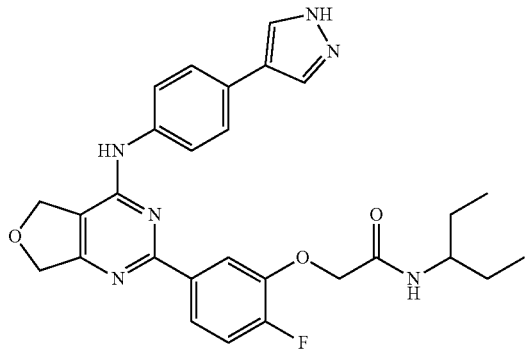 [SMILES: CCC(CC)NC(=O)COc1cc(-c2nc3c(c(Nc4ccc(-c5cn[nH]c5)cc4)n2)COC3)ccc1F]

To the mixture of 2-(2-fluoro-5-(4-((4-(1-(tetrahydro-2H-pyran-2-yl)-1H-pyrazol-4-yl)phenyl)amino)-5,7-dihydrofuro[3,4-d]pyrimidin-2-yl)phenoxy)-N-(pentan-3-yl)acetamide (63.00 mg, 104.88 umol) in CH$_2$Cl$_2$ (5.00 mL) was added HCl/dioxane (4 N, 5.00 mL). The mixture was stirred at 30° C. for 1 h. LCMS showed about 65% desired product and about 35% starting material. To the mixture was added HCl/dioxane (4 N, 2 mL). The mixture was stirred at 30° C. for 30 min. LCMS showed one main peak of desired product. The residue was concentrated under reduced pressure to give a residue. The residue was purified by prep-HPLC (FA conditions) to give the title compound (33.8 mg, 61%) as an off-white solid. $^1$H NMR (400 MHz, DMSO-d$_6$) δ 12.91 (s, 1H), 9.23 (s, 1H), 8.16 (s, 1H), 8.04 (d, J=7.2 Hz, 1H), 7.98-7.95 (m, 2H), 7.78 (d, J=8.4 Hz, 3H), 7.66 (d, J=8.4 Hz, 2H), 7.38-7.33 (m, 1H), 5.07 (s, 2H), 4.91 (s, 2H), 4.70 (s, 2H), 3.64-3.59 (m, 1H), 1.45-1.31 (m, 4H), 0.76 (t, J=7.2 Hz, 6H). (ES+) m/e 517.2 (M+H)$^+$.

Example 98

2-(3-(4-((4-(1H-pyrazol-4-yl)phenyl)amino)-5,6,7,8-tetrahydropyrido[4,3-d]pyrimidin-2-yl)phenoxy)-N-(tert-butyl)acetamide

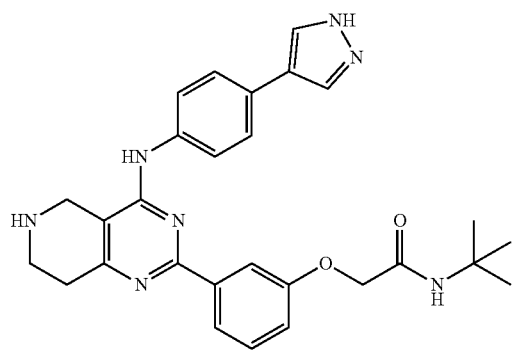

Example 98A tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylate

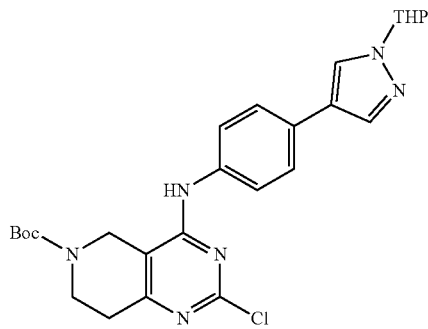

To the mixture of tert-butyl 2,4-dichloro-7,8-dihydropyrido[4,3-d]pyrimidine-6(5H)-carboxylate (2.20 g, 7.23 mmol) and 4-(1-(tetrahydro-2H-pyran-2-yl)-1H-pyrazol-4-yl)aniline (1.76 g, 7.23 mmol) in n-BuOH (20.00 mL) was added DIPEA (1.87 g, 14.46 mmol, 2.53 mL). The mixture was stirred under N$_2$ at 100° C. for 16 h. TLC (petroleum ether/EtOAc=1:1, RF=0.45) showed one main spot was detected. The reaction mixture was cooled to room temperature and diluted with water (30 mL). The resulting mixture was extracted with EtOAc (30 mL×3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=100:1 to 1:1) to afford the title compound (3.03 g, 82%) as a yellow solid. $^1$H NMR (400 MHz, DMSO-d$_6$) δ 8.97 (s, 1H), 8.32 (s, 1H), 7.94 (s, 1H), 7.63-7.58 (m, 4H), 5.42-5.39 (m, 1H), 4.43 (s, 2H), 3.94 (d, J=11.6 Hz, 1H), 3.68-3.62 (m, 3H), 2.69 (t, J=5.6 Hz, 2H), 2.16-2.08 (m, 1H), 1.96-1.93 (m, 2H), 1.71-1.64 (m, 1H), 1.56-1.55 (m, 2H), 1.48 (s, 9H), 1.45 (s, 9H).

Example 98B tert-butyl 2-(3-(2-(tert-butylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate

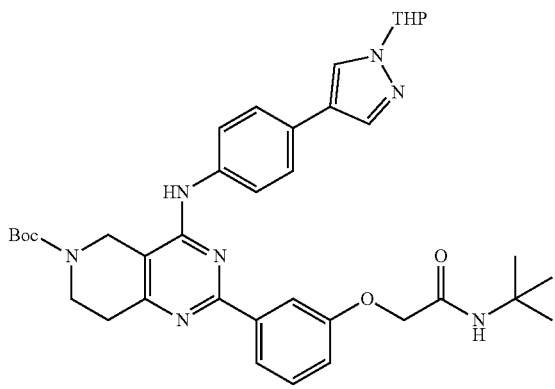

To the mixture of tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (1.50 g, 2.94 mmol) and N-(tert-butyl)-2-(3-(4,4,5,5-tetramethyl-1,3,2-dioxaborolan-2-yl)phenoxy)acetamide (1.18 g, 3.53 mmol) in dioxane (10.00 mL), H$_2$O (1.00 mL) was added K$_2$CO$_3$ (812.67 mg, 5.88 mmol), Pd(dppf)Cl$_2$ (215.12 mg, 294.00 umol). The mixture was stirred under N$_2$ at 90° C. for 16 h. TLC (petroleum ether/EtOAc=1:1, Rf=0.30) showed one new main spot. The reaction mixture was cooled to room temperature and diluted with water (30 mL). The resulting mixture was extracted with EtOAc (30 mL×3). The combined organic layers were washed with brine (50 mL×2), dried over Na$_2$SO$_4$, filtered and concentrated under reduced pressure to give a residue. The residue was purified by column chromatography (SiO$_2$, petroleum ether/EtOAc=50:1 to 1:1) to afford the title compound (1.40 g, 70%) as a light yellow solid. $^1$H NMR (400 MHz, DMSO-d$_6$) δ 8.35-8.31 (m, 1H), 7.94-7.89 (m, 2H), 7.79 (d, J=8.0 Hz, 2H), 7.66-7.56 (m, 3H), 7.48 (s, 1H), 7.38 (t, J=8.0 Hz, 1H), 7.06-7.03 (m, 1H), 5.42-5.39 (m, 1H), 4.52-4.47 (m, 3H), 3.96-3.93 (m, 1H), 3.71-3.62 (m, 3H), 2.82-2.67 (m, 2H), 2.18-2.12 (m, 1H), 1.96-1.94 (m, 2H), 1.74-1.63 (m, 1H), 1.56-1.54 (m, 2H), 1.46-1.45 (m, 9H), 1.30 (s, 9H).

Example 98C 2-(3-(4-((4-(1H-pyrazol-4-yl)phenyl)amino)-5,6,7,8-tetrahydropyrido[4,3-d]pyrimidin-2-yl)phenoxy)-N-(tert-butyl)acetamide

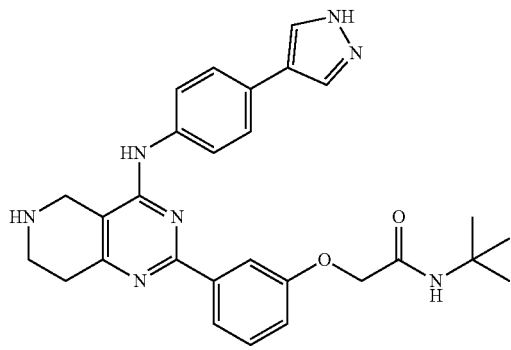 [SMILES: CC(C)(C)NC(=O)COc1cccc(-c2nc3c(c(Nc4ccc(-c5cn[nH]c5)cc4)n2)CNCC3)c1]

To a mixture of tert-butyl 2-(3-(2-(tert-butylamino)-2-oxoethoxy)phenyl)-4-((4-(1-(tetrahydro-2H-pyrazol-2-yl)-1H-pyrazol-4-yl)phenyl)amino)-7,8-dihydropyrido[4,3-d]pyrimidine-6(5H)-carboxylate (1.40 g, 2.05 mmol) in CH$_2$Cl$_2$ (15.00 mL) was added HCl/dioxane (4 N, 10.00 mL). The mixture was stirred at 20° C. for 15 h. LCMS showed about 70% desired product and about 12% THP-protected product. To the mixture was added HCl/dioxane (4 N, 20 mL) and the mixture was stirred at 20° C. for another 2 h. LCMS showed about 81% of desired product. The mixture was filtered to give compound 6 (1.2 g, HCl salt, crude). 100 mg of compound 6 was purified by prep-HPLC (FA conditions) to give the title compound (31.8 mg) as a light yellow solid. $^1$H NMR (400 MHz, DMSO-d$_6$) δ 8.44 (s, 1H), 8.21 (s, 1H), 8.05 (s, 2H), 7.90-7.88 (m, 2H), 7.78 (d, J=8.4 Hz, 2H), 7.63 (d, J=8.4 Hz, 2H), 7.53 (s, 1H), 7.38 (t, J=7.8 Hz, 1H), 7.02 (d, J=6.8 Hz, 1H), 4.46 (s, 2H), 3.50 (s, 2H), 2.83 (s, 2H), 2.73 (s, 2H), 2.47 (s, 3H), 1.29 (s, 9H). (ES+) m/e 498.2 (M+H)$^+$.

Example 99

2-(3-(4-((4-(1H-pyrazol-4-yl)phenyl)amino)-6-methyl-5,6,7,8-tetrahydropyrido[4,3-d]pyrimidin-2-yl)phenoxy)-N-(tert-butyl)acetamide

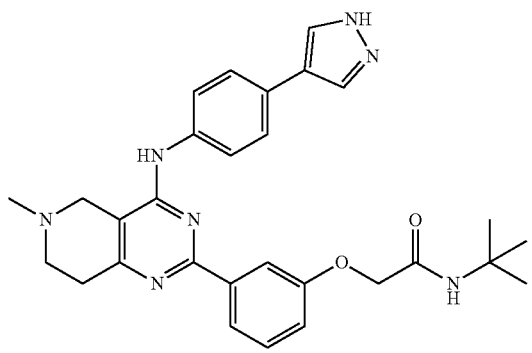 [SMILES: CN1CCc2nc(-c3cccc(OCC(=O)NC(C)(C)C)c3)nc(Nc3ccc(-c4cn[nH]c4)cc3)c2C1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-(tert-butyl)acetamide (200.00 mg, 374.50 umol, HCl salt) in MeOH (2.00 mL) was added TEA (75.79 mg, 748.99 umol, 103.82 uL). The mixture was stirred at 15° C. for 10 min. Then to the mixture was added HCHO (84.35 mg, 1.12 mmol, 77.38 uL, 40% purity), HOAc (89.95 mg, 1.50 mmol, 85.67 uL). The mixture was stirred at 15° C. for 20 min. Then to the mixture was added NaBH$_3$CN (117.67 mg, 1.87 mmol). The resulting mixture was stirred at 15° C. for 15.5 h. LCMS showed one main peak of desired product. The reaction mixture was diluted with water (30 mL) and the mixture was extracted with EtOAc (30 mL×3). The combined organic layers were dried over Na$_2$SO$_4$, filtered and concentrated under reduced pressure to give a residue. The residue was purified by prep-HPLC (FA conditions) to afford the title compound (74.4 mg, 32%) as a light yellow solid. $^1$H NMR (400 MHz, DMSO-d$_6$) δ 8.44 (s, 1H), 8.20 (s, 1H), 8.05 (s, 2H), 7.95-7.90 (m, 3H), 7.78 (d, J=8.8 Hz, 2H), 7.38 (t, J=8.2 Hz, 1H), 7.06-7.04 (m, 1H), 4.50 (s, 2H), 4.02-3.94 (m, 1H), 3.50 (s, 2H), 2.83 (d, J=5.2 Hz, 2H), 2.73 (d, J=5.2 Hz, 2H), 2.47 (s, 3H), 1.09 (d, J=6.4 Hz, 6H). (ES+) m/e 512.2 (M+H)$^+$.

Example 100

2-(3-(4-((4-(1H-pyrazol-4-yl)phenyl)amino)-6-methyl-5,6,7,8-tetrahydropyrido[4,3-d]pyrimidin-2-yl)phenoxy)-N-(pentan-3-yl)acetamide

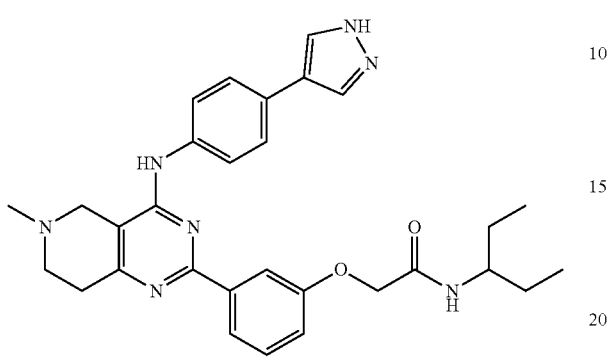

The title compound was synthesized using essentially the same procedure as described for the synthesis of Example 99.

Yellow solid; Yield: 11% (3 steps). $^1$H NMR (400 MHz, DMSO-$d_6$) δ 8.43 (s, 1H), 8.25 (s, 1H), 8.04 (s, 2H), 7.91-7.90 (m, 2H), 7.79-7.72 (m, 3H), 7.63 (d, J=8.4 Hz, 2H), 7.38 (t, J=8.2 Hz, 1H), 7.06-7.03 (m, 1H), 4.56 (s, 2H), 3.64-3.60 (m, 1H), 3.50 (s, 2H), 2.82 (d, J=5.2 Hz, 2H), 2.73 (d, J=5.2 Hz, 2H), 2.47 (s, 3H), 1.48-1.34 (m, 4H), 0.77 (t, J=7.4 Hz, 6H). (ES+) m/e 526.4 (M+H)$^+$.

Example 101

2-(3-(4-((4-(1H-pyrazol-4-yl)phenyl)amino)-6-methyl-5,6,7,8-tetrahydropyrido[4,3-d]pyrimidin-2-yl)phenoxy)-N-isopropylacetamide

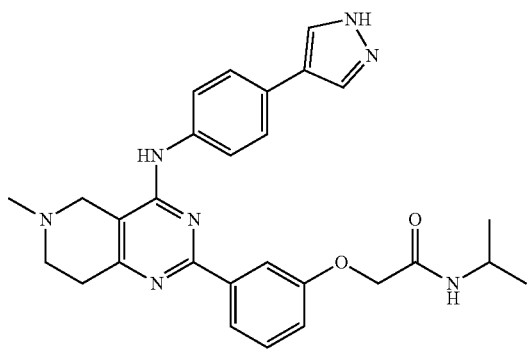 [SMILES: CC(C)NC(=O)COc1cccc(-c2nc3c(c(Nc4ccc(-c5cn[nH]c5)cc4)n2)CN(C)CC3)c1]

The title compound was synthesized using essentially the same procedure as described for the synthesis of Example 99.

Light Yellow solid; Yield: 19% (3 steps). $^1$H NMR (400 MHz, DMSO-$d_6$) δ 8.44 (s, 1H), 8.20 (s, 1H), 8.05 (s, 2H), 7.95-7.90 (m, 3H), 7.78 (d, J=8.8 Hz, 2H), 7.38 (t, J=8.2 Hz, 1H), 7.06-7.04 (m, 1H), 4.50 (s, 2H), 4.02-3.94 (m, 1H), 3.50 (s, 2H), 2.83 (d, J=5.2 Hz, 2H), 2.73 (d, J=5.2 Hz, 2H), 2.47 (s, 3H), 1.09 (d, J=6.4 Hz, 6H). (ES+) m/e 498.3 (M+H)$^+$.

Example 102

2-(3-(4-((4-(1H-pyrazol-4-yl)phenyl)amino)-7,8-dihydro-5H-pyrano[4,3-d]pyrimidin-2-yl)phenoxy)-N-isopropylacetamide

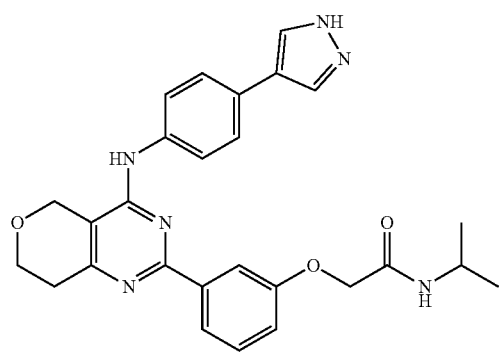 [SMILES: CC(C)NC(=O)COc1cccc(-c2nc3c(c(Nc4ccc(-c5cn[nH]c5)cc4)n2)COCC3)c1]

Example 102A methyl 4-oxotetrahydro-2H-pyran-3-carboxylate

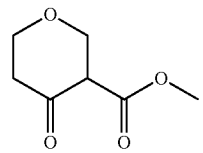

To the mixture of tetrahydro-4H-pyran-4-one (15.00 g, 149.82 mmol), dimethyl carbonate (33.74 g, 374.55 mmol) in THF (300.00 mL) was added NaH (14.98 g, 374.55 mmol, 60% purity) by protions at 0° C. The mixture was stirred under N$_2$ at 0° C. for 30 min, then at 15° C. for 30 min. Then the mixture was warmed to 45° C. and stirred for 15 h. TLC (petroleum ether/EtOAc=3:1, Rf=0.6) showed one new main spot. The reaction mixture was poured into the mixture of icy 1 N HCl (600 mL) and extracted with EtOAc (600 mL×3). The combined organic layers were washed with brine (800 mL×2), dried over Na$_2$SO$_4$, filtered and concentrated under reduced pressure to give a residue. The residue was purified by column chromatography (SiO$_2$, petroleum ether/EtOAc=1:0 to 10:1) to afford the title compound (7.75 g 33%) as colorless oil. $^1$H NMR (400 MHz, DMSO-$d_6$) δ 11.78 (s, 1H), 4.14-4.10 (m, 1H), 4.07-3.95 (m, 1H), 3.86 (t, J=5.6 Hz, 2H), 3.78-3.77 (m, 3H), 2.40 (t, J=5.6 Hz, 2H).

Example 102B 2-(ethylthio)-7,8-dihydro-5H-pyrano[4,3-d]pyrimidin-4-ol

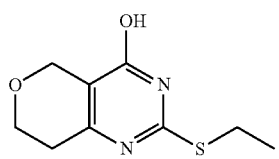

To the mixture of 2-ethylisothiourea (9.07 g, 49.00 mmol, HBr salt) in H$_2$O (50.00 mL) under dark was added Na$_2$CO$_3$ (5.19 g, 49.00 mmol). Then to the mixture was added methyl 4-oxotetrahydro-2H-pyran-3-carboxylate (7.75 g, 49.00 mmol). The mixture was stirred under dark at 25° C. for 16 h TLC (petroleum ether/EtOAc=1:1, Rf=0.3) showed one new main spot. The mixture was filtered, the solid was washed with water (30 mL), petroleum ether/EtOAc=20:1 (20 mL). Then the solid was dried under reduced pressure to afford the title compound (8.01 g, crude) as an off-white solid. $^1$H NMR (400 MHz, DMSO-d$_6$) δ 10.69 (s, 1H), 5.87 (s, 1H), 3.83 (s, 1H), 3.63-3.49 (m, 3H), 3.00-2.89 (m, 2H), 2.40 (s, 1H), 1.24 (t, J=7.2 Hz, 3H).

Example 102C 7,8-dihydro-5H-pyrano[4,3-d]pyrimidine-2,4-diol

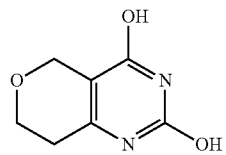 [SMILES: Oc1nc(O)c2c(n1)CCOC2]

To the mixture of 2-(ethylthio)-7,8-dihydro-5H-pyrano[4,3-d]pyrimidin-4-ol (8.01 g, 37.73 mmol) in H$_2$O (100.00 mL) was added conc.HCl (3.82 g, 37.73 mmol, 3.75 mL), AcOH (13.60 g, 226.38 mmol, 12.95 mL). The mixture was stirred at 100° C. for 16 h. The mixture was cooled to room temperature and filtered. The solid was washed with water (80 mL), dried over with toluene to afford the title compound (5.30 g, crude) as a white solid. $^1$H NMR (400 MHz, DMSO-d$_6$) δ 10.99 (s, 1H), 10.85 (s, 1H), 4.19 (s, 2H), 3.77 (t, J=5.2 Hz, 2H), 2.38 (t, J=5.0 Hz, 2H).

Example 102D 2,4-dichloro-7,8-dihydro-5H-pyrano[4,3-d]pyrimidine

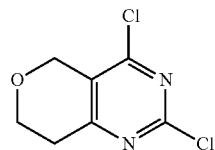 [SMILES: Clc1nc(Cl)c2c(n1)CCOC2]

To POCl$_3$ (50.00 mL) was added 7,8-dihydro-5H-pyrano[4,3-d]pyrimidine-2,4-diol (4.80 g, 28.55 mmol), DIPEA (7.38 g, 57.10 mmol, 9.97 mL). The mixture was stirred under N$_2$ at 80° C. for 16 h. TLC (petroleum ether/EtOAc=3:1, Rf=0.55) showed one main spot was detected. The mixture was concentrated under reduced pressure to remove most of POCl$_3$ to give a residue. With the addition of ice, the residue was neutralized with sat.NaHCO$_3$ to pH-7 and the resulting mixture was extracted with EtOAc (100 mL×3). The combined organic layers were dried over Na$_2$SO$_4$, filtered and concentrated under reduced pressure to give a residue. The residue was purified by column chromatography (SiO$_2$, petroleum ether/EtOAc=10:1 to 3:1) to give the title compound (5.10 g, 87%) as a light yellow solid.

Example 102E 2-chloro-N-(4-(1-(tetrahydro-2H-pyran-2-yl)-1H-pyrazol-4-yl)phenyl)-7,8-dihydro-5H-pyrano[4,3-d]pyrimidin-4-amine

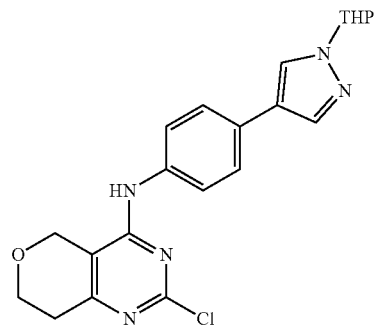

To the mixture of 2,4-dichloro-7,8-dihydro-5H-pyrano[4,3-d]pyrimidine (5.10 g, 24.87 mmol) and 4-(1-(tetrahydro-2H-pyran-2-yl)-1H-pyrazol-4-yl)aniline (6.05 g, 24.87 mmol) in n-BuOH (40.00 mL) was added DIPEA (6.43 g, 49.74 mmol, 8.69 mL). The mixture was stirred under N$_2$ at 100° C. for 16 h. TLC (petroleum ether/EtOAc=1:2, Rf=0.46) showed one main spot was detected. The mixture was cooled to room temperature and filtered. The solid was purified by recrystallization (petroleum ether/EtOAc=10:1, 200 mL) to give the title compound (4.93 g) as a light yellow solid. $^1$H NMR (400 MHz, DMSO-d$_6$) δ 8.71 (s, 1H), 8.31 (s, 1H), 7.93 (s, 1H), 7.62-7.55 (m, 4H), 5.42-5.39 (m, 1H), 4.61 (s, 2H), 3.95-3.91 (m, 3H), 3.68-3.61 (m, 1H), 2.71 (t, J=5.2 Hz, 2H), 2.14-2.07 (m, 1H), 1.95-1.94 (m, 2H), 1.71-1.66 (m, 1H), 1.56-1.55 (m, 1H).

Example 102F 2-(3-(4-((4-(1H-pyrazol-4-yl)phenyl)amino)-7,8-dihydro-5H-pyrano[4,3-d]pyrimidin-2-yl)phenoxy)-N-isopropylacetamide

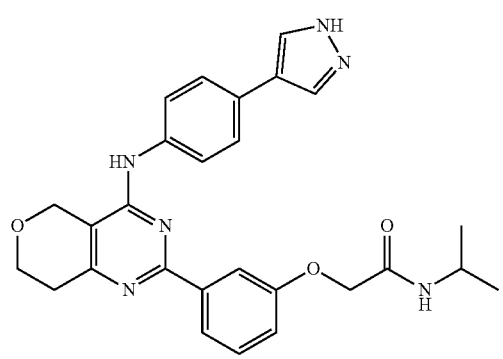

To the mixture of 2-chloro-N-(4-(1-(tetrahydro-2H-pyran-2-yl)-1H-pyrazol-4-yl)phenyl)-7,8-dihydro-5H-pyrano[4,3-d]pyrimidin-4-amine (1.00 eq) and N-isopropyl-2-(3-(4,4,5,5-tetramethyl-1,3,2-dioxaborolan-2-yl)phenoxy)

acetamide (1.20 eq) in dioxane (3.00 mL), H₂O (300.00 uL) was added K₂CO₃ (2.00 eq) and Pd(dppf)Cl₂ (0.10 eq). The mixture was stirred under N₂ at 90° C. for 16 h. The reaction mixture was cooled to room temperature and diluted with water. The resulting mixture was extracted with EtOAc. The combined organic layers were washed with brine, dried over Na₂SO₄, filtered and concentrated under reduced pressure to give a residue. The residue was purified by column chromatography to afford N-isopropyl-2-(3-(4-((4-(1-(tetrahydro-2H-pyran-2-yl)-1H-pyrazol-4-yl)phenyl)amino)-7,8-dihydro-5H-pyrano[4,3-d]pyrimidin-2-yl)phenoxy)acetamide.

To the mixture of N-isopropyl-2-(3-(4-((4-(1-(tetrahydro-2H-pyran-2-yl)-1H-pyrazol-4-yl)phenyl)amino)-7,8-dihydro-5H-pyrano[4,3-d]pyrimidin-2-yl)phenoxy)acetamide (1.00 eq) in CH₂Cl₂ was added HCl/dioxane. The mixture was stirred at 15° C. for 0.5-16 h. The mixture was concentrated under reduced pressure to give a residue. The residue was purified by prep-HPLC (FA conditions) to afford the title compound. Yellow solid; Yield: 23% (2 steps). ¹H NMR (400 MHz, DMSO-d₆) δ 8.42 (s, 1H), 8.06 (s, 2H), 7.97 (d, J=8.0 Hz, 1H), 7.91 (d, J=7.2 Hz, 2H), 7.76 (d, J=8.8 Hz, 2H), 7.64 (d, J=8.4 Hz, 2H), 7.39 (t, J=8.2 Hz, 1H), 7.07-7.04 (m, 1H), 4.71 (s, 2H), 4.50 (s, 2H), 4.01-3.96 (m, 3H), 2.82 (t, J=5.0 Hz, 2H), 1.09 (d, J=6.8 Hz, 6H). (ES+) m/e 485.1 (M+H)⁺.

Example 103

2-(3-(4-((4-(1H-pyrazol-4-yl)phenyl)amino)-7,8-dihydro-5H-pyrano[4,3-d]pyrimidin-2-yl)phenoxy)-N-(sec-butyl)acetamide

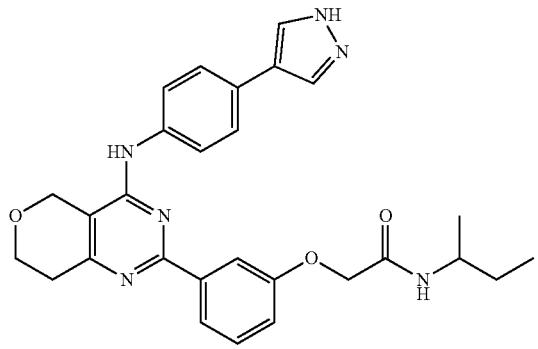 [SMILES: CCC(C)NC(=O)COc1cccc(-c2nc3c(c(Nc4ccc(-c5cn[nH]c5)cc4)n2)COCC3)c1]

The compound was synthesized using essentially the same procedure described for the synthesis of Example 102.

Yellow solid; Yield: 13% (2 steps). ¹H NMR (400 MHz, DMSO-d₆) δ 12.77 (s, 1H), 8.40 (s, 1H), 8.05 (s, 2H), 7.92-7.86 (m, 3H), 7.75 (d, J=8.4 Hz, 2H), 7.39 (t, J=8.2 Hz, 1H), 7.07-7.04 (m, 1H), 4.71 (s, 2H), 4.53 (s, 2H), 3.99 (t, J=5.4 Hz, 2H), 3.80-3.77 (m, 1H), 2.82 (d, J=4.8 Hz, 2H), 1.44-1.40 (m, 2H), 1.05 (d, J=6.8 Hz, 3H), 0.78 (t, J=7.4 Hz, 3H). (ES+) m/e 499.1 (M+H)⁺.

Example 104

2-(3-(4-((4-(1H-pyrazol-4-yl)phenyl)amino)-7,8-dihydro-5H-pyrano[4,3-d]pyrimidin-2-yl)phenoxy)-N-isobutylacetamide

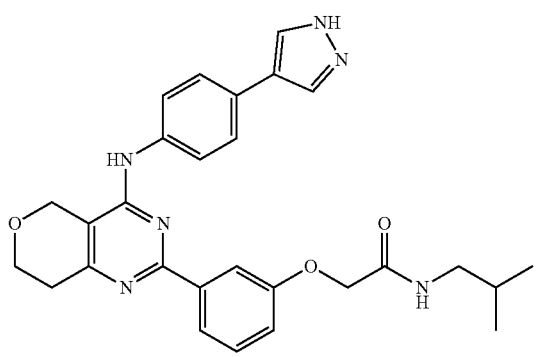 [SMILES: CC(C)CNC(=O)COc1cccc(-c2nc3c(c(Nc4ccc(-c5cn[nH]c5)cc4)n2)COCC3)c1]

The compound was synthesized using essentially the same procedure described for the synthesis of Example 102.

Light Yellow solid; Yield: 9.3% (2 steps). ¹H NMR (400 MHz, DMSO-d₆) δ 12.90 (s, 1H), 8.40 (s, 1H), 8.14-8.05 (m, 3H), 7.92-7.90 (m, 2H), 7.75 (d, J=8.4 Hz, 2H), 7.63 (d, J=8.4 Hz, 2H), 7.39 (t, J=8.2 Hz, 1H), 7.07-7.05 (m, 1H), 4.71 (s, 2H), 4.55 (s, 2H), 3.99 (t, J=5.6 Hz, 2H), 2.96 (t, J=6.4 Hz, 2H), 2.82 (t, J=5.2 Hz, 2H), 1.78-1.70 (m, 1H), 0.80 (d, J=6.8 Hz, 6H). (ES+) m/e 499.2 (M+H)⁺.

Example 105

2-(3-(4-((4-(1H-pyrazol-4-yl)phenyl)amino)-7,8-dihydro-5H-pyrano[4,3-d]pyrimidin-2-yl)phenoxy)-N-neopentylacetamide

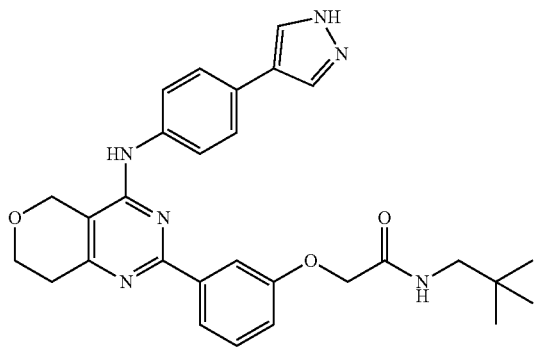 [SMILES: CC(C)(C)CNC(=O)COc1cccc(-c2nc3c(c(Nc4ccc(-c5cn[nH]c5)cc4)n2)COCC3)c1]

The compound was synthesized using essentially the same procedure described for the synthesis of Example 102.

Light Yellow solid; Yield: 39% (2 steps). ¹H NMR (400 MHz, DMSO-d₆) δ 12.90 (s, 1H), 8.39 (s, 1H), 8.04-7.95 (m, 3H), 7.92-7.90 (m, 2H), 7.75 (d, J=8.4 Hz, 2H), 7.63 (d, J=8.8 Hz, 2H), 7.39 (t, J=8.2 Hz, 1H), 7.07-7.04 (m, 1H), 4.71 (s, 2H), 4.60 (s, 2H), 3.99 (t, J=5.6 Hz, 2H), 2.95 (d, J=6.4 Hz, 2H), 2.81 (t, J=5.2 Hz, 2H), 0.80 (s, 9H). (ES+) m/e 513.2 (M+H)⁺.

Example 106

2-(3-(4-((4-(1H-pyrazol-4-yl)phenyl)amino)-7,8-dihydro-5H-pyrano[4,3-d]pyrimidin-2-yl)phenoxy)-N-(pentan-3-yl)acetamide

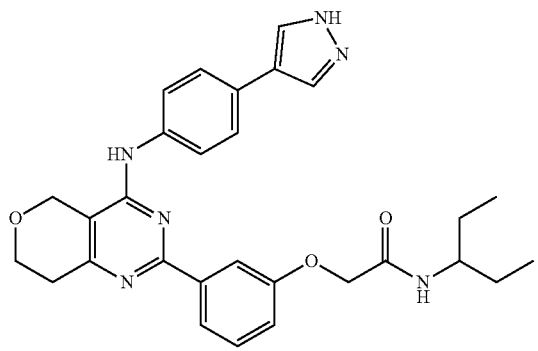 [SMILES: CCC(CC)NC(=O)COc1cccc(-c2nc3c(c(Nc4ccc(-c5cn[nH]c5)cc4)n2)COCC3)c1]

The compound was synthesized using essentially the same procedure described for the synthesis of Example 102.

Light Yellow solid; Yield: 13% (2 steps). $^1$H NMR (400 MHz, DMSO-$d_6$) δ 8.40 (s, 1H), 8.05 (s, 2H), 7.92-7.91 (m, 2H), 7.77-7.73 (m, 3H), 7.64 (d, J=8.4 Hz, 2H), 7.39 (t, J=8.2 Hz, 1H), 7.07-7.04 (m, 1H), 4.71 (s, 2H), 4.56 (s, 2H), 3.99 (t, J=5.4 Hz, 2H), 3.65-3.60 (m, 1H), 2.81 (s, 2H), 1.47-1.34 (m, 4H), 0.78 (t, J=7.4 Hz, 6H). (ES+) m/e 513.2 (M+H)$^+$.

Example 107

2-(3-(4-((4-(1H-pyrazol-4-yl)phenyl)amino)-7,8-dihydro-5H-pyrano[4,3-d]pyrimidin-2-yl)phenoxy)-N-(tert-butyl)acetamide

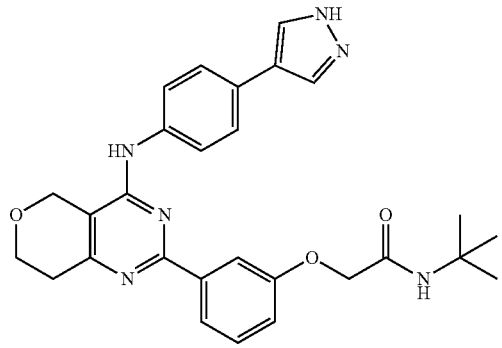 [SMILES: CC(C)(C)NC(=O)COc1cccc(-c2nc3c(c(Nc4ccc(-c5cn[nH]c5)cc4)n2)COCC3)c1]

The compound was synthesized using essentially the same procedure described for the synthesis of Example 102.

Light Yellow solid; Yield: 5.6% (2 steps). $^1$H NMR (400 MHz, DMSO-$d_6$) δ 8.41 (s, 1H), 8.04 (s, 2H), 7.91-7.88 (m, 2H), 7.75 (d, J=8.8 Hz, 2H), 7.63 (d, J=8.4 Hz, 2H), 7.52 (s, 1H), 7.38 (t, J=8.2 Hz, 1H), 7.05-7.02 (m, 1H), 4.71 (s, 2H), 4.46 (s, 2H), 3.99 (t, J=5.4 Hz, 2H), 2.82 (t, J=5.0 Hz, 2H), 1.29 (s, 9H). (ES+) m/e 499.2 (M+H)$^+$.

Example 108

2-(3-(4-((4-(1H-pyrazol-4-yl)phenyl)amino)-7,8-dihydro-5H-pyrano[4,3-d]pyrimidin-2-yl)phenoxy)-N-cyclopentylacetamide

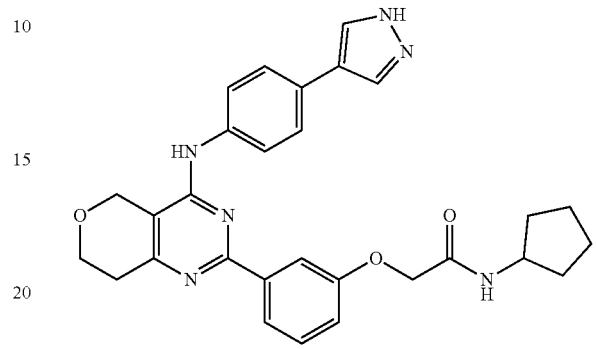

The compound was synthesized using essentially the same procedure described for the synthesis of Example 102.

Light Yellow solid; Yield: 38% (2 steps). $^1$H NMR (400 MHz, DMSO-$d_6$) δ 8.40 (s, 1H), 8.05-8.01 (m, 3H), 7.92-7.90 (m, 2H), 7.76 (d, J=8.8 Hz, 2H), 7.63 (d, J=8.8 Hz, 2H), 7.39 (t, J=8.2 Hz, 1H), 7.06-7.04 (m, 1H), 4.71 (s, 2H), 4.51 (s, 2H), 4.13-4.08 (m, 1H), 4.01-3.98 (m, 2H), 2.82 (s, 2H), 1.81-1.79 (m, 2H), 1.62-1.61 (m, 2H), 1.50-1.44 (m, 4H). (ES+) m/e 511.2 (M+H)$^+$.

Example 109

2-(3-(4-((4-(1H-pyrazol-4-yl)phenyl)amino)-7,8-dihydro-5H-pyrano[4,3-d]pyrimidin-2-yl)phenoxy)-N-cyclobutylacetamide

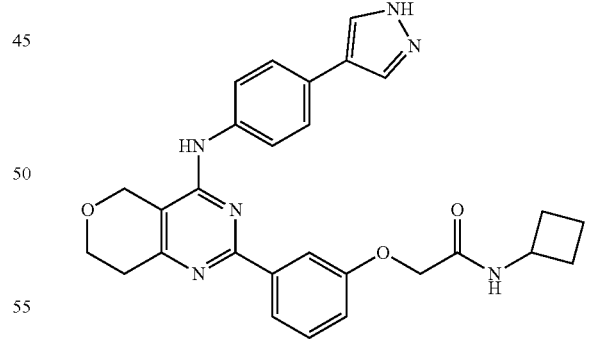

The compound was synthesized using essentially the same procedure described for the synthesis of Example 102.

Light Yellow solid; Yield: 20% (2 steps). $^1$H NMR (400 MHz, DMSO-$d_6$) δ 12.82 (s, 1H), 8.41-8.35 (m, 2H), 8.05 (s, 2H), 7.92-7.90 (m, 2H), 7.76 (d, J=8.4 Hz, 2H), 7.64 (d, J=8.8 Hz, 2H), 7.39 (t, J=8.0 Hz, 1H), 7.07-7.05 (m, 1H), 4.71 (s, 2H), 4.50 (s, 2H), 4.36-4.28 (m, 1H), 4.01-3.98 (m, 2H), 2.82 (s, 2H), 2.14-2.12 (m, 2H), 2.04-1.99 (m, 2H), 1.63-1.56 (m, 2H). (ES+) m/e 497.2 (M+H)$^+$.

Example 110

2-(3-(4-((4-(1H-pyrazol-4-yl)phenyl)amino)thieno[3,2-d]pyrimidin-2-yl)phenoxy)-N-(tert-butyl)acetamide

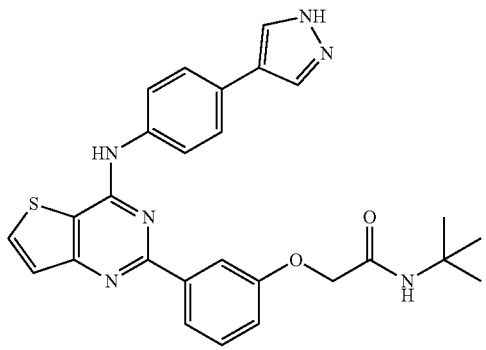 [SMILES: CC(C)(C)NC(=O)COc1cccc(-c2nc(Nc3ccc(-c4cn[nH]c4)cc3)c3sccc3n2)c1]

To the mixture of 2-chloro-N-(4-(1-(tetrahydro-2H-pyran-2-yl)-1H-pyrazol-4-yl)phenyl)thieno[3,2-d]pyrimidin-4-amine (1.00 eq) and N-(tert-butyl)-2-(3-(4,4,5,5-tetramethyl-1,3,2-dioxaborolan-2-yl)phenoxy)acetamide (1.20 eq) in dioxane (5.00 mL), H$_2$O (500.00 uL) was added K$_2$CO$_3$ (2.00 eq), Pd(dppf)Cl$_2$ (0.10 eq). The mixture was stirred under N$_2$ at 90° C. for 16 h. The reaction mixture was cooled to room temperature and diluted with water. The resulting mixture was extracted with EtOAc. The combined organic layers were washed with brine, dried over Na$_2$SO$_4$, filtered and concentrated under reduced pressure to give a residue. The residue was purified by column chromatography to afford N-(tert-butyl)-2-(3-(4-((4-(1-(tetrahydro-2H-pyran-2-yl)-1H-pyrazol-4-yl)phenyl)amino)thieno[3,2-d]pyrimidin-2-yl)phenoxy)acetamide.

To the mixture of N-(tert-butyl)-2-(3-(4-((4-(1-(tetrahydro-2H-pyran-2-yl)-1H-pyrazol-4-yl)phenyl)amino)thieno[3,2-d]pyrimidin-2-yl)phenoxy)acetamide (1.00 eq) in CH$_2$Cl$_2$ (5.00 mL) was added HCl/dioxane (4 M, 5.00 mL). The mixture was stirred at 20° C. for 0.5 h. The mixture was concentrated under reduced pressure to give a residue. The residue was purified by prep-HPLC (FA conditions) to provide the title compound. $^1$H NMR (400 MHz, DMSO-d$_6$) δ 9.82 (s, 1H), 8.26 (d, J=5.2 Hz, 1H), 8.08-8.02 (m, 4H), 7.89 (d, J=8.4 Hz, 2H), 7.69 (d, J=8.4 Hz, 2H), 7.56 (s, 1H), 7.52 (d, J=5.2 Hz, 1H), 7.43 (t, J=7.4 Hz, 1H), 7.08-7.06 (m, 1H), 4.50 (s, 2H), 1.31 (s, 9H). (ES+) m/e 499.2 (M+H)$^+$.

Example 111

2-(3-(4-((4-(1H-pyrazol-4-yl)phenyl)amino)thieno[3,2-d]pyrimidin-2-yl)phenoxy)-N-(tert-pentyl)acetamide

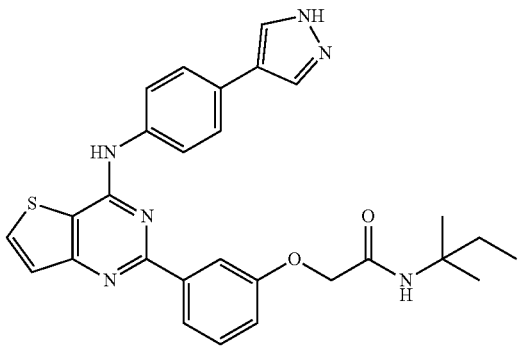 [SMILES: CCC(C)(C)NC(=O)COc1cccc(-c2nc(Nc3ccc(-c4cn[nH]c4)cc3)c3sccc3n2)c1]

The compound was synthesized using essentially the same procedure described for the synthesis of Example 110.

Yellow solid; Yield: 8.8% (2 steps). $^1$H NMR (400 MHz, DMSO-d6) δ 9.82 (s, 1H), 8.26 (d, J=5.2 Hz, 1H), 8.08-8.02 (m, 4H), 7.89 (d, J=8.4 Hz, 2H), 7.68 (d, J=8.4 Hz, 2H), 7.52 (d, J=5.6 Hz, 1H), 7.45-7.38 (m, 2H), 7.08-7.05 (m, 1H), 4.52 (s, 2H), 1.70-1.65 (m, 2H), 1.24 (s, 6H), 0.76 (t, J=7.4 Hz, 3H). (ES+) m/e 513.2 (M+H)$^+$.

Example 112

2-(3-(4-((4-(1H-pyrazol-4-yl)phenyl)amino)-6-acetyl-5,6,7,8-tetrahydropyrido[4,3-d]pyrimidin-2-yl)phenoxy)-N-isopropylacetamide

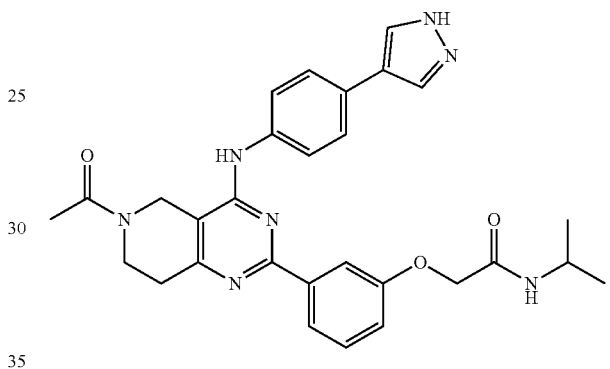

To the mixture of acetic acid (20.79 mg, 346.14 umol, 19.80 uL), HATU (164.52 mg, 432.67 umol) and DIPEA (74.56 mg, 576.90 umol, 100.76 uL) in DMF (2 mL) was added the mixture of 2-(3-(4-((4-(1H-pyrazol-4-yl)phenyl)amino)-5,6,7,8-tetrahydropyrido[4,3-d]pyrimidin-2-yl)phenoxy)-N-isopropylacetamide (150.00 mg, 288.45 umol, HCl salt) and DIPEA (74.56 mg, 576.90 umol, 100.76 uL) in DMF (1 mL). The mixture was stirred at 25° C. for 16 h. LCMS showed one peak with desired mass and one peak of Ms+1=610. The reaction mixture was diluted with water (30 mL) and extracted with EtOAc (30 mL×3). The combined organic layers were washed with brine (40 mL×2), dried over Na$_2$SO$_4$, filtered and concentrated under reduced pressure to give a residue. The residue was dissolved with CH$_2$Cl$_2$ (5 mL) and HCl/dioxane (5 mL, 4 N) was added. The mixture was stirred at 25° C. for 0.5 h. LCMS showed one main peak of desired product. The mixture was concentrated under reduced pressure to give a residue. The residue was purified by prep-HPLC (FA conditions) to afford the title compound (34.5 mg, 22%) as a light yellow solid. $^1$H NMR (400 MHz, DMSO-d$_6$) δ 7.98-7.96 (m, 3H), 7.89-7.87 (m, 2H), 7.76-7.73 (m, 2H), 7.63 (t, J=9.4 Hz, 2H), 7.53 (s, 1H), 7.38 (t, J=7.8 Hz, 1H), 7.05 (d, J=8.0 Hz, 1H), 4.59 (s, 2H), 4.48 (s, 2H), 3.99-3.91 (m, 1H), 3.80-3.77 (m, 2H), 2.89 (s, 1H), 2.76 (s, 1H), 2.16 (d, J=11.2 Hz, 3H), 1.06 (d, J=6.8 Hz, 6H). (ES+) m/e 526.4 (M+H)$^+$.

Example 113

2-(3-(4-((4-(1H-pyrazol-4-yl)phenyl)amino)-6-acetyl-5,6,7,8-tetrahydropyrido[4,3-d]pyrimidin-2-yl)phenoxy)-N-(pentan-3-yl)acetamide

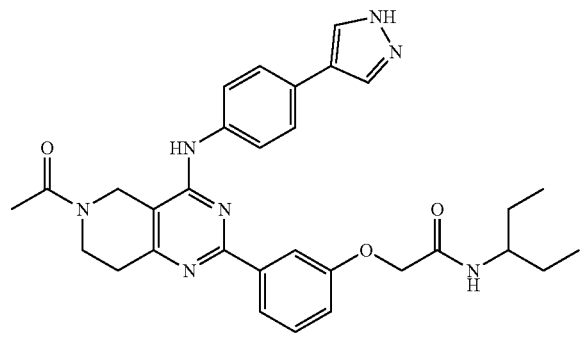 [SMILES: CCC(CC)NC(=O)COc1cccc(-c2nc3c(c(Nc4ccc(-c5cn[nH]c5)cc4)n2)CN(C(C)=O)CC3)c1]

To the mixture of acetic acid (19.72 mg, 328.42 umol, 18.78 uL), HATU (156.09 mg, 410.52 umol) and DIPEA (70.74 mg, 547.36 umol, 95.59 uL) in DMF (2 mL) was added the mixture of 2-(3-(4-((4-(1H-pyrazol-4-yl)phenyl)amino)-5,6,7,8-tetrahydropyrido[4,3-d]pyrimidin-2-yl)phenoxy)-N-(pentan-3-yl)acetamide (150.00 mg, 273.68 umol, HCl salt) and DIPEA (70.74 mg, 547.36 umol, 95.59 uL) in DMF (1 mL). The mixture was stirred at 25° C. for 16 h. LCMS showed one peak with desired mass and one peak of Ms+1=638. The reaction mixture was diluted with water (30 mL) and the resulting mixture was extracted with EtOAc (30 mL×3). The combined organic layers were washed with brine (40 mL×2), dried over Na$_2$SO$_4$, filtered and concentrated under reduced pressure to give a residue. The residue was dissolved with CH$_2$Cl$_2$ (5 mL) and HCl/dioxane (5 mL, 4 N) was added. The mixture was stirred at 25° C. for 0.5 h. LCMS showed one main peak of desired product. The mixture was concentrated under reduced pressure to give a residue. The residue was purified by prep-HPLC (FA conditions) to afford the title compound (29.1 mg, 19%) as a light yellow solid. $^1$H NMR (400 MHz, DMSO-d$_6$) δ 8.46 (s, 1H), 7.97-7.92 (m, 4H), 7.79 (d, J=8.4 Hz, 2H), 7.61 (d, J=8.4 Hz, 2H), 7.40-7.36 (m, 2H), 7.08-7.06 (m, 1H), 4.64 (s, 2H), 4.54 (s, 2H), 3.83-3.80 (m, 2H), 3.68-3.63 (m, 1H), 2.88 (s, 2H), 2.18 (s, 3H), 1.51-1.38 (m, 4H), 0.81 (t, J=7.4 Hz, 6H). (ES+) m/e 554.1 (M+H)$^+$.

Example 114

2-(3-(4-((4-(1H-pyrazol-4-yl)phenyl)amino)-6-acetyl-5,6,7,8-tetrahydropyrido[4,3-d]pyrimidin-2-yl)phenoxy)-N-(tert-butyl)acetamide

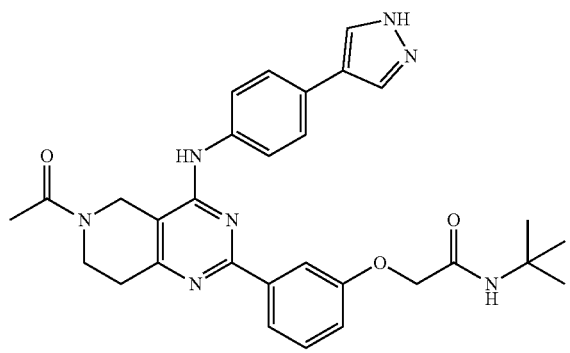 [SMILES: CC(=O)N1CCc2nc(-c3cccc(OCC(=O)NC(C)(C)C)c3)nc(Nc3ccc(-c4cn[nH]c4)cc3)c2C1]

To the mixture of acetic acid (13.49 mg, 224.70 umol, 12.85 uL), HATU (106.80 mg, 280.88 umol) and DIPEA (48.40 mg, 374.50 umol, 65.41 uL) in DMF (1 mL) was added the mixture of 2-(3-(4-((4-(1H-pyrazol-4-yl)phenyl)amino)-5,6,7,8-tetrahydropyrido[4,3-d]pyrimidin-2-yl)phenoxy)-N-(tert-butyl)acetamide (100.00 mg, 187.25 umol, HCl salt) and DIPEA (48.40 mg, 374.50 umol, 65.41 uL) in DMF (1 mL). The mixture was stirred at 15° C. for 16 h. LCMS showed two main peaks. The reaction mixture was diluted with water (30 mL) and extracted with EtOAc (30 mL×3). The combined organic layers were washed with brine (40 mL×2), dried over Na$_2$SO$_4$, filtered and concentrated under reduced pressure to give a residue. The residue was purified by prep-HPLC (FA conditions) to separate the two peaks. HPLC and LCMS showed one peak was the mixture of desired product and THP-protected product. The solid after lyophilization was used in the next step. To the solid in CH$_2$Cl$_2$ (2.00 mL) was added HCl/dioxane (4 N, 3.00 mL). The mixture was stirred at 25° C. for 1 h. LCMS showed one main peak of desired product. The mixture was concentrated under reduced pressure to give a residue (Part A). HPLC and LCMS showed the other peak was the mixture of desired product and di-substituted product. The solid after lyophilization was used in next step. To the solid in THF (2.00 mL) and MeOH (2.00 mL) was added NaOH (2 M, 2.00 mL). The mixture was stirred at 25° C. for 1 h. LCMS showed one main peak of desired product. The reaction was diluted with water (20 mL) and the mixture was extracted with EtOAc (30 mL×3). The combined organic layers were dried over Na2SO4, filtered and concentrated under reduced pressure to give a residue. The residue which was combined with Part A was purified by prep-HPLC (FA conditions) to afford the title compound (11.6 mg) as a light yellow solid. $^1$H NMR (400 MHz, DMSO-d$_6$) δ 7.88-7.84 (m, 4H), 7.76-7.73 (m, 2H), 7.63 (t, J=9.6 Hz, 2H), 7.50-7.49 (m, 1H), 7.38 (t, J=8.0 Hz, 1H), 7.02 (d, J=6.4 Hz, 1H), 7.06-7.04 (m, 1H), 4.59 (s, 2H), 4.44 (s, 2H), 3.80-3.77 (m, 2H), 2.89 (s, 1H), 2.76 (s, 1H), 2.16 (d, J=11.2 Hz, 3H), 1.26 (s, 9H). (ES+) m/e 540.3 (M+H)$^+$.

Example 115

2-(3-(4-((4-(1H-pyrazol-4-yl)phenyl)amino)-6-ethyl-5,6,7,8-tetrahydropyrido[4,3-d]pyrimidin-2-yl)phenoxy)-N-(tert-butyl)acetamide

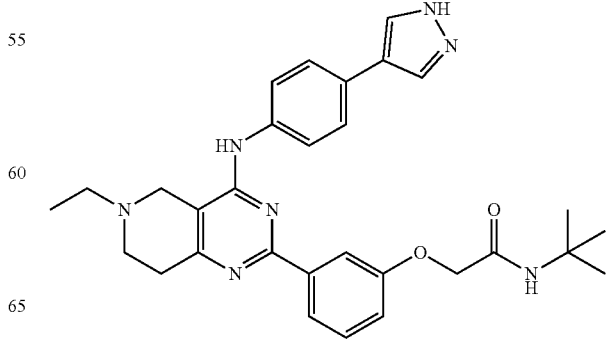

To the mixture of 2-(3-(4-((4-(1H-pyrazol-4-yl)phenyl)amino)-5,6,7,8-tetrahydropyrido[4,3-d]pyrimidin-2-yl)phenoxy)-N-(tert-butyl)acetamide (200.00 mg, 374.50 umol, HCl salt) in MeOH (2.00 mL) was added TEA (75.79 mg, 748.99 umol, 103.82 uL). The mixture was stirred at 15° C. for 10 min. Then to the mixture was added acetaldehyde (123.34 mg, 1.12 mmol, 156.13 uL, 40% purity) and HOAc (89.95 mg, 1.50 mmol, 85.67 uL). The mixture was stirred at 15° C. for 20 min. Then to the mixture was added NaBH₃CN (117.67 mg, 1.87 mmol). The mixture was stirred at 15° C. for 15.5 h. LCMS showed the reaction was a little messy and one main peak of desired product. The reaction mixture was diluted with water (30 mL) and extracted with EtOAc (30 mL×3). The combined organic layers were dried over Na₂SO₄, filtered and concentrated under reduced pressure to give a residue. The residue was purified by prep-HPLC (TFA conditions) to afford the title compound (23.2 mg, 9.2%) as a yellow solid. ¹H NMR (400 MHz, DMSO-d₆) δ 8.44 (s, 1H), 8.20 (s, 1H), 8.05 (s, 2H), 7.95-7.90 (m, 3H), 7.78 (d, J=8.8 Hz, 2H), 7.38 (t, J=8.2 Hz, 1H), 7.06-7.04 (m, 1H), 4.50 (s, 2H), 4.02-3.94 (m, 1H), 3.50 (s, 2H), 2.83 (d, J=5.2 Hz, 2H), 2.73 (d, J=5.2 Hz, 2H), 2.47 (s, 3H), 1.09 (d, J=6.4 Hz, 6H). (ES+) m/e 526.3 (M+H)⁺.

Example 116

2-(3-(4-((4-(1H-pyrazol-4-yl)phenyl)amino)-6-isopropyl-5,6,7,8-tetrahydropyrido[4,3-d]pyrimidin-2-yl)phenoxy)-N-(tert-butyl)acetamide

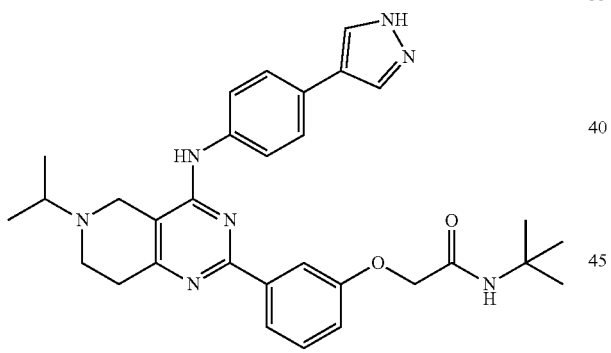

To the mixture of 2-(3-(4-((4-(1H-pyrazol-4-yl)phenyl)amino)-5,6,7,8-tetrahydropyrido[4,3-d]pyrimidin-2-yl)phenoxy)-N-(tert-butyl)acetamide (200.00 mg, 374.50 umol, HCl salt) in MeOH (2.00 mL) was added TEA (75.79 mg, 748.99 umol, 103.82 uL). The mixture was stirred at 15° C. for 10 min. Then to the mixture was added acetone (65.25 mg, 1.12 mmol, 82.59 uL), HOAc (89.95 mg, 1.50 mmol, 85.67 uL). The mixture was stirred at 15° C. for 20 min. To the mixture was added NaBH₃CN (117.67 mg, 1.87 mmol). The mixture was stirred at 15° C. for 15.5 h. LCMS showed one main peak of desired product. The reaction mixture was diluted with water (30 mL) and the mixture was extracted with EtOAc (30 mL×3). The combined organic layers were dried over Na₂SO₄, filtered and concentrated under reduced pressure to give a residue. The residue was purified by prep-HPLC (TFA conditions) to afford the title compound (59.9 mg, 25%) as a light yellow solid. ¹H NMR (400 MHz, DMSO-d₆) δ 8.44 (s, 1H), 8.20 (s, 1H), 8.05 (s, 2H), 7.95-7.90 (m, 3H), 7.78 (d, J=8.8 Hz, 2H), 7.38 (t, J=8.2 Hz, 1H), 7.06-7.04 (m, 1H), 4.50 (s, 2H), 4.02-3.94 (m, 1H), 3.50 (s, 2H), 2.83 (d, J=5.2 Hz, 2H), 2.73 (d, J=5.2 Hz, 2H), 2.47 (s, 3H), 1.09 (d, J=6.4 Hz, 6H). (ES+) m/e 540.3 (M+H)⁺.

Example 117

2-(3-(4-((4-(1H-pyrazol-4-yl)phenyl)amino)-5,6,7,8-tetrahydropyrido[4,3-d]pyrimidin-2-yl)phenoxy)-N-(pentan-3-yl)acetamide

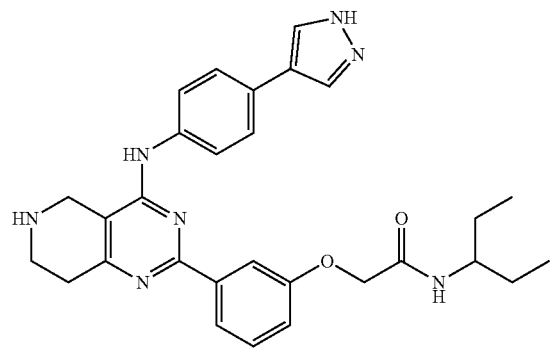 [SMILES: CCC(CC)NC(=O)COc1cccc(-c2nc3c(c(Nc4ccc(-c5cn[nH]c5)cc4)n2)CNCC3)c1]

Example 117A tert-butyl 2-(3-(2-oxo-2-(pentan-3-ylamino)ethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate

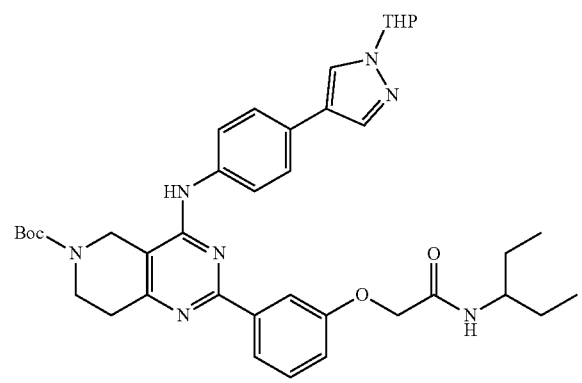

To the mixture of tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (1.50 g, 2.94 mmol) and N-(pentan-3-yl)-2-(3-(4,4,5,5-tetramethyl-1,3,2-dioxaborolan-2-yl)phenoxy)acetamide (1.23 g, 3.53 mmol) in dioxane (10.00 mL), H₂O (1.00 mL) was added K₂CO₃ (811.39 mg, 5.87 mmol), Pd(dppf)Cl₂ (214.78 mg, 293.54 umol). The mixture was stirred under N₂ at 90° C. for 16 h.

TLC (petroleum ether/EtOAc=1:1, Rf=0.30) showed one new main spot. The reaction mixture was cooled to room temperature and diluted with water (30 mL). The resulting mixture was extracted with EtOAc (30 mL×3). The combined organic layers were washed with brine (50 mL×2), dried over Na$_2$SO$_4$, filtered and concentrated under reduced pressure to give a residue The residue was purified by column chromatography (SiO$_2$, petroleum ether/EtOAc=50:1 to 1:1) to afford the title compound (1.3 g, 63%) as a light yellow solid. $^1$H NMR (400 MHz, DMSO-d$_6$) δ 8.65 (s, 1H), 8.34 (s, 1H), 7.95-7.90 (m, 3H), 7.79 (d, J=8.0 Hz, 2H), 7.72-7.65 (m, 3H), 7.39 (t, J=8.2 Hz, 1H), 7.08-7.06 (m, 1H), 5.43-5.40 (m, 1H), 4.58-4.53 (m, 4H), 3.95 (d, J=11.6 Hz, 1H), 3.72-3.59 (m, 4H), 2.81 (t, J=5.2 Hz, 2H), 2.18-2.11 (m, 1H), 1.98-1.92 (m, 2H), 1.73-1.66 (m, 1H), 1.59-1.57 (m, 2H), 1.48 (s, 9H), 1.41-1.32 (m, 4H), 0.78 (t, J=7.4 Hz, 6H).

Example 117B 2-(3-(4-((4-(1H-pyrazol-4-yl)phenyl)amino)-5,6,7,8-tetrahydropyrido[4,3-d]pyrimidin-2-yl)phenoxy)-N-(pentan-3-yl)acetamide

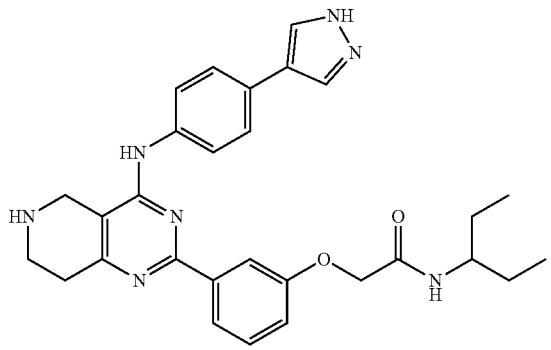 [SMILES: CCC(CC)NC(=O)COc1cccc(-c2nc3c(c(Nc4ccc(-c5cn[nH]c5)cc4)n2)CNCC3)c1]

To the mixture of tert-butyl 2-(3-(2-oxo-2-(pentan-3-ylamino)ethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (1.30 g, 1.87 mmol) in CH$_2$Cl$_2$ (15.00 mL) was added HCl/dioxane (4 N, 10.00 mL). The mixture was stirred at 20° C. for 15 h. LCMS showed about 77% of desired product and about 14% of THP-protected product. To the mixture was added additional HCl/dioxane (4 N, 2 mL) and the reaction was stirred at 20° C. for another 2 h. LCMS showed about 91% desired product. The mixture was filtered to afford the title compound (1.2, crude, HCl salt) as a yellow solid. 100 mg of the crude material was purified by prep-HPLC (FA conditions) to afford the pure title compound as a white solid. $^1$H NMR (400 MHz, DMSO-d$_6$) δ 8.35 (s, 1H), 8.29 (s, 1H), 8.03 (s, 2H), 7.91-7.90 (m, 2H), 7.78 (d, J=8.8 Hz, 2H), 7.71 (d, J=9.2 Hz, 1H), 7.62 (d, J=8.4 Hz, 2H), 7.38 (t, J=8.0 Hz, 1H), 7.05-7.03 (dd, J=8.0, 2.0 Hz, 1H), 4.55 (s, 2H), 3.83 (s, 2H), 3.65-3.60 (m, 1H), 3.06 (s, 2H), 2.72 (s, 2H), 1.48-1.34 (m, 4H), 0.78 (t, J=7.2 Hz, 6H). (ES+) m/e 512.2 (M+H)$^+$.

Example 118

2-(3-(4-((4-(1H-pyrazol-4-yl)phenyl)amino)-6-ethyl-5,6,7,8-tetrahydropyrido[4,3-d]pyrimidin-2-yl)phenoxy)-N-(pentan-3-yl)acetamide

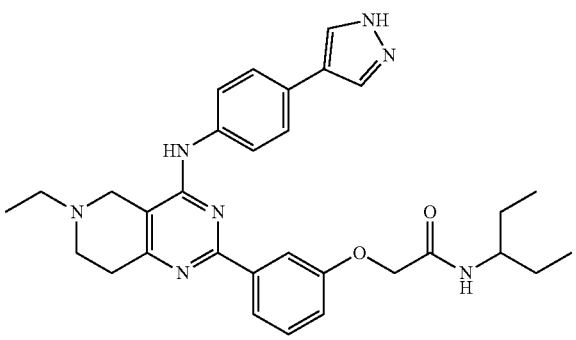 [SMILES: CCC(CC)NC(=O)COc1cccc(-c2nc3c(c(Nc4ccc(-c5cn[nH]c5)cc4)n2)CN(CC)CC3)c1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-(pentan-3-yl)acetamide (200.00 mg, 364.91 umol, HCl salt) in MeOH (2.00 mL) was added TEA (73.85 mg, 729.82 umol, 101.17 uL). The mixture was stirred at 15° C. for 10 min. Then to the mixture was added acetaldehyde (120.56 mg, 1.09 mmol, 152.60 uL, 40% purity) and HOAc (87.65 mg, 1.46 mmol, 83.48 uL). The mixture was stirred at 15° C. for 20 min. Then NaBH$_3$CN (114.65 mg, 1.82 mmol) was added. The mixture was stirred at 15° C. for another 15.5 h. LCMS showed about 53% of desired product. The reaction was diluted with water (30 mL) and the mixture was extracted with EtOAc (30 mL×3). The combined organic layers were dried over Na$_2$SO$_4$, filtered and concentrated under reduced pressure to give a residue. The residue was purified by prep-HPLC (FA conditions) to afford the title compound (37.0 mg, 16%) as a light yellow solid. $^1$H NMR (400 MHz, DMSO-d$_6$) δ 8.44 (s, 1H), 8.27 (s, 1H), 8.04 (s, 2H), 7.91-7.90 (m, 2H), 7.77 (d, J=8.8 Hz, 2H), 7.72 (d, J=8.8 Hz, 1H), 7.64 (d, J=8.8 Hz, 2H), 7.38 (t, J=8.2 Hz, 1H), 7.06-7.03 (m, 1H), 4.56 (s, 2H), 3.64 (s, 1H), 3.52 (s, 2H), 2.82-2.77 (m, 4H), 2.66-2.62 (m, 2H), 1.47-1.36 (m, 4H), 1.18 (t, J=7.2 Hz, 3H), 0.78 (t, J=7.4 Hz, 6H). (ES+) m/e 540.4 (M+H)$^+$.

Example 119

2-(3-(4-((4-(1H-pyrazol-4-yl)phenyl)amino)-6-isopropyl-5,6,7,8-tetrahydropyrido[4,3-d]pyrimidin-2-yl)phenoxy)-N-(pentan-3-yl)acetamide

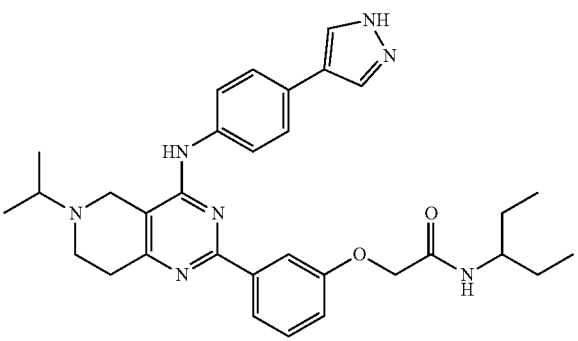 [SMILES: CCC(CC)NC(=O)COc1cccc(-c2nc3c(c(Nc4ccc(-c5cn[nH]c5)cc4)n2)CN(C(C)C)CC3)c1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-(pentan-3-yl)acetamide (200.00 mg, 364.91 umol, HCl salt) in MeOH (2.00 mL) was added TEA (73.85 mg, 729.82 umol, 101.17 uL). The mixture was stirred at 15° C. for 10 min. Then to the mixture was added acetone (63.58 mg, 1.09 mmol, 80.48 uL) and HOAc (87.65 mg, 1.46 mmol, 83.48 uL). The mixture was stirred at 15° C. for 20 min. Then NaBH₃CN (114.65 mg, 1.82 mmol) was added. The mixture was stirred at 15° C. for another 15.5 h. LCMS showed desired product was major and 2-(3-(4-((4-(1H-pyrazol-4-yl)phenyl)amino)-5,6,7,8-tetrahydropyrido[4,3-d]pyrimidin-2-yl)phenoxy)-N-(pentan-3-yl)acetamideremained (two peaks were hard to separate). To the mixture was added acetone (40 mg). The mixture was stirred at 15° C. for 2 h. LCMS showed 2-(3-(4-((4-(1H-pyrazol-4-yl)phenyl)amino)-5,6,7,8-tetrahydropyrido[4,3-d]pyrimidin-2-yl)phenoxy)-N-(pentan-3-yl)acetamide still remained and one main peak of desired product. The mixture was stirred at 15° C. for 16 h. LCMS showed 2-(3-(4-((4-(1H-pyrazol-4-yl)phenyl)amino)-5,6,7,8-tetrahydropyrido[4,3-d]pyrimidin-2-yl)phenoxy)-N-(pentan-3-yl)acetamide was consumed completely and desired product was major. The reaction was diluted with water (30 mL) and the mixture was extracted with EtOAc (30 mL×3). The combined organic layers were dried over Na₂SO₄, filtered and concentrated under reduced pressure to give a residue. The residue was purified by prep-HPLC (FA conditions) to afford the title compound (84.3 mg, 35%) as a light yellow solid. $^1$H NMR (400 MHz, DMSO-d₆) δ 8.41 (s, 1H), 8.24 (s, 1H), 8.04 (s, 2H), 7.91-7.89 (m, 2H), 7.76 (d, J=8.4 Hz, 2H), 7.71 (d, J=8.8 Hz, 1H), 7.64 (d, J=8.8 Hz, 2H), 7.37 (t, J=8.0 Hz, 1H), 7.04 (d, J=7.2 Hz, 1H), 4.55 (s, 2H), 3.64-3.63 (m, 1H), 3.60 (s, 2H), 2.99-2.96 (m, 1H), 2.80 (s, 4H), 1.47-1.34 (m, 4H), 1.14 (d, J=6.4 Hz, 6H), 0.78 (t, J=7.4 Hz, 6H). (ES+) m/e 554.3 (M+H)⁺.

Example 120

2-(3-(4-((4-(1H-pyrazol-4-yl)phenyl)amino)-5,6,7,8-tetrahydropyrido[4,3-d]pyrimidin-2-yl)phenoxy)-N-isopropylacetamide Example 120A tert-butyl 2-(3-(2-(isopropylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate

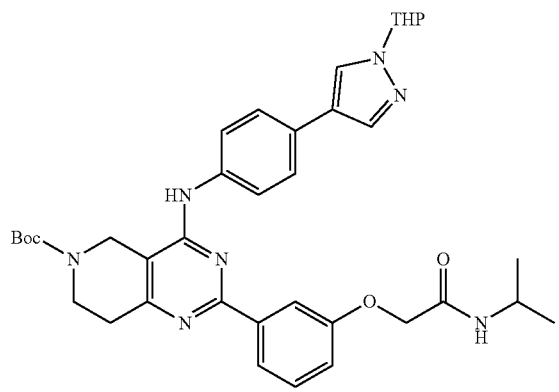

To the mixture of tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (700.00 mg, 1.37 mmol) and N-isopropyl-2-(3-(4,4,5,5-tetramethyl-1,3,2-dioxaborolan-2-yl)phenoxy)acetamide (524.76 mg, 1.64 mmol) in dioxane (8.00 mL), H₂O (800.00 uL) was added K₂CO₃ (378.70 mg, 2.74 mmol), Pd(dppf)Cl₂ (100.24 mg, 137.00 umol). The mixture was stirred under N₂ at 90° C. for 16 h. TLC (petroleum ether/EtOAc=1:2, Rf=0.59) showed one new main spot. The reaction mixture was cooled to room temperature and diluted with water (40 mL). The resulting mixture was extracted with EtOAc (40 mL×3). The combined organic layers were washed with brine (60 mL), dried over Na₂SO₄, filtered and concentrated under reduced pressure to give a residue. The residue was purified by column chromatography (SiO₂, petroleum ether/EtOAc=100:1 to 1:2) to afford the title compound (890.00 mg, 97%) as a light yellow solid. $^1$H NMR (400 MHz, DMSO-d₆) δ 8.66 (s, 1H), 8.34 (s, 1H), 7.94-7.89 (m, 4H), 7.78 (d, J=7.4 Hz, 2H), 7.65 (d, J=8.4 Hz, 2H), 7.41-7.37 (m, 1H), 7.07-7.05 (m, 1H), 5.42-5.39 (m, 1H), 4.52-4.50 (m, 4H), 3.98-3.94 (m, 1H), 3.72-3.60 (m, 3H), 2.81 (t, J=5.2 Hz, 2H), 2.17-2.11 (m, 1H), 1.97-1.91 (m, 2H), 1.72-1.65 (m, 1H), 1.58-1.56 (m, 2H), 1.47 (s, 9H), 1.11-1.09 (m, 6H).

Example 120B 2-(3-(4-((4-(1H-pyrazol-4-yl)phenyl)amino)-5,6,7,8-tetrahydropyrido[4,3-d]pyrimidin-2-yl)phenoxy)-N-isopropylacetamide

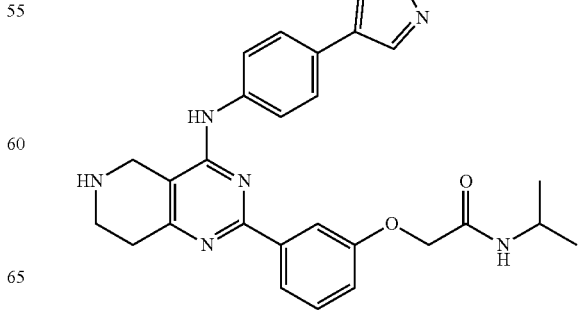

To a mixture of tert-butyl 2-(3-(2-(isopropylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (890.00 mg, 1.33 mmol) in $CH_2Cl_2$ (10.00 mL) was added HCl/dioxane (4 N, 10.00 mL). The mixture was stirred at 20° C. for 15 h. LCMS showed one main peak of desired product. The mixture was filtered to afford the crude product (626 mg, HCl salt, crude). 100 mg of the crude material was purified by prep-HPLC (FA conditions) to afford the pure title compound (34.7 mg) as a light yellow solid. $^1$H NMR (400 MHz, DMSO-$d_6$) δ 8.38 (s, 1H), 8.27 (s, 1H), 8.04 (s, 2H), 7.93-7.89 (m, 3H), 7.78 (d, J=8.8 Hz, 2H), 7.62 (d, J=8.8 Hz, 2H), 7.40-7.36 (m, 1H), 7.06-7.03 (m, 1H), 4.50 (s, 2H), 4.01-3.95 (m, 1H), 3.85 (s, 2H), 3.08 (t, J=5.6 Hz, 2H), 2.74 (t, J=5.2 Hz, 2H), 1.09 (d, J=6.4 Hz, 6H). (ES+) m/e 484.3 (M+H)$^+$.

Example 121

2-(3-(4-((4-(1H-pyrazol-4-yl)phenyl)amino)-6-isopropyl-5,6,7,8-tetrahydropyrido[4,3-d]pyrimidin-2-yl)phenoxy)-N-isopropylacetamide

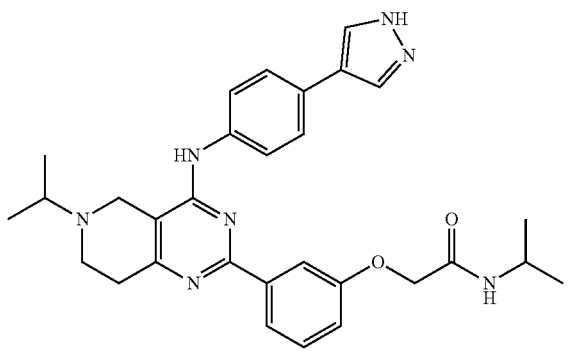 [SMILES: CC(C)NC(=O)COc1cccc(-c2nc3c(c(Nc4ccc(-c5cn[nH]c5)cc4)n2)CN(C(C)C)CC3)c1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-isopropylacetamide (200.00 mg, 384.60 umol, HCl salt) in MeOH (2.00 mL) was added TEA (77.84 mg, 769.20 umol, 106.62 uL). The mixture was stirred at 15° C. for 10 min. Then to the mixture was added acetone (89.35 mg, 1.54 mmol, 113.10 uL) and HOAc (92.38 mg, 1.54 mmol, 87.98 uL). The mixture was stirred at 15° C. for 20 min. Then NaBH$_3$CN (120.84 mg, 1.92 mmol) was added. The mixture was stirred at 15° C. for 15.5 h. LCMS showed one main peak of desired product. The reaction mixture was diluted with water (20 mL) and the mixture was extracted with EtOAc (30 mL×3). The combined organic layers were dried over Na$_2$SO$_4$, filtered and concentrated under reduced pressure to give a residue. The residue was purified by prep-HPLC (FA conditions) to afford the title compound (27.6 mg, 11%) as a yellow solid. $^1$H NMR (400 MHz, DMSO-$d_6$) δ 8.42 (s, 1H), 8.23 (s, 2H), 8.05 (s, 2H), 7.94-7.89 (m, 3H), 7.76 (d, J=8.4 Hz, 2H), 7.64 (d, J=8.4 Hz, 2H), 7.38 (t, J=8.0 Hz, 1H), 7.04 (d, J=7.2 Hz, 1H), 4.50 (s, 2H), 4.00-3.95 (m, 1H), 3.60 (s, 2H), 3.00-2.97 (m, 1H), 2.80 (s, 4H), 1.14 (d, J=6.4 Hz, 6H), 1.09 (d, J=6.4 Hz, 6H). (ES+) m/e 526.3 (M+H)$^+$.

Example 122

2-(3-(4-((4-(1H-pyrazol-4-yl)phenyl)amino)-6-ethyl-5,6,7,8-tetrahydropyrido[4,3-d]pyrimidin-2-yl)phenoxy)-N-isopropylacetamide

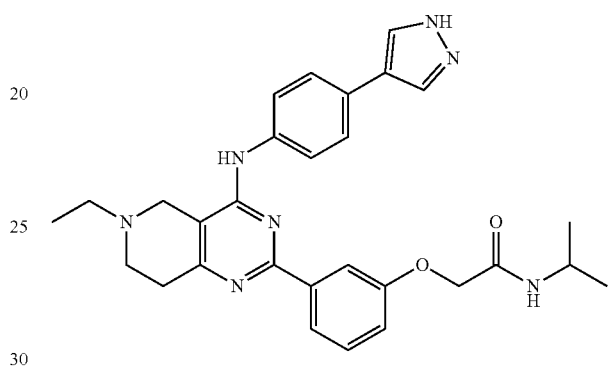

To 2-(3-(4-((4-(1H-pyrazol-4-yl)phenyl)amino)-5,6,7,8-tetrahydropyrido[4,3-d]pyrimidin-2-yl)phenoxy)-N-isopropylacetamide (120.00 mg, 230.76 umol, HCl salt) was added sat.NaHCO$_3$ (about 15 mL) and the mixture was stirred at 20° C. for 10 min. The mixture was filtered to get the solid and the solid was dried with toluene to provide 2-(3-(4-((4-(1H-pyrazol-4-yl)phenyl)amino)-5,6,7,8-tetrahydropyrido[4,3-d]pyrimidin-2-yl)phenoxy)-N-isopropylacetamide (free base). To the mixture of 2-(3-(4-((4-(1H-pyrazol-4-yl)phenyl)amino)-5,6,7,8-tetrahydropyrido[4,3-d]pyrimidin-2-yl)phenoxy)-N-isopropylacetamide (free base) in MeOH (3.00 mL) was added HOAc (55.43 mg, 923.04 umol, 52.79 uL), acetaldehyde (127.06 mg, 1.15 mmol, 160.84 uL, 40% purity). The resulting mixture was stirred at 20° C. for 10 min. Then to the mixture was added NaBH$_3$CN (72.50 mg, 1.15 mmol, 5.00 eq) and the reaction was stirred at 20° C. for 16 h. LCMS showed about 52% of the desired product. The reaction mixture was diluted with water (20 mL) and extracted with EtOAc (20 mL×3). The combined organic layers were dried over Na$_2$SO$_4$, filtered and concentrated under reduced pressure to give a residue. The residue was purified by prep-HPLC (FA conditions) to give the title compound (14.8 mg, 10%) as a yellow solid. $^1$H NMR (400 MHz, DMSO-$d_6$) δ 8.46 (s, 1H), 8.26 (s, 1H), 8.05 (s, 2H), 7.95 (d, J=8.0 Hz, 1H), 7.91-7.89 (m, 2H), 7.77 (d, J=8.4 Hz, 2H), 7.64 (d, J=8.8 Hz, 2H), 7.40-7.36 (m, 1H), 7.06-7.03 (m, 1H), 4.50 (s, 2H), 4.02-3.95 (m, 1H), 3.52 (s, 2H), 2.82-2.77 (m, 4H), 2.66-2.61 (m, 2H), 1.18 (t, J=6.8 Hz, 3H), 1.09 (d, J=6.8 Hz, 6H). (ES+) m/e 512.1 (M+H)$^+$.

Example 123

2-(3-(4-((4-(1H-pyrazol-4-yl)phenyl)amino)-5,6,7,8-tetrahydropyrido[4,3-d]pyrimidin-2-yl)phenoxy)-N-cyclopentylacetamide

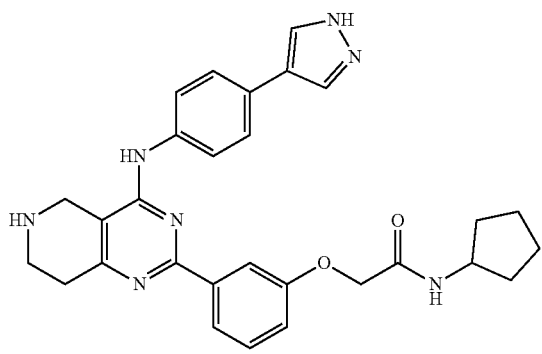 [SMILES: O=C(COc1cccc(-c2nc3c(c(Nc4ccc(-c5cn[nH]c5)cc4)n2)CNCC3)c1)NC1CCCC1]

Example 123A tert-butyl 2-(3-(2-(cyclopentylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate

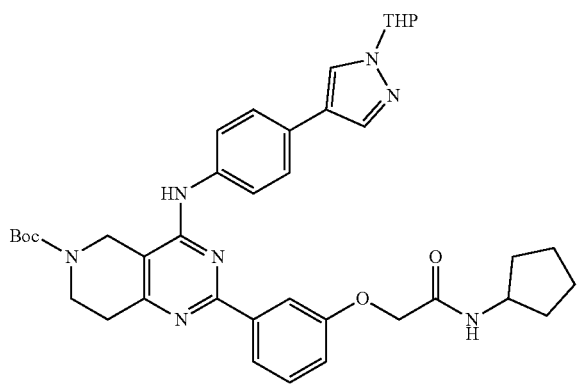

To the mixture of tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (900.00 mg, 1.76 mmol) and N-cyclopentyl-2-(3-(4,4,5,5-tetramethyl-1,3,2-dioxaborolan-2-yl)phenoxy)acetamide (729.15 mg, 2.11 mmol) in dioxane (10.00 mL), H$_2$O (1.00 mL) was added K$_2$CO$_3$ (486.50 mg, 3.52 mmol) and Pd(dppf)Cl$_2$ (128.78 mg, 176.00 umol). The mixture was stirred under N$_2$ at 90° C. for 16 h. TLC (petroleum ether/EtOAc=1:2, Rf=0.59) showed one new main spot. The reaction mixture was cooled to room temperature and diluted with water (40 mL). The resulting mixture was extracted with EtOAc (40 mL×3). The combined organic layers were washed with brine (60 mL), dried over Na$_2$SO$_4$, filtered and concentrated under reduced pressure to give a residue. The residue was purified by column chromatography (SiO$_2$, petroleum ether/EtOAc=100:1 to 1:2) to give the title compound (926.00 mg, 76%) as a light yellow solid. $^1$H NMR (400 MHz, DMSO-d$_6$) δ 8.69 (s, 1H), 8.36 (s, 1H), 8.05 (d, J=7.6 Hz, 1H), 7.96 (s, 1H), 7.91-7.90 (m, 2H), 7.80-7.78 (m, 2H), 7.66 (d, J=8.4 Hz, 2H), 7.39 (t, J=8.4 Hz, 1H), 7.07-7.04 (m, 1H), 5.43-5.40 (m, 1H), 4.52 (s, 4H), 3.97-3.94 (m, 1H), 3.72-3.65 (m, 3H), 2.82-2.81 (m, 2H), 2.20-2.12 (m, 1H), 1.97-1.94 (m, 2H), 1.80-1.77 (m, 2H), 1.66-1.53 (m, 6H), 1.47 (s, 9H).

Example 123B 2-(3-(4-((4-(1H-pyrazol-4-yl)phenyl)amino)-5,6,7,8-tetrahydropyrido[4,3-d]pyrimidin-2-yl)phenoxy)-N-cyclopentylacetamide

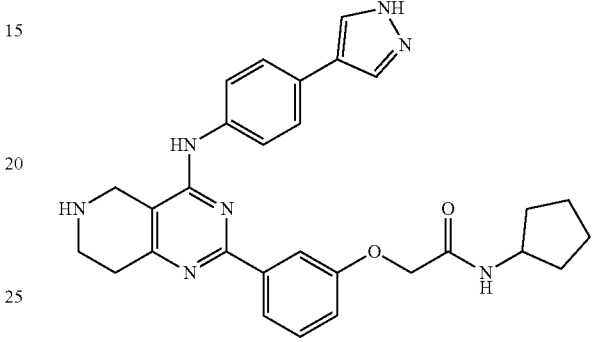

To a mixture of tert-butyl 2-(3-(2-(cyclopentylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (926.00 mg, 1.33 mmol) in CH$_2$Cl$_2$ (10.00 mL) was added HCl/dioxane (4 N, 10.00 mL). The mixture was stirred at 20° C. for 15 h. LCMS showed one main peak of desired product. The mixture was filtered to crude title compound (810 mg, HCl salt, crude). 100 mg of the crude material was purified by prep-HPLC (FA conditions) to afford pure title compound (42.3 mg) as a light yellow solid. $^1$H NMR (400 MHz, DMSO-d$_6$) δ 8.40 (s, 1H), 8.30 (s, 1H), 8.04-8.00 (m, 3H), 7.92-7.90 (m, 2H), 7.79 (d, J=8.4 Hz, 2H), 7.63 (d, J=8.8 Hz, 2H), 7.39 (t, J=8.0 Hz, 1H), 7.06-7.04 (m, 1H), 4.52 (s, 2H), 4.14-4.08 (m, 1H), 3.87 (s, 2H), 3.09 (t, J=5.6 Hz, 2H), 2.76-2.75 (m, 2H), 1.83-1.77 (m, 2H), 1.63-1.62 (m, 2H), 1.51-1.43 (m, 4H). (ES+) m/e 510.3 (M+H)$^+$.

Example 124

2-(3-(4-((4-(1H-pyrazol-4-yl)phenyl)amino)-6-methyl-5,6,7,8-tetrahydropyrido[4,3-d]pyrimidin-2-yl)phenoxy)-N-cyclopentylacetamide

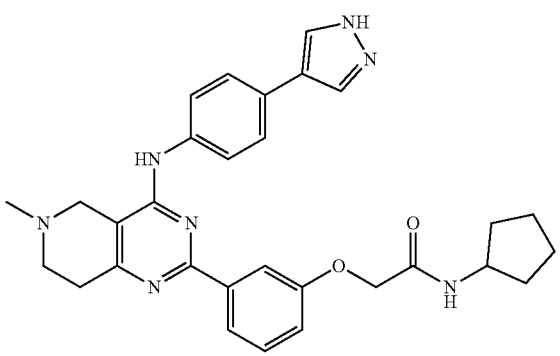 [SMILES: CN1CCc2nc(-c3cccc(OCC(=O)NC4CCCC4)c3)nc(Nc3ccc(-c4cn[nH]c4)cc3)c2C1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-cyclopentylacetamide (200.00 mg, 366.26 umol, HCl salt) in MeOH (2.00 mL) was added TEA (74.12 mg, 732.52 umol, 101.54 uL). The mixture was stirred at 15° C. for 10 min. Then to the mixture were added formaldehyde (82.49 mg, 1.10 mmol, 75.68 uL, 40% purity) and HOAc (87.98 mg, 1.47 mmol, 83.79 uL). The mixture was stirred at 15° C. for 20 min. Then NaBH$_3$CN (115.08 mg, 1.83 mmol) was added. The mixture was stirred at 15° C. for 15.5 h. LCMS showed about 72% desired product. The reaction mixture was diluted with water (20 mL) and the mixture was extracted with EtOAc (20 mL×3). The combined organic layers were washed with brine (30 mL), dried over Na$_2$SO$_4$, filtered and concentrated under reduced pressure to give a residue. The residue was purified by prep-HPLC (FA conditions) to afford the title compound (50.7 mg) as a light yellow solid. $^1$H NMR (400 MHz, DMSO-d$_6$) δ 8.44 (s, 1H), 8.22 (s, 1H), 8.05-8.02 (m, 3H), 7.91-7.89 (m, 2H), 7.78 (d, J=8.8 Hz, 2H), 7.63 (d, J=8.8 Hz, 2H), 7.38 (t, J=8.0 Hz, 1H), 7.05-7.03 (m, 1H), 4.51 (s, 2H), 4.13-4.08 (m, 1H), 3.50 (s, 2H), 2.8-2.82 (m, 2H), 2.74-2.72 (m, 2H), 2.47 (s, 3H), 1.82-1.76 (m, 2H), 1.62-1.61 (m, 2H), 1.49-1.45 (m, 4H). (ES+) m/e 524.3 (M+H)$^+$.

Example 125

2-(3-(4-((4-(1H-pyrazol-4-yl)phenyl)amino)-6-ethyl-5,6,7,8-tetrahydropyrido[4,3-d]pyrimidin-2-yl)phenoxy)-N-cyclopentylacetamide

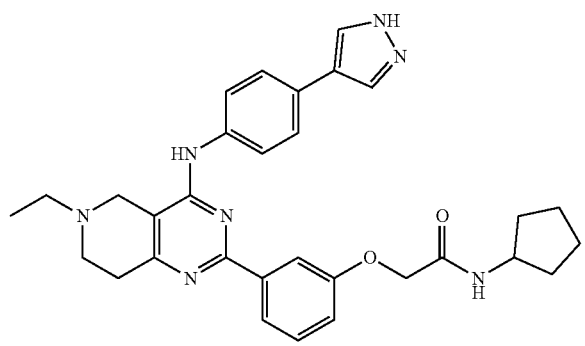 [SMILES: CCN1CCc2nc(-c3cccc(OCC(=O)NC4CCCC4)c3)nc(Nc3ccc(-c4cn[nH]c4)cc3)c2C1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-cyclopentylacetamide (200.00 mg, 366.26 umol, HCl salt) in MeOH (2.00 mL) was added TEA (74.12 mg, 732.52 umol, 101.53 uL). The mixture was stirred at 15° C. for 10 min. Then to the mixture was added acetaldehyde (161.34 mg, 1.47 mmol, 204.23 uL 40% purity) and HOAc (87.98 mg, 1.47 mmol, 83.79 uL). The mixture was stirred at 15° C. for 20 min. Then NaBH$_3$CN (115.08 mg, 1.83 mmol) was added. The mixture was stirred at 15° C. for another 15.5 h. LCMS showed about 74% of desired product. The reaction mixture was diluted with water (20 mL) and the resulting mixture was extracted with EtOAc (20 mL×3). The combined organic layers were washed with brine (30 mL), dried over Na$_2$SO$_4$, filtered and concentrated under reduced pressure to give a residue. The residue was purified by prep-HPLC (FA conditions) to afford the title compound (35.9 mg, 15%) as a light yellow solid. $^1$H NMR (400 MHz, DMSO-d$_6$) δ 8.46 (s, 1H), 8.20 (s, 1H), 8.05-8.02 (m, 3H), 7.91-7.89 (m, 2H), 7.77 (d, J=8.8 Hz, 2H), 7.64 (d, J=8.4 Hz, 2H), 7.40-7.36 (m, 1H), 7.05-7.03 (m, 1H), 4.51 (s, 2H), 4.10 (m, 1H), 3.54 (s, 2H), 2.83-2.78 (m, 4H), 2.67-2.62 (m, 2H), 1.82-1.76 (m, 2H), 1.64-1.58 (m, 2H), 1.50-1.42 (m, 4H), 1.18 (t, J=6.8 Hz, 3H). (ES+) m/e 538.4 (M+H)$^+$.

Example 126

2-(3-(4-((4-(1H-pyrazol-4-yl)phenyl)amino)-6-isopropyl-5,6,7,8-tetrahydropyrido[4,3-d]pyrimidin-2-yl)phenoxy)-N-cyclopentylacetamide

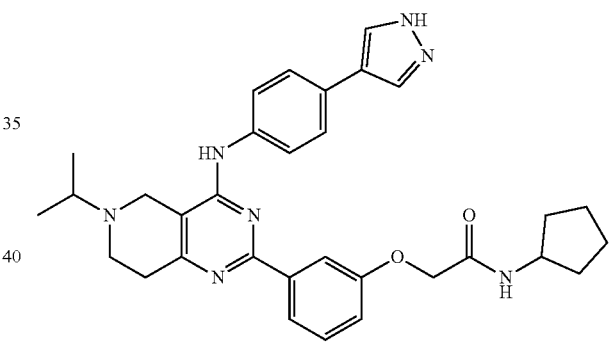

To the mixture of 2-(3-(4-((4-(1H-pyrazol-4-yl)phenyl)amino)-5,6,7,8-tetrahydropyrido[4,3-d]pyrimidin-2-yl)phenoxy)-N-cyclopentylacetamide (200.00 mg, 366.26 umol, HCl salt) in MeOH (2.00 mL) was added TEA (74.12 mg, 732.52 umol, 101.53 uL). The mixture was stirred at 15° C. for 10 min. Then to the mixture was added acetone (85.09 mg, 1.47 mmol, 107.71 uL) and HOAc (87.98 mg, 1.47 mmol, 83.79 uL). The mixture was stirred at 15° C. for 20 min. Then NaBH$_3$CN (115.08 mg, 1.83 mmol) was added and the reaction was stirred at 15° C. for 15.5 h. LCMS showed about 82% desired product. The reaction mixture was diluted with water (20 mL) and the resulting mixture was extracted with EtOAc (20 mL×3). The combined organic layers were washed with brine (30 mL), dried over Na$_2$SO$_4$, filtered and concentrated under reduced pressure to give a residue. The residue was purified by prep-HPLC (FA conditions) to afford the title compound (31.3 mg, 14%) as a light yellow solid. $^1$H NMR (400 MHz, DMSO-d$_6$) δ 8.43 (s, 1H), 8.20 (s, 1H), 8.05-8.01 (m, 3H), 7.90-7.89 (m, 2H), 7.76 (d, J=8.4 Hz, 2H), 7.64 (d, J=8.4 Hz, 2H), 7.38 (t, J=8.0 Hz, 1H), 7.05-7.02 (m, 1H), 4.50 (s, 2H), 4.13-4.08 (m, 1H), 3.60 (s, 2H), 3.02-2.95 (m, 1H), 2.80 (s, 4H), 1.82-1.76 (m, 2H), 1.62-1.61 (m, 2H), 1.49-1.42 (m, 4H), 1.14 (d, J=6.8 Hz, 6H). (ES+) m/e 552.2 (M+H)+.

Example 127

N-(4-(1H-pyrazol-4-yl)phenyl)-2-(3-(2-methoxyethoxy)phenyl)-7,8-dihydro-5H-pyrano[4,3-d]pyrimidin-4-amine

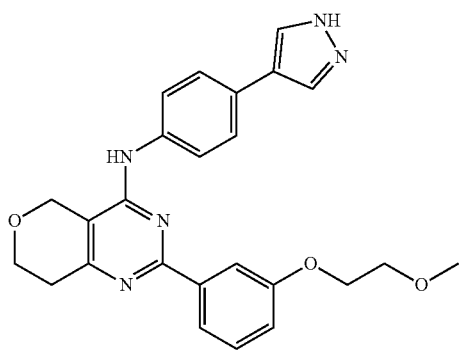 [SMILES: COCCOc1cccc(-c2nc3c(c(Nc4ccc(-c5cn[nH]c5)cc4)n2)COCC3)c1]

Example 127A 2-(3-(2-methoxyethoxy)phenyl)-N-(4-(1-(tetrahydro-2H-pyran-2-yl)-1H-pyrazol-4-yl)phenyl)-7,8-dihydro-5H-pyrano[4,3-d]pyrimidin-4-amine

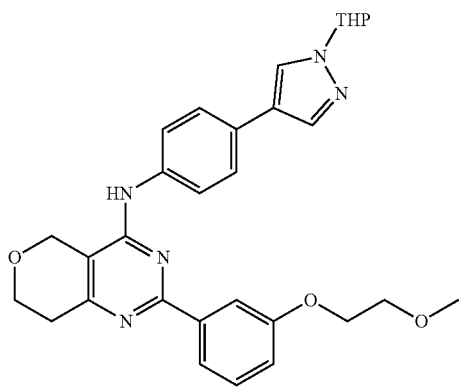

A mixture of 2-chloro-N-(4-(1-(tetrahydro-2H-pyran-2-yl)-1H-pyrazol-4-yl)phenyl)-7,8-dihydro-5H-pyrano[4,3-d]pyrimidin-4-amine (300.00 mg, 728.35 umol), 2-(3-(2-methoxyethoxy)phenyl)-4,4,5,5-tetramethyl-1,3,2-dioxaborolane (243.11 mg, 874.02 umol,), K$_2$CO$_3$ (201.33 mg, 1.46 mmol) and Pd(dppf)Cl$_2$ (53.29 mg, 72.83 umol) in dioxane (10.00 mL)/H$_2$O (1.00 mL) was degassed and purged with N$_2$ 3 times, then the mixture was stirred at 100° C. for 16 hour under N$_2$ atmosphere. LCMS showed ~21% of the desired compound and ~32% of 2-chloro-N-(4-(1-(tetrahydro-2H-pyran-2-yl)-1H-pyrazol-4-yl)phenyl)-7,8-dihydro-5H-pyrano[4,3-d]pyrimidin-4-amine. The mixture was cooled to room temperature and diluted with EtOAc (50 mL). The resulting mixture was washed with H$_2$O (50 mL), brine (50 mL), dried over Na$_2$SO$_4$, filtered and concentrated under reduced pressure to give a residue. The residue was purified by column chromatography (SiO$_2$, Petroleum ether/Ethyl acetate=5/1 to 0/1; Petroleum ether/Ethyl acetate=1/2, Rf=0.45) to afford the title compound (0.28 g, 34%, LCMS) as a yellow solid.

Example 127B

N-(4-(1H-pyrazol-4-yl)phenyl)-2-(3-(2-methoxyethoxy)phenyl)-7,8-dihydro-5H-pyrano[4,3-d]pyrimidin-4-amine

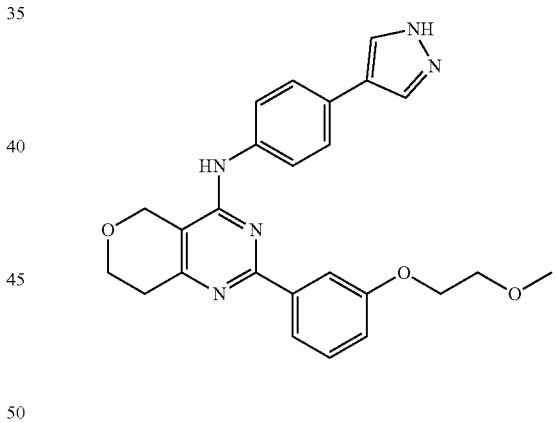

To a mixture of 2-(3-(2-methoxyethoxy)phenyl)-N-(4-(1-(tetrahydro-2H-pyran-2-yl)-1H-pyrazol-4-yl)phenyl)-7,8-dihydro-5H-pyrano[4,3-d]pyrimidin-4-amine (280.00 mg, 244.12 umol; purity: 46%) in CH$_2$Cl$_2$ (10.00 mL) was added HCl/dioxane (4 N, 5.00 mL) dropwise. The mixture was stirred at 20° C. for 16 h. LCMS showed ~50% desired compound was detected. The mixture was concentrated under vacuum to give a residue. The residue was purified by prep-HPLC (FA conditions) to afford the title compound (79.1 mg, 66%) as an off-white solid. $^1$H NMR (400 MHz, DMSO-d$_6$) δ 8.42 (s, 1H), 8.39 (s, 1H), 8.05-7.85 (m, 4H), 7.73 (d, J=8.8 Hz, 2H), 7.62 (d, J=8.8 Hz, 2H), 7.37 (t, J=8.0 Hz, 1H), 7.05-7.02 (m, 1H), 4.71 (s, 2H), 4.14 (t, J=4.8 Hz, 2H), 3.99 (t, J=5.6 Hz, 2H), 3.70-3.67 (m, 2H), 3.33 (s, 3H), 2.82 (t, J=5.4 Hz, 2H). (ES+) m/e 444.1 (M+H)⁺.

Example 128

2-(3-(4-((4-(1H-pyrazol-4-yl)phenyl)amino)-5,6,7,8-tetrahydropyrido[4,3-d]pyrimidin-2-yl)phenoxy)-N-(tert-pentyl)acetamide

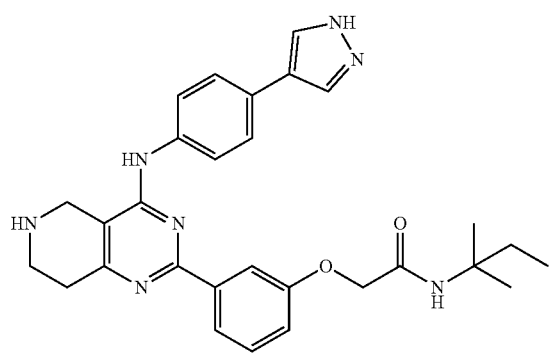 [SMILES: CCC(C)(C)NC(=O)COc1cccc(-c2nc3c(c(Nc4ccc(-c5cn[nH]c5)cc4)n2)CNCC3)c1]

Example 128A tert-butyl 2-(3-(2-oxo-2-(tert-pentylamino)ethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate

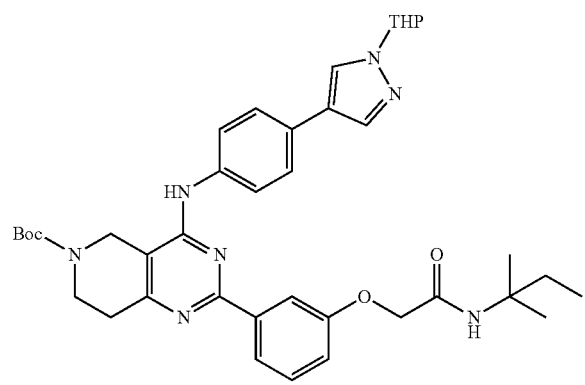

To the mixture of tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (900.00 mg, 1.76 mmol) and N-(tert-pentyl)-2-(3-(4,4,5,5-tetramethyl-1,3,2-dioxaborolan-2-yl)phenoxy)acetamide (733.91 mg, 2.11 mmol) in dioxane (10.00 mL), H₂O (1.00 mL) was added K₂CO₃ (486.50 mg, 3.52 mmol), Pd(dppf)Cl₂ (128.78 mg, 176.00 umol). The mixture was degassed and purged with N₂ 3 times and stirred under N₂ at 90° C. for 16 h. TLC (petroleum ether/EtOAc=1:1) showed tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (Rf=0.35) was consumed completely and one main new spot (Rf=0.3) was detected. The reaction mixture was cooled to room temperature and diluted with water (30 mL). The resulting mixture was extracted with EtOAc (30 mL×3). The combined organic layers were washed with brine (60 mL), dried over Na₂SO₄, filtered and concentrated under reduced pressure to give a residue. The residue was purified by column chromatography (SiO₂, petroleum ether/EtOAc=1:0 to 0:1) to give the title compound (884.00 mg, 72%) as a brown solid. ¹H NMR (400 MHz, DMSO-d₆) δ 8.67 (s, 1H), 8.35 (s, 1H), 7.94 (s, 1H), 7.90-7.87 (m, 2H), 7.79-7.77 (m, 2H), 7.65 (d, J=8.8 Hz, 2H), 7.40-7.30 (m, 2H), 7.06-7.03 (m, 1H), 5.41 (d, J=8.8 Hz, 1H), 4.52-4.48 (m, 4H), 3.97-3.94 (m, 1H), 3.72-3.62 (m, 3H), 2.80-2.67 (m, 2H), 2.20-2.11 (m, 1H), 1.96-1.94 (m, 2H), 1.70-1.62 (m, 3H), 1.56 (s, 2H), 1.47 (s, 9H), 1.24 (s, 6H), 0.75 (t, J=7.2 Hz, 3H).

Example 128B 2-(3-(4-((4-(1H-pyrazol-4-yl)phenyl)amino)-5,6,7,8-tetrahydropyrido[4,3-d]pyrimidin-2-yl)phenoxy)-N-(tert-pentyl)acetamide

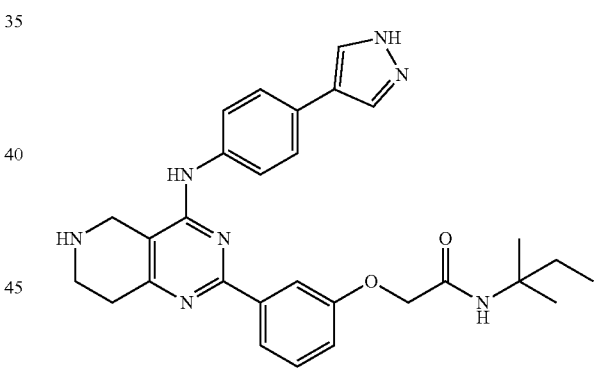

To a mixture of tert-butyl 2-(3-(2-oxo-2-(tert-pentylamino)ethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (884.00 mg, 1.27 mmol) in CH₂Cl₂ (10.00 mL) was added HCl/dioxane (4 N, 8.00 mL). The mixture was stirred at 20° C. for 16 h. LCMS showed about 83% desired product and about 12% THP-protected product. To the mixture was added additional HCl/dioxane (4 N, 2 mL) and the reaction was stirred at 20° C. for another 4 h. LCMS showed about 92% desired product and 7% THP-protected product. The mixture was stirred at 20° C. for another 16 h. LCMS showed one main peak of the desired product. The mixture was filtered to give crude title compound (640 mg, HCl salt, crude). 100 mg of the crude material was purified by prep-HPLC (TFA conditions) to afford pure title compound (52.6 mg) as a yellow solid. $^1$H NMR (400 MHz, DMSO-$d_6$) δ 9.35 (s, 2H), 8.82 (s, 1H), 8.06 (s, 2H), 7.90-7.86 (m, 2H), 7.74-7.72 (m, 2H), 7.67-7.65 (m, 2H), 7.40 (t, J=8.0 Hz, 1H), 7.34 (s, 1H), 7.07-7.05 (m, 1H), 4.49 (s, 2H), 4.26 (s, 2H), 3.53 (s, 2H), 3.04-3.01 (m, 2H), 1.69-1.63 (m, 2H), 1.22 (s, 6H), 0.75 (t, J=7.2 Hz, 3H). (ES+) m/e 512.2 (M+H)$^+$.

Example 129

2-(3-(4-((4-(1H-pyrazol-4-yl)phenyl)amino)-6-methyl-5,6,7,8-tetrahydropyrido[4,3-d]pyrimidin-2-yl)phenoxy)-N-(tert-pentyl)acetamide

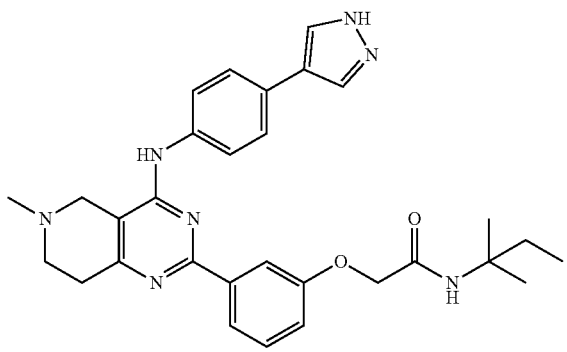 [SMILES: CCC(C)(C)NC(=O)COc1cccc(-c2nc3c(c(Nc4ccc(-c5cn[nH]c5)cc4)n2)CN(C)CC3)c1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-(tert-pentyl)acetamide (180.00 mg, 328.42 umol, HCl salt) in MeOH (2.00 mL) was added TEA (66.47 mg, 656.84 umol, 91.05 uL). The mixture was stirred at 15° C. for 10 min. Then to the mixture were added formaldehyde (73.97 mg, 985.26 umol, 67.86 uL, 40% purity) and HOAc (78.89 mg, 1.31 mmol, 75.13 uL). The mixture was stirred at 15° C. for 20 min. Then NaBH$_3$CN (103.19 mg, 1.64 mmol) was added. The mixture was stirred at 15° C. for another 15.5 h. LCMS showed one main peak of desired product. The reaction mixture was diluted with water (20 mL) and extracted with EtOAc (30 mL×3). The combined organic layers were dried over Na$_2$SO$_4$, filtered and concentrated under reduced pressure to give a residue. The residue was purified by prep-HPLC (FA conditions) to give desired product. But HNMR showed product contained some MeCN. The product was dissolved with deionized water (about 30 mL) to afford the title compound (54.00 mg, 28%) as a white solid by lyophilization. $^1$H NMR (400 MHz, DMSO-$d_6$) δ 8.42 (s, 1H), 8.04 (s, 2H), 7.91-7.87 (m, 2H), 7.78 (d, J=8.8 Hz, 2H), 7.63 (d, J=8.4 Hz, 2H), 7.39-7.32 (m, 2H), 7.04-7.01 (m, 1H), 4.48 (s, 2H), 3.50 (s, 2H), 2.84-2.82 (m, 2H), 2.74-2.72 (m, 2H), 2.47 (s, 3H), 1.69-1.64 (m, 2H), 1.23 (s, 6H), 0.75 (t, J=7.6 Hz, 3H). (ES+) m/e 526.2 (M+H)$^+$.

Example 130

2-(3-(4-((4-(1H-pyrazol-4-yl)phenyl)amino)-6-ethyl-5,6,7,8-tetrahydropyrido[4,3-d]pyrimidin-2-yl)phenoxy)-N-(tert-pentyl)acetamide

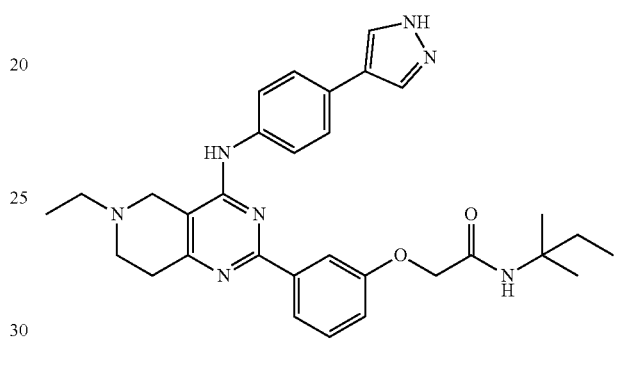

To the mixture of 2-(3-(4-((4-(1H-pyrazol-4-yl)phenyl)amino)-5,6,7,8-tetrahydropyrido[4,3-d]pyrimidin-2-yl)phenoxy)-N-(tert-pentyl)acetamide (180.00 mg, 328.42 umol, HCl salt) in MeOH (2.00 mL) was added TEA (66.47 mg, 656.84 umol, 91.05 uL). The mixture was stirred at 15° C. for 10 min. Then to the mixture was added acetaldehyde (144.67 mg, 1.31 mmol, 183.12 uL, 40% purity) and HOAc (78.89 mg, 1.31 mmol, 75.13 uL). The mixture was stirred at 15° C. for 20 min. Then NaBH$_3$CN (103.19 mg, 1.64 mmol) was added and the reaction was stirred at 15° C. for 15.5 h. LCMS showed reaction was a little messy and one major peak of desired product. The reaction mixture was diluted with water (20 mL) and extracted with EtOAc (30 mL×3). The combined organic layers were dried over Na$_2$SO$_4$, filtered and concentrated under reduced pressure to give a residue. The residue was purified by prep-HPLC (FA conditions) to give a light yellow solid. Since HNMR showed that the product contained some MeCN, it was dissolved in deionized water (about 20 mL) to afford the desired product by lyophilization (22.1 mg, 10%) as a yellow solid. $^1$H NMR (400 MHz, DMSO-$d_6$) δ 8.43-8.42 (m, 2H), 8.04-7.87 (m, 4H), 7.76 (d, J=8.8 Hz, 2H), 7.63 (d, J=8.8 Hz, 2H), 7.37 (t, J=8.0 Hz, 1H), 7.32 (s, 1H), 7.04-7.01 (m, 1H), 4.48 (s, 2H), 3.52 (s, 2H), 2.82-2.77 (m, 4H), 2.66-3.61 (m, 2H), 1.69-1.64 (m, 2H), 1.23 (s, 6H), 1.18 (t, J=7.2 Hz, 3H), 0.75 (t, J=7.2 Hz, 3H). (ES+) m/e 540.3 (M+H)$^+$.

Example 131

2-(3-(4-((4-(1H-pyrazol-4-yl)phenyl)amino)-6-isopropyl-5,6,7,8-tetrahydropyrido[4,3-d]pyrimidin-2-yl)phenoxy)-N-(tert-pentyl)acetamide

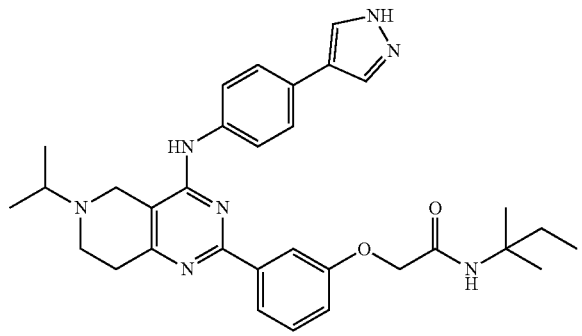 [SMILES: CCC(C)(C)NC(=O)COc1cccc(-c2nc3c(c(Nc4ccc(-c5cn[nH]c5)cc4)n2)CN(C(C)C)CC3)c1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-(tert-pentyl)acetamide (180.00 mg, 328.42 umol, HCl salt) in MeOH (2.00 mL) was added TEA (66.47 mg, 656.84 umol, 91.05 uL). The mixture was stirred at 15° C. for 10 min. Then to the mixture was added acetone (76.30 mg, 1.31 mmol, 96.58 uL) and HOAc (78.89 mg, 1.31 mmol, 75.13 uL). The mixture was stirred at 15° C. for 20 min. Then NaBH$_3$CN (103.19 mg, 1.64 mmol) was added and the mixture was stirred at 15° C. for another 15.5 h. LCMS showed one main peak of desired product. The reaction mixture was diluted with water (20 mL) and extracted with EtOAc (30 mL×3). The combined organic layers were dried over Na$_2$SO$_4$, filtered and concentrated under reduced pressure to give a residue. The residue was purified by prep-HPLC (FA conditions) to afford the title compound (64.8 mg, 30%) as a white solid. $^1$H NMR (400 MHz, DMSO-d$_6$) δ 8.42 (s, 1H), 8.23 (s, 2H), 8.04 (s, 2H), 7.90-7.87 (m, 2H), 7.76 (d, J=8.4 Hz, 2H), 7.64 (d, J=8.4 Hz, 2H), 7.37 (t, J=8.0 Hz, 1H), 7.32 (s, 1H), 7.03-7.01 (m, 1H), 4.48 (s, 2H), 3.60 (s, 2H), 3.02-2.97 (m, 1H), 2.80 (s, 4H), 1.69-1.64 (m, 2H), 1.23 (s, 6H), 1.15 (d, J=6.8 Hz, 6H), 0.75 (t, J=7.6 Hz, 3H). (ES+) m/e 554.3 (M+H)$^+$.

Example 132

2-(3-(4-((4-(1H-pyrazol-4-yl)phenyl)amino)-6-propionyl-5,6,7,8-tetrahydropyrido[4,3-d]pyrimidin-2-yl)phenoxy)-N-(tert-pentyl)acetamide

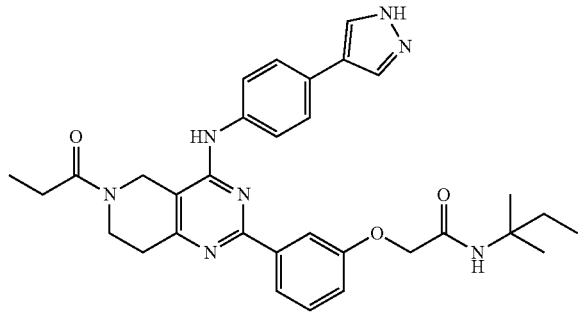 [SMILES: CCC(=O)N1CCc2nc(-c3cccc(OCC(=O)NC(C)(C)CC)c3)nc(Nc3ccc(-c4cn[nH]c4)cc3)c2C1]

Example 132A 1-(2,4-dichloro-7,8-dihydropyrido[4,3-d]pyrimidin-6(5H)-yl)propan-1-one

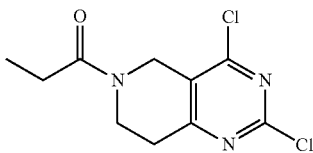 [SMILES: CCC(=O)N1CCc2nc(Cl)nc(Cl)c2C1]

To the mixture of 2,4-dichloro-5,6,7,8-tetrahydropyrido[4,3-d]pyrimidine (270.00 mg, 1.12 mmol, HCl salt) in CH$_2$Cl$_2$ (15.00 mL) was added dropwise TEA (340.00 mg, 3.36 mmol, 465.75 uL) at 0° C. Then the mixture was stirred under N$_2$ at 0° C. for 5 min. To the mixture was added propanoyl chloride (124.35 mg, 1.34 mmol, 124.35 uL) at 0° C. The mixture was stirred under N$_2$ at 0° C. for 2 h. TLC (petroleum ether/EtOAc=1:1, Rf=0.6) showed one new main spot. The mixture was diluted with CH$_2$Cl$_2$ (30 mL) and washed with water (30 mL×2), citric acid (10%, 30 mL×3), sat.NaHCO$_3$ (30 mL), brine (30 mL). The organic layer was dried over Na$_2$SO$_4$, filtered and concentrated under reduced pressure to afford the title compound (276.00 mg, crude) as light brown oil which was used in the next step without further purification. $^1$H NMR (400 MHz, DMSO-d$_6$) δ 4.60 (s, 2H), 3.78 (t, J=5.6 Hz, 2H), 3.00-2.85 (m, 2H), 2.47-2.43 (m, 2H), 1.03-0.99 (m, 3H).

Example 132B 1-(2-chloro-4-((4-(1-(tetrahydro-2H-pyran-2-yl)-1H-pyrazol-4-yl)phenyl)amino)-7,8-dihydropyrido[4,3-d]pyrimidin-6(5H)-yl)propan-1-one

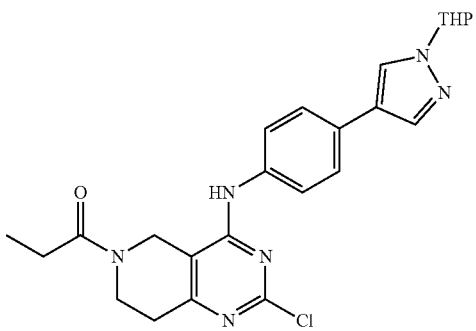

To the mixture of 1-(2,4-dichloro-7,8-dihydropyrido[4,3-d]pyrimidin-6(5H)-yl)propan-1-one (270.00 mg, 1.04 mmol) and 4-(1-(tetrahydro-2H-pyran-2-yl)-1H-pyrazol-4-yl)aniline (227.73 mg, 936.00 umol) in n-BuOH (5.00 mL) was added DIPEA (268.82 mg, 2.08 mmol, 363.27 uL). The mixture was stirred at 100° C. for 16 h under N$_2$. The reaction mixture was cooled to room temperature and diluted with water (30 mL). The resulting mixture was extracted with EtOAc (30 mL×3). The combined organic layers were washed with brine (40 mL), dried over Na$_2$SO$_4$, filtered and concentrated under reduced pressure to give a residue. The residue was purified by combi-flash (SiO$_2$) to afford the title compound (280.00 mg, 58%) as a yellow solid and the structure was confirmed by NOE. $^1$H NMR (400 MHz, DMSO-d$_6$) δ 9.06-8.90 (m, 1H), 8.33-8.32 (m, 1H), 7.93 (s, 1H), 7.63-7.57 (m, 4H), 5.41 (d, J=9.6 Hz, 1H), 4.55-4.52 (m, 2H), 3.94 (d, J=11.6 Hz, 1H), 3.75-3.74 (m, 2H), 3.66-3.62 (m, 1H), 2.78-2.66 (m, 2H), 2.48-2.46 (m, 2H), 2.16-2.09 (m, 1H), 1.96-1.91 (m, 2H), 1.70-1.67 (m, 1H), 1.56-1.55 (m, 2H), 1.04 (t, J=7.2 Hz, 3H).

Example 132C

N-(tert-pentyl)-2-(3-(6-propionyl-4-((4-(1-(tetrahydro-2H-pyran-2-yl)-1H-pyrazol-4-yl)phenyl)amino)-5,6,7,8-tetrahydropyrido[4,3-d]pyrimidin-2-yl)phenoxy)acetamide

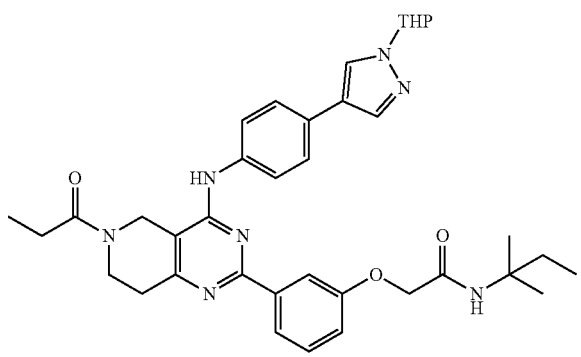

To the mixture of 1-(2-chloro-4-((4-(1-(tetrahydro-2H-pyran-2-yl)-1H-pyrazol-4-yl)phenyl)amino)-7,8-dihydropyrido[4,3-d]pyrimidin-6(5H)-yl)propan-1-one (250.00 mg, 535.38 umol) and N-(tert-pentyl)-2-(3-(4,4,5,5-tetramethyl-1,3,2-dioxaborolan-2-yl)phenoxy)acetamide (223.10 mg, 642.45 umol) in dioxane (5.00 mL), H$_2$O (500.00 uL) was added K$_2$CO$_3$ (147.99 mg, 1.07 mmol), Pd(dppf)Cl$_2$ (39.17 mg, 53.54 umol, 0.10 eq). The mixture was stirred under N$_2$ at 90° C. for 16 h. TLC (petroleum ether/EtOAc=0:1, Rf=0.4) showed one new main spot. The reaction mixture was cooled to room temperature and diluted with water (30 mL). The resulting mixture was extracted with EtOAc (30 mL×3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=20:1 to 0:1) to give the title compound (230.00 mg, 66%) as a light brown solid. $^1$H NMR (400 MHz, DMSO-d$_6$) δ 8.77-8.62 (m, 1H), 8.36-8.35 (m, 1H), 7.95-7.94 (m, 1H), 7.91-7.88 (m, 2H), 7.79 (t, J=8.8 Hz, 2H), 7.69-7.63 (m, 2H), 7.38 (t, J=8.0 Hz, 1H), 7.32-7.31 (m, 1H), 7.06-7.03 (m, 1H), 5.42-5.40 (m, 1H), 4.63-4.61 (m, 2H), 4.49 (s, 2H), 3.97-3.94 (m, 1H), 3.82-3.80 (m, 2H), 3.68-3.62 (m, 1H), 2.89-2.77 (m, 1H), 2.59 (s, 2H), 2.20-2.12 (m, 1H), 1.97-1.94 (m, 1H), 1.70-1.66 (m, 3H), 1.57-1.56 (m, 2H), 1.23 (s, 6H), 1.06 (t, J=7.2 Hz, 3H), 0.75 (t, J=7.6 Hz, 3H).

Example 132D 2-(3-(4-((4-(1H-pyrazol-4-yl)phenyl)amino)-6-propionyl-5,6,7,8-tetrahydropyrido[4,3-d]pyrimidin-2-yl)phenoxy)-N-(tert-pentyl)acetamide

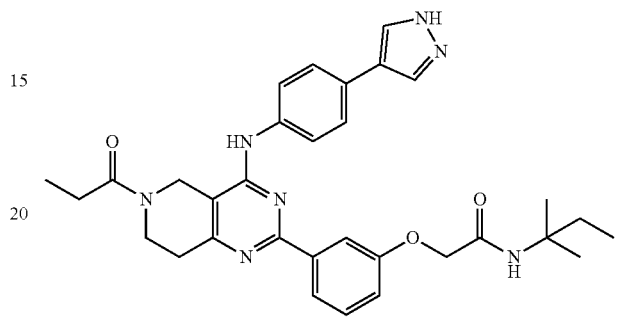

To the mixture of N-(tert-pentyl)-2-(3-(6-propionyl-4-((4-(1-(tetrahydro-2H-pyran-2-yl)-1H-pyrazol-4-yl)phenyl)amino)-5,6,7,8-tetrahydropyrido[4,3-d]pyrimidin-2-yl)phenoxy)acetamide (230.00 mg, 352.87 umol) in CH$_2$Cl$_2$ (5.00 mL) was added HCl/dioxane (4 N, 5.00 mL). The mixture was stirred at 20° C. for 2 h. LCMS showed about 81% of desired product. The mixture was concentrated under reduced pressure to give a residue. The residue was purified by prep-HPLC (FA conditions) to afford the title compound (35.50 mg, 16%, 99% purity, FA salt) as a yellow solid. $^1$H NMR (400 MHz, DMSO-d$_6$) δ 8.74-8.61 (m, 1H), 8.05 (s, 2H), 7.91-7.87 (m, 2H), 7.77 (t, J=9.4 Hz, 2H), 7.64 (t, J=8.4 Hz, 2H), 7.38 (t, J=8.0 Hz, 1H), 7.31 (s, 1H), 7.05-7.02 (m, 1H), 4.63-4.61 (m, 2H), 4.48 (s, 2H), 3.81 (d, J=5.6 Hz, 2H), 2.89-2.77 (m, 2H), 2.54 (s, 2H), 1.69-1.63 (m, 2H), 1.23 (s, 6H), 1.06 (t, J=7.4 Hz, 3H), 0.75 (t, J=7.4 Hz, 3H). (ES+) m/e 568.2 (M+H)$^+$.

Example 133

2-(3-(4-((4-(1H-pyrazol-4-yl)phenyl)amino)-6-acetyl-5,6,7,8-tetrahydropyrido[4,3-d]pyrimidin-2-yl)phenoxy)-N-(tert-butyl)acetamide

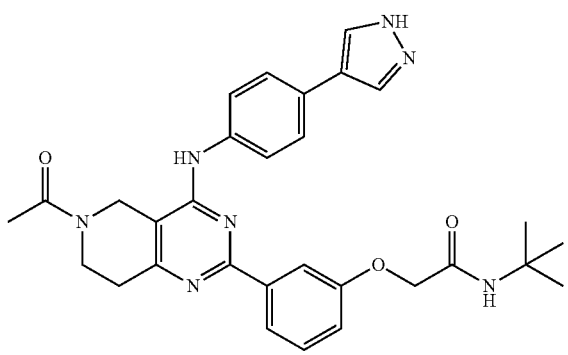 [SMILES: CC(=O)N1CCc2nc(-c3cccc(OCC(=O)NC(C)(C)C)c3)nc(Nc3ccc(-c4cn[nH]c4)cc3)c2C1]

To the mixture of acetic acid (13.49 mg, 224.70 umol, 12.85 uL), HATU (106.80 mg, 280.88 umol) and DIPEA (48.40 mg, 374.50 umol, 65.41 uL) in DMF (1 mL) was added the mixture of 2-(3-(4-((4-(1H-pyrazol-4-yl)phenyl)amino)-5,6,7,8-tetrahydropyrido[4,3-d]pyrimidin-2-yl)phenoxy)-N-(tert-butyl)acetamide (100.00 mg, 187.25 umol, HCl salt) and DIPEA (48.40 mg, 374.50 umol, 65.41 uL) in DMF (1 mL). The mixture was stirred at 15° C. for 16 h. LCMS showed two main peaks. The reaction mixture was diluted with water (30 mL) and extracted with EtOAc (30 mL×3). The combined organic layers were washed with brine (40 mL×2), dried over Na$_2$SO$_4$, filtered and concentrated under reduced pressure to give a residue. The residue was purified by prep-HPLC (FA conditions) to separate the two peaks. (1). HPLC and LCMS showed one peak was the mixture of desired product and THP-protected product. The solid after lyophilization was used into next step. To the solid in CH$_2$Cl$_2$ (2.00 mL) was added HCl/dioxane (4 N, 3.00 mL). The mixture was stirred at 25° C. for 1 h. LCMS showed one main peak of desired product. The mixture was concentrated under reduced pressure to give a residue (Part A). HPLC and LCMS showed the other peak was the mixture of desired product and bi-substituted product. The solid after lyophilization was used into next step. To the solid in THF (2.00 mL) and MeOH (2.00 mL) was added NaOH (2 M, 2.00 mL). The mixture was stirred at 25° C. for 1 h. LCMS showed one main peak of desired product. The reaction was diluted with water (20 mL) and the mixture was extracted with EtOAc (30 mL×3). The combined organic layers were dried over Na2SO4, filtered and concentrated under reduced pressure to give a residue (Part B). The residue which was combined with Part A was purified by prep-HPLC (FA conditions) to afford the title compound (11.6 mg) as a light yellow solid. $^1$H NMR (400 MHz, DMSO-d$_6$) δ 7.88-7.84 (m, 4H), 7.76-7.73 (m, 2H), 7.63 (t, J=9.6 Hz, 2H), 7.50-7.49 (m, 1H), 7.38 (t, J=8.0 Hz, 1H), 7.02 (d, J=6.4 Hz, 1H), 7.06-7.04 (m, 1H), 4.59 (s, 2H), 4.44 (s, 2H), 3.80-3.77 (m, 2H), 2.89 (s, 1H), 2.76 (s, 1H), 2.16 (d, J=11.2 Hz, 3H), 1.26 (s, 9H). (ES+) m/e 540.3 (M+H)$^-$.

Example 134

2-(3-(4-((4-(1H-pyrazol-4-yl)phenyl)amino)pyrido[4,3-d]pyrimidin-2-yl)phenoxy)-N-isopropylacetamide

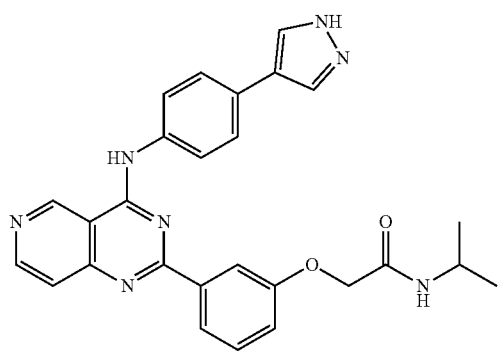 [SMILES: CC(C)NC(=O)COc1cccc(-c2nc(Nc3ccc(-c4cn[nH]c4)cc3)c3cnccc3n2)c1]

Example 134A methyl 4-(3-methoxybenzamido)nicotinate

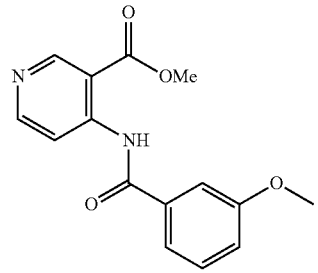 [SMILES: COC(=O)c1cnccc1NC(=O)c1cccc(OC)c1]

To a solution of methyl 4-aminonicotinate (8.00 g, 52.58 mmol) and TEA (10.60 g, 105.16 mmol, 14.58 mL) in DCM (100 mL) was added dropwise the solution of 3-methoxybenzoyl chloride (8.97 g, 52.58 mmol) in CH$_2$Cl$_2$ (50 mL) at 23° C. The mixture was stirred at 23° C. for 16 hours. LCMS showed the desired product was major. The reaction mixture was quenched by addition of water (100 mL) and the mixture was extracted with CH$_2$Cl$_2$ (120 mL×3). The combined organic layers were dried over Na$_2$SO$_4$, filtered and concentrated under reduced pressure to give a residue. The residue was dispersed in CH$_2$Cl$_2$ (80 mL) and stirred for about 4 hours. The suspension was filtered and the resulting solid was dried to afford the title compound (14.00 g, 93%) as a white solid.

Example 134B 4-(3-methoxybenzamido)nicotinamide

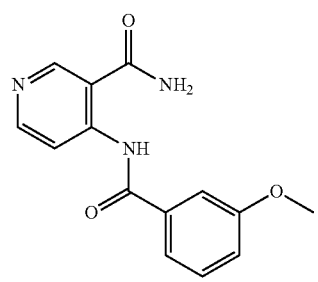 [SMILES: COc1cccc(C(=O)Nc2ccncc2C(N)=O)c1]

To MeOH (450 mL) was bubbled NH$_3$ for at room temperature for 30 minutes and about NH$_3$ (50 g) was bubbled into MeOH. To the NH$_3$/MeOH solution was added methyl 4-(3-methoxybenzamido)nicotinate (14.00 g, 48.90 mmol). Then the reaction was stirred at room temperature for 16 hours. LC/MS (EW991-1067-P1A) showed the desired product as the major product. TLC (EtOAc Rf=0.4) showed that the starting materials were consumed completely and there was a main new spot. The reaction mixture was concentrated to remove most of MeOH. The resulting suspension was filtered, the solid was washed with MeOH, dried under reduce pressure to afford the title compound (11.50 g, 87%) as a white solid.

Example 134C 2-(3-methoxyphenyl)pyrido[4,3-d]pyrimidin-4-ol

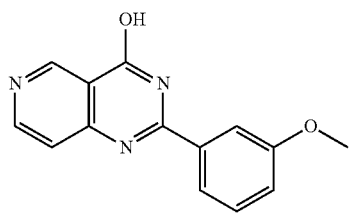

To the solution of 2-(3-methoxyphenyl)pyrido[4,3-d]pyrimidin-4-ol (11.50 g, 42.39 mmol) in i-PrOH (100 mL) was added aqueous NaOH (2 M, 127.17 mL). Then the reaction was stirred at 90° C. for 3 hours. LCMS showed the desired product was major. TLC (EtOAc Rf=0.45) showed the starting materials were consumed completely and there was a main new spot. The reaction mixture was concentrated to remove most of i-PrOH. The resulting mixture was adjusted to pH=7 with addition of 6 N HCl. The resulting suspension was filtered. The solid was collected and dried under reduce pressure to give the title compound (9.50 g, 89%) as a white solid. $^1$H NMR (400 MHz, DMSO-d$_6$) δ 12.80 (s, 1H), 9.27 (s, 1H), 8.77 (d, J=8.0 Hz, 1H), 7.85 (d, J=8.0 Hz, 1H), 7.81 (s, 1H), 7.58 (d, J=5.6 Hz, 1H), 7.47 (d, J=8.0, 8.0 Hz, 1H), 7.18 (d, J=8.0, 5.6 Hz, 1H), 3.87 (s, 3H).

Example 134D 4-chloro-2-(3-methoxyphenyl)pyrido[4,3-d]pyrimidine

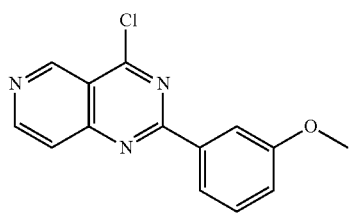 [SMILES: COc1cccc(-c2nc(Cl)c3cnccc3n2)c1]

To the mixture of 2-(3-methoxyphenyl)pyrido[4,3-d]pyrimidin-4-ol (9.00 g, 35.54 mmol) in POCl$_3$ (115.50 g, 753.28 mmol, 70.00 mL) was added DIPEA (9.19 g, 71.07 mmol, 12.41 mL). Then the reaction was stirred at 80° C. for 2 hours. LCMS showed there was 55% MeO replaced product and about 45% starting material remained. So the reaction was stirred at 80° C. for another 14 hours. LCMS showed there was 85% MeO replaced product. The reaction mixture was concentrated to give the title compound (9.60 g, crude) as a light brown solid which was used in the next step directly.

Example 134E

N-(4-bromophenyl)-2-(3-methoxyphenyl)pyrido[4,3-d]pyrimidin-4-amine

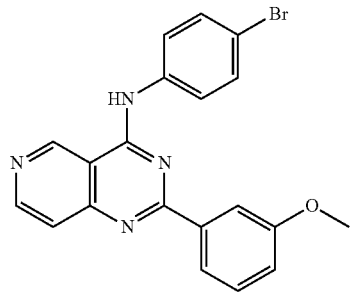 [SMILES: COc1cccc(-c2nc(Nc3ccc(Br)cc3)c3cnccc3n2)c1]

The mixture of 4-chloro-2-(3-methoxyphenyl)pyrido[4,3-d]pyrimidine (9.60 g, 35.33 mmol), 4-bromoaniline (9.12 g, 53.00 mmol) and DIPEA (18.27 g, 141.32 mmol, 24.69 mL) in THF (150 mL) was stirred at 10° C. for 2 hours. LCMS showed the starting materials were major and the reaction was stirred at 60° C. for another 16 hours. LCMS showed there were still all starting materials. The reaction mixture was concentrated to give a residue and the residue was purified roughly via silica chromatography (CH$_2$Cl$_2$) to recover the mixture of the two starting materials (18 g) as a black brown solid.

The recovered the mixture of the two starting materials (18 g) and DIPEA (8.56 g, 66.24 mmol, 11.57 mL) in n-BuOH (150 mL) was stirred at 100° C. for 16 hours. LCMS showed the desired product was major. The reaction was cooled to room temperature and water (150 mL) was added. The resulting mixture was extracted with EtOAc (150 mL×4). The combined organic layers were washed with brine (100 mL), dried over Na$_2$SO$_4$, concentrated to give a residue. The residue was dispersed in EtOAc (150 mL) and the mixture was stirred at room temperature for 30 minutes. The yellow solid (3.8 g) was collected by filtration and the filtrate was concentrated. The residue was purified via silica chromatography (petroleum ether/EtOAc=10:1 to 3:1, then CH$_2$Cl$_2$ to CH$_2$Cl$_2$:MeOH=20:1). The obtained title compound was re-purified via recrystallization (petroleum ether/EtOAc=1:1) to afford 1.4 g product (purity: ~80%) as a light brown solid. $^1$H NMR (400 MHz, DMSO-d$_6$) δ 10.46 (s, 1H), 9.86 (s, 1H), 8.81 (d, J=5.6 Hz, 1H), 8.04 (d, J=8.0 Hz, 1H), 7.99 (s, 1H), 7.94 (d, J=8.0 Hz, 2H), 7.73 (d, J=5.6 Hz, 1H), 7.68 (d, J=8.0 Hz, 2H), 7.46 (d, J=8.0, 8.0 Hz, 1H), 7.13 (d, J=8.0, 5.6 Hz, 1H), 3.86 (s, 3H).

Example 134F 3-(4-((4-bromophenyl)amino)pyrido[4,3-d]pyrimidin-2-yl)phenol

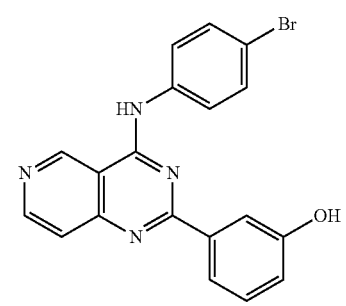 [SMILES: Oc1cccc(-c2nc(Nc3ccc(Br)cc3)c3cnccc3n2)c1]

To the suspension of N-(4-bromophenyl)-2-(3-methoxyphenyl)pyrido[4,3-d]pyrimidin-4-amine (3.50 g, 8.59 mmol) in CH₂Cl₂ (60 mL) was added BBr₃ (10.76 g, 42.95 mmol, 4.14 mL) at 0° C. under N₂. The reaction was stirred at 35° C. for 5 hrs. LCMS showed that there was 33% desired product and 37% starting materials remaining. After the reaction was stirred for another 16 hr, LCMS still showed 35% starting materials although there was 34% desired product as well. Additional BBr₃ (10.76 g, 42.95 mmol, 4.14 mL) was added and the reaction was stirred at 35° C. for another 5 hours. LCMS showed there was 38% desired product and still 25% starting materials remained. The reaction was quenched with ice water (150 mL) and adjusted to pH=7 with sat.Na₂CO₃. The resulted suspension was extracted with the mixed solvent (CH₂Cl₂:MeOH=10:1 200 mL×3). The combined organic layers were filtered. The filtrate was washed with brine (150 mL), dried over Na₂SO₄ and concentrated to give the crude yellow solid. The crude yellow solid was dispersed in EtOAc (50 mL). The mixture was stirred at room temperature for 20 minutes and filtered to get a yellow solid. The solid was dispersed in CH₂Cl₂ (500 mL) and water (100 mL) and the resulting mixture was extracted with CH₂Cl₂ (200 mL×5). The combined organic layers were dried over Na₂SO₄, filtered and concentrated to give the title compound (2.40 g, crude) as a yellow solid. HNMR showed there was about 25% starting materials remained, and the obtained mixture of product was used in the next step directly.

Example 134G methyl 2-(3-(4-((4-bromophenyl)amino)pyrido[4,3-d]pyrimidin-2-yl)phenoxy)acetate

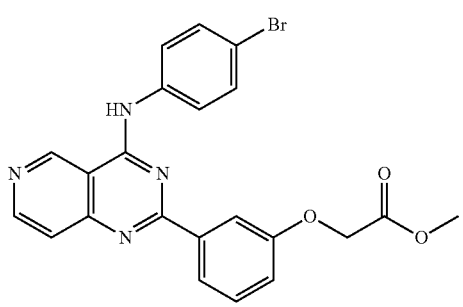 [SMILES: COC(=O)COc1cccc(-c2nc(Nc3ccc(Br)cc3)c3cnccc3n2)c1]

The mixture of 3-(4-((4-bromophenyl)amino)pyrido[4,3-d]pyrimidin-2-yl)phenol (2.00 g, 5.09 mmol, purity: 75%), methyl 2-bromoacetate (544.60 mg, 3.56 mmol, 336.17 uL) and K₂CO₃ (1.06 g, 7.64 mmol) in DMF (20 mL) was stirred at 40° C. for 1 hour. LCMS showed there were 20% desired product and 30% di-substituted byproduct. The reaction mixture of another small scale reaction was combined with this reaction. Water (20 mL) was added and the resulting mixture was extracted with EtOAc (100 mL×3). The combined organic layers were washed with brine (20 mL), dried over Na₂SO₄, concentrated to give a residue. The residue was purified via prep-MPLC. The purified aqueous solution of desired product was basified with sat.Na₂CO₃ to pH=9 and the resulting mixtures were extracted with EtOAc (100 mL×4). The combined organic layers were washed with brine (20 mL), dried over Na₂SO₄, filtered and concentrated to afford the title compound (420 mg, HNMR: EW991-1136-P1B) as a yellow solid altogether. ¹H NMR (400 MHz, DMSO-d₆) δ 10.41 (s, 1H), 9.84 (s, 1H), 8.81 (d, J=5.6 Hz, 1H), 8.08 (d, J=8.0 Hz, 1H), 7.94 (s, 1H), 7.92 (d, J=8.0 Hz, 2H), 7.71 (d, J=5.6 Hz, 1H), 7.68 (d, J=8.0 Hz, 2H), 7.47 (d, J=8.0, 8.0 Hz, 1H), 7.14 (d, J=8.0, 5.6 Hz, 1H), 4.92 (s, 2H), 3.70 (s, 3H).

Example 134H methyl 2-(3-(4-((4-(1-(tetrahydro-2H-pyran-2-yl)-1H-pyrazol-4-yl)phenyl)amino)pyrido[4,3-d]pyrimidin-2-yl)phenoxy)acetate

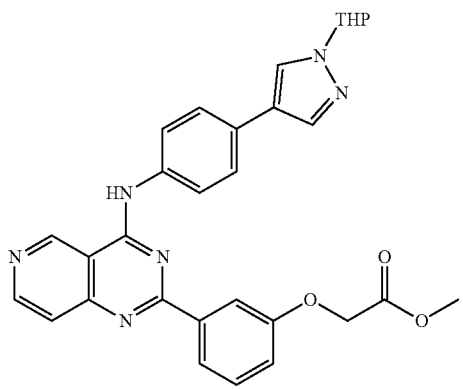

The mixture of methyl 2-(3-(4-((4-bromophenyl)amino)pyrido[4,3-d]pyrimidin-2-yl)phenoxy)acetate (370.00 mg, 795.19 umol), 1-(tetrahydro-2H-pyran-2-yl)-4-(4,4,5,5-tetramethyl-1,3,2-dioxaborolan-2-yl)-1H-pyrazole (287.54 mg, 1.03 mmol), K₂CO₃ (219.81 mg, 1.59 mmol) and Pd(dppf)Cl₂ (116.37 mg, 159.04 umol) in dioxane (10 mL) and H₂O (1 mL) was stirred at 100° C. under N₂ 16 hours. TLC (DCM:MeOH=10:1 Rf=0.46) showed there was a main new spot. The reaction was cooled to room temperature and water (15 mL) was added. The resulting mixture was extracted with EtOAc (30 mL×3). The combined organic layers were washed with brine (20 mL), dried over Na₂SO₄, filtered, concentrated to give the crude product which was purified via silica chromotagraphy (CH₂Cl₂ to CH₂Cl₂:MeOH=20:1) to give the title compound (380.00 mg, purity: 80%) as a yellow solid.

Example 134I 2-(3-(4-((4-(1-(tetrahydro-2H-pyran-2-yl)-1H-pyrazol-4-yl)phenyl)amino)pyrido[4,3-d]pyrimidin-2-yl)phenoxy)acetic acid

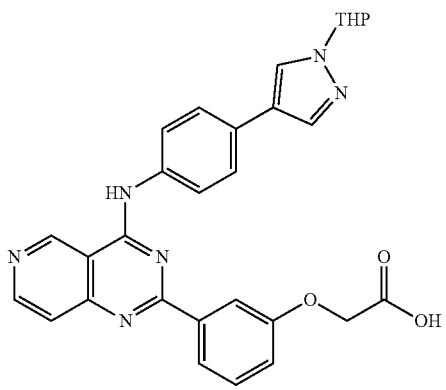

The mixture of methyl 2-(3-(4-((4-(1-(tetrahydro-2H-pyran-2-yl)-1H-pyrazol-4-yl)phenyl)amino)pyrido[4,3-d]pyrimidin-2-yl)phenoxy)acetate (350.00 mg, 652.28 umol) and LiOH (46.87 mg, 1.96 mmol) in THF (5 mL) and H₂O (1 mL) was stirred at 15° C. for 16 hours. LCMS showed the desired product was major. The reaction mixture was concentrated to give a residue. The residue was dispersed in water (10 mL), acidified to pH=5 with 1 N HCl and the resulting yellow solid was filtered, washed with water and dried under azeotropic condition with toluene to give the title compound (180 mg).

Example 134J

N-isopropyl-2-(3-(4-((4-(1-(tetrahydro-2H-pyran-2-yl)-1H-pyrazol-4-yl)phenyl)amino)pyrido[4,3-d]pyrimidin-2-yl)phenoxy)acetamide

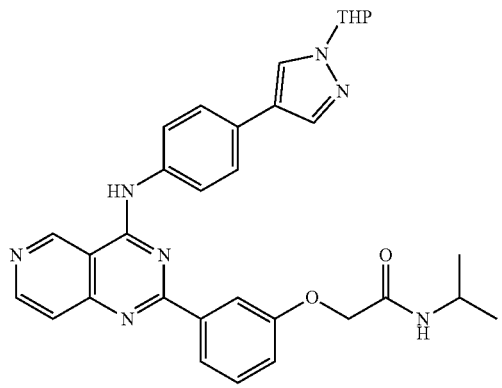

After the solution of 2-(3-(4-((4-(1-(tetrahydro-2H-pyran-2-yl)-1H-pyrazol-4-yl)phenyl)amino)pyrido[4,3-d]pyrimidin-2-yl)phenoxy)acetic acid (100.00 mg, 191.37 umol), HATU (109.15 mg, 287.05 umol) and DIPEA (74.20 mg, 574.11 umol, 100.27 uL) in DMF (1 mL) stirring at 15° C. for 15 minutes, propan-2-amine (22.62 mg, 382.74 umol, 32.79 uL) was added. Then the reaction was stirred at 15° C. for another 15.8 hours. LCMS showed the desired product was the major component. Water (15 mL) was added and the resulting mixture was extracted with EtOAc (20 mL×2). The combined organic layers were washed with brine (15 mL×2), dried over Na₂SO₄, filtered, concentrated to give the title compound (130 mg, crude) as a brown solid which was used in the next step directly.

Example 134K 2-(3-(4-((4-(1H-pyrazol-4-yl)phenyl)amino)pyrido[4,3-d]pyrimidin-2-yl)phenoxy)-N-isopropylacetamide

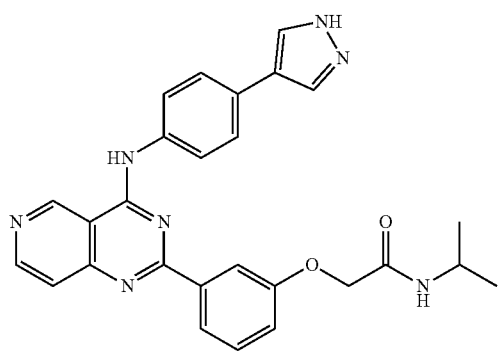 [SMILES: CC(C)NC(=O)COc1cccc(-c2nc(Nc3ccc(-c4cn[nH]c4)cc3)c3cnccc3n2)c1]

To the solution of N-isopropyl-2-(3-(4-((4-(1-(tetrahydro-2H-pyran-2-yl)-1H-pyrazol-4-yl)phenyl)amino)pyrido[4,3-d]pyrimidin-2-yl)phenoxy)acetamide (100.00 mg, 177.42 umol) in CH₂Cl₂ (3.00 mL) was added HCl/dioxane (4 N, 3.00 mL). Then the reaction was stirred at 15° C. for 1 hour. LCMS showed the desired product was major. The reaction mixture was concentrated to give a residue which was basified with 1 M NaOH to pH=10. The resulting mixture was extracted with EtOAc (50 mL×3). The combined organic layers were washed with brine (15 mL), dried over Na₂SO₄, filtered and concentrated to give the crude product which was purified via prep-HPLC (FA conditions) to afford the title compound (28.00 mg, 29%) as a red solid. ¹H NMR (400 MHz, DMSO-d₆) δ 10.40 (s, 1H), 9.88 (s, 1H), 8.81 (d, J=5.6 Hz, 1H), 8.36 (s, 1H), 8.12-8.08 (m, 4H), 8.01-7.96 (m, 3H), 7.76 (d, J=8.0 Hz, 2H), 7.70 (d, J=5.6 Hz, 1H), 7.47 (d, J=8.0, 8.0 Hz, 1H), 7.16 (d, J=8.0, 5.6 Hz, 1H), 4.56 (s, 2H), 4.05-3.96 (m, 1H), 1.11 (d, J=6.4 Hz, 6H). (ES+) m/e 480.1 (M+H)⁺.

Example 135

2-(3-(4-((4-(1H-pyrazol-4-yl)phenyl)amino)pyrido[4,3-d]pyrimidin-2-yl)phenoxy)-N-(tert-butyl)acetamide

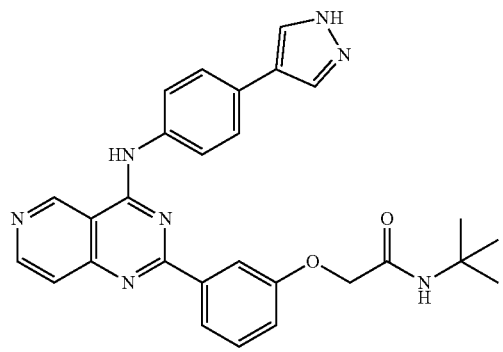 [SMILES: CC(C)(C)NC(=O)COc1cccc(-c2nc(Nc3ccc(-c4cn[nH]c4)cc3)c3cnccc3n2)c1]

The title compound was synthesized using the same procedure as described in Example 134.

¹H NMR (400 MHz, DMSO-d₆) δ 10.69 (s, 1H), 9.87 (s, 1H), 8.81 (d, J=5.6 Hz, 1H), 8.14-8.06 (m, 4H), 7.96 (d, J=8.0 Hz, 2H), 7.76 (d, J=8.0 Hz, 2H), 7.71 (d, J=5.6 Hz, 1H), 7.57 (s, 1H), 7.47 (d, J=8.0, 8.0 Hz, 1H), 7.14 (d, J=8.0, 5.6 Hz, 1H), 4.52 (s, 2H), 1.32 (s, 9H). (ES+) m/e 494.2 (M+H)⁺.

Example 136

2-(3-(4-((4-(1H-pyrazol-4-yl)phenyl)amino)pyrido[3,4-d]pyrimidin-2-yl)phenoxy)-N-(tert-butyl)acetamide

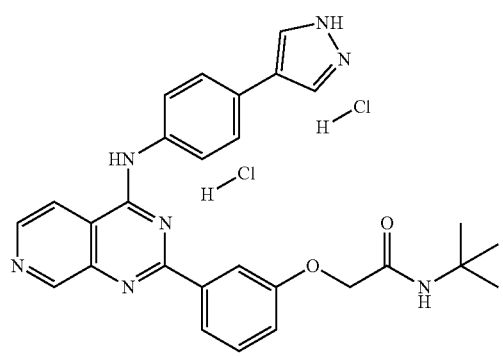

Example 136A pyrido[3,4-d]pyrimidine-2,4-diol

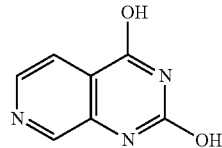

The mixture of 3-aminoisonicotinic acid (4.00 g, 28.96 mmol) in urea (26.09 g, 434.40 mmol, 23.29 mL) was stirred at 175° C. for 3 h. LCMS showed one main peak was detected. The reaction mixture was cooled to 40° C. and the solid was suspended with water (1000 mL). A mixture of light brown solid suspension was stirred at 20° C. for 16 h, filtered and the solid was washed with water (500 mL), dried with toluene to afford the title compound (2.3 g, first batch) as a light yellow solid. $^1$H NMR (400 MHz, DMSO-d$_6$) δ 11.50 (s, 2H), 8.56 (s, 1H), 8.37 (d, J=4.8 Hz, 1H), 7.74 (d, J=5.2 Hz, 1H).

Example 136B 2,4-dichloropyrido[3,4-d]pyrimidine

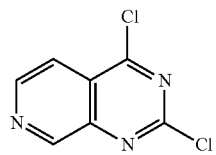 [SMILES: Clc1nc(Cl)c2ccncc2n1]

To the mixture of pyrido[3,4-d]pyrimidine-2,4-diol (1.30 g, 7.97 mmol), POCl$_3$ (14.59 g, 95.13 mmol, 8.84 mL) in toluene (10.00 mL) was added dropwise DIPEA (2.06 g, 15.94 mmol, 2.78 mL). The mixture was stirred under N$_2$ at 15° C. for 64 h. TLC (petroleum:EtOAc=0:1, Rf=0.4) showed one main spot was detected. The reaction mixture was quenched by addition of ice and the mixture was neutralized with sat.NaHCO$_3$ to about pH=7. The mixture was extracted with EtOAc (40 mL×3). The combined organic layers were dried over Na$_2$SO$_4$, filtered and concentrated under reduced pressure to give a residue. The residue was purified by column chromatography (SiO$_2$, petroleum:EtOAc=10:1 to 3:1) to afford the title compound (420 mg, 26%) as a light yellow solid. $^1$H NMR (400 MHz, DMSO-d$_6$) δ 9.02 (m, 1H), 8.70 (d, J=4.8 Hz, 1H), 7.97 (d, J=5.2 Hz, 1H).

Example 136C 2-chloro-N-(4-(1-(tetrahydro-2H-pyran-2-yl)-1H-pyrazol-4-yl)phenyl)pyrido[3,4-d]pyrimidin-4-amine

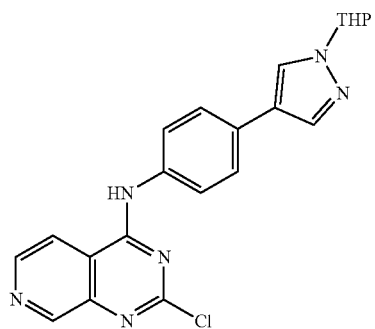

To the mixture of 2,4-dichloropyrido[3,4-d]pyrimidine (420.00 mg, 2.10 mmol) and 4-(1-(tetrahydro-2H-pyran-2-yl)-1H-pyrazol-4-yl)aniline (408.70 mg, 1.68 mmol) in THF (10.00 mL) was added DIPEA (542.75 mg, 4.20 mmol, 733.45 uL). The mixture was stirred under N$_2$ at 15° C. for 16 h. TLC (petroleum:EtOAc=0:1, Rf=0.40) showed one new main spot. The reaction mixture was diluted with water (30 mL) and the mixture was extracted with EtOAc (40 mL×3). The combined organic layers were washed dried over Na$_2$SO$_4$, filtered and concentrated under reduced pressure to give a residue. The residue was purified by recrystallization (petroleum:EtOAc=10:1, 20 mL) to afford the title compound (620.00 mg, 72%) as a yellow solid. $^1$H NMR (400 MHz, DMSO-d$_6$) δ 10.51 (s, 1H), 9.10 (s, 1H), 8.74 (d, J=6.0 Hz, 1H), 8.45 (d, J=5.6 Hz, 1H), 8.37 (s, 1H), 7.98 (s, 1H), 7.81 (d, J=8.4 Hz, 2H), 7.71 (d, J=8.8 Hz, 2H), 5.43-5.41 (m, 1H), 3.97-3.94 (m, 1H), 3.69-3.62 (m, 1H), 2.15-2.12 (m, 1H), 1.99-1.94 (m, 2H), 1.72-1.65 (m, 1H), 1.57-1.56 (m, 2H).

Example 136D 2-(3-(4-((4-(1H-pyrazol-4-yl)phenyl)amino)pyrido[3,4-d]pyrimidin-2-yl)phenoxy)-N-(tert-butyl)acetamide dihydrochloride

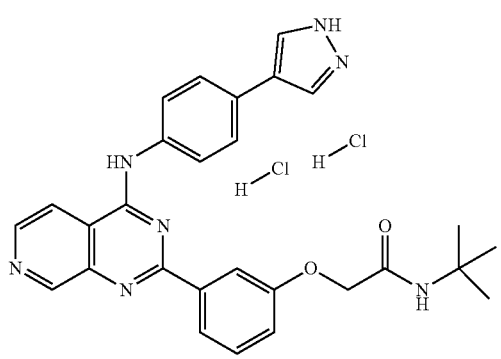

To the mixture of 2-chloro-N-(4-(1-(tetrahydro-2H-pyran-2-yl)-1H-pyrazol-4-yl)phenyl)pyrido[3,4-d]pyrimidin-4-amine (1.00 eq) and N-(tert-butyl)-2-(3-(4,4,5,5-tetramethyl-1,3,2-dioxaborolan-2-yl)phenoxy)acetamide (1.20 eq) in dioxane/H₂O (10:1) was added K₂CO₃ (2.00 eq) and Pd(dppf)Cl₂ (0.10 eq). The mixture was stirred under N₂ at 90° C. for 16 h. The reaction mixture was cooled to room temperature and diluted with water. The resulting mixture was extracted with EtOAc. The combined organic layers were washed with brine, dried over Na₂SO₄, filtered and concentrated under reduced pressure to give a residue. The residue was purified by column chromatography to afford N-(tert-butyl)-2-(3-(4-((4-(1-(tetrahydro-2H-pyran-2-yl)-1H-pyrazol-4-yl)phenyl)amino)pyrido[3,4-d]pyrimidin-2-yl)phenoxy)acetamide.

To the mixture of N-(tert-butyl)-2-(3-(4-((4-(1-(tetrahydro-2H-pyran-2-yl)-1H-pyrazol-4-yl)phenyl)amino)pyrido[3,4-d]pyrimidin-2-yl)phenoxy)acetamide (1.00 eq) in CH₂Cl₂ (5.00 mL) was added HCl/dioxane (4 N, 5.00 mL). The mixture was stirred at 15° C. for 16 h, and then concentrated under reduced pressure to give a residue. The residue was purified by prep-HPLC (FA conditions) to give 2-(3-(4-((4-(1H-pyrazol-4-yl)phenyl)amino)pyrido[3,4-d]pyrimidin-2-yl)phenoxy)-N-(tert-butyl)acetamide.

To the mixture of 2-(3-(4-((4-(1H-pyrazol-4-yl)phenyl)amino)pyrido[3,4-d]pyrimidin-2-yl)phenoxy)-N-(tert-butyl)acetamide (1.00 eq) in THF (or addition of a little MeOH) was added HCl/dioxane (4 A, 5.00 eq). The mixture was stirred at 15° C. for 2 h and solid separated out after the addition of HCl/dioxane. Deion water was added and the resulting mixture was concentrated under reduce pressure to remove the organic solvent. The aqueous layer was lyophilized to give the title compound.

Deep red solid; Yield: 7.5% (3 steps). ¹H NMR (400 MHz, DMSO-d₆) δ 10.89 (s, 1H), 9.43 (s, 1H), 8.80 (d, J=5.6 Hz, 1H), 8.76 (d, J=5.6 Hz, 1H), 8.17 (s, 2H), 8.07-8.05 (m, 2H), 7.99 (d, J=8.4 Hz, 2H), 7.78 (d, J=8.4 Hz, 2H), 7.59 (s, 1H), 7.50 (t, J=8.0 Hz, 1H), 7.19-7.17 (m, 1H), 4.54 (s, 2H), 1.30 (s, 9H). (ES+) m/e 494.2 (M+H)⁺.

Example 137

2-(3-(4-((4-(1H-pyrazol-4-yl)phenyl)amino)pyrido[3,4-d]pyrimidin-2-yl)phenoxy)-N-(pentan-3-yl)acetamide dihydrochloride

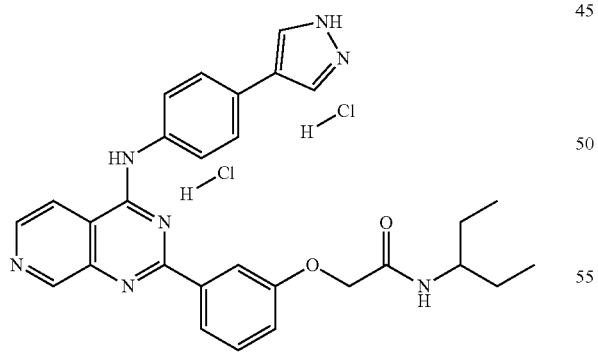

The title compound was synthesized using essentially the same procedure as described in Example 136.

Deep red solid; Yield: 19% (3 steps). ¹H NMR (400 MHz, DMSO-d₆) δ 10.96 (s, 1H), 9.45 (s, 1H), 8.81 (s, 2H), 8.19 (s, 2H), 8.08-8.07 (m, 2H), 7.99 (d, J=8.4 Hz, 2H), 7.83-7.77 (m, 3H), 7.51 (t, J=8.2 Hz, 1H), 7.22-7.19 (m, 1H), 4.64 (s, 2H), 3.65-3.61 (m, 1H), 1.48-1.35 (m, 4H), 0.78 (t, J=7.4 Hz, 6H). (ES+) m/e 508.2 (M+H)⁺.

Example 138

2-(3-(4-((4-(1H-pyrazol-4-yl)phenyl)amino)pyrido[3,4-d]pyrimidin-2-yl)phenoxy)-N-cyclohexylacetamide dihydrochloride

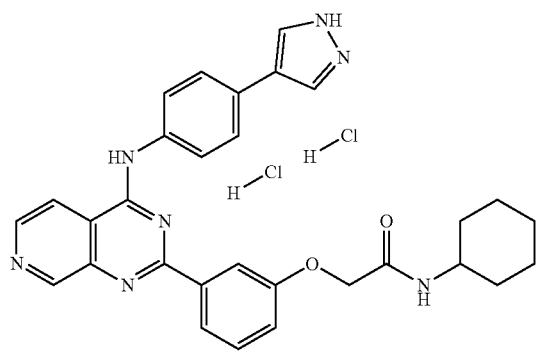

The title compound was synthesized using essentially the same procedure as described in Example 136.

Deep red solid; Yield: 25% (3 steps). ¹H NMR (400 MHz, DMSO-d₆) δ 10.62 (s, 1H), 9.35 (s, 1H), 8.77 (d, J=5.6 Hz, 1H), 8.65 (d, J=5.6 Hz, 1H), 8.15 (s, 2H), 8.09-8.06 (m, 2H), 8.00-7.97 (m, 3H), 7.50 (t, J=8.2 Hz, 1H), 7.19-7.16 (m, 1H), 4.58 (s, 2H), 3.66-3.64 (m, 1H), 1.71-1.67 (m, 4H), 1.56-1.53 (m, 1H), 1.30-1.19 (m, 4H), 1.10 (s, 1H). (ES+) m/e 520.2 (M+H)⁺.

Example 139

2-(3-(4-((4-(1H-pyrazol-4-yl)phenyl)amino)thieno[3,2-d]pyrimidin-2-yl)phenoxy)acetamide

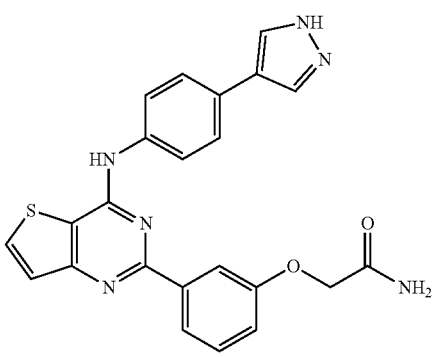 [SMILES: NC(=O)COc1cccc(-c2nc(Nc3ccc(-c4cn[nH]c4)cc3)c3sccc3n2)c1]

Example 139A tert-butyl 2-(3-bromophenoxy)acetate

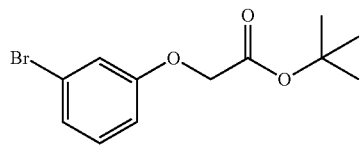 [SMILES: CC(C)(C)OC(=O)COc1cccc(Br)c1]

To a solution of tert-butyl 2-bromoacetate (5.93 g, 30.42 mmol, 4.49 mL) and 3-bromophenol (5.00 g, 28.90 mmol) in MeCN (150.00 mL) was added K$_2$CO$_3$ (8.41 g, 60.84 mmol). The mixture was stirred at 80° C. for 16 hour. LCMS showed one main peak, but no desired mass was detected. TLC (Petroleum ether/Ethyl acetate=5:1, Rf=0.75) showed one main spot. The reaction mixture was cooled to room temperature and diluted with H$_2$O (100 mL). The resulting mixture was extracted with EtOAc (100 mL×2). The combined organic layers were washed with brine (100 mL×2), dried over Na$_2$SO$_4$, filtered and concentrated under reduced pressure to give a residue. The residue was purified by column chromatography (SiO$_2$, Petroleum ether/Ethyl acetate=20/1 to 1:1) to afford the title compound (8 g, 96%) as colorless oil. $^1$H NMR (400 MHz, DMSO-d$_6$) δ 7.25 (t, J=8.0 Hz, 1H), 7.17-7.12 (m, 2H), 6.95 (d, J=8.0 Hz, 1H), 4.71 (s, 2H), 1.42 (s, 9H).

Example 139B tert-butyl 2-(3-(4,4,5,5-tetramethyl-1,3,2-dioxaborolan-2-yl)phenoxy)acetate

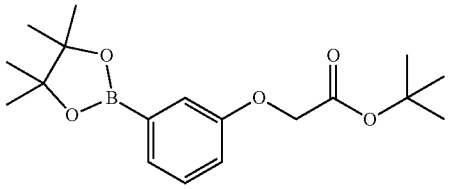 [SMILES: CC(C)(C)OC(=O)COc1cccc(B2OC(C)(C)C(C)(C)O2)c1]

A mixture of tert-butyl 2-(3-bromophenoxy)acetate (1.00 g, 3.48 mmol), B$_2$(pin$_2$) (972.78 mg, 3.83 mmol), AcOK (683.55 mg, 6.96 mmol) and Pd(dppf)Cl$_2$ (254.82 mg, 348.00 umol) in dioxane (20.00 mL) was degassed and purged with N$_2$ 3 times, and then the mixture was stirred at 85° C. for 16 hour under N$_2$ atmosphere. LCMS showed tert-butyl 2-(3-bromophenoxy)acetate was consumed completely and one main peak with desired mass was detected. The reaction mixture was cooled to room temperature and diluted with water (30 mL). The resulting mixture was extracted with EtOAc (30 mL×3). The combined organic layers were washed with brine (30 mL×3), dried over Na$_2$SO$_4$, filtered and concentrated under reduced pressure to give a residue. The residue was purified by column chromatography (SiO$_2$, Petroleum ether/Ethyl acetate=50/1 to 20/1) to afford the title compound (990 mg, 85%) as a white solid. $^1$H NMR (400 MHz, DMSO-d$_6$) δ 7.34-7.26 (m, 2H), 7.10 (d, J=2.8 Hz, 1H), 7.06-7.03 (m, 1H), 4.65 (s, 2H), 1.43 (s, 9H), 1.29 (s, 12H).

Example 139C tert-butyl 2-(3-(4-((4-(1-(tetrahydro-2H-pyran-2-yl)-1H-pyrazol-4-yl)phenyl)amino)thieno[3,2-d]pyrimidin-2-yl)phenoxy)acetate

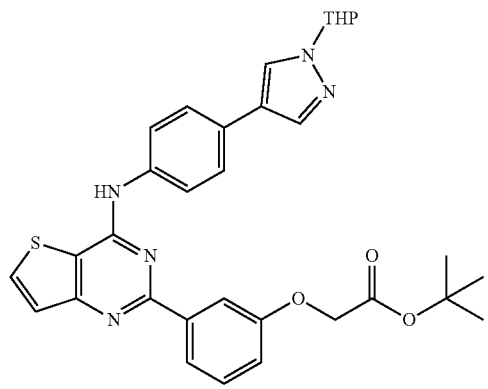

A mixture of 2-chloro-N-(4-(1-(tetrahydro-2H-pyran-2-yl)-1H-pyrazol-4-yl)phenyl)thieno[3,2-d]pyrimidin-4-amine (300.00 mg, 728.31 umol), tert-butyl 2-(3-(4,4,5,5-tetramethyl-1,3,2-dioxaborolan-2-yl)phenoxy)acetate (292.10 mg, 873.97 umol), K$_2$CO$_3$ (201.32 mg, 1.46 mmol) and Pd(dppf)Cl$_2$ (53.29 mg, 72.83 umol) in dioxane (10.00 mL)/H$_2$O (1.00 mL) was degassed and purged with N$_2$ 3 times, then the mixture was stirred at 85° C. for 16 hour under N$_2$ atmosphere. LCMS showed 2-chloro-N-(4-(1-(tetrahydro-2H-pyran-2-yl)-1H-pyrazol-4-yl)phenyl)thieno[3,2-d]pyrimidin-4-amine was consumed and ~77% desired compound was detected. The reaction mixture was cooled to room temperatue and diluted with H$_2$O (20 mL). The resulting mixture was extracted with EtOAc (20 mL×3). The combined organic layers were washed with brine (20 mL×3), dried over Na$_2$SO$_4$, filtered and concentrated under reduced pressure to give a residue. The residue was purified by column chromatography (SiO$_2$, Petroleum ether/Ethyl acetate=5/1 to 2/3) to afford the title compound (990 mg, 85%) as an off-white solid.

Example 139D 2-(3-(4-((4-(1H-pyrazol-4-yl)phenyl)amino)thieno[3,2-d]pyrimidin-2-yl)phenoxy)acetic acid

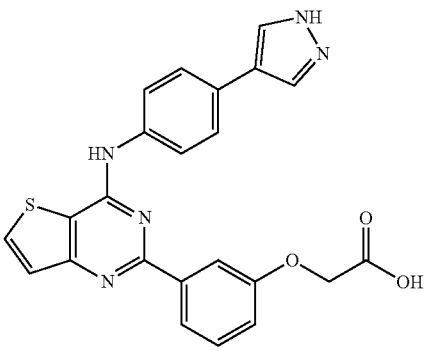 [SMILES: O=C(O)COc1cccc(-c2nc(Nc3ccc(-c4cn[nH]c4)cc3)c3sccc3n2)c1]

To a solution of tert-butyl 2-(3-(4-((4-(1-(tetrahydro-2H-pyran-2-yl)-1H-pyrazol-4-yl)phenyl)amino)thieno[3,2-d]pyrimidin-2-yl)phenoxy)acetate (280.00 mg, 479.70 umol) in CH₂Cl₂ (5.00 mL) was added HCl/dioxane (4 N, 5.00 mL). The mixture was stirred at 20° C. for 16 hour. LCMS showed ~90% peak with methyl ester product was detected. The reaction mixture was concentrated under reduced pressure to give a residue. The residue was added H₂O (3 mL), THF (3 mL) and LiOH.H₂O (~2 eq, 40 mg). The mixture was stirred at 20° C. for 2 h. LCMS showed ~77% desired compound. So the mixture was concentrated under reduced pressure to remove THF. The result mixture was filtered to obtain a yellow solid (150 mg). 50 mg yellow solid was purified by prep-HPLC (FA conditions) to afford the title compound (13.7 mg) as a yellow solid. ¹H NMR (400 MHz, DMSO-d₆) δ 9.80 (s, 1H), 8.26 (d, J=5.2 Hz, 1H), 8.08-8.01 (m, 3H), 7.96 (s, 1H), 7.90 (d, J=8.4 Hz, 2H), 7.70 (d, J=8.4 Hz, 2H), 7.55 (d, J=5.2 Hz, 1H), 7.41 (t, J=8.0 Hz, 1H), 7.03 (d, J=6.0 Hz, 1H), 4.68 (s, 2H). (ES+) m/e 444.0 (M+H)⁺.

Example 139E 2-(3-(4-((4-(1H-pyrazol-4-yl)phenyl)amino)thieno[3,2-d]pyrimidin-2-yl)phenoxy)acetamide

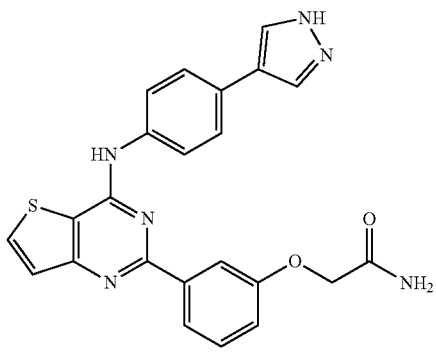 [SMILES: NC(=O)COc1cccc(-c2nc(Nc3ccc(-c4cn[nH]c4)cc3)c3sccc3n2)c1]

To a solution of 2-(3-(4-((4-(1H-pyrazol-4-yl)phenyl)amino)thieno[3,2-d]pyrimidin-2-yl)phenoxy)acetic acid (50.00 mg, 112.74 umol) in DMF (3.00 mL) was added EDCI (28.10 mg, 146.56 umol), DIEA (29.14 mg, 225.48 umol, 39.38 uL), HOBt (30.47 mg, 225.48 umol). The mixture was stirred at 20° C. for 10 min, then NH₃.H₂O (600.00 uL) was added. The mixture was stirred at 20° C. for 16 h. LCMS showed no desired compound was detected. Additional 1 mL NH₃.H₂O was added. The mixture was stirred at 50° C. for another 16 h. LCMS showed ~67% desired compound was detected. The mixture was concentrated under reduced pressure to give a residue. The residue was purified by prep-HPLC (FA conditions) to afford the title compound (21.4 mg) as a yellow solid. ¹H NMR (400 MHz, DMSO-d₆) δ 9.83 (s, 1H), 8.35 (s, 1H), 8.27 (d, J=5.6 Hz, 1H), 8.10-8.04 (m, 4H), 7.91 (d, J=8.8 Hz, 2H), 7.70 (d, J=8.8 Hz, 2H), 7.64 (s, 1H), 7.55 (d, J=5.2 Hz, 1H), 7.45 (t, J=8.4 Hz, 2H), 7.11-7.08 (m, 1H), 4.55 (s, 2H). (ES+) m/e 443.1 (M+H)⁺.

Example 140

2-(3-(4-((4-(1H-pyrazol-4-yl)phenyl)amino)-6-acetyl-6,7-dihydro-5H-pyrrolo[3,4-d]pyrimidin-2-yl)phenoxy)-N-isopropylacetamide

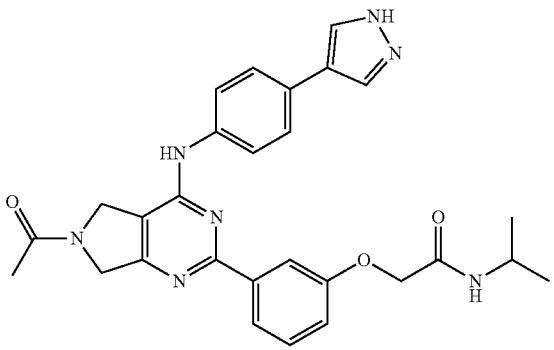 [SMILES: CC(=O)N1Cc2nc(-c3cccc(OCC(=O)NC(C)C)c3)nc(Nc3ccc(-c4cn[nH]c4)cc3)c2C1]

Example 140A 2,4-dichloro-6,7-dihydro-5H-pyrrolo[3,4-d]pyrimidine

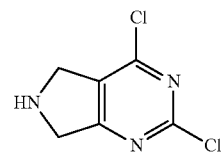 [SMILES: Clc1nc(Cl)c2c(n1)CNC2]

The mixture of tert-butyl 2,4-dichloro-5,7-dihydro-6H-pyrrolo[3,4-d]pyrimidine-6-carboxylate (2.00 g, 6.89 mmol) in CH₂Cl₂ (15.00 mL) was added HCl/dioxane (4 N, 10.00 mL). The mxiture was stirred at 15° C. for 2 h. LCMS showed one peak of desired product was detected. The mixture was concentrated under reduced pressure to afford the title compound (2.10 g, crude, HCl salt) as a light yellow solid which was used into next step without further purification.

Example 140B 1-(2,4-dichloro-5,7-dihydro-6H-pyrrolo[3,4-d]pyrimidin-6-yl)ethan-1-one

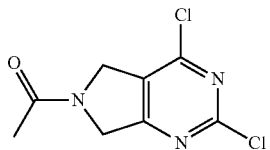

To the mixture of 2,4-dichloro-6,7-dihydro-5H-pyrrolo[3,4-d]pyrimidine (2.10 g, 9.27 mmol, HCl salt) in CH₂Cl₂ (30.00 mL) was added dropwise TEA (2.81 g, 27.81 mmol, 3.85 mL) at 0° C. The mixture was stirred at 0° C. for 5 min. Then to the mixture was added dropwise acetyl chloride (873.42 mg, 11.13 mmol, 794.01 uL) at 0° C. The mixture was stirred under N₂ at 0° C. for 1.5 h. TLC (petroleum ether/EtOAc=1:1, Rf=0.35) showed that one new main spot was detected. The mixture was diluted with CH$_2$Cl$_2$ (30 mL) and washed with water (30 mL×2), citric acid (10%, 30 mL×3), sat.NaHCO$_3$ (30 mL×2), brine (30 mL×2). The organic layer was dried over Na$_2$SO$_4$, filtered and concentrated under reduced pressure to give a residue. The residue was purified by column chromatography (SiO$_2$, petroleum ether/EtOAc=40:1 to 0:1) to afford the title compound (1.1 g, 51%) as a light yellow solid. $^1$H NMR (400 MHz, DMSO-d6) δ 4.96 (s, 1H), 4.91 (s, 1H), 4.68 (s, 1H), 4.62 (s, 1H), 2.09-2.07 (m, 3H).

Example 140C 1-(2-chloro-4-((4-(1-(tetrahydro-2H-pyran-2-yl)-1H-pyrazol-4-yl)phenyl)amino)-5,7-dihydro-6H-pyrrolo[3,4-d]pyrimidin-6-yl)ethan-1-one

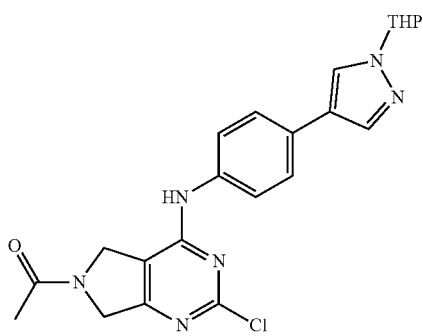

To the mixture of 1-(2,4-dichloro-5,7-dihydro-6H-pyrrolo[3,4-d]pyrimidin-6-yl)ethan-1-one (1.10 g, 4.74 mmol) and 4-(1-(tetrahydro-2H-pyran-2-yl)-1H-pyrazol-4-yl)aniline (980.25 mg, 4.03 mmol) in n-BuOH (10.00 mL) was added DIPEA (1.84 g, 14.22 mmol, 2.48 mL). The mixture was stirred under N$_2$ at 100° C. for 16 h. The mixture was cooled to room temperature and filtered. The solid was washed with petroleum ether/EtOAc=8:1 (60 mL) and dried over under vacuum to give the title compound (1.5 g, 72%) as brownish yellow solid. $^1$H NMR (400 MHz, DMSO-d$_6$) δ 8.57 (m, 1H), 8.31 (s, 1H), 7.93 (s, 1H), 7.69-7.61 (m, 4H), 5.40 (d, J=8.0 Hz, 1H), 4.73 (s, 2H), 4.53-4.47 (m, 2H), 3.96-3.93 (m, 1H), 3.68-3.62 (m, 1H), 2.14-2.06 (m, 4H), 1.96-1.94 (m, 2H), 1.57-1.52 (m, 3H).

Example 140D 2-(3-(4-((4-(1H-pyrazol-4-yl)phenyl)amino)-6-acetyl-6,7-dihydro-5H-pyrrolo[3,4-d]pyrimidin-2-yl)phenoxy)-N-isopropylacetamide

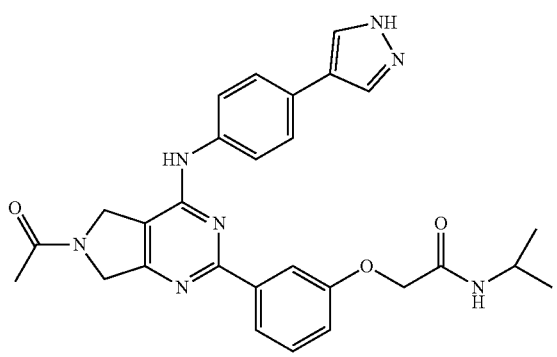 [SMILES: CC(=O)N1Cc2nc(-c3cccc(OCC(=O)NC(C)C)c3)nc(Nc3ccc(-c4cn[nH]c4)cc3)c2C1]

To the mixture of 1-(2-chloro-4-((4-(1-(tetrahydro-2H-pyran-2-yl)-1H-pyrazol-4-yl)phenyl)amino)-5,7-dihydro-6H-pyrrolo[3,4-d]pyrimidin-6-yl)ethan-1-one (1.00 eq) and N-isopropyl-2-(3-(4,4,5,5-tetramethyl-1,3,2-dioxaborolan-2-yl)phenoxy)acetamide (1.20 eq) in dioxane (5.00 mL), H$_2$O (500.00 uL) was added K$_2$CO$_3$ (2.00 eq), Pd(dppf)Cl$_2$ (0.10 eq). The mixture was stirred under N$_2$ at 90° C. for 16 h. The reaction mixture was cooled to room temperature and diluted with water. The resulting mixture was extracted with CH$_2$Cl$_2$. The combined organic layers were washed with brine, dried over Na$_2$SO$_4$, filtered and concentrated under reduced pressure to give a residue. The residue was purified by column chromatography or recrystallization to afford 2-(3-(6-acetyl-4-((4-(1-(tetrahydro-2H-pyran-2-yl)-1H-pyrazol-4-yl)phenyl)amino)-6,7-dihydro-5H-pyrrolo[3,4-d]pyrimidin-2-yl)phenoxy)-N-isopropylacetamide.

To the mixture of 2-(3-(6-acetyl-4-((4-(1-(tetrahydro-2H-pyran-2-yl)-1H-pyrazol-4-yl)phenyl)amino)-6,7-dihydro-5H-pyrrolo[3,4-d]pyrimidin-2-yl)phenoxy)-N-isopropylacetamide (1.00 eq) in CH$_2$Cl$_2$ (5.00 mL) was added HCl/dioxane (4 N, 5.00 mL). The mixture was stirred at 15° C. for 2-16 h. The mixture was concentrated under reduced pressure to give a residue. The residue was purified by prep-HPLC (FA conditions) to give the title compound.

Off-white solid; Yield: 5% (2 steps). $^1$H NMR (400 MHz, DMSO-d$_6$) δ 12.93 (s, 1H), 9.26 (d, J=14.4 Hz, 1H), 8.46 (s, 1H), 8.16-7.93 (m, 5H), 7.86 (t, J=8.8 Hz, 2H), 7.68-7.63 (m, 2H), 7.46-7.40 (m, 1H), 7.10 (dt, J=8.0, 1.2 Hz, 1H), 4.82 (d, J=8.0 Hz, 2H), 4.63 (s, 1H) 4.57-4.49 (m, 3H), 4.01-3.94 (m, 1H), 2.13-2.09 (m, 3H), 1.09 (d, J=6.4 Hz, 6H). (ES+) m/e 512.2 (M+H)$^+$.

Example 141

2-(3-(4-((4-(1H-pyrazol-4-yl)phenyl)amino)-6-acetyl-6,7-dihydro-5H-pyrrolo[3,4-d]pyrimidin-2-yl)phenoxy)-N-(pentan-3-yl)acetamide

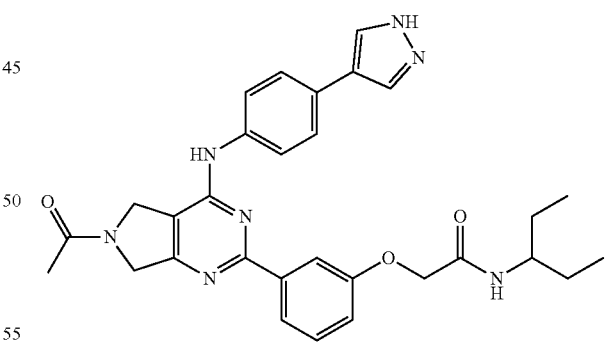

The title compound was synthesized using essentially the same procedure as described in Example 140.

Off-white solid; Yield: 40% (2 steps). $^1$H NMR (400 MHz, DMSO-d$_6$) δ 12.92 (s, 1H), 9.30-9.20 (m, 1H), 8.25-7.91 (m, 4H), 7.85 (t, J=8.4 Hz, 2H), 7.79-7.71 (m, 1H), 7.66 (dd, J=8.8, 5.2 Hz, 2H), 7.43 (dt, J=8.2, 2.8 Hz, 1H), 7.10 (d, J=8.2 Hz, 1H), 4.82 (d, J=9.6 Hz, 2H), 4.68-4.48 (m, 4H), 3.70-3.55 (m, 1H), 2.11 (d, J=7.2 Hz, 3H), 1.53-1.29 (m, 4H), 0.78 (t, J=7.2 Hz, 6H). $^1$H NMR (400 MHz, DMSO-d$_6$) (ES+) m/e 540.2 (M+H)$^+$.

Example 142

2-(3-(4-((4-(1H-pyrazol-4-yl)phenyl)amino)-6-acetyl-6,7-dihydro-5H-pyrrolo[3,4-d]pyrimidin-2-yl)phenoxy)-N-(tert-butyl)acetamide

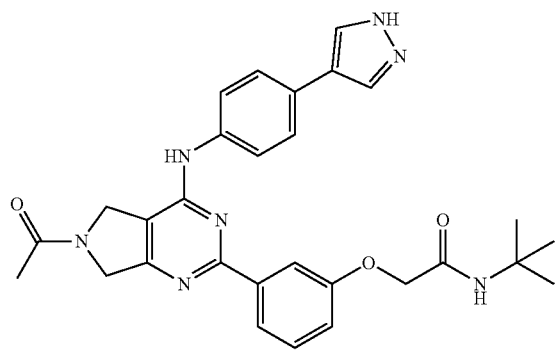 [SMILES: CC(=O)N1Cc2nc(-c3cccc(OCC(=O)NC(C)(C)C)c3)nc(Nc3ccc(-c4cn[nH]c4)cc3)c2C1]

The title compound was synthesized using essentially the same procedure as described in Example 140.

Off-white solid; Yield: 15% (2 steps). $^1$H NMR (400 MHz, DMSO-$d_6$) δ 12.89 (s, 1H), 9.30-9.21 (m, 1H), 8.14-7.90 (m, 4H), 7.90-7.81 (m, 2H), 7.65 (dd, J=8.4, 4.8 Hz, 2H), 7.53 (d, J=12.8 Hz, 1H), 7.42 (dt, J=8.0, 3.2 Hz, 1H), 7.07 (d, J=8.4 Hz, 1H), 4.87-4.77 (m, 2H), 4.66-4.47 (m, 4H), 2.15-2.07 (m, 3H), 1.30 (s, 9H). (ES+) m/e 526.2 (M+H)$^+$.

Example 143

2-(3-(4-((4-(1H-pyrazol-4-yl)phenyl)amino)-6-acetyl-6,7-dihydro-5H-pyrrolo[3,4-d]pyrimidin-2-yl)phenoxy)-N-cyclopentylacetamide

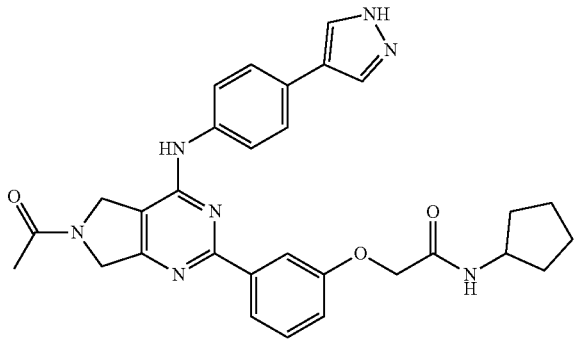 [SMILES: CC(=O)N1Cc2nc(-c3cccc(OCC(=O)NC4CCCC4)c3)nc(Nc3ccc(-c4cn[nH]c4)cc3)c2C1]

The title compound was synthesized using essentially the same procedure as described in Example 140.

Earth yellow solid; Yield: 20% (2 steps). $^1$H NMR (400 MHz, DMSO-$d_6$) δ 9.04 (s, 1H), 8.49 (s, 1H), 8.05-7.91 (m, 4H), 7.87-7.8 (m, 2H), 7.70-7.59 (m, 3H), 7.42 (t, J=8.2 Hz, 1H), 7.13-7.07 (m, 1H), 4.82 (d, J=14.0 Hz, 2H), 4.66 (s, 1H), 4.59-4.50 (m, 3H), 4.17-4.09 (m, 1H), 2.16-2.08 (m, 3H), 1.89-1.79 (m, 2H), 1.69-1.60 (m, 2H), 1.56-1.42 (m, 4H). (ES+) m/e 538.2 (M+H)$^+$.

Example 144

2-(3-(4-((4-(1H-pyrazol-4-yl)phenyl)amino)-6-acetyl-5,6,7,8-tetrahydropyrido[4,3-d]pyrimidin-2-yl)phenoxy)-N-(tert-butyl)acetamide

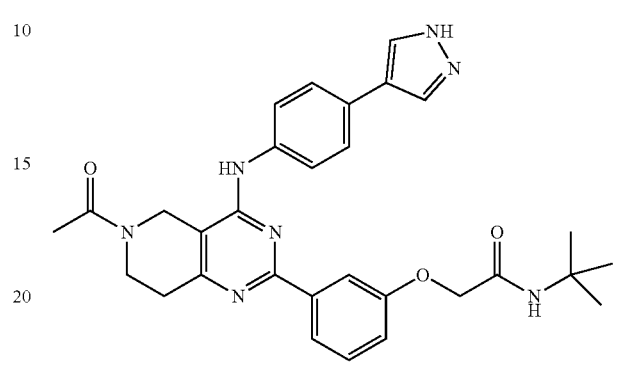

Example 144A 2,4-dichloro-5,6,7,8-tetrahydropyrido[4,3-d]pyrimidine

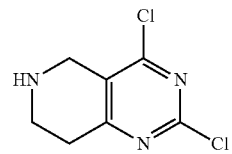 [SMILES: Clc1nc(Cl)c2c(n1)CCNC2]

To the mixture of tert-butyl 2,4-dichloro-7,8-dihydropyrido[4,3-d]pyrimidine-6(5H)-carboxylate (4.00 g, 13.15 mmol) in CH$_2$Cl$_2$ (15.00 mL) was added HCl/dioxane (4 N, 15.00 mL). The mixture was stirred at 15° C. for 15 h. LCMS showed one main peak of desired product and about 5% of starting material. The mixture was stirred at 30° C. for 1 h. LCMS showed desired product was major. The mixture was concentrated under reduced pressure to afford the title compound (3.07 g, crude, HCl salt) as a white solid which was used in the next step without further purification.

Example 144B 1-(2,4-dichloro-7,8-dihydropyrido[4,3-d]pyrimidin-6(5H)-yl)ethan-1-one

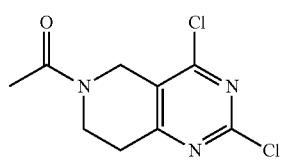

To the mixture of 2,4-dichloro-5,6,7,8-tetrahydropyrido[4,3-d]pyrimidine (1.10 g, 4.57 mmol, HCl) in CH₂Cl₂ (30.00 mL) was added dropwise TEA (1.39 g, 13.71 mmol, 1.90 mL) at 0° C. The mixture was stirred at 0° C. for 5 min. Then to the mixture was added dropwise acetyl chloride (430.82 mg, 5.48 mmol, 391.65 uL) at 0° C. The mixture was stirred under N₂ at 0° C. for 2 hour. TLC (petroleum ether/EtOAc=1:1, Rf=0.3) showed one main spot. The mixture was diluted with CH₂Cl₂ (30 mL) and washed with water (30 mL×2), citric acid (10%, 30 mL×2), sat.NaHCO₃ (30 mL×2), brine (30 mL×2). The organic layer was dried over Na₂SO₄, filtered and concentrated under reduced pressure to give the title compound (960 mg, crude) as a light brown solid which was used in the next step without further purification. ¹H NMR (400 MHz, DMSO-d₆) δ 4.59-4.58 (m, 2H), 3.78-3.75 (m, 2H), 3.01-2.83 (m, 2H), 2.13 (s, 3H).

Example 144C 1-(2-chloro-4-((4-(1-(tetrahydro-2H-pyran-2-yl)-1H-pyrazol-4-yl)phenyl)amino)-7,8-dihydropyrido[4,3-d]pyrimidin-6(5H)-yl)ethan-1-one

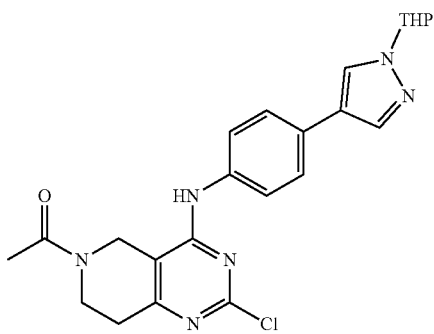

To the mixture of 1-(2,4-dichloro-7,8-dihydropyrido[4,3-d]pyrimidin-6(5H)-yl)ethan-1-one (960.00 mg, 3.90 mmol) and 4-(1-(tetrahydro-2H-pyran-2-yl)-1H-pyrazol-4-yl)aniline (901.43 mg, 3.70 mmol) in n-BuOH (15.00 mL) was added DIPEA (1.01 g, 7.80 mmol, 1.36 mL). The mixture was stirred at 100° C. for 16 h. TLC (petroleum ether/EtOAc=1:1) showed pyrimidine starting material (Rf=0.2) and 4-(1-(tetrahydro-2H-pyran-2-yl)-1H-pyrazol-4-yl)aniline (Rf=0.68) were still present and one main new spot (Rf=0.11) was observed. The mixture was stirred under N₂ at 100° C. for 20 h. TLC (petroleum ether/EtOAc=0:1) showed 1-(2,4-dichloro-7,8-dihydropyrido[4,3-d]pyrimidin-6(5H)-yl)ethan-1-one was consumed completely and one main new spot (Rf=0.3) was detected. The mixture was cooled to room temperature and filtered to collect solid. The solid was washed with petroleum ether/EtOAc=10:1 (20 mL) dried over under vacuum to give the title compound (900 mg) as a yellow solid. ¹H NMR (400 MHz, DMSO-d₆) δ 9.04-8.90 (m, 1H), 8.33-8.31 (s, 1H), 7.94-7.93 (m, 1H), 7.65-7.55 (m, 4H), 5.40 (d, J=9.6 Hz, 1H), 4.53-4.52 (m, 2H), 3.96-3.94 (m, 1H), 3.75-3.72 (m, 2H), 3.68-3.64 (m, 1H), 2.81-2.66 (m, 2H), 2.16-2.11 (m, 4H), 1.96-1.94 (m, 2H), 1.57-1.55 (m, 3H).

Example 144D 2-(3-(4-((4-(1H-pyrazol-4-yl)phenyl)amino)-6-acetyl-5,6,7,8-tetrahydropyrido[4,3-d]pyrimidin-2-yl)phenoxy)-N-(tert-butyl)acetamide

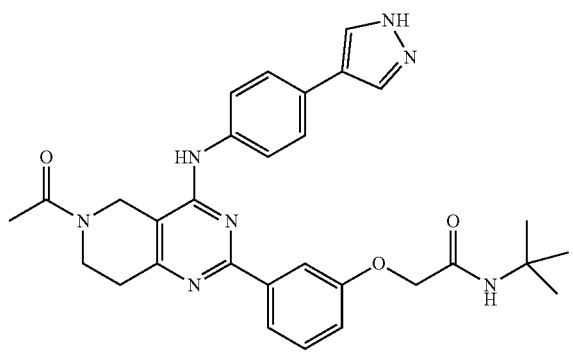 [SMILES: CC(=O)N1CCc2nc(-c3cccc(OCC(=O)NC(C)(C)C)c3)nc(Nc3ccc(-c4cn[nH]c4)cc3)c2C1]

To the mixture of 1-(2-chloro-4-((4-(1-(tetrahydro-2H-pyran-2-yl)-1H-pyrazol-4-yl)phenyl)amino)-7,8-dihydropyrido[4,3-d]pyrimidin-6(5H)-yl)ethan-1-one (1.00 eq) and N-(tert-butyl)-2-(3-(4,4,5,5-tetramethyl-1,3,2-dioxaborolan-2-yl)phenoxy)acetamide (1.20 eq) in dioxane/H₂O (10:1) was added K₂CO₃ (2.00 eq), Pd(dppf)Cl₂ (0.10 eq). The mixture was stirred under N₂ at 90° C. for 16 h. The reaction mixture was cooled to room temperature and diluted with water. The resulting mixture was extracted with EtOAc. The combined organic layers were washed with brine, dried over Na₂SO₄, filtered and concentrated under reduced pressure to give a residue. The residue was purified by column chromatography to afford 2-(3-(6-acetyl-4-((4-(1-(tetrahydro-2H-pyran-2-yl)-1H-pyrazol-4-yl)phenyl)amino)-5,6,7,8-tetrahydropyrido[4,3-d]pyrimidin-2-yl)phenoxy)-N-(tert-butyl)acetamide.

To the mixture of 2-(3-(6-acetyl-4-((4-(1-(tetrahydro-2H-pyran-2-yl)-1H-pyrazol-4-yl)phenyl)amino)-5,6,7,8-tetrahydropyrido[4,3-d]pyrimidin-2-yl)phenoxy)-N-(tert-butyl)acetamide (1.00 eq) in CH₂Cl₂ (5.00-10.00 mL) was added HCl/dioxane (4 N, 5.00-10.00 mL). The mixture was stirred at 20° C. for 2-16 h. The mixture was concentrated under reduced pressure to give a residue. The residue was purified prep-HPLC (FA conditions) to give the title compound.

Light yellow solid; Yield: 11% (2 steps). ¹H NMR (400 MHz, DMSO-d₆) δ 8.74 (s, 1H), 8.61 (s, 1H), 8.45 (s, 1H), 8.05-7.87 (m, 4H), 7.77 (dd, J=8.8 Hz, 8.8 Hz, 2H), 7.67-7.62 (m, 2H), 7.52 (d, J=3.6 Hz, 1H), 7.38 (dd, J=8.0 Hz, 8.0 Hz, 1H), 7.04-7.02 (dd, J=8.4 Hz, 2.4 Hz, 1H), 4.62 (s, 2H), 4.46 (s, 2H), 3.79 (t, J=5.6 Hz, 2H), 2.90-2.76 (m, 2H), 2.18 (d, J=9.6 Hz, 3H), 1.29 (s, 9H). (ES+) m/e 540.2 (M+H)⁺.

Example 145

2-(3-(4-((4-(1H-pyrazol-4-yl)phenyl)amino)-6-acetyl-5,6,7,8-tetrahydropyrido[4,3-d]pyrimidin-2-yl)phenoxy)-N-cyclopentylacetamide

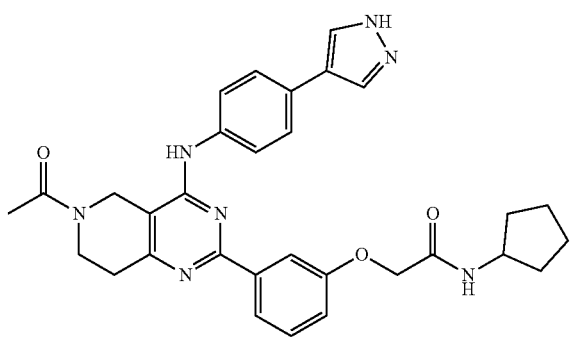 [SMILES: CC(=O)N1CCc2nc(-c3cccc(OCC(=O)NC4CCCC4)c3)nc(Nc3ccc(-c4cn[nH]c4)cc3)c2C1]

The title compound was synthesized using the same procedure as described in Example 144.

Light yellow solid; Yield: 11% (2 steps). ¹H NMR (400 MHz, DMSO-d₆) δ 8.80-8.58 (m, 1H), 8.42 (s, 1H), 8.13-7.98 (m, 3H), 7.93-7.87 (m, 2H), 7.82-7.73 (m, 2H), 7.69-7.60 (m, 2H), 7.39 (t, J=8.2 Hz, 1H), 7.08-7.03 (m, 1H), 4.62 (s, 2H), 4.51 (s, 2H), 4.10 (d, J=14.0, 7.2 Hz, 1H), 3.80 (t, J=5.2 Hz, 2H), 2.95-2.72 (m, 2H), 2.23-2.14 (m, 3H), 1.88-1.74 (m, 2H), 1.68-1.56 (m, 2H), 1.54-1.38 (m, 4H). (ES+) m/e 552.3 (M+H)⁺.

Example 146

2-(3-(4-((4-(1H-pyrazol-4-yl)phenyl)amino)-6-acetyl-5,6,7,8-tetrahydropyrido[4,3-d]pyrimidin-2-yl)phenoxy)-N-isobutylacetamide

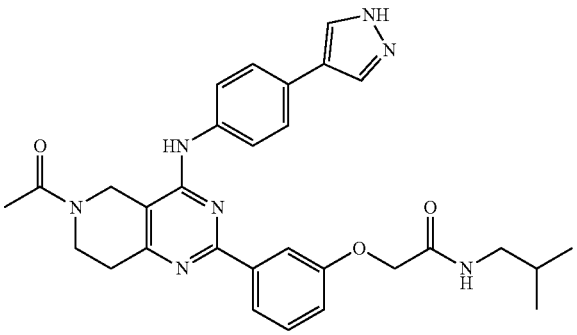 [SMILES: CC(=O)N1CCc2nc(-c3cccc(OCC(=O)NCC(C)C)c3)nc(Nc3ccc(-c4cn[nH]c4)cc3)c2C1]

The title compound was synthesized using the same procedure as described in Example 144.

Light yellow solid; Yield: 9.9% (2 steps). ¹H NMR (400 MHz, DMSO-d₆) δ 8.76-8.65 (m, 1H), 8.39 (s, 1H), 8.14 (t, J=5.6 Hz, 1H), 8.06 (s, 2H), 7.92 (d, J=6.8 Hz, 2H), 7.78 (t, J=8.8 Hz, 2H), 7.69-7.63 (m, 2H), 7.40 (t, J=8.0 Hz, 1H), 7.08-7.05 (m, 1H), 4.63 (s, 2H), 4.56 (s, 2H), 3.80 (t, J=5.2 Hz, 2H), 2.96 (t, J=6.8 Hz, 2H), 2.92-2.76 (m, 2H), 2.19 (d, J=10.0 Hz, 3H), 1.75-1.72 (m, 1H), 0.80 (d, J=6.4 Hz, 6H). (ES+) m/e 540.3 (M+H)⁺.

Example 147

2-(3-(4-((4-(1H-pyrazol-4-yl)phenyl)amino)-6-acetyl-5,6,7,8-tetrahydropyrido[4,3-d]pyrimidin-2-yl)phenoxy)-N-neopentylacetamide

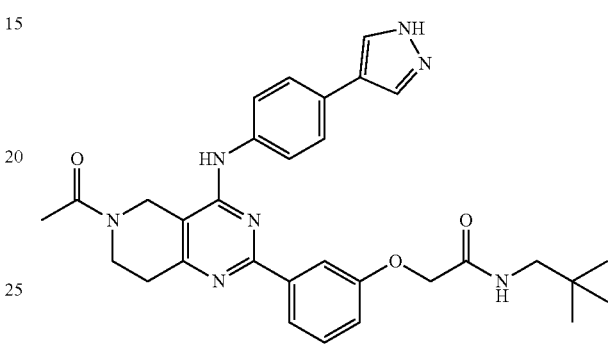

The title compound was synthesized using the same procedure as described in Example 144.

Yellow solid; Yield: 18% (2 steps). ¹H NMR (400 MHz, DMSO-d₆) δ 8.76-8.60 (m, 1H), 8.42 (s, 1H), 8.12-7.89 (m, 5H), 7.81-7.73 (m, 2H), 7.69-7.61 (m, 2H), 7.39 (t, J=8.0 Hz, 1H), 7.06 (dd, J=8.0, 1.6 Hz, 1H), 4.64-4.57 (m, 4H), 3.80 (t, J=5.2 Hz, 2H), 2.95 (d, J=6.40 Hz, 2H), 2.92-2.75 (m, 2H), 2.21-2.15 (m, 3H), 0.79 (s, 9H). (ES+) m/e 554.2 (M+H)⁺.

Example 148

2-(3-(4-((4-(1H-pyrazol-4-yl)phenyl)amino)-6-acetyl-5,6,7,8-tetrahydropyrido[4,3-d]pyrimidin-2-yl)phenoxy)-N-(tert-pentyl)acetamide

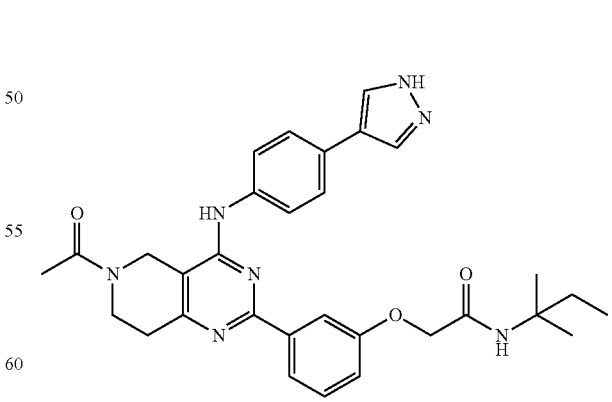

The title compound was synthesized using the same procedure as described in Example 144.

White solid; Yield: 7.7% (2 steps). ¹H NMR (400 MHz, DMSO-d₆) δ 12.90 (s, 1H), 8.73-8.59 (m, 1H), 8.05 (s, 1H), 7.91-7.87 (m, 2H), 7.79 (d, J=8.4 Hz, 1H), 7.76 (d, J=8.8 Hz, 1H), 7.68-7.62 (m, 2H), 7.38 (t, J=8.0 Hz, 1H), 7.33-7.32 (m, 1H), 7.05-7.02 (m, 1H), 4.62-4.48 (m, 2H), 3.80 (t, J=5.6 Hz, 2H), 2.92-2.77 (m, 2H), 2.19-2.17 (m, 3H), 1.69-1.63 (m, 2H), 1.23 (s, 6H), 0.75 (t, J=7.6 Hz, 3H). (ES+) m/e 554.1 (M+H)⁺.

Example 149

2-(3-(4-((4-(1H-pyrazol-4-yl)phenyl)amino)-6-isobutyryl-5,6,7,8-tetrahydropyrido[4,3-d]pyrimidin-2-yl)phenoxy)-N-isopropylacetamide

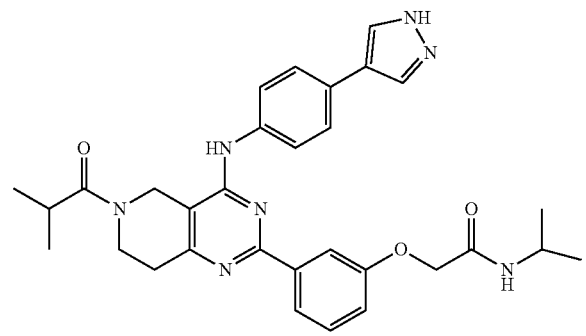 [SMILES: CC(C)NC(=O)COc1cccc(-c2nc3c(c(Nc4ccc(-c5cn[nH]c5)cc4)n2)CN(C(=O)C(C)C)CC3)c1]

Example 149A 1-(2,4-dichloro-7,8-dihydropyrido[4,3-d]pyrimidin-6 (5H)-yl)-2-methylpropan-1-one

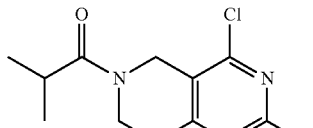

To the mixture of 2,4-dichloro-5,6,7,8-tetrahydropyrido[4,3-d]pyrimidine (2.20 g, 9.15 mmol, HCl salt) in CH₂Cl₂ (30.00 mL) was added dropwise TEA (2.78 g, 27.45 mmol, 3.81 mL) at 0° C. Then the mixture was stirred under N₂ at 0° C. for 5 min. To the mixture was added 2-methylpropanoyl chloride (1.17 g, 10.98 mmol, 1.15 mL) at 0° C. The mixture was stirred under N₂ at 0° C. for 2 h. LCMS showed one main peak of desired product. TLC (petroleum ether/EtOAc=1:1, Rf=0.6) showed one new main spot. The mixture was diluted with CH₂Cl₂ (40 mL) and washed with water (40 mL×2), citric acid (10%, 40 mL×3), sat.NaHCO₃ (40 mL×2), brine (40 mL). The organic layer was dried over Na₂SO₄, filtered and concentrated under reduced pressure to afford the title compund (2.50 g, crude) as a light yellow solid which was used in the next step without further purification. ¹H NMR (400 MHz, DMSO-d₆) δ 4.67-4.59 (m, 2H), 3.85-3.79 (m, 2H), 3.03-2.99 (m, 2H), 2.89-2.85 (m, 1H), 1.04 (d, J=6.4 Hz, 6H).

Example 149B 1-(2-chloro-4-((4-(1-(tetrahydro-2H-pyran-2-yl)-1H-pyrazol-4-yl)phenyl)amino)-7,8-dihydropyrido[4,3-d]pyrimidin-6(5H)-yl)-2-methylpropan-1-one

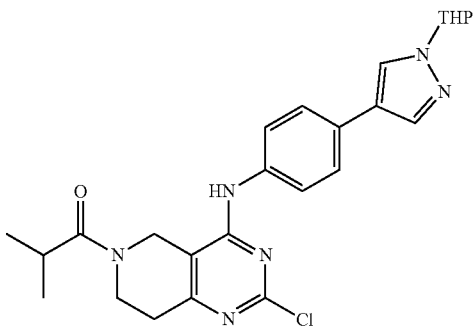

To the mixture of 1-(2,4-dichloro-7,8-dihydropyrido[4,3-d]pyrimidin-6(5H)-yl)-2-methylpropan-1-one (2.50 g, 9.12 mmol) and 4-(1-(tetrahydro-2H-pyran-2-yl)-1H-pyrazol-4-yl)aniline (2.00 g, 8.21 mmol) in n-BuOH (20.00 mL) was added DIPEA (2.36 g, 18.24 mmol, 3.19 mL). The mixture was stirred under N₂ at 100° C. for 16 h. LCMS showed one main peak of desired product. TLC (petroleum ether/EtOAc=1:1, Rf=0.2) showed that one new main spot was detected. The reaction mixture was cooled to room temperature and diluted with water (30 mL). The resulting mixture was extracted with EtOAc (40 mL×3). The combined organic layers were washed with brine (50 mL), dried over Na₂SO₄, filtered and concentrated under reduced pressure to give a residue which was purified by column chromatography (SiO₂, petroleum ether/EtOAc=100:1 to 0:1) to give the title compound (2.8 g, 64%) as a light yellow solid. ¹H NMR (400 MHz, DMSO-d₆) δ 9.06-8.93 (m, 1H), 8.32 (s, 1H), 7.94 (s, 1H), 7.63-7.55 (m, 4H), 5.41 (d, J=8.8 Hz, 1H), 4.58-4.54 (m, 2H), 3.96-3.93 (m, 1H), 3.81-3.76 (m, 2H), 3.68-3.62 (m, 1H), 3.06-3.00 (m, 1H), 2.78-2.66 (m, 2H), 2.16-2.08 (m, 1H), 1.96-1.94 (m, 2H), 1.70-1.67 (m, 1H), 1.50 (s, 2H), 1.05 (d, J=6.4 Hz, 6H).

Example 149C 2-(3-(4-((4-(1H-pyrazol-4-yl)phenyl)amino)-6-isobutyryl-5,6,7,8-tetrahydropyrido[4,3-d]pyrimidin-2-yl)phenoxy)-N-isopropylacetamide

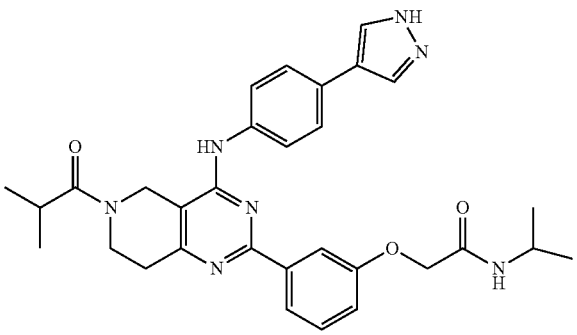 [SMILES: CC(C)NC(=O)COc1cccc(-c2nc3c(c(Nc4ccc(-c5cn[nH]c5)cc4)n2)CN(C(=O)C(C)C)CC3)c1]

To the mixture of 1-(2-chloro-4-((4-(1-(tetrahydro-2H-pyran-2-yl)-1H-pyrazol-4-yl)phenyl)amino)-7,8-dihydropyrido[4,3-d]pyrimidin-6(5H)-yl)-2-methylpropan-1-one (1.00 eq) and N-isopropyl-2-(3-(4,4,5,5-tetramethyl-1,3,2-dioxaborolan-2-yl)phenoxy)acetamide (1.20 eq) in dioxane/H$_2$O (10:1) was added K$_2$CO$_3$ (2.00 eq), Pd(dppf)Cl$_2$ (0.10 eq). The mixture was stirred under N$_2$ at 90° C. for 16 h. The reaction mixture was cooled to room temperature and diluted with water. The resulting mixture was extracted with EtOAc. The combined organic layers were washed with brine, dried over Na$_2$SO$_4$, filtered and concentrated under reduced pressure to give a residue. The residue was purified by column chromatography to give 2-(3-(6-isobutyryl-4-((4-(1-(tetrahydro-2H-pyran-2-yl)-1H-pyrazol-4-yl)phenyl)amino)-5,6,7,8-tetrahydropyrido[4,3-d]pyrimidin-2-yl)phenoxy)-N-isopropylacetamide.

To the mixture of 2-(3-(6-isobutyryl-4-((4-(1-(tetrahydro-2H-pyran-2-yl)-1H-pyrazol-4-yl)phenyl)amino)-5,6,7,8-tetrahydropyrido[4,3-d]pyrimidin-2-yl)phenoxy)-N-isopropylacetamide (1.00 eq) in CH$_2$Cl$_2$ (5.00-10.00 mL) was added HCl/dioxane (4 M, 5.00-10.00 mL). The mixture was stirred at 20° C. for 1-16 h. The mixture was concentrated under reduced pressure to give a residue. The residue was purified by prep-HPLC (FA conditions) to afford the title compound.

Light yellow solid; Yield: 24% (2 steps). $^1$H NMR (400 MHz, DMSO-d$_6$) δ 8.76-8.65 (m, 1H), 8.06-7.89 (m, 5H), 7.77 (dd, J=9.2 Hz, 8.0 Hz, 2H), 7.68-7.63 (m, 2H), 7.41-7.37 (m, 1H), 7.09-7.04 (m, 1H), 4.68-4.63 (m, 2H), 4.50 (s, 2H), 4.02-3.94 (m, 1H), 3.87-3.82 (m, 2H), 3.14-3.04 (m, 1H), 2.90-2.76 (m, 2H), 1.08 (t, J=4.4 Hz, 12H). (ES+) m/e 554.2 (M+H)$^+$.

Example 150

2-(3-(4-((4-(1H-pyrazol-4-yl)phenyl)amino)-6-isobutyryl-5,6,7,8-tetrahydropyrido[4,3-d]pyrimidin-2-yl)phenoxy)-N-cyclopentylacetamide

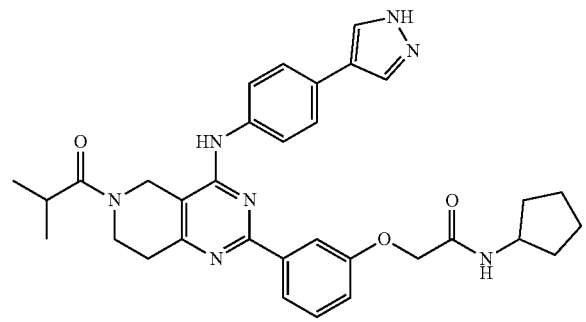 [SMILES: CC(C)C(=O)N1CCc2nc(-c3cccc(OCC(=O)NC4CCCC4)c3)nc(Nc3ccc(-c4cn[nH]c4)cc3)c2C1]

The title compound was synthesized using the same procedure as described in Example 149.

Light yellow solid; Yield: 15% (2 steps). $^1$H NMR (400 MHz, DMSO-d$_6$) δ 12.90 (s, 1H), 8.74-8.62 (m, 1H), 8.16-7.89 (m, 5H), 7.77 (dd, J=8.4 Hz, 7.6 Hz, 2H), 7.68-7.62 (m, 2H), 7.38 (t, J=8.4 Hz, 1H), 7.06-7.04 (m, 1H), 4.68-4.63 (m, 2H), 4.50 (s, 2H), 4.12-4.07 (m, 1H), 3.87-3.82 (m, 2H), 3.14-3.05 (m, 1H), 2.90-2.77 (m, 2H), 1.82-1.76 (m, 2H), 1.64-1.57 (m, 2H), 1.50-1.42 (m, 4H), 1.07 (d, J=6.4 Hz, 6H). (ES+) m/e 580.3 (M+H)$^+$.

Example 151

2-(3-(4-((4-(1H-pyrazol-4-yl)phenyl)amino)-6-isobutyryl-5,6,7,8-tetrahydropyrido[4,3-d]pyrimidin-2-yl)phenoxy)-N-(tert-butyl)acetamide

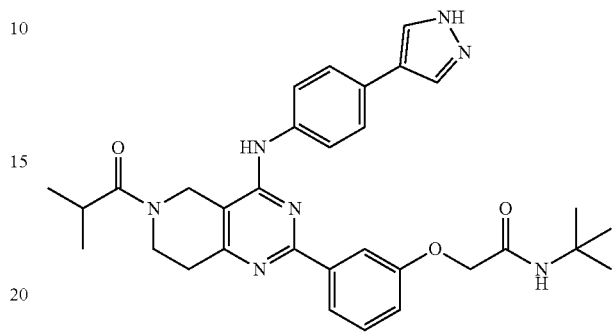

The title compound was synthesized using the same procedure as described in Example 149.

Faint yellow solid; Yield: 29% (2 steps). $^1$H NMR (400 MHz, DMSO-d$_6$) δ 12.92 (s, 1H), 8.75-8.65 (m, 1H), 8.02-7.87 (m, 4H), 7.77 (t, J=8.0 Hz, 2H), 7.68-7.64 (m, 1H), 7.51 (s, 1H), 7.39-7.37 (m, 1H), 7.04-7.02 (m, 1H), 4.68-4.63 (m, 2H), 4.46 (s, 2H), 3.87-3.82 (m, 2H), 3.12-3.05 (m, 1H), 2.89-2.65 (m, 1H), 1.29 (s, 9H), 1.07 (d, J=6.4 Hz, 6H). (ES+) m/e 568.4 (M+H)$^+$.

Example 152

2-(3-(4-((4-(1H-pyrazol-4-yl)phenyl)amino)-6-isobutyryl-5,6,7,8-tetrahydropyrido[4,3-d]pyrimidin-2-yl)phenoxy)-N-cyclobutylacetamide The title compound was synthesized using the same procedure as described in Example 149.

Faint yellow solid; Yield: 28% (2 steps). $^1$H NMR (400 MHz, DMSO-d$_6$) δ 12.93 (s, 1H), 8.76-8.65 (m, 1H), 8.36 (d, J=7.6 Hz, 1H), 8.06-7.89 (m, 4H), 7.77 (t, J=7.6 Hz, 2H), 7.65 (t, J=8.0 Hz, 2H), 7.39 (t, J=8.4 Hz, 1H), 7.05 (d, J=8.8 Hz, 1H), 4.68-4.63 (m, 2H), 4.49 (s, 2H), 4.33-4.27 (m, 1H), 3.87-3.82 (m, 2H), 3.12-3.05 (m, 1H), 2.90-2.77 (m, 2H), 2.14-2.12 (m, 2H), 2.04-1.99 (m, 2H), 1.62-1.56 (m, 2H), 1.07 (d, J=6.0 Hz, 6H). (ES+) m/e 566.4 (M+H)$^+$.

Example 153

2-(3-(4-((4-(1H-pyrazol-4-yl)phenyl)amino)-6-isobutyryl-5,6,7,8-tetrahydropyrido[4,3-d]pyrimidin-2-yl)phenoxy)-N-(pentan-3-yl)acetamide

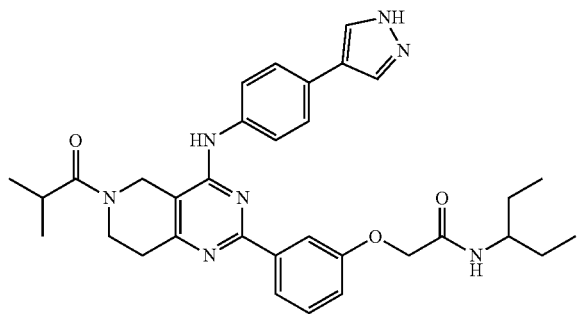 [SMILES: CCC(CC)NC(=O)COc1cccc(-c2nc3c(c(Nc4ccc(-c5cn[nH]c5)cc4)n2)CN(C(=O)C(C)C)CC3)c1]

The title compound was synthesized using the same procedure as described in Example 149.

Off-white solid; Yield: 17% (2 steps). $^1$H NMR (400 MHz, DMSO-d$_6$) δ 12.95 (s, 1H), 8.76-8.66 (m, 1H), 8.18-7.91 (m, 4H), 7.79-7.73 (m, 3H), 7.69-7.64 (m, 2H), 7.39 (t, J=8.0 Hz, 1H), 7.06 (d, J=6.8 Hz, 1H), 4.68-4.64 (m, 2H), 4.56 (s, 2H), 3.88-3.83 (m, 2H), 3.64-3.62 (m, 1H), 3.13-3.06 (m, 1H), 2.90-2.77 (m, 2H), 1.46-1.36 (m, 4H), 1.08 (d, J=5.6 Hz, 6H), 0.78 (t, J=7.2 Hz, 6H). (ES+) m/e 582.2 (M+H)$^+$.

Example 154

2-(3-(4-((4-(1H-pyrazol-4-yl)phenyl)amino)-6-isobutyryl-5,6,7,8-tetrahydropyrido[4,3-d]pyrimidin-2-yl)phenoxy)-N-isobutylacetamide

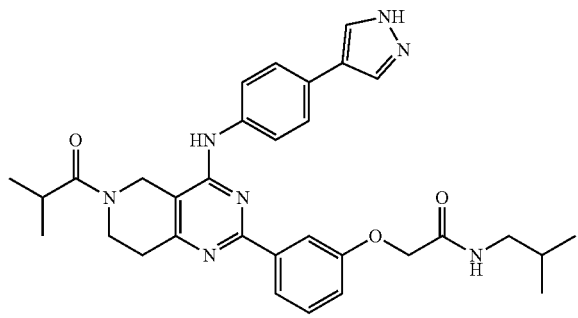 [SMILES: CC(C)CNC(=O)COc1cccc(-c2nc3c(c(Nc4ccc(-c5cn[nH]c5)cc4)n2)CN(C(=O)C(C)C)CC3)c1]

The title compound was synthesized using the same procedure as described in Example 149.

Off-white solid; Yield: 9.3% (2 steps). $^1$H NMR (400 MHz, DMSO-d$_6$) δ 12.92 (s, 1H), 8.76-8.66 (m, 1H), 8.14-8.11 (m, 2H), 7.92-7.90 (m, 3H), 7.77 (t, J=8.0 Hz, 2H), 7.65 (t, J=8.4 Hz, 2H), 7.40 (t, J=8.0 Hz, 1H), 7.08-7.05 (m, 1H), 4.69-4.64 (m, 2H), 4.56 (s, 2H), 3.88-3.83 (m, 2H), 3.13-3.04 (m, 1H), 2.97-2.94 (m, 2H), 2.90-2.77 (m, 2H), 1.79-1.70 (m, 1H), 1.08 (d, J=6.4 Hz, 6H), 0.80 (d, J=6.8 Hz, 6H). (ES+) m/e 568.2 (M+H)$^+$.

Example 155

2-(3-(4-((4-(1H-pyrazol-4-yl)phenyl)amino)-6-isobutyryl-5,6,7,8-tetrahydropyrido[4,3-d]pyrimidin-2-yl)phenoxy)-N-neopentylacetamide

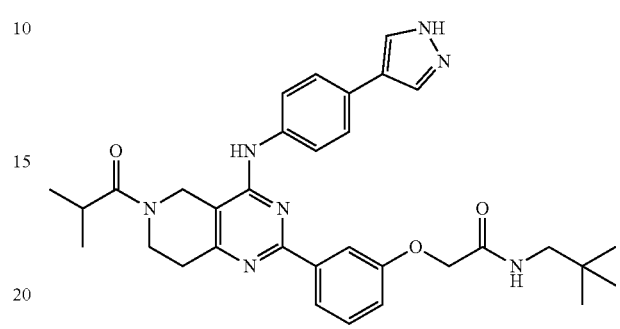

The title compound was synthesized using the same procedure as described in Example 149.

Off-white solid; Yield: 19% (2 steps). $^1$H NMR (400 MHz, DMSO-d$_6$) δ 12.93 (s, 1H), 8.75-8.65 (m, 1H), 8.18-7.90 (m, 5H), 7.77 (t, J=8.4 Hz, 2H), 7.65 (t, J=8.4 Hz, 2H), 7.40 (t, J=8.0 Hz, 1H), 7.08-7.05 (m, 1H), 4.69-4.60 (m, 4H), 3.88-3.83 (m, 2H), 3.13-3.06 (m, 1H), 2.97-2.96 (m, 2H), 2.90-2.77 (m, 2H), 1.08 (d, J=6.0 Hz, 6H), 0.80 (s, 9H). (ES+) m/e 582.2 (M+H)$^+$.

Example 156

2-(3-(4-((4-(1H-pyrazol-4-yl)phenyl)amino)-6-isobutyryl-5,6,7,8-tetrahydropyrido[4,3-d]pyrimidin-2-yl)phenoxy)-N-(tert-pentyl)acetamide

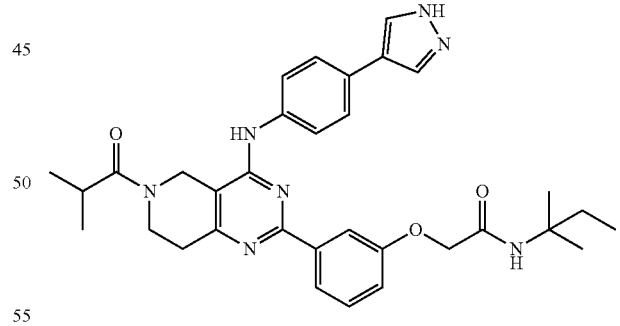

The title compound was synthesized using the same procedure as described in Example 149.

Off-white solid; Yield: 26% (2 steps). $^1$H NMR (400 MHz, DMSO-d$_6$) δ 12.93 (s, 1H), 8.76-8.66 (m, 1H), 8.16-7.87 (m, 4H), 7.77 (t, J=8.4 Hz, 2H), 7.65 (t, J=8.8 Hz, 2H), 7.41-7.34 (m, 1H), 7.05-7.03 (m, 1H), 4.69-4.64 (m, 2H), 4.49 (s, 2H), 3.88-3.83 (m, 2H), 3.13-3.04 (m, 1H), 2.90-2.77 (m, 2H), 1.70-1.64 (m, 2H), 1.23 (s, 6H), 1.08 (d, J=6.4 Hz, 6H), 0.76 (t, J=7.6 Hz, 3H). (ES+) m/e 582.3 (M+H)$^+$.

Example 157

2-(3-(4-((4-(1H-pyrazol-4-yl)phenyl)amino)-5,6,7,8-tetrahydropyrido[4,3-d]pyrimidin-2-yl)phenoxy)-N-cyclobutylacetamide

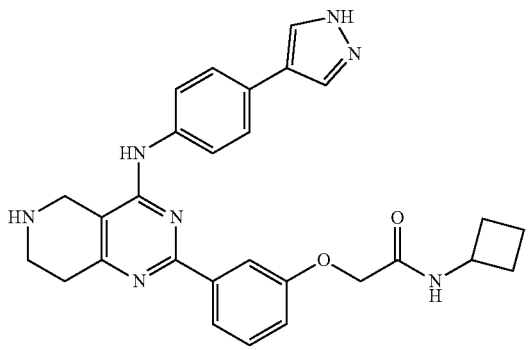 [SMILES: O=C(COc1cccc(-c2nc3c(c(Nc4ccc(-c5cn[nH]c5)cc4)n2)CNCC3)c1)NC1CCC1]

Example 157A tert-butyl 2-(3-(2-(cyclobutylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate

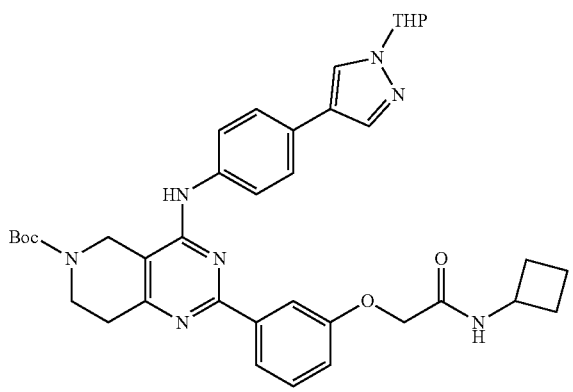

To the mixture of tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (900.00 mg, 1.76 mmol) and N-cyclobutyl-2-(3-(4,4,5,5-tetramethyl-1,3,2-dioxaborolan-2-yl)phenoxy)acetamide (699.52 mg, 2.11 mmol) in dioxane (10.00 mL), H$_2$O (1.00 mL) was added K$_2$CO$_3$ (486.50 mg, 3.52 mmol), Pd(dppf)Cl$_2$ (128.78 mg, 176.00 umol). The mixture was stirred under N$_2$ at 90° C. for 16 h. TLC (petroleum ether/EtOAc=1:1, Rf=0.5) showed one new main spot. The reaction mixture was cooled to room temperature and diluted with water (30 mL). The resulting mixture was extracted with EtOAc (30 mL×3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=100:1 to 1:1) to give the title compound (834.00 mg, 69%) as a light brown solid. $^1$H NMR (400 MHz, DMSO-d$_6$) δ 8.67 (s, 1H), 8.37-8.34 (m, 2H), 7.95 (s, 1H), 7.91-7.89 (m, 2H), 7.79-7.77 (m, 2H), 7.65 (d, J=8.4 Hz, 2H), 7.39 (t, J=8.0 Hz, 1H), 7.07-7.05 (m, 1H), 5.42-5.39 (m, 1H), 4.52-4.50 (m, 4H), 4.34-4.28 (m, 1H), 3.97-3.94 (m, 1H), 3.72-3.62 (m, 3H), 2.81-2.80 (m, 2H), 2.19-2.12 (m, 4H), 2.04-2.02 (m, 2H), 1.97-1.95 (m, 2H), 1.70-1.53 (m, 4H), 1.47 (s, 9H).

Example 157B 2-(3-(4-((4-(1H-pyrazol-4-yl)phenyl)amino)-5,6,7,8-tetrahydropyrido[4,3-d]pyrimidin-2-yl)phenoxy)-N-cyclobutylacetamide

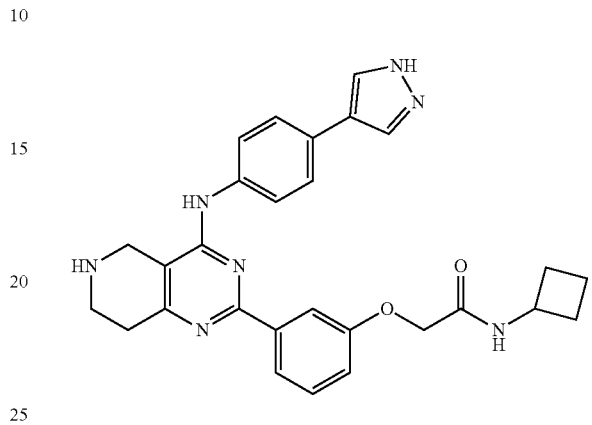

To a mixture of tert-butyl 2-(3-(2-(cyclobutylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (830.00 mg, 1.22 mmol) in CH$_2$Cl$_2$ (15.00 mL) was added HCl/dioxane (4 N, 10.00 mL). The mixture was stirred at 20° C. for 15 h. LCMS showed one main peak of desired product. The mixture was filtered to give the crude title compound (740 mg, HCl salt, crude) as a yellow solid. 100 mg of the title compound was purified by prep-HPLC (FA conditions) to pure title compound (39.8 mg) as a white solid. $^1$H NMR (400 MHz, DMSO-d$_6$) δ 8.41 (s, 1H), 8.35 (d, J=7.6 Hz, 1H), 8.23 (s, 1H), 8.04 (s, 2H), 7.92-7.90 (m, 2H), 7.78 (d, J=8.4 Hz, 2H), 7.63 (d, J=8.4 Hz, 2H), 7.39 (t, J=8.4 Hz, 1H), 7.06-7.04 (m, 1H), 4.50 (s, 2H), 4.34-4.27 (m, 1H), 3.88 (s, 2H), 3.10 (t, J=5.2 Hz, 2H), 2.77-2.76 (m, 2H), 2.16-2.10 (m, 2H), 2.06-1.97 (m, 2H), 1.65-1.58 (m, 2H). (ES+) m/e 496.2 (M+H)$^+$.

Example 158

2-(3-(4-((4-(1H-pyrazol-4-yl)phenyl)amino)-6-methyl-5,6,7,8-tetrahydropyrido[4,3-d]pyrimidin-2-yl)phenoxy)-N-cyclobutylacetamide

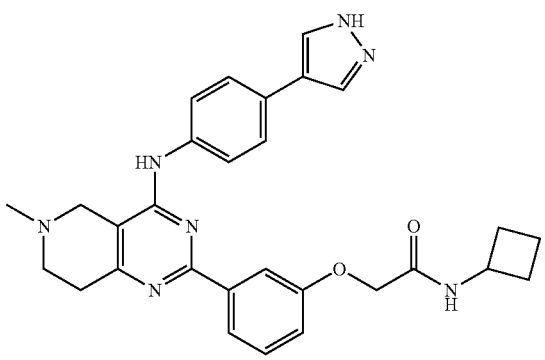 [SMILES: CN1CCc2nc(-c3cccc(OCC(=O)NC4CCC4)c3)nc(Nc3ccc(-c4cn[nH]c4)cc3)c2C1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-cyclobutylacetamide (180.00 mg, 338.32 umol, HCl salt) in MeOH (2.00 mL) was added TEA (68.47 mg, 676.64 umol, 93.79 uL) and the mixture was stirred at 15° C. for 10 min. Then to the mixture were added formaldehyde (76.20 mg, 1.01 mmol, 69.91 uL, 40% purity) and HOAc (81.26 mg, 1.35 mmol, 77.39 uL). The mixture was stirred at 15° C. for 20 min. Then NaBH$_3$CN (106.30 mg, 1.69 mmol) was added. The mixture was stirred at 15° C. for another 15.5 h. LCMS showed one main peak of desired product. The reaction mixture was diluted with water (20 mL) and extracted with EtOAc (30 mL×3). The combined organic layers were dried over Na$_2$SO$_4$, filtered and concentrated under reduced pressure to give a residue. The residue was purified by prep-HPLC (FA conditions) to afford the title comound (36.9 mg, 18%) as a yellow solid. $^1$H NMR (400 MHz, DMSO-d6) δ 8.43 (s, 1H), 8.36 (d, J=8.0 Hz, 1H), 8.18-8.17 (m, 2H), 8.05 (s, 2H), 7.92-7.90 (m, 2H), 7.78 (d, J=8.8 Hz, 2H), 7.63 (d, J=8.8 Hz, 2H), 7.39 (t, J=8.4 Hz, 1H), 7.06-7.04 (m, 1H), 4.50 (s, 2H), 4.34-4.28 (m, 1H), 3.50 (s, 2H), 2.84-2.83 (m, 2H), 2.74-2.73 (m, 2H), 2.47 (s, 3H), 2.14-2.11 (m, 2H), 2.04-1.99 (m, 2H), 1.63-1.61 (m, 2H). (ES+) m/e 510.1 (M+H)$^+$.

Example 159

2-(3-(4-((4-(1H-pyrazol-4-yl)phenyl)amino)-6-isopropyl-5,6,7,8-tetrahydropyrido[4,3-d]pyrimidin-2-yl)phenoxy)-N-cyclobutylacetamide

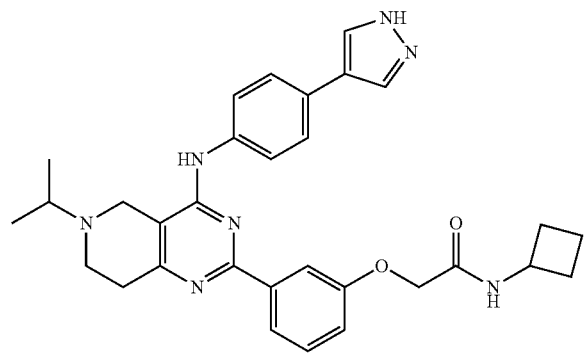 [SMILES: CC(C)N1CCc2nc(-c3cccc(OCC(=O)NC4CCC4)c3)nc(Nc3ccc(-c4cn[nH]c4)cc3)c2C1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-cyclobutylacetamide (180.00 mg, 338.32 umol, HCl salt) in MeOH (2.00 mL) was added TEA (68.47 mg, 676.64 umol, 93.79 uL) and the mixture was stirred at 15° C. for 10 min. Then to the mixture was added acetone (78.60 mg, 1.35 mmol, 99.49 uL) and HOAc (81.26 mg, 1.35 mmol, 77.39 uL). The mixture was stirred at 15° C. for 20 min. Then NaBH$_3$CN (106.30 mg, 1.69 mmol) was added. The mixture was stirred at 15° C. for another 15.5 h. LCMS showed one main peak of desired product. The reaction mixture was diluted with water (20 mL) and extracted with EtOAc (30 mL×3). The combined organic layers were dried over Na$_2$SO$_4$, filtered and concentrated under reduced pressure to give a residue. The residue was purified by prep-HPLC (FA conditions) to give the title compound (54.0 mg, 24%) as a yellow solid. $^1$H NMR (400 MHz, DMSO-d$_6$) δ 8.44 (s, 1H), 8.36 (d, J=7.6 Hz, 1H), 8.17 (s, 1H), 8.06 (s, 2H), 7.92-7.89 (m, 2H), 7.77 (d, J=8.8 Hz, 2H), 7.65-7.63 (m, 2H), 7.38 (t, J=8.4 Hz, 1H), 7.06-7.03 (m, 1H), 4.50 (s, 2H), 4.34-4.28 (m, 1H), 3.62 (s, 2H), 3.03-2.97 (m, 1H), 2.82 (s, 4H), 2.15-2.10 (m, 2H), 2.04-1.99 (m, 2H), 1.65-1.58 (m, 2H), 1.15 (d, J=6.8 Hz, 6H). (ES+) m/e 538.1 (M+H)$^+$.

Example 160

2-(3-(4-((4-(1H-pyrazol-4-yl)phenyl)amino)-6-ethyl-5,6,7,8-tetrahydropyrido[4,3-d]pyrimidin-2-yl)phenoxy)-N-cyclobutylacetamide

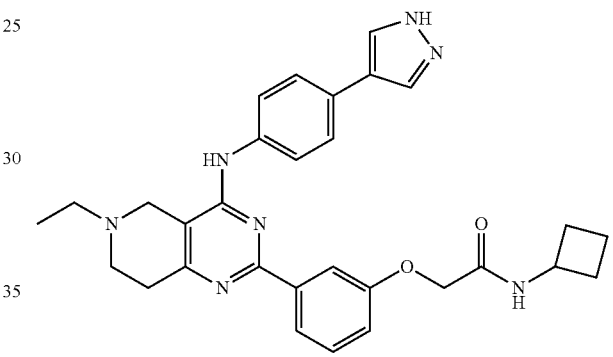

To the mixture of 2-(3-(4-((4-(1H-pyrazol-4-yl)phenyl)amino)-5,6,7,8-tetrahydropyrido[4,3-d]pyrimidin-2-yl)phenoxy)-N-cyclobutylacetamide (200.00 mg, 375.91 umol, HCl salt) in MeOH (2.00 mL) was added TEA (76.08 mg, 751.82 umol, 104.22 uL). The mixture was stirred at 20° C. for 10 min. Then to the mixture was added acetaldehyde (124.19 mg, 1.13 mmol, 157.20 uL, 40% purity) and HOAc (90.29 mg, 1.50 mmol, 85.99 uL). The mixture was stirred at 20° C. for 20 min. Then NaBH$_3$CN (118.11 mg, 1.88 mmol) was added. The mixture was stirred at 20° C. for 15.5 h. LCMS showed one main peak of desired product. The reaction mixture was diluted with water (20 mL) and extracted with EtOAc (20 mL×3). The combined organic layers were dried over Na$_2$SO$_4$, filtered and concentrated under reduced pressure to give a residue. The residue was purified by prep-HPLC (FA conditions) to give product as a yellow solid. HNMR showed product contained MeCN. The product was dissolved with deionized water (about 30 mL) and dried over with lyophilization to give the title compound (82.2 mg, 38%) as a yellow solid. $^1$H NMR (400 MHz, DMSO-d$_6$) δ 8.45 (s, 1H), 8.36 (d, J=8.0 Hz, 1H), 8.18 (s, 1H), 8.05 (s, 2H), 7.91-7.89 (m, 2H), 7.77 (d, J=8.8 Hz, 2H), 7.64 (d, J=8.4 Hz, 2H), 7.38 (t, J=8.4 Hz, 1H), 7.06-7.04 (m, 1H), 4.50 (s, 2H), 4.34-4.28 (m, 1H), 3.54 (s, 2H), 2.83-2.78

(m, 4H), 2.67-2.62 (m, 2H), 2.14-2.10 (m, 2H), 2.06-1.99 (m, 2H), 1.65-1.58 (m, 2H), 1.18 (t, J=7.2 Hz, 3H). (ES+) m/e 524.2 (M+H)+.

Example 161

2-(3-(4-((4-(1H-pyrazol-4-yl)phenyl)amino)-5,6,7,8-tetrahydropyrido[4,3-d]pyrimidin-2-yl)phenoxy)-N-isobutylacetamide

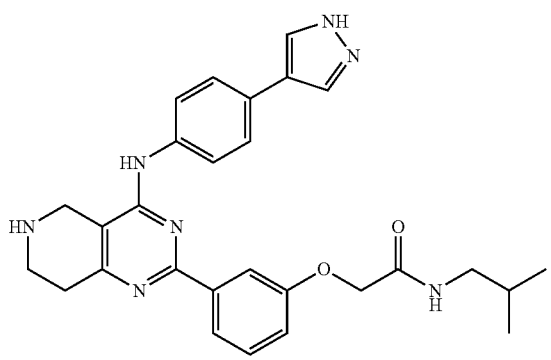 [SMILES: CC(C)CNC(=O)COc1cccc(-c2nc3c(c(Nc4ccc(-c5cn[nH]c5)cc4)n2)CNCC3)c1]

Example 161A tert-butyl 2-(3-(2-(isobutylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate

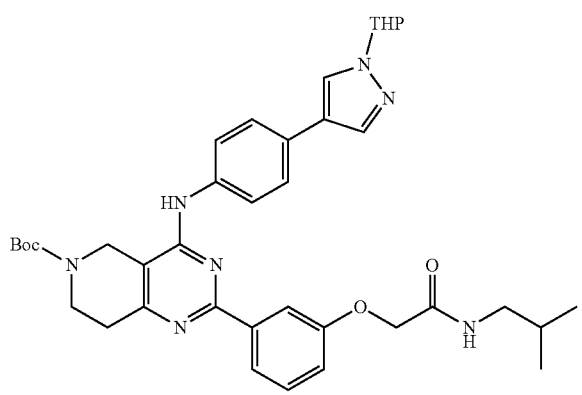

To the mixture of tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (900.00 mg, 1.76 mmol) and N-isobutyl-2-(3-(4,4,5,5-tetramethyl-1,3,2-dioxaborolan-2-yl)phenoxy)acetamide (703.78 mg, 2.11 mmol) in dioxane (10.00 mL), H$_2$O (1.00 mL) was added K$_2$CO$_3$ (486.50 mg, 3.52 mmol), Pd(dppf)Cl$_2$ (128.78 mg, 176.00 umol). The mixture was stirred under N$_2$ at 90° C. for 16 h. TLC (petroleum ether/EtOAc=1:1, Rf=0.5) showed one new main spot. The reaction mixture was cooled to room temperature and diluted with water (30 mL). The resulting mixture was extracted with EtOAc (30 mL×3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=100:1 to 1:1) to give the title compound (1.02 g, 85%) as light brown oil. $^1$H NMR (400 MHz, DMSO-d$_6$) δ 8.67 (brs, 1H), 8.35 (s, 1H), 8.12 (t, J=6.0 Hz, 1H), 7.94-7.89 (m, 3H), 7.79-7.77 (m, 2H), 7.65 (d, J=8.4 Hz, 2H), 7.41-7.37 (m, 1H), 7.07-7.05 (m, 1H), 5.42-5.39 (m, 1H), 4.55-4.52 (m, 3H), 3.93 (s, 2H), 3.73-3.62 (m, 3H), 2.96 (t, J=6.4 Hz, 2H), 2.82-2.80 (m, 2H), 2.18-2.11 (m, 1H), 1.96-1.94 (m, 2H), 1.77-1.68 (m, 2H), 1.58-1.56 (m, 2H), 1.47 (s, 9H), 0.82-0.79 (m, 6H).

Example 161B 2-(3-(4-((4-(1H-pyrazol-4-yl)phenyl)amino)-5,6,7,8-tetrahydropyrido[4,3-d]pyrimidin-2-yl)phenoxy)-N-isobutylacetamide

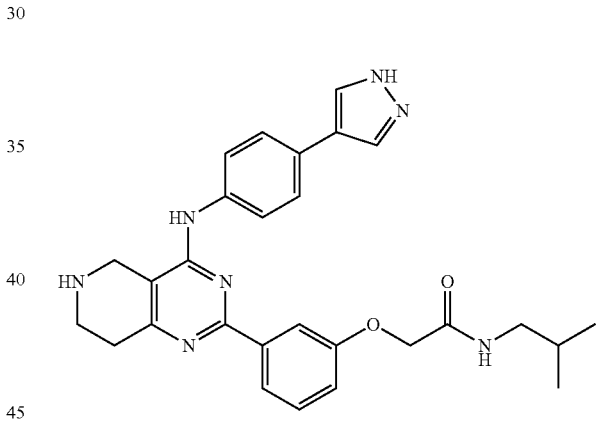

To a mixture of tert-butyl 2-(3-(2-(isobutylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (1.02 g, 1.50 mmol) in CH$_2$Cl$_2$ (15.00 mL) was added HCl/dioxane (4 N, 10.00 mL). The mixture was stirred at 20° C. for 15 h. LCMS showed about 85% of desired product. The mixture was filtered and dried over under vacuum to give the crude title compound (1.0 g, HCl salt, crude) as a yellow solid. 100 mg of crude product was purified by prep-HPLC (FA conditions) to give pure title compound (16.0 mg) as a yellow solid. $^1$H NMR (400 MHz, DMSO-d$_6$) δ 8.39 (s, 1H), 8.25 (s, 1H), 8.10 (t, J=6.0 Hz, 1H), 8.04 (s, 2H), 7.92-7.90 (m, 2H), 7.77 (d, J=8.8 Hz, 2H), 7.62 (d, J=8.4 Hz, 2H), 7.38 (t, J=8.0 Hz, 1H), 7.06-7.04 (m, 1H), 4.55 (s, 2H), 3.86 (s, 2H), 3.08 (s, 2H), 2.96 (t, J=6.4 Hz, 2H), 2.74 (s, 1H), 1.77-1.70 (m, 1H), 0.80 (d, J=6.4 Hz, 6H). (ES+) m/e 498.1 (M+H)+.

Example 162

2-(3-(4-((4-(1H-pyrazol-4-yl)phenyl)amino)-6-methyl-5,6,7,8-tetrahydropyrido[4,3-d]pyrimidin-2-yl)phenoxy)-N-isobutylacetamide

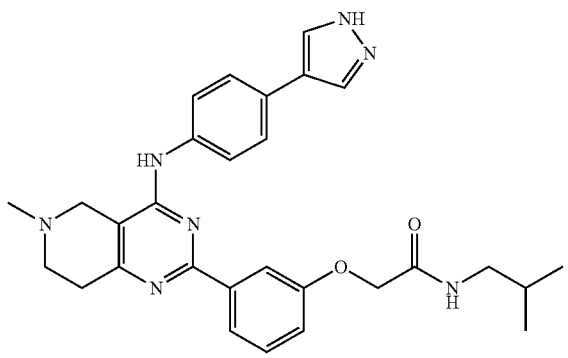 [SMILES: CC(C)CNC(=O)COc1cccc(-c2nc3c(c(Nc4ccc(-c5cn[nH]c5)cc4)n2)CN(C)CC3)c1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-isobutylacetamide (200.00 mg, 374.50 umol, HCl salt) in MeOH (2.00 mL) was added TEA (75.79 mg, 748.99 umol, 103.82 uL). The mixture was stirred at 15° C. for 10 min. Then to the mixture were added HCHO (84.35 mg, 1.12 mmol, 77.38 uL, 40% purity) and HOAc (89.95 mg, 1.50 mmol, 85.67 uL). The mixture was stirred at 15° C. for 20 min. Then NaBH$_3$CN (117.67 mg, 1.87 mmol) was added. The mixture was stirred at 15° C. for another 15.5 h. LCMS showed about 66% of desired product. The reaction mixture was diluted with water (20 mL) and extracted with EtOAc (20 mL×3). The combined organic layers were dried over Na$_2$SO$_4$, filtered and concentrated under reduced pressure to give a residue. The residue was purified by prep-HPLC (FA conditions) to give desired product as a yellow solid. HNMR showed product was contained MeCN. The product was dissolved with deionized water (about 30 mL) and dried over with lyophilization to give the title compound (65.2 mg, 28%) as a yellow solid. $^1$H NMR (400 MHz, DMSO-d$_6$) δ 8.44 (s, 1H), 8.16-8.15 (m, 2H), 8.12 (t, J=5.6 Hz, 1H), 8.05 (s, 2H), 7.92-7.90 (m, 2H), 7.78 (d, J=8.8 Hz, 2H), 7.63 (d, J=8.8 Hz, 2H), 7.38 (t, J=8.0 Hz, 1H), 7.06-7.04 (m, 1H), 4.55 (s, 2H), 3.50 (s, 2H), 2.95 (t, J=6.0 Hz, 2H), 2.84-2.82 (m, 2H), 2.73 (s, 2H), 2.47 (s, 3H), 1.76-1.70 (m, 1H), 0.80 (d, J=6.8 Hz, 6H). (ES+) m/e 512.1 (M+H)$^+$.

Example 163

2-(3-(4-((4-(1H-pyrazol-4-yl)phenyl)amino)-6-isopropyl-5,6,7,8-tetrahydropyrido[4,3-d]pyrimidin-2-yl)phenoxy)-N-isobutylacetamide

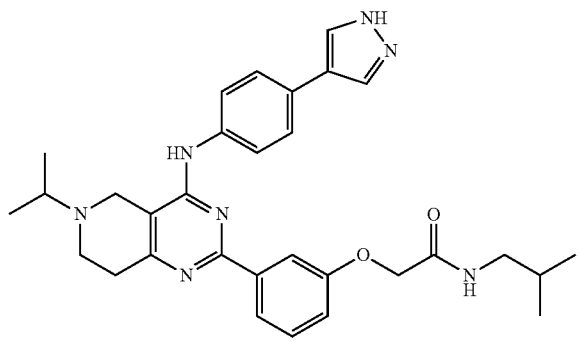 [SMILES: CC(C)CNC(=O)COc1cccc(-c2nc3c(c(Nc4ccc(-c5cn[nH]c5)cc4)n2)CN(C(C)C)CC3)c1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-isobutylacetamide (200.00 mg, 374.50 umol, HCl salt) in MeOH (2.00 mL) was added TEA (75.79 mg, 748.99 umol, 103.82 uL). The mixture was stirred at 15° C. for 10 min. Then to the mixture was added acetone (87.00 mg, 1.50 mmol, 110.13 uL) and HOAc (89.95 mg, 1.50 mmol, 85.67 uL). The mixture was stirred at 15° C. for 20 min. Then NaBH$_3$CN (117.67 mg, 1.87 mmol) was added. The mixture was stirred at 15° C. for another 15.5 h. LCMS showed about 76% of desired product. The reaction mixture was diluted with water (20 mL) and extracted with EtOAc (20 mL×3). The combined organic layers were dried over Na$_2$SO$_4$, filtered and concentrated under reduced pressure to give a residue. The residue was purified by prep-HPLC (FA conditions) to give the title compound (58.4 mg, 26%) as a yellow solid. $^1$H NMR (400 MHz, DMSO-d$_6$) δ 8.42 (s, 1H), 8.17 (s, 1H), 8.11 (t, J=6.0 Hz, 1H), 8.05 (s, 2H), 7.92-7.90 (m, 2H), 7.76 (d, J=8.4 Hz, 2H), 7.64 (d, J=8.4 Hz, 2H), 7.38 (t, J=8.0 Hz, 1H), 7.05-7.03 (m, 1H), 4.55 (s, 2H), 3.61 (s, 2H), 3.01-2.94 (m, 3H), 2.81 (s, 4H), 1.76-1.70 (m, 1H), 1.15 (d, J=6.8 Hz, 6H), 0.80 (d, J=6.8 Hz, 6H). (ES+) m/e 540.2 (M+H)$^+$.

Example 164

2-(3-(4-((4-(1H-pyrazol-4-yl)phenyl)amino)-6-ethyl-5,6,7,8-tetrahydropyrido[4,3-d]pyrimidin-2-yl)phenoxy)-N-isobutylacetamide

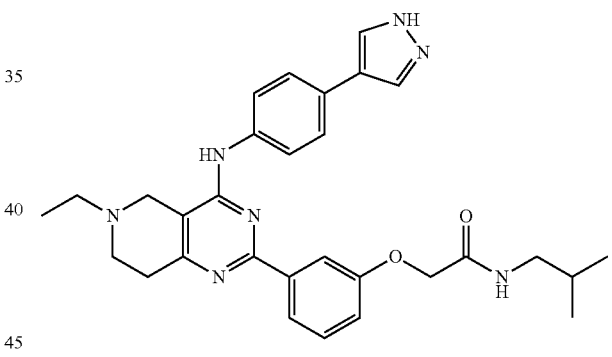

To the mixture of 2-(3-(4-((4-(1H-pyrazol-4-yl)phenyl)amino)-5,6,7,8-tetrahydropyrido[4,3-d]pyrimidin-2-yl)phenoxy)-N-isobutylacetamide (150.00 mg, 280.87 umol, HCl salt) in MeOH (2.00 mL) was added TEA (56.84 mg, 561.75 umol, 77.87 uL). The mixture was stirred at 20° C. for 10 min. Then to the mixture was added acetaldehyde (92.79 mg, 842.62 umol, 117.46 uL, 40% purity) and HOAc (67.47 mg, 1.12 mmol, 64.25 uL). The mixture was stirred at 20° C. for 20 min. Then NaBH$_3$CN (88.25 mg, 1.40 mmol) was added. The mixture was stirred at 20° C. for another 15.5 h. LCMS showed one main peak of desired product. The reaction mixture was diluted with water (20 mL) and extracted with EtOAc (20 mL×3). The combined organic layers were dried over Na$_2$SO$_4$, filtered and concentrated under reduced pressure to give a residue. The residue was purified by prep-HPLC (FA conditions) to give the title compound (16.1 mg, 9.2%) as a yellow solid. $^1$H NMR (400 MHz, DMSO-d6) δ 8.45 (s, 1H), 8.25 (s, 1H), 8.12 (t, J=6.0 Hz, 1H), 8.05 (s, 2H), 7.92-7.90 (m, 2H), 7.76 (d, J=8.4 Hz, 2H), 7.64 (d, J=8.8 Hz, 2H), 7.38 (t, J=8.0 Hz, 1H), 7.06-7.03 (m, 1H), 4.55 (s, 2H), 3.53 (s, 2H), 2.96 (t, J=6.4

Hz, 2H), 2.82-2.77 (m, 4H), 2.66-2.61 (m, 2H), 1.76-1.70 (m, 1H), 1.18 (t, J=7.2 Hz, 3H), 0.80 (d, J=6.8 Hz, 6H). (ES+) m/e 526.2 (M+H)⁺.

Example 165

2-(3-(4-((4-(1H-pyrazol-4-yl)phenyl)amino)pyrido[3,4-d]pyrimidin-2-yl)phenoxy)-N-(tert-pentyl)acetamide

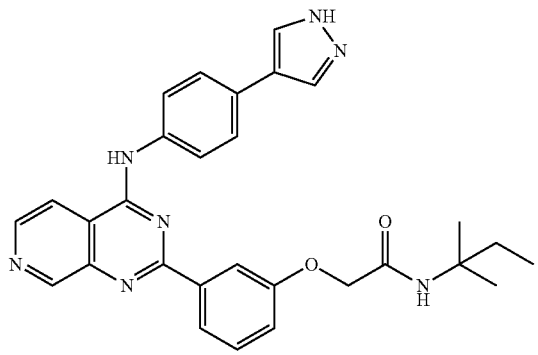 [SMILES: CCC(C)(C)NC(=O)COc1cccc(-c2nc(Nc3ccc(-c4cn[nH]c4)cc3)c3ccncc3n2)c1]

Example 165A

N-(tert-pentyl)-2-(3-(4-((4-(1-(tetrahydro-2H-pyran-2-yl)-1H-pyrazol-4-yl)phenyl)amino)pyrido[3,4-d]pyrimidin-2-yl)phenoxy)acetamide

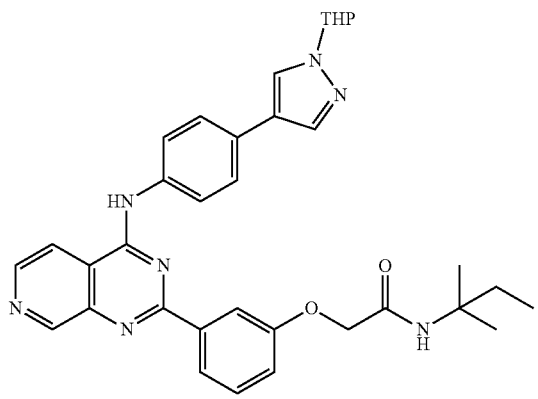

To the solution of 2-chloro-N-(4-(1-(tetrahydro-2H-pyran-2-yl)-1H-pyrazol-4-yl)phenyl)pyrido[3,4-d]pyrimidin-4-amine (180.00 mg, 442.40 umol) in dioxane (10.00 mL) was added N-(tert-pentyl)-2-(3-(4,4,5,5-tetramethyl-1,3,2-dioxaborolan-2-yl)phenoxy)acetamide (184.35 mg, 530.88 umol), K₂CO₃ (122.29 mg, 884.80 umol), Pd(dppf)Cl₂ (32.37 mg, 44.24 umol) and H₂O (4.00 mL). The mixture was stirred for 12 hr at 90° C. under N₂. LCMS showed that ~75% was the desired product. The mixture was cooled to room temperature and water (100 mL) was added. The resulting mixture was extracted with EtOAc (100 mL×2). The combined organic layers were dried over Na₂SO₄, filtered and concentrated under reduced pressure to give the title compound (340 mg, crude) as yellow oil.

Example 165B 2-(3-(4-((4-(1H-pyrazol-4-yl)phenyl)amino)pyrido[3,4-d]pyrimidin-2-yl)phenoxy)-N-(tert-pentyl)acetamide

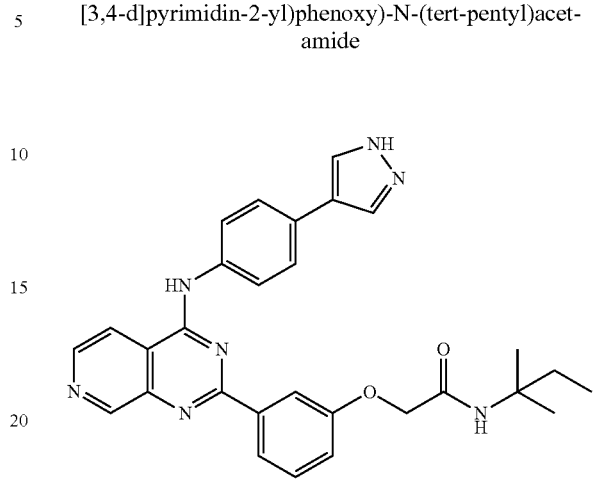

To the solution of N-(tert-pentyl)-2-(3-(4-((4-(1-(tetrahydro-2H-pyran-2-yl)-1H-pyrazol-4-yl)phenyl)amino)pyrido[3,4-d]pyrimidin-2-yl)phenoxy)acetamide (340.00 mg, 574.62 umol) in CH₂Cl₂ (8.00 mL) was added HCl/dioxane (4 N, 8.00 mL) dropwise at 0° C. After addition the mixture was stirred for 12 hr at 20° C. LCMS showed ~62% of product. The mixture was concentrated and MeOH (30 mL) was added. The mixture was adjusted to pH=7 with NH₃·H₂O (6 M). The mixture was concentrated and dried in reduced pressure to give a crude product. The crude product was purified by prep-HPLC (FA conditions) to afford the title compound (27.00 mg) as a yellow solid. ¹H NMR (400 MHz, DMSO-d₆) δ 12.98 (s, 1H), 10.20 (s, 1H), 9.23 (s, 1H), 8.48 (d, J=5.6 Hz, 1H), 8.44 (s, 1H), 8.27-8.06 (m, 4H), 7.99 (d, J=8.4 Hz, 2H), 7.75 (d, J=8.8 Hz, 2H), 7.47 (t, J=8.0 Hz, 1H), 7.34 (s, 1H), 7.13-7.11 (dd, J=8.0, 2.0 Hz, 1H), 4.54 (s, 2H), 1.71-1.65. (m, 2H), 1.65 (s, 6H), 0.77 (t, J=6.8, 3H). (ES+) m/e 508.2 (M+H)⁺.

1.1.3

Example 166

2-(3-(4-((4-(1H-pyrazol-4-yl)phenyl)amino)-7,8-dihydro-5H-pyrano[4,3-d]pyrimidin-2-yl)phenoxy)-N-(tert-pentyl)acetamide

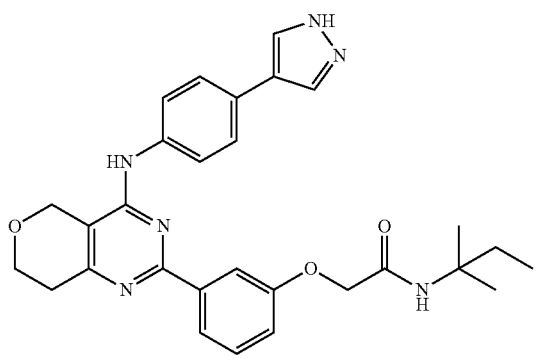 [SMILES: CCC(C)(C)NC(=O)COc1cccc(-c2nc3c(c(Nc4ccc(-c5cn[nH]c5)cc4)n2)COCC3)c1]

Example 166A

N-(tert-pentyl)-2-(3-(4-((4-(1-(tetrahydro-2H-pyran-2-yl)-1H-pyrazol-4-yl)phenyl)amino)-7,8-dihydro-5H-pyrano[4,3-d]pyrimidin-2-yl)phenoxy)acetamide

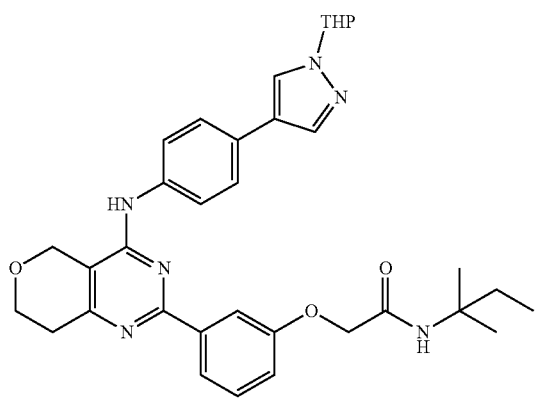

To the solution of 2-chloro-N-(4-(1-(tetrahydro-2H-pyran-2-yl)-1H-pyrazol-4-yl)phenyl)-7,8-dihydro-5H-pyrano[4,3-d]pyrimidin-4-amine (200.00 mg, 485.57 umol) in dioxane (15.00 mL) was added N-(tert-pentyl)-2-(3-(4,4,5,5-tetramethyl-1,3,2-dioxaborolan-2-yl)phenoxy)acetamide (219.20 mg, 631.24 umol), $K_2CO_3$ (134.22 mg, 971.14 umol) and Pd(dppf)Cl$_2$ (35.53 mg, 48.56 umol) and H$_2$O (3.00 mL). The mixture was stirred at 90° C. for 12 hr under N$_2$. LCMS showed ~67% of product. The mixture was cooled to room temperature and water (100 mL) was added. The resulting mixture was extracted with EtOAc (100 mL×2). The organic layer was dried over Na$_2$SO$_4$ and filtered through thin silica pad. The filtrate was concentrated and dried under reduced pressure to give the title compound (340 mg, crude) as a yellow solid.

Example 166B 2-(3-(4-((4-(1H-pyrazol-4-yl)phenyl)amino)-7,8-dihydro-5H-pyrano[4,3-d]pyrimidin-2-yl)phenoxy)-N-(tert-pentyl)acetamide

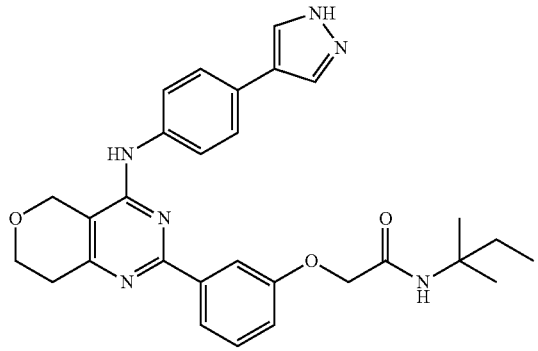 [SMILES: CCC(C)(C)NC(=O)COc1cccc(-c2nc3c(c(Nc4ccc(-c5cn[nH]c5)cc4)n2)COCC3)c1]

To the solution of N-(tert-pentyl)-2-(3-(4-((4-(1-(tetrahydro-2H-pyran-2-yl)-1H-pyrazol-4-yl)phenyl)amino)-7,8-dihydro-5H-pyrano[4,3-d]pyrimidin-2-yl)phenoxy)acetamide (340.00 mg, 569.78 umol) in CH$_2$Cl$_2$ (8.00 mL) was added HCl/dioxane (4 N, 10.00 mL) dropwise at 0° C. Then the mixture was stirred at 20° C. for 12 hr. LCMS showed ~56% of product. The mixture was concentrated and MeOH (20 mL) was added. The mixture was adjusted to pH=8 with NH$_4$OH (6 M). The mixture was concentrated and dried in reduced pressure to give a residue. The residue was purified by prep-HPLC (TFA conditions) to give 120 mg of crude product which was further purified by prep-HPLC (HCl conditions) to afford the title compound (79.5.00 mg) as a yellow solid. $^1$H NMR (400 MHz, DMSO-d$_6$) δ 9.83 (s, 1H), 8.12 (s, 2H), 7.83-7.80 (m, 2H), 7.72 (d, J=8.8 Hz, 2H), 7.67 (d, J=8.8 Hz, 2H), 7.51 (t, J=8.4 Hz, 1H), 7.43 (s, 1H), 7.23-7.20 (dd, J=8.0, 2.0 Hz, 1H), 4.75 (s, 2H), 4.55 (s, 2H), 4.01 (t, J=5.6 Hz, 2H), 3.01 (t, J=4.8 Hz, 2H), 1.68-1.62 (m, 2H), 1.21 (s, 6H), 0.74 (t, J=7.6 Hz, 3H). (ES+) m/e 513.2 (M+H)$^+$.

Example 167

2-(3-(4-((4-(1H-pyrazol-4-yl)phenyl)amino)-5,6,7,8-tetrahydropyrido[4,3-d]pyrimidin-2-yl)phenoxy)-N-neopentylacetamide

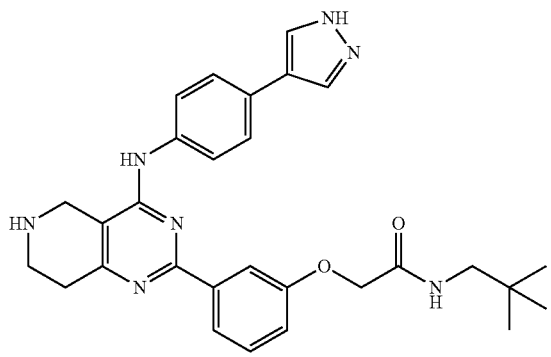 [SMILES: CC(C)(C)CNC(=O)COc1cccc(-c2nc3c(c(Nc4ccc(-c5cn[nH]c5)cc4)n2)CNCC3)c1]

Example 167A tert-butyl 2-(3-(2-(neopentylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate

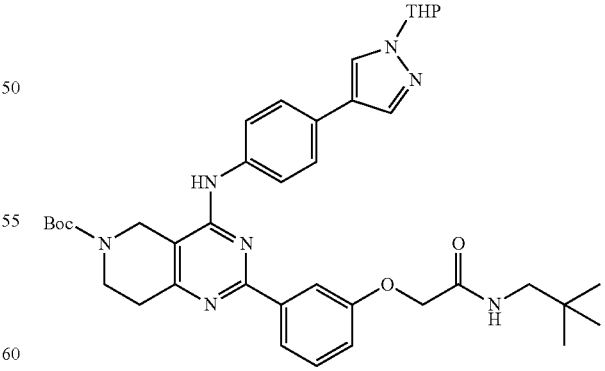

To the mixture of tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (900.00 mg, 1.76 mmol) and N-neopentyl-2-(3-(4,4,5,5-tetramethyl-1,3,2-dioxaborolan-2-yl)phenoxy)acetamide (733.41 mg, 2.11 mmol) in dioxane (10.00 mL), H₂O (1.00 mL) was added K₂CO₃ (486.50 mg, 3.52 mmol) and Pd(dppf)Cl₂ (128.78 mg, 176.00 umol). The mixture was stirred under N₂ at 90° C. for 16 h. LCMS showed about 58% of desired product and about 22% of tert-butyl 2-chloro-4-((4-(1-(tetrahydro-2H-pyran-2-yl)-1H-pyrazol-4-yl)phenyl)amino)-7,8-dihydropyrido[4,3-d]pyrimidine-6(5H)-carboxylateremained. To the mixture was added additional N-neopentyl-2-(3-(4,4,5,5-tetramethyl-1,3,2-dioxaborolan-2-yl)phenoxy)acetamide (160 mg), K₂CO₃ (120 mg) and Pd(dppf)Cl₂ (30 mg). The mixture was stirred under N₂ at 90° C. for another 2 h TLC (petroleum ether/EtOAc=2:1, Rf=0.15) showed one new main spot. The reaction mixture was cooled to room temperature and diluted with water (30 mL). The resulting mixture was extracted with EtOAc (30 mL×3). The combined organic layers were washed with brine (50 mL), dried over Na₂SO₄, filtered and concentrated under reduced pressure to give a residue. The residue was purified by column chromatography (SiO₂, petroleum ether/EtOAc=100:1 to 1:1) to give the title compound (820 mg, 49%) as a brown solid.

Example 167B 2-(3-(4-((4-(1H-pyrazol-4-yl)phenyl)amino)-5,6,7,8-tetrahydropyrido[4,3-d]pyrimidin-2-yl)phenoxy)-N-neopentylacetamide

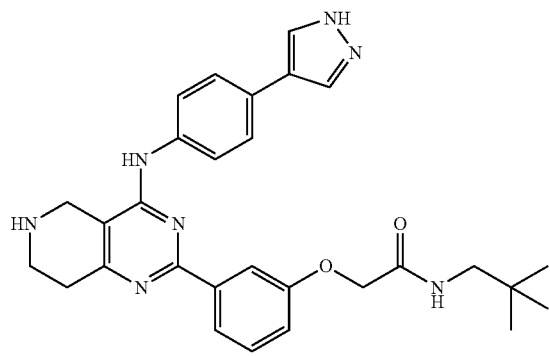 [SMILES: CC(C)(C)CNC(=O)COc1cccc(-c2nc3c(c(Nc4ccc(-c5cn[nH]c5)cc4)n2)CNCC3)c1]

To a mixture of tert-butyl 2-(3-(2-(neopentylamino)-2-oxoethoxy)phenyl)-4-((4-(1-(tetrahydro-2H-pyran-2-yl)-1H-pyrazol-4-yl)phenyl)amino)-7,8-dihydropyrido[4,3-d]pyrimidine-6(5H)-carboxylate (820.00 mg, 1.18 mmol) in CH₂Cl₂ (10.00 mL) was added HCl/dioxane (4 N, 10.00 mL). The mixture was stirred at 20° C. for 16 h. LCMS showed one main peak of desired product. The mixture was filtered to give the crude product (810 mg, HCl salt, crude) as a yellow solid. 100 mg of crude material was purified by prep-HPLC (FA conditions) and concentrate was dissolved with deionized water (about 30 mL) and dried over with lyophilization to afford the title compound (36.6 mg) as an off-white solid. ¹H NMR (400 MHz, DMSO-d₆) δ 8.39 (s, 1H), 8.27 (s, 1H), 8.04 (s, 2H), 7.96 (t, J=6.0 Hz, 1H), 7.92-7.90 (m, 2H), 7.77 (d, J=8.4 Hz, 2H), 7.63 (d, J=8.4 Hz, 2H), 7.38 (t, J=8.0 Hz, 1H), 7.06-7.04 (m, 1H), 4.59 (s, 2H), 3.86 (s, 2H), 3.09 (s, 2H), 2.96 (d, J=6.4 Hz, 2H), 2.74 (s, 2H), 0.80 (s, 9H). (ES+) m/e 512.1 (M+H)⁺.

Example 168

2-(3-(4-((4-(1H-pyrazol-4-yl)phenyl)amino)-6-methyl-5,6,7,8-tetrahydropyrido[4,3-d]pyrimidin-2-yl)phenoxy)-N-neopentylacetamide

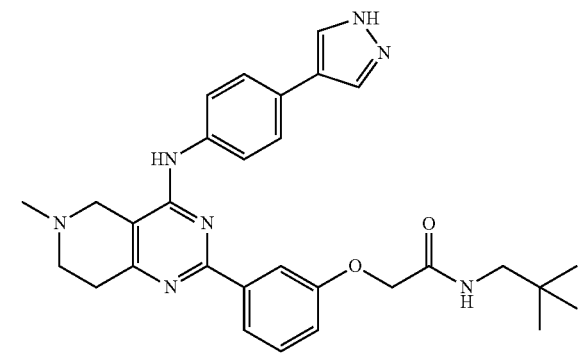 [SMILES: CN1CCc2nc(-c3cccc(OCC(=O)NCC(C)(C)C)c3)nc(Nc3ccc(-c4cn[nH]c4)cc3)c2C1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-neopentylacetamide (200.00 mg, 364.91 umol, HCl salt) in MeOH (2.00 mL) was added TEA (73.85 mg, 729.82 umol, 101.16 uL). The mixture was stirred at 20° C. for 10 min. Then to the mixture was added HCHO (82.19 mg, 1.09 mmol, 75.40 uL, 40% purity) and HOAc (87.65 mg, 1.46 mmol, 83.48 uL). The mixture was stirred at 20° C. for 20 min. Then NaBH₃CN (117.67 mg, 1.87 mmol) was added. The mixture was stirred at 15° C. for another 15.5 h. LCMS showed one main peak of the desired product. The reaction mixture was diluted with water (20 mL) and extracted with EtOAc (20 mL×3). The combined organic layers were dried over Na₂SO₄, filtered and concentrated under reduced pressure to give a residue. The residue was purified by prep-HPLC (FA conditions) to give desired product as yellow solid. HNMR showed product was contained MeCN. The product was dissolved with deionized water (about 30 mL) and dried over with lyophilization to afford the title compound (48.8 mg, 23%) as a yellow solid. ¹H NMR (400 MHz, DMSO-d₆) δ 8.43 (s, 1H), 8.31 (s, 1H), 8.04 (s, 2H), 7.96 (t, J=6.0 Hz, 1H), 7.92-7.90 (m, 2H), 7.78 (d, J=8.5 Hz, 2H), 7.63 (d, J=8.8 Hz, 2H), 7.38 (t, J=8.0 Hz, 1H), 7.06-7.04 (m, 1H), 4.59 (s, 2H), 3.50 (s, 2H), 2.95 (d, J=6.4 Hz, 2H), 2.82 (d, J=5.2 Hz, 2H), 2.74-2.71 (m, 2H), 2.47 (s, 3H), 0.79 (s, 9H). (ES+) m/e 526.3 (M+H)⁺.

Example 169

2-(3-(4-((4-(1H-pyrazol-4-yl)phenyl)amino)-6-isopropyl-5,6,7,8-tetrahydropyrido[4,3-d]pyrimidin-2-yl)phenoxy)-N-neopentylacetamide

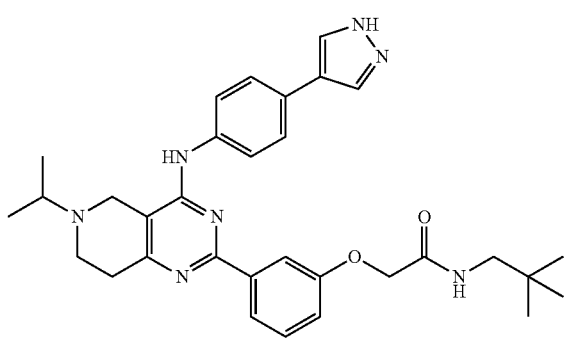 [SMILES: CC(C)N1CCc2nc(-c3cccc(OCC(=O)NCC(C)(C)C)c3)nc(Nc3ccc(-c4cn[nH]c4)cc3)c2C1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-neopentylacetamide (200.00 mg, 364.91 umol, HCl salt) in MeOH (2.00 mL) was added TEA (73.85 mg, 729.82 umol, 101.17 uL). The mixture was stirred at 15° C. for 10 min. Then to the mixture was added acetone (84.78 mg, 1.46 mmol, 107.31 uL), HOAc (87.65 mg, 1.46 mmol, 83.48 uL). The mixture was stirred at 15° C. for 20 min. Then NaBH$_3$CN (114.65 mg, 1.82 mmol) was added. The mixture was stirred at 15° C. for another 15.5 h. LCMS showed one main peak of desired product. The reaction mixture was diluted with water (20 mL) and extracted with EtOAc (20 mL×3). The combined organic layers were dried over Na$_2$SO$_4$, filtered and concentrated under reduced pressure to give a residue. The residue was purified by prep-HPLC (FA conditions) to give the title compound (41.4 mg, 17%) as a yellow solid. $^1$H NMR (400 MHz, DMSO-d$_6$) δ 8.42 (s, 1H), 8.22 (s, 1H), 8.04 (s, 2H), 7.95 (t, J=6.8 Hz, 1H), 7.91-7.90 (m, 2H), 7.76 (d, J=8.8 Hz, 2H), 7.64 (d, J=8.8 Hz, 2H), 7.38 (t, J=8.0 Hz, 1H), 7.05-7.03 (m, 1H), 4.59 (s, 2H), 3.60 (s, 2H), 2.96 (d, J=6.4 Hz, 3H), 2.80 (s, 4H), 1.15 (d, J=6.8 Hz, 6H), 0.79 (s, 9H). (ES+) m/e 554.2 (M+H)$^+$.

Example 170

2-(3-(4-((4-(1H-pyrazol-4-yl)phenyl)amino)-6-ethyl-5,6,7,8-tetrahydropyrido[4,3-d]pyrimidin-2-yl)phenoxy)-N-neopentylacetamide

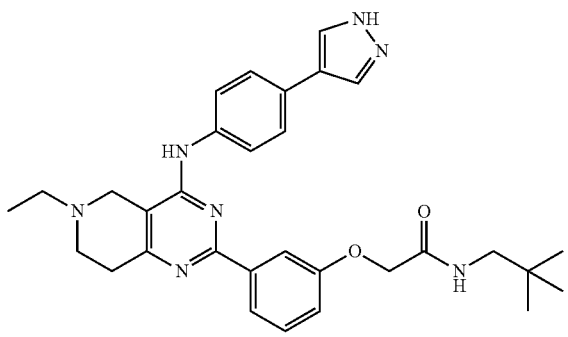 [SMILES: CCN1CCc2nc(-c3cccc(OCC(=O)NCC(C)(C)C)c3)nc(Nc3ccc(-c4cn[nH]c4)cc3)c2C1]

To the mixture of 2-(3-(4-((4-(1H-pyrazol-4-yl)phenyl)amino)-5,6,7,8-tetrahydropyrido[4,3-d]pyrimidin-2-yl)phenoxy)-N-neopentylacetamide (200.00 mg, 364.91 umol, HCl salt) in MeOH (2.00 mL) was added TEA (73.85 mg, 729.82 umol, 101.17 uL). The mixture was stirred at 20° C. for 10 min. Then to the mixture was added acetaldehyde (160.74 mg, 1.46 mmol, 203.47 uL, 40% purity), HOAc (87.65 mg, 1.46 mmol, 83.48 uL). The mixture was stirred at 20° C. for 20 min. Then NaBH$_3$CN (114.65 mg, 1.42 mmol) was added. The reaction mixture was diluted with water (20 mL) and extracted with EtOAc (20 mL×3). The combined organic layers were dried over Na$_2$SO$_4$, filtered and concentrated under reduced pressure to give a residue. The residue was dissolved with CH$_2$Cl$_2$ (5 mL). To the mixture was added HCl/dioxane (4 N, 5 mL) and the mixture was stirred at 20° C. for 1 h. LCMS showed about 51% of the desired product. The mixture was concentrated to afford a which was purified by prep-HPLC (FA conditions) to give the title compound (15.3 mg, 7.1%) as a yellow solid. $^1$H NMR (400 MHz, DMSO-d$_6$) δ 8.43 (s, 1H), 8.23 (s, 1H), 8.04 (s, 2H), 7.95 (t, J=6.0 Hz, 1H), 7.91-7.90 (m, 2H), 7.76 (d, J=8.8 Hz, 2H), 7.63 (d, J=8.4 Hz, 2H), 7.38 (t, J=8.0 Hz, 1H), 7.06-7.03 (m, 1H), 4.59 (s, 2H), 3.52 (s, 2H), 2.95 (d, J=6.8 Hz, 2H), 2.82-2.77 (m, 4H), 2.66-2.61 (m, 2H), 1.18 (t, J=7.2 Hz, 3H), 0.79 (s, 9H). (ES+) m/e 540.2 (M+H)$^+$.

Example 171

N-(3-(4-((4-(1H-pyrazol-4-yl)phenyl)amino)-5,7-dihydrofuro[3,4-d]pyrimidin-2-yl)phenyl)-2-morpholinopropanamide

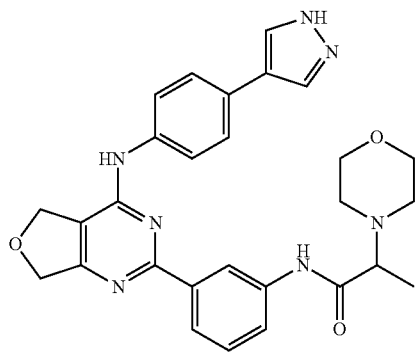 [SMILES: CC(C(=O)Nc1cccc(-c2nc3c(c(Nc4ccc(-c5cn[nH]c5)cc4)n2)COC3)c1)N1CCOCC1]

To N-(4-(1H-pyrazol-4-yl)phenyl)-2-chloro-5,7-dihydrofuro[3,4-d]pyrimidin-4-amine (24 mg, 0.078 mmol) in a 10 mL microwave vessel was added 2-morpholino-N-(3-(4,4,5,5-tetramethyl-1,3,2-dioxaborolan-2-yl)phenyl)propanamide (28 mg, 0.078 mmol), 1,4-dioxane (0.78 mL), a solution of sodium carbonate in water (2M, 0.080 mL), and water (0.078 mL). The vessel was flushed with nitrogen then Pd(PPh$_3$)$_4$ (9 mg, 0.0078 mmol, 10 mol %) was added and the vessel was under microwave irradiation at 180° C. for 2 h after which LC-MS of the reaction showed the desired product mass was present along with some of the starting boronic ester. The reaction mixture was transferred to a 20 mL vial with addition of dioxane and the solvent was removed in vacuo. Then water was added to the residue and the material was filtered to give a grey gummy residue. After being left on the filter for at least 30 min, the residue was dissolved in a 10:1 DMSO/MeOH solution (1.65 mL) then filtered through a 0.45 μm syringe filter. HPLC (10% A 90% B to 100% A where A is water with 0.1% TFA and B is MeCN with 0.1% TFA) gave 11.8 mg of the product as a sticky TFA salt. This material was converted into its HCl salt by dissolving the TFA salt in THF (2 mL) and adding 4.0 M HCl in dioxane (0.039 mL, 10 eq.). The mixture was stirred for 10 min then it was centrifuged in a Genevac and the supernatant was pipetted off. The remaining solid was dried in vacuo to give 5.1 mg, 11%, of the title compound as a yellow solid. $^1$H NMR (400 MHz, DMSO-d$_6$) δ 11.02 (s, 1H), 10.66 (s, 1H), 9.32 (d, J=6.1 Hz, 1H), 8.75 (dt, J=3.8, 1.9 Hz, 1H), 8.12 (d, J=7.7 Hz, 1H), 8.06 (s, 1H), 7.90-7.83 (m, 2H), 7.77 (dd, J=8.1, 2.4 Hz, 1H), 7.70-7.65 (m, 2H), 7.52 (t, J=7.9 Hz, 1H), 5.10 (s, 2H), 4.96 (d, J=2.5 Hz, 2H), 4.20 (s, 1H), 4.08-3.17 (m, 8H), 1.62 (d, J=6.9 Hz, 3H). MS (ES+) m/e 512 (M+H)$^+$.

Example 172

N-(3-(4-((4-(1H-pyrazol-4-yl)phenyl)aminoguro[3,2-d]pyrimidin-2-yl)phenyl)-2-morpholinopropanamide

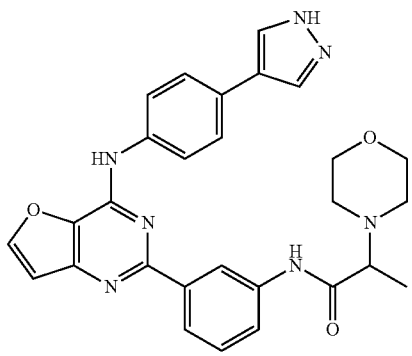 [SMILES: CC(C(=O)Nc1cccc(-c2nc(Nc3ccc(-c4cn[nH]c4)cc3)c3occc3n2)c1)N1CCOCC1]

To N-(4-(1H-pyrazol-4-yl)phenyl)-2-chlorofuro[3,2-d]pyrimidin-4-amine (24 mg, 0.078 mmol) in a 10 mL microwave vessel was added 2-morpholino-N-(3-(4,4,5,5-tetramethyl-1,3,2-dioxaborolan-2-yl)phenyl)propanamide (28 mg, 0.078 mmol), 1,4-dioxane (0.78 mL), a solution of sodium carbonate in water (2M, 0.080 mL), and water (0.078 mL). The vessel was flushed with nitrogen then Pd(PPh$_3$)$_4$ (9 mg, 0.0078 mmol, 10 mol %) was added to the vessel and the vessel was irradiated in the microwave (CEM) at 180° C. for 2 h after which LC-MS of the reaction showed the desired product mass was present along with some of the starting boronic ester. The reaction mixture was transferred to a 20 mL vial with addition of dioxane (there was a grey solid stuck to the inside of the vessel that was not transferred to the 20 mL vial) and the solvent was removed in vacuo. Then water was added to the residue and the material was filtered to give a solid. After being left on the filter for at least 30 min, the solid was dissolved in a 10:1 DMSO/MeOH solution (1.65 mL) then filtered through a 0.45 µm syringe filter. HPLC (10% A 90% B to 100% A where A is water with 0.1% TFA and B is MeCN with 0.1% TFA) gave 30.3 mg of the product as a sticky TFA salt. This material was converted into its HCl salt by dissolving the TFA salt in THF (2 mL) and adding 4.0 M HCl in dioxane (0.103 mL, 10 eq.). The mixture was stirred for 10 min then it was centrifuged in a Genevac and the supernatant was pipetted off. The remaining solid was dried in vacuo to give 25.1 mg, 55%, of the title compound as a dark yellow solid. $^1$H NMR (500 MHz, DMSO-d$_6$) δ 11.11 (s, 1H), 10.81 (s, 1H), 10.23 (s, 1H), 8.81 (t, J=1.9 Hz, 1H), 8.46 (d, J=2.2 Hz, 1H), 8.16 (dt, J=7.7, 1.3 Hz, 1H), 8.09 (s, 2H), 8.03-7.98 (m, 2H), 7.75 (dd, J=8.5, 2.2 Hz, 1H), 7.72-7.66 (m, 2H), 7.53 (t, J=7.9 Hz, 1H), 7.18 (d, J=2.2 Hz, 1H), 4.81-3.12 (m, 9H), 1.64 (d, J=6.9 Hz, 3H). MS (ES+) m/e 510 (M+H)$^+$.

Example 173

N-(3-(4-((4-(1H-pyrazol-4-yl)phenyl)amino)thieno[3,2-d]pyrimidin-2-yl)phenyl)-2-morpholinopropanamide

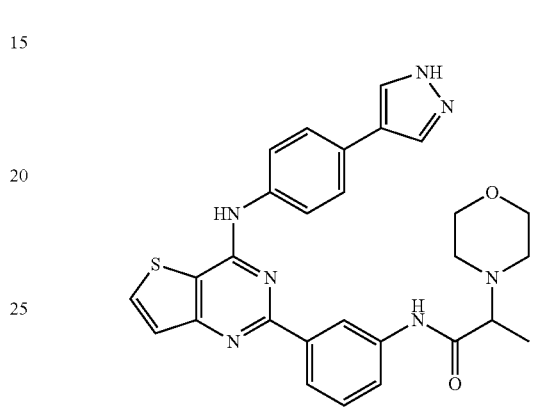

To N-(4-(1H-pyrazol-4-yl)phenyl)-2-chlorothieno[3,2-d]pyrimidin-4-amine (25.5 mg, 0.078 mmol) in a 10 mL microwave vessel was added 2-morpholino-N-(3-(4,4,5,5-tetramethyl-1,3,2-dioxaborolan-2-yl)phenyl)propanamide (28 mg, 0.078 mmol), 1,4-dioxane (0.78 mL), a solution of sodium carbonate in water (2M, 0.080 mL), and water (0.078 mL). The vessel was flushed with nitrogen then Pd(PPh$_3$)$_4$ (9 mg, 0.0078 mmol, 10 mol %) was added to the vessel and the vessel was irradiated at 180° C. for 2 h after which LC-MS of the reaction showed the desired product mass was present along with some of the starting boronic ester. The reaction mixture was transferred to a 20 mL vial with addition of dioxane and the solvent was removed in vacuo, while resulting yellow solid left on the inside of the microwave vial was transferred out and treated separately. Then water was added to the residue and the material was filtered to give a solid. After being left on the filter for at least 30 min, the solid was dissolved in a 10:1 DMSO/MeOH solution (1.65 mL) then filtered through a 0.45 mm syringe filter. HPLC (10% A 90% B to 100% A where A is water with 0.1% TFA and B is MeCN with 0.1% TFA) gave 27 mg of the product as a sticky TFA salt. HCl salt was generated by dissolving the TFA salt in a solution of THF/MeOH (4:1, 2.5 mL total volume) and adding 4.0 M HCl in dioxane (0.090 mL, 10 eq.). The mixture was stirred for 10 min then it was centrifuged in a Genevac and the supernatant was pipetted off. The remaining solid was dried in vacuo to give 16.4 mg, 35%, of the title compound as a yellow solid. $^1$H NMR (400 MHz, DMSO-d$_6$) δ 11.15 (s, 1H), 10.82 (s, 1H), 10.21 (s, 1H), 8.80 (t, J=2.0 Hz, 1H), 8.34 (d, J=5.2 Hz, 1H), 8.19 (dt, J=7.8, 1.3 Hz, 1H), 8.11 (s, 2H), 7.92 (d, J=8.1 Hz, 2H), 7.80

(dd, J=8.0, 2.3 Hz, 1H), 7.75-7.69 (m, 2H), 7.62-7.52 (m, 2H), 4.62-2.94 (m, 9H), 1.63 (d, J=6.9 Hz, 3H). MS (ES+) m/e 526 (M+H)+.

Example 174

N-(3-(4-((4-(1H-pyrazol-4-yl)phenyl)amino)thieno[3,2-d]pyrimidin-2-yl)phenyl)isonicotinamide

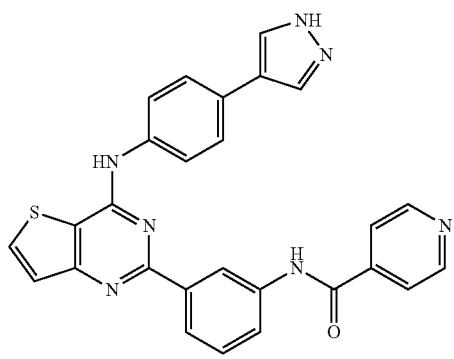 [SMILES: O=C(Nc1cccc(-c2nc(Nc3ccc(-c4cn[nH]c4)cc3)c3sccc3n2)c1)c1ccncc1]

Example 174A

N-(3-(4,4,5,5-tetramethyl-1,3,2-dioxaborolan-2-yl)phenyl)isonicotinamide

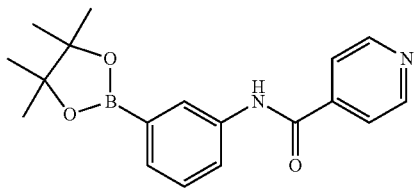 [SMILES: CC1(C)OB(c2cccc(NC(=O)c3ccncc3)c2)OC1(C)C]

To a mixture of 3-aminophenylboronic acid pinacol ester (43 mg, 0.20 mmol) in a 1-dram vial was added dry CHCl$_3$ (0.80 mL) followed by nicotinyl chloride hydrochloride (37 mg, 0.21 mmol) followed by TEA (64 mg, 0.088 mL, 0.63 mmol) dropwise at rt. The reaction mixture was stirred overnight at rt. LCMS showed one peak for the desired product mass. The reaction mixture was diluted with water and extracted with EtOAc. The aqueous layer was separated and extracted once with EtOAc. The organic layers were combined, dried over sodium sulfate, decanted from the drying agent, and concentrated in vacuo to give dark yellow oil. This oil was dissolved in DCM and subjected to column chromatography on silica gel to give 39.7 mg, 62%, of the title compound as a yellow oil. MS (ES+) m/e 325 (M+H)+.

Example 174B

N-(3-(4-((4-(1H-pyrazol-4-yl)phenyl)amino)thieno[3,2-d]pyrimidin-2-yl)phenyl)isonicotinamide

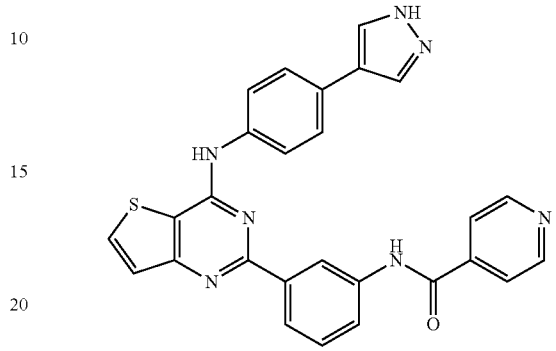

To a solution of N-(3-(4,4,5,5-tetramethyl-1,3,2-dioxaborolan-2-yl)phenyl)isonicotinamide (20 mg, 0.061 mmol) in dioxane (0.61 mL) in a 10-mL microwave vials was added N-(4-(1H-pyrazol-4-yl)phenyl)-2-chlorothieno[3,2-d]pyrimidin-4-amine (20 mg, 0.061 mmol), a solution of sodium carbonate (13 mg, 0.12 mmol) in water (0.061 mL), and water (0.061 mL). The vessel was flushed with nitrogen then Pd(PPh$_3$)$_4$ (7.5 mg, 0.0061 mmol, 10 mol %) was added to the vessel and the vessel was irradiated in the microwave at 180° C. for 2 h then cooled to rt. LC-MS of the reaction showed one peak corresponding to the desired product mass in the reaction. The reaction mixture was transferred to a separate 20-mL vial with the addition of dioxane then concentrated in vacuo to give a residue. The residue was diluted with water and the resulting solid was filtered, washed with water, and dried on the filter. The crude material was dissolved in DMSO/MeOH (10:1, total volume 2.2 mL) and subjected to HPLC (10% B 90% A to 100% B where A is water with 0.1% TFA and B is MeCN with 0.1% TFA with a gradient time of 13 min and a run time of 15 min). There yielded 14 mg of the product as a sticky TFA salt. This salt was converted to the HCl salt by dissolving the material in THF (2 mL) and adding 10 eq of 4.0 M HCl in dioxane (0.0487 mL) and stirring for 15 minutes. Hexanes were added and the suspension was centrifuged in a Genevac and the supernatant was pipetted off. The residue left in the vial was dried in vacuo for 3 h. There yielded 6.7 mg, 20%, of the title compound as a rust-colored solid. $^1$H NMR (400 MHz, DMSO-d$_6$) δ 10.86 (s, 1H), 9.29 (d, J=2.2 Hz, 1H), 8.94 (t, J=2.0 Hz, 1H), 8.88 (ddd, J=12.2, 5.1, 1.6 Hz, 1H), 8.59 (dt, J=8.1, 1.9 Hz, 1H), 8.37 (d, J=5.4 Hz, 1H), 8.17 (dt, J=7.8, 1.3 Hz, 1H), 8.10 (s, 2H), 7.98-7.88 (m, 3H), 7.80-7.68 (m, 4H), 7.64-7.53 (m, 2H), 7.39 (dd, J=8.5, 7.4 Hz, 1H). MS (ES+) m/e 490 (M+H)+.

Example 175

N-(3-(4-((4-(1H-pyrazol-4-yl)phenyl)amino)-5,7-dihydrofuro[3,4-d]pyrimidin-2-yl)phenyl)isonicotinamide

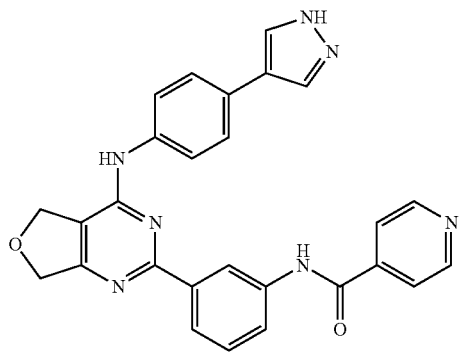 [SMILES: O=C(Nc1cccc(-c2nc3c(c(Nc4ccc(-c5cn[nH]c5)cc4)n2)COC3)c1)c1ccncc1]

This compound was made in a similar manner to Example 4C using N-(3-(4,4,5,5-tetramethyl-1,3,2-dioxaborolan-2-yl)phenyl)isonicotinamide (20 mg, 0.061 mmol) in dioxane (0.61 mL), N-(4-(1H-pyrazol-4-yl)phenyl)-2-chloro-5,7-dihydrofuro[3,4-d]pyrimidin-4-amine (19 mg, 0.061 mmol), a solution of sodium carbonate (13 mg, 0.12 mmol) in water (0.061 mL), and water (0.061 mL), Pd(PPh$_3$)$_4$ (7.0 mg, 0.0061 mmol, 10 mol %), and 4.0M HCl in dioxane (0.0394 mL, for HCl salt formation from the TFA salt) to give 6.6 mg, 20%, of the title compound as a golden yellow solid. $^1$H NMR (400 MHz, DMSO-d$_6$) δ 10.78 (s, 1H), 9.37 (s, 1H), 9.28 (d, J=2.1 Hz, 1H), 8.90-8.86 (m, 2H), 8.59 (d, J=8.0 Hz, 1H), 8.12 (dt, J=7.8, 1.3 Hz, 1H), 8.07 (s, 2H), 7.96 (dd, J=8.0, 2.1 Hz, 1H), 7.88 (dd, J=8.5, 6.1 Hz, 2H), 7.79 (dd, J=8.1, 5.1 Hz, 1H), 7.71-7.65 (m, 2H), 7.54 (t, J=8.0 Hz, 1H), 5.10 (t, J=2.5 Hz, 2H), 4.98 (t, J=2.5 Hz, 2H). MS (ES+) m/e 476 (M+H)$^+$.

Example 176

N-(3-(4-((4-(1H-pyrazol-4-yl)phenyl)amino)thieno[3,2-d]pyrimidin-2-yl)phenyl)picolinamide

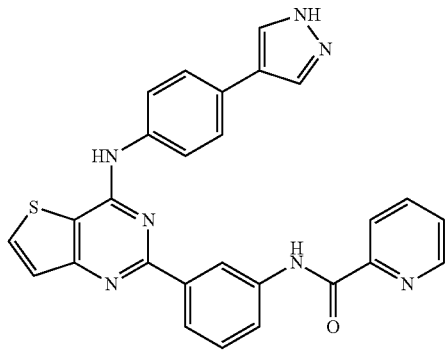 [SMILES: O=C(Nc1cccc(-c2nc(Nc3ccc(-c4cn[nH]c4)cc3)c3sccc3n2)c1)c1ccccn1]

Example 176A

N-(3-(4,4,5,5-tetramethyl-1,3,2-dioxaborolan-2-yl)phenyl)picolinamide

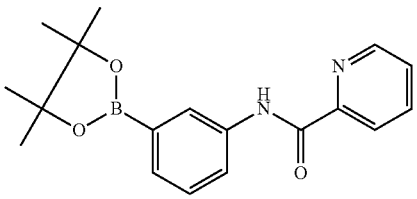 [SMILES: CC1(C)OB(c2cccc(NC(=O)c3ccccn3)c2)OC1(C)C]

To a solution of 3-aminophenylboronic acid pinacol ester, (110 mg, 0.50 mmol) and B, 2-picolinic acid, (65 mg, 0.53 mmol) in dry DMF (2.5 mL) was added TEA (152 mg, 1.51 mmol, 0.21 mL) followed by HATU (191 mg, 0.50 mmol) at rt. The mixture was stirred overnight at rt then checked by LC-MS. The desired product mass was not observed by LC-MS, but TLC showed that the starting boronic ester was consumed and a new spot formed. The reaction mixture was diluted with water and extracted with EtOAc. The aqueous layer was separated and extracted with EtOAc once. The combined organic layers were washed with water twice, dried over sodium sulfate, decanted from the drying agent, and concentrated in vacuo to give yellow oil. The oil was dissolved in DCM and loaded onto a silica gel column. Column chromatography (Hexanes to EtOAc gradient) gave 85 mg, 52% of the title compound as a white solid. $^1$H NMR (400 MHz, DMSO-d$_6$) δ 10.82 (s, 1H), 10.05 (s, 1H), 9.12 (t, J=2.0 Hz, 1H), 8.78 (dt, J=4.7, 1.3 Hz, 1H), 8.32 (d, J=5.4 Hz, 1H), 8.26-8.23 (m, 1H), 8.18-8.04 (m, 5H), 7.94 (d, J=8.1 Hz, 3H), 7.77-7.69 (m, 3H), 7.61-7.51 (m, 2H). MS (ES+) m/e 325 (M+H)$^+$.

Example 176B

N-(3-(4-((4-(1H-pyrazol-4-yl)phenyl)amino)thieno[3,2-d]pyrimidin-2-yl)phenyl)picolinamide

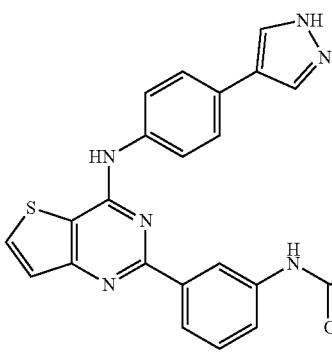

To a solution of N-(3-(4,4,5,5-tetramethyl-1,3,2-dioxaborolan-2-yl)phenyl)picolinamide (20 mg, 0.062 mmol) in dioxane (0.62 mL) in a 10-mL microwave vial was added N-(4-(1H-pyrazol-4-yl)phenyl)-2-chlorothieno[3,2-d]pyrimidin-4-amine (20 mg, 0.062 mmol), a solution of sodium carbonate (13 mg, 0.12 mmol) in water (0.061 mL), and water (0.062 mL). The vessel was flushed with nitrogen then Pd(PPh₃)₄ (7.1 mg, 0.0062 mmol, 10 mol %) was added to the vessel and the vessel was irradiated in the microwave at 180° C. for 2 h. LC-MS showed one peak for the desired product mass of the product. The reaction mixture was transferred to a 20-mL vial with the addition of dioxane and concentrated down in vacuo. Water was added to the residue yielding an orange solid. The solid was filtered and washed with water and dried on the filter then dissolved in DMSO/MeOH (15:1, 3.2 mL total volume). HPLC (10% B 90% A to 100% B where A is water with 0.1% TFA and B is MeCN with 0.1% TFA) gave 19.9 mg, 45%, of the title compound as a yellow solid. ¹H NMR (500 MHz, DMSO-d6) δ 10.82 (s, 1H), 10.05 (b, 1H), 9.12 (t, J=Hz, 1H), 8.78 (dt, J=Hz, Hz, 1H), 8.31 (d, J=Hz, 1H), 8.26 (dd, J=Hz, Hz, 1H), 8.17-8.06 (m, 4H), 7.96-7.91 (m, 3H), 7.75-7.70 (m, 3H), 7.60-7.53 (m, 2H). MS (ES+) m/e 490 (M+H)+.

Example 177

N-(3-(4-((4-(1H-pyrazol-4-yl)phenyl)amino)-5,7-dihydrofuro[3,4-d]pyrimidin-2-yl)phenyl)picolinamide

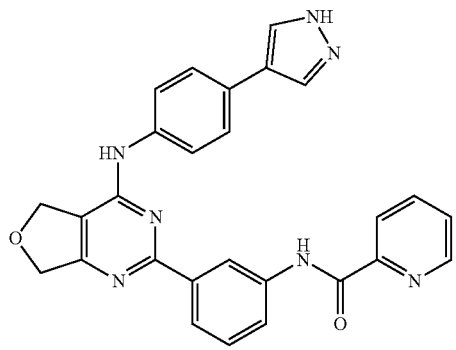 [SMILES: O=C(Nc1cccc(-c2nc3c(c(Nc4ccc(-c5cn[nH]c5)cc4)n2)COC3)c1)c1ccccn1]

To a solution of N-(3-(4,4,5,5-tetramethyl-1,3,2-dioxaborolan-2-yl)phenyl)picolinamide (20 mg, 0.062 mmol) in dioxane (0.62 mL) in a 10-mL microwave vials was added N-(4-(1H-pyrazol-4-yl)phenyl)-2-chloro-5,7-dihydrofuro[3,4-d]pyrimidin-4-amine (19 mg, 0.062 mmol), a solution of sodium carbonate (13 mg, 0.12 mmol) in water (0.061 mL), and water (0.062 mL). The vessel was flushed with nitrogen then Pd(PPh₃)₄ (7.1 mg, 0.0062 mmol, 10 mol %) was added to the vessel and the vessel was irradiated in the microwave at 180° C. for 2 h. LC-MS showed one peak for the desired product mass. The reaction mixture was transferred to a 20-mL vial with the addition of dioxane and concentrated down in vacuo. Water was added to the residue yielding dark grey sticky gum which was dissolved in DMSO/MeOH (15:1, total volume 3.2 mL). HPLC (10% B 90% A to 100% B where A is water with 0.1% TFA and B is MeCN with 0.1% TFA) gave 16.8 mg, 39%, of the title compound as a yellow solid. ¹H NMR (400 MHz, DMSO-d₆) δ 10.80 (s, 1H), 9.27 (s, 1H), 9.10 (t, J=1.9 Hz, 1H), 8.79-8.76 (m, 1H), 8.23 (d, J=7.8 Hz, 1H), 8.11 (td, J=7.8, 1.7 Hz, 2H), 8.05 (s, 2H), 7.94-7.85 (m, 3H), 7.73-7.66 (m, 3H), 7.50 (t, J=7.9 Hz, 1H), 5.10 (t, J=2.5 Hz, 2H), 4.98 (d, J=2.6 Hz, 2H). MS (ES+) m/e 476 (M+H)+.

Example 178

N-(3-(4-((4-(1H-pyrazol-4-yl)phenyl)amino)thieno[3,2-d]pyrimidin-2-yl)phenyl)nicotinamide

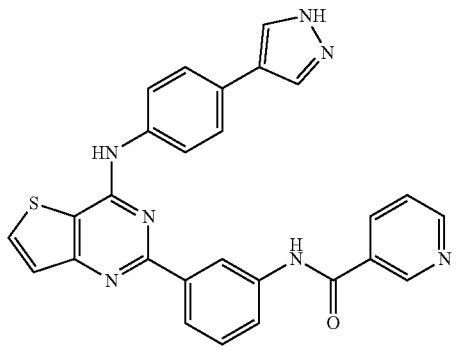 [SMILES: O=C(Nc1cccc(-c2nc(Nc3ccc(-c4cn[nH]c4)cc3)c3sccc3n2)c1)c1cccnc1]

This compound was made in a similar manner to Example 4C using N-(4-(1H-pyrazol-4-yl)phenyl)-2-chlorothieno[3,2-d]pyrimidin-4-amine (33 mg, 0.10 mmol) in dioxane (1 mL), N-(3-(4,4,5,5-tetramethyl-1,3,2-dioxaborolan-2-yl)phenyl)nicotinamide (32 mg, 0.10 mmol), a solution of sodium carbonate (21 mg, 0.20 mmol) in water (0.10 mL), and water (0.10 mL), Pd(PPh₃)₄ (12 mg, 0.010 mmol, 10 mol %) to give 19.3 mg, 27%, of the title compound as a yellow solid. MS (ES+) m/e 490 (M+H)+.

Example 179

2-(3-(4-((4-(1H-pyrazol-4-yl)phenyl)amino)thieno[3,2-d]pyrimidin-2-yl)phenoxy)-N-(3,3-difluorocyclobutyl)acetamide

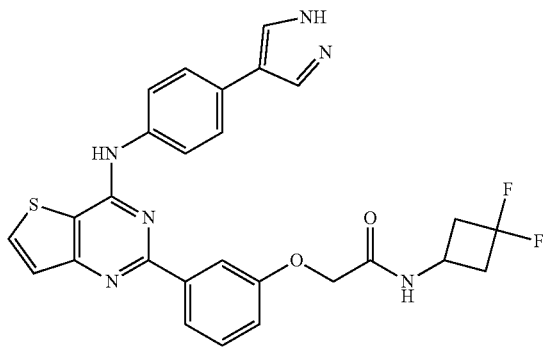 [SMILES: N=C/C(=C\N)c1ccc(Nc2nc(-c3cccc(OCC(=O)NC4CC(F)(F)C4)c3)nc3ccsc23)cc1]

Into a 10 mL microwave vessel was added N-(4-(1H-pyrazol-4-yl)phenyl)-2-chlorothieno[3,2-d]pyrimidin-4-amine (35 mg, 0.095 mmol) and 1,4-dioxane (0.95 mL). Then N-(3,3-difluorocyclobutyl)-2-(3-(4,4,5,5-tetramethyl-1,3,2-dioxaborolan-2-yl)phenoxy)acetamide (32 mg, 0.095 mmol) was added to the vessel followed by a solution of Na₂CO₃ (20.2 mg, 0.19 mmol) in water (0.095 mL) and water (0.095 mL). The vessel was flushed with nitrogen then Pd(PPh₃)₄ (11.6 mg, 0.0095 mmol) was added and the reaction mixture was irradiated at 180° C. for 2 h then checked by LC-MS. The LC-MS of the reaction showed a peak that corresponded to the desired product mass. The mixture was transferred to a 20-mL vial with the aid of dioxane and the solvent was removed in vacuo to give a residue. The residue was stirred with DMSO/MeOH (10:1, 2.75 mL total volume) for at least 30 min. HPLC (10% B 90% A to 100% B gradient where A is water (0.1% TFA) and B is MeCN (0.1% TFA)) gave 30.4 mg, 49%, of the title compound as a yellow solid. MS (ES+) m/e 533 (M+H)⁺.

Example 180

2-(3-(4-((4-(1H-pyrazol-4-yl)phenyl)amino)thieno[3,2-d]pyrimidin-2-yl)phenoxy)-N-cyclohexylacetamide

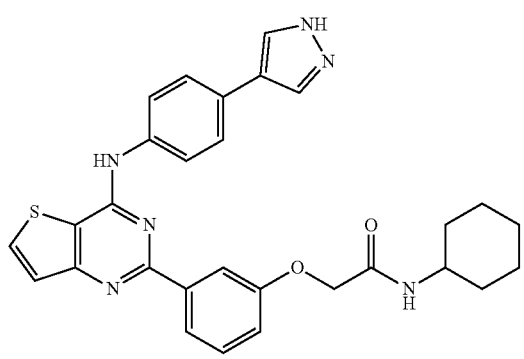 [SMILES: O=C(COc1cccc(-c2nc(Nc3ccc(-c4cn[nH]c4)cc3)c3sccc3n2)c1)NC1CCCCC1]

The title compound was made in a similar manner to Example 179 using N-(4-(1H-pyrazol-4-yl)phenyl)-2-chlorothieno[3,2-d]pyrimidin-4-amine (35 mg, 0.095 mmol), N-cyclohexyl-2-(3-(4,4,5,5-tetramethyl-1,3,2-dioxaborolan-2-yl)phenoxy)acetamide (34.2 mg, 0.095 mmol), water (0.10 mL), a solution of Na₂CO₃ (21.2 mg, 0.20 mmol) in water (0.10 mL), Pd(PPh₃)₄ (11.6 mg, 0.010 mmol), and 0.95 mL 1,4-dioxane to give 33.2 mg, 55%, of the title compound as a yellow solid. MS (ES+) m/e 525 (M+H)⁺.

Example 181

2-(3-(4-((4-(1H-pyrazol-4-yl)phenyl)amino)thieno[3,2-d]pyrimidin-2-yl)phenoxy)-N-(pentan-3-yl)acetamide

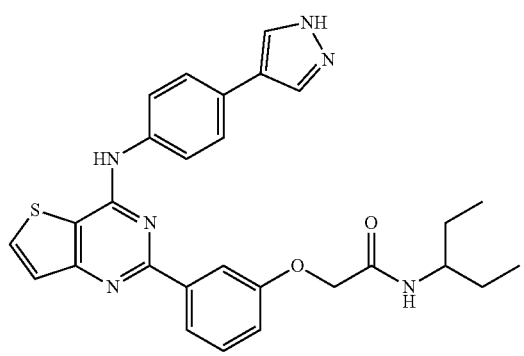 [SMILES: CCC(CC)NC(=O)COc1cccc(-c2nc(Nc3ccc(-c4cn[nH]c4)cc3)c3sccc3n2)c1]

The title compound was made in a similar manner to Example 179 using N-(4-(1H-pyrazol-4-yl)phenyl)-2-chlorothieno[3,2-d]pyrimidin-4-amine (35 mg, 0.095 mmol), N-(pentan-3-yl)-2-(3-(4,4,5,5-tetramethyl-1,3,2-dioxaborolan-2-yl)phenoxy)acetamide (33.1 mg, 0.095 mmol), water (0.10 mL), a solution of Na₂CO₃ (21.2 mg, 0.20 mmol) in water (0.10 mL), Pd(PPh₃)₄ (11.6 mg, 0.010 mmol), and 1,4-dioxane (0.95 mL) to give 26.7 mg, 5%, of the title compound as a yellow solid. MS (ES+) m/e 513 (M+H)⁺.

Example 182

2-((5-(4-((4-(1H-pyrazol-4-yl)phenyl)amino)thieno[2,3-d]pyrimidin-2-yl)pyridin-3-yl)oxy)-N-isopropylacetamide

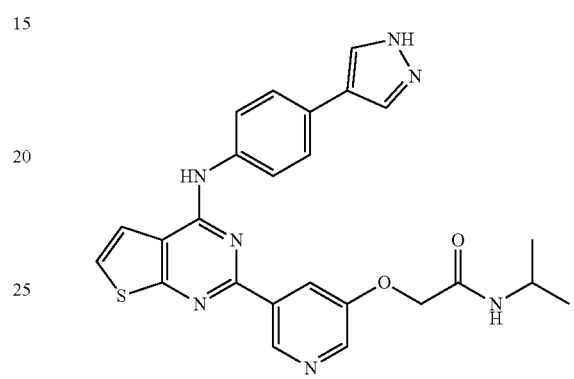

Example 182A 2-((5-bromopyridin-3-yl)oxy)-N-isopropylacetamide

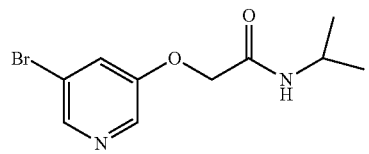

To a mixture of 3-bromo-5-hydroxypyridine (1.39 g, 8.00 mmol) and N-isopropyl-2-bromoacetamide (1.44 g, 8.00 mmol) in DMF (26.7 mL) was added Cs₂CO₃ (3.9 g, 12.00 mmol). The mixture was heated overnight at 50° C. and checked by LC-MS and TLC. LC-MS showed one major peak with the desired product mass. There were two minor peaks that had the same mass as the desired product. TLC showed one major spot and a few minor spots. No starting material was present according to the TLC. The reaction mixture was cooled to rt and poured into water. The aqueous mixture was extracted 3 times with EtOAc and the combined organic layers were washed with water twice. The organic solution was dried over sodium sulfate, decanted from the drying agent, and concentrated in vacuo to give dark red oil. The oil was loaded onto Celite and column chromatography (DCM to 10% MeOH/DCM gradient) to give the product which contained some starting bromide by LC-MS. The material was subjected to column chromatography again (silica gel, DCM to 10% MeOH/DCM gradient) to give 800 mg, 37%, of the title compound as a light yellow solid. MS (ES+) m/e 273/275 (M+H)⁺.

Example 182B

N-isopropyl-2-((5-(4,4,5,5-tetramethyl-1,3,2-dioxaborolan-2-yl)pyridin-3-yl)oxy)acetamide

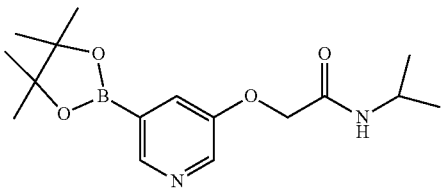 [SMILES: CC(C)NC(=O)COc1cncc(B2OC(C)(C)C(C)(C)O2)c1]

To a solution of 2-((5-bromopyridin-3-yl)oxy)-N-isopropylacetamide (1.12 g, 4.10 mmol) in 1,4-dioxane (21 mL) was added bis(pinacolato)diboron (1.25 g, 4.92 mmol), KOAc (1.70 g, 12.30 mmol) and PdCl$_2$(dppf) (150 mg, 0.21 mmol). The reaction was heated at 90° C. overnight then checked by LC-MS and TLC. LC-MS showed the starting bromide was consumed and a minor amount of the dimer of the starting bromide was present. None of the starting bromide was seen by TLC. The reaction mixture was cooled to rt and poured into water. The aqueous mixture was extracted with EtOAc three times and the combined organic layers were dried over sodium sulfate. After decanting the solution from the drying agent, it was concentrated in vacuo to give 1.74 g of dark brown oil. The oil was dissolved in DCM and loaded onto an 80 g silica gel column. The column was eluted with a gradient of DCM to 10% MeOH/DCM solvent. After about 35 min of elution, nothing had eluted from the column so the material on the column was recovered by washing the silica gel with 25% MeOH/DCM and EtOAc. The filtrate was concentrated to give back the title compound as brown oil containing multiple components by TLC. Column chromatography on a 20 mg sample (10% MeOH/DCM to 20% MeOH/DCM gradient) was unsuccessful in generating any pure compound. As such, the crude product was used directly used in the next step. MS (ES+) m/e 321 (M+H)$^+$.

Example 182C 2-((5-(4-((4-(1H-pyrazol-4-yl)phenyl)amino)thieno[2,3-d]pyrimidin-2-yl)pyridin-3-yl)oxy)-N-isopropylacetamide

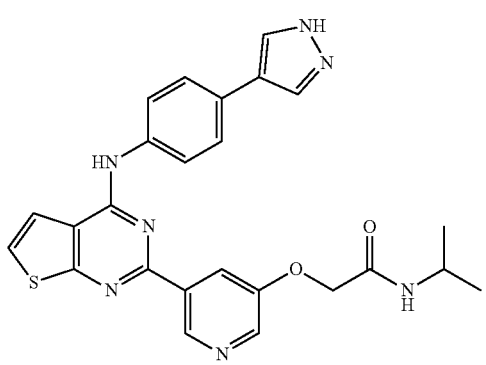 [SMILES: CC(C)NC(=O)COc1cncc(-c2nc(Nc3ccc(-c4cn[nH]c4)cc3)c3ccsc3n2)c1]

To N-(4-(1H-pyrazol-4-yl)phenyl)-2-chlorothieno[2,3-d]pyrimidin-4-amine (32.8 mg, 0.10 mmol) in a 10 mL microwave vessel was added crude N-isopropyl-2-((5-(4,4,5,5-tetramethyl-1,3,2-dioxaborolan-2-yl)pyridin-3-yl)oxy)acetamide from Example 13B (32 mg, 0.10 mmol), dioxane (1.0 mL), and a solution of sodium carbonate in water (2M, 0.10 mL). The vessel was flushed with nitrogen then Pd(PPh$_3$)$_4$ (11.5 mg, 0.10 mmol) was added to the vessel and the reaction mixture was irradiated in the microwave at 180° C. for 2 h. After the reaction was cooled to rt, the reaction was checked by LC-MS. There was one main peak in the LC-MS that corresponded to the mass of the desired product as well as additional peaks. The mixture was diluted with water and extracted with EtOAc twice. The combined organic layers were dried over sodium sulfate, decanted from the drying agent, and concentrated in vacuo to give 19 mg of a residue. The residue was dissolved in DMSO (1.1 mL). HPLC (10% B 90% A to 100% B gradient where A is water (0.1% TFA) and B is MeCN (0.1% TFA)) gave 3.4 mg, 5%, of the title compound as a yellow solid. MS (ES+) m/e 486 (M+H)$^+$.

Example 183

N-(3-(4-((4-(1H-pyrazol-4-yl)phenyl)amino)thieno[3,2-d]pyrimidin-2-yl)phenyl)-2-(4-methylpiperazin-1-yl)acetamide

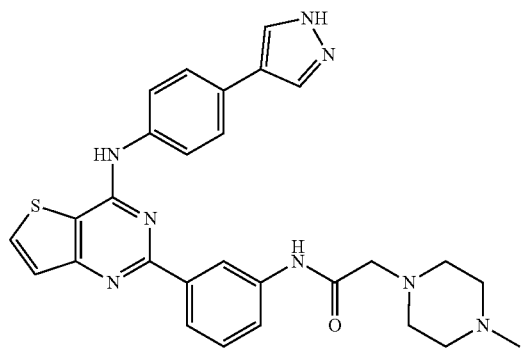

Example 183A 2-chloro-N-(3-(4,4,5,5-tetramethyl-1,3,2-dioxaborolan-2-yl)phenyl)acetamide

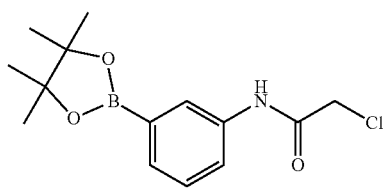 [SMILES: CC1(C)OB(c2cccc(NC(=O)CCl)c2)OC1(C)C]

To a mixture of 3-(4,4,5,5-tetramethyl-1,3,2-dioxaborolan-2-yl)aniline (548 mg, 2.50 mmol) in dry DCM (10 mL) was added TEA (278 mg, 2.75 mmol, 0.38 mL). The solution was cooled to 0° C. then chloroacetyl chloride (311 mg, 2.75 mmol, 0.219 mL) was added dropwise. The reaction mixture was stirred overnight for 2.5 d. TLC of the reaction mixture showed the starting aniline had been consumed. The reaction mixture was washed with 1 N HCl once then water twice and the combined aqueous washes were extracted once with DCM. The combined organic layers were dried over sodium sulfate, decanted from the drying agent, and concentrated in vacuo to give 705 mg, 95%, of the title compound as a tan solid. This crude material is used as is in the next reaction. MS (ES+) m/e 296/298 (M+H)$^+$.

Example 183B 2-(4-methylpiperazin-1-yl)-N-(3-(4,4,5,5-tetramethyl-1,3,2-dioxaborolan-2-yl)phenyl)acetamide

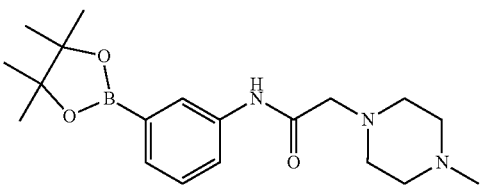

To a solution of 2-chloro-N-(3-(4,4,5,5-tetramethyl-1,3,2-dioxaborolan-2-yl)phenyl)acetamide (443 mg, 1.50 mmol) in dry MeCN (15 mL) in a 35-mL microwave vessel was added TEA (228 mg, 2.25 mmol, 0.313 mL) followed by 1-methylpiperazine (150 mg, 0.166 mL, 1.50 mmol). The solution was irradiated at 100° C. for 10 min after which point LC-MS showed one major peak that corresponded to the desired product mass. No starting boronic ester was seen in the LC-MS. The mixture was diluted with water and extracted with EtOAc. The aqueous layer was separated and extracted once with EtOAc. The combined organic layers were washed once with brine (this brine layer was not combined with the other aqueous layer), dried over sodium sulfate, decanted from the drying agent, and concentrated in vacuo to give 259 mg of an oil as the crude material. It was noticed that some of the desired product (as the boronic ester and the boronic acid) was present in the non-brine aqueous layer. This layer was concentrated in vacuo to give 500 mg of brown oil. The crude material from the organic layer was dissolved in DCM and loaded onto a silica gel column. Column chromatography (DCM to 20% MeOH/DCM gradient) gave 141 mg of light brown oil as the product. The brown oil from the non-brine aqueous layer was absorbed onto Celite and column chromatography (silica gel, DCM to 20% MeOH/DCM) gave 222 mg of beige solid. Total yield of the title compound is 363 mg, 67%. MS (ES+) m/e 360 (M+H)$^+$.

Example 183C

N-(3-(4-((4-(1H-pyrazol-4-yl)phenyl)amino)thieno[3,2-d]pyrimidin-2-yl)phenyl)-2-(4-methylpiperazin-1-yl)acetamide

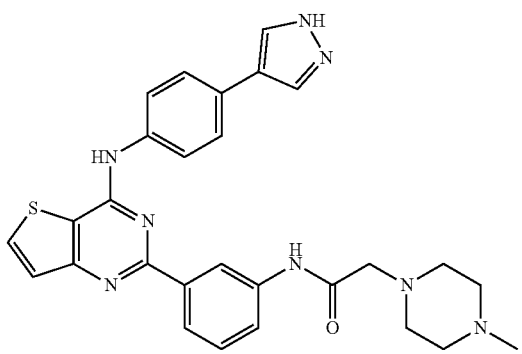 [SMILES: CN1CCN(CC(=O)Nc2cccc(-c3nc(Nc4ccc(-c5cn[nH]c5)cc4)c4sccc4n3)c2)CC1]

The title compound was made in a similar manner to Example 179 using N-(4-(1H-pyrazol-4-yl)phenyl)-2-chlorothieno[3,2-d]pyrimidin-4-amine (33 mg, 0.10 mmol), 2-chloro-N-(3-(4,4,5,5-tetramethyl-1,3,2-dioxaborolan-2-yl)phenyl)acetamide (36 mg, 0.10 mmol), a solution of Na$_2$CO$_3$ (21.2 mg, 0.20 mmol) in water (0.10 mmol), water (0.10 mmol), and Pd(PPh$_3$)$_4$ (12 mg, 0.010 mmol, 10 mol %) to give 22.9 mg, 26%, of the title compound as a yellow solid. MS (ES+) m/e 525 (M+H)$^+$.

Example 184

N-(3-(4-((4-(1H-pyrazol-4-yl)phenyl)amino)furo[3,2-d]pyrimidin-2-yl)phenyl)-2-(4-methylpiperazin-1-yl)acetamide

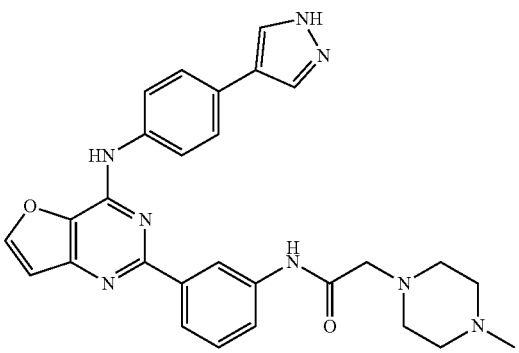 [SMILES: CN1CCN(CC(=O)Nc2cccc(-c3nc(Nc4ccc(-c5cn[nH]c5)cc4)c4occc4n3)c2)CC1]

The title compound was made in a similar manner to Example 179 using N-(4-(1H-pyrazol-4-yl)phenyl)-2-chlorofuro[3,2-d]pyrimidin-4-amine (31 mg, 0.10 mmol), 2-chloro-N-(3-(4,4,5,5-tetramethyl-1,3,2-dioxaborolan-2-yl)phenyl)acetamide (36 mg, 0.10 mmol), a solution of Na$_2$CO$_3$ (21.2 mg, 0.20 mmol) in water (0.10 mmol), water (0.10 mmol), and Pd(PPh$_3$)$_4$ (12 mg, 0.010 mmol, 10 mol %) to give 10.1 mg, 12%, of the title compound as a yellow solid. MS (ES+) m/e 509 (M+H)$^+$.

Example 185

2-(3-(4-((4-(1H-pyrazol-4-yl)phenyl)amino)-5,7-dihydrofuro[3,4-d]pyrimidin-2-yl)phenoxy)-N-isopropylpropanamide

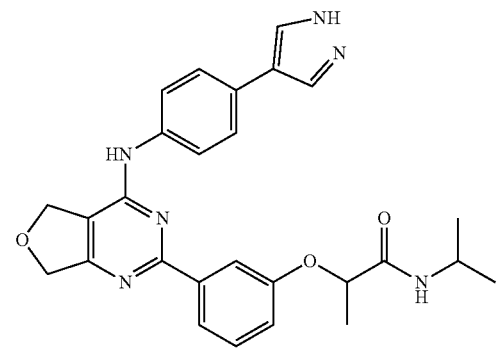 [SMILES: CC(C)NC(=O)C(C)Oc1cccc(-c2nc3c(c(Nc4ccc(/C(C=N)=C/N)cc4)n2)COC3)c1]

Example 185A 2-chloro-N-isopropylpropanamide

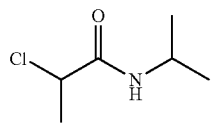

To a solution of isopropylamine (443 mg, 7.49 mmol, 0.644 mL) in dry THF (30 mL) was added TEA (834 mg, 8.24 mmol, 1.15 mL) at rt. The reaction mixture was cooled to 0° C. and 2-chloropropionyl chloride (1.05 g, 8.24 mmol, 0.80 mL) was added dropwise at the same temperature. Then the mixture was allowed to warm up to rt and stir for an additional 1.5 h. The reaction mixture was concentrated in vacuo and the residue was diluted with water and extracted with EtOAc. The aqueous layer was separated and extracted once with EtOAc. The combined organic layers were washed with 1 M aqueous HCl and saturated NaCl then dried over sodium sulfate. The solution was decanted from the drying agent and removed in vacuo to give the crude product. If the product is an oil or a semisolid, column chromatography (silica gel, Hexanes to EtOAc gradient) was carried out to afford the title compound otherwise the crude product was used as is in the next step. There was 1.14 g, 102%, of the crude title compound obtained as a white solid. MS (ES+) m/e 150/152 (M+H)$^+$.

Example 185B 2-(3-bromophenoxy)-N-isopropylpropanamide

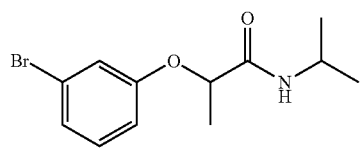 [SMILES: CC(C)NC(=O)C(C)Oc1cccc(Br)c1]

To a solution of 3-bromophenol (432 mg, 2.50 mmol, 0.265 mL) in DMF (8.3 mL) in a 20 mL vial was added K$_2$CO$_3$ (518 mg, 3.75 mmol) and the mixture was stirred for 15 min at rt. Then 2-chloro-N-isopropylpropanamide (374 mg, 2.5 mmol) was added to the reaction mixture. The mixture was then heated overnight at 70° C. and checked by LC-MS and TLC. LC-MS showed a peak in the reaction that corresponded to the desired product mass. TLC showed the starting phenol was still present. Heating of the reaction was continued for another 4 h after which the starting phenol was still present in each reaction. The reaction mixture was cooled to rt and worked up. Work up was done by pouring the reaction mixture into water and extracting the aqueous mixture with EtOAc. The aqueous layer was separated and extracted twice with EtOAc. The combined organic layers were washed once with saturated NaCl, dried over sodium sulfate, decanted from the drying agent, and concentrated in vacuo to give the crude product. The material was dissolved in DCM and column chromatography (Hexanes to EtOAc gradient) gave 338 mg, 47%, of the title compound as a solid. MS (ES+) m/e 286/288 (M+H)$^+$.

Example 185C

N-isopropyl-2-(3-(4,4,5,5-tetramethyl-1,3,2-dioxaborolan-2-yl)phenoxy)propanamide

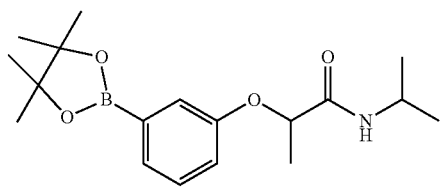 [SMILES: CC(C)NC(=O)C(C)Oc1cccc(B2OC(C)(C)C(C)(C)O2)c1]

A mixture of 2-(3-bromophenoxy)-N-isopropylpropanamide (338 mg, 1.18 mmol), bis(pinacolato)diboron (365 mg, 1.44 mmol), KOAc (497 mg, 3.60 mmol), PdCl$_2$(dppf) (44 mg, 0.060 mmol), and 1,4-dioxane (6 mL) was stirred at 90° C. for 18 h after which LC-MS showed all of the starting bromide was consumed and one major peak corresponding to the desired product mass. The mixture was diluted with water and extracted twice with EtOAc and the combined organic layers were dried over sodium sulfate, decanted from the drying agent, and concentrated in vacuo followed by column chromatography (Hexanes to EtOAc gradient) afforded the title compound (310 mg, 79%) as a beige solid. $^1$H NMR (400 MHz, DMSO-d$_6$) δ 7.98 (d, J=8.1 Hz, 1H), 7.33-7.22 (m, 2H), 7.16 (d, J=2.7 Hz, 1H), 7.03 (ddd, J=8.1, 2.8, 1.3 Hz, 1H), 4.62 (q, J=6.6 Hz, 1H), 3.87 (dp, J=8.2, 6.5 Hz, 1H), 1.40 (d, J=6.6 Hz, 3H), 1.28 (d, J=4.4 Hz, 12H), 1.09 (d, J=6.6 Hz, 3H), 1.02 (d, J=6.6 Hz, 3H). MS (ES+) m/e 334 (M+H)$^+$.

Example 185D 2-(3-(4-((4-(1H-pyrazol-4-yl)phenyl)amino)-5,7-dihydrofuro[3,4-d]pyrimidin-2-yl)phenoxy)-N-isopropylpropanamide

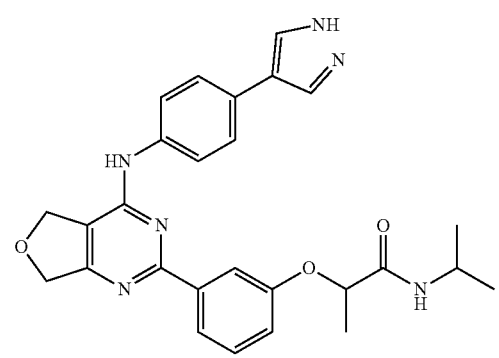 [SMILES: CC(C)NC(=O)C(C)Oc1cccc(-c2nc3c(c(Nc4ccc(/C(C=N)=C/N)cc4)n2)COC3)c1]

The title compound was made in a similar fashion to Example 179 using N-isopropyl-2-(3-(4,4,5,5-tetramethyl-1,3,2-dioxaborolan-2-yl)phenoxy)propanamide (50 mg, 0.150 mmol), N-(4-(1H-pyrazol-4-yl)phenyl)-2-chloro-5,7-dihydrofuro[3,4-d]pyrimidin-4-amine (47 mg, 0.150 mmol), water (0.15 mL), and a solution of Na$_2$CO$_3$ (31.8 mg, 0.300 mmol) in water (0.15 mL), Pd(PPh$_3$)$_4$ (17.3 mg, 0.0150 mmol), and dioxane (1.5 mL) to give 26.4 mg, 29%, of the title compound as a yellow solid. MS (ES+) m/e 485 (M+H)$^+$.

Example 186

2-(3-(4-((4-(1H-pyrazol-4-yl)phenyl)amino)-5,7-dihydrofuro[3,4-d]pyrimidin-2-yl)phenoxy)-N-isobutylpropanamide

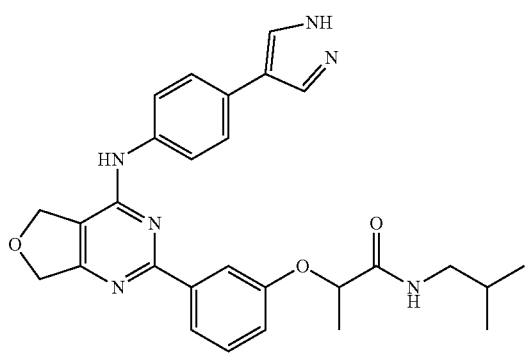 [SMILES: CC(C)CNC(=O)C(C)Oc1cccc(-c2nc3c(c(Nc4ccc(/C(C=N)=C/N)cc4)n2)COC3)c1]

The title compound was synthesized in a similar manner to Example 185 using the appropriate starting material and intermediates. MS (ES+) m/e 499 (M+H)+.

Example 187

2-(3-(4-((4-(1H-pyrazol-4-yl)phenyl)amino)-5,7-dihydrofuro[3,4-d]pyrimidin-2-yl)phenoxy)-N-(sec-butyl)propanamide

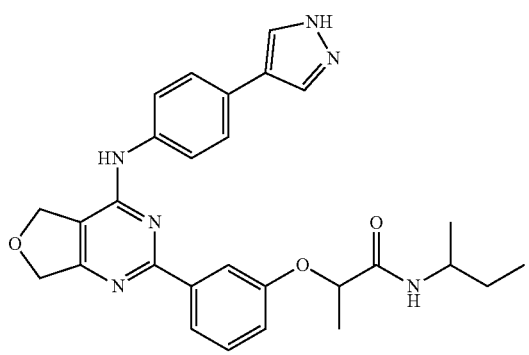 [SMILES: CCC(C)NC(=O)C(C)Oc1cccc(-c2nc3c(c(Nc4ccc(-c5cn[nH]c5)cc4)n2)COC3)c1]

The title compound was synthesized in a similar manner to Example 185 using the appropriate starting material and intermediates. MS (ES+) m/e 499 (M+H)+.

Example 188

2-(3-(4-((4-(1H-pyrazol-4-yl)phenyl)amino)-5,7-dihydrofuro[3,4-d]pyrimidin-2-yl)phenoxy)-N-(tert-butyl)propanamide

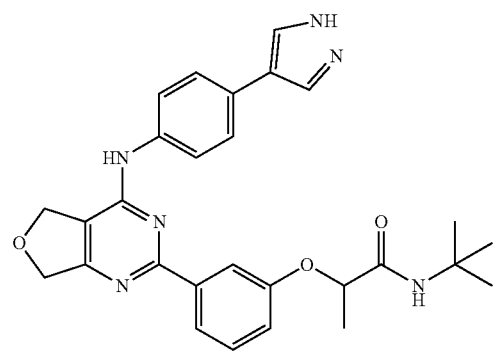 [SMILES: CC(Oc1cccc(-c2nc3c(c(Nc4ccc(/C(C=N)=C/N)cc4)n2)COC3)c1)C(=O)NC(C)(C)C]

The title compound was synthesized in a similar manner to Example 185 using the appropriate starting material and intermediates. MS (ES+) m/e 499 (M+H)+.

Example 189

2-(3-(4-((4-(1H-pyrazol-4-yl)phenyl)amino)-5,7-dihydrofuro[3,4-d]pyrimidin-2-yl)phenoxy)-N-neo-pentylpropanamide

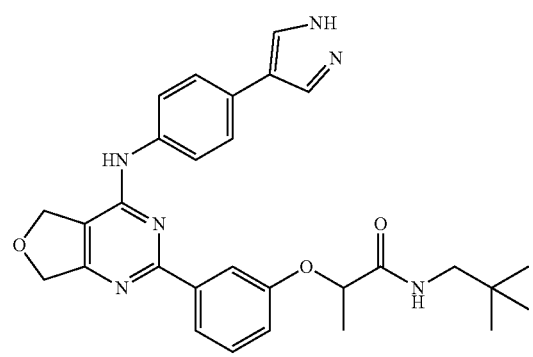 [SMILES: CC(Oc1cccc(-c2nc3c(c(Nc4ccc(/C(C=N)=C/N)cc4)n2)COC3)c1)C(=O)NCC(C)(C)C]

The title compound was synthesized in a similar manner to Example 185 using the appropriate starting material and intermediates. MS (ES+) m/e 513 (M+H)+.

Example 190

2-(3-(4-((4-(1H-pyrazol-4-yl)phenyl)amino)thieno[3,2-d]pyrimidin-2-yl)phenoxy)-N-(tert-pentyl)acetamide

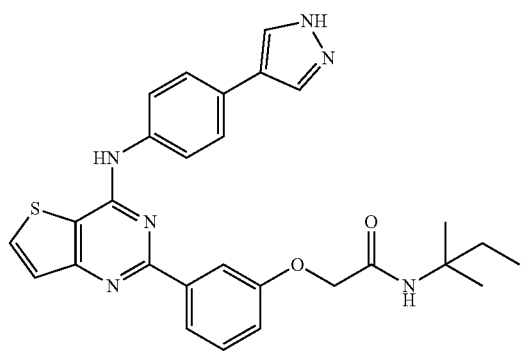 [SMILES: CCC(C)(C)NC(=O)COc1cccc(-c2nc(Nc3ccc(-c4cn[nH]c4)cc3)c3sccc3n2)c1]

The title compound was synthesized in a similar manner to Example 179. MS (ES+) m/e 513 (M+H)+.

Example 191 (Assays)

The combination of inhibitors of both oxidative phosphorylation and glycolysis synergistically suppress cellular ATP levels. Therefore, an assay was developed that utilizes the combination of the glucose uptake inhibitors disclosed herein with oligomycin, a well-characterized inhibitor of ATP synthase. Because oligomycin inhibits ATP derived from oxidative phosphorylation, any remaining ATP production is derived from glycolysis. By reading out cellular ATP levels using the Promega Cell Titer Glo kit, the extent of glycolysis inhibition by the glucose uptake inhibitors disclosed herein can be assessed. Note that neither oligomycin alone nor control GLUT1 inhibitors substantially decrease cellular ATP levels in HT1080 cells in one hour. When oligomycin and control GLUT1 inhibitor/glucose uptake inhibitors disclosed herein are combined, the two agents strikingly decrease cellular ATP levels in one hour. Utilizing this experimental set-up, the IC50 of glycolysis inhibition for each compound can be determined. The values for example compounds can be found in Table 1 (nM).

TABLE 1

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 1 | 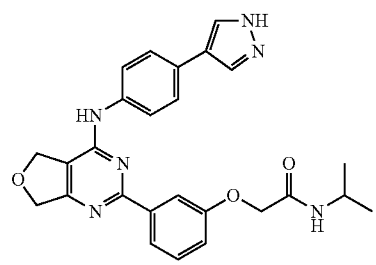 [SMILES: CC(C)NC(=O)COc1cccc(-c2nc3c(c(Nc4ccc(-c5cn[nH]c5)cc4)n2)COC3)c1] | A |
| Example 2 | 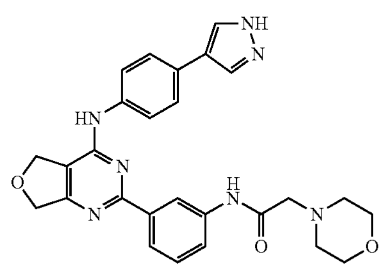 [SMILES: O=C(CN1CCOCC1)Nc1cccc(-c2nc3c(c(Nc4ccc(-c5cn[nH]c5)cc4)n2)COC3)c1] | E |
| Example 3 | 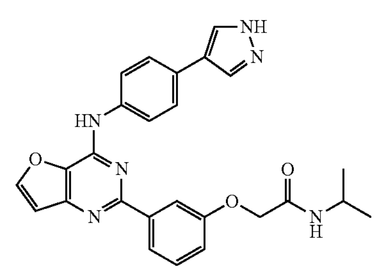 [SMILES: CC(C)NC(=O)COc1cccc(-c2nc(Nc3ccc(-c4cn[nH]c4)cc3)c3occc3n2)c1] | C |

TABLE 1-continued
Glycolysis IC50 values (nM)
| Example Number | Structure | Glycolysis IC50 A = 10-100 nM; B = 101-250 Nm; C = 251-500 nM; D = 501-1,000 nM; E = >1,000 nM |
|---|---|---|
| Example 4 | 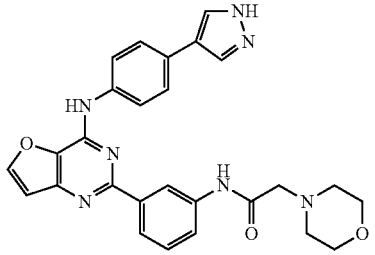 [SMILES: O=C(CN1CCOCC1)Nc1cccc(-c2nc(Nc3ccc(-c4cn[nH]c4)cc3)c3occc3n2)c1] | E |
| Example 5 | 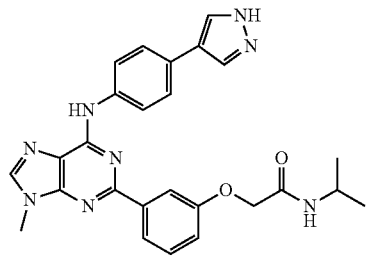 [SMILES: CC(C)NC(=O)COc1cccc(-c2nc(Nc3ccc(-c4cn[nH]c4)cc3)c3ncn(C)c3n2)c1] | C |
| Example 6 | 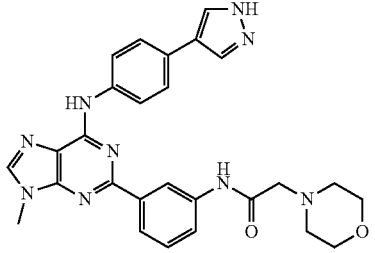 [SMILES: Cn1cnc2c(Nc3ccc(-c4cn[nH]c4)cc3)nc(-c3cccc(NC(=O)CN4CCOCC4)c3)nc21] | E |
| Example 7 | 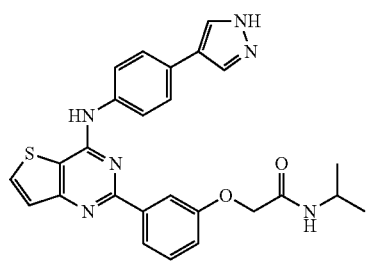 | A |
| Example 8 | 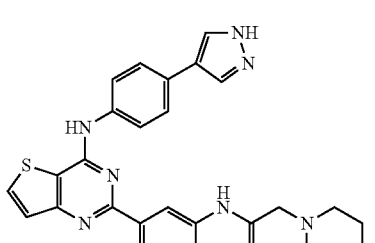 | E |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 9 | 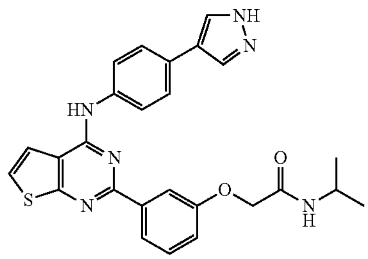 [SMILES: CC(C)NC(=O)COc1cccc(-c2nc(Nc3ccc(-c4cn[nH]c4)cc3)c3ccsc3n2)c1] | B |
| Example 10 | 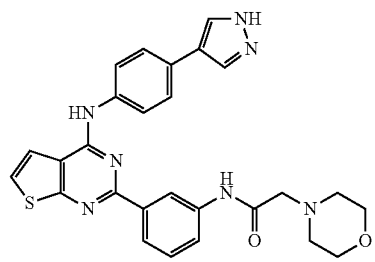 [SMILES: O=C(CN1CCOCC1)Nc1cccc(-c2nc(Nc3ccc(-c4cn[nH]c4)cc3)c3ccsc3n2)c1] | E |
| Example 11 | 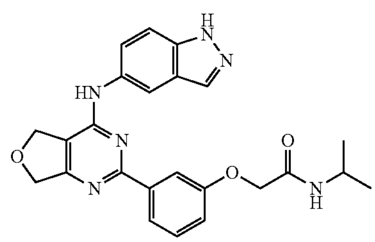 [SMILES: CC(C)NC(=O)COc1cccc(-c2nc3c(c(Nc4ccc5[nH]ncc5c4)n2)COC3)c1] | E |
| Example 12 | 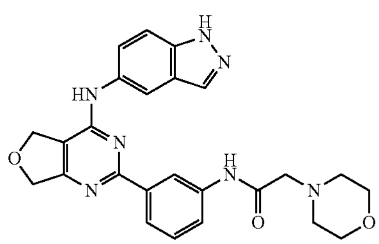 [SMILES: O=C(CN1CCOCC1)Nc1cccc(-c2nc3c(c(Nc4ccc5[nH]ncc5c4)n2)COC3)c1] | N.A |
| Example 13 | 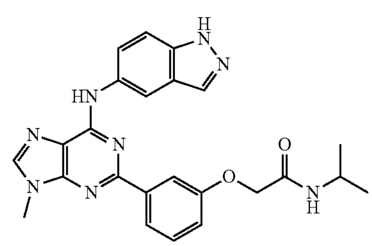 [SMILES: CC(C)NC(=O)COc1cccc(-c2nc(Nc3ccc4[nH]ncc4c3)c3ncn(C)c3n2)c1] | E |
| Example 14 | 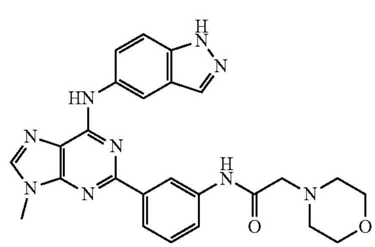 [SMILES: Cn1cnc2c(Nc3ccc4[nH]ncc4c3)nc(-c3cccc(NC(=O)CN4CCOCC4)c3)nc21] | E |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 15 | 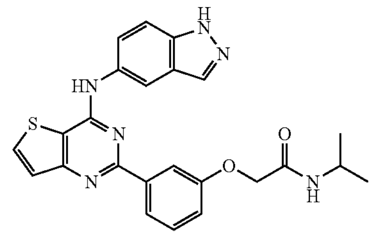 [SMILES: CC(C)NC(=O)COc1cccc(-c2nc(Nc3ccc4[nH]ncc4c3)c3sccc3n2)c1] | E |
| Example 16 | 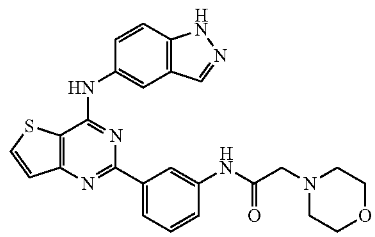 [SMILES: O=C(CN1CCOCC1)Nc1cccc(-c2nc(Nc3ccc4[nH]ncc4c3)c3sccc3n2)c1] | E |
| Example 17 | 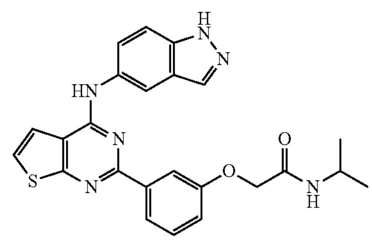 [SMILES: CC(C)NC(=O)COc1cccc(-c2nc(Nc3ccc4[nH]ncc4c3)c3ccsc3n2)c1] | E |
| Example 18 | 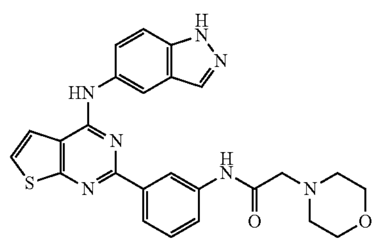 [SMILES: O=C(CN1CCOCC1)Nc1cccc(-c2nc(Nc3ccc4[nH]ncc4c3)c3ccsc3n2)c1] | E |
| Example 19 | 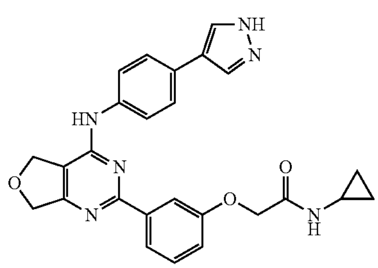 [SMILES: O=C(COc1cccc(-c2nc3c(c(Nc4ccc(-c5cn[nH]c5)cc4)n2)COC3)c1)NC1CC1] | D |
| Example 20 | 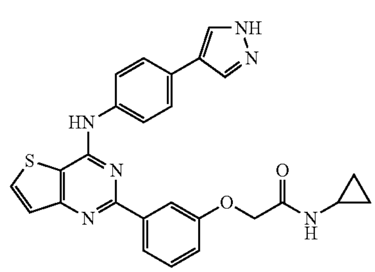 [SMILES: O=C(COc1cccc(-c2nc(Nc3ccc(-c4cn[nH]c4)cc3)c3sccc3n2)c1)NC1CC1] | D |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 21 | 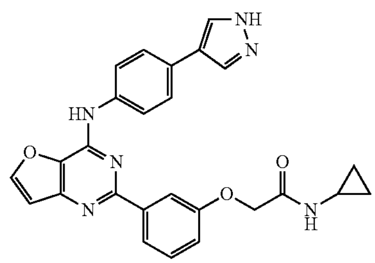 [SMILES: O=C(COc1cccc(-c2nc(Nc3ccc(-c4cn[nH]c4)cc3)c3occc3n2)c1)NC1CC1] | D |
| Example 22 | 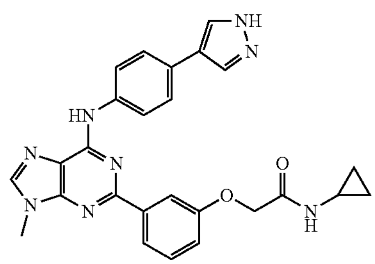 [SMILES: Cn1cnc2c(Nc3ccc(-c4cn[nH]c4)cc3)nc(-c3cccc(OCC(=O)NC4CC4)c3)nc21] | E |
| Example 23 | 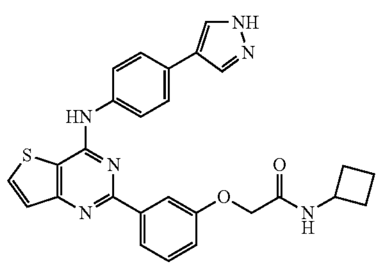 [SMILES: O=C(COc1cccc(-c2nc(Nc3ccc(-c4cn[nH]c4)cc3)c3sccc3n2)c1)NC1CCC1] | B |
| Example 24 | 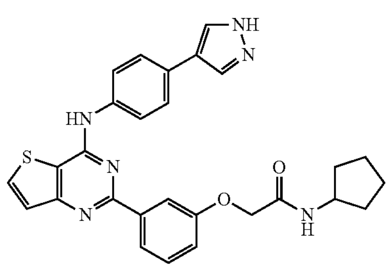 [SMILES: O=C(COc1cccc(-c2nc(Nc3ccc(-c4cn[nH]c4)cc3)c3sccc3n2)c1)NC1CCCC1] | A |
| Example 25 | 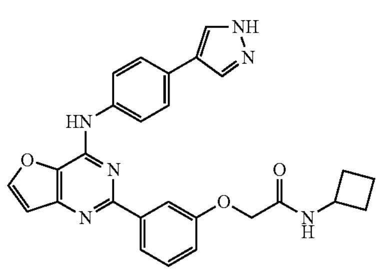 [SMILES: O=C(COc1cccc(-c2nc(Nc3ccc(-c4cn[nH]c4)cc3)c3occc3n2)c1)NC1CCC1] | C |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 26 | 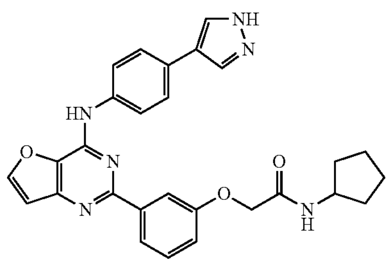 [SMILES: O=C(COc1cccc(-c2nc(Nc3ccc(-c4cn[nH]c4)cc3)c3occc3n2)c1)NC1CCCC1] | C |
| Example 27 | 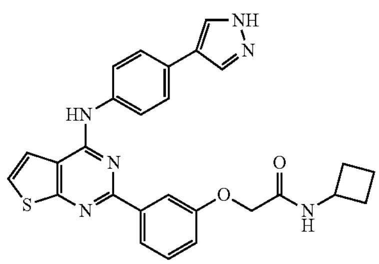 [SMILES: O=C(COc1cccc(-c2nc(Nc3ccc(-c4cn[nH]c4)cc3)c3ccsc3n2)c1)NC1CCC1] | B |
| Example 28 | 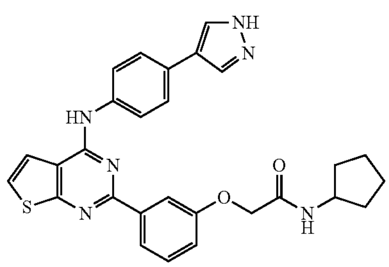 [SMILES: O=C(COc1cccc(-c2nc(Nc3ccc(-c4cn[nH]c4)cc3)c3ccsc3n2)c1)NC1CCCC1] | B |
| Example 29 | 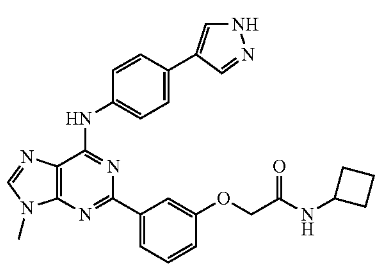 [SMILES: Cn1cnc2c(Nc3ccc(-c4cn[nH]c4)cc3)nc(-c3cccc(OCC(=O)NC4CCC4)c3)nc21] | C |
| Example 30 | 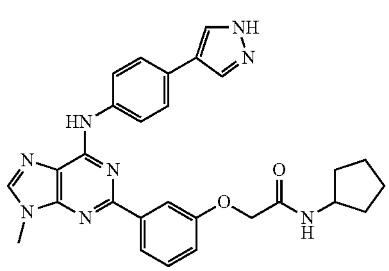 [SMILES: Cn1cnc2c(Nc3ccc(-c4cn[nH]c4)cc3)nc(-c3cccc(OCC(=O)NC4CCCC4)c3)nc21] | B |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 31 | 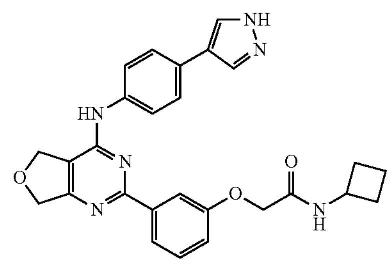 [SMILES: O=C(COc1cccc(-c2nc3c(c(Nc4ccc(-c5cn[nH]c5)cc4)n2)COC3)c1)NC1CCC1] | A |
| Example 32 | 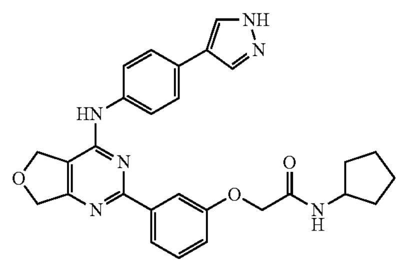 [SMILES: O=C(COc1cccc(-c2nc3c(c(Nc4ccc(-c5cn[nH]c5)cc4)n2)COC3)c1)NC1CCCC1] | A |
| Example 33 | 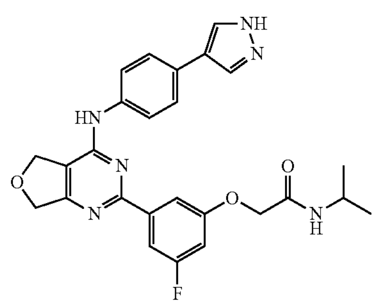 [SMILES: CC(C)NC(=O)COc1cc(F)cc(-c2nc3c(c(Nc4ccc(-c5cn[nH]c5)cc4)n2)COC3)c1] | D |
| Example 34 | 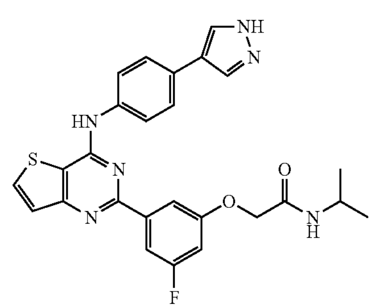 [SMILES: CC(C)NC(=O)COc1cc(F)cc(-c2nc(Nc3ccc(-c4cn[nH]c4)cc3)c3sccc3n2)c1] | E |
| Example 35 | 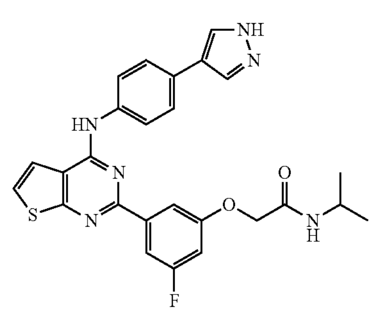 [SMILES: CC(C)NC(=O)COc1cc(F)cc(-c2nc(Nc3ccc(-c4cn[nH]c4)cc3)c3ccsc3n2)c1] | E |

TABLE 1-continued
Glycolysis IC50 values (nM)
| Example Number | Structure | Glycolysis IC50 A = 10-100 nM; B = 101-250 Nm; C = 251-500 nM; D = 501-1,000 nM; E = >1,000 nM |
|---|---|---|
| Example 36 | 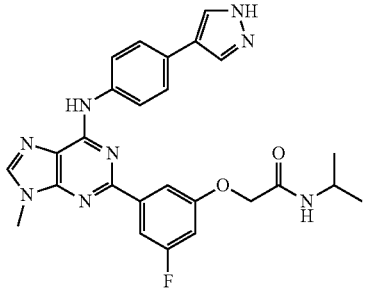 [SMILES: CC(C)NC(=O)COc1cc(F)cc(-c2nc(Nc3ccc(-c4cn[nH]c4)cc3)c3ncn(C)c3n2)c1] | E |
| Example 37 | 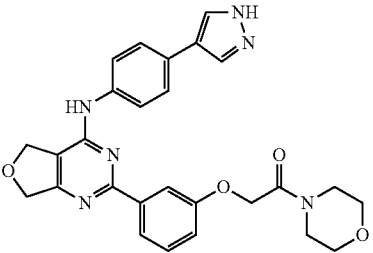 [SMILES: O=C(COc1cccc(-c2nc3c(c(Nc4ccc(-c5cn[nH]c5)cc4)n2)COC3)c1)N1CCOCC1] | E |
| Example 38 | 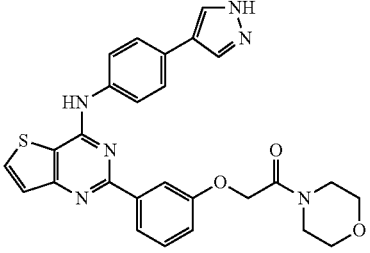 [SMILES: O=C(COc1cccc(-c2nc(Nc3ccc(-c4cn[nH]c4)cc3)c3sccc3n2)c1)N1CCOCC1] | D |
| Example 39 | 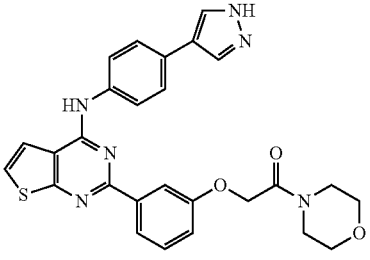 [SMILES: O=C(COc1cccc(-c2nc(Nc3ccc(-c4cn[nH]c4)cc3)c3ccsc3n2)c1)N1CCOCC1] | E |
| Example 40 | 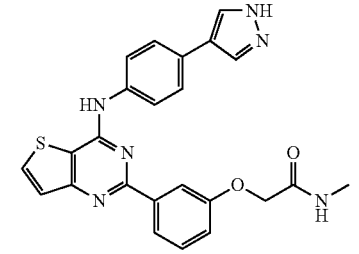 | E |

TABLE 1-continued

| | | Glycolysis IC50 A = 10-100 nM; |
|Example Number | Structure | B = 101-250 Nm; C = 251-500 nM; D = 501-1,000 nM; E = >1,000 nM |
|---|---|---|
| Example 41 | 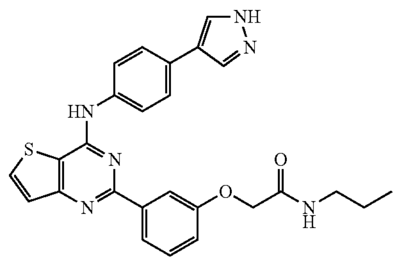 [SMILES: CCCNC(=O)COc1cccc(-c2nc(Nc3ccc(-c4cn[nH]c4)cc3)c3sccc3n2)c1] | E |
| Example 42 | 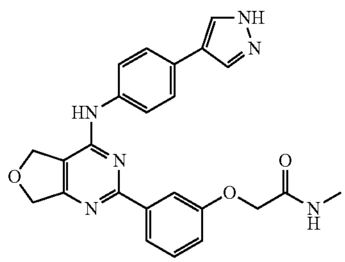 [SMILES: CNC(=O)COc1cccc(-c2nc3c(c(Nc4ccc(-c5cn[nH]c5)cc4)n2)COC3)c1] | E |
| Example 43 | 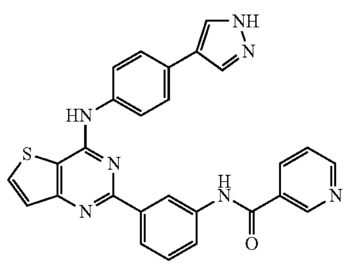 [SMILES: O=C(Nc1cccc(-c2nc(Nc3ccc(-c4cn[nH]c4)cc3)c3sccc3n2)c1)c1cccnc1] | B |
| Example 44 | 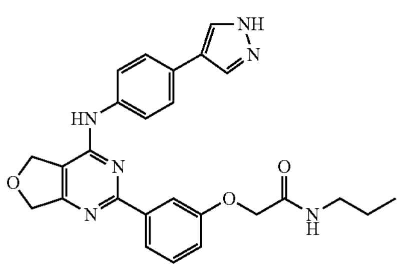 | C |
| Example 45 | 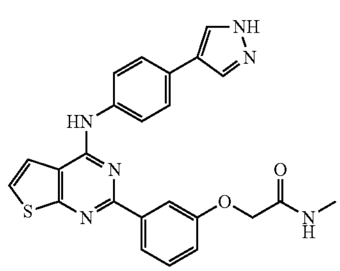 [SMILES: CNC(=O)COc1cccc(-c2nc(Nc3ccc(-c4cn[nH]c4)cc3)c3ccsc3n2)c1] | E |

TABLE 1-continued

| | | Glycolysis IC50 A = 10-100 nM; |
| Example Number | Structure | B = 101-250 Nm; C = 251-500 nM; D = 501-1,000 nM; E = >1,000 nM |
| --- | --- | --- |
| Example 46 | [structure] | D |
| Example 47 | [structure] | A |
| Example 48 | [structure] | E |
| Example 49 | [structure] | B |
| Example 50 | [structure] | D |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 51 | 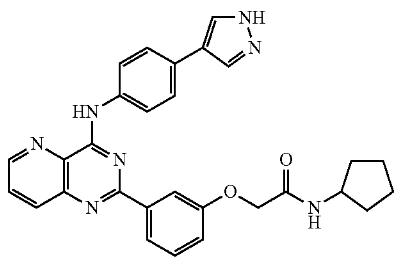 [SMILES: O=C(COc1cccc(-c2nc(Nc3ccc(-c4cn[nH]c4)cc3)c3ncccc3n2)c1)NC1CCCC1] | A |
| Example 52 | 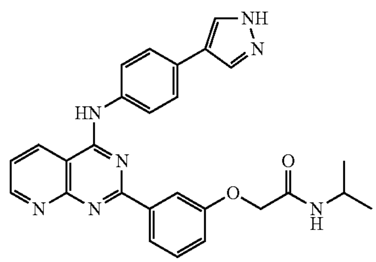 [SMILES: CC(C)NC(=O)COc1cccc(-c2nc(Nc3ccc(-c4cn[nH]c4)cc3)c3cccnc3n2)c1] | D |
| Example 53 | 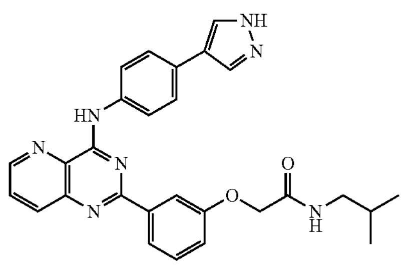 [SMILES: CC(C)CNC(=O)COc1cccc(-c2nc(Nc3ccc(-c4cn[nH]c4)cc3)c3ncccc3n2)c1] | B |
| Example 54 | 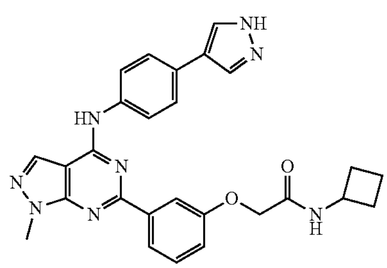 [SMILES: Cn1ncc2c(Nc3ccc(-c4cn[nH]c4)cc3)nc(-c3cccc(OCC(=O)NC4CCC4)c3)nc21] | C |
| Example 55 | 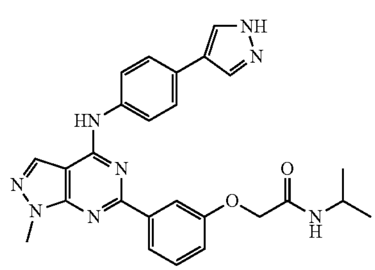 [SMILES: CC(C)NC(=O)COc1cccc(-c2nc(Nc3ccc(-c4cn[nH]c4)cc3)c3cnn(C)c3n2)c1] | C |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 56 | 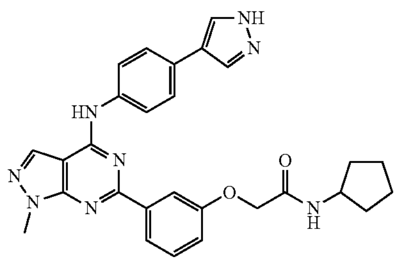 [SMILES: Cn1ncc2c(Nc3ccc(-c4cn[nH]c4)cc3)nc(-c3cccc(OCC(=O)NC4CCCC4)c3)nc21] | B |
| Example 57 | 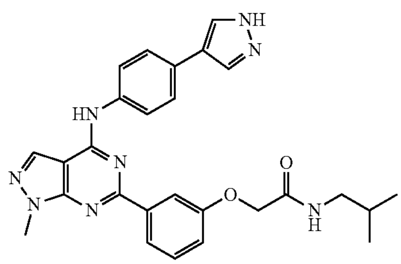 [SMILES: CC(C)CNC(=O)COc1cccc(-c2nc(Nc3ccc(-c4cn[nH]c4)cc3)c3cnn(C)c3n2)c1] | B |
| Example 58 | 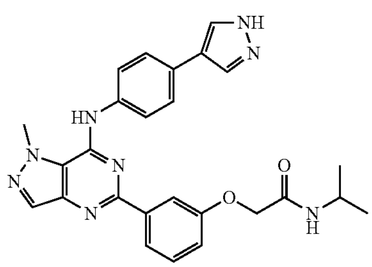 | E |
| Example 59 | 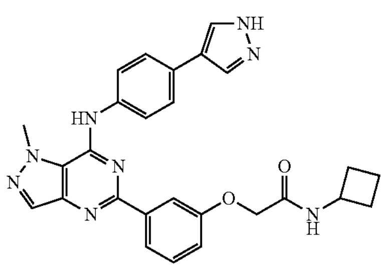 [SMILES: Cn1ncc2nc(-c3cccc(OCC(=O)NC4CCC4)c3)nc(Nc3ccc(-c4cn[nH]c4)cc3)c21] | E |
| Example 60 | 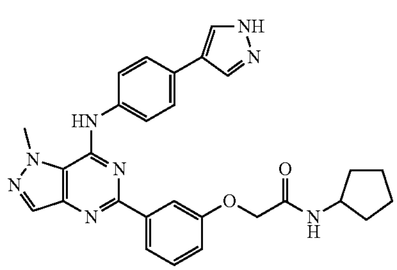 [SMILES: Cn1ncc2nc(-c3cccc(OCC(=O)NC4CCCC4)c3)nc(Nc3ccc(-c4cn[nH]c4)cc3)c21] | D |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 61 | 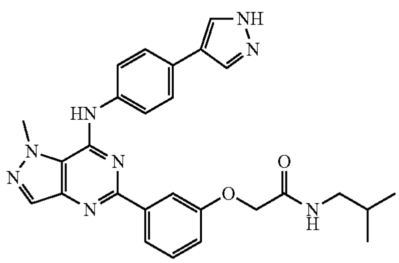 [SMILES: CC(C)CNC(=O)COc1cccc(-c2nc(Nc3ccc(-c4cn[nH]c4)cc3)c3c(cnn3C)n2)c1] | E |
| Example 62 | 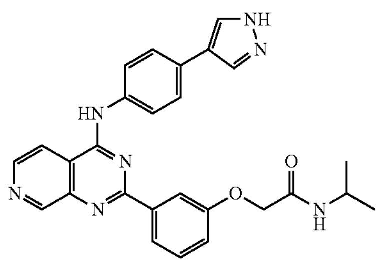 [SMILES: CC(C)NC(=O)COc1cccc(-c2nc(Nc3ccc(-c4cn[nH]c4)cc3)c3ccncc3n2)c1] | A |
| Example 63 | 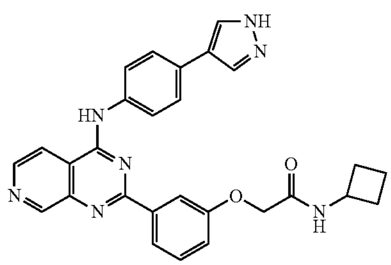 [SMILES: O=C(COc1cccc(-c2nc(Nc3ccc(-c4cn[nH]c4)cc3)c3ccncc3n2)c1)NC1CCC1] | A |
| Example 64 | 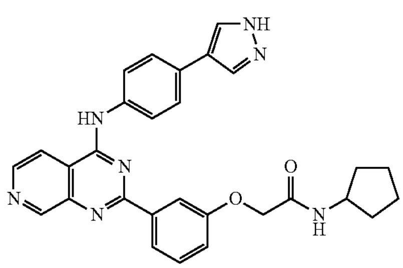 [SMILES: O=C(COc1cccc(-c2nc(Nc3ccc(-c4cn[nH]c4)cc3)c3ccncc3n2)c1)NC1CCCC1] | A |
| Example 65 | 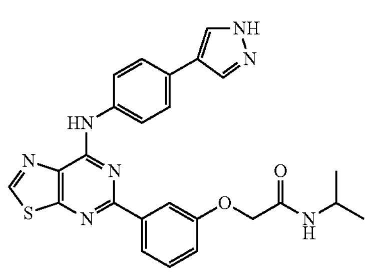 | C |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 66 | 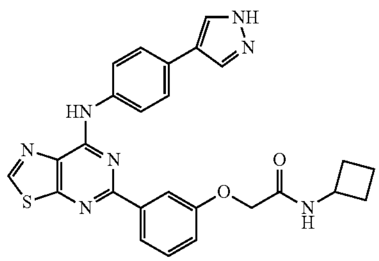 [SMILES: O=C(COc1cccc(-c2nc(Nc3ccc(-c4cn[nH]c4)cc3)c3ncsc3n2)c1)NC1CCC1] | C |
| Example 67 | 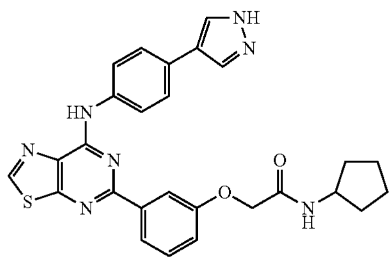 [SMILES: O=C(COc1cccc(-c2nc(Nc3ccc(-c4cn[nH]c4)cc3)c3ncsc3n2)c1)NC1CCCC1] | B |
| Example 68 | 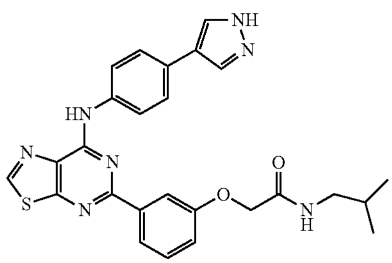 [SMILES: CC(C)CNC(=O)COc1cccc(-c2nc(Nc3ccc(-c4cn[nH]c4)cc3)c3ncsc3n2)c1] | C |
| Example 69 | 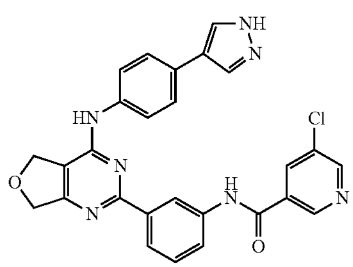 | A |
| Example 70 | 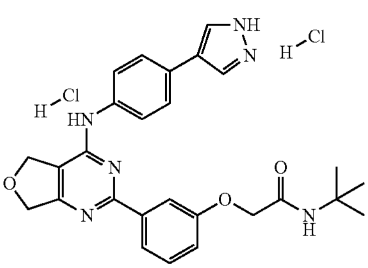 | A |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 71 | 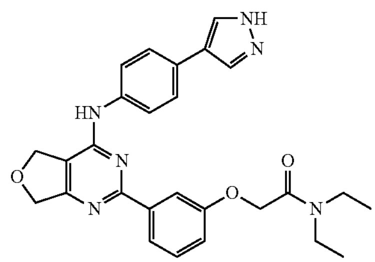 [SMILES: CCN(CC)C(=O)COc1cccc(-c2nc3c(c(Nc4ccc(-c5cn[nH]c5)cc4)n2)COC3)c1] | D |
| Example 72 | 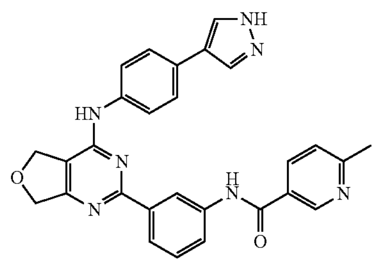 [SMILES: Cc1ccc(C(=O)Nc2cccc(-c3nc4c(c(Nc5ccc(-c6cn[nH]c6)cc5)n3)COC4)c2)cn1] | A |
| Example 73 | 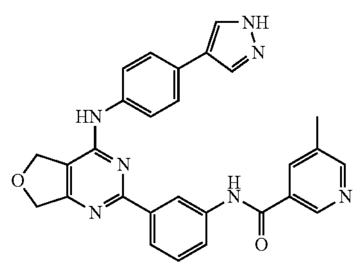 [SMILES: Cc1cncc(C(=O)Nc2cccc(-c3nc4c(c(Nc5ccc(-c6cn[nH]c6)cc5)n3)COC4)c2)c1] | A |
| Example 74 | 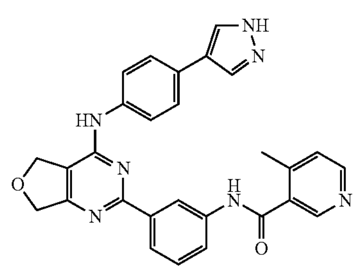 [SMILES: Cc1ccncc1C(=O)Nc1cccc(-c2nc3c(c(Nc4ccc(-c5cn[nH]c5)cc4)n2)COC3)c1] | B |
| Example 75 | 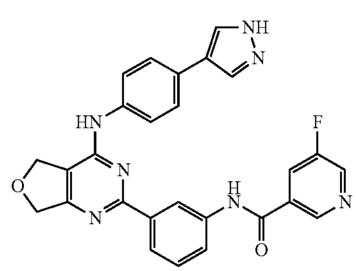 [SMILES: O=C(Nc1cccc(-c2nc3c(c(Nc4ccc(-c5cn[nH]c5)cc4)n2)COC3)c1)c1cncc(F)c1] | A |

TABLE 1-continued
Glycolysis IC50 values (nM)
| Example Number | Structure | Glycolysis IC50 A = 10-100 nM; B = 101-250 Nm; C = 251-500 nM; D = 501-1,000 nM; E = >1,000 nM |
|---|---|---|
| Example 76 | 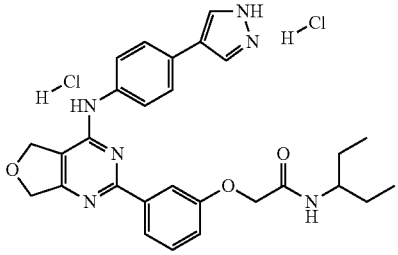 | A |
| Example 77 | 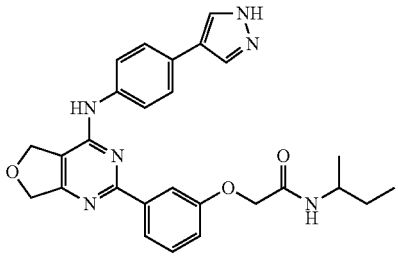 | A |
| Example 78 | 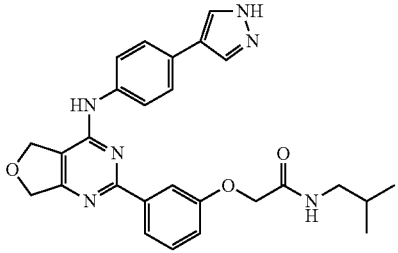 [SMILES: CC(C)CNC(=O)COc1cccc(-c2nc3c(c(Nc4ccc(-c5cn[nH]c5)cc4)n2)COC3)c1] | A |
| Example 79 | 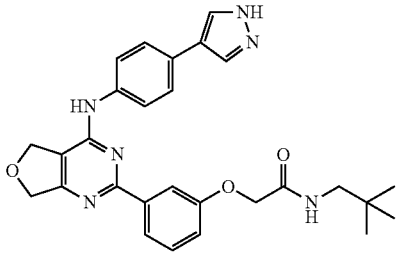 | A |
| Example 80 | 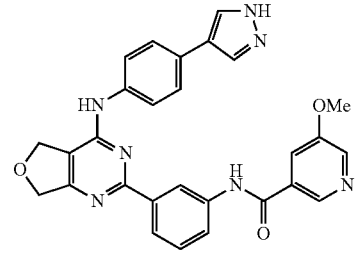 [SMILES: COc1cncc(C(=O)Nc2cccc(-c3nc4c(c(Nc5ccc(-c6cn[nH]c6)cc5)n3)COC4)c2)c1] | A |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 81 | 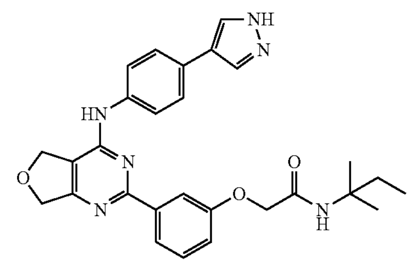 [SMILES: CCC(C)(C)NC(=O)COc1cccc(-c2nc3c(c(Nc4ccc(-c5cn[nH]c5)cc4)n2)COC3)c1] | A |
| Example 82 | 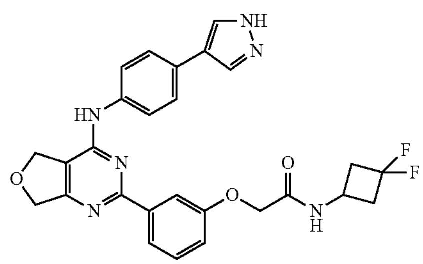 [SMILES: O=C(COc1cccc(-c2nc3c(c(Nc4ccc(-c5cn[nH]c5)cc4)n2)COC3)c1)NC1CC(F)(F)C1] | B |
| Example 83 | 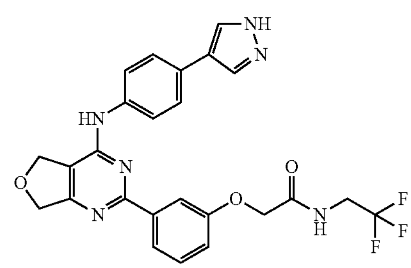 [SMILES: O=C(COc1cccc(-c2nc3c(c(Nc4ccc(-c5cn[nH]c5)cc4)n2)COC3)c1)NCC(F)(F)F] | D |
| Example 84 | 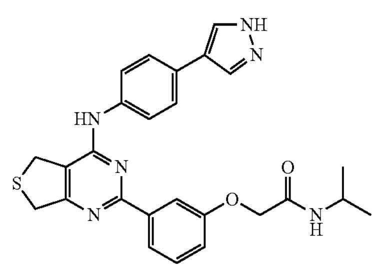 [SMILES: CC(C)NC(=O)COc1cccc(-c2nc3c(c(Nc4ccc(-c5cn[nH]c5)cc4)n2)CSC3)c1] | C |
| Example 85 | 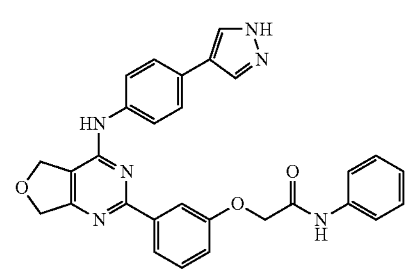 [SMILES: O=C(COc1cccc(-c2nc3c(c(Nc4ccc(-c5cn[nH]c5)cc4)n2)COC3)c1)Nc1ccccc1] | D |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 86 | 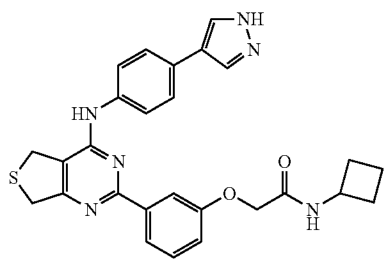 [SMILES: O=C(COc1cccc(-c2nc3c(c(Nc4ccc(-c5cn[nH]c5)cc4)n2)CSC3)c1)NC1CCC1] | B |
| Example 87 | 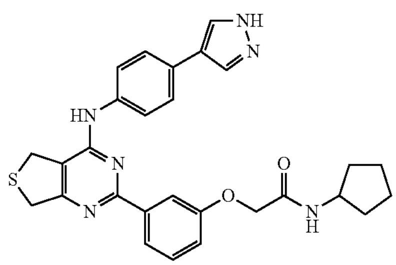 [SMILES: O=C(COc1cccc(-c2nc3c(c(Nc4ccc(-c5cn[nH]c5)cc4)n2)CSC3)c1)NC1CCCC1] | B |
| Example 88 | 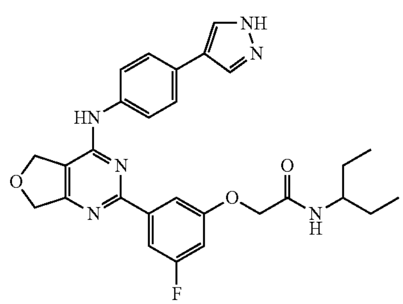 [SMILES: CCC(CC)NC(=O)COc1cc(F)cc(-c2nc3c(c(Nc4ccc(-c5cn[nH]c5)cc4)n2)COC3)c1] | D |
| Example 89 | 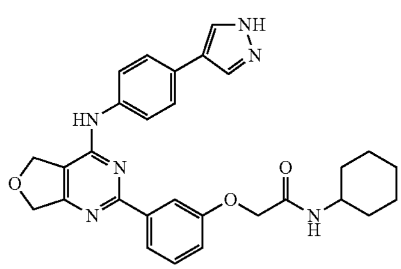 [SMILES: O=C(COc1cccc(-c2nc3c(c(Nc4ccc(-c5cn[nH]c5)cc4)n2)COC3)c1)NC1CCCCC1] | A |
| Example 90 | 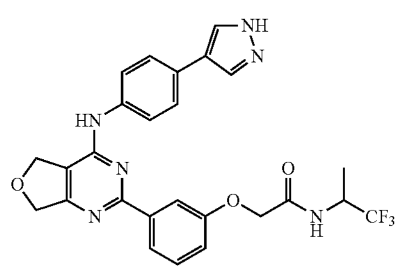 [SMILES: CC(NC(=O)COc1cccc(-c2nc3c(c(Nc4ccc(-c5cn[nH]c5)cc4)n2)COC3)c1)C(F)(F)F] | A |

TABLE 1-continued

| | | Glycolysis IC50 values (nM) | |
|---|---|---|---|
| Example Number | Structure | | Glycolysis IC50 A = 10-100 nM; B = 101-250 Nm; C = 251-500 nM; D = 501-1,000 nM; E = >1,000 nM |

| Example Number | Structure | Glycolysis IC50 |
|---|---|---|
| Example 91 | 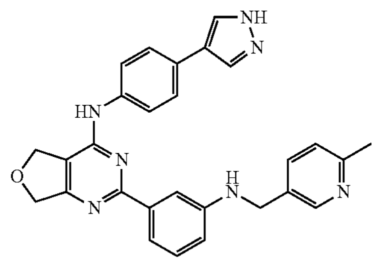 [SMILES: Cc1ccc(CNc2cccc(-c3nc4c(c(Nc5ccc(-c6cn[nH]c6)cc5)n3)COC4)c2)cn1] | E |
| Example 92 | 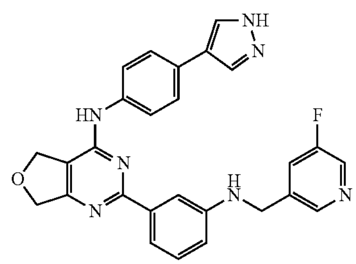 [SMILES: Fc1cncc(CNc2cccc(-c3nc4c(c(Nc5ccc(-c6cn[nH]c6)cc5)n3)COC4)c2)c1] | D |
| Example 93 | 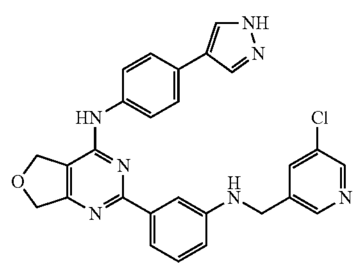 [SMILES: Clc1cncc(CNc2cccc(-c3nc4c(c(Nc5ccc(-c6cn[nH]c6)cc5)n3)COC4)c2)c1] | D |
| Example 94 | 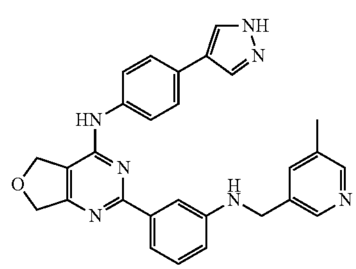 [SMILES: Cc1cncc(CNc2cccc(-c3nc4c(c(Nc5ccc(-c6cn[nH]c6)cc5)n3)COC4)c2)c1] | D |
| Example 95 | 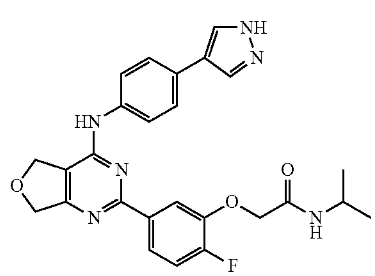 [SMILES: CC(C)NC(=O)COc1cc(-c2nc3c(c(Nc4ccc(-c5cn[nH]c5)cc4)n2)COC3)ccc1F] | E |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 96 | 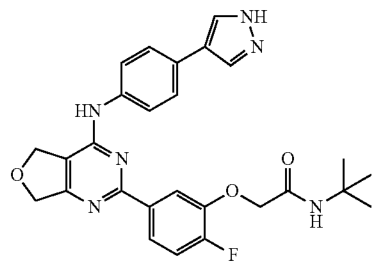 [SMILES: CC(C)(C)NC(=O)COc1cc(-c2nc3c(c(Nc4ccc(-c5cn[nH]c5)cc4)n2)COC3)ccc1F] | E |
| Example 97 | 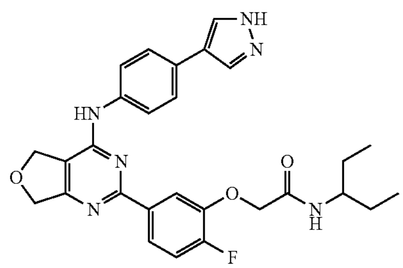 [SMILES: CCC(CC)NC(=O)COc1cc(-c2nc3c(c(Nc4ccc(-c5cn[nH]c5)cc4)n2)COC3)ccc1F] | E |
| Example 98 | 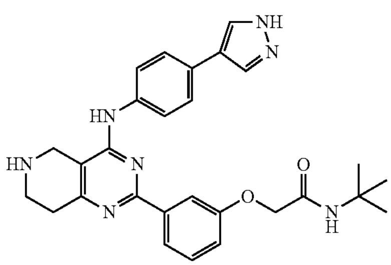 [SMILES: CC(C)(C)NC(=O)COc1cccc(-c2nc3c(c(Nc4ccc(-c5cn[nH]c5)cc4)n2)CNCC3)c1] | A |
| Example 99 | 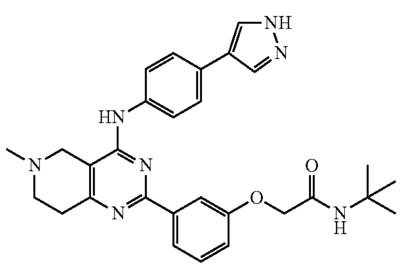 [SMILES: CN1CCc2nc(-c3cccc(OCC(=O)NC(C)(C)C)c3)nc(Nc3ccc(-c4cn[nH]c4)cc3)c2C1] | B |
| Example 100 | 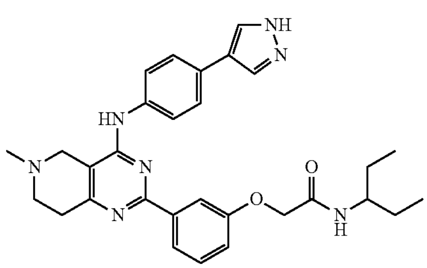 [SMILES: CCC(CC)NC(=O)COc1cccc(-c2nc3c(c(Nc4ccc(-c5cn[nH]c5)cc4)n2)CN(C)CC3)c1] | C |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 101 | 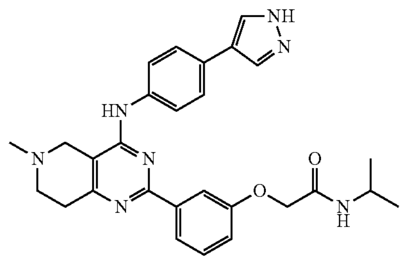 [SMILES: CC(C)NC(=O)COc1cccc(-c2nc3c(c(Nc4ccc(-c5cn[nH]c5)cc4)n2)CN(C)CC3)c1] | C |
| Example 102 | 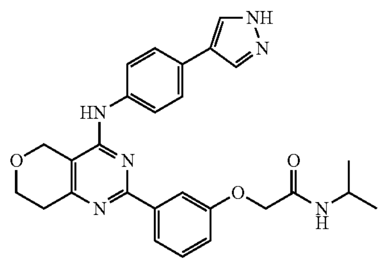 [SMILES: CC(C)NC(=O)COc1cccc(-c2nc3c(c(Nc4ccc(-c5cn[nH]c5)cc4)n2)COCC3)c1] | A |
| Example 103 | 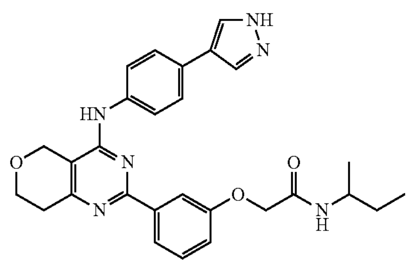 [SMILES: CCC(C)NC(=O)COc1cccc(-c2nc3c(c(Nc4ccc(-c5cn[nH]c5)cc4)n2)COCC3)c1] | A |
| Example 104 | 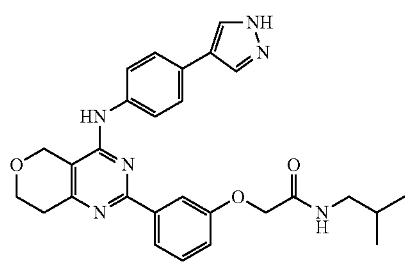 [SMILES: CC(C)CNC(=O)COc1cccc(-c2nc3c(c(Nc4ccc(-c5cn[nH]c5)cc4)n2)COCC3)c1] | A |
| Example 105 | 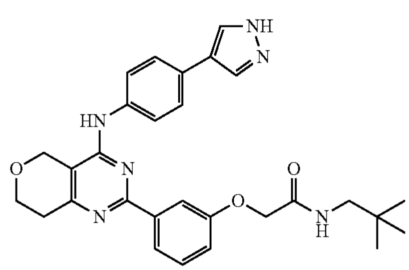 [SMILES: CC(C)(C)CNC(=O)COc1cccc(-c2nc3c(c(Nc4ccc(-c5cn[nH]c5)cc4)n2)COCC3)c1] | A |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 106 | 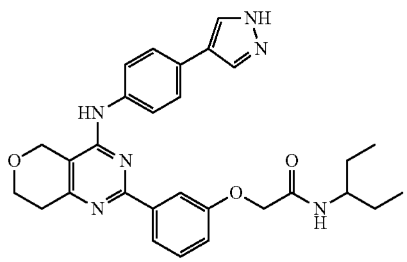 [SMILES: CCC(CC)NC(=O)COc1cccc(-c2nc3c(c(Nc4ccc(-c5cn[nH]c5)cc4)n2)COCC3)c1] | A |
| Example 107 | 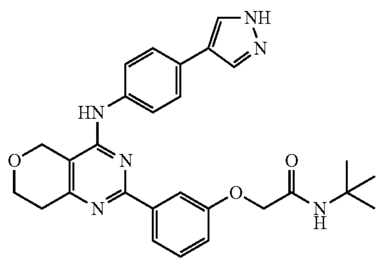 [SMILES: CC(C)(C)NC(=O)COc1cccc(-c2nc3c(c(Nc4ccc(-c5cn[nH]c5)cc4)n2)COCC3)c1] | A |
| Example 108 | 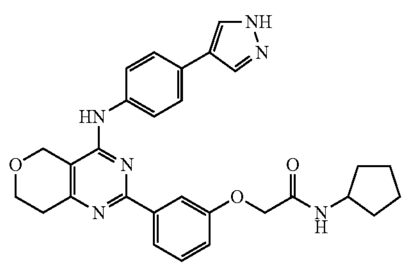 [SMILES: O=C(COc1cccc(-c2nc3c(c(Nc4ccc(-c5cn[nH]c5)cc4)n2)COCC3)c1)NC1CCCC1] | A |
| Example 109 | 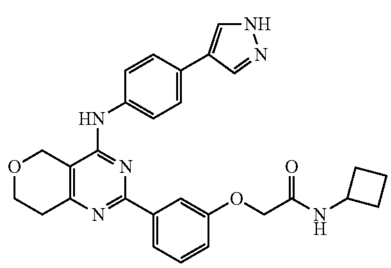 [SMILES: O=C(COc1cccc(-c2nc3c(c(Nc4ccc(-c5cn[nH]c5)cc4)n2)COCC3)c1)NC1CCC1] | A |
| Example 110 | 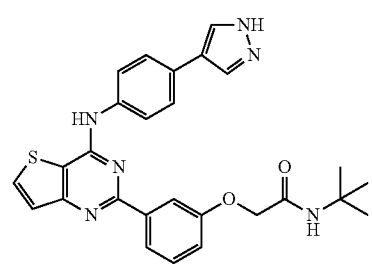 | B |

TABLE 1-continued

| Example Number | Structure | Glycolysis IC50 A = 10-100 nM; B = 101-250 Nm; C = 251-500 nM; D = 501-1,000 nM; E = >1,000 nM |
|---|---|---|
| Example 111 | *(structure)* | B |
| Example 112 | *(structure)* | B |
| Example 113 | *(structure)* | A |
| Example 114 | *(structure)* | A |
| Example 115 | *(structure)* | B |

TABLE 1-continued
Glycolysis IC50 values (nM)
| Example Number | Structure | Glycolysis IC50 A = 10-100 nM; B = 101-250 Nm; C = 251-500 nM; D = 501-1,000 nM; E = >1,000 nM |
|---|---|---|
| Example 116 | 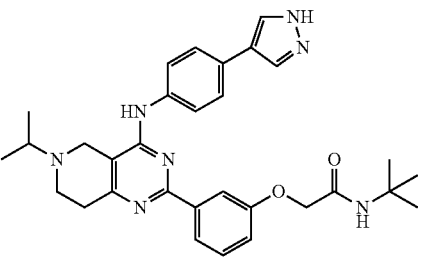 | B |
| Example 117 | 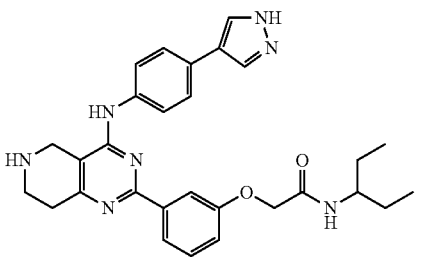 [SMILES: CCC(CC)NC(=O)COc1cccc(-c2nc3c(c(Nc4ccc(-c5cn[nH]c5)cc4)n2)CNCC3)c1] | A |
| Example 118 | 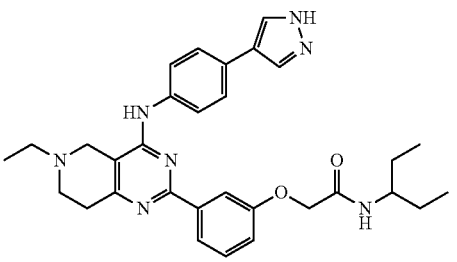 [SMILES: CCC(CC)NC(=O)COc1cccc(-c2nc3c(c(Nc4ccc(-c5cn[nH]c5)cc4)n2)CN(CC)CC3)c1] | D |
| Example 119 | 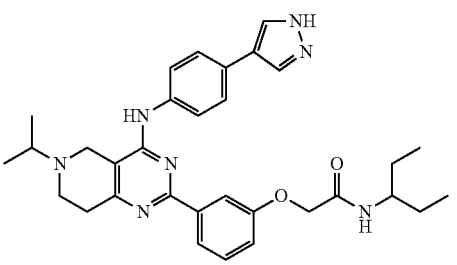 [SMILES: CCC(CC)NC(=O)COc1cccc(-c2nc3c(c(Nc4ccc(-c5cn[nH]c5)cc4)n2)CN(C(C)C)CC3)c1] | D |
| Example 120 | 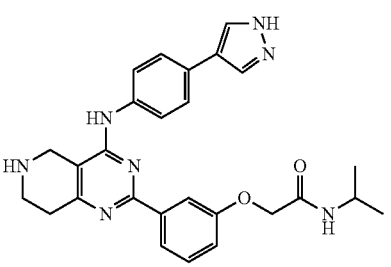 | C |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 121 | 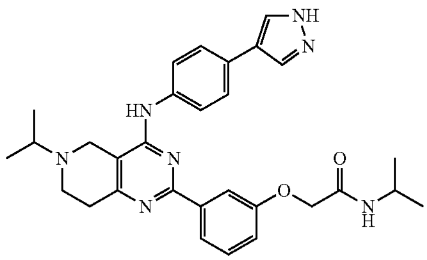 [SMILES: CC(C)NC(=O)COc1cccc(-c2nc3c(c(Nc4ccc(-c5cn[nH]c5)cc4)n2)CN(C(C)C)CC3)c1] | D |
| Example 122 | 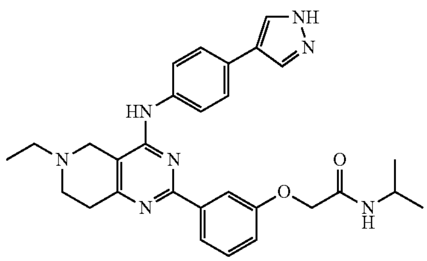 [SMILES: CCN1CCc2nc(-c3cccc(OCC(=O)NC(C)C)c3)nc(Nc3ccc(-c4cn[nH]c4)cc3)c2C1] | D |
| Example 123 | 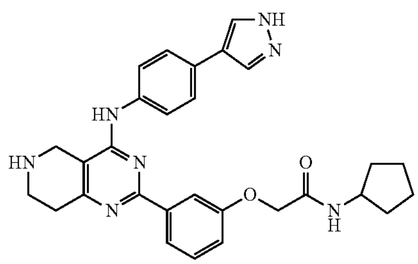 [SMILES: O=C(COc1cccc(-c2nc3c(c(Nc4ccc(-c5cn[nH]c5)cc4)n2)CNCC3)c1)NC1CCCC1] | A |
| Example 124 | 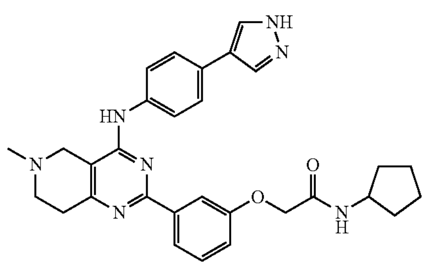 [SMILES: CN1CCc2nc(-c3cccc(OCC(=O)NC4CCCC4)c3)nc(Nc3ccc(-c4cn[nH]c4)cc3)c2C1] | B |
| Example 125 | 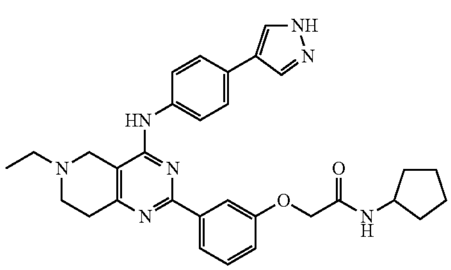 [SMILES: CCN1CCc2nc(-c3cccc(OCC(=O)NC4CCCC4)c3)nc(Nc3ccc(-c4cn[nH]c4)cc3)c2C1] | B |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 126 | 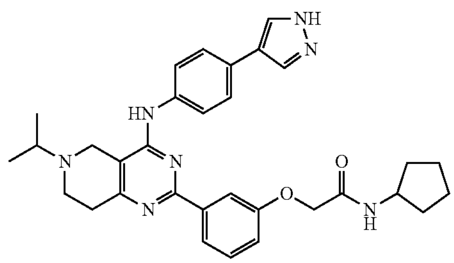 | C |
| Example 127 | 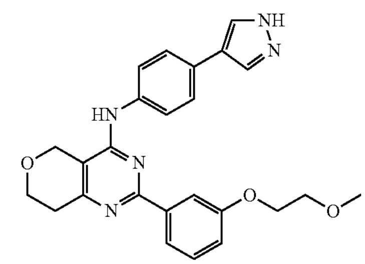 [SMILES: COCCOc1cccc(-c2nc3c(c(Nc4ccc(-c5cn[nH]c5)cc4)n2)COCC3)c1] | E |
| Example 128 | 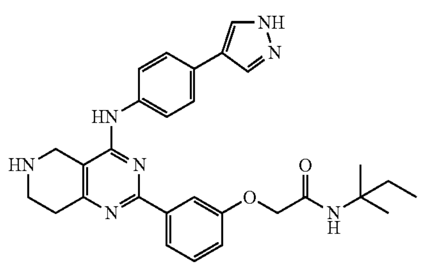 [SMILES: CCC(C)(C)NC(=O)COc1cccc(-c2nc3c(c(Nc4ccc(-c5cn[nH]c5)cc4)n2)CNCC3)c1] | A |
| Example 129 | 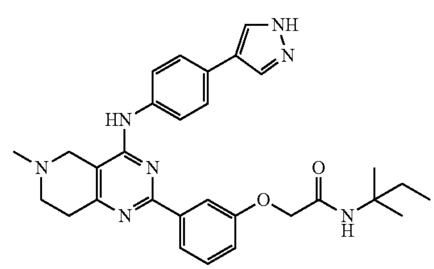 [SMILES: CCC(C)(C)NC(=O)COc1cccc(-c2nc3c(c(Nc4ccc(-c5cn[nH]c5)cc4)n2)CN(C)CC3)c1] | A |
| Example 130 | 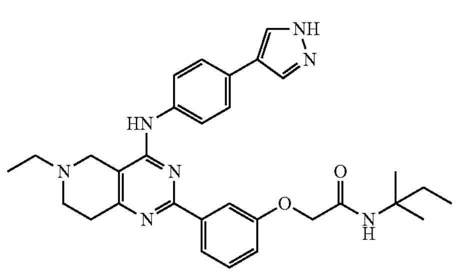 | A |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 131 | 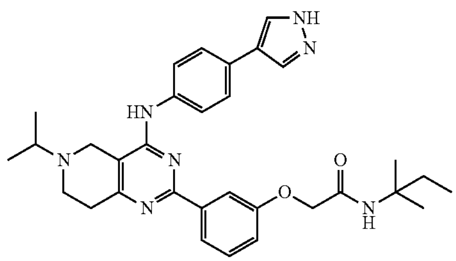 [SMILES: CCC(C)(C)NC(=O)COc1cccc(-c2nc3c(c(Nc4ccc(-c5cn[nH]c5)cc4)n2)CN(C(C)C)CC3)c1] | B |
| Example 132 | 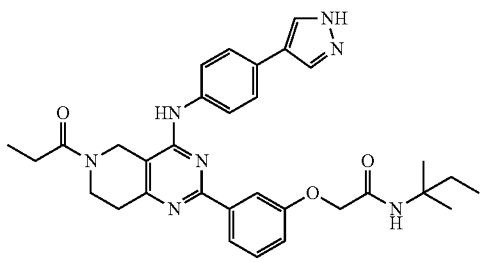 [SMILES: CCC(=O)N1CCc2nc(-c3cccc(OCC(=O)NC(C)(C)CC)c3)nc(Nc3ccc(-c4cn[nH]c4)cc3)c2C1] | A |
| Example 133 | 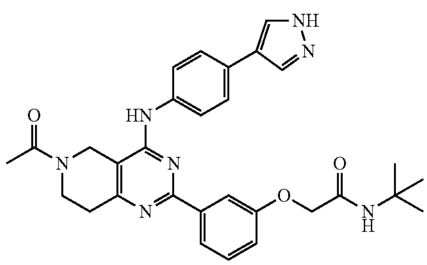 [SMILES: CC(=O)N1CCc2nc(-c3cccc(OCC(=O)NC(C)(C)C)c3)nc(Nc3ccc(-c4cn[nH]c4)cc3)c2C1] | A |
| Example 134 | 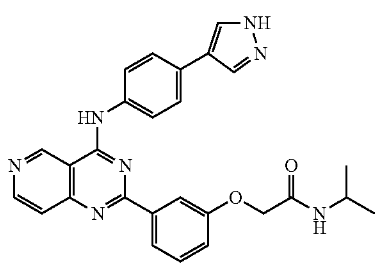 [SMILES: CC(C)NC(=O)COc1cccc(-c2nc(Nc3ccc(-c4cn[nH]c4)cc3)c3cnccc3n2)c1] | A |
| Example 135 | 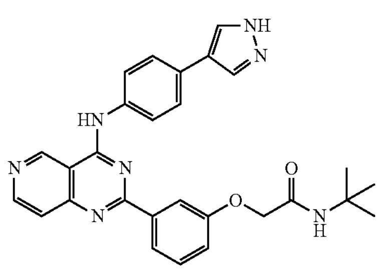 [SMILES: CC(C)(C)NC(=O)COc1cccc(-c2nc(Nc3ccc(-c4cn[nH]c4)cc3)c3cnccc3n2)c1] | A |

TABLE 1-continued
Glycolysis IC50 values (nM)
| Example Number | Structure | Glycolysis IC50 A = 10-100 nM; B = 101-250 Nm; C = 251-500 nM; D = 501-1,000 nM; E = >1,000 nM |
|---|---|---|
| Example 136 | 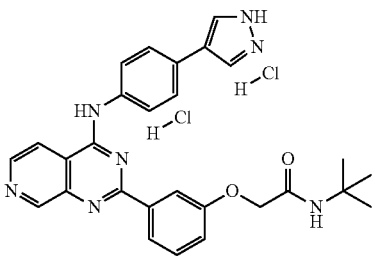 | A |
| Example 137 | 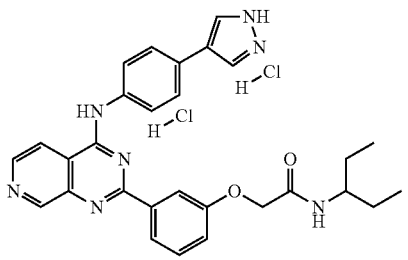 | A |
| Example 138 | 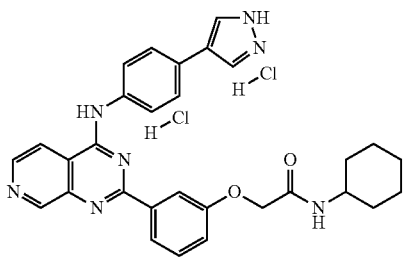 | A |
| Example 139 | 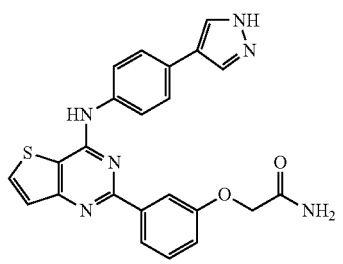 [SMILES: NC(=O)COc1cccc(-c2nc(Nc3ccc(-c4cn[nH]c4)cc3)c3sccc3n2)c1] | E |
| Example 140 | 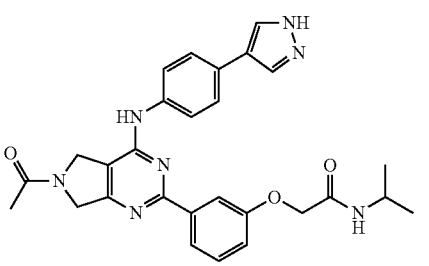 [SMILES: CC(=O)N1Cc2nc(-c3cccc(OCC(=O)NC(C)C)c3)nc(Nc3ccc(-c4cn[nH]c4)cc3)c2C1] | B |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
| --- | --- | --- |
| Example 141 | 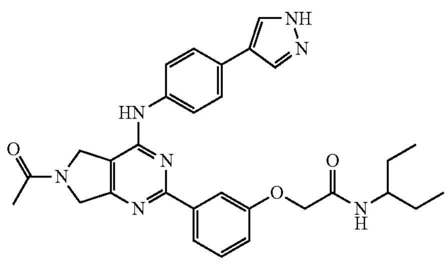 [SMILES: CCC(CC)NC(=O)COc1cccc(-c2nc3c(c(Nc4ccc(-c5cn[nH]c5)cc4)n2)CN(C(C)=O)C3)c1] | A |
| Example 142 | 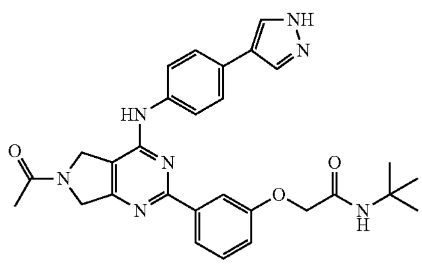 [SMILES: CC(=O)N1Cc2nc(-c3cccc(OCC(=O)NC(C)(C)C)c3)nc(Nc3ccc(-c4cn[nH]c4)cc3)c2C1] | A |
| Example 143 | 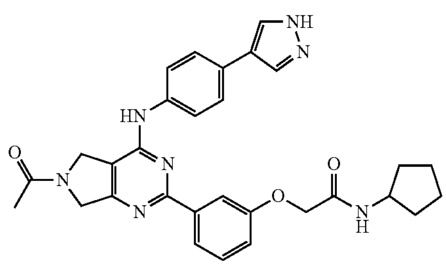 [SMILES: CC(=O)N1Cc2nc(-c3cccc(OCC(=O)NC4CCCC4)c3)nc(Nc3ccc(-c4cn[nH]c4)cc3)c2C1] | A |
| Example 144 | 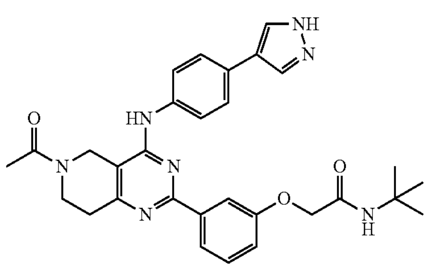 [SMILES: CC(=O)N1CCc2nc(-c3cccc(OCC(=O)NC(C)(C)C)c3)nc(Nc3ccc(-c4cn[nH]c4)cc3)c2C1] | A |
| Example 145 | 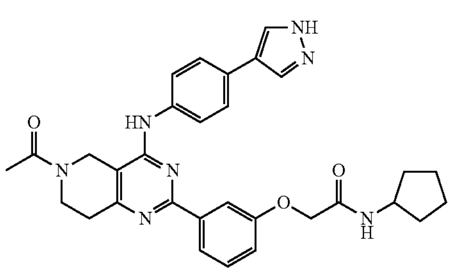 [SMILES: CC(=O)N1CCc2nc(-c3cccc(OCC(=O)NC4CCCC4)c3)nc(Nc3ccc(-c4cn[nH]c4)cc3)c2C1] | A |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 146 | 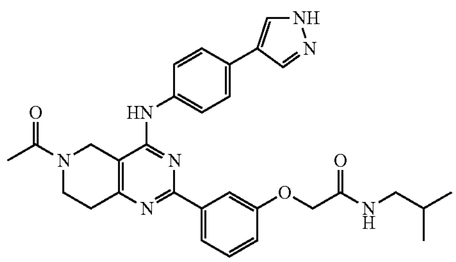 | A |
| Example 147 | 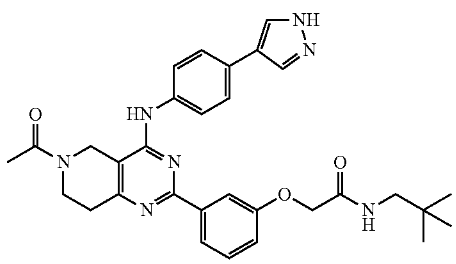 [SMILES: CC(=O)N1CCc2nc(-c3cccc(OCC(=O)NCC(C)(C)C)c3)nc(Nc3ccc(-c4cn[nH]c4)cc3)c2C1] | A |
| Example 148 | 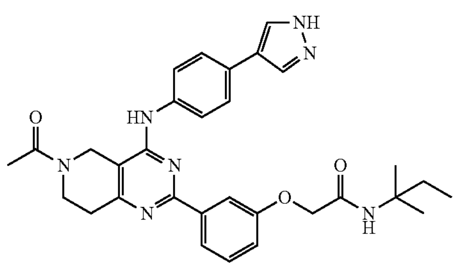 [SMILES: CCC(C)(C)NC(=O)COc1cccc(-c2nc3c(c(Nc4ccc(-c5cn[nH]c5)cc4)n2)CN(C(C)=O)CC3)c1] | A |
| Example 149 | 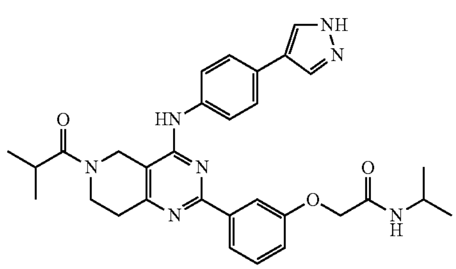 | A |
| Example 150 | 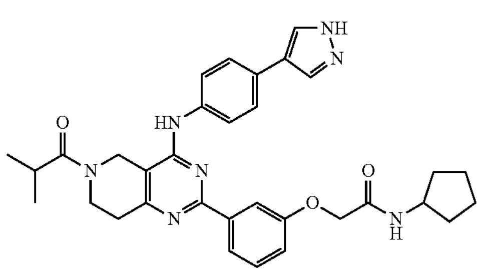 [SMILES: CC(C)C(=O)N1CCc2nc(-c3cccc(OCC(=O)NC4CCCC4)c3)nc(Nc3ccc(-c4cn[nH]c4)cc3)c2C1] | 28 |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 151 | 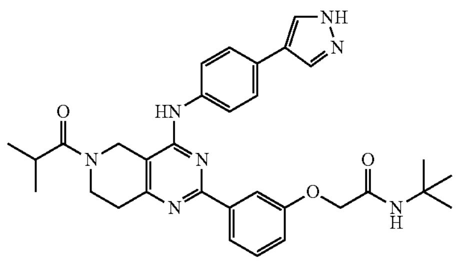 [SMILES: CC(C)C(=O)N1CCc2nc(-c3cccc(OCC(=O)NC(C)(C)C)c3)nc(Nc3ccc(-c4cn[nH]c4)cc3)c2C1] | A |
| Example 152 | 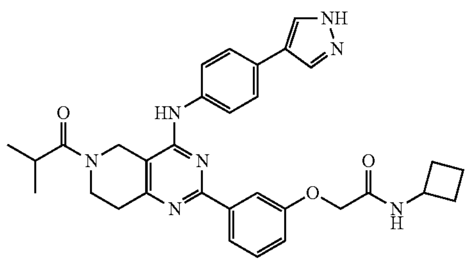 [SMILES: CC(C)C(=O)N1CCc2nc(-c3cccc(OCC(=O)NC4CCC4)c3)nc(Nc3ccc(-c4cn[nH]c4)cc3)c2C1] | A |
| Example 153 | 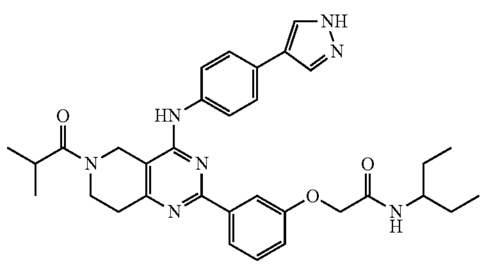 [SMILES: CCC(CC)NC(=O)COc1cccc(-c2nc3c(c(Nc4ccc(-c5cn[nH]c5)cc4)n2)CN(C(=O)C(C)C)CC3)c1] | A |
| Example 154 | 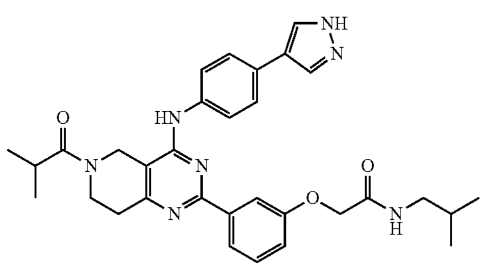 [SMILES: CC(C)CNC(=O)COc1cccc(-c2nc3c(c(Nc4ccc(-c5cn[nH]c5)cc4)n2)CN(C(=O)C(C)C)CC3)c1] | A |
| Example 155 | 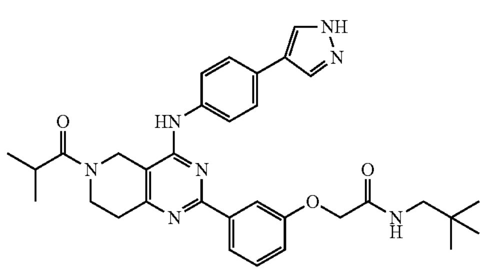 | A |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 156 | 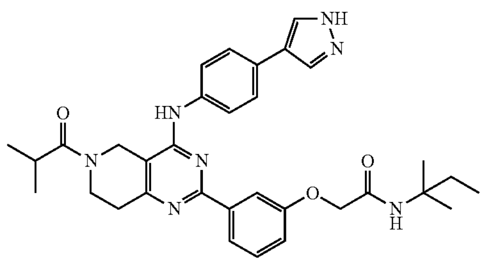 | A |
| Example 157 | 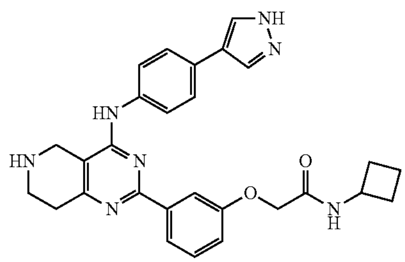 [SMILES: O=C(COc1cccc(-c2nc3c(c(Nc4ccc(-c5cn[nH]c5)cc4)n2)CNCC3)c1)NC1CCC1] | B |
| Example 158 | 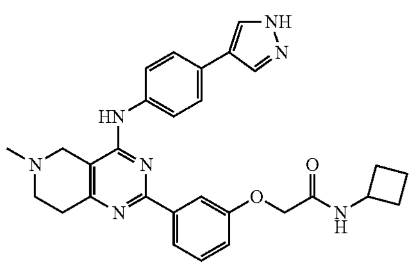 [SMILES: CN1CCc2nc(-c3cccc(OCC(=O)NC4CCC4)c3)nc(Nc3ccc(-c4cn[nH]c4)cc3)c2C1] | C |
| Example 159 | 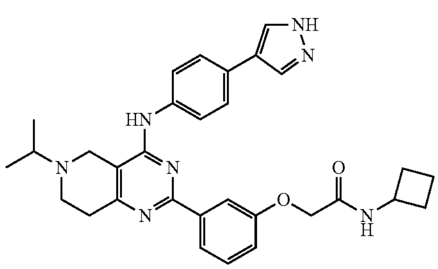 [SMILES: CC(C)N1CCc2nc(-c3cccc(OCC(=O)NC4CCC4)c3)nc(Nc3ccc(-c4cn[nH]c4)cc3)c2C1] | C |
| Example 160 | 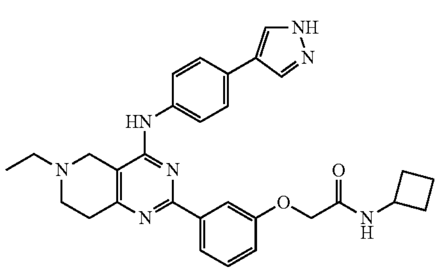 [SMILES: CCN1CCc2nc(-c3cccc(OCC(=O)NC4CCC4)c3)nc(Nc3ccc(-c4cn[nH]c4)cc3)c2C1] | C |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 161 | 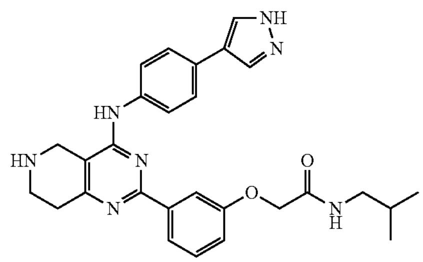 [SMILES: CC(C)CNC(=O)COc1cccc(-c2nc3c(c(Nc4ccc(-c5cn[nH]c5)cc4)n2)CNCC3)c1] | C |
| Example 162 | 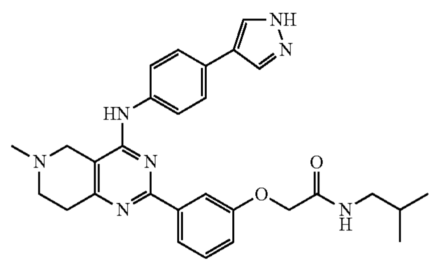 [SMILES: CC(C)CNC(=O)COc1cccc(-c2nc3c(c(Nc4ccc(-c5cn[nH]c5)cc4)n2)CN(C)CC3)c1] | C |
| Example 163 | 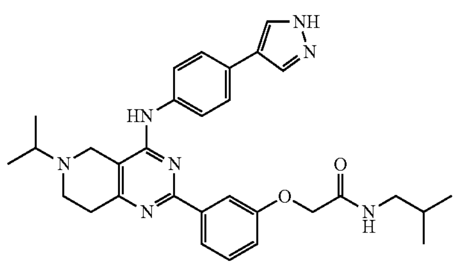 [SMILES: CC(C)CNC(=O)COc1cccc(-c2nc3c(c(Nc4ccc(-c5cn[nH]c5)cc4)n2)CN(C(C)C)CC3)c1] | D |
| Example 164 | 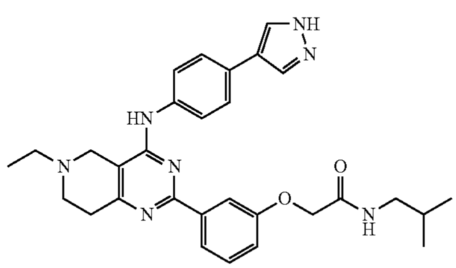 [SMILES: CCN1CCc2nc(-c3cccc(OCC(=O)NCC(C)C)c3)nc(Nc3ccc(-c4cn[nH]c4)cc3)c2C1] | C |
| Example 165 | 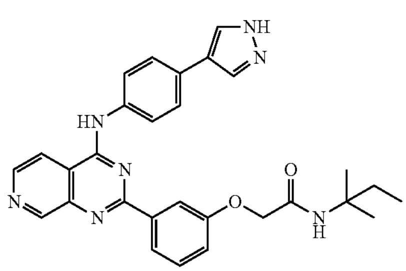 [SMILES: CCC(C)(C)NC(=O)COc1cccc(-c2nc(Nc3ccc(-c4cn[nH]c4)cc3)c3ccncc3n2)c1] | A |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 166 | 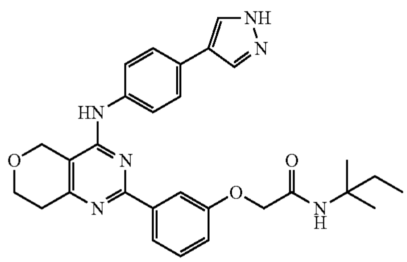 [SMILES: CCC(C)(C)NC(=O)COc1cccc(-c2nc3c(c(Nc4ccc(-c5cn[nH]c5)cc4)n2)COCC3)c1] | A |
| Example 167 | 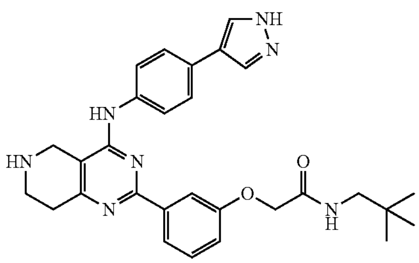 [SMILES: CC(C)(C)CNC(=O)COc1cccc(-c2nc3c(c(Nc4ccc(-c5cn[nH]c5)cc4)n2)CNCC3)c1] | A |
| Example 168 | 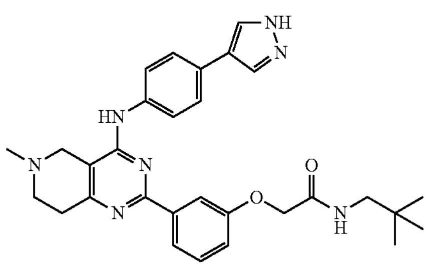 [SMILES: CN1CCc2nc(-c3cccc(OCC(=O)NCC(C)(C)C)c3)nc(Nc3ccc(-c4cn[nH]c4)cc3)c2C1] | B |
| Example 169 | 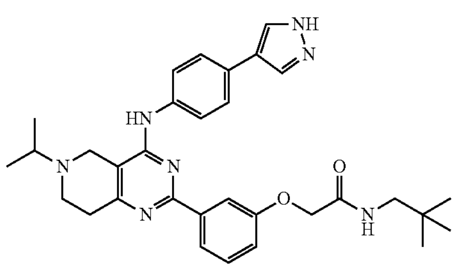 [SMILES: CC(C)N1CCc2nc(-c3cccc(OCC(=O)NCC(C)(C)C)c3)nc(Nc3ccc(-c4cn[nH]c4)cc3)c2C1] | 290 |
| Example 170 | 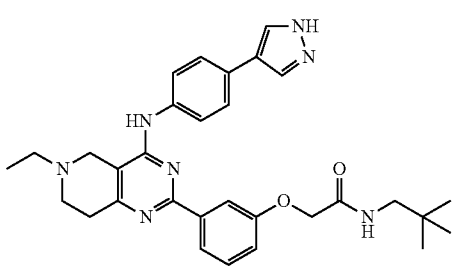 [SMILES: CCN1CCc2nc(-c3cccc(OCC(=O)NCC(C)(C)C)c3)nc(Nc3ccc(-c4cn[nH]c4)cc3)c2C1] | B |

TABLE 1-continued
Glycolysis IC50 values (nM)
| Example Number | Structure | Glycolysis IC50 A = 10-100 nM; B = 101-250 Nm; C = 251-500 nM; D = 501-1,000 nM; E = >1,000 nM |
|---|---|---|
| Example 171 | 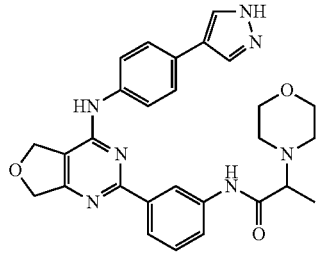 [SMILES: CC(C(=O)Nc1cccc(-c2nc3c(c(Nc4ccc(-c5cn[nH]c5)cc4)n2)COC3)c1)N1CCOCC1] | D |
| Example 172 | 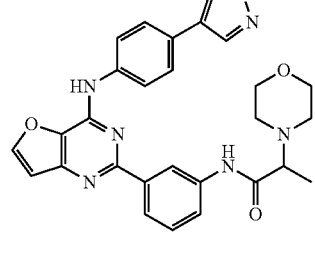 | B |
| Example 173 | 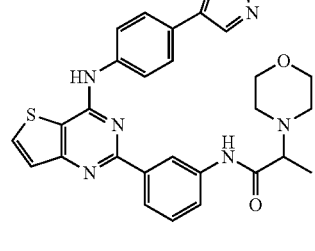 | C |
| Example 174 | 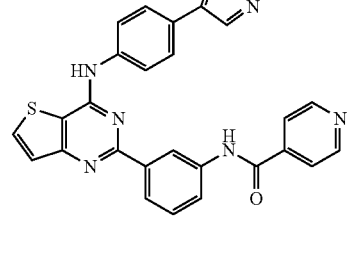 | D |
| Example 175 | 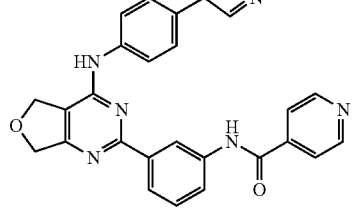 | D |

TABLE 1-continued
Glycolysis IC50 values (nM)
| Example Number | Structure | Glycolysis IC50 A = 10-100 nM; B = 101-250 Nm; C = 251-500 nM; D = 501-1,000 nM; E = >1,000 nM |
|---|---|---|
| Example 176 | 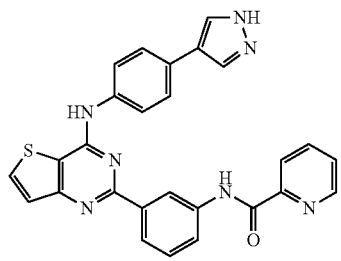 [SMILES: O=C(Nc1cccc(-c2nc(Nc3ccc(-c4cn[nH]c4)cc3)c3sccc3n2)c1)c1ccccn1] | E |
| Example 177 | 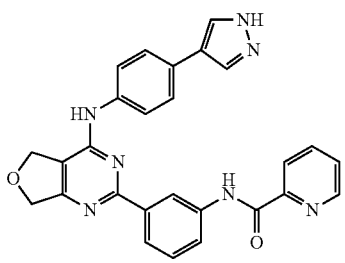 [SMILES: O=C(Nc1cccc(-c2nc3c(c(Nc4ccc(-c5cn[nH]c5)cc4)n2)COC3)c1)c1ccccn1] | A |
| Example 178 | 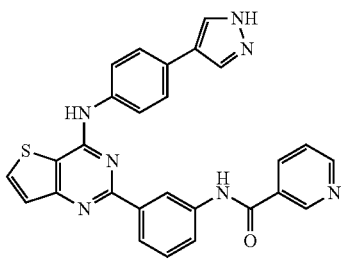 [SMILES: O=C(Nc1cccc(-c2nc(Nc3ccc(-c4cn[nH]c4)cc3)c3sccc3n2)c1)c1cccnc1] | A |
| Example 179 | 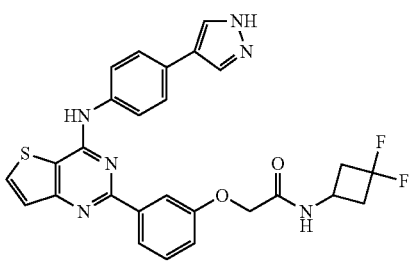 [SMILES: O=C(COc1cccc(-c2nc(Nc3ccc(-c4cn[nH]c4)cc3)c3sccc3n2)c1)NC1CC(F)(F)C1] | C |
| Example 180 | 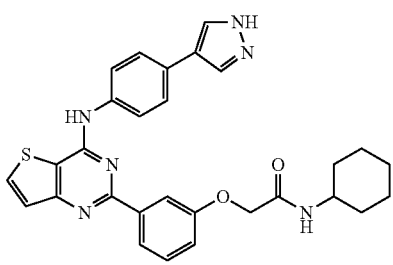 [SMILES: O=C(COc1cccc(-c2nc(Nc3ccc(-c4cn[nH]c4)cc3)c3sccc3n2)c1)NC1CCCCC1] | B |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 181 | 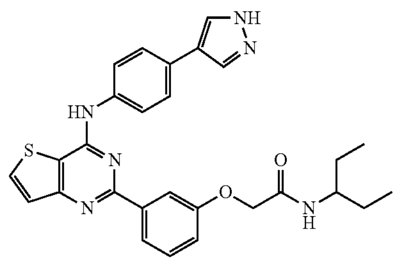 [SMILES: CCC(CC)NC(=O)COc1cccc(-c2nc(Nc3ccc(-c4cn[nH]c4)cc3)c3sccc3n2)c1] | C |
| Example 182 | 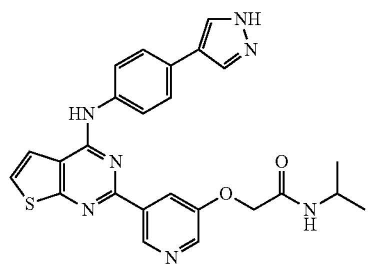 [SMILES: CC(C)NC(=O)COc1cncc(-c2nc(Nc3ccc(-c4cn[nH]c4)cc3)c3ccsc3n2)c1] | E |
| Example 183 | 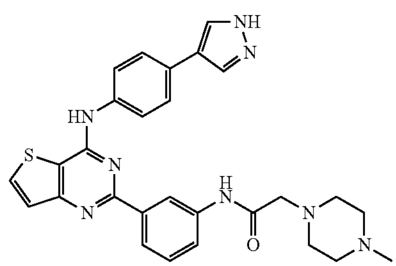 [SMILES: CN1CCN(CC(=O)Nc2cccc(-c3nc(Nc4ccc(-c5cn[nH]c5)cc4)c4sccc4n3)c2)CC1] | D |
| Example 184 | 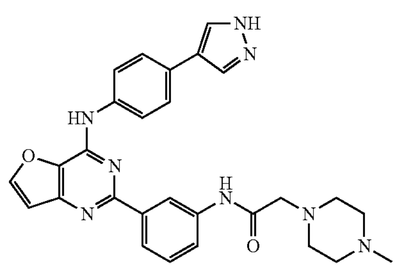 [SMILES: CN1CCN(CC(=O)Nc2cccc(-c3nc(Nc4ccc(-c5cn[nH]c5)cc4)c4occc4n3)c2)CC1] | D |
| Example 185 | 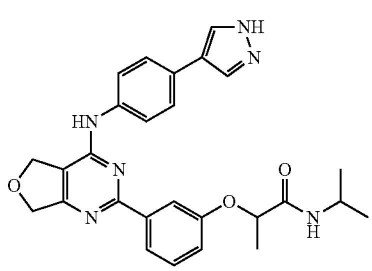 [SMILES: CC(C)NC(=O)C(C)Oc1cccc(-c2nc3c(c(Nc4ccc(-c5cn[nH]c5)cc4)n2)COC3)c1] | E |

TABLE 1-continued

Glycolysis IC50 values (nM)

| Example Number | Structure | Glycolysis IC50 A = 10-100 nM; B = 101-250 Nm; C = 251-500 nM; D = 501-1,000 nM; E = >1,000 nM |
|---|---|---|
| Example 186 | 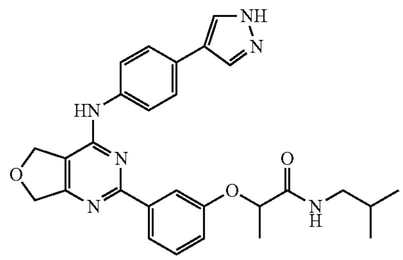 | E |
| Example 187 | 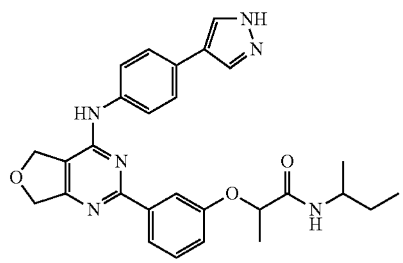 [SMILES: CCC(C)NC(=O)C(C)Oc1cccc(-c2nc3c(c(Nc4ccc(-c5cn[nH]c5)cc4)n2)COC3)c1] | E |
| Example 188 | 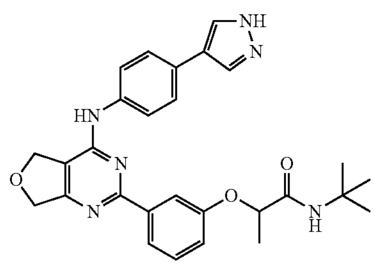 [SMILES: CC(Oc1cccc(-c2nc3c(c(Nc4ccc(-c5cn[nH]c5)cc4)n2)COC3)c1)C(=O)NC(C)(C)C] | E |
| Example 189 | 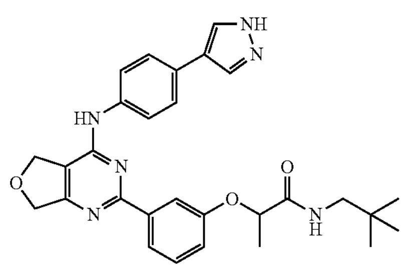 [SMILES: CC(Oc1cccc(-c2nc3c(c(Nc4ccc(-c5cn[nH]c5)cc4)n2)COC3)c1)C(=O)NCC(C)(C)C] | C |
| Example 190 | 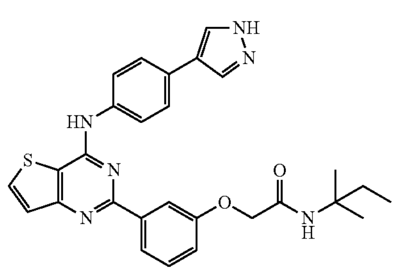 [SMILES: CCC(C)(C)NC(=O)COc1cccc(-c2nc(Nc3ccc(-c4cn[nH]c4)cc3)c3sccc3n2)c1] | B |

Example 192 (Cell-Based Efficacy)

As previously discussed, glucose is the major energy source for cancer cells and, compared to normal cells, cancer cells rely on increased rates of glycolysis for survival and cell growth. The glucose transport inhibitors disclosed herein strongly inhibit the growth of multiple cancer cell lines in tissue culture. Table 2 summarizes these findings for multiple compounds:

TABLE 2

Proliferation IC50 values (nM) for each compound on various cell lines (72 hrs)

| Compound | Jurkat | MOLT-4 | U937 |
| --- | --- | --- | --- |
| Example 1 | 629.8 | 1623 | N/A |
| Example 5 | 397 | N/A | N/A |
| Example 7 | 499.8 | 822.8 | 387.5 |
| Example 19 | 2200 | N/A | N/A |
| Example 21 | 9400 | N/A | N/A |
| Example 23 | 162 | N/A | N/A |
| Example 24 | 215.5 | 416.7 | 233.5 |
| Example 31 | 293.5 | 385 | 256 |
| Example 32 | 169.6 | 264.3 | 123 |

Figure 2A:
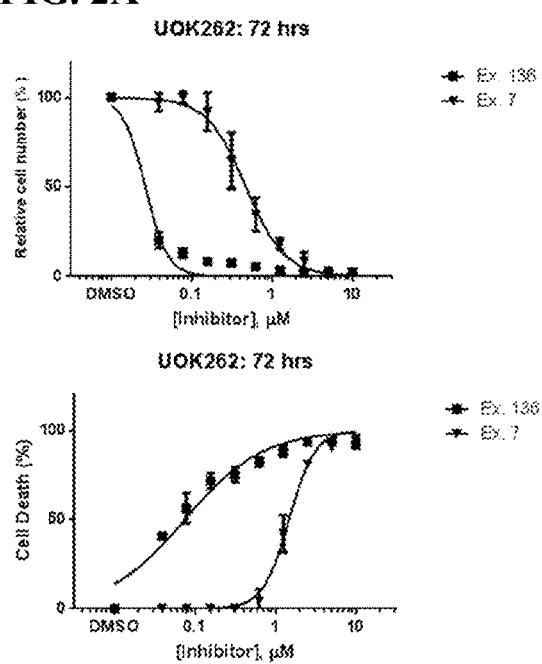
FIG. 2A-B shows a 72 hour proliferation assay for two mitochondrial deficient cell lines (FIG. 2A=UOK262, FIG. 2B=UOK269) treated with a dose-curve of the compound of Example 136 (-■-) and the compound of Example 7 (-▼-). Both IC50 and LD50 values are displayed.
Figure 2B:
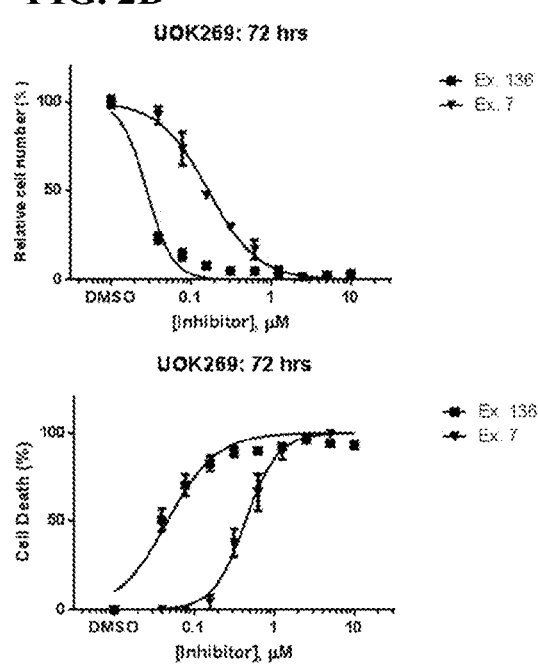

In addition to the cell lines summarized in Table 2, the glucose uptake inhibitors disclosed herein have a potent inhibitory effect on the growth of cancer cell lines derived from tumors that have compromised mitochondrial function. In the defined genetic background of mutant FH (UOK262 cell line) or mutant SDHB (UOK269 cell line), glucose uptake inhibitors disclosed herein deplete ATP levels in 4 hours without the addition of oligomycin (FIG. 1) and inhibit cell growth and cause cell death at nanomolar concentrations (FIG. 2).

Example 193 (Rational Combination Strategies)

In addition to inhibition of cell growth as single agents, the glucose transport inhibitors disclosed herein display robust effects on cell growth and survival when used within rational combination strategies. The following examples describe the use of the glucose transport inhibitors disclosed herein in targeted combinatorial approaches.

Figure 3A:
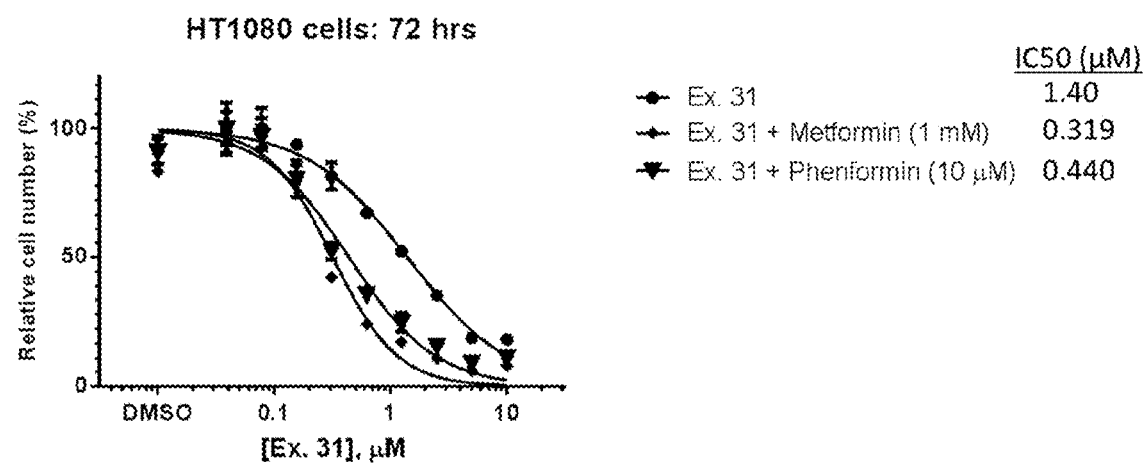
FIG. 3A-B shows a dose-response curve for HT1080 cells that were treated (72 hours) with the compound of Example 31 (FIG. 3A) or Example 7 (FIG. 3B) −/+1 mM Metformin or 10 µM Phenformin.
Figure 3B:
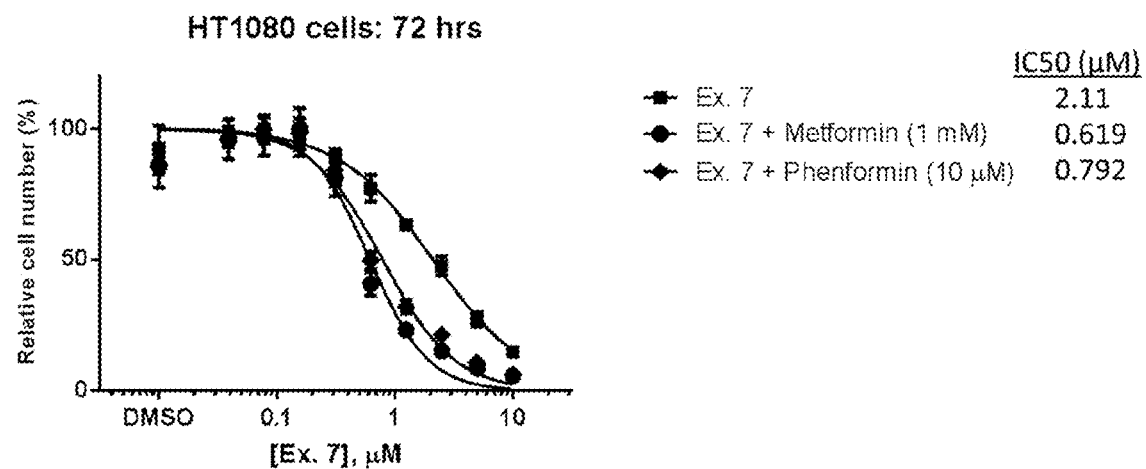

Simultaneous inhibition of glucose transport and Complex I of oxidative phosphorylation: The principle employed in the cellular glycolysis assay described above can be implemented to reduce cancer cell viability. Cell growth and survival depends on ATP and the simultaneous targeting of glycolysis and oxidative phosphorylation is known to synergistically reduce intracellular ATP levels. This was demonstrated by the ability of the glucose transport inhibitors disclosed herein combined with oligomycin to synergistically reduce ATP levels in one hour. However, the ATP synthase inhibitor oligomycin is not a viable therapeutic agent. In contrast, biguanides such as phenformin and metformin represent viable therapeutic agents that target Complex I of the electron transport chain (ETC). Inhibition of complex I reduces electron flow through the ETC and leads to decreased ATP production from oxidative phosphorylation. Similar to what has been observed with the glycolysis inhibitor 2-Deoxyglucose (2-DG) (Cheong, J. H., et al., *Dual inhibition of tumor energy pathway by 2-deoxyglucose and metformin is effective against a broad spectrum of preclinical cancer models*. Mol Cancer Ther, 2011. 10(12): p. 2350-62), the combination of the glucose transport inhibitors disclosed herein and inhibitors of complex I robustly inhibit cancer cell growth over 72 hrs. FIG. 3 shows an example of a dose-response curve of the compound of Example 31 (Ex. 31) in combination with 1 mM Metformin, 10 μM Phenformin. In addition, the glucose transport inhibitors disclosed herein robustly inhibit cancer cell growth when combined with 20 nM Rotenone (a well-established inhibitor of Complex I, data not shown). Note that at these concentrations, the complex I inhibitors had no effect on viability and minimal effect on cell number as single agents.

Figure 4A:
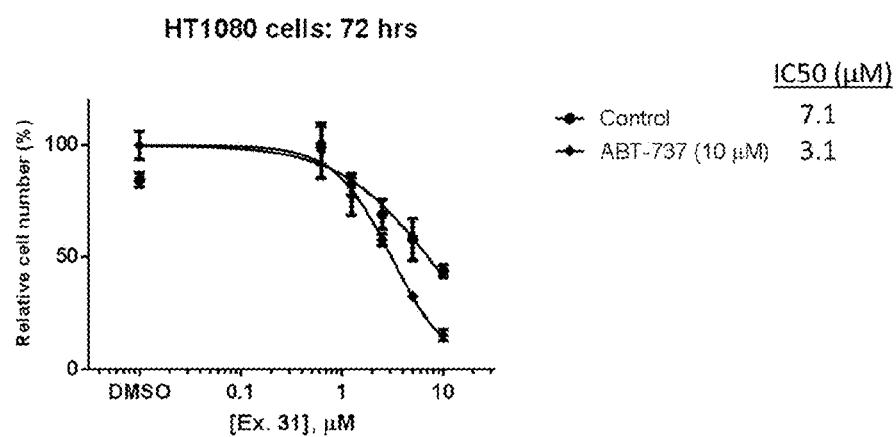
FIG. 4A-B shows a dose-response curve for HT1080 cells that were treated (72 hours) with the compound of Example 31−/+10 µM ABT-737.
Figure 4B:
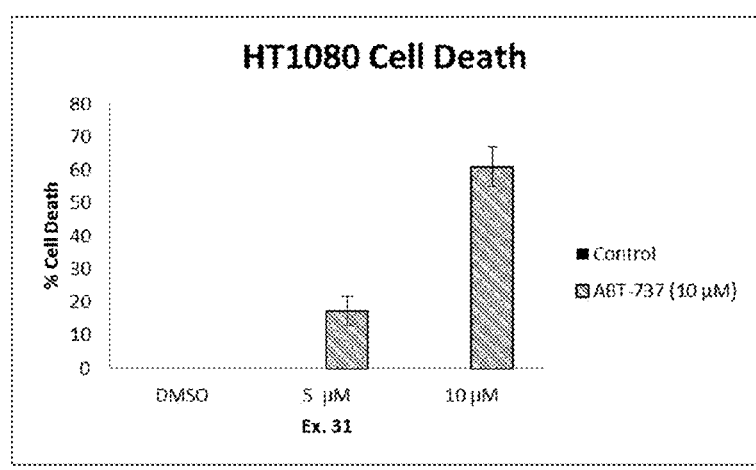

Simultaneous inhibition of glucose transport and pro-survival Bcl-2 family members: Because deprivation of glucose interferes with N-linked protein glycosylation, pharmacological inhibition of glucose transport causes ER stress (Palorini, R., et al., *Glucose starvation induces cell death in K-ras-transformed cells by interfering with the hexosamine biosynthesis pathway and activating the unfolded protein response*. Cell Death Dis, 2013. 4: p. e732; Saito, S., et al., *Chemical genomics identifies the unfolded protein response as a target for selective cancer cell killing during glucose deprivation*. Cancer Res, 2009. 69(10): p. 4225-34). Upon ER stress, cells activate the unfolded protein response, an adaptive response that protects cells until the ER stress has become too severe or too prolonged. Pro-survival Bcl-2 family members play a large role in this adaptive response (Xu, C., B. Bailly-Maitre, and J. C. Reed, *Endoplasmic reticulum stress: cell life and death decisions*. J Clin Invest, 2005. 115(10): p. 2656-64; Szegezdi, E., et al., *Mediators of endoplasmic reticulum stress-induced apoptosis*. EMBO Rep, 2006. 7(9): p. 880-5). Therefore, the simultaneous induction of ER stress by inhibition of glucose transport and inhibition of pro-survival Bcl-2 family members is likely to lead to increased cell death. We have demonstrated a synergistic effect between ABT-737, a Bcl-2 family inhibitor, and the glucose transport inhibitors disclosed herein. Despite the observation that HT-1080 cells were relatively resistant to ABT-737 as a single agent (IC50 of ~8.5 μM), FIG. 4 shows that ABT-737 greatly sensitized these cells to Ex. 31. Not only is the IC50 of Ex. 31 reduced by more than two-fold, but the combination of these two agents caused ~60% cell death. Note that under these conditions, neither Ex. 31 nor ABT-737 (10 μM) caused cell death as single agents. In addition, the glucose transport inhibitors disclosed herein also synergize with an analog of ABT-737, ABT-263 (data not shown).

Figure 5A:
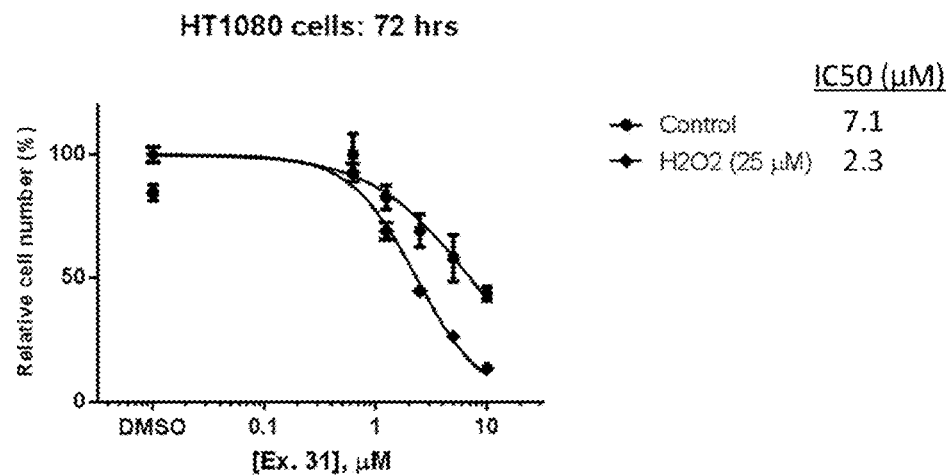
FIG. 5A-B shows a dose-response curve for HT1080 cells that were treated (72 hours) with the compound of Example 31−/+25 µM $H_2O_2$.
Figure 5B:
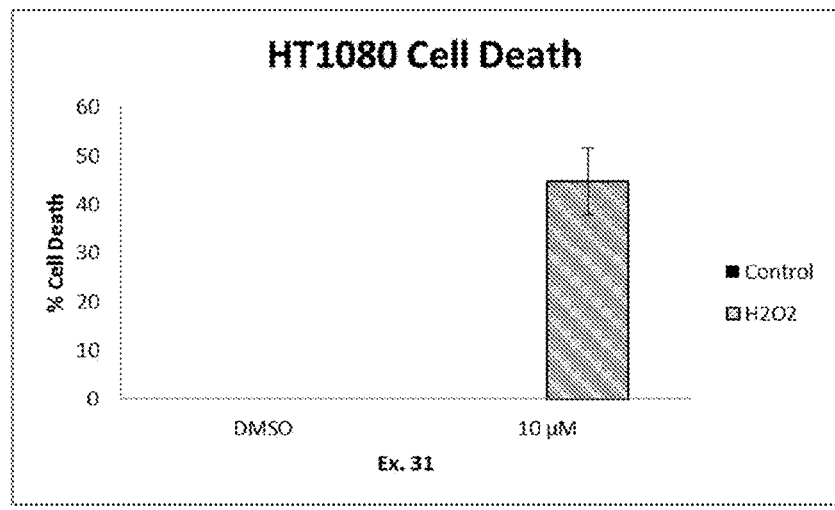

Inhibition of glucose transport combined with pro-oxidant compounds (ROS): Glucose is an extremely important nutrient not only for generating intracellular ATP but also for maintenance of cellular antioxidant responses. Both glycolysis and the pentose phosphate pathway (PPP) utilize glucose to produce antioxidant molecules. The end product of glycolysis is pyruvate, which is a scavenger for reactive oxygen species (ROS). The PPP produces NAPDH, an essential co-factor for both the thioredoxin and glutathione antioxidant systems. Unlike enzymatic inhibitors of glycolysis that work downstream of glucose uptake (e.g. 2-DG, lonidamine, etc.), the glucose uptake inhibitors disclosed herein simultaneously inhibit both glycolysis and the PPP. Accordingly, it may be hypothesized that glucose transport inhibition would greatly sensitize cells to ROS. To demonstrate this principle, the combination of Hydrogen Peroxide ($H_2O_2$) and the glucose uptake inhibitors disclosed herein was utilized. FIG. 5 demonstrates that the glucose transport inhibitors disclosed herein sensitize cells to ROS. In FIG. 5A, HT-1080 cells were treated with a dose-response curve of Ex. 31 −/+25 μM $H_2O_2$. This treatment shifted the IC50 of Ex. 31 by more than two-fold. In addition, FIG. 5B demonstrates that the glucose transport inhibitors disclosed herein sensitize HT1080 cells to cell death by ROS. While neither 10 μM Ex. 31 nor 25 μM $H_2O_2$ caused cell death under these conditions, the combination resulted in ~45% cell death.

Figure 6A:
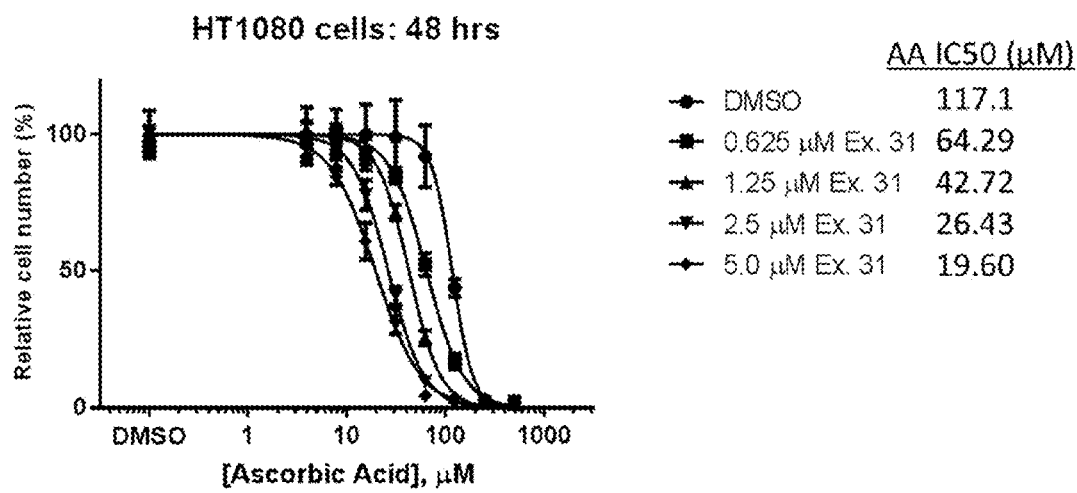
FIG. 6A-B shows a dose response curve for HT1080 cells that were treated (48 hrs) with of ascorbic acid −/+ the indicated concentrations of the compound of Example 31.
Figure 6B:
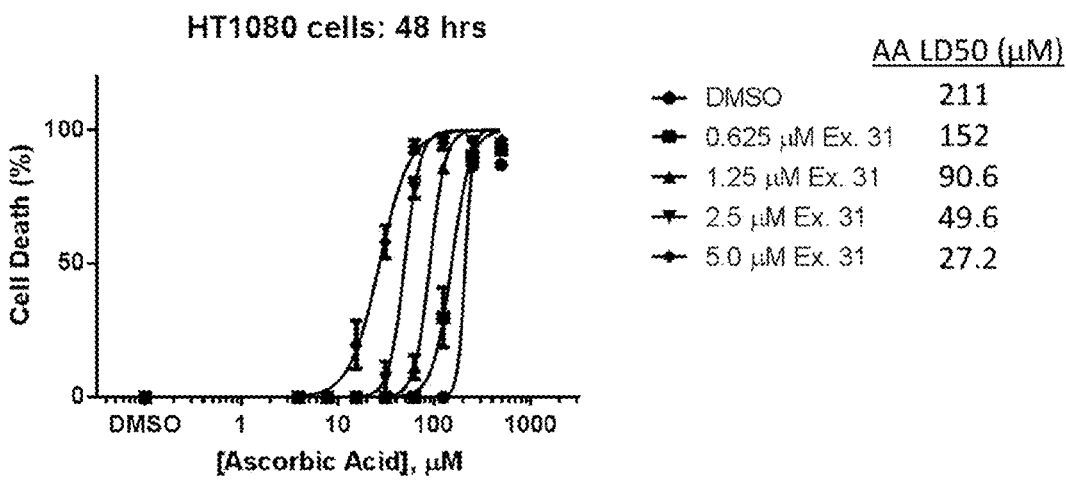

One physiologically relevant pro-oxidant is high-dose ascorbic acid. While at low concentrations ascorbic acid acts as an antioxidant, at high-doses (pharmacological doses) it exerts pro-oxidant effects. Accorindgly, it has been shown that the glucose uptake inhibitors disclosed herein synergize with ascorbic acid treatment of cancer cells. FIG. 6 demonstrates that both the IC50 (FIG. 6A) and LD50 (FIG. 6B) of ascorbic acid are greatly shifted by increasing doses of Ex. 31.

In addition to $H_2O_2$ and high-dose ascorbic acid, it has been found that the glucose transport inhibitors disclosed herein synergize with all pro-oxidant compounds tested to date, including high-dose ascorbic acid, menadione and beta-lapachone. At low concentrations, ascorbic acid acts as an antioxidant but at high-doses (pharmacological doses) exerts pro-oxidant effects. Therefore, any therapeutic that produces ROS (including ionizing radiation) or lowers ROS defenses would be predicted have synergistic effects with the glucose transport inhibitors disclosed herein.

Collectively, the data herein demonstrate that the glucose transport inhibitors disclosed herein have single agent efficacy across multiple cancer cell lines, and are amenable, but not limited to, the specific combination strategies outlined above.

Example 194 (Malaria)

Figure 7A:
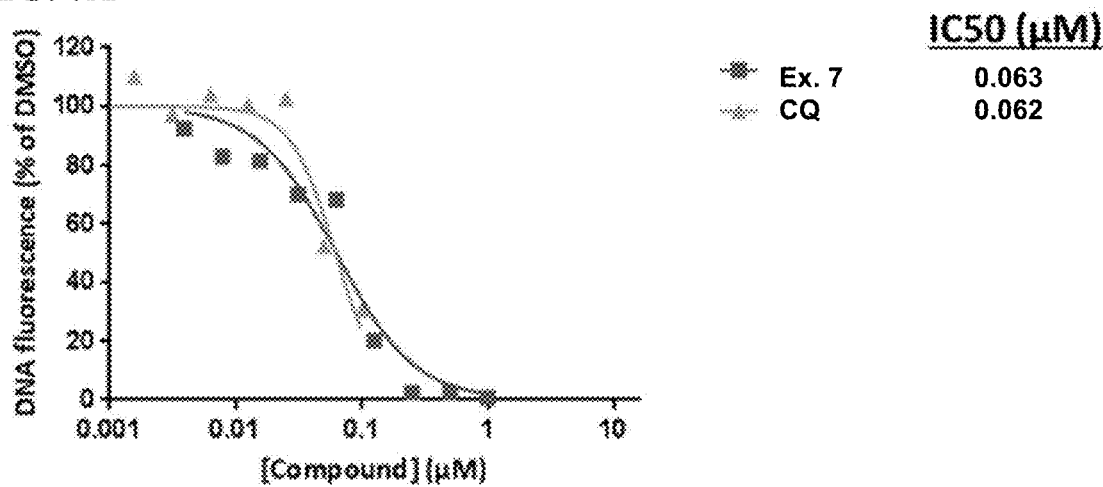
FIG. 7A-B shows that cultured *Plasmodium falciparum* is sensitive to glucose uptake inhibition.
Figure 7B:
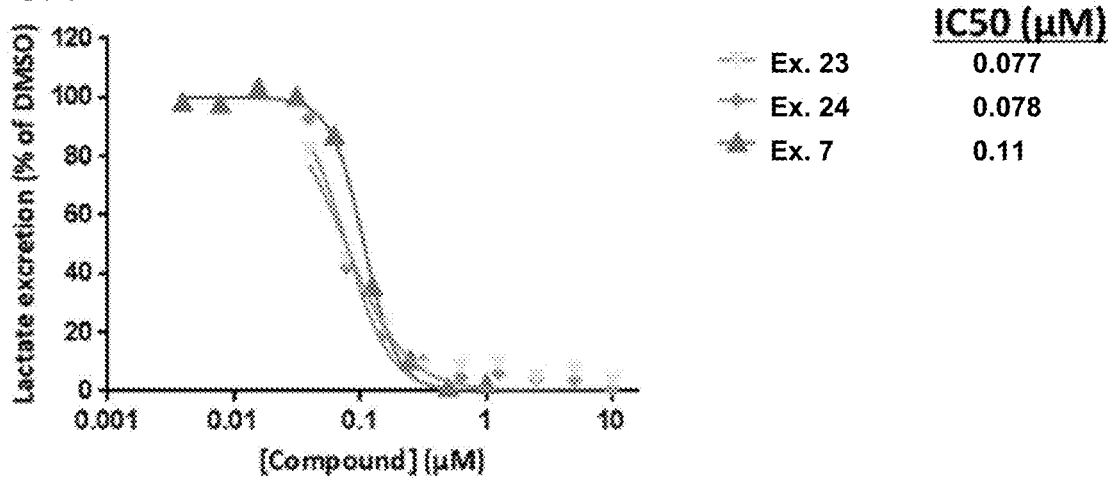

As previously discussed, malaria parasites rely on glucose that is first imported by host transporters in the erythrocyte membrane (i.e. GLUT1) and subsequently transported into the parasite through its own hexose transporters. As shown below, the glucose uptake inhibitors disclosed herein display striking inhibition of both parasite proliferation (FIG. 7A) and lactate excretion (FIG. 7B), a downstream maker of glucose consumption/glycolysis.

Example 195 (Activated T Cells)

Figures 8A, 8B:
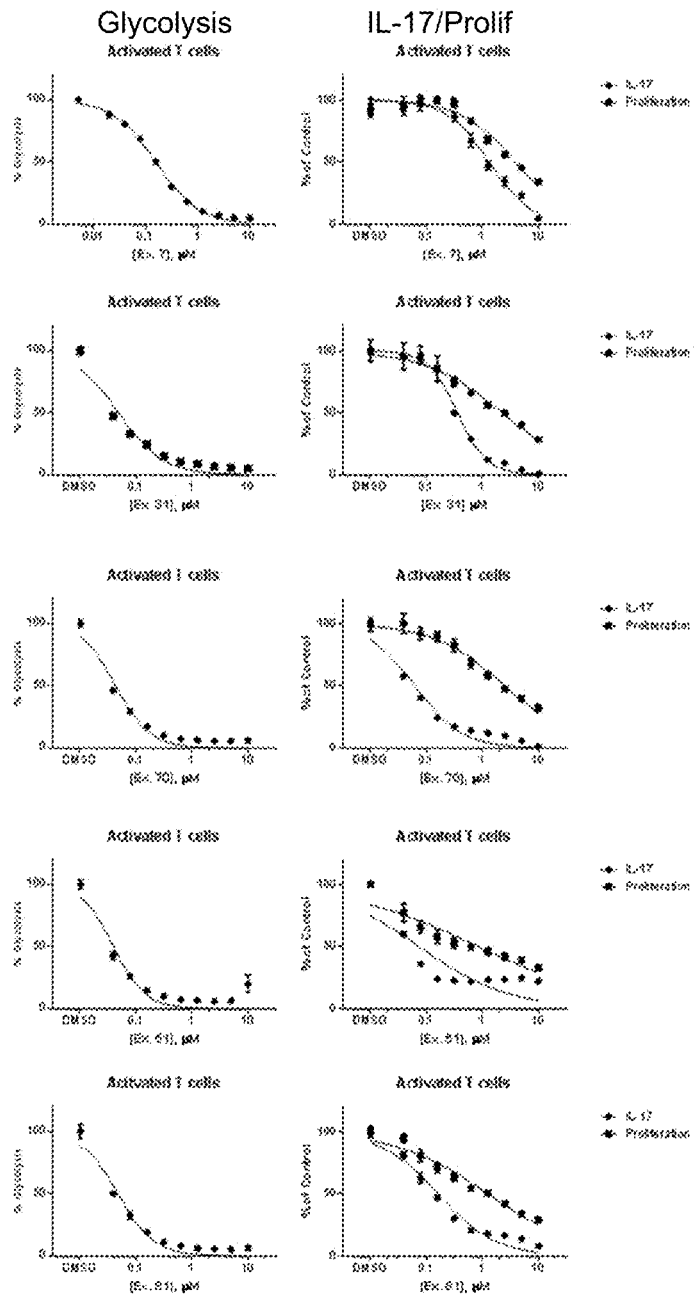
FIG. 8A-B shows that the metabolism, function and proliferation of activated T cells are suppressed by compounds disclosed herein.

As previously described, activated T cells rely on aerobic glycolysis to meet their energetic demands. As shown below, the glucose uptake inhibitors disclosed herein down-regulate glycolysis of activated T cells and inhibit their effector function. In FIG. 8, human CD4 positive T cells were activated by anti-CD3 and anti-CD28 antibodies in the presence of IL1β and TGFβ (activating conditions). Under these conditions, CD4+ T cells rapidly divide and produce many cytokines, including IL-17. 24 hours post-activation, the glucose uptake inhibitors disclosed herein were applied in the one-hour glycolysis assay described above for HT1080 cells. As can be seen in FIG. 8A (left panel), these inhibitors potentially suppressed glycolysis in activated T cells. Alternatively, resting T cells were activated and treated simultaneously with the glucose uptake inhibitors disclosed herein for 48 hours. At this time, secreted IL-17 and relative cell number were measured (FIG. 8A, right panel). The glucose uptake inhibitors disclosed herein down-regulated both IL-17 secretion and proliferation (at higher concentrations). In FIG. 8B, the IC50s for each compound against glycolysis, IL-17 secretion and proliferation are listed. Therefore, the glucose uptake inhibitors disclosed herein are likely to have utility against inflammatory disorders, including but not limited to diseases characterized by highly glycolytic immune cells and/or Th17/IL-17 driven pathologies.

Example 196 (Activated T Cells)

Figure 9:
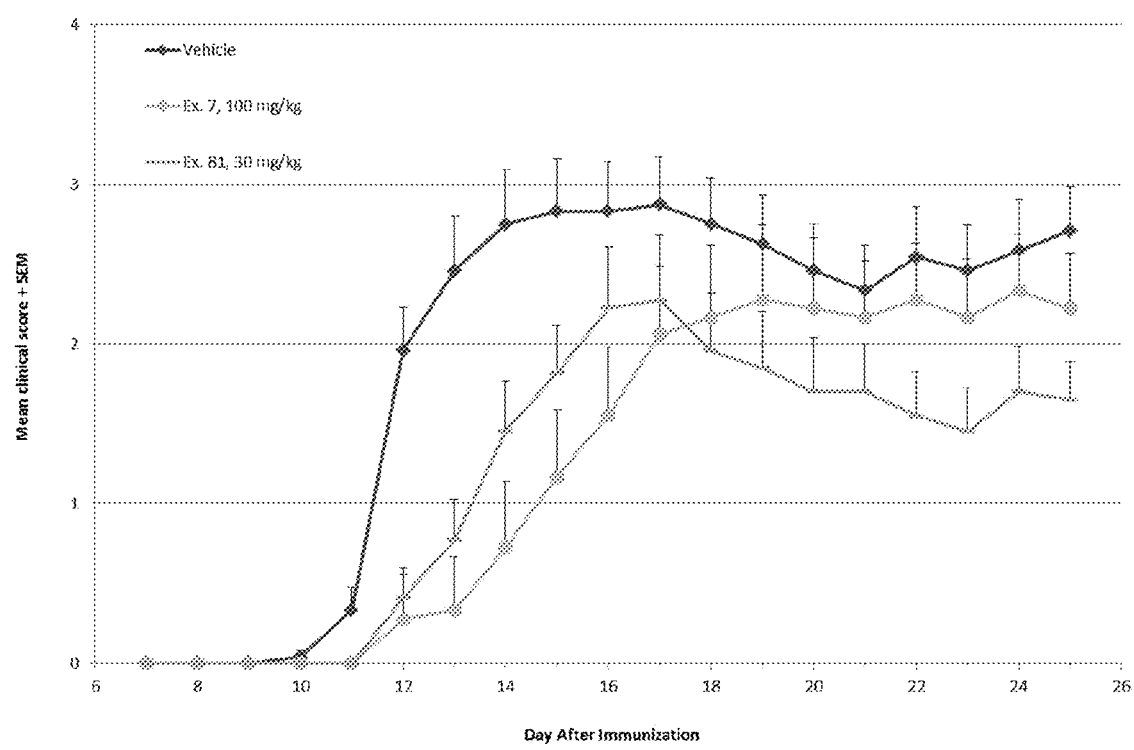
FIG. 9 demonstrates in vivo efficacy for glucose uptake inhibitors disclosed herein in a model of mouse Myelin Oligodendrocyte Glycoprotein (MOG)-induced experimental autoimmune encephalitis (EAE). Two specific glucose uptake inhibitors, the compound of Example 7 (-●-) and the compound of Example 81 ( - - - ) either delayed the onset or lowered the end clinical score (compared to the vehicle control, -♦-=vehicle) in this model.

As described above, the glucose uptake inhibitors disclosed herein possess anti-inflammatory properties and inhibit metabolism, effector function and proliferation of activated T cells. In FIG. 9, two of the glucose uptake inhibitors disclosed herein are shown to have efficacy against an in vivo mouse model of inflammation, MOG-induced experimental autoimmune encephalitis. The glucose uptake inhibitors disclosed herein delay the onset or lower the end clinical score of inflammation in this model. These in vivo data confirm the observations made in cell-based assays and further demonstrate the utility of these compounds against inflammatory disorders, including but not limited to those driven by Th17 CD4+ T cells.

Example 197 (Methods)

Determination of glucose uptake/GLUT activity (glycolysis assay): HT1080 cells (as well as other cell types) were plated to confluency in 96-well plates. Cells were exposed to the combination of 10 μM Oligomycin (to block mitochondrial-derived ATP) and the glucose uptake inhibitors disclosed herein for one-hour, after which glycolytically-derived ATP was measured with the Cell Titer-Glo assay kit (Promega). Dose-response curves of the glucose uptake inhibitors disclosed herein were used to determine the IC50 for GLUT activity.

Cell proliferation and cell death assays: HT1080 cells (or other cell types) were plated in 96-well format at cell densities suitable for culture from 24-72 hrs. For IC50 of cellular proliferation, cells were fixed with TCA and stained with SRB to quantify relative viability. At the end of the specified assay time, the percentage of drug-treated cells was calculated relative to the DMSO control. For cell death assays, viability was assessed relative to the 0-hour time-point T cell assays: Human CD4 T cells were purified using RossetteSep Human CD4 T cell Enrichment Cocktail. Resting T cells were activated with 5 μg/ml plate-bound anti-CD3 and anti-CD28, 50 ng/ml IL-1β and 5 ng/ml TGF-β. The previously described glycolysis assay was performed 24 hours post-activation. IL-17 levels were measured by ELISA (R&D systems, Human IL-17 Quantikine ELISA kit). Proliferation was measured by Cell Titer Glo (Promega)

Mouse Prophylactic MOG-EAE Model: Performed at Hooke laboratories. Briefly, mice were immunized with MOG peptide on day 0 and subsequently injected with pertussis toxin. Compounds were dosed orally beginning on day 3 continuing until day 25.

What is claimed is:
1. A compound having the formula I:

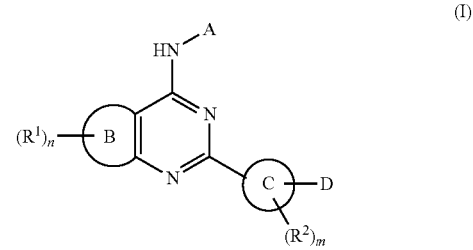

(I)

or a pharmaceutically acceptable salt thereof,
wherein:
A is a group having the formula:

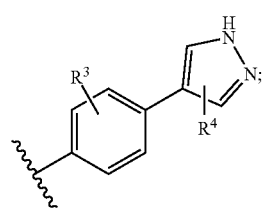

Ring B is a five- or six-membered ring containing 1 or 2 heteroatoms selected from the group consisting of N, O and S;

Ring C is a five- or six-membered aryl or heteroaryl ring containing from 0 to 2 heteroatoms selected from the group consisting of N, O and S;

each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

n is selected from 0, 1, or 2;

each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

m is selected from 0, 1, or 2;

$R^3$ and $R^4$ are H;

D is selected from the group consisting of —O—$(CH_2)_y$—C(=O)$NR^5R^6$, —O—C(=O)—$(CH_2)_y$—$NR^5R^6$, —O—$(CH_2)_y$—$NR^5R^6$, —NH—C(=O)—$(CH_2)_y$—$NR^5R^6$, —NH—C(=O)—$(CH_2)_y$—$R^7$, and —NH—$(CH_2)_y$—$NR^5R^6$;

y is selected from 1, 2, or 3;

$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl, or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and $R^7$ is selected from the group consisting of aryl, heteroaryl, and a hetercyclic group.

2. The compound of claim 1, wherein the sub-structure

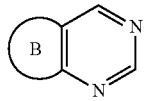

is selected from the group consisting of:

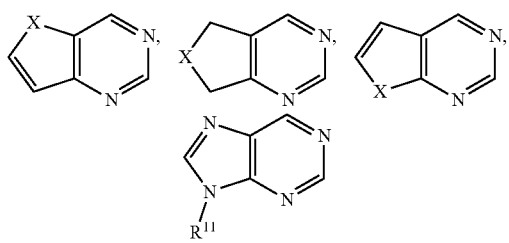

wherein X is selected from O and S, and $R^{11}$ is selected from H and $C_1$ to $C_6$ alkyl,

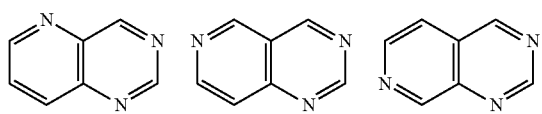

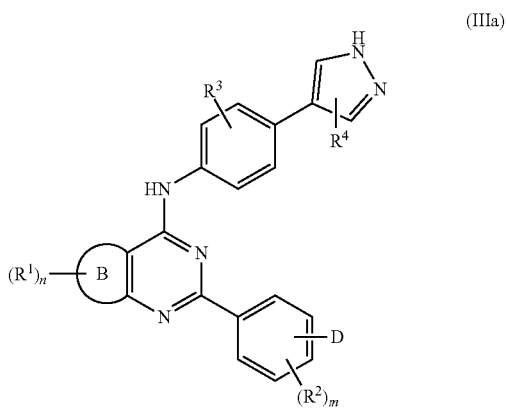

wherein R is selected from $C_1$-$C_6$ alkyl, and $C_3$-$C_6$ cycloalkyl.

3. The compound of claim 1, having the formula III$_a$:

(IIIa)

or a pharmaceutically acceptable salt thereof, wherein:

Ring B is a five- or six-membered ring containing 1 or 2 heteroatoms selected from the group consisting of N, O and S;

each $R^1$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

n is selected from 0, 1, or 2;

each $R^2$ is independently selected from the group consisting of halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl;

m is selected from 0, 1, or 2;

$R^3$ and $R^4$ are H;

D is selected from the group consisting of —O—$(CH_2)_y$—C(=O)$NR^5R^6$, —O—C(=O)—$(CH_2)_y$—

$NR^5R^6$, —O—$(CH_2)_y$—$NR^5R^6$, —NH—C(=O)—$(CH_2)_y$—$NR^5R^6$, —NH—C(=O)—$(CH_2)_y$—$R^7$, and —NH—$(CH_2)_y$—$NR^5R^6$;

y is selected from 1, 2, or 3;

$R^5$ and $R^6$ are independently selected from the group consisting of H, $C_1$-$C_6$ alkyl, $C_2$-$C_6$ alkenyl, $C_2$-$C_6$ alkynyl, —($C_1$-$C_6$ alkyl)-O—($C_1$-$C_6$ alkyl), aryl, aralkyl, heteroaryl, and $C_3$-$C_6$ cycloalkyl, or $R^5$ and $R^6$ may be taken together with the nitrogen to which they are attached to form a 5- to 6-membered heterocyclic ring having up to 3 heteroatoms selected from N, O, and S, and which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_6$ cycloalkyl, oxo, hydroxy, amino, cyano and $C_1$-$C_3$ perfluoro alkyl; and $R^7$ is selected from the group consisting of aryl, heteroaryl, and a hetercyclic group.

4. A pharmaceutical composition comprising the compound of claim 1 and a pharmaceutically acceptable excipient.

5. A method of inhibiting tumor growth or metastasis comprising administering to a patient in need thereof a therapeutically effect amount of the pharmaceutical composition of claim 4.

6. A method of inhibiting angiogenesis comprising administering to a patient in need thereof a therapeutically effect amount of the pharmaceutical composition of claim 4.

7. A method of inhibiting inflammation comprising administering to a patient in need thereof a therapeutically effect amount of the pharmaceutical composition of claim 4.

\* \* \* \* \*